United States Patent
Feng et al.

(10) Patent No.: US 9,974,782 B2
(45) Date of Patent: May 22, 2018

(54) PHOSPHODIESTERASE INHIBITORS AND USES THEREOF

(71) Applicant: THE TRUSTEES OF COLUMBIA UNIVERSITY IN THE CITY OF NEW YORK, New York, NY (US)

(72) Inventors: Yan Feng, Shanghai (CN); Ottavio Arancio, New York, NY (US); Shixian Deng, White Plains, NY (US); Donald W. Landry, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days. days.

(21) Appl. No.: 15/235,736

(22) Filed: Aug. 12, 2016

(65) Prior Publication Data

US 2017/0216275 A1    Aug. 3, 2017

Related U.S. Application Data

(63) Continuation of application No. 14/224,702, filed on Mar. 25, 2014, now Pat. No. 9,422,242, which is a continuation of application No. 13/167,540, filed on Jun. 23, 2011, now Pat. No. 8,697,875, which is a continuation-in-part of application No. PCT/US2009/058813, filed on Sep. 29, 2009.

(60) Provisional application No. 61/140,315, filed on Dec. 23, 2008.

(30) Foreign Application Priority Data

Apr. 1, 2009    (WO) ................ PCT/US2009/039129

(51) Int. Cl.
    *A61K 31/4706*    (2006.01)
(52) U.S. Cl.
    CPC ............... *A61K 31/4706* (2013.01)
(58) Field of Classification Search
    CPC ............................................. A61K 31/4706
    See application file for complete search history.

(56) References Cited

U.S. PATENT DOCUMENTS

| | | |
|---|---|---|
| 5,294,612 A | 3/1994 | Bacon et al. |
| 5,296,479 A | 3/1994 | Cain et al. |
| 5,346,901 A | 9/1994 | Bell et al. |
| 5,492,915 A | 2/1996 | Dereu et al. |
| 5,565,325 A | 10/1996 | Blake |
| 5,576,322 A | 11/1996 | Takase et al. |
| 5,693,652 A | 12/1997 | Takase et al. |
| 5,712,171 A | 1/1998 | Zambias et al. |
| 5,801,180 A | 9/1998 | Takase et al. |
| 6,302,837 B1 | 10/2001 | De Nanteuil et al. |
| 6,573,278 B2 | 6/2003 | Mittendorf et al. |
| 6,576,644 B2 | 6/2003 | Bi et al. |
| 6,835,737 B2 | 12/2004 | Bi et al. |
| 6,921,759 B2 | 7/2005 | Anthony et al. |
| 7,173,042 B2 | 2/2007 | Bi et al. |
| 7,378,430 B2 | 5/2008 | Bi et al. |
| 7,384,958 B2 | 6/2008 | Bi et al. |
| 2002/0106676 A1 | 8/2002 | Roch et al. |
| 2002/0133008 A1 | 9/2002 | Macor et al. |
| 2002/0177587 A1* | 11/2002 | Bi ................... A61K 31/47 514/210.21 |
| 2003/0166644 A1 | 9/2003 | Ebdrup et al. |
| 2003/0199693 A1 | 10/2003 | Chen |
| 2004/0014774 A1 | 1/2004 | Myers et al. |
| 2004/0038856 A1 | 2/2004 | Chakravarty et al. |
| 2004/0039035 A1 | 2/2004 | Collins et al. |
| 2004/0043983 A1 | 3/2004 | Li |
| 2004/0043985 A1 | 3/2004 | Hicks et al. |
| 2004/0171881 A1 | 9/2004 | John et al. |
| 2005/0009163 A1 | 1/2005 | Tong et al. |
| 2005/0009815 A1 | 1/2005 | DeVita et al. |
| 2005/0202549 A1 | 9/2005 | Brown et al. |
| 2005/0261298 A1 | 11/2005 | Solow-Cordero et al. |
| 2006/0222647 A1 | 10/2006 | Beavo et al. |
| 2006/0281901 A1 | 12/2006 | Yoo et al. |
| 2007/0172484 A1 | 7/2007 | Solomon |
| 2007/0208029 A1* | 9/2007 | Barlow ............. A61K 31/40 514/252.15 |
| 2008/0009467 A1 | 1/2008 | Henderson |

(Continued)

FOREIGN PATENT DOCUMENTS

| | | |
|---|---|---|
| EP | 636626 | 2/1995 |
| EP | 995750 | 4/2000 |
| EP | 995751 | 4/2000 |

(Continued)

OTHER PUBLICATIONS

Baltrons et al., "β-amyloid peptides decrease Soluble Guanylyl Cyclase Expression in Astroglial Cells," Neurobiol. Dis., 10, pp. 139-149 (2002).

Baltrons et al., "Regulation of NO-dependent cyclic GMP formation by inflammatory agents in neural cells," Toxicol. Lett., 139, pp. 191-198 (2003).

Barad et al., "Rolipram, a type IV-specific phosphodiesterase inhibitor, facilitates the establishment of long-lasting long-term potentiation and improves memory," Proc. Natl. Acad. Sci. USA, 95, pp. 15020-15025 (1998).

Baratti and Boccia, "Effects of sildenafil on long-term retention of an inhibitory avoidance response in mice," Behav. Pharmacol., 10, 731-737 (1999).

Barrios Sosa et al., "Synthesis and inhibition of Src kinase activity by 7-ethenyl and 7-ethynyl-4-anilino-3-quinolinecarbonitriles," Bioorg. Med. Chem. Lett., 14, pp. 2155-2158 (2004).

(Continued)

*Primary Examiner* — Timothy R Rozof

(74) *Attorney, Agent, or Firm* — Wilmer Cutler Pickering Hale and Dorr LLP

(57) ABSTRACT

The invention provides for compounds that are phosphodiesterase inhibitors. The invention further provides for a method for screening compounds that bind to and modulate a phosphosdiesterase protein. The invention also provides methods for treating conditions associated with accumulated amyloid-beta peptide deposit accumulations by administering a phosphodiesterase-binding compound to a subject.

28 Claims, 58 Drawing Sheets
(21 of 58 Drawing Sheet(s) Filed in Color)

(56) References Cited

U.S. PATENT DOCUMENTS

| 2009/0017546 A1 | 1/2009 | Agnew et al. |
| 2009/0076077 A1 | 3/2009 | Kaila et al. |

FOREIGN PATENT DOCUMENTS

| EP | 1092718 | 4/2001 |
| JP | 2000072675 | 3/2000 |
| JP | 2002308877 | 10/2002 |
| WO | WO-91/05058 | 4/1991 |
| WO | WO-93/07124 | 4/1993 |
| WO | WO-93/07149 | 4/1993 |
| WO | WO-93/20242 | 10/1993 |
| WO | WO-94/18318 | 8/1994 |
| WO | WO-95/18972 | 7/1995 |
| WO | WO-95/19978 | 7/1995 |
| WO | WO-96/22529 | 7/1996 |
| WO | WO-98/07430 | 2/1998 |
| WO | WO-9816514 | 4/1998 |
| WO | WO-98/38168 | 9/1998 |
| WO | WO-98/49166 | 11/1998 |
| WO | WO-99/07409 | 2/1999 |
| WO | WO-99/24433 | 5/1999 |
| WO | WO-99/32619 | 7/1999 |
| WO | WO-99/54333 | 10/1999 |
| WO | WO-00/01846 | 1/2000 |
| WO | WO-00/015222 | 3/2000 |
| WO | WO-00/042026 | 7/2000 |
| WO | WO-00/44895 | 8/2000 |
| WO | WO-00/44914 | 8/2000 |
| WO | WO-01/12608 | 2/2001 |
| WO | WO-01/27112 | 4/2001 |
| WO | WO-01/27113 | 4/2001 |
| WO | WO-01/29058 | 4/2001 |
| WO | WO-01/36646 | 5/2001 |
| WO | WO-01/081311 | 11/2001 |
| WO | WO-01/087882 | 11/2001 |
| WO | WO-02/020489 | 3/2002 |
| WO | WO-02/074312 | 9/2002 |
| WO | WO-02/074774 | 9/2002 |
| WO | WO-04/010929 | 2/2004 |
| WO | WO-05/087742 | 9/2005 |
| WO | WO-08/067389 | 6/2008 |
| WO | WO-08/154221 | 12/2008 |
| WO | WO-09/124119 | 10/2009 |

OTHER PUBLICATIONS

Bass, "RNA interference: The short answer," Nature, 411, pp. 428-429 (2001).
Basun et al., "Plasma Levels of Aβ42 and Aβ40 in Alzheimer Patients during Treatment with the Acetylcholinesterase Inhibitor Tacrine," Dement. Geriatr. Cogn. Disord., 14, pp. 156-160 (2002).
Battaglioli et al., "REST Repression of Neuronal Genes Requires Components of the hSWI.SNF Complex," The Journal of Biological Chemistry, 277(43), pp. 41038-41045 (2002).
Bennett et al., "Cognitive Deficits in Rats after Forebrain Cholinergic Depletion are Reversed by a Novel NO Mimetic Nitrate Ester," Neuropsychopharmacology, 32, pp. 505-513 (2007).
Billings et al., "Intraneuronal Aβ Causes the Onset of Early Alzheimer's Disease-Related Cognitive Deficits in Transgenic Mice," Neuron, 45(5), pp. 675-688 (2005).
Blaney and Martin, "Computational approaches for combinatorial library design and molecular diversity analysis," Curr. Opin. Chem. Biol., 1 (1): pp. 54-59 (1997).
Bliss and Collingridge, "A synaptic model of memory: long-term potentiation in the hippocampus," Nature, 361, pp. 31-39 (1993).
Blondelle and Houghten, "Novel antimicrobial compounds identified using synthetic combinatorial library technology," Trends Biotechnol., 14, pp. 60-65 (1996).
Bon and Garthwaite, "On the Role of Nitric Oxide in Hippocampal Long-Term Potentiation," J. Neurosci., 23(5), pp. 1941-1948 (2003).
Bonkale et al., "Reduced nitric oxide responsive soluble guanylyl cyclase activity in the superior temporal cortex of patients with Alzheimer's disease," Neuroscience Letters, 187, pp. 5-8 (1995).
Borchelt et al., "Accelerated Amyloid Deposition in the Brains of Transgenic Mice Coexpressing Mutant Presenilin 1 and Amyloid Precursor Proteins," Neuron, 19, pp. 939-945 (1997).
Boschelli et al., "Synthesis and Src Kinase Inhibitory Activity of a Series of 4-Phenylamino-3-Quinolinecarbonitriles," J. Med. Chem., 44, pp. 822-833 (2001).
Bourtchuladze et al., "Deficient Long-Term Memory in Mice with a Targeted Mutation of the cAMP-Responsive Element-Binding Protein," Cell, 79, pp. 59-68 (1994).
Brenner and Lerner, "Encoded combinatorial chemistry," Proc. Natl. Acad. Sci. USA, 89, pp. 5381-5383 (1992).
Bunin et al., "The combinatorial synthesis and chemical and biological evaluation of a 1,4-benzodiazepine library," Proc. Natl. Acad. Sci. USA 91, pp. 4708-4712 (1994).
Burnett et al., "Long-term oral phosphodiesterase 5 inhibitor therapy alleviates recurrent priapism," Urology, 67(5), 1043-1048 (2006).
Böhm, "LUDI: rule-based automatic design of new substituents for enzyme inhibitor leads," J. Computer-Aided Mol. Des., 6, pp. 593-606 (1992).
Böhm, "On the use of LUDI to search the Fine Chemicals Directory for ligands of proteins of known three-dimensional structure," J. Computer-Aided Mol. Des., 8, pp. 623-632 (1994).
Böhm, "The computer program LUDI: a new method for the de novo design of enzyme inhibitors," J. Computer-Aided Mol. Des., 6, pp. 61-78 (1992).
Card et al., "Structural Basis for the Activity of Drugs that Inhibit Phosphodiesterases," Structure, 12(12) pp. 2233-2247 (2004).
Case et al., "The Amber Biomolecular Simulation Programs," Author Manuscript, published in final edited form as: J. Comput. Chem., 26(16), pp. 1668-1688 (2005).
Champion et al. "Phosphodiesterase-5A dysregulation in penile erectile tissue is a mechanism of priapism," Proc. Natl. Acad. Sci. USA, 102(5), pp. 1661-1666 (2005).
Chang et al., "AMPA receptor downscaling at the onset of Alzheimer's disease pathology in double knockin mice," Proceedings of the National Academy of Sciences of the United States of America, 103(9), pp. 3410-3415 (2006).
Chapman et al., "Impaired synaptic plasticity and learning in aged amyloid precursor protein transgenic mice," Nat. Neurosci., 2(3), pp. 271-276 (1999).
Chen and Wang, "The Use of Bioisosteric Groups in Lead Optimization," Ann. Reports Med. Chem., 38, pp. 333-346 (2003).
Chen and Zhan, "Fundamental reaction pathways and free energy barriers for ester hydrolysis of intracellular second messenger 3',5'-cyclic nucleotide," J. Phys. Chem. A, 108, pp. 3789-3797 (2004).
Chen and Zhan, "Theoretical Determination of Activation Free Energies for Alkaline Hydrolysis of Cyclic and Acyclic Phosphodiesters in Aqueous Solution," J. Phys. Chem. A, 108, pp. 6407-6413 (2004).
Choi et al., "Efficacy of Vardenafil and Sildenafil in Facilitating Penile Erection in an Animal Model," J. Androl., 23(3), pp. 332-337 (2002).
Christian et al., "Simplified Methods for Construction, Assessment and Rapid Screening of Peptide Libraries in Bacteriophage," J. Mol. Biol., 227, pp. 711-718 (1992).
Colton et al. "NO synthase 2 (NOS2) deletion promotes multiple pathologies in a mouse model of Alzheimer's disease," Proceedings of the National Academy of Sciences of the United States of America, 103, pp. 12867-12872 (2006).
Contestabile et al., "Brain Nitric Oxide and its Dual Role in Neurodegeneration/Neuroprotection: Understanding Molecular Mechanisms to Devise Drug Approaches," Curr. Med. Chem., 10, pp. 2147-2174 (2003).
Corbin and Francis, "Pharmacology of phosphodiesterase-5 inhibitors," Int. J. Clin. Pract., 56(6), pp. 453-459 (2002).
Cornell et al., "A Second Generation Force Field for the Simulation of Proteins, Nucleic Acids, and Organic Molecules," J. Am. Chem. Soc., 117, pp. 5179-5197 (1995).

(56) References Cited

OTHER PUBLICATIONS

Coste and Grondin, "Characterization of a novel potent and specific inhibitor of type V phosphodiesterase," Biochem. Pharmacol., 50(10), pp. 1577-1585 (1995).
Cullen et al., "Block of LTP in rat hippocampus in vivo by β-amyloid precursor protein fragments," Neuroreport, 8, pp. 3213-3217 (1997).
Dahiyat and Mayo, "De Novo Protein Design: Fully Automated Sequence Selection," Science, 278, 82-87 (1997).
Dallas and Vlassov, "RNAi: a novel antisense technology and its therapeutic potential," Med. Sci. Monit., 12(4), RA67-RA74 (2006).
Daugan et al., "The discovery of tadalafil: a novel and highly selective PDE5 inhibitor. 1: 5,6,11,11a-tetrahydro-1H-imidazo[1',5':1,6]pyrido[3,4-b]indole-1,3(2H)-dione analogues," J. Med. Chem., 46, pp. 4525-4532 (2003).
Davis et al., "The cyclic AMP system and *Drosophila* learning," Mol. Cell Biochem., 149/150, pp. 271-278 (1995).
Davis, "Physiology and biochemistry of *Drosophila* learning mutants," Physiol. Rev., 76(2), pp. 299-317 (1996).
Degerman et al., "Structure, Localization, and Regulation of cGMP-inhibited Phosphodiesterase (PDE3)," J. Biol. Chem., 272(11), pp. 6823-6826 (1997).
Devlin et al., "Random Peptide Libraries: a Source of Specific Protein Binding Molecules," Science, 249, pp. 404-406 (1990).
Di Rosa et al., "Calpain Inhibitors: A Treatment for Alzheimer's Disease," J. Mol. Neurosci., 19, pp. 135-141 (2002).
Diamond et al., "Exposing Rats to a Predator Impairs Spatial Working Memory in the Radial Arm Water Maze," Hippocampus, 9, pp. 542-552 (1999).
Dineley et al., "β-amyloid Activates the Mitogen-Activated Protein Kinase Cascade via Hippocampal α7 Nicotinic Acetylcholine Receptors: In Vitro and In Vivo Mechanisms Related to Alzheimer's Disease," J. Neurosci., 21(12), pp. 4125-4133 (2001).
Dineley et al., "Accelerated Plaque Accumulation, Associative Learning Deficits, and Up-regulation of α7 Nicotinic Receptor Protein in Transgenic Mice Co-expressing Mutant Human Presenilin 1 and Amyloid Precursor Proteins," J. Biol. Chem., 277(25), pp. 22768-22780 (2002).
Dixon et al., "Decomposition Pathways of Peroxynitrous Acid: Gas-Phase and Solution Energetics," J. Phys. Chem. A, 106, pp. 3191-3196 (2002).
Dixon et al., "The gas and solution phase acidities of HNO, HOONO, HONO, and $HONO_2$," Int. J. Mass Spectrom., 227, pp. 421-438 (2003).
Duff et al., "Increased amyloid-beta42(43) in brains of mice expressing mutant presenilin 1," Nature, 383, pp. 710-713 (1996).
Elbashir et al., "Duplexes of 21-nucleotide RNAs mediate RNA interference in cultured mammalian cells," Nature, 411, pp. 494-498 (2001).
Erb et al., "Recursive deconvolution of combinatorial chemical libraries," Proc. Natl. Acad. Sci. USA, 91, pp. 11422-11426 (1994).
Evans et al. "Drug-Protein Adducts: An Industry Perspective on Minimizing the Potential for Drug Bioactivation in Drug Discovery and Development," Chem. Res. Toxicol., 17, pp. 3-16 (2004).
Ewing et al., "Dock 4.0: search strategies for automated molecular docking of flexible molecule databases," J. Computer-Aided. Mol. Des., 15, pp. 411-428 (2001).
Fadrná et al., "Molecular Dynamics Simulations of Guanine Quadruplex Loops: Advances and Force Field Limitations," Biophys. J., 87, pp. 227-242 (2004).
FDA, "Review and evaluation of pharmacology and toxicology data. Viagra tablets (sildenafil citrate)," Report from the Division of Cardio-renal Drug Products (HFD-10). Center for Drug Evaluation and Research in Food and Drug Administration, 26 pages (1998).
Francis et al. "Beneficial effect of the histone deacetylase inhibitor TSA in a mouse model of Alzheimer's disease," Soc. Neurosci. Abstr., 1 page (2007).
Freir et al., "Blockade of Long-Term Potentiation by β-Amyloid Peptides in the CA1 Region of the Rat Hippocampus In Vivo," J. Neurophysiol., 85, pp. 708-713 (2001).
Gallop et al., "Applications of Combinatorial Technologies to Drug Discovery. 1. Background and Peptide Combinatorial Libraries," J. Med. Chem., 37(9), pp. 1233-1251 (1994).
Gao et al., "Computational design of a human butyrylcholinesterase mutant for accelerating cocaine hydrolysis based on the transition-state simulation," Author Manuscript, published in final edited form as: Angew Chem. Int. Ed. Engl., 45(4), pp. 653-657 (2006).
Gillet et al., Sprout: recent developments in the de novo design of molecules, J. Chem. Inf. Comput. Sci., 34(1), pp. 207-217 (1994).
Gong et al., "Persistent improvement in synaptic and cognitive functions in an Alzheimer mouse model after rolipram treatment," J. Clin. Invest., 114, pp. 1624-1634 (2004).
Gong et al., "Ubiquitin Hydrolase Uch-L1 Rescues β-Amyloid-Induced Decreases in Synaptic Function and Contextual Memory," Cell, 126, pp. 775-788 (2006).
Gresser and Gleiter, "Erectile Dysfunction: Comparison of Efficacy and Side Effects of the PDE-5 Inhibitors Sildenafil, Vardenafil and Tadalafil Review of the Literature," Eur. J. Med. Res., 7, pp. 435-446 (2002).
Haas et al., "Inducible nitric oxide synthase and argininosuccinate synthetase: co-induction in brain tissue of patients with Alzheimer's dementia and following stimulation with β-amyloid 1-42 in vitro," Neuroscience Letters, 322, pp. 121-125 (2002).
Hamza and Zhan, "How can (−)-Epigallocatechin Gallate from Green Tea Prevent HIV-1 Infection? Mechanistic Insights from Computational Modeling and the Implication for Rational Design of Anti-HIV-1 Entry Inhibitors," J. Phys. Chem. B, 110, pp. 2910-2917 (2006).
Hamza et al., "Molecular Dynamics Simulation of Cocaine Binding with Human Butyrylcholinesterase and Its Mutants," J. Phys. Chem. B., 109, pp. 4776-4782 (2005).
Hamza et al., "Understanding human 15-hydroxyprostaglandin dehydrogenase binding with $NAD^+$ and $PGE_2$ by homology modeling, docking and molecular dynamics simulation," Bioorg. Med. Chem., 13, pp. 4544-4551 (2005).
Hansen, "Towards Selective Kir6.2/SUR1 Potassium Channel Openers, Medicinal Chemistry and Therapeutic Perspectives," Curr. Med. Chem. 13, pp. 361-376 (2006).
Harris et al., "Theoretical Study of the Ligand-CYP2B4 Complexes: Effect of Structure on Binding Free Energies and Heme Spin State," Proteins, 55, pp. 895-914 (2004).
Herman et al., "Analysis of a Mutation in Phosphodiesterase Type 4 that Alters Both Inhibitor Activity and Nucleotide Selectivity," Mol. Pharmacol., 57, pp. 991-999 (2000).
Ho and Marshall, "Foundation: A program to retrieve all possible structures containing a user-defined minimum number of matching query elements from three-dimensional databases," J. Computer-Aided Mol. Des., 7, pp. 3-22 (1993).
Hodgson, "ADMET-turning chemicals into drugs," Nat. Biotechnol., 19(8), pp. 722-726 (2001).
Houghten et al., "Generation and use of synthetic peptide combinatorial libraries for basic research and drug discovery," Nature 354, pp. 84-86 (1991).
Houghten et al., "The use of synthetic peptide combinatorial libraries for the identification of bioactive peptides," Biotechniques 13(3), 412-421 (1992).
Hsia et al., "Plaque-independent disruption of neural circuits in Alzheimer's disease mouse models," Proc. Natl. Acad. Sci. USA, 96, pp. 3228-3233 (1999).
Hsiao et al., "Correlative memory deficits, Aβ elevation, and amyloid plaques in transgenic mice," Science, 274, pp. 99-102 (1996).
Hsieh et al., "AMPA-R Removal Underlies Aβ-induced Synaptic Depression and Dendritic Spine loss," Author Manuscript, published in final edited form as: Neuron, 52(5), pp. 831-843 (2006).
Österberg and Norinder, "Prediction of Polar Surface Area and Drug Transport Processes Using Simple Parameters and PLS Statistics," J. Chem. Inf. Comput. Sci., 40(6), pp. 1408-1411 (2000).

(56) References Cited

OTHER PUBLICATIONS

Huai et al., "Crystal structure of phosphodiesterase 9 shows orientation variation of inhibitor 3-isobutyl-1-methylxanthine binding," PNAS, 101(26), pp. 9624-9629 (2004).

Huai et al., "Crystal Structures of Phosphodiesterases 4 and 5 in Complex with Inhibitor 3-Isobutyl-1-Methylxanthine Suggest a Conformation Determinant of Inhibitor Selectivity," J. Biol. Chem., 279(13) pp. 13095-13101 (2004).

Huai et al., "The Crystal Structure of AMP-Bound PDE4 Suggests a Mechanism for Phosphodiesterase Catalysis," Biochemistry, 42, pp. 13220-13226 (2003).

Huang et al., "Structural and functional characterization of human microsomal prostaglandin E synthase-1 by computational modeling and site-directed mutagenesis," Bioorg. Med. Chem., 14, pp. 3553-3562 (2006).

Hudson, "Recombinant antibody fragments," Curr. Opin. Biotechnol., 9, pp. 395-402 (1998).

International Search Report and Written Opinion for International Application No. PCT/US09/58813 dated Mar. 3, 2010 (8 pages).

Irwin and Shoichet, "ZINC—A Free Database of Commercially Available Compounds for Virtual Screening," Author Manuscript, published in final edited form as: J. Chem. Inf. Model, 45(1), pp. 177-182 (2005).

Itoh et al., "Impairments of long-term potentiation in hippocampal slices of β-amyloid-infused rats," Eur. J. Pharmacol., 382(3), pp. 167-175 (1999).

Janeway et al., *Immunobiology: The Immune System in Heath and Disease*, 5th ed., Garland Publishing, Table of contents, 15 pages (2001).

Jantzen et al. "Microglial Activation and B-Amyloid Deposit Reduction Caused by a Nitric Oxide-Releasing Nonsteroidal Anti-Inflammatory Drug in Amyloid Precursor Protein Plus Presenilin-1 Transgenic Mice," J. Neurosci., 22(6), pp. 2246-2254 (2002).

Janus et al., "Aβ peptide immunization reduces behavioural impairment and plaques in a model of Alzheimer's disease, Nature, 408, pp. 979-982 (2000).

Jayawickreme et al., "Creation and functional screening of a multi-use peptide library," Proc. Natl. Acad. Sci. USA, 91, pp. 1614-1618 (1994).

Jolas et al., "Long-Term Potentiation is Increased in the CA1 Area of the Hippocampus of $APP_{swe/ind}$ CRND8 Mice," Neurobiol. Dis., 11, pp. 394-409 (2002).

Kalaria, "Vascular Factors in Alzheimer's Disease," Int. Psychogeriatr., 15(Suppl. 1), pp. 47-52 (2003).

Kalota et al., "Progress in the development of nucleic acid therapeutics," Handb. Exp. Pharmacol., 173, pp. 173-196 (2006).

Kalé et al., "NAMD2: Greater Scalability for Parallel Molecular Dynamics," J. Comp. Phys., 151, pp. 283-312 (1999).

Kamenetz et al., "APP Processing and Synaptic Function," Neuron, 37, pp. 925-937 (2003).

Kay et al., "An M13 phage library displaying random 38-amino-acid peptides as a source of novel sequences with affinity to selected targets," Gene, 128, 59-65 (1993).

Kemenes et al., "Critical Time-Window for NO-cGMP-Dependent Long-Term Memory Formation after One-Trial Appetitive Conditioning," J. Neurosci., 22(4), pp. 1414-1425 (2002).

Khalil et al., "Mechanisms of peripheral microvascular dysfunction in transgenic mice overexpressing the Alzheimers disease amyloid Aβ protein," J. Alzheimer's Dis., 4, pp. 467-478 (2002).

Kim et al., "Use-Dependent Effects of Amyloidogenic Fragments of β-Amyloid Precursor Protein on Synaptic Plasticity in Rat Hippocampus In Vivo," J. Neurosci., 21(4), pp. 1327-1333 (2001).

Kloner et al., "Cardiovascular Safety Update of Tadalafil: Retrospective Analysis of Data from Placebo-Controlled and Open-Label Clinical Trials of Tadalafil With As Needed, Three Times-per-Week or Once-a-Day Dosing," Am. J. Cardiol., 97(12) pp. 1778-1784 (2006).

Koča et al., Mobility of the Active Site Bound Paraoxon and Sarin in Zinc-Phosphotriesterase by Molecular Dynamics Simulation and Quantum Chemical Calculation, J. Am. Chem. Soc., 123, pp. 817-826 (2001).

Koglin et al., "BAY 41/2272 Activates Two Isoforms of Nitric Oxide-Sensitive Guanylyl Cyclase," Biochem. Biophys. Res. Commun., 292, pp. 1057-1062 (2002).

Kowalska and Badellino, "Beta-Amyloid protein induces platelet aggregation and supports platelet adhesion," Biochem. Biophys. Res. Commun., 205(3), pp. 1829-1835 (1994).

Kubinyi, "Drug research: myths, hype and reality," Nat. Rev. Drug Discov., 2(8), pp. 665-668 (2003).

Lam et al., "A new type of synthetic peptide library for identifying ligand-binding activity," Nature, 354, pp. 82-84 (1991).

Larson et al., "Alterations in synaptic transmission and long-term potentiation in hippocampal slices from young and aged PDAPP mice," Brain Res., 840(1-2), pp. 23-35 (1999).

Lawrence and Davis, "CLIX: A Search Algorithm for Finding Novel Ligands Capable of Binding Proteins of Known Three-Dimensional Structure," Proteins: Structure, Function, and Genetics, 12, pp. 31-41 (1992).

Lee and O'Dowd, "cAMP-Dependent Plasticity at Excitatory Cholinergic Synapses in *Drosophila* Neurons: Alterations in the Memory Mutant Dunce," J. Neurosci., 20(6), pp. 2104-2111 (2000).

Lee et al., "Crystal structure of phosphodiesterase 4D and inhibitor complex1," FEBS Lett., 530, pp. 53-58 (2002).

Lenstra et al. "Isolation of sequences from a random-sequence expression library that mimic viral epitopes," J. Immunol. Meth., 152, pp. 149-157 (1992).

Lipinski et al., "Experimental and computational approaches to estimate solubility and permeability in drug discovery and development settings," Adv. Drug Deliv. Rev., 23, pp. 3-25 (1997).

Lipinski, "Drug-like properties and the causes of poor solubility and poor permeability," J. Pharmacol. Toxicol. Methods, 44, pp. 235-249 (2000).

Liu et al., "α-Synuclein produces a long-lasting increase in neurotransmitter release," EMBO J., 23, pp. 4506-4516 (2004).

Liu et al., "Aβ levels in serum, CSF and brain, and cognitive deficits in APP + PSI transgenic mice," Neuroreport, 14(1), pp. 163-166 (2003).

Liu et al., "Dissecting the Cofactor-Dependent and Independent Bindings of PDE4 Inhibitors," Biochemistry, 40, pp. 10179-10186 (2001).

Lu et al., "Nitric Oxide Signaling Contributes to Late-Phase LTP and CREB Phosphorylation in the Hippocampus," J. Neurosci., 19, 10250-10261 (1999).

Lunyak et al., "Corepressor-Dependent Silencing of Chromosomal Regions Encoding Neuronal Genes," Science, 298(29), pp. 1747-1752 (2002).

Lustbader et al., "ABAD Directly Links Aβ to Mitochondrial Toxicity in Alzheimer's Disease," Science, 304, pp. 448-452 (2004).

Lützelburger and Kjems, "Strategies to identify potential therapeutic target sites in RNA," Handb. Exp. Pharmacol., 173, pp. 243-259 (2006).

Mannhold, "Structure-Activity Relationships of $K_{ATP}$ Channel Openers," Curr. Top. Med. Chem., 6, pp. 1031-1047 (2006).

Martin et al., "Measuring Diversity: Experimental Design of Combinatorial Libraries for Drug Discovery," J. Med. Chem., 38, pp. 1431-1436 (1995).

Martin, "A bioavailability score," J. Med. Chem., 48, pp. 3164-3170 (2005).

Masliah, "Mechanisms of synaptic dysfunction in Alzheimer's disease," Histol. Histopathol., 10, pp. 509-519 (1995).

Mattheakis et al.,"An in vitro polysome display system for identifying ligands from very large peptide libraries," Proc. Natl. Acad. Sci. USA, 91, pp. 9022-9026 (1994).

Mattson et al., "Secreted Form of Amyloid Precursor Protein Enhances Basal Glucose and Glutamate Transport and Protects Against Oxidative Impairment of Glucose and Glutamate Transport in Synaptosomes by a Cyclic GMP-Mediated Mechanism," J. Neurochem., 73(2), pp. 532-537 (1999).

(56) References Cited

OTHER PUBLICATIONS

Mattson, "Cellular Actions of β-Amyloid Precursor Protein and Its Soluble and Fibrillogenic Derivatives," Physiol. Rev., 77(4), pp. 1081-1132 (1997).
Maynard and Georgiou, "Antibody engineering," Ann. Rev. Biomed. Eng., 2, pp. 339-376 (2000).
McCann, "The nitric oxide hypothesis of brain aging," Exp. Gerontol., 32, pp. 431-440 (1997).
McCarty, "Vascular nitric oxide may lessen Alzheimer's risk," Med. Hypotheses, 51, pp. 465-476 (1998).
Medynski, "Synthetic peptide combinatorial libraries," Bio/Technology, 12, pp. 709-710 (1994).
Moechars et al., "Early phenotypic changes in transgenic mice that overexpress different mutants of amyloid precursor protein in brain," J. Biol. Chem., 274(10), pp. 6483-6492 (1999).
Monsonego et al., "Microglia-Mediated Nitric Oxide Cytotoxicity of T Cells Following Amyloid β-Peptide Presentation to Th1 cells," J. Immunol., 171, pp. 2216-2224 (2003).
Moreno et al "Adapting fMRI so that normal and abnormal hippocampal circuits can be investigated in transgenic mice," Soc. Neurosci. Abstr., 2 pages (2004).
Moreno et al., "Imaging Hippocampal Dysfunction in Transgenic Mice with MRI," The 9th International Conference on Alzheimer's Disease and Related Disorders, Poster Session P2: Animal and Cellular Models—Animal Models, Transgenic, p. S239 (2004).
Morgan, et al. "Aβpeptide vaccination prevents memory loss in an animal model of Alzheimer's disease," Nature, 408, pp. 982-985 (2000).
Mosbach, "Molecular imprinting," Trends in Biochem. Sci., 19, pp. 9-14 (1994).
Murthy et al., "PKA-dependent activation of PDE3A and PDE4 and inhibition of adenylyl cyclase V/VI in smooth muscle," Am. J. Physiol. Cell Physiol., 282, pp. C508-C517 (2002).
Nakagami et al., "A novel β-sheet breaker, RS-0406, reverses amyloid β-induced cytotoxicity and impairment of long-term potentiation in vitro," Br., J., Pharmacol., 137, pp. 676-682 (2002).
Nalbantoglu et al., "Impaired learning and LTP in mice expressing the carboxy terminus of the Alzheimer amyloid precursor protein," Nature, 387, pp. 500-505 (1997).
Nehlig et al., "Caffeine and the central nervous system: mechanisms of action, biochemical, metabolic and psychostimulant effects," Brain. Res. Rev., 17, pp. 139-170 (1992).
Nicholson, "Pharmacology of nootropics and metabolically active compounds in relation to their use in dementia," Psychopharmacology (Berl) 101, pp. 147-159 (1990).
Ninan and Arancio, "Presynaptic CaMKII Is Necessary for Synaptic Plasticity in Cultured Hippocampal Neurons," Neuron, 42, pp. 129-141 (2004).
Oddo et al., "Triple-Transgenic Model of Alzheimer's Disease with Plaques and Tangles: Intracellular Aβ and Synaptic Dysfunction," Neuron, 39, pp. 409-421 (2003).
Ohlmeyer et al., "Complex synthetic chemical libraries indexed with molecular tags," Proc. Natl. Acad. Sci. USA, 90, pp. 10922-10926 (1993).
Oprea et al., "Is There a Difference Between Leads and Drugs? A Historical Perspective," J. Chem. Inf. Comput. Sci., 41(5), pp. 1308-1315 (2001).
Ostresh et al., ""Libraries from libraries": Chemical transformation of combinatorial libraries to extend the range and repertoire of chemical diversity," Proc. Natl. Acad. Sci. USA 91, pp. 11138-11142 (1994).
Paakkari and Lindsberg, "Nitric Oxide in the Central Nervous System," Ann. Med., 27, pp. 369-377 (1995).
Pan et al., "Computational redesign of human butyrylcholinesterase for anticocaine medication," PNAS, 102(46), pp. 16656-16661 (2005).
Pardridge, "Blood-brain barrier drug targeting: the future of brain drug development," Mol. Interv., 3(2), pp. 90-105, 51 (2003).
Paris et al., "Inhibition of Alzheimer's β-Amyloid Induced Vasoactivity and Proinflammatory Response in Microglia by a cGMP-Dependent Mechanism," Exp. Neurol., 157, pp. 211-221 (1999).
Park et al., Sildenafil inhibits Phosphodiesterase Type 5 in Human Clitoral Corpus Cavernosum Smooth Muscle, Biochem. Biophys. Res. Commun., 249, pp. 612-617 (1998).
Pasquier and Leys, "Pression arterielle et maladie d' Alzheimer," [Blood pressure and Alzheimer's disease], Rev Neurol (Paris), 154, 743-751 (1998).
Passer, et al., "Generation of an Apoptotic Intracellular Peptide by γ-Secretase Cleavage of Alzheimer's Amyloid β Protein Precursor," J. Alzheimer's Dis., 2, pp. 289-301 (2000).
Paterno et al., "Role of $Ca^{2+}$-Dependent $K^+$ Channels in Cerebral Vasodilatation Induced by Increases in Cyclic GMP and Cyclic AMP in the Rat," Stroke, 27(9), pp. 1603-1608 (1996).
Phillips and LeDoux, "Differential Contribution of Amygdala and Hippocampus to Cued and Contextual Fear Conditioning," Behav. Neurosci., 106(2), pp. 274-285 (1992).
Price et al., "Aging enhances vascular dysfunction induced by the Alzheimer's peptide β-amyloid," Neurol. Res., 26, pp. 305-311 (2004).
Prickaerts et al., "cGMP, but not cAMP, in rat hippocampus is involved in early stages of object memory consolidation," Eur. J. Pharmacol., 436, pp. 83-87 (2002).
Prickaerts et al., "Effects of two selective phosphodiesterase type 5 inhibitors, sildenafil and vardenafil, on object recognition memory and hippocampal cyclic GMP levels in the rat," Neuroscience, 113(2), pp. 351-361 (2002).
Prickaerts et al., "Phosphodiesterase type 5 inhibition improves early memory consolidation of object information," Neurochem. Int., 45, pp. 915-928 (2004).
Puolivali et al., "Hippocampal Aβ42 Levels Correlate with Spatial Memory Deficit in APP and PS1 Double Transgenic Mice," Neurobiol. Dis., 9, p. 339-47 (2002).
Puzzo et al., "Amyloid-beta peptide inhibits activation of the nitric oxide/cGMP/cAMP-responsive element-binding protein pathway during hippocampal synaptic plasticity," J. Neurosci. 25(29), pp. 6887-6897 (2005).
Puzzo et al., "Picomolar amyloid-β Positively Modulates Synaptic Plasticity and Memory in Hippocampus," J. Neurosci. 28(53), pp. 14537-14545 (2008).
Rajfer et al., "Case report: Avoidance of palpable corporal fibrosis due to priapism with upregulators of nitric oxide," J. Sex Med., 3, pp. 173-176 (2006).
Randt et al., "Brain Cyclic AMP and Memory in Mice," Pharmacology Biochemistry and Behavior, 17, 677-680 (1982).
Richter et al., "Identification of inhibitor binding sites of the cAMP-specific phosphodiesterase 4," Cell Signal, 13, pp. 287-297 (2001).
Robinett et al., "The discovery of substituted 4-(3-hydroxyanilino)-quinolines as potent RET kinase inhibitors," Bioorg. Med. Chem. Lett., 17, pp. 5886-5893 (2007).
Rostein and Murcko, "GroupBuild: A Fragment-Based Method for De NoVo Drug Design," J. Med. Chem., 36, pp. 1700-1710 (1993).
Rotella, "N-3-substituted imidazoquinazolinones: potent and selective PDE5 inhibitors as potential agents for treatment of erectile dysfunction," J. Med. Chem., 43, pp. 1257-1263 (2000).
Rotella, "Phosphodiesterase 5 inhibitors: Current status and potential applications," Nat. Rev. Drug Discov., 1, pp. 674-682 (2002).
Russo et al., "Signal Transduction through Tyrosine-Phosphorylated C-terminal Fragments of Amyloid Precursor Protein via an Enhanced Interaction with Shc/Grb2 Adaptor Proteins in Reactive Astrocytes of Alzheimer's Disease Brain," The Journal of Biological Chemistry, 277(38), pp. 35282-35288 (2002).
Saenz de Tejada et al., "The phosphodiesterase inhibitory selectivity and the in vitro and in vivo potency of the new PDE5 inhibitor vardenafil," Int. J. Impot. Res., 13, pp. 282-290 (2001).
Salmon et al., "Discovery of biologically active peptides in random libraries: Solution-phase testing after staged orthogonal release from resin beads," Proc. Natl. Acad. Sci. USA, 90, 11708-11712 (1993).

(56) References Cited

OTHER PUBLICATIONS

Sant'Angelo and Arancio, "Usefulness of Behavioral and Electrophysiological Studies in Transgenic Models of Alzheimer's Disease," Neurochem. Res., 28(7), pp. 1009-1015 (2003).
Scapin et al., "Crystal structure of human phosphodiesterase 3B: atomic basis for substrate and inhibitor specificity," Biochemistry, 43, pp. 6091-6100 (2004).
Schenk et al., "Immunization with amyloid-β attenuates Alzheimer-disease-like pathology in the PDAPP mouse," Nature, 400(6740), pp. 173-177 (1999).
Schenk, "Dissociation between components of spatial memory in rats after recovery from the effects of retrohippocampal lesions," Exp. Brain. Res. 58, pp. 11-28 (1985).
Schiefer and Sparing, "Transient global amnesia after intake of tadalafil, a PDE-5 inhibitor: a possible association?" Int. J. Impot. Res., 17, pp. 383-384 (2005).
Schudt et al., "Zardaverine as a selective inhibitor of phosphodiesterase isozymes," Biochem. Pharmacol., 42(1), pp. 153-162 (1991).
Schultheiss et al., "Central effects of sildenafil (Viagra) on auditory selective attention and verbal recognition memory in humans: a study with event-related brain potentials," World J. Urol., 19, pp. 46-50 (2001).
Schwardt et al., "Drug discovery today," Curr. Top. Med. Chem., 3, pp. 1-9 (2003).
Scott et al., "Searching for Peptide Ligands with an Epitope Library," Science, 249, pp. 386-390 (1990).
Selig et al., "Examination of the Role of cGMP in Long-term Potentiation in the CA1 Region of the Hippocampus," Learn. Mem., 3, pp. 42-48 (1996).
Selkoe, "Alzheimer's disease is a synaptic failure," Science, 298, pp. 789-791 2002.
Shankar et al., "Natural Oligomers of the Alzheimer Amyloid-β Protein Induce Reversible Synapse Loss by Modulating an NMDA-Type Glutamate Receptor-Dependent Signaling Pathway," J. Neurosci., 27(11), pp. 2866-2875 (2007).
Shea, "Molecular Imprinting of Synthetic Network Polymers: The De Novo Synthesis of Macromolecular Binding and Catalytic Sites," Trends in Polymer Science, 2(5), pp. 166-173 (1994).
Silva et al., "CREB and Memory," Ann. Rev. Neurosci., 21, pp. 127-148 (1998).
Simon et al., "Peptoids: A modular approach to drug discovery," Proc. Natl. Acad. Sci. USA, 89, pp. 9367-9371 (1992).
Simons et al. "Amyloidogenic Processing of the Human Amyloid Precursor Protein in Primary Cultures of Rat Hippocampal Neurons," J. Neurosci. 16(3), pp. 899-908 (1996).
Smith et al., "Soluble β-amyloid (Aβ) 40 causes attenuation or potentiation of noradrenaline-induced vasoconstriction in rats depending upon the concentration employed," Neuroscience Letters, 367, pp. 129-132 (2004).
Snyder at al., "The role of cyclic nucleotide phosphodiesterases in the regulation of adipocyte lipolysis," Journal of Lipid Research, 46, pp. 494-503 (2005).
Snyder et al., "Regulation of NMDA receptor trafficking by amyloid-β," Nature Neuroscience, 8(8), pp. 1051-1058 (2005).
Soderling and Beavo, "Regulation of cAMP and cGMP signaling: new phosphodiesterases and new functions," Curr. Opin. Cell. Biol., 12, pp. 174-179 (2000).
Stéphan et al., "Generation of Aggregated β-Amyloid in the Rat Hippocampus Impairs Synaptic Transmission and Plasticity and Causes Memory Deficits," J. Neurosci., 21(15), pp. 5703-5714 (2001).
Suhara et al., "Aβ42 generation is toxic to endothelial cells and inhibits eNOS function through an Akt/GSK-3β signaling-dependent mechanism," Neurobiol. Aging, 24, pp. 437-451 (2003).
Sung et al., "Structure of the catalytic domain of human phosphodiesterase 5 with bound drug molecules," Nature, 425, pp. 98-102 (2003).
Suter, "Predictive value of in vitro safety studies," Curr. Opin. Chem. Biol., 10, pp. 362-366 (2006).
Takahashi et al., "Oligomerization of Alzheimer's β-Amyloid within Processes and Synapses of Cultured Neurons and Brain," The Journal of Neuroscience, 24(14), pp. 3592-3599 (2004).
Takuma et al., "ABAD enhances Aβ-induced cell stress via mitochondrial dysfunction," FASEB J., 19, pp. 597-598 (2005).
Taylor et al., "A review of protein-small molecule docking methods," J. Computer-Aided. Mol. Des., 16, pp. 151-166 (2002).
Teague et al., "The Design of Leadlike Combinatorial Libraries," Angew. Chem. Int. Ed., 38(24), pp. 3743-3748 (1999).
Terrett et al., "Sildenafil (Viagra™), a potent and selective inhibitor of type 5 cGMP phosphodiesterase with utility for the treatment of male erectile dysfunction," Bioorg. Med. Chem. Lett., 6(15), pp. 1819-1824 (1996).
Thatcher et al., "Nitric oxide mimetic molecules as therapeutic agents in Alzheimer's disease," Curr. Alzheimer. Res., 2, pp. 171-182 (2005).
Thatcher et al., "Novel nitrates as NO mimetics directed at Alzheimers disease," J. Alzheimers. Dis., 6, pp. S75-S84 (2004).
Tran et al., "Amyloid β-peptide induces nitric oxide production in rat hippocampus: association with cholinergic dysfunction and amelioration by inducible nitric oxide synthase inhibitors," Faseb J., 15, pp. 1407-1409 (2001).
Trinchese et al. "Alzheimer Aβ Increases Neurotransmitter Release and Blocks Synaptic Plasticity in Hippocampal Cultures," The 9th International Conference on Alzheimers Disease and Related Disorders, Poster Session P3: Molecular Mechanisms of Neurodegeneration—Synpatic Disruption, 1 page (2004).
Trinchese et al., "Progressive Age-Related Development of Alzheimer-like Pathology in APP/PS1 Mice," Ann. Neurol. 55(6), pp. 801-814 (2004).
Troy et al. "Caspase-2 Mediates Neuronal Cell Death Induced by β-Amyloid," J. Neurosci., 20(4), pp. 1386-1392 (2000).
Tully et al., "Targeting the CREB pathway for memory enhancers," Nat. Rev. Drug. Discov., 2, pp. 267-277 (2003).
Turko et al., "Potential roles of conserved amino acids in the catalytic domain of the cGMP-binding cGMP-specific phosphodiesterase (PDE5)," J. Biol. Chem., 273(11), pp. 6460-6466 (1998).
Turner, "Cellular Memory and the Histone Code," Cell, 111, pp. 285-291 (2002).
Ukita et al.,"1,7- and 2,7-Naphthyridine Derivatives as Potent and Highly Specific PDE5 Inhibitors," Bioorg. Med. Chem. Lett., 13, pp. 2341-2345 (2003).
van de Waterbeemd and Gifford, "ADMET in silico modelling: towards prediction paradise?" Nat. Rev. Drug. Discov., 2, pp. 192-204 (2003).
van Staveren et al., "mRNA Expression Patterns of the cGMP-Hydrolyzing Phosphodiesterases Types 2, 5, and 9 during Development of the rat Brain," J. Comp. Neurol., 467, pp. 566-580 (2003).
van Staveren et al., "Species differences in the localization of cGMP-producing and NO-responsive elements in the mouse and rat hippocampus using cGMP immunocytochemistry," Eur. J. Neurosci., 19, pp. 2155-2168 (2004).
Venturini et al., "β-Amyloid inhibits NOS activity by subtracting NADPH availability," Faseb J., 16, pp. 1970-1972 (2002).
Villiger and Dunn, "Phosphodiesterase Inhibitors Facilitate Memory for Passive Avoidance Conditioning," Behavioral and Neural Biology, 31, pp. 354-359 (1981).
Vitolo et al., "Amyloid β-peptide inhibition of the PKA/CREB pathway and long-term potentiation: Reversibility by drugs that enhance cAMP signaling," PNAS, 99(20), pp. 13217-13221 (2002).
Walker et al., "Pharmacokinetics and metabolism of sildenafil in mouse, rat, rabbit, dog and man," Xenobiotica, 29(3), pp. 297-310 (1999).
Walsh et al., "Certain inhibitors of synthetic amyloid β-peptide (Aβ) fibrillogenesis block oligomerization of natural Aβ and thereby rescue long-term potentiation," J. Neurosci., 25(10), pp. 2455-2462 (2005).
Walsh et al., "Naturally secreted oligomers of amyloid β protein potently inhibit hippocampal long-term potentiation in vivo," Nature, 416, pp. 535-539 (2002).

(56) References Cited

OTHER PUBLICATIONS

Wang et al., "β-Amyloid-Mediated Inhibition of NMDA Receptor-Dependent Long-Term Potentiation Induction Involves Activation of Microglia and Stimulation of Inducible Nitric Oxide Synthase and Superoxide," J. Neurosci., 24(27), pp. 6049-6056 (2004).

Wang et al., "Characterization of human, dog and rabbit corpus cavernosum type 5 phosphodiesterases," Life Sci., 68, pp. 1977-1987 (2001).

Wang et al., "Inhibitors of Src Tyrosine Kinase: The Preparation and Structure-Activity Relationship of 4-Anilino-3-cyanoquinolines and 4-Anilinoquinazolines," Bioorg. Med. Chem. Lett., 10, pp. 2477-2480 (2000).

Wells et al., "Cyclic nucleotide phosphodiesterase activities of pig coronary arteries," Biochim. Biophys. Acta., 384, pp. 430-442 (1975).

Werner and Nelson, "Joining high-throughput technology with in silico modelling advances genome-wide screening towards targeted discovery," Brief. Funct., Genomic Proteomic, 5(1), pp. 32-36 (2006).

Wirtz-Brugger and Giovanni, "Guanosine 3',5'-cyclic monophosphate mediated inhibition of cell death induced by nerve growth factor withdrawal and (β-amyloid: protective effects of propentofylline," Neuroscience, 99, pp. 737-750 (2000).

Wong et al. "Advanced glycation endproducts co-localize with inducible nitric oxide synthase in Alzheimer's Disease," Brain Res., 920, pp. 32-40 (2001).

Wu et al., "β-amyloid-(1-40) increases long-term potentiation in rat hippocampus in vitro," Eur. J. Pharmacol., 284, pp. R1-R3 (1995).

Wulff, "Molecular Recognition in Polymers prepared by imprinting with Templates," Polymeric Reagents and Catalysts (Ford, W. T., Ed.) ACS Symposium Series No. 308, pp. 186-230 (1986).

Xie et al., "Peroxynitrite Mediates Neurotoxicity of Amyloid (β-Peptides-$_{1-42}$- and Lipopolysaccharide-Activated Microglia," J. Neurosci., 22(9), pp. 3484-3492 (2002).

Xiong et al., "Characterization of a Catalytic Ligand Bridging Metal Ions in Phosphodiesterases 4 and 5 by Molecular Dynamics Simulations and Hybrid Quantum Mechanical/Molecular Mechanical Calculations," Biophys. J., 91, pp. 1858-1867 (2006).

Xiong et al., "Dynamic Structures of Phosphodiesterase-5 Active Site by Combined Molecular Dynamics Simulations and Hybrid Quantum Mechanical/Molecular Mechanical Calculations," J. Comp. Chem., 29(8), pp. 1259-1267 (2007).

Xu et al., "Atomic Structure of PDE4: Insights into Phosphodiesterase Mechanism and Specificity," Science, 288(5472), pp. 1822-1825 (2000).

Yang et al., "Understanding the structure-activity and structure-selectivity correlation of cyclic guanine derivatives as phosphodiesterase-5 inhibitors by molecular docking, CoMFA and CoMSIA analyses," Bioorg. Med. Chem., 14, pp. 1462-1473 (2006).

Yin et al., "Induction of a Dominant Negative CREB Transgene Specifically Blocks Long-Term Memory in *Drosophila*," Cell, 79, pp. 49-58 (1994).

Yu et al., "The retromer and Alzheimer's disease: characterizing retromer knock-down mice with and without APP mutations," Soc. Neurosci. Abstr., 2 pages (2005).

Zhan and Chipman, "Cavity size in reaction field theory," J. Chem. Phys., 109(23), pp. 10543-10558 (1998).

Zhan and Chipman, "Effect of Hydrogen Bonding on the Vibrations of p-Benzosemiquinone Radical Anion," J. Phys. Chem. A, 102, pp. 1230-1235 (1998).

Zhan and Dixon, "Absolute Hydration Free Energy of the Proton from First-Principles Electronic Structure Calculations," J. Phys. Chem. A, 105, pp. 11534-11540 (2001).

Zhan and Dixon, "First-Principles Determination of Absolute Hydration Free Energy of Hydroxide Ion," J. Phys. Chem. A, 106, pp. 9737-9744 (2002).

Zhan and Dixon, "Hydration of the Fluoride Anion: Structures and Absolute Hydration Free Energy from First-Principles Electronic Structure Calculations," J. Phys. Chem. A, 108, pp. 2020-2029 (2004).

Zhan and Dixon, "The Nature and Absolute Hydration Free Energy of the Solvated Electron in Water," J. Phys. Chem. B, 107, pp. 4403-4417 (2003).

Zhan and Gao, "Catalytic Mechanism and Energy Barriers for Butyrylcholinesterase-Catalyzed Hydrolysis of Cocaine," Biophys. J., 89, pp. 3863-3872 (2005).

Zhan and Zheng, "First Computational Evidence for a Catalytic Bridging Hydroxide Ion in a Phosphodiesterase Active Site," J. Am. Chem. Soc., 123, pp. 2835-2838 (2001).

Zhan et al., "Chromogenic and Neurotoxic Effects of an Aliphatic γ-Diketone: Computational Insights into the Molecular Structures and Mechanism," J. Phys. Chem. B, 108, pp. 6098-6104 (2004).

Zhan et al., "Computational insights into the Chemical Structures and Mechanisms of the Chromogenic and Neurotoxic Effects of Aromatic γ-diketones," J. Phys. Chem. B, 107, pp. 2853-2861 (2003).

Zhan et al., "Determination of Two Structural Forms of Catalytic Bridging Ligand in Zinc-Phosphotriesterase by Molecular Dynamics Simulation and Quantum Chemical Calculation," J. Am. Chem. Soc., 121(32), pp. 7279-7282 (1999).

Zhan et al., "Energy Barriers for Alkaline Hydrolysis of Carboxylic Acid Esters in Aqueous Solution by Reaction Field Calculations," J. Phys. Chem. A, 104, pp. 7672-7678 (2000).

Zhan et al., "Theoretical Determination of Chromophores in the Chromogenic Effects of Neurotoxicants," J. Am. Chem. Soc., 124(11), pp. 2744-2752 (2002).

Zhan et al., "Theoretical studies of photoelectron spectra of $SO^2_4$-$(H_2O)_n$ clusters and the extrapolation to bulk solution," J. Chem. Phys., 119, pp. 781-793 (2003).

Zhan et al., "Volume polarization in reaction field theory," J. Chem. Phys., 108, pp. 177-192 (1998).

Zhang et al., "A Glutamine Switch Mechanism for Nucleotide Selectivity by Phosphodiesterases," Mol. Cell, 15, pp. 279-286 (2004).

Zhang et al., "Efficacy and Selectivity of Phosphodiesterase-Targeted Drugs in Inhibiting Photoreceptor Phosphodiesterase (PDE6) in Retinal Photoreceptors," Invest. Ophthalmol. Vis. Sci., 46(9), pp. 3060-3066 (2005).

Zhang et al., "Inhibition of Cyclic AMP Phosphodiesterase (PDE4) Reverses Memory Deficits Associated with NMDA Receptor Antagonism," Neuropsychopharmacology, 23(2), pp. 198-204 (2000).

\* cited by examiner

FIG. 3A
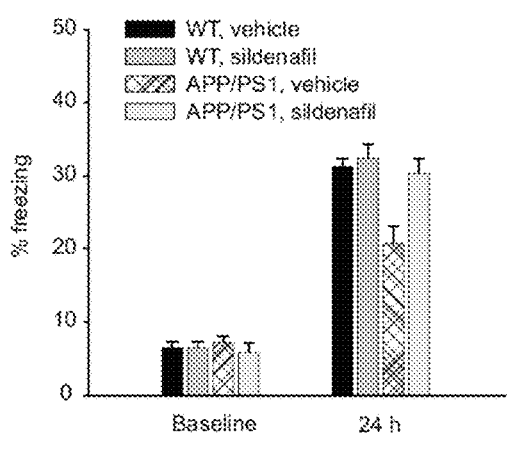
FIG. 3B
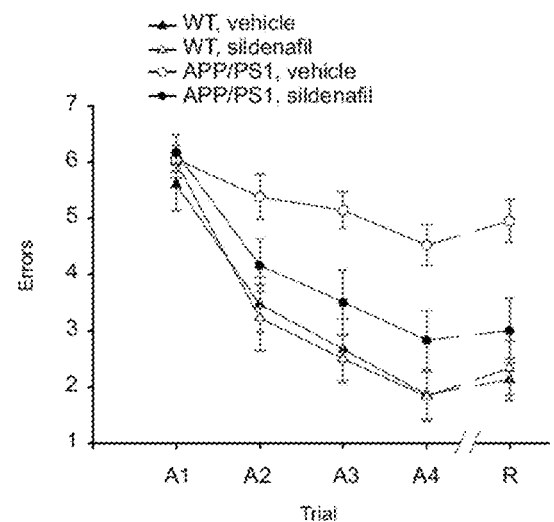
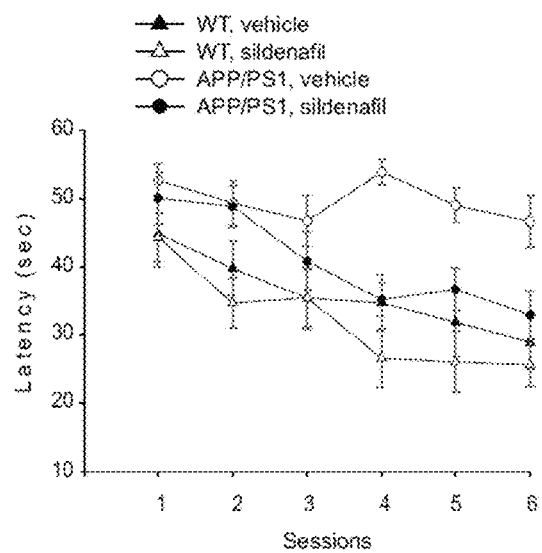
FIG. 3C
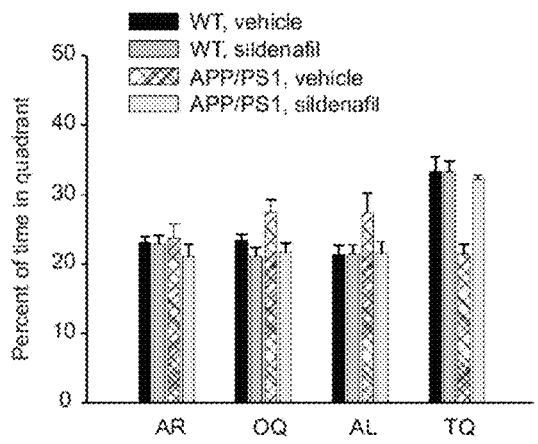
FIG. 3D

FIG. 6A  FIG. 6B  FIG. 6C
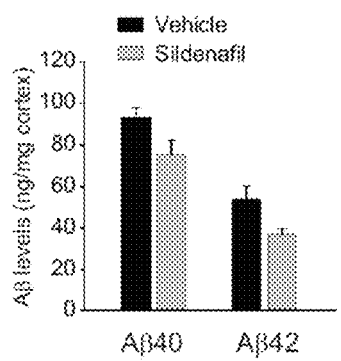
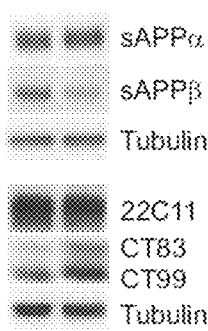
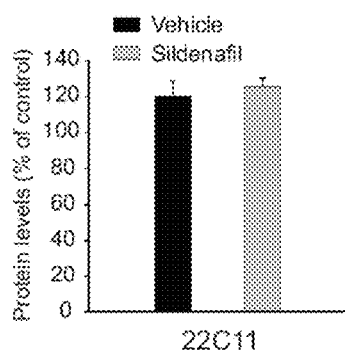
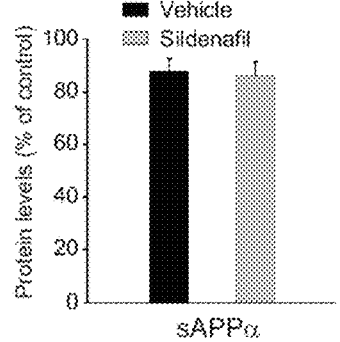
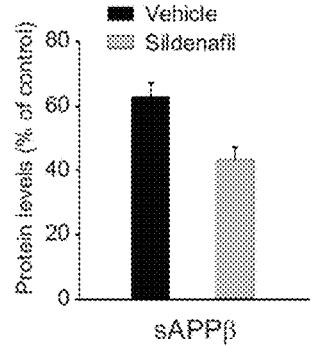
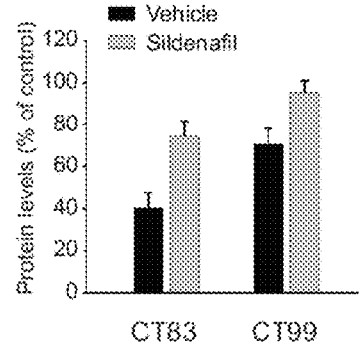
FIG. 6D  FIG. 6E  FIG. 6F

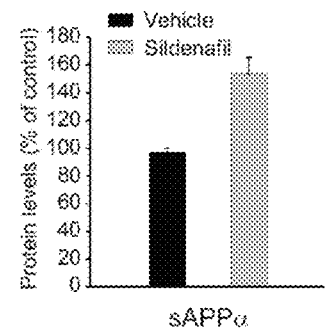
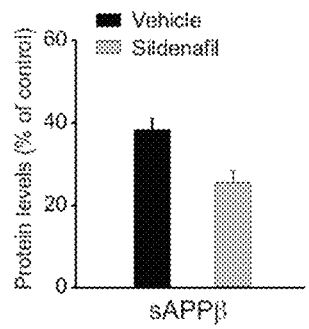
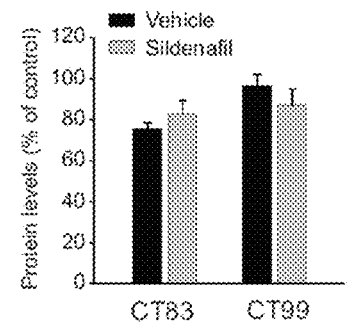
FIG. 7D
FIG. 7E
FIG. 7F

Scheme Ia

Scheme IIa-c

Scheme IId

Scheme III

Scheme IVa

| Compound | | PDE1 | PDE2 | PDE3 | PDE4 | PDE5 | PDE6 | PDE7 | PDE8 | PDE9 | PDE10 | PDE11 |
|---|---|---|---|---|---|---|---|---|---|---|---|---|
| YF012403[a] | IC50 (nM) | >10⁴ | >10⁴ | >10⁴ | >10⁴ | 0.27 | 339 | >10⁴ | >10⁴ | >10⁴ | >10⁴ | >10⁴ |
| | PDEX/PDE5 | >10⁴ | >10⁴ | >10⁴ | >10⁴ | 1 | 1256 | >10⁴ | >10⁴ | >10⁴ | >10⁴ | >10⁴ |
| YF016203[a] | IC50 (nM) | >10⁴ | >10⁴ | >10⁴ | >10⁴ | 0.40 | 5100 | >10⁴ | >10⁴ | >10⁴ | >10⁴ | >10⁴ |
| | PDEX/PDE5 | >10⁴ | >10⁴ | >10⁴ | >10⁴ | 1 | 12750 | >10⁴ | >10⁴ | >10⁴ | >10⁴ | >10⁴ |
| Sildenafil[b] | IC50 (nM) | 1500 | 35000 | 15000 | 20000 | 2.20 | 9.5[a] | 78000 | >10⁴ | 5600 | 6800 | 6100 |
| | PDEX/PDE5 | 682 | 15909 | 6818 | 9091 | 1 | 4 | 35455 | >10⁴ | 2545 | 3091 | 2773 |
| Vardenafil[b] | IC50 (nM) | 300 | 3100 | 380 | 3800 | 1.00 | 11.0[c] | 1900 | 57000 | 680 | 880 | 240 |
| | PDEX/PDE5 | 300 | 3100 | 380 | 3800 | 1 | 11 | 1900 | >10⁴ | 680 | 880 | 240 |
| Tadalafil[b] | IC50 (nM) | >10⁴ | >10⁴ | >10⁴ | 9200 | 1.2 | 5200[d] | 74000 | >[c] | >10⁴ | 19000 | 10 |
| | PDEX/PDE5 | >10⁴ | >10⁴ | >10⁴ | 7667 | 1 | 4333 | 61667 | >10³ | >10³ | 15833 | 8 |

FIG. 27

| Parameters | | YF012403 | | | Sildenafil | | |
|---|---|---|---|---|---|---|---|
| | | Brain | Plasma | Ratio* | Brain | Plasma | Ratio* |
| $T_{max}$ | (h) | 0.5 | 0.5 | - | 0.5 | 0.25 | - |
| $C_{max}$ | (ng/mL or ng/g) | 385 | 1022 | 0.38 | 2413 | 5910 | 0.41 |
| $AUC_{0-t}$ | (ng·h/mL or ng·h/g) | 418 | 1014 | 0.41 | 3901 | 12543 | 0.31 |
| $AUC_{0-\infty}$ | (ng·h/mL or ng·h/g) | 420 | 1133 | 0.37 | 4058 | 14123 | 0.29 |
| t1/2 | (h) | 1.04 | 1.33 | - | 0.84 | 1.21 | - |
| MRT | (h) | 1.66 | 1.61 | - | 1.31 | 1.87 | - |

*Ratio = brain/plasma
** 50 mg/kg, p.o.; Vehicle for YF012403 is 0.5% methylcellulose aqueous solution; Vehicle for sildenafil is 0.2M HCl.

FIG. 28

R = H, alkyl, cycloalkyl, alkenyl, alkynyl, heterocyclyl, aryl, heteroaryl, R₁R₂N, R₃S, R₄O
R₁, R₂, R₃, R₄ = H, alkyl, cycloalkyl, acyl; R', R" = H, alkyl, acyl, sulfonyl FIG. 61A
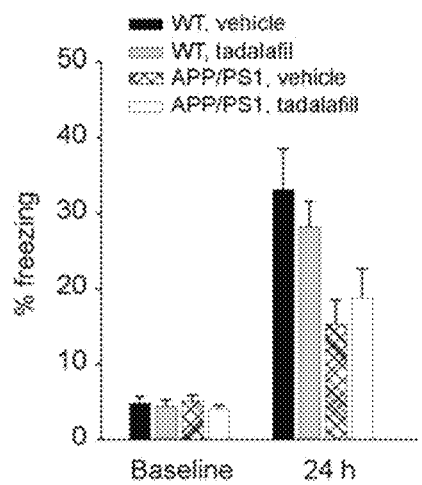
FIG. 61B
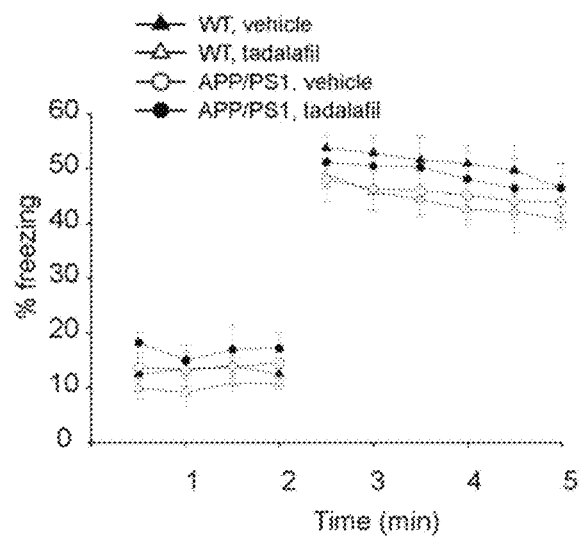
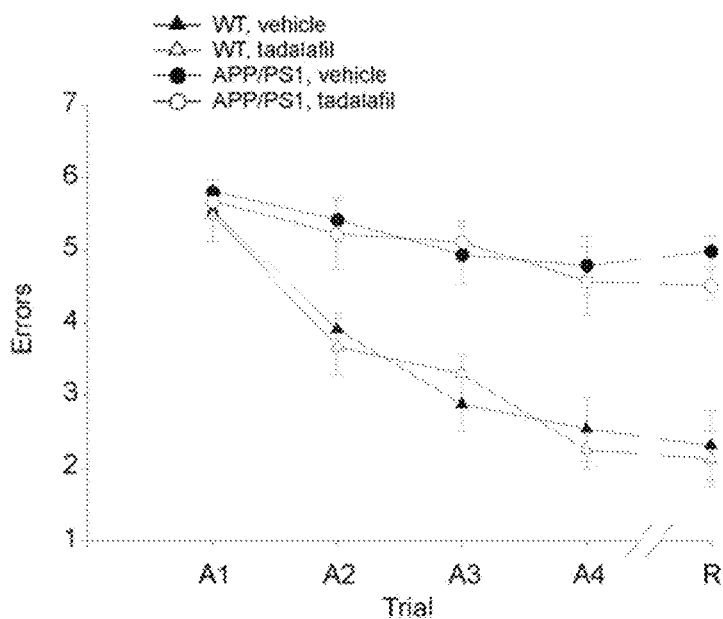
FIG. 61C FIG. 62A
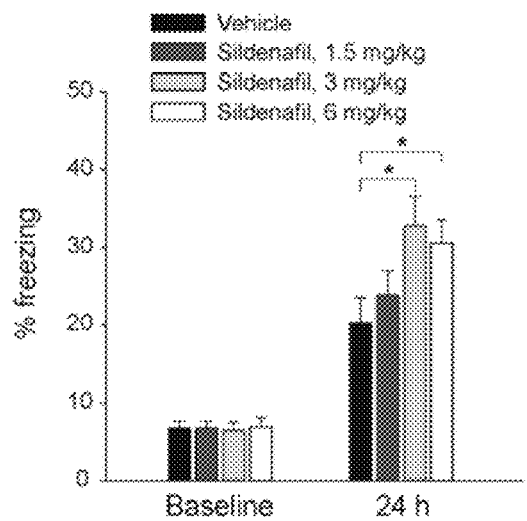
FIG. 62B
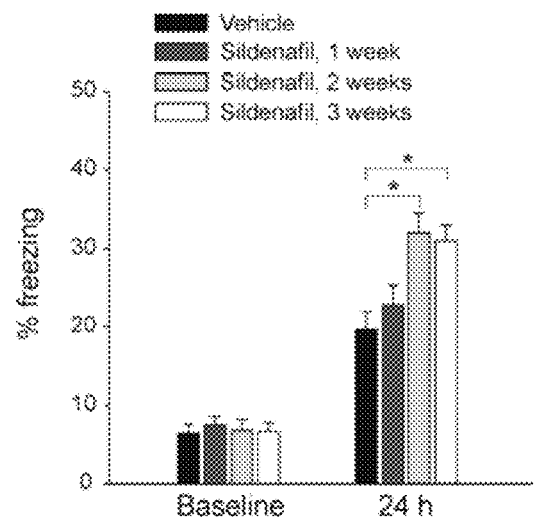
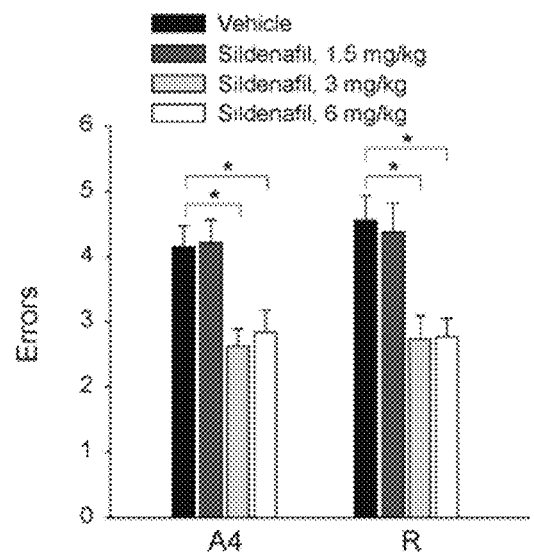
FIG. 62C
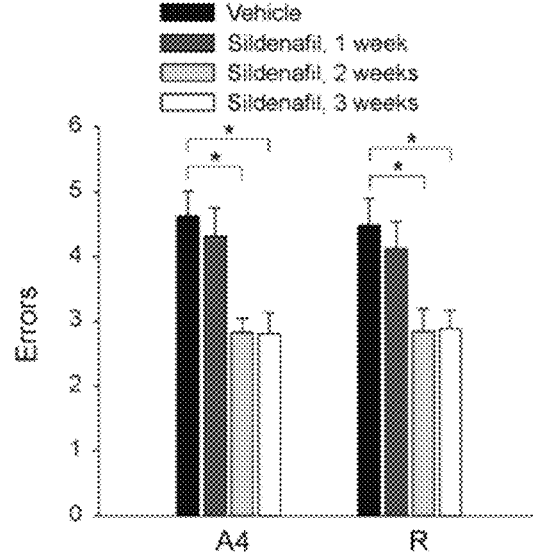
FIG. 62D

FIG. 62E
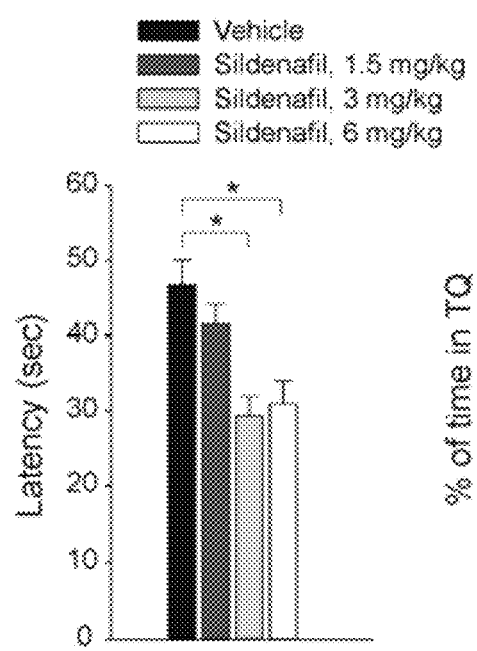
FIG. 62F
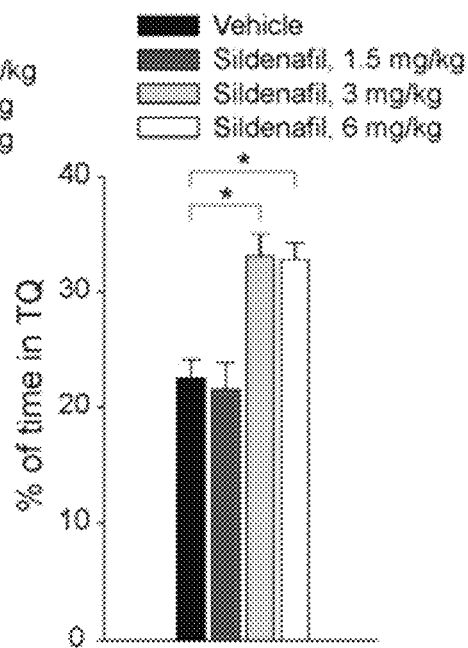
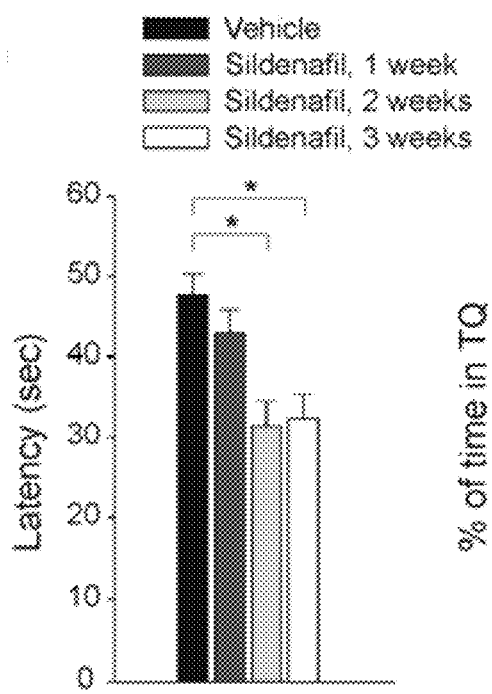
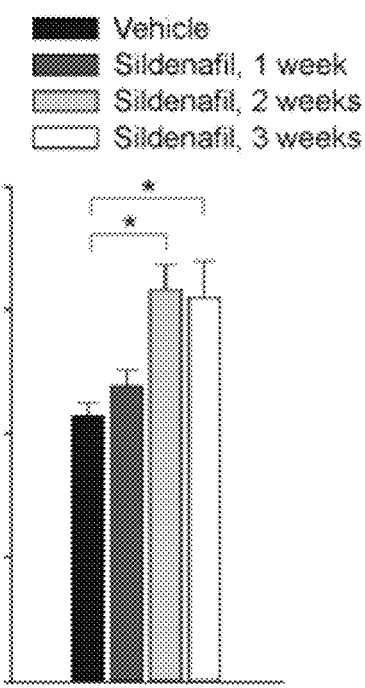
FIG. 62G
FIG. 62H

FIG. 65A
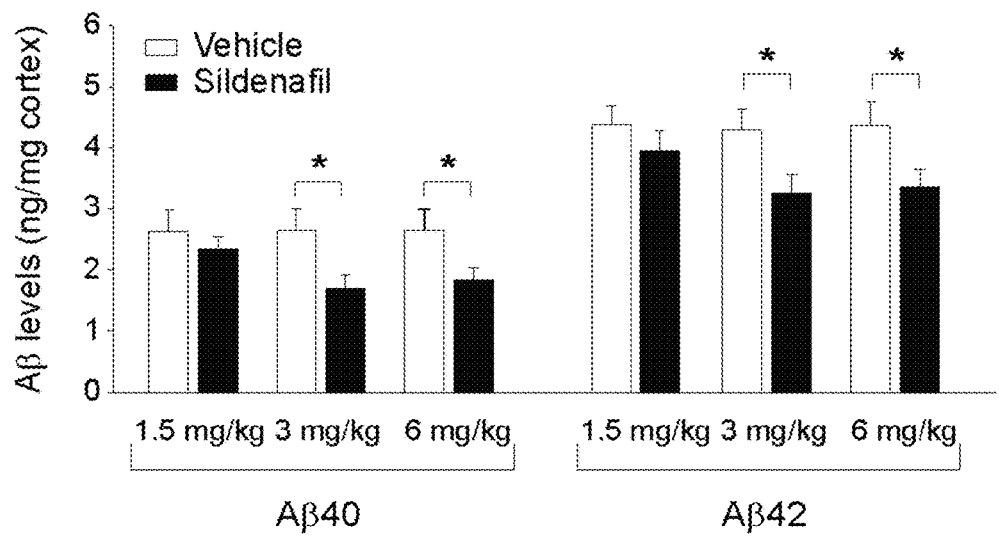
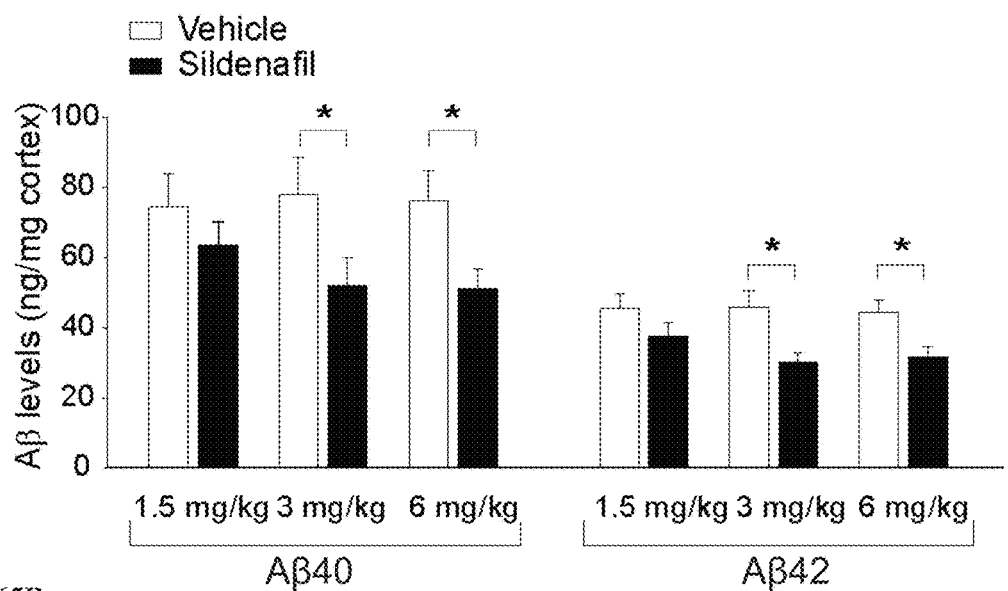
FIG. 65B

FIG. 65C
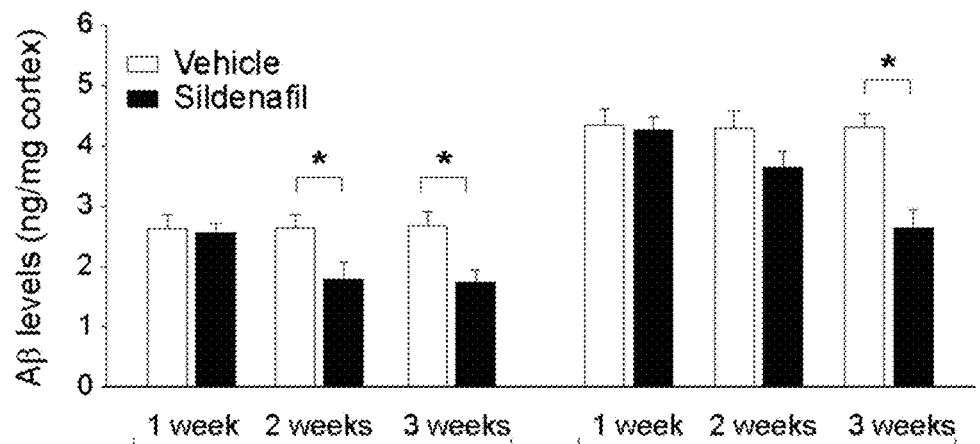
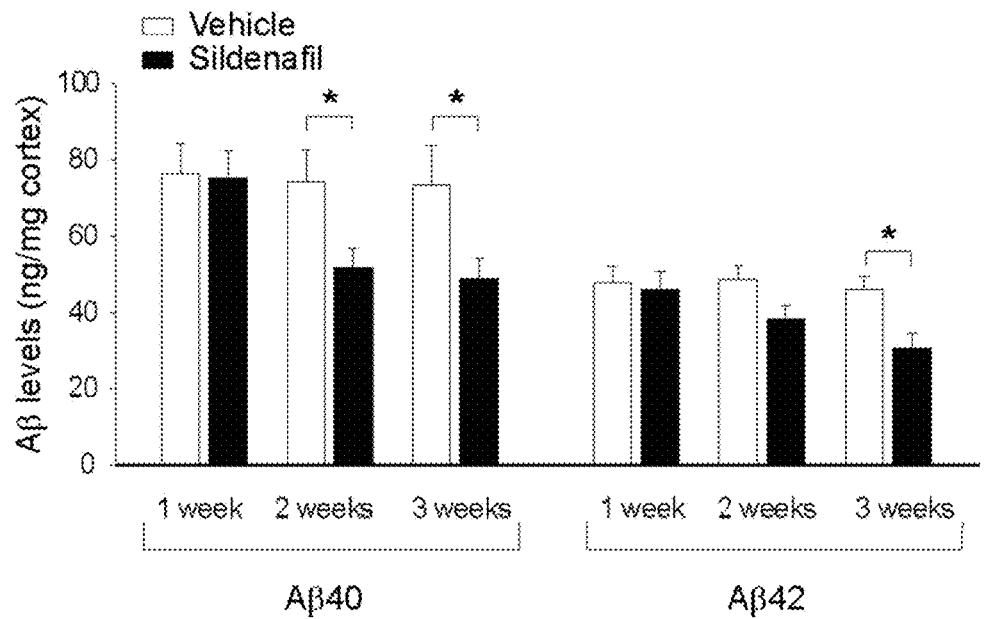
FIG. 65D

PHOSPHODIESTERASE INHIBITORS AND USES THEREOF

This application is a continuation of U.S. patent application Ser. No. 14/224,702, filed on Mar. 25, 2014, which is a continuation of U.S. patent application Ser. No. 13/167,540, filed on Jun. 23, 2011, now U.S. Pat. No. 8,697,875, which is a continuation-in-part of International Application No. PCT/US2009/058813, filed Sep. 29, 2009, which claims priority to U.S. Provisional Application Ser. No. 61/140,315, filed Dec. 23, 2008, and International Application No. PCT/US2009/039129, filed Apr. 1, 2009, each of which are hereby incorporated by reference in their entireties.

GOVERNMENT SUPPORT

This invention was made with government support under Grant No. AG027468 awarded by the National Institutes of Health. The Government has certain rights in this invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

Alzheimer's disease (AD) is a neurodegenerative disorder characterized by memory loss, synaptic dysfunction and accumulation of amyloid β-peptides (Aβ). It is caused in part by increased levels of amyloid-β-peptide 1-42 (Aβ42). Phosphodiesterase 5 (PDE5) inhibitors are widely used drugs against erectile dysfunction and pulmonary hypertension. These inhibitors are believed to increase cGMP levels which enhances phosphorylation of the transcription factor and memory-affecting molecule cAMP-responsive element binding (CREB) through activation of cGMP-dependent-protein kinases.

Cyclic adenosine monophosphate (cAMP) and cyclic guanosine monophosphate (cGMP), nucleotide biological second messengers, regulate various biological processes, such as blood flow regulation, cardiac muscle contraction, cell differentiation, neural transmission, glandular secretion, and gene expression. Intracellular receptors for these molecules include cyclic nucleotide phosphodiesterases (PDEs), cyclic nucleotide dependent protein kinases (PGK), and cyclic nucleotide-gated channels. PDEs are a large family of proteins that catalyze the hydrolysis of 3',5'-cyclic nucleotides to the corresponding 5' monophosphates. There are eleven related, but biochemically distinct, human PDE gene groups. Some PDEs are specific for hydrolysis of cAMP (such as PDE4, PDE7, and PDE8), and some are cGMP specific (such as PDE5, PDE6, and PDE9), while some PDEs have mixed specificity (such as PDE1, PDE2, PDE3, PDE10, and PDE11).

PDE 5 inhibitors are cyclic guanosine 3',5'-monophosphate type five cGMP PDE inhibitors, which include, but are not limited to, sildenafil, tadalafil, zaprinast, and vardenafil. PDE5 inhibitors increase cGMP levels by inhibiting the degradative action of PDE5 on cGMP. No PDE inhibitor has reached the marketplace for diseases of the CNS, and no PDE5 inhibitors have been used for the treatment of Ad.

SUMMARY OF THE INVENTION

The invention is directed to a class of quinoline-containing compounds with PDE5 inhibitory potency, high selectivity, and blood-brain-barrier (BBB) permeability. In one aspect, the compound is Formula V as described herein. In one embodiment, the compound is Formula V-1 as described herein. In another embodiment, the compound is Formula V-1a as described herein. In a further embodiment, the compound is Formula V-1a1 as described herein. In some embodiments, the compound is selected from Formula V, Formula V-1, Formula V-1a, and Formula V1a1 as described herein; wherein $R^1$ is $C_3$-$C_8$ cycloalkyl, —$NR^7R^8$, or —$SR^7$. In some embodiments, $R^1$ is $C_3$-$C_8$ cycloalkyl. In some embodiments, $R^1$ is $C_3$-$C_8$ cycloalkyl or —$NR^7R^8$. In some embodiments, $R^1$ is —$NR^7R^8$. In some embodiments, the compounds are those compounds depicted as compounds 1-18 as described herein. In specific embodiments, the compound is compound 3 (YF012403) or compound 8 (YF016203).

In various aspects, the invention provides a method for screening compounds to treat conditions associated with accumulated amyloid-beta peptide deposits, the method comprising: (a) selecting (or identifying or screening for) a PDE5 inhibitor compound that can modulate secretase activity for at least 1 month after completion of administration of the PDE5 inhibitor compound in an animal model of amyloid-beta peptide deposit accumulation.

In one aspect, the invention provides a method for screening compounds to treat conditions associated with accumulated amyloid-beta peptide deposits, the method comprising: (a) selecting a PDE5 inhibitor compound that comprises one or both of the following features: (i) the compound interacts with two or more amino acid residues of a phosphodiesterase protein, wherein the amino acid residues comprise F787, L804, I813, M816, or a combination thereof; or (ii) the 2nd bridging ligand (BL2) between the compound and a phosphodiesterase protein is OH—.

In one aspect, the invention provides a method for identifying a phosphodiesterase-binding compound to treat conditions associated with accumulated amyloid-beta peptide deposits, wherein the method comprises selecting a PDE5 inhibitor compound having one or more of the following features: (a) the $IC_{50}$ of the compound is no more than about 1000 nM; (b) the selectivity of the compound is at least a 50 fold greater potency towards PDE5 relative to PDE1, PDE2, PDE3, PDE4, PDE6, PDE7, PDE8, PDE9, PDE10, or PDE11; (c) the PDE5 inhibitory activity in vitro has an $IC_{50}$ no more than about 50 nM; (d) the compound penetrates the blood brain barrier; (e) the compound hydrolyzes cGMP by about 20% to about 80%; (f) the 2nd bridging ligand (BL2) between the compound and a phosphodiesterase protein is OH—; or (g) the compound interacts with two or more amino acid residues of a phosphodiesterase protein, wherein the amino acid residues comprise F787, L804, I813, M816, or a combination thereof. The phosphodiesterase in feature (g) can comprise, for example, phosphodiesterase type V (PDE5) or even another PDE. In one aspect, feature (g) is where the compound interacts with at least all four amino acid residues F787, L804, I813, and M816 of PDE5. In one aspect, the compound can decrease the activity or expression of a phosphodiesterase type V (PDE5) protein In some aspects, the above described methods further comprise testing whether the selected PDE5 inhibitor can modulate secretase activity for at least 1 month after administration in an animal model of amyloid-beta peptide deposit accumulation. The secretase can be α-secretase or β-secretase. The modulation can comprise a decrease in β-secretase activity or expression levels and/or an increase in α-secretase activity or expression levels. In some aspects, the modulated secretase activity or expression of β-secretase remains decreased. In some aspects, the modulated secretase activity or expression of α-secretase remains increased. In some aspects, the modulated secretase activity persists more than 2 months, 3 months, 4 months, 5 months, 6 months, or 7 months after completion of the dosage period.

In some aspects of the above described methods, the animal model of amyloid-beta peptide deposit accumulation comprises an APP/PS1 double transgenic mouse. Where the animal model comprises this transgenic mouse, in some aspects, the step of testing whether the selected PDE5 inhibitor can modulate secretase activity for at least 1 month after administration in the APP/PS1 double transgenic mouse comprises: (a) administering the selected PDE5 inhibitor to APP/PS1 double transgenic mice for a dosage period up to about 21 days; (b) testing whether the selected PDE5 inhibitor modulates secretase activity or expression in the APP/PS1 double transgenic mice immediately after completion of the dosage period as compared to a negative control; and (c) testing whether modulated secretase activity or expression in the APP/PS1 double transgenic mice from step (b) persists more than 1 month after completion of the dosage period as compared to a negative control.

In some aspects for the above methods, the selecting step of the compound based on features can involve in silico screening, molecular docking, in vivo screening, in vitro screening, or a combination thereof.

In some aspects relating to the above methods, a dosage period of the PDE5 inhibitor compound to the animal model subject is up to about 5 days, up to about 6 days, up to about 7 days, up to about 8 days, up to about 9 days, up to about 10 days, up to about 11 days, up to about 12 days, up to about 13 days, up to about 14 days, up to about 15 days, up to about 16 days, up to about 17 days, up to about 18 days, up to about 19 days, or up to about 20 days.

In some aspects relating to the above methods, the compound has a molecular mass less than about 500 Da, a polar surface area less than about 90 Å$^2$, less than 8 hydrogen bonds, or a combination thereof in order to penetrate the blood brain barrier.

In some aspects relating to the above methods, the PDE5 inhibitor compound has been first pre-screened by a method comprising: (a) providing an electronic library of test compounds; (b) providing atomic coordinates listed in Table 1 for at least 20 amino acid residues for the active site of the PDE5 protein, wherein the coordinates have a root mean square deviation therefrom, with respect to at least 50% of Cα atoms, of not greater than about 2 Å, in a computer readable format; (c) converting the atomic coordinates into electrical signals readable by a computer processor to generate a three dimensional model of the PDE5 protein; (d) performing a data processing method, wherein electronic test compounds from the library are docked onto the three dimensional model of the PDE5 protein; and (e) determining which test compound fits into the active site of the three dimensional model of the PDE5 protein, thereby identifying which compound would bind to PDE5. In one aspect, this method can further comprise: (f) synthesizing or obtaining the compound determined to dock to the active site of the PDE5 protein; (g) contacting the PDE5 protein with the compound under a condition suitable for binding; and (h) determining whether the compound modulates PDE5 protein expression or mRNA expression, or PDE5 protein activity using a diagnostic assay.

In some aspects of the present methods, the PDE5 inhibitor compound comprises Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18), as described herein. In some embodiments, the compound is selected from Formula V, Formula V-1, Formula V-1a, and Formula VIaI as described herein; wherein $R^1$ is $C_3$-$C_8$ cycloalkyl, —$NR^7R^8$, or —$SR^7$. In some embodiments, $R^1$ is $C_3$-$C_8$ cycloalkyl. In some embodiments, $R^1$ is $C_3$-$C_8$ cycloalkyl or —$NR^7R^8$. In some embodiments, $R^1$ is —$NR^7R^8$.

In some aspects, the PDE5 inhibitor decreases PDE5 protein or mRNA expression, or PDE5 activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

In some aspects, the PDE5 inhibitor has an $IC_{50}$ at least about 0.1 nM, at least about 1 nM, at least about 5 nM, at least about 10 nM, at least about 25 nM, at least about 50 nM, at least about 100 nM, at least about 200 nM, at least about 300 nM, at least about 400 nM, at least about 500 nM, at least about 600 nM, at least about 700 nM, at least about 800 nM, at least about 900 nM, or at least about 1000 nM.

In some aspects, methods for selecting a PDE5 inhibitor can comprise detecting whether the inhibitor can cause an increase or decease in a secondary messenger concentration. The secondary messenger can comprise, for example, cyclic GMP, protein kinase G (PKG), or a combination thereof. The detection can comprise an assay that measures an intracellular concentration of GTP, cyclic GMP, protein kinase G (PKG), or CREB.

In some aspects, the PDE5 inhibitor compound binds to the active site of phosphodiesterase type V (PDE5).

In some aspects, the compound has an IC50 at least about 0.1 nM, at least about 1 nM, at least about 5 nM, at least about 10 nM, at least about 25 nM, at least about 50 nM, at least about 100 nM, at least about 200 nM, at least about 300 nM, at least about 400 nM, at least about 500 nM, at least about 600 nM, at least about 700 nM, at least about 800 nM, at least about 900 nM, or at least about 1000 nM.

In one aspect, the invention provides a method for increasing α-secretase protein activity or expression in a subject, the method comprising: (a) administering to the subject an effective amount of a composition comprising a PDE5 inhibitor compound, thereby increasing α-secretase protein activity or expression in the subject.

In one aspect, the invention provides a method for decreasing β-secretase protein activity or expression in a subject, the method comprising: (a) administering to the subject an effective amount of a composition comprising a PDE5 inhibitor compound, thereby decreasing β-secretase protein activity or expression in the subject.

In one aspect, the invention provides a method for reducing amyloid beta (Aβ) protein deposits in a subject, the method comprising: (a) administering to the subject an effective amount of a composition comprising a PDE5 inhibitor compound, thereby decreasing Aβ protein deposits in the subject.

In some aspects, the subject exhibits abnormally elevated amyloid beta plaques. In some aspects, the subject is afflicted with Alzheimer's disease, Lewy body dementia, inclusion body myositis, or cerebral amyloid angiopathy. In some aspect, the subject is a mouse, dog, cat, horse, cow, sheep, or human.

In some aspects, the compound that is administered to the subject comprises Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18). In some embodiments, the compound is selected from Formula V, Formula V-1, Formula V-1a, and Formula V1a1 as described herein; wherein $R^1$ is $C_3$-$C_8$ cycloalkyl, —$NR^7R^8$, or —$SR^7$. In some embodiments, $R^1$ is $C_3$-$C_8$ cycloalkyl. In some embodiments, $R^1$ is $C_3$-$C_8$ cycloalkyl or —$NR^7R^8$. In some embodiments, $R^1$ is —$NR^7R^8$. In some aspects, the compound is sildenafil, tadalafil, or vardenafil. In some aspects, the administration comprises subcutaneous, intra-muscular, intra-peritoneal, or intravenous injection; infusion; oral or nasal delivery; or a combination thereof. In some aspects the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, or at least about 10 mg/kg body weight. In other aspects, the effective amount of the administered compound is at least about 3 mg/kg body weight. In some aspects, the composition is administered at least once daily for up to 18 days, up to 19 days, up to 20 days, up to 21 days, up to 22 days, up to 23 days, up to 24 days, or up to 25 days. In some aspects, the α-secretase protein activity or expression is increased up to 3 months post-treatment, up to 4 months post-treatment, up to 5 months post-treatment, or up to 6 months post-treatment. In some aspects, the β-secretase protein activity or expression is decreased up to 3 months post-treatment, up to 4 months post-treatment, up to 5 months post-treatment, or up to 6 months post-treatment. In some aspects, the Aβ protein deposit comprises an Aβ40 isomer, an Aβ42 isomer, or a combination thereof.

In some aspects, PDE5 inhibitor compounds that are administered to subjects to modulate secretase activity or expression are administered infrequently due to the finding provided herein that PDE5 inhibitors can cause a long-lasting or sustained affect on secretase activity long-after administration. Thus, in some aspects, methods of treatment are provided where subjects are administered PDE5 inhibitors for short-term periods on a regular, but infrequent basis. For example, administration can comprise a dosage regimen comprising 1 week, 2 weeks, 3 weeks, a month, or more, followed by a period of no administration that comprises 1 week, 2 weeks, 3 weeks, a month, 2 months, 3 months, 4 months, 5 months, 6 months, 1 year, or more, wherein this dosage regimen can then be repeated and varied. Namely, the dosage regimen comprises a period of PDE5 inhibitor administration followed a period of no drug administration, optionally followed by further cycles. The benefit of such a cyclic regimen can be, for example, to lessen the possibility of side-effects due to total drug intake-load over time.

BRIEF DESCRIPTION OF THE FIGURES

The patent or application file contains at least one drawing executed in color. Copies of this patent or patent application publication with color drawing(s) will be provided by the Office upon request and payment of the necessary fee.

(11 males and 9 females), $F_{(1,39)}=6.64$, P=0.01]. Treatment with sildenafil ameliorates deficit in freezing responses in APP/PS1 mice (the freezing time of sildenafil-treated APP/PS1 mice was about 87% of vehicle-treated WT mice: 28.95±3.94%, n=22 (12 males and 10 females), $F_{(1,40)}=0.73$, P=0.39). Sildenafil has no effect on the freezing responses of WT mice compared to vehicle-treated WT littermates [about 89% of vehicle-treated WT mice: 30.1±3.11%, n=20 (11 males and 9 females), $F_{(1,38)}=0.52$, P=0.47). Cued fear conditioning was similar among the four groups [$F_{(3,79)}=0.89$, P=0.44].

Figure 2A:
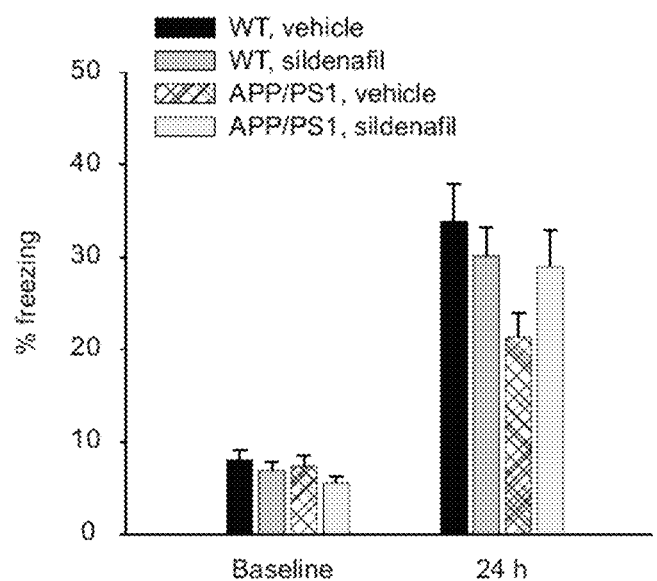
FIG. 2A is a graph that shows sildenafil ameliorates cognitive dysfunction in 3-month-old APP/PS1 mice. Sildenafil (3 mg/Kg, i.p.) improves contextual fear conditioning in 3 month-old APP/PS1 mice. APP/PS1 and WT littermates treated with sildenafil or vehicle show no difference in freezing prior to training (baseline; one-way ANOVA among the four groups: $F_{(3,79)}$=2.39, P=0.07), whereas contextual FC performed 24 hrs after training shows a reduction of freezing responses in APP/PS1 mice treated with vehicle compared to vehicle-treated WT littermates [the freezing time of vehicle-treated APP/PS1 mice was ~63% of vehicle-treated WT mice; 21.36±3.94% in APP/PS1, n=21 (12 males and 9 females), vs. 33.81±4.05% in WT littermates, n=20
Figure 2B:
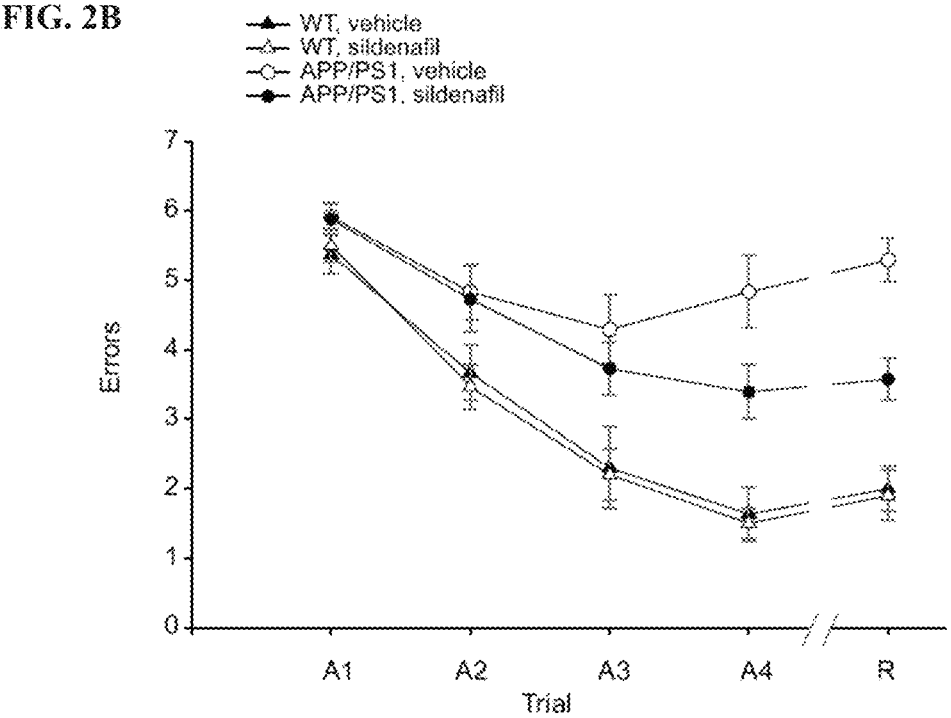

FIG. 2B is a graph demonstrating that sildenafil ameliorates cognitive dysfunction in 3-month-old APP/PS1 mice. Sildenafil (3 mg/Kg, i.p.) improves spatial working memory in 3 month-old APP/PS1 mice. APP/PS1 mice treated with vehicle do not learn the position of the hidden platform compared to vehicle-treated WT littermates [APP/PS1: 5.91±0.19 errors in the first acquisition trial (A1), 4.83±0.52 errors by the fourth consecutive trial (A4), and 5.29±0.31 errors by the recall trial (R), n=8 (4 males and females); WT: A1=5.36±0.27 errors, A4=1.63±0.39 errors, R=2.00±0.32 errors, n=10 (5 males and females)]. Two-way ANOVA showed a significant difference between the performance of vehicle-treated APP/PS1 mice and that of vehicle-treated WT littermates ($F_{(1,16)}=39.66$, P<0.0001), and planned comparisons showed that the 2 groups were significantly different at trial A2 (P=0.05), Aβ (P=0.02), A4 and R (P=<0.0001). However, treatment with sildenafil ameliorates the performance of double transgenic littermates compared to vehicle-treated APP/PS1 [A1=5.87±0.22 errors, A4=3.39±0.39 errors, R=3.57±0.31 errors, n=11 (6 males and 5 females), $F_{(1,17)}=5.99$, P=0.02]. Planned comparisons showed that the 2 groups were significantly different at trial A4 (P=0.03) and R (P=0.001). Sildenafil does not affect the performance of WT mice compared to vehicle-treated WT mice [sildenafil: A1=5.5±0.23 errors, A4=1.5±0.21 errors, R=1.9±0.35 errors, n=10 (5 males and females), $F_{(1,18)}=0.09$, P=0.76).

FIG. 3A is a bar graph that shows sildenafil (3 mg/Kg, i.p. for 3 weeks at the age of 3 months) ameliorates contextual fear conditioning in transgenic mice. After 24 hours, there is a reduction of freezing behavior in APP/PS1 mice compared to WT, rescued by sildenafil treatment [~97% of vehicle-treated WT mice in sildenafil-treated APP/PS1 mice, vs. ~66% in vehicle-treated APP/PS1 mice; 30.32±1.98%, n=12 (7 males and 5 females) in sildenafil-treated APP/PS1 mice, 20.66±2.42%, n=17 (10 males and 7 females) in vehicle-treated APP/PS1 mice, $F_{(1,27)}=7.10$, P=0.013]. Sildenafil did not increase the freezing time in WT littermates compared to WT mice treated with vehicle [~104% of vehicle-treated WT mice; 32.41±1.88%, n=17 (10 males and 7 females) vs. 31.16±1.21%, n=14 (8 males and 6 females), $F_{(1,29)}=0.28$, P=0.06]. There were no significant differences between the 4 groups in the cued conditioning test [$F_{(3,56)}=0.07$, P=0.097].

FIG. 3B is a graph that shows impairment of performance during radial-arm water maze testing in APP/PS1 mice is rescued by treatment with sildenafil (3 mg/Kg, i.p. for 3 weeks at the age of 3 months). There was a significant difference between the number of errors made by vehicle-treated APP/PS1 and WT littermates [APP/PS1: 6.04±0.21 errors in the first acquisition trial A1, 5.38±0.34 errors in A2, 5.14±0.36 in A3, 4.52±0.33 by the fourth consecutive trial A4, and 4.95±0.28 errors by the recall trial R, n=7 (4 males and 3 females); WT: A1=5.60±0.62 errors, A2=3.46±0.34 errors, A3=2.66±0.82 errors, A4=1.86±0.16 errors, R=2.13±0.34 errors, n=5 (3 males and 2 females)]. Two-way ANOVA revealed a significant overall difference between the performance of the two groups [$F_{(1,10)}=33.98$, P=0.0001] and planned comparison showed that the difference became pronounced since the second acquisition trial A2 (P=0.003) and in the recall trial (P=0.0001). Sildenafil improves the performance of APP/PS1 mice and does not affect the performance of WT mice [sildenafil-treated APP/PS1: A1=6.16±0.39, A2=4.16±0.53, A3=3.5±0.41, A4=2.83±0.61, R=3±0.75 errors, n=4 (3 males 1 female); sildenafil-treated WT animal: A1=6±0.29, A2=3.22±0.56, A3=2.5±0.36, A4=1.83±0.16, R=2.33±0.36 errors, n=6 (4 males and 2 females), $F_{(1,7)}=3.42$, P=0.1 and $F_{(1,8)}=4.04$, P=0.07 compared to vehicle-treated WT animals]. Statistical analysis revealed a strong effect of treatment in APP/PS1 mice treated with sildenafil compared to APP/PS1 animals treated with vehicle ($F_{(1,9)}=18.53$, P=0.002), and planned comparisons showed that the groups were significantly different at Aβ (P=0.019), A4 (P=0.026) and R (P=0.017).

FIG. 3C is a graph depicting that the performance of APP/PS1 mice in the Morris water maze is improved by previous treatment with sildenafil (3 mg/Kg, i.p. for 3 weeks at the age of 3 months). Vehicle-treated transgenic mice needed 44.83±3.77 seconds to find the hidden platform after six sessions compared to 28.91±3.94 seconds required by WT littermates [~155% of the time needed by the vehicle-treated WT mice; $F_{(1,21)}=13.73$, P=0.001; planned comparisons showed that the groups were significantly different at the fourth, fifth and sixth sessions; P=0.001, P=0.009, P=0.008, respectively]. Previous treatment with sildenafil reduces the time needed to find the platform in APP/PS1 mice (32.92±3.50 seconds, ~114% of the time required by vehicle-treated WT mice; $F_{(1,16)}=2.97$; P=0.10). Sildenafil did not affect the performance in WT littermates that needed 25.64±3.16 seconds (~89% of the time required by vehicle-treated WT mice; $F_{(1,23)}=0.981$; P=0.37). Statistical analysis revealed a significant difference in the overall performance of sildenafil-treated APP/PS1 mice compared to that of vehicle-treated APP/PS1 mice [$F_{(1,15)}=0.85$, P=0.02)] and planned comparisons of latency on each individual session revealed that the difference was significant at the fourth, fifth and sixth session (P=0.0001, P=0.011, P=0.034, respectively).

FIG. 3D is a bar graph demonstrating that APP/PS1 mice previously treated with sildenafil search significantly more time in the target quadrant (TQ), where the platform was located during training, than do vehicle-treated APP/PS1 littermates, during the probe test. ($F_{(1,16)}=8.42$, P=0.01). WT mice spent 33.37±2.10% of their time given in the TQ then in other quadrants [$F_{(3,44)}=3.85$, P=0.016]. Planned comparisons confirmed that they spent significantly more time in the TQ than in the adjacent quadrant to the right (AR), in the adjacent quadrant to the left (AL), or in the opposite quadrant (OQ) (TQ versus AR, P=0.03; TQ versus OQ, P=0.04; TQ versus AL, P=0.02). Sildenafil improved the performance of the APP/PS1 mice [32.25±0.58% of their time given spent in TQ, or ~97% of the time used by vehicle-treated WT littermates, than in other quadrants; $F_{(3,24)}=14.73$; P<0.0001]. Planned comparisons confirmed that they spent significantly more time in the TQ than in the AR, in the AL, or in the OQ (P<0.0001). Vehicle-treated APP/PS1 mice spent only 21.39±1.46% of the time in the TQ [$F_{(3,40)}=0.52$, P=0.66], or ~64% of the time used by vehicle-treated WT littermates. Sildenafil-treated WT mice spent 33.35±1.38% of the time in the TQ [$F_{(3,48)}=3.63$, P=0.019; planned comparisons TQ versus AR, P=0.03; TQ versus OQ, P=0.04; TQ versus AL, P=0.02], or ~100% of the time used by vehicle-treated WT littermates. Statistic revealed a significant difference in the percent of time spent in the TQ by sildenafil-treated APP/PS1 mice compared with that of vehicle-treated APP/PS1 mice ($F_{(1,16)}$=8.42, P=0.01). No statistically significant difference was found in the percent of time spent in the TQ by sildenafil-treated APP/PS1 mice compared with vehicle-treated and sildenafil-treated WT mice ($F_{(1,17)}$=0.04, P=0.84; $F_{(1,18)}$=0.03, P=0.85, respectively).

Figure 4A:
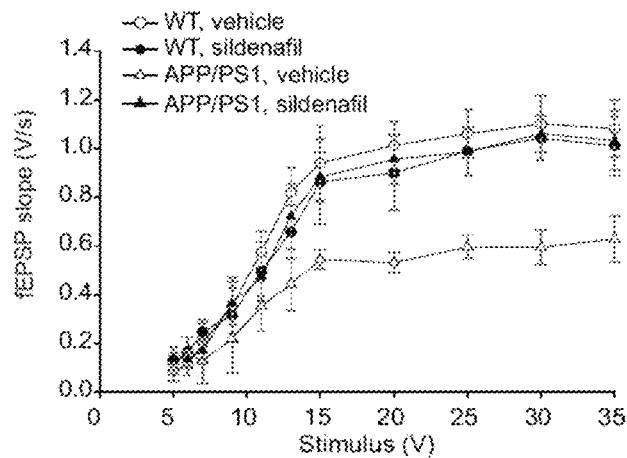

FIG. 4A is a graph showing that BST impairment in 6-8 month-old APP/PS1 animals is improved by sildenafil-treatment (3 mg/Kg, i.p. for 3 weeks at the age of 3 months) [APP/PS1: ~57% of vehicle-treated WT mice; 0.62±0.09 V/sec., (n=6 slices from 5 males), $F_{(1,9)}$=7.26, P=0.02; compared to vehicle-treated WT mice; APP/PS1+ sildenafil: ~160% of vehicle-treated APP/PS1 mice; 1.03±0.12 V/sec., (n=8 slices from 6 males), $F_{(1,12)}$=5.51, P=0.03 compared to vehicle-treated transgenic mice]. No statistically significant difference was found in the values of fEPSP slope in sildenafil-treated APP/PS1 mice compared to vehicle-treated and sildenafil-treated WT mice ($F_{(1,11)}$=0.07, P=0.79; $F_{(1,12)}$=0.03, P=0.84, respectively). Sildenafil does not change BST in WT mice [slope of the input-output curve in sildenafil-treated WT mice: ~94% of vehicle-treated WT mice; sildenafil-treated WT mice: 1.01±0.12 V/sec. (n=6 from 5 males), vehicle-treated mice: 1.08±0.11 V/sec. (n=5 slices from 5 males); two-way ANOVA $F_{(1,9)}$=0.34, P=0.57]. Similar results were observed when plotting the fEPSP slope versus the amplitude of the fiber afferent volley.

Figure 4B:
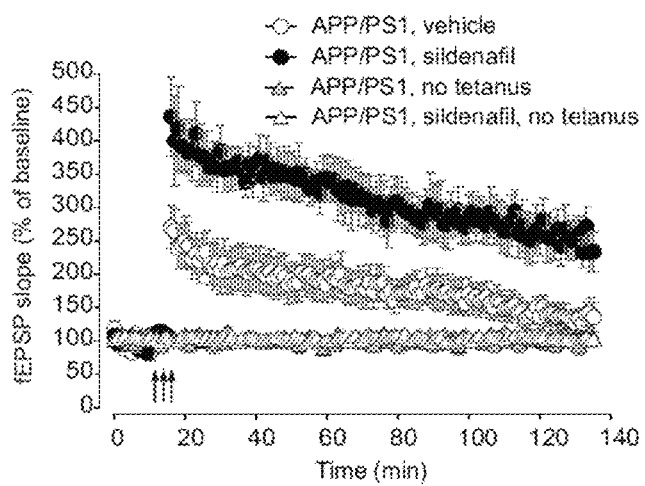

FIG. 4B is a graph demonstrating that sildenafil (3 mg/Kg, i.p. for 3 weeks at the age of 3 months) rescues the LTP impairment in 6-8 month-old APP/PS1 mice [APP/PS1+ sildenafil: ~100% of sildenafil-treated WT mice, 233.81±30.47% of baseline at 120 min, n=7 slices from 6 males, $F_{(1,12)}$=1.18, P=0.29 compared to sildenafil treated-WT littermates; APP/PS 1+ vehicle: ~65% of vehicle-treated WT mice, 135.56±22.02% of baseline, n=7 slices from 6 males, $F_{(1,12)}$=14.82, P=0.002 compared to vehicle-treated WT littermates].

Figure 4C:
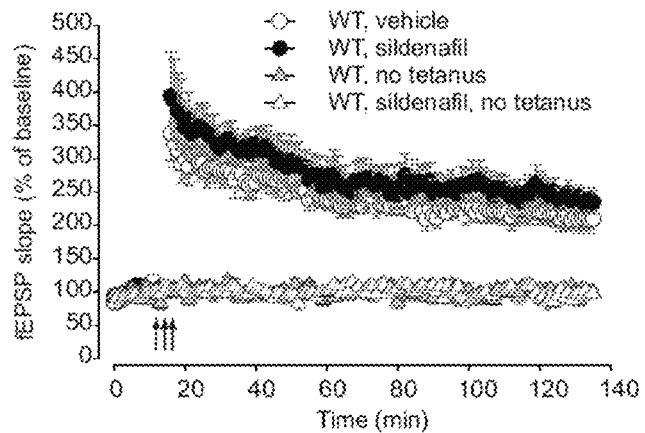

FIG. 4C is a graph depicting that sildenafil (3 mg/Kg, i.p. for 3 weeks at the age of 3 months) does not affect LTP in 6-8 month-old WT mice [~112% of vehicle-treated mice in sildenafil-treated mice; sildenafil-treated mice: 234.67±17.19% of baseline, n=7 slices from 6 males; vehicle-treated mice: 210.01±16.62% of baseline, n=7 slices from 6 males, $F_{(1,12)}$=2.16, P=0.16]. No differences were noted in the baseline transmission of the four groups of mice in the absence of tetanus (n=4 slices from 4 animals for each group, $F_{(3,12)}$=0.17, P=0.91).

Figure 5A:
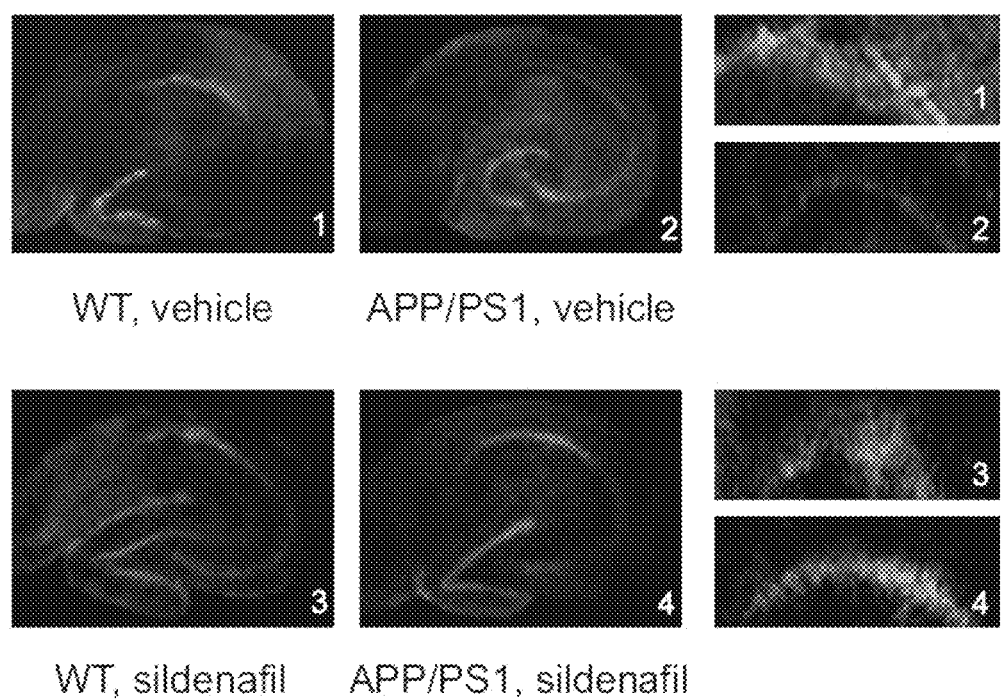

FIG. 5A are immunofluorescence photographs showing representative examples of hippocampal slices stained with a phospho-CREB antibody. The slices are fixed 60 minute after either vehicle or sildenafil (50 nM) with tetanus in 3-months old WT and APP/PS1 animals. Left, lower-power (4×) view of the entire slice. Right, higher power (16×) view of CA1 cell pyramidal area. Sildenafil re-establishes normal increase in CREB phosphorylation following tetanic stimulation in APP/PS1 mice.

Figure 5B:
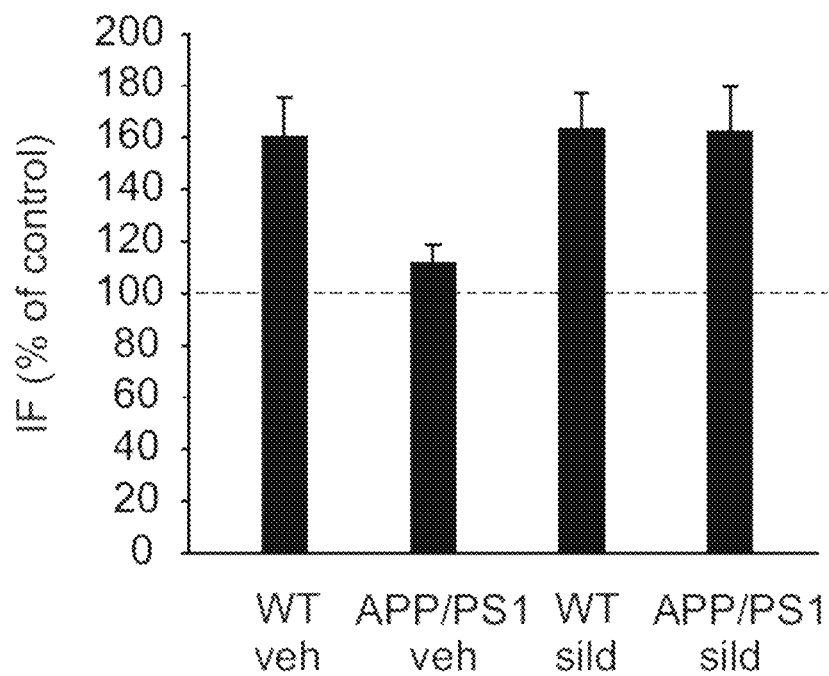

FIG. 5B is a bar graph showing that the increase in the intensity of immunofluorescence (IF) in the CA1 cell body area after application of the tetanus does not appear in 3 month old APP/PS1 mice (WT: 160.51±14.96% of control, n=4; $t_{(6)}$=3.44, P=0.014 compared to control non-tetanized slices; APP/PS1: 111.89±6.62% of control, n=4; $t_{(6)}$=2.96, P=0.025 compared to tetanized slices). Sildenafil (sild) re-establishes increase in CREB phosphorylation in APP/PS1 mice after tetanus whereas it does not affect phospho-CREB levels in WT tetanized slices (APP/PS1+ sildenafil: 162.58±17.09% of control, n=4; $t_{(6)}$=0.09, P=0.93; WT+sildenafil: 163.54±13.52% of control, n=4; $t_{(6)}$=0.15, P=0.88 compared to tetanized slices of WT mice).

Figure 5C:
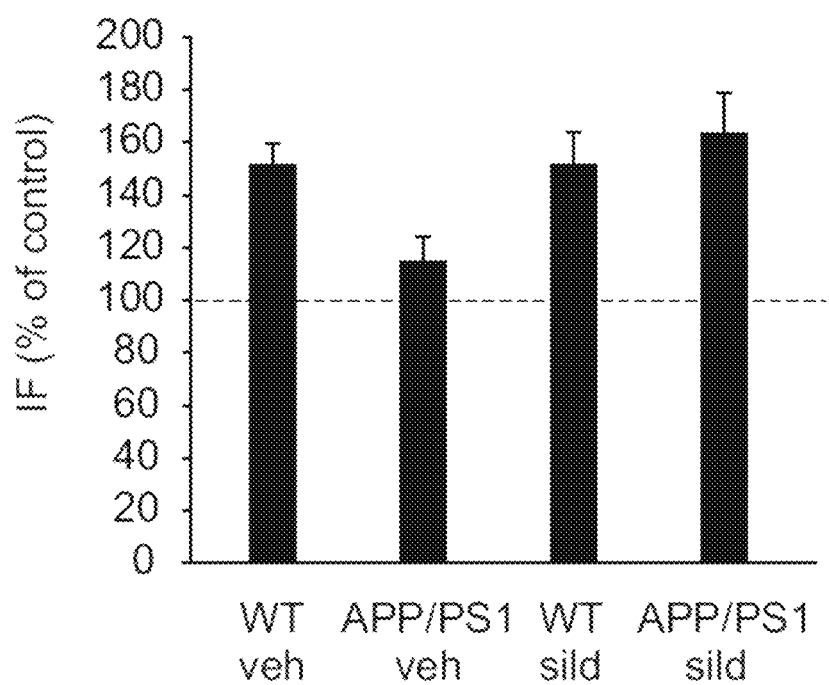

FIG. 5C is a bar graph demonstrating that daily injections of sildenafil (3 mg/Kg, i.p. for 3 weeks in 3-month-old APP/PS1 mice) re-establish the tetanus-induced increase in CREB phosphorylation in hippocampal slices from the same mice at 6-8 months of age (WT: 151.60±8.25% of control, n=4/4; $t_{(6)}$=4.70, P=0.003 compared to non-tetanized slices; APP/PS1: 114.96±9.12% of control, n=4, $t_{(6)}$=2.96, P=0.025, compared to tetanized slices from their WT littermates; APP/PS1+ sildenafil: 163.6±15.14% of control, n=4; $t_{(6)}$=0.69, P=0.53 compared to tetanized slices of vehicle-treated WT animals, ($t_{(6)}$=2.75, P=0.041 compared to tetanized slices of vehicle-treated APP/PS1 animals). Sildenafil does not affect the increase in CREB phosphorylation in WT mice (151.73±12.24% of control, n=4, $t_{(6)}$=0.009, P=0.993, compared to tetanized slices from WT mice).

FIG. 6A is a bar graph showing that daily injections of sildenafil for 3 weeks decreases $A\beta_{40}$ and $A\beta_{42}$ levels in 3-month-old transgenic mice ($A\beta_{40}$: ~64% of vehicle-treated APP/PS1 mice, $A\beta_{42}$: ~80%; $A\beta_{40}$ and $A\beta_{42}$ values were 1.71±0.22 and 3.56±0.23 ng/mg cortex, respectively, in sildenafil-treated APP/PS1 mice, n=7, versus 2.67±0.35 and 4.43±0.34 ng/mg cortex in vehicle-treated APP/PS1 mice, n=7, $t_{(12)}$=2.26, P=0.043, and $t_{(12)}$=2.09, P=0.058, respectively). Sildenafil decreased Aβ levels in 3-4 month-old APP/PS1.

FIG. 6B are photographs of immunoblots from the brains of APP/PS1 3-month-old transgenic mice treated with sildenafil (Right Column) or vehicle (Left Column) stained for APP full length, sAPPα, sAPPβ, CT83, CT99. Tubulin was used as a control.

FIG. 6C is a bar graph demonstrating that sildenafil treated 3-month-old transgenic mice do not show a change in APP levels (125.75±4.44% of control in vehicle-treated mice vs. 119.75±8.99% in vehicle-treated mice, n=4/4, $t_{(6)}$=0.59, P=0.572).

FIG. 6D is a bar graph demonstrating that sildenafil treated 3-month-old transgenic mice do not show a change in sAPPα (86.25±5.02% vs. 87.75±4.90, n=4/4, $t_{(6)}$=0.21, P=0.838).

FIG. 6E is a bar graph demonstrating that sAPPβ is decreased in 3-month old transgenic animals treated with sildenafil (43.25±3.90% vs. 62.75±4.58%, n=4/4, $t_{(6)}$=3.68, P=0.010). Sildenafil modifies β-secretase activity in 3-4 month-old APP/PS1.

FIG. 6F is a bar graph demonstrating that CT83 and CT99 fragments show an increase after sildenafil treatment of 3-month-old transgenics (CT83: 74.5±6.73% vs. 40.00±7.73%, n=4/4, $t_{(6)}$=3.36, P=0.015; CT99: 95.25±5.66% vs. 70.5±7.70%, n=4/4, $t_{(6)}$=2.58, P=0.041).

Figure 7A:
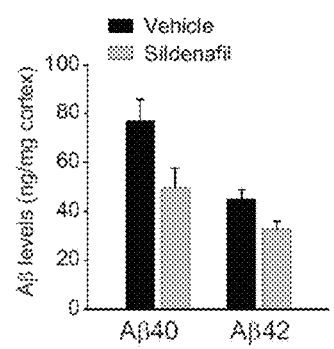

FIG. 7A is a bar graph showing that daily injections of sildenafil at age 3 months for 3 weeks decrease $A\beta_{40}$ and $A\beta_{42}$ levels in mice at 7-10 months of age ($A\beta_{40}$: ~65% of vehicle-treated APP/PS1 mice, $A\beta_{42}$: ~73%; $A\beta_{40}$ and $A\beta_{42}$ values were 49.59±7.93 and 32.55±3.27 ng/mg cortex, respectively, in sildenafil-treated APP/PS1 mice, n=6, versus 76.98±8.88 and 44.77±4.08 ng/mg in vehicle-treated APP/PS1 mice, n=7, $t_{(11)}$=2.26, P=0.045, and $t_{(11)}$=2.24, P=0.047, respectively).

Figure 7B:
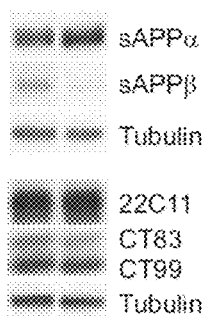

FIG. 7B are photographs of immunoblots from the brains of APP/PS1 mice at 7-10 months of age that were treated with sildenafil or vehicle for 3 weeks at 3-months of age, which were stained for APP full length, sAPPα, sAPPβ, CT83, CT99.

Figure 7C:
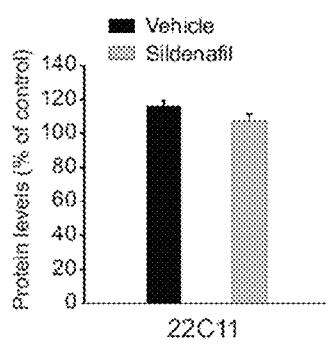

FIG. 7C is a bar graph showing that sildenafil treated mice do not show a change in APP levels (116.33±3.32% vs. 107.4±3.88%, n=3/5, $t_{(6)}$=1.51, P=0.180). Daily injections of sildenafil for 3 weeks in 3-month-old APP/PS1 mice did not change APP in the same mice at 7-10 months of age.

FIG. 7D is a bar graph showing that sAPPα is increased (97±3.12% vs. 153.65±11.95, n=3/4, $t_{(5)}$=3.52, P=0.017) in APP/PS1 mice at 7-10 months of age that received daily injections of sildenafil for 3 weeks at 3-months of age.

FIG. 7E is a bar graph showing that sAPPβ is decreased in APP/PS1 mice at 7-10 months of age that received daily injections of sildenafil for 3 weeks at 3-months of age (28.33±2.84% vs. 25.6±2.83%, n=3/5, $t_{(6)}$=2.84, P=0.029).

FIG. 7F is a bar graph showing that no differences are observed for CTFs (CT83: 75.66±1.92% vs. 82.75±6.78%, n=3/5, $t_{(6)}$=1.13, P=0.299; CT99: 96.66±5.29% vs. 87.2±7.63%, n=3/5, $t_{(6)}$=0.85, P=0.427) in APP/PS1 mice at 7-10 months of age that received daily injections of sildenafil for 3 weeks at 3-months of age.

Figure 8A:
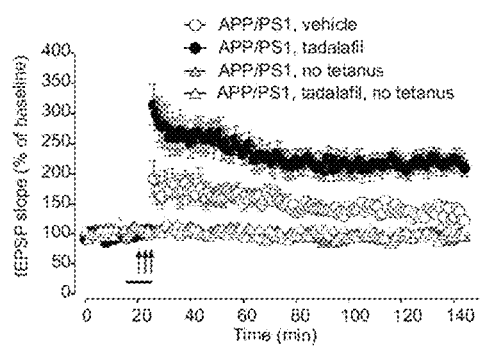

FIG. 8A is a graph demonstrating that tadalafil (50 nM) reverses LTP impairment in APP/PS1 mice (levels of LTP: tadalafil-treated APP/PS1 mice equal to ~96% of vehicle-treated WT littermates at 120 min. after tetanus, vs. ~56% in vehicle-treated APP/PS1 mice; tadalafil-treated APP/PS1 mice: 209.49±13.89% at 120 min. after tetanus, n=8 slices from 6 males; vehicle-treated APP/PS1 mice: 123.14±5.98%, n=8 slices from 7 males; vehicle-treated WT mice: 219.88±19.35%, n=8 slices from 7 males, $F_{(1,14)}$=15.57, P=0.001]. Tadalafil does not change basal neurotransmission either during its application or 120 minutes after the end of the application in experiments where no tetanic stimulation is applied [$F_{(1,6)}$=1.007, P=0.93]. PDE5 inhibition reverses the impairment of LTP in the CA1 region of slices from 3-month-old APP/PS1 mice.

Figure 8B:
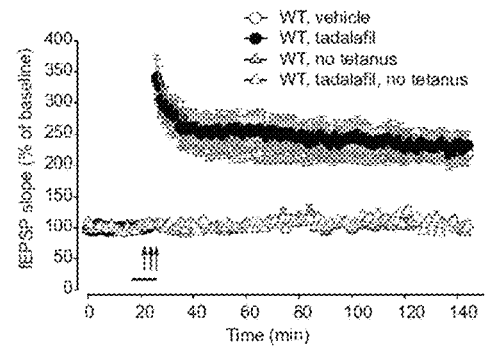

FIG. 8B is a graph showing that ten minutes perfusion with tadalafil (50 nM) does not change the amplitude of LTP [~106% of vehicle-treated tetanized WT slices, 232.45±21.92% vs. 219.88±19.35%, n=8/8, $F_{(1,14)}$=0.24, P=0.62) and baseline in WT mice (~98% of vehicle-treated WT slices, 103.65±1.63% vs. 104.71±6.13, n=4/4, $F_{(1,6)}$=1.05, P=0.34]. These experiments were interleaved with those of APP/PS1 mice.

Figure 8C:
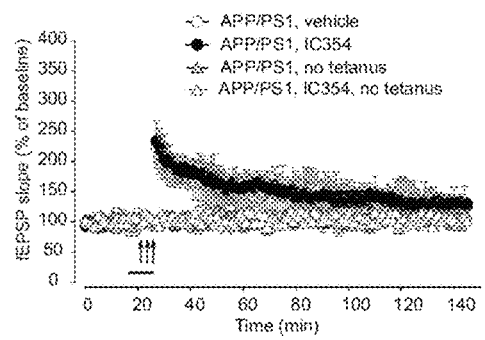

FIG. 8C is a graph demonstrating that IC354 (1 μM) does not reverse LTP impairment in APP/PS1 mice [levels of LTP: IC354-treated APP/PS1 mice equal to ~58% of vehicle-treated WT littermates at 120 min. after tetanus, vs. ~57% in vehicle-treated APP/PS1 mice; IC354-treated APP/PS1 mice: 129.33±8.71% at 120 min. after tetanus, n=5 slices from 5 males; vehicle-treated APP/PS1 mice: 126.81±12.39%, n=5 slices from 5 males; vehicle-treated WT mice: 220.82±9.49%, n=5 slices from 5 males, $F_{(1,8)}$=0.03, P=0.85]. IC354 does not affect basal neurotransmission either during its application or 120 minutes after the end of the application in experiments where no tetanic stimulation is applied [$F_{(1,6)}$=0.006, P=0.94].

Figure 8D:
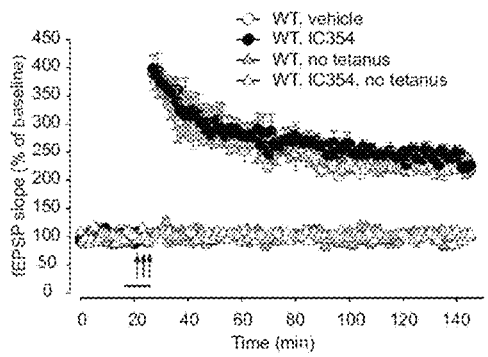

FIG. 8D is a graph depicting a ten minutes perfusion with IC354 (1 μM) does not affect LTP in WT mice [~102% of vehicle-treated WT slices, 226.05±18.76%, n=5 slices from 5 males, $F_{(1,8)}$=0.84, P=0.38]. The inhibitor has no effect on basal synaptic responses either during its application or 120 minutes after the end of the application in experiments where no tetanic stimulation is applied [$F_{(1,6)}$=0.072, P=0.79]. These experiments were interleaved with those of APP/PS1 mice.

Figure 9:
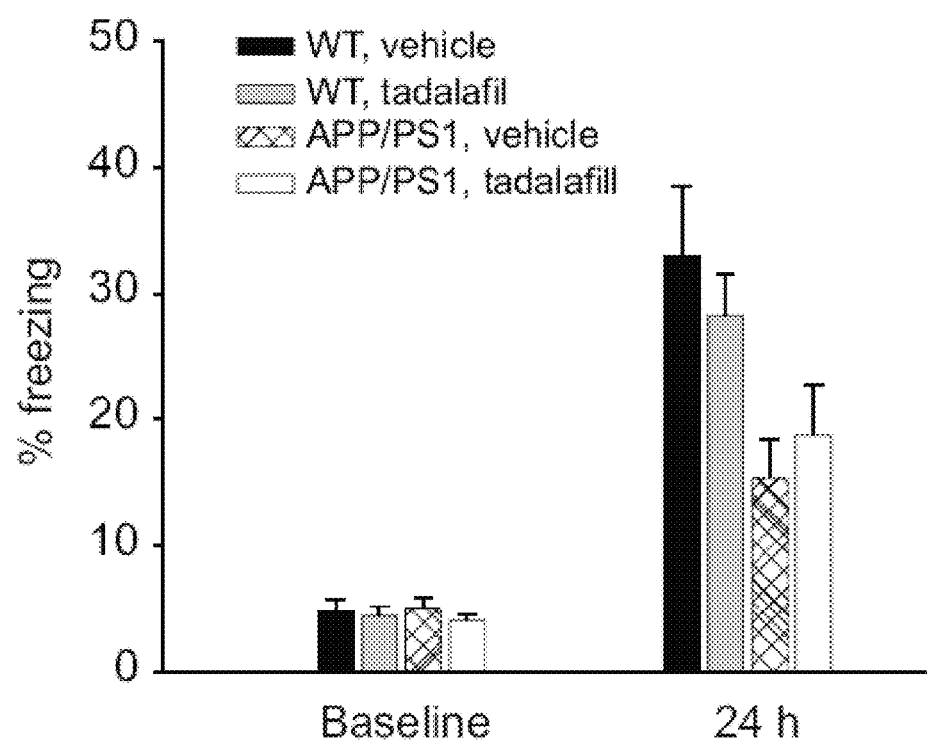

FIG. 9 is a bar graph that tadalafil does not ameliorate cognition in 3-month-old APP/PS1 mice. Tadalafil (1 mg/Kg, i.p.) does not modify contextual fear conditioning in 3 month-old APP/PS1 mice. APP/PS1 and WT littermates treated with tadalafil or vehicle show no difference in freezing prior to training [$F_{(3,39)}$=0.26, P=0.853]. Fear conditioning performed 24 hrs after training shows a reduction of freezing responses in APP/PS1 mice treated with vehicle compared to vehicle-treated WT littermates [freezing time in vehicle-treated APP/PS1 mice is ~47% of vehicle-treated WT mice; 15.34±3.15% in APP/PS1, n=12 (6 males, 6 females), vs. 33.03±5.52% in WT littermates, n=10 (5 males, 5 females), $F_{(1,20)}$=8.19, P=0.011]. Treatment with tadalafil does not rescue freezing behavior in APP/PS1 mice compared to vehicle-treated APP/PS1 animals [freezing time of tadalafil-treated APP/PS1 mice is ~122% of vehicle-treated APP/PS1 mice: 18.76±3.89%, n=8 (4 males, 4 females), $F_{(1,18)}$=0.08, P=0.778]. Tadalafil does not affect the freezing responses of WT mice [~85% of vehicle-treated WT mice: 28.29±3.30%, n=13 (7 males, 6 females), $F_{(1,21)}$=0.58, P=0.453]. Cued fear conditioning was similar among the four groups [$F_{(3, 39)}$=0.21, P=0.884].

Figure 10A:
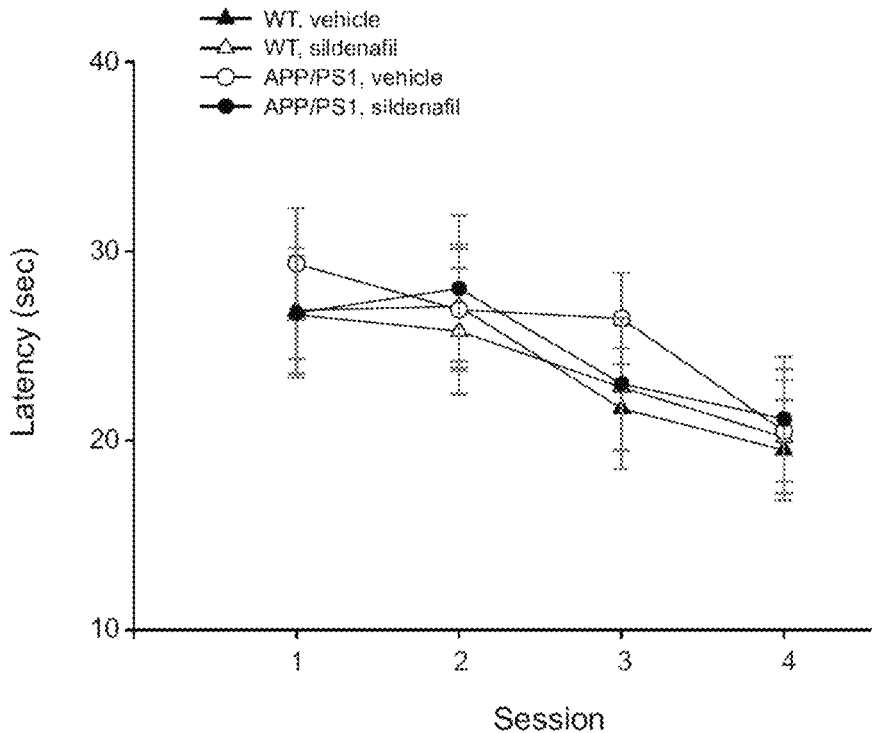

FIG. 10A is a graph that demonstrates that four groups of mice show no difference in the time needed to find a visible platform [APP/PS1 mice treated with sildenafil, 26.73±3.43 seconds in the first session of testing and 21.14±3.28 seconds in the fourth one; APP/PS1 mice treated with vehicle, 29.33±4.62 seconds and 20.49±4.20 seconds in the first and fourth sessions, respectively; WT mice treated with sildenafil, 26.64±3.11 seconds and 20.17±4.01 seconds in the first and fourth sessions, respectively; WT mice treated with vehicle, 26.88±2.58 seconds and 19.49±2.65 seconds in the first and fourth sessions, respectively, $F_{(3,35)}$=0.02, P=0.994]. APP/PS1 mice do not show any sensory impairment at 3 months of age.

Figure 10B:
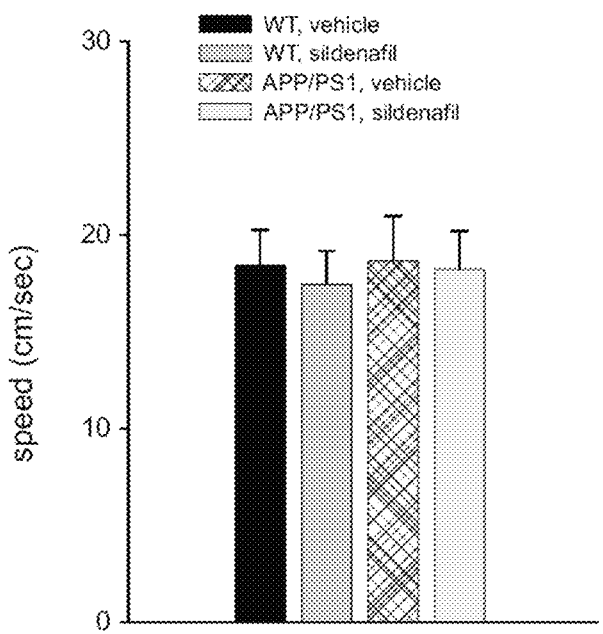

FIG. 10B is a bar graph that shows no difference in swimming speed among the four groups was also found [APP/PS1 mice treated with sildenafil, 18.21±1.96 cm/s, APP/PS1 mice treated with vehicle, 18.65±2.31 cm/s, WT mice treated with sildenafil, 17.42±1.72 cm/s, and WT mice treated with vehicle, 18.42±1.81 cm/s, $F_{(3,35)}$=0.073; P=0.974]. APP/PS1 mice do not show any motor impairment at 3 months of age.

Figure 11A:
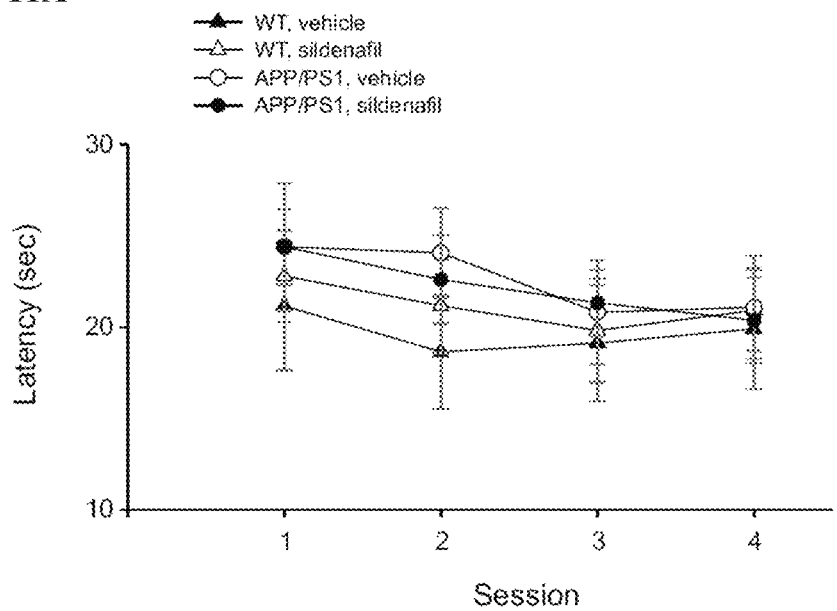

FIG. 11A is a graph demonstrating visible platform trials do not reveal any significant difference in the time to reach the platform among the 4 groups [APP/PS1 mice treated with sildenafil, 24.40±2.06 seconds in the first session of testing and 20.37±2.35 seconds in the fourth one; APP/PS1 mice treated with vehicle, 24.40±3.49 seconds and 21.09±2.83 seconds in the first and fourth sessions, respectively; WT mice treated with sildenafil, 22.79±2.51 seconds and 20.91±2.21 seconds in the first and fourth sessions, respectively; WT mice treated with vehicle, 21.16±3.11 seconds and 19.90±2.50 seconds in the first and fourth sessions, respectively; $F_{(3,39)}$=0.01, P=0.997]. APP/PS1 mice do not show any sensory impairment at 7-10 months of age. These animals received daily injections of sildenafil for 3 weeks at 3 months of age.

Figure 11B:
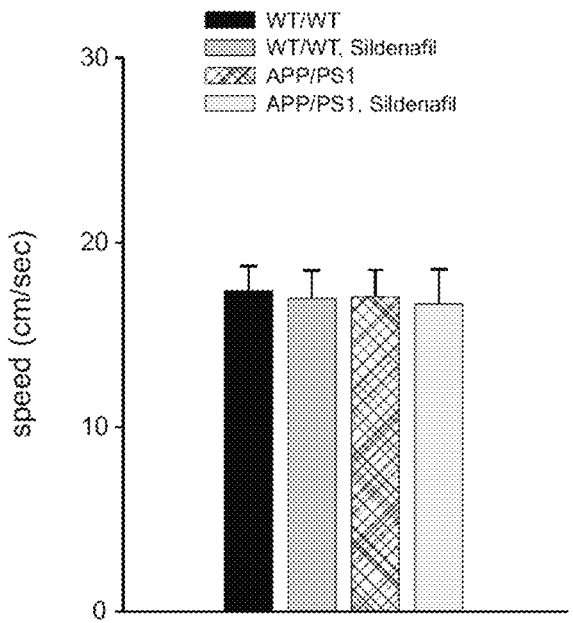

FIG. 11B is a bar graph depicting that the four groups of mice do not show any difference in swimming speed [APP/PS1 mice treated with sildenafil, 15.81±1.88 cm/s, APP/PS1 mice treated with vehicle, 17.05±1.45 cm/s, WT mice treated with sildenafil, 16.97±1.49 cm/s, and WT mice treated with vehicle, 17.36±1.34 cm/s, $F_{(3,39)}$=0.023; P=0.995]. APP/PS1 mice do not show any/motor impairment at 7-10 months of age. These animals received daily injections of sildenafil for 3 weeks at 3 months of age.

Figure 12:
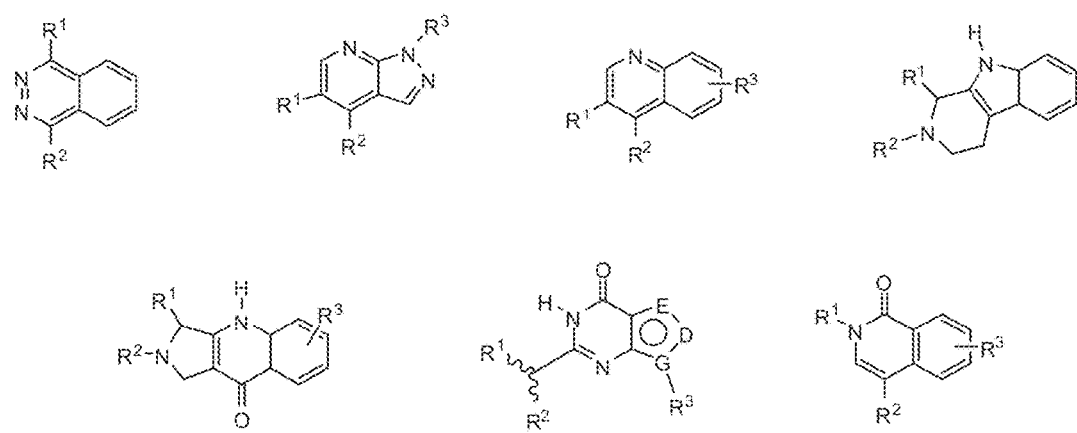

FIG. 12 is a schematic showing the fused planar ring system structures in reported PDE5 inhibitors.

Figure 13:
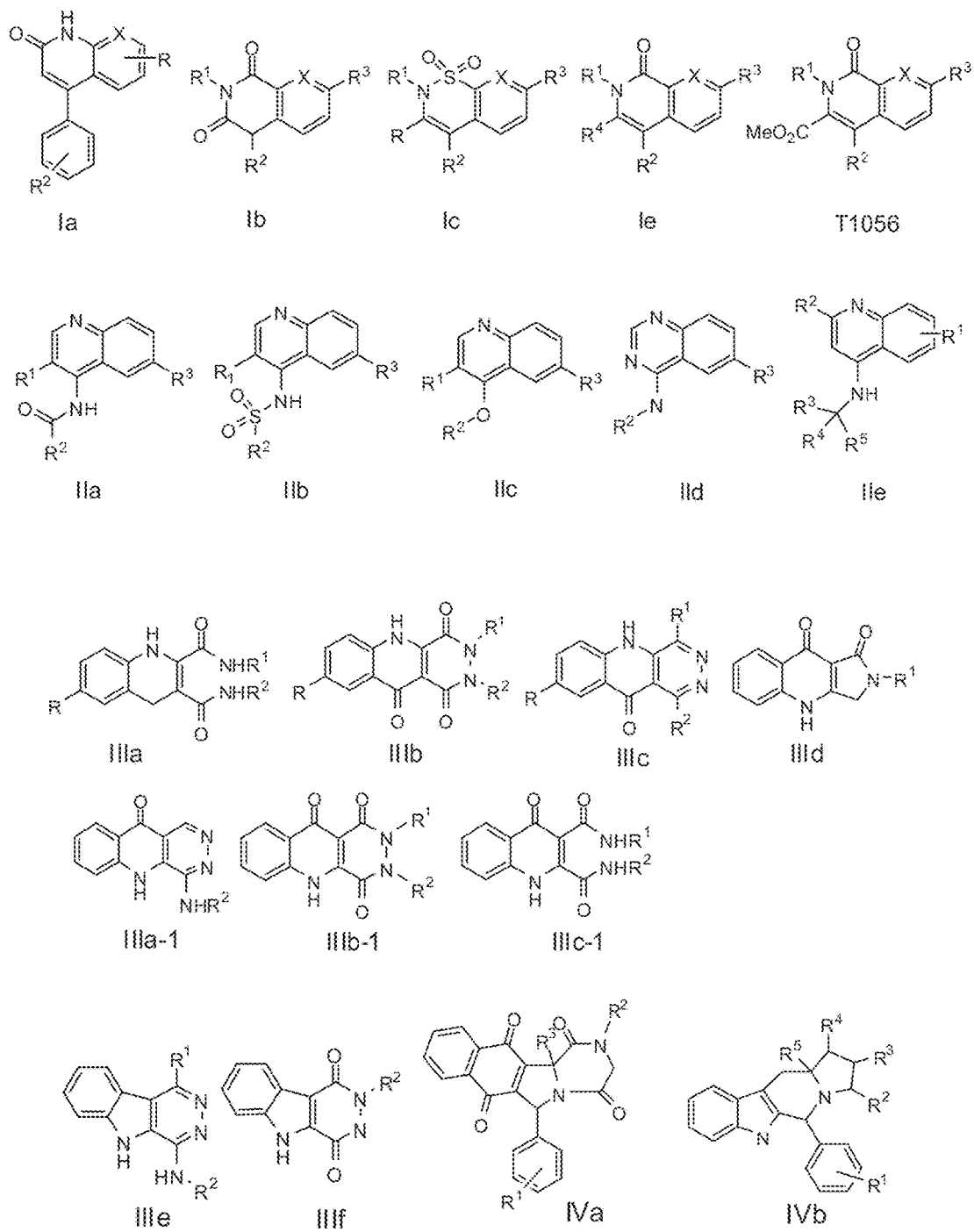

FIG. 13 are chemical structures depicting four classes of structurally related, and formally independent scaffolds (I-IV) based on structure analysis of reported PDE5 inhibitors and known Structure-Activity Relationship (SAR) data.

Figure 14:
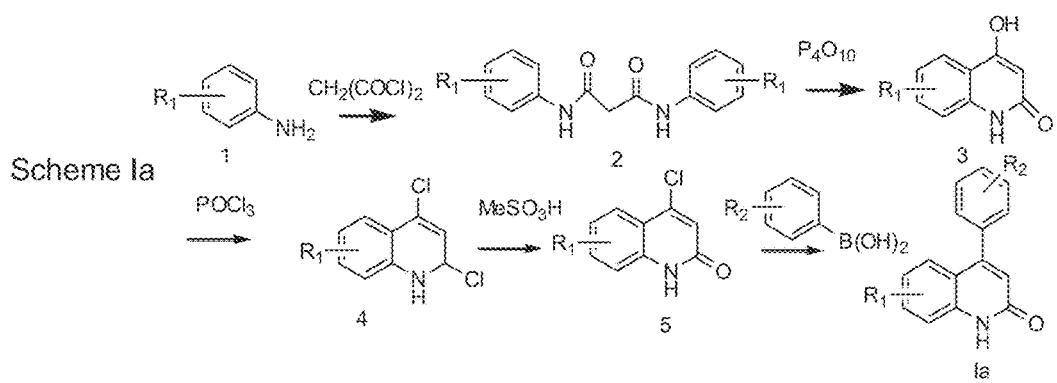

FIG. 14 is a schematic showing the synthesis of compounds comprising scaffold Ia.

Figure 15:
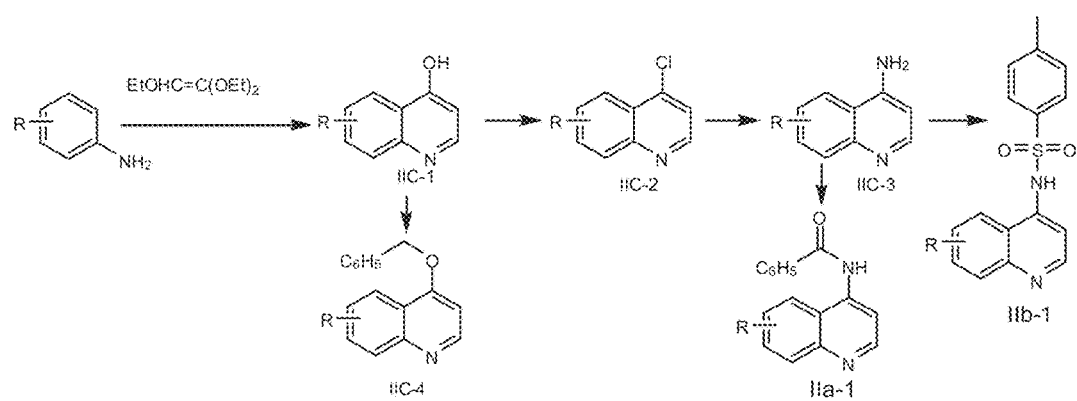

FIG. 15 is a schematic showing the synthesis of compounds comprising scaffold IIa-c.

Figure 16:
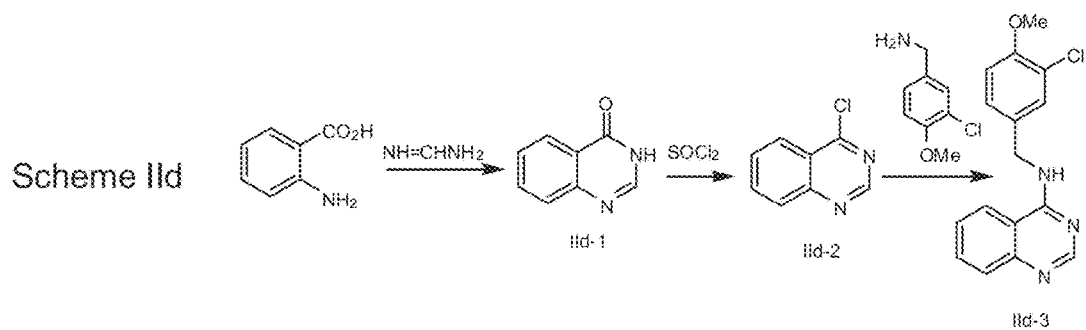

FIG. 16 is a schematic showing the synthesis of compounds comprising scaffold IId.

Figure 17:
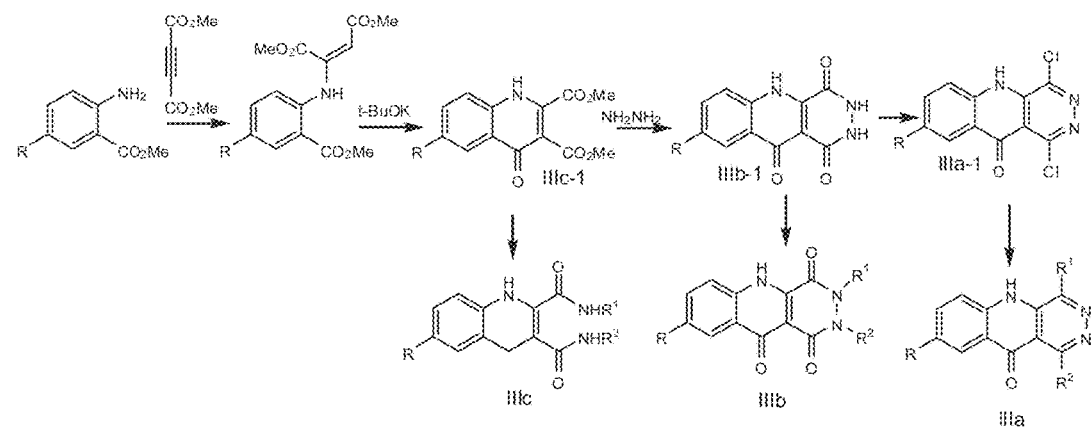

FIG. 17 is a schematic showing the synthesis of compounds comprising scaffold III.

Figure 18:
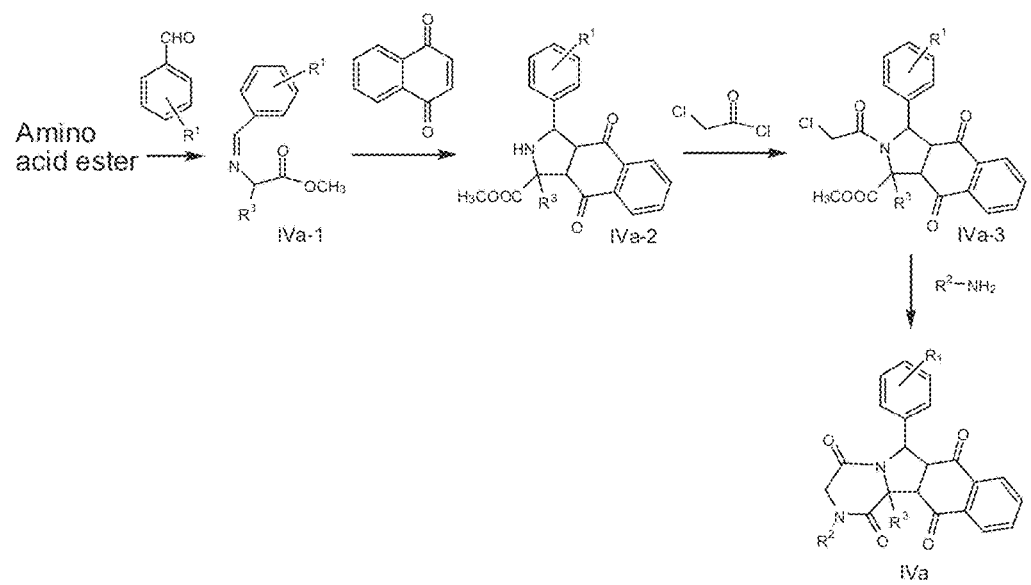

FIG. 18 is a schematic showing the synthesis of compounds comprising scaffold IVa.

Figure 19:
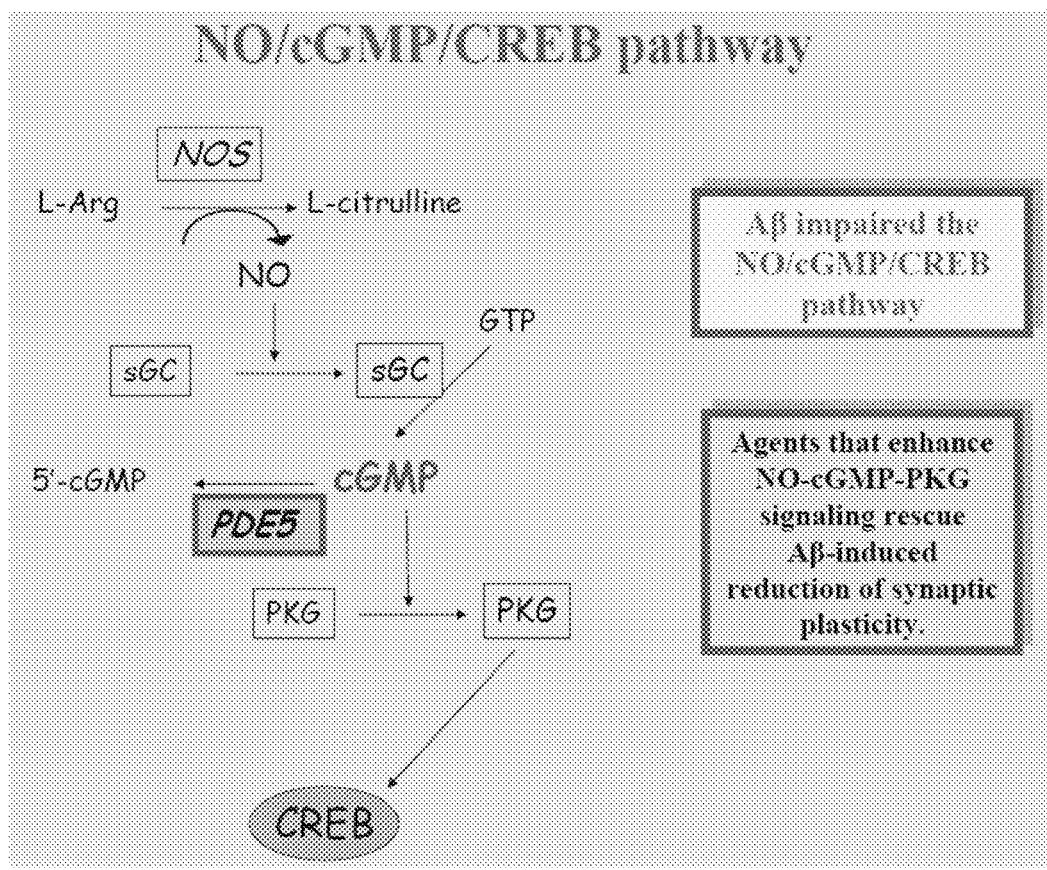

FIG. 19 is a schematic of the NO/cGMP/CREB pathway.

Figure 20:
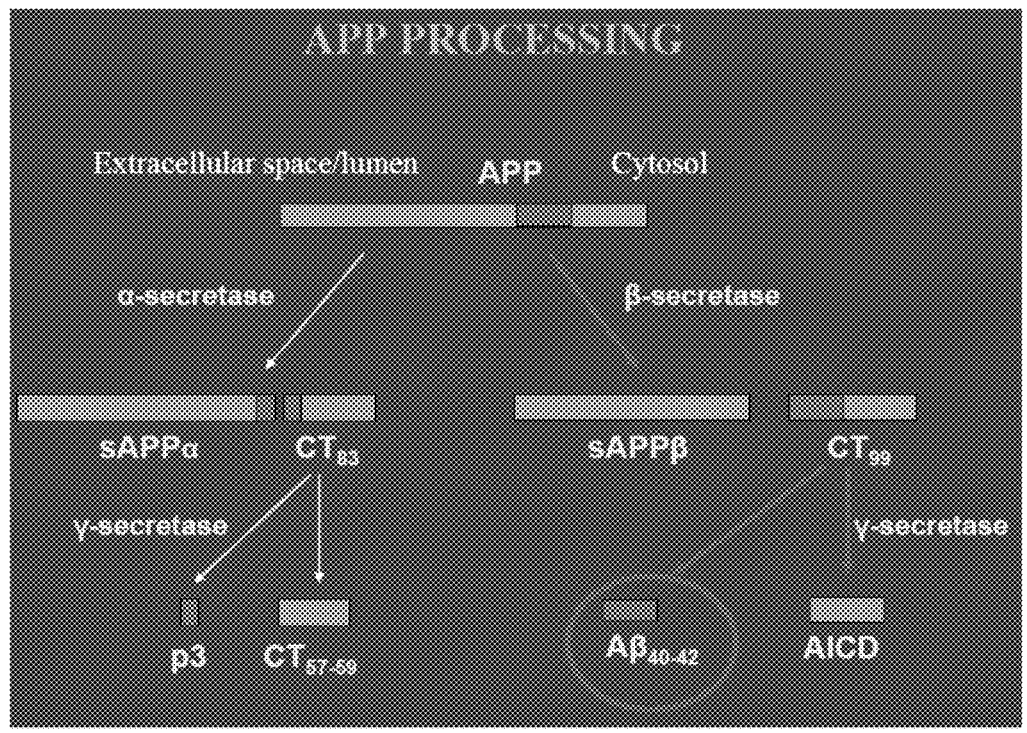

FIG. 20 is a schematic of APP processing. Administration of the PDE5 inhibitor sildenafil modifies APP process in APP/PS1 mice. A decrease in sAPPβ levels was detected in 3-month-old APP/PS1 mice treated with sildenafil, while an increase in CT83 and CT99 fragments was observed. A persistent decrease in sAPPβ levels and a persistent increase in sAPPα levels was detected at 7-10 months of age in APP/PS1 mice that were previously treated with sildenafil when 3 months old.

Figure 21:
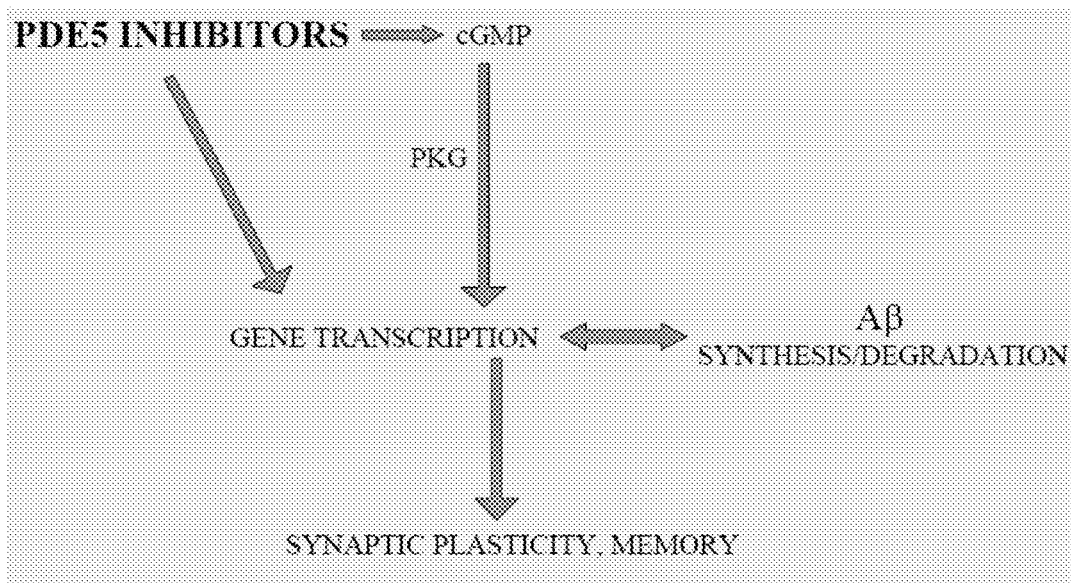

FIG. 21 is a schematic of a model depicting the action of PDE5 inhibitors on synaptic plasticity, memory, and amyloid-beta (Aβ) peptide synthesis and degradation. PDE5 inhibitors can increase synaptic plasticity in APP/PS1 mice; increase memory, fear conditioning and RAWM in APP/PS1 mice; increase CREB phosphorylation in APP/PS1 mice; and can decrease Aβ peptide levels in APP/PS1 mice.

Figure 22A:
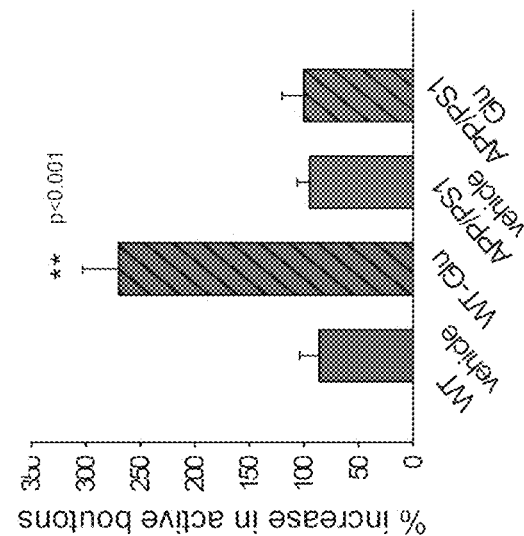
Figure 22B:
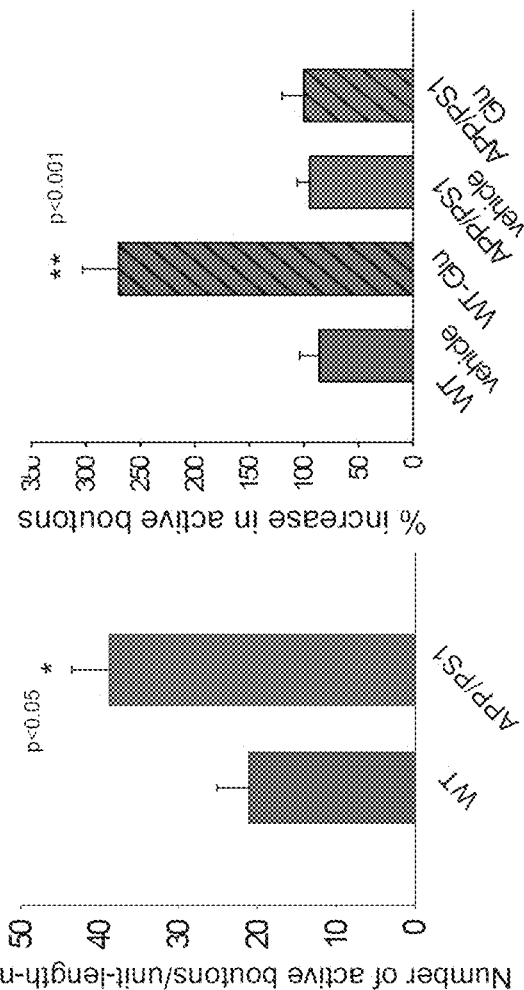
Figure 22C:
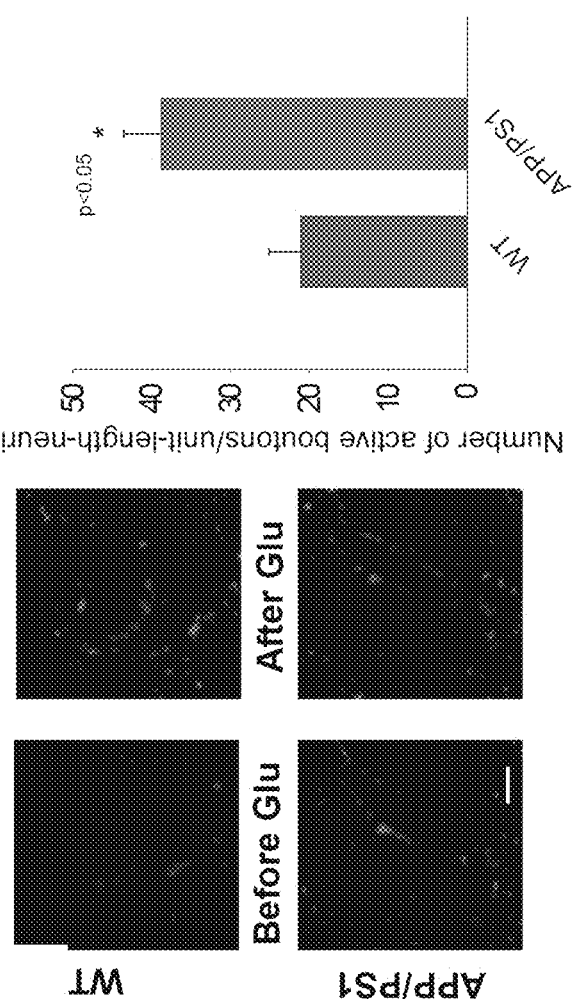

FIGS. 22A-C shows the effect of APP and PS1 transgene overexpression onto active boutons in cell cultures. FIG. 22A are photographs of Examples of FM 1-43 staining of active release sites before and after glutamate in WT and APP/PS1 hippocampal cultures. Scale bar, 15 μm. FIG. 22B is a graph showing basal number of active boutons per unit-length-neurite was higher in cultures from Tg mice compared to WT littermates. FIG. 22C is a graph demonstrating the percent increase in presynaptic active boutons 30 min after glutamate in 0 Mg++ in WT and APP/PS1 cultures. Glutamate increased active bouton number in WT but not in APP/PS1 cultures.

Figure 23:
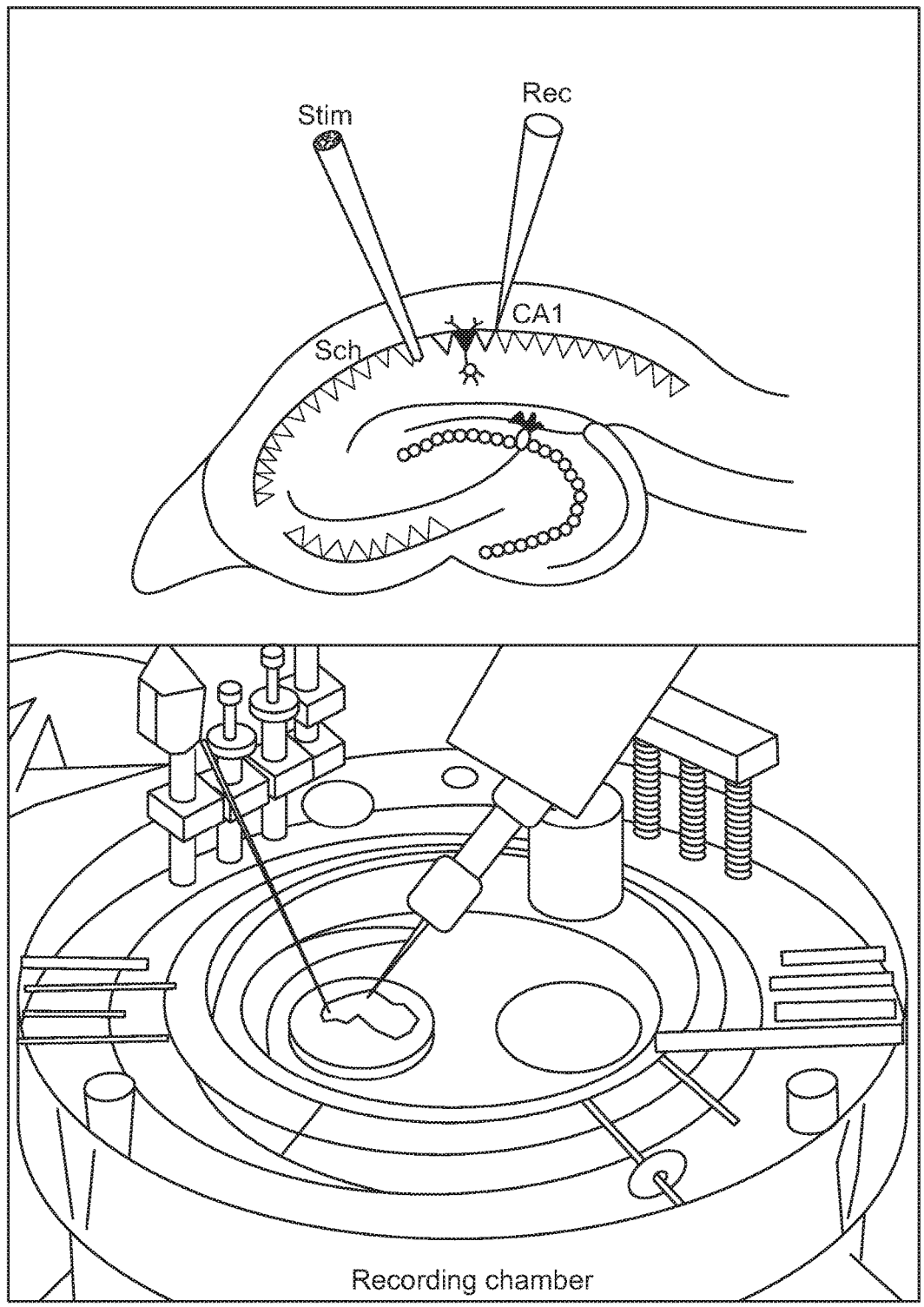

FIG. 23 represents the experimental set-up. A schematic drawing of a transverse hippocampal slice is shown in the top image. Schaeffer collateral fibers and CA1 stratum radiatum are marked. Positions of the stimulating and recording electrodes are indicated. Long-term potentiation (LTP) was induced by a theta-burst stimulation of Schaeffer collateral fibers. Photograph of the interface recording chamber used for electrophysiological experiments is shown in the bottom image.

Figure 24:
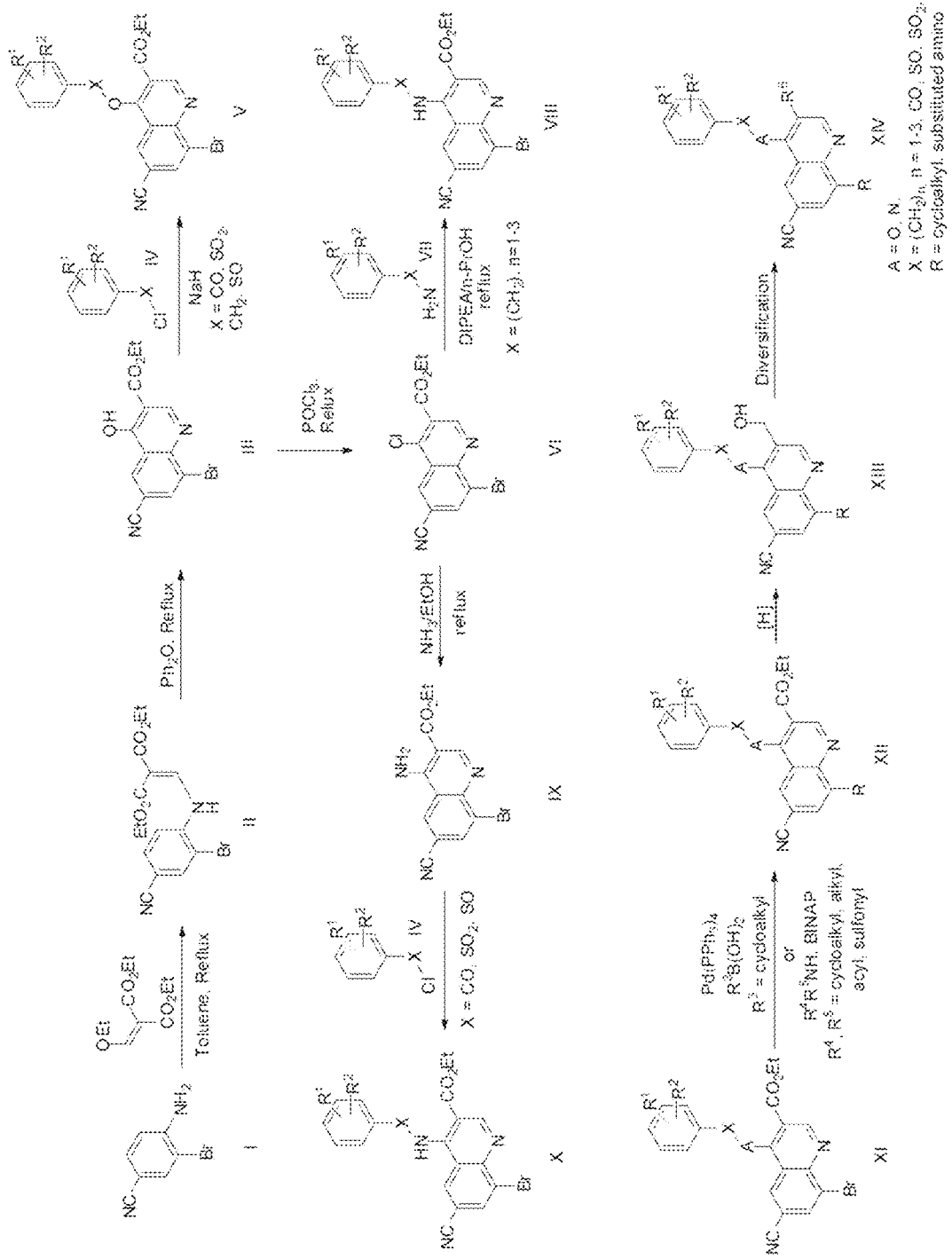

FIG. 24 represents a synthetic Scheme of new PDE5 inhibitors. Based on the requirement for new PDE5 inhibitors, a class of quinoline derivatives was designed.

Figure 25:
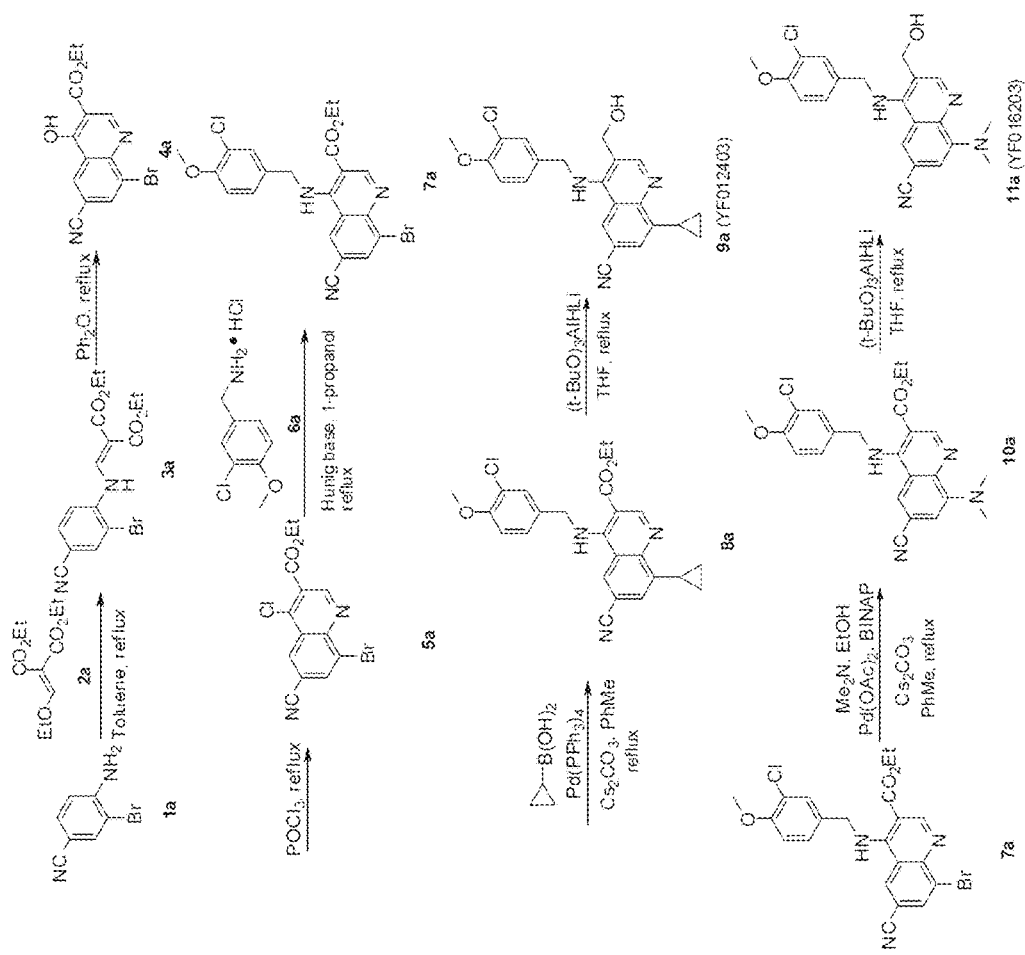

FIG. 25 depicts some synthetic scheme examples. Based on the SAR, YF012403 (cyclopropyl lead) and YF016203 (dimethylamino lead). were picked for further investigation.

Figure 26:
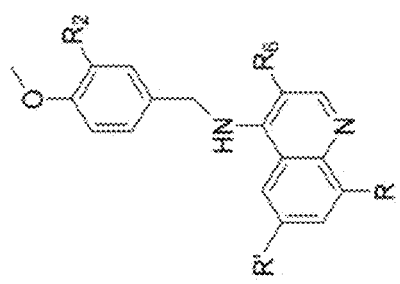

FIG. 26 represents the $IC_{50}$s of synthesized compounds. YF012403 and YF016203 are highlighted in red.

FIG. 27 depicts the in vitro selectivity of PDE5 inhibitors. Two compounds, YF012403 and YF016203, were picked up based on the SAR for selectivity profiling. a) Data obtained by BPS Bioscience; b) Graeme L. Card, et. al. *Structure*, 2004, 12, 2233-2247; c) I Saenz de Tejada, et al., *International Journal of Impotence Research*, 2001, 13, 282-290; d) Alain, Daugan, et. Al, *Journal of Medicinal Chemistry*, 2003, 46, 4533-4542.

FIG. 28 represents a pharmacokinetics profile. One compound, YF012403, was identified based on the in vitro activity and selectivity for PK profiling as compared to sildenafil.

Figure 29:
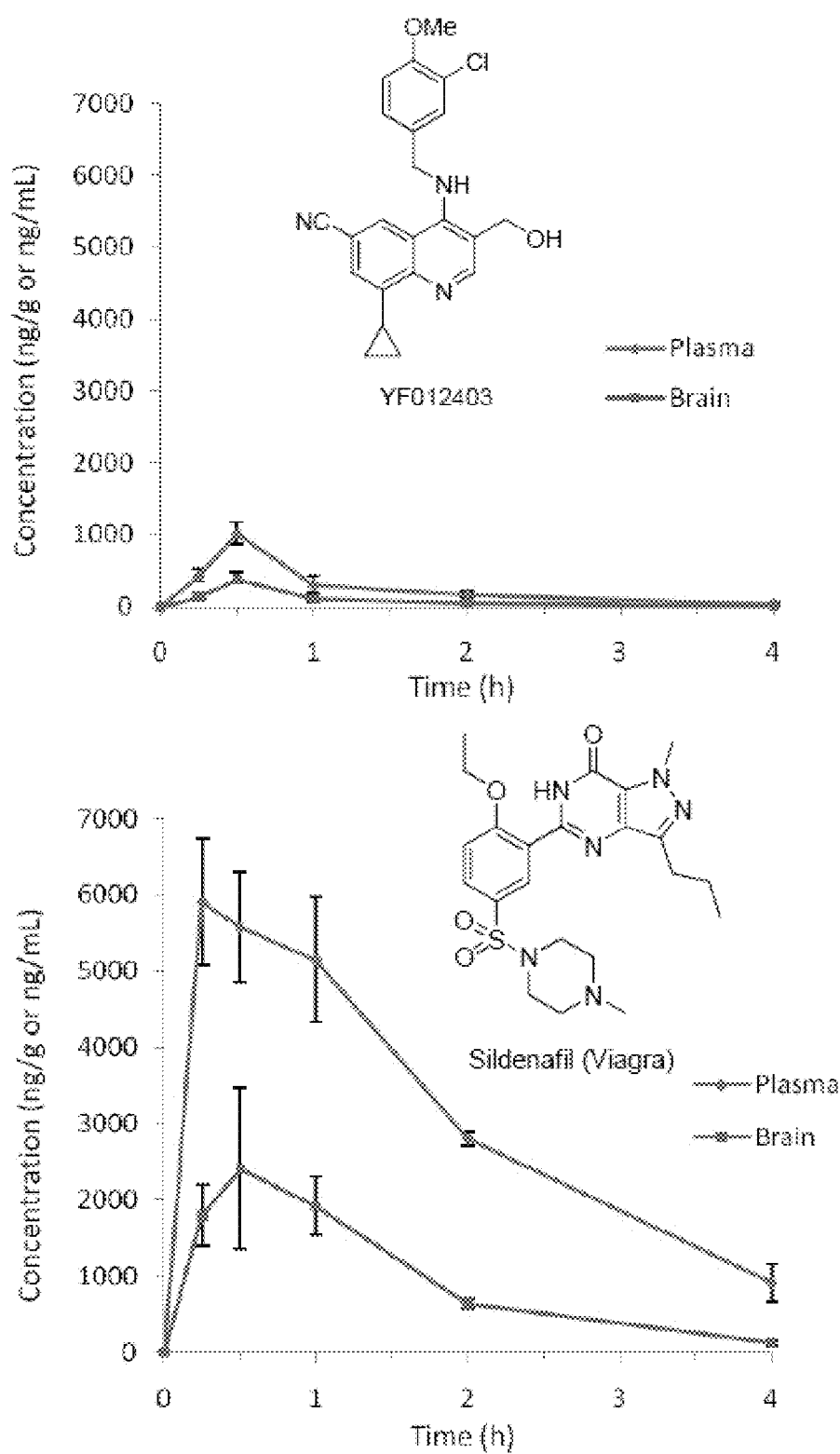

FIG. 29 represents a pharmacokinetics profile. The graphs depicts a concentration/time curve of candidate YF012403 and sildenafil in brain tissue and plasma. The data were collected with male C57/BALB/c mice; three mice for each point.

Figure 30:
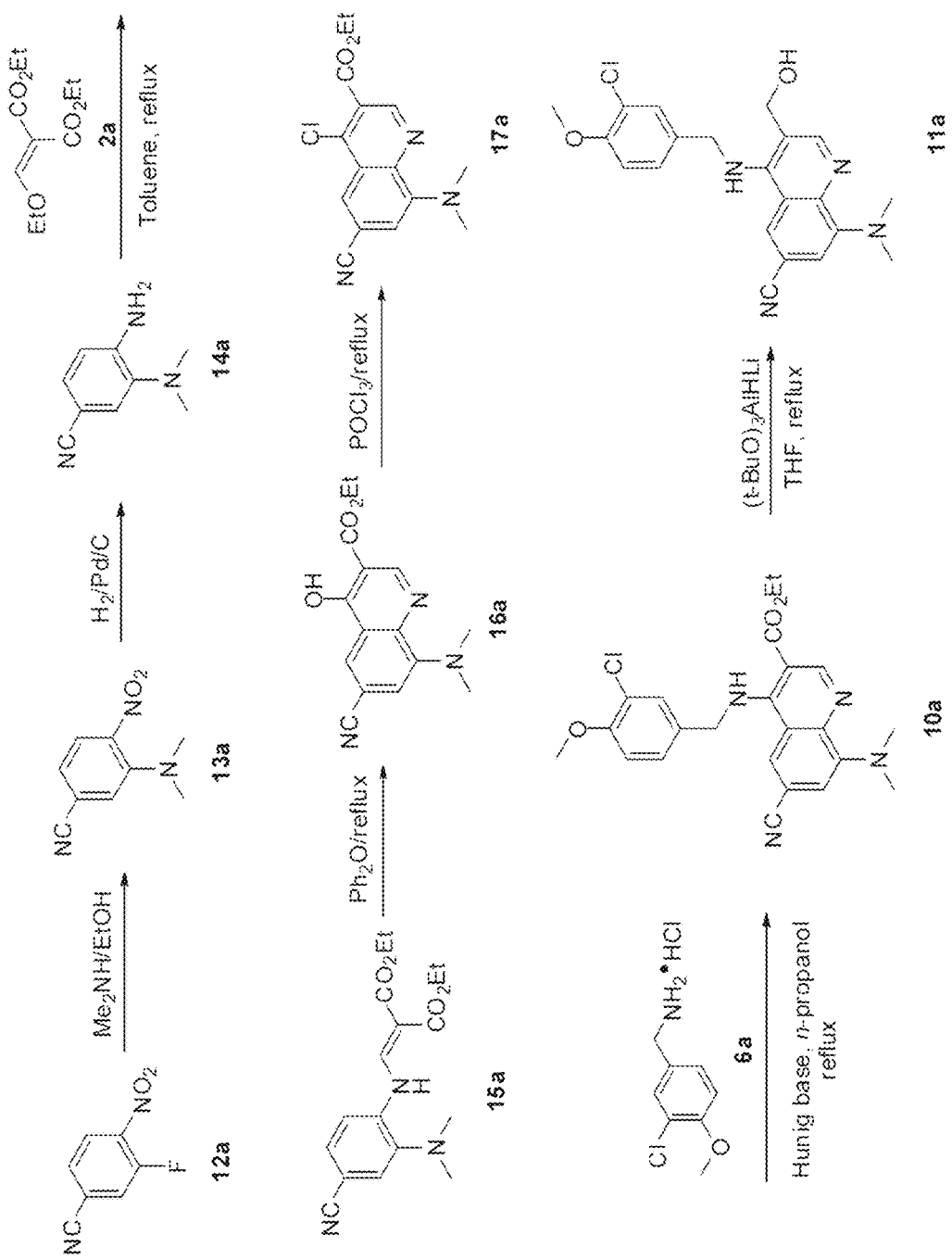

FIG. 30 depicts a synthetic route for process chemistry of the dimethylamino derivative (YF016203).

Figure 31:
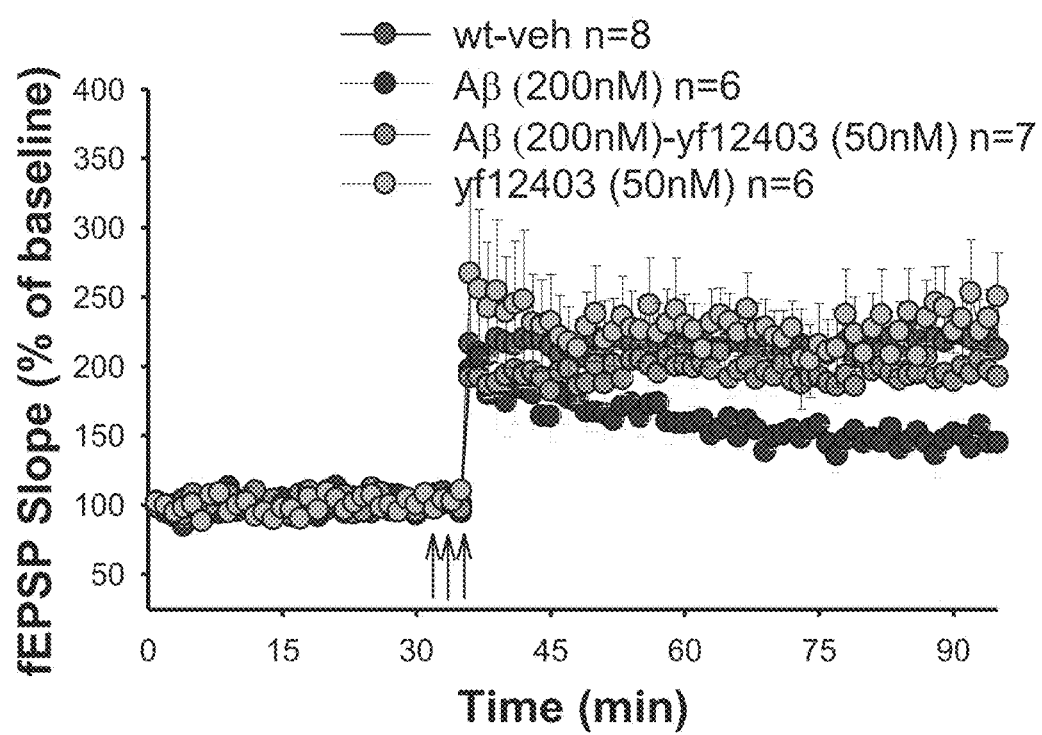

FIG. 31 is a graph showing electrophysiology data. YF012403 reverses LTP impairment in the CA1 region of slices from 3-4 month-old mice treated with 200 nM oligomeric Aβ 42. A Two-way ANOVA was carried out: Aβ compared to Aβ plus YF012403=$F(1,11)$=6.073; p=0.0314.

Figure 32:
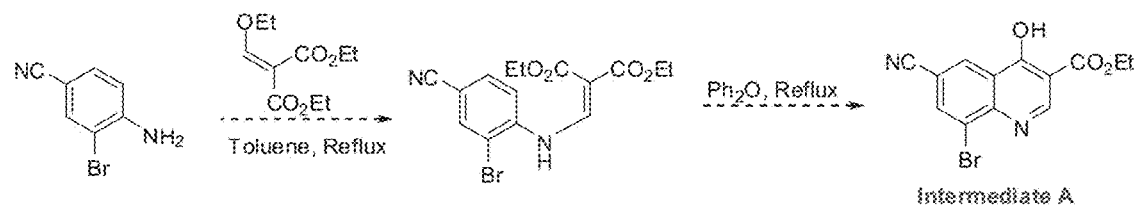

FIG. 32 depicts a synthesis scheme of Intermediate A. Dashed lines in the scheme indicate a prophetic reaction.

Figure 33:
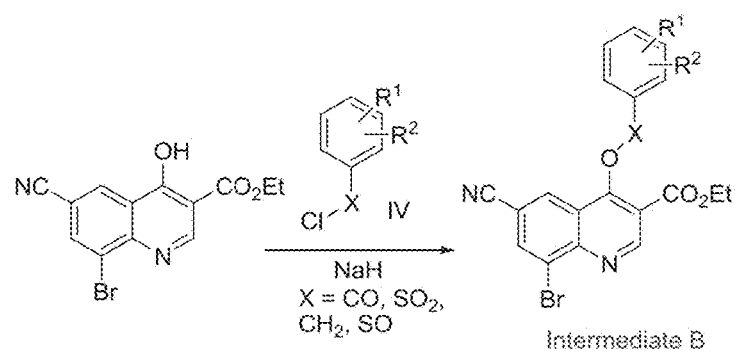

FIG. 33 depicts a synthesis scheme of Intermediate B.

Figure 34:
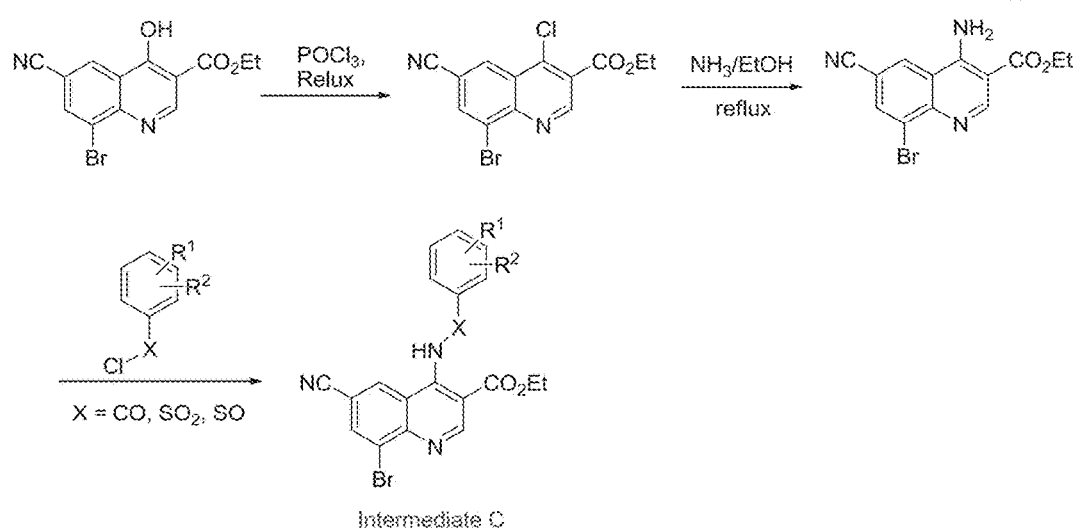

FIG. 34 depicts a synthesis scheme of Intermediate C.

Figure 35:
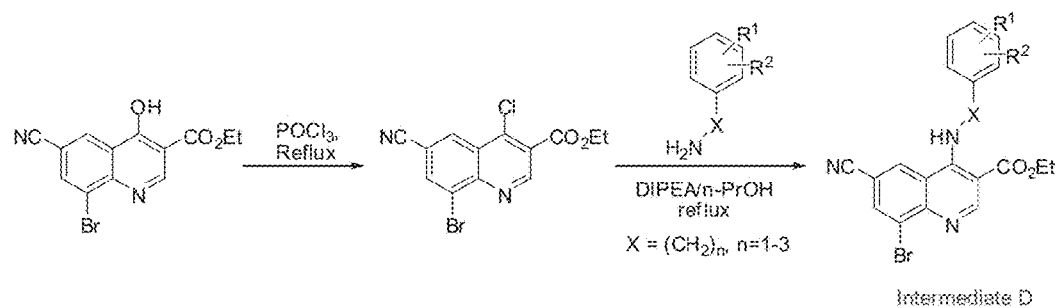

FIG. 35 depicts a synthesis scheme of Intermediate D.

Figure 36:
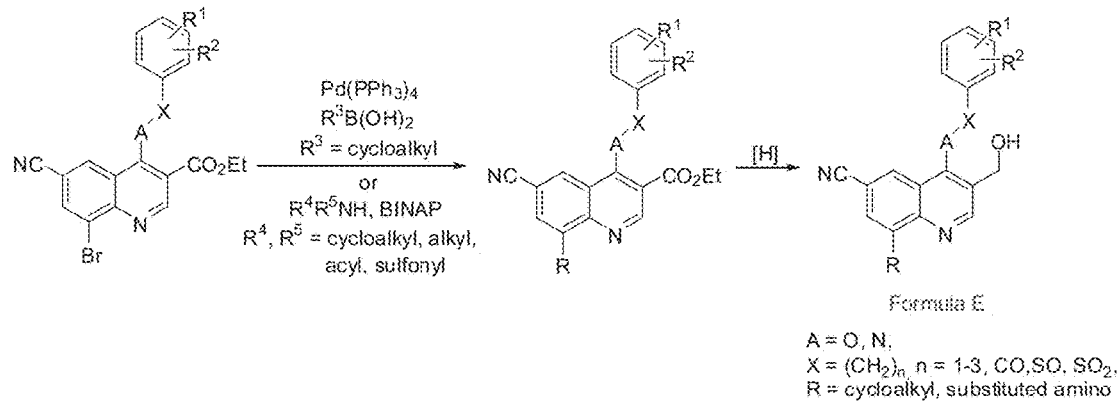

FIG. 36 depicts a synthesis scheme of Formula E.

Figure 37:
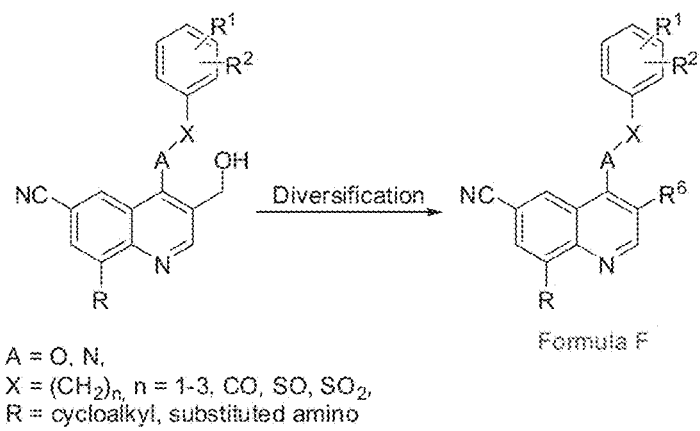

FIG. 37 depicts a synthesis scheme of Formula F.

Figure 38:
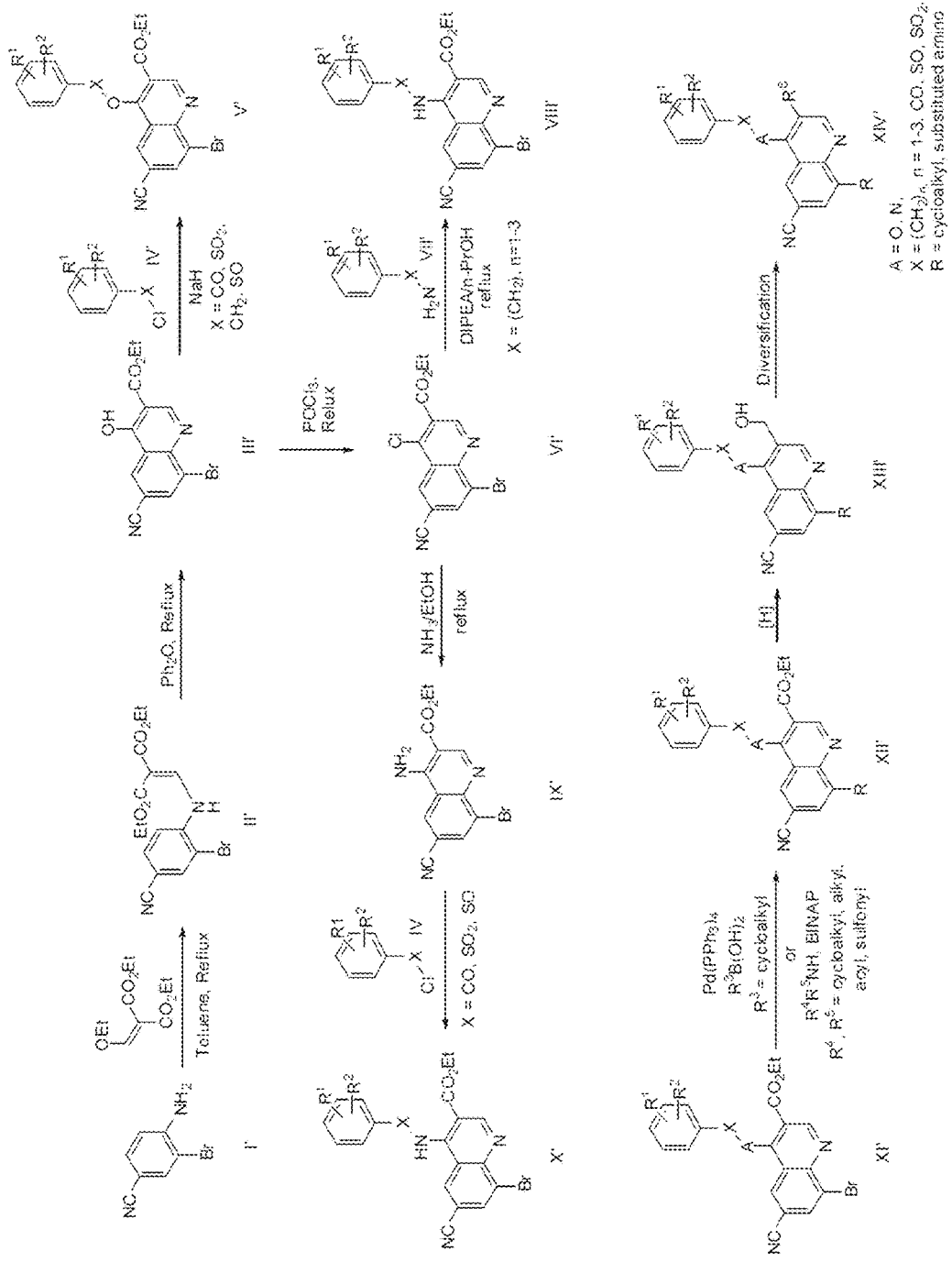

FIG. 38 depicts the general synthesis method of scheme A.

Figure 39:
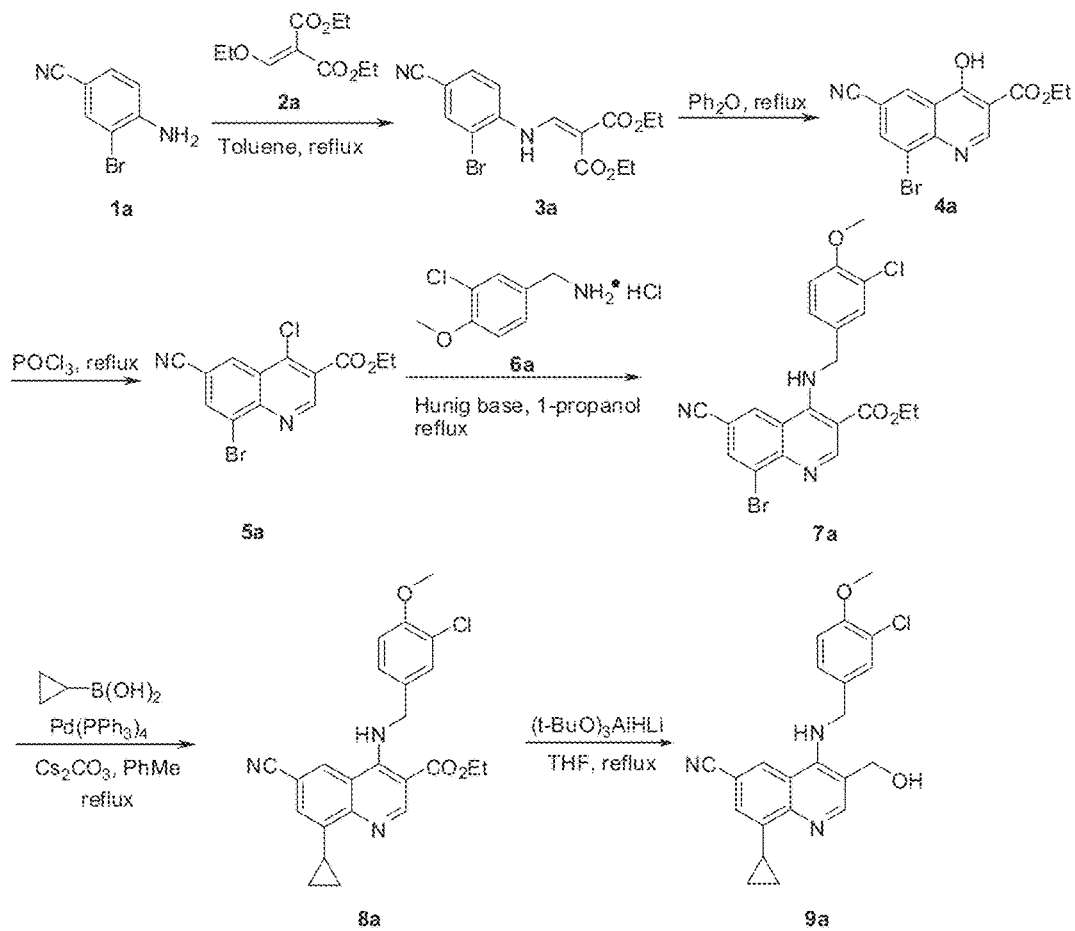

FIG. 39 depicts synthesis Scheme I for compound 9a (YF012403; the cyclopropyl lead).

Figure 40:
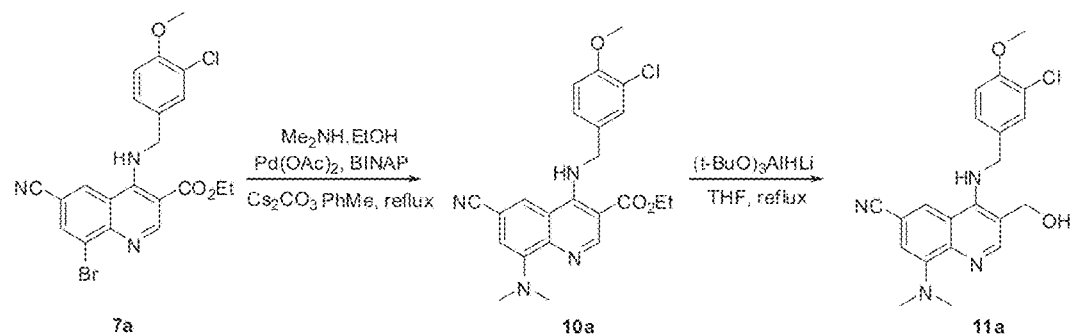

FIG. 40 depicts synthesis Scheme II for compound 11a (YF016203; dimethylamino lead).

Figure 41:
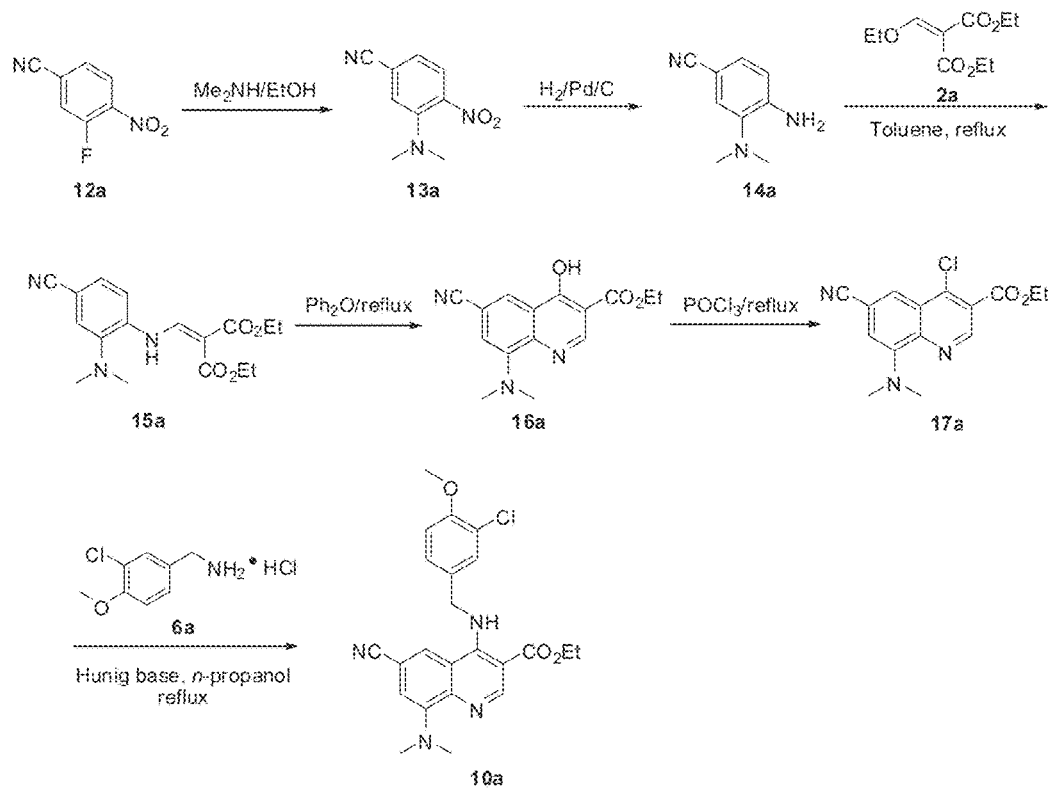

FIG. 41 depicts synthesis Scheme III-A1 for intermediate 10a.

Figure 42A:
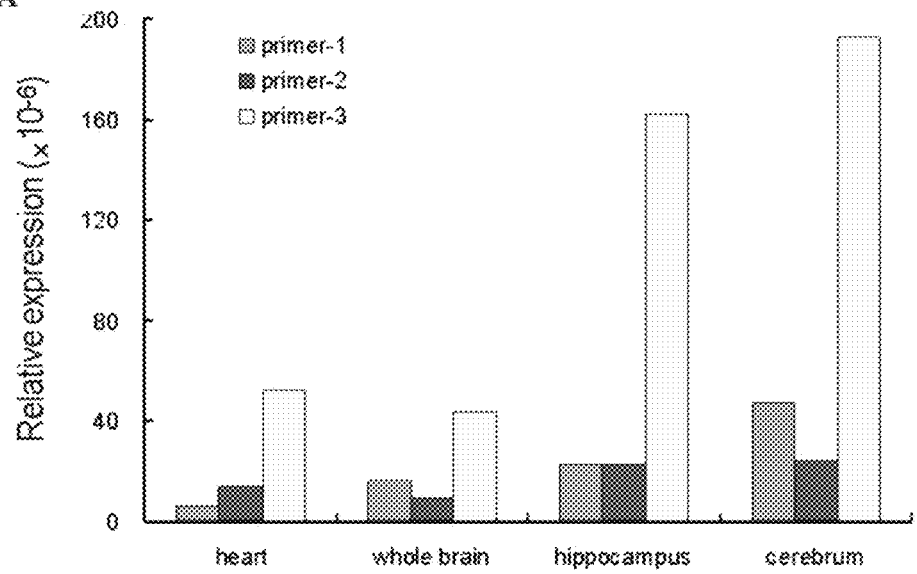
Figure 42B:
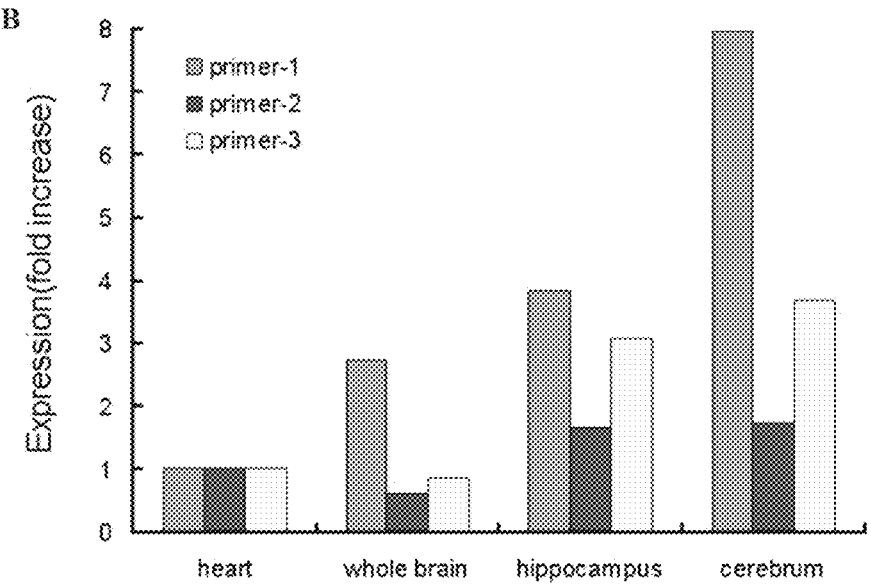

FIGS. 42A-B are graphs that show the expression levels of PDE5 mRNA in heart, whole brain, hippocampus and cerebrum of humans. In FIG. 42A, the values were normalized to β-actin mRNA. In FIG. 42B, the values shown in FIG. 42A were normalized to respective heart mRNA levels.

Figure 43:
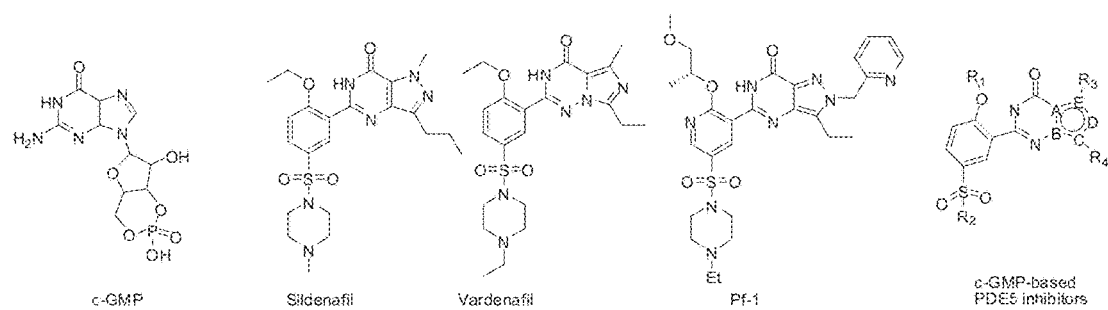

FIG. 43 shows the structures of cGMP-based molecules.

Figure 44:
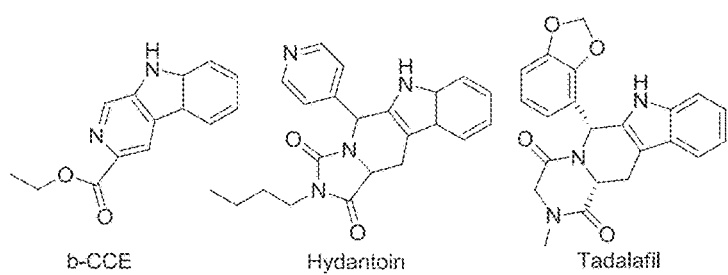

FIG. 44 shows the structures of β-carbolines-derived molecules.

Figure 45:
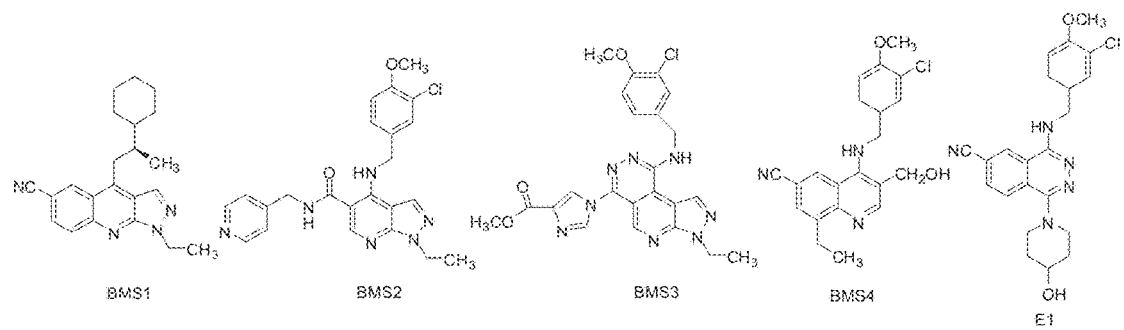

FIG. 45 shows the structures of pyrazolopyridine, phthalazine and quinoline derivatives.

Figure 46:
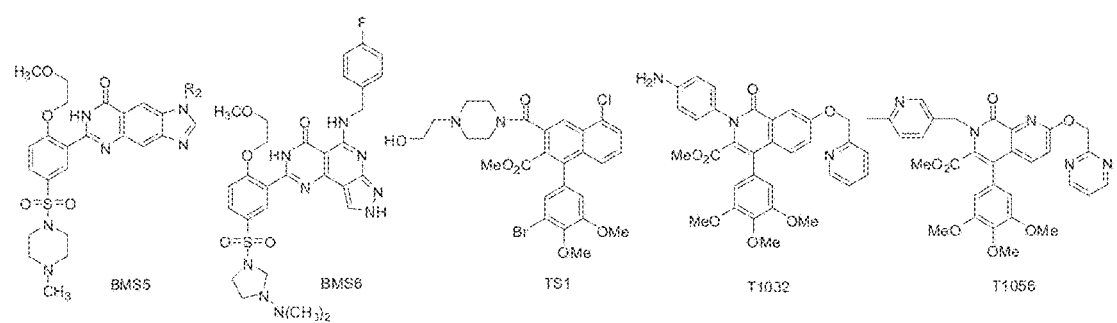

FIG. 46 shows the structures of isoquinazolinone and isoquinolinone derivatives.

Figure 47:
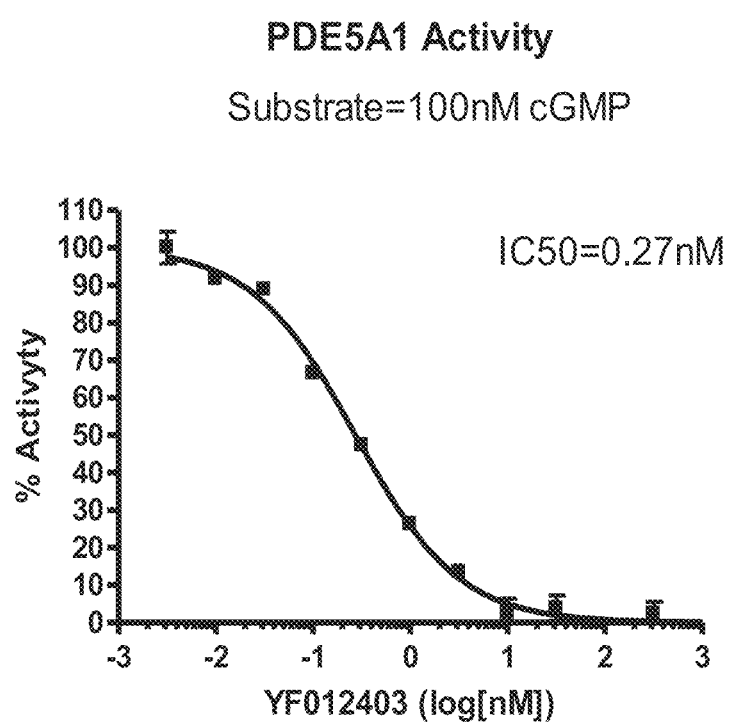

FIG. 47 is a graph depicting PDE5 activity where 100 nM of cGMP substrate was used.

Figure 48:
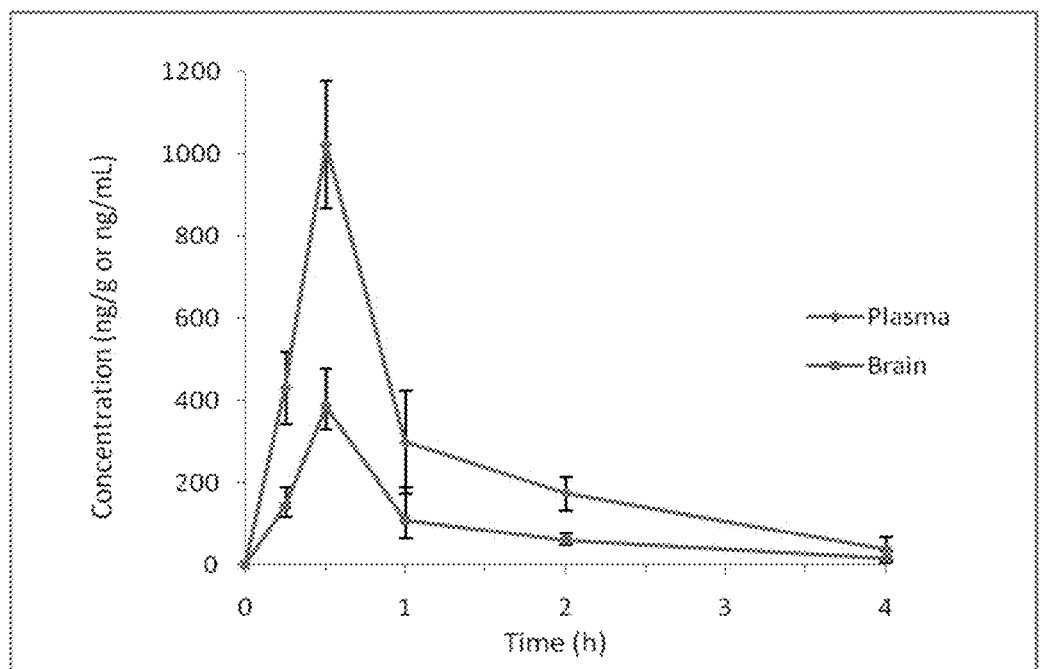

FIG. 48 is a Concentration-Time curve of YF012403 in mouse brain tissue and plasma (n=3 mice per group).

Figure 49A:
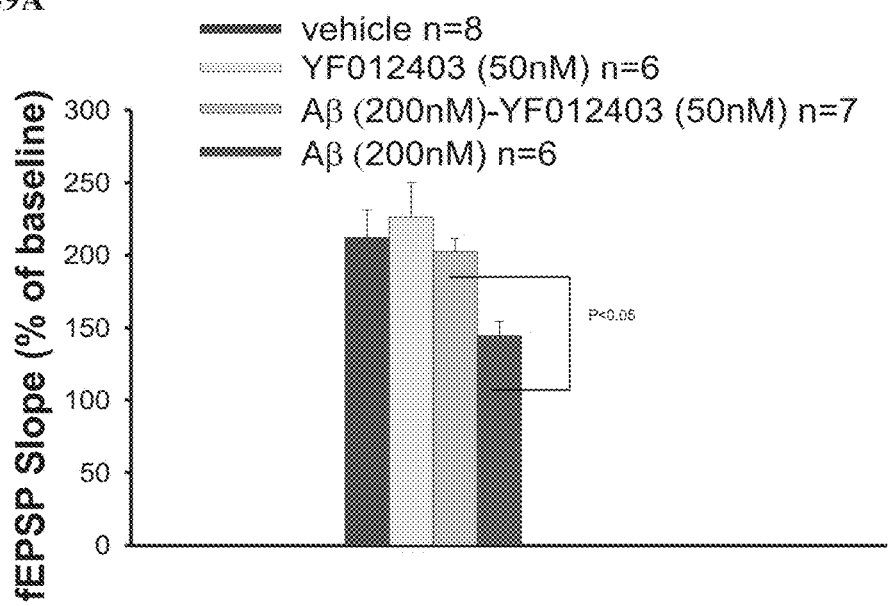
Figure 49B:
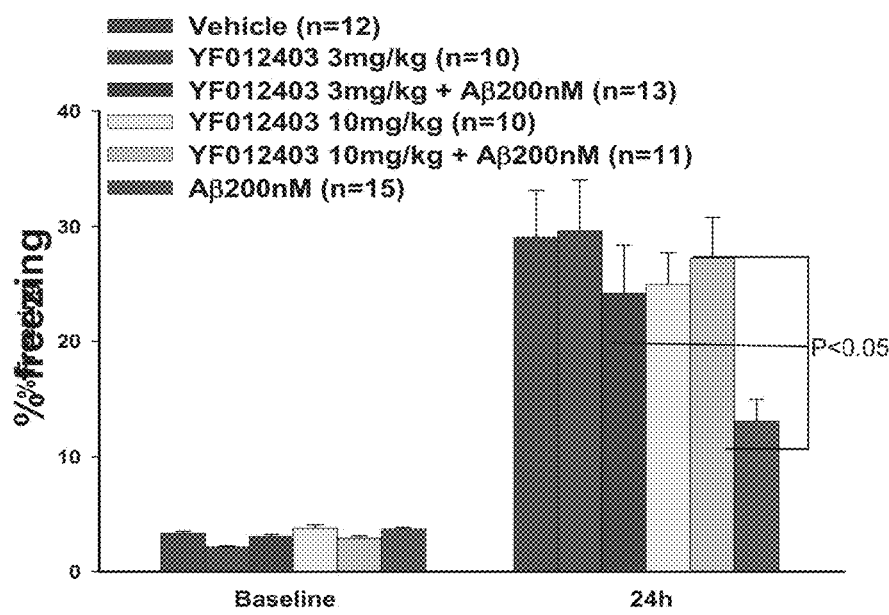

FIGS. 49A-B are graphs that show the beneficial effect of YF012403 on Aβ42-induced synaptic and cognitive dysfunction. FIG. 49A shows that YF012403 ameliorates the LTP deficit in Aβ42-treated slices. The graph represents the average of the last 5 min of recording at 60 min after the tetanus. FIG. 49B shows that YF012403 ameliorates the contextual fear memory deficit in Aβ42-infused mice.

Figure 50:
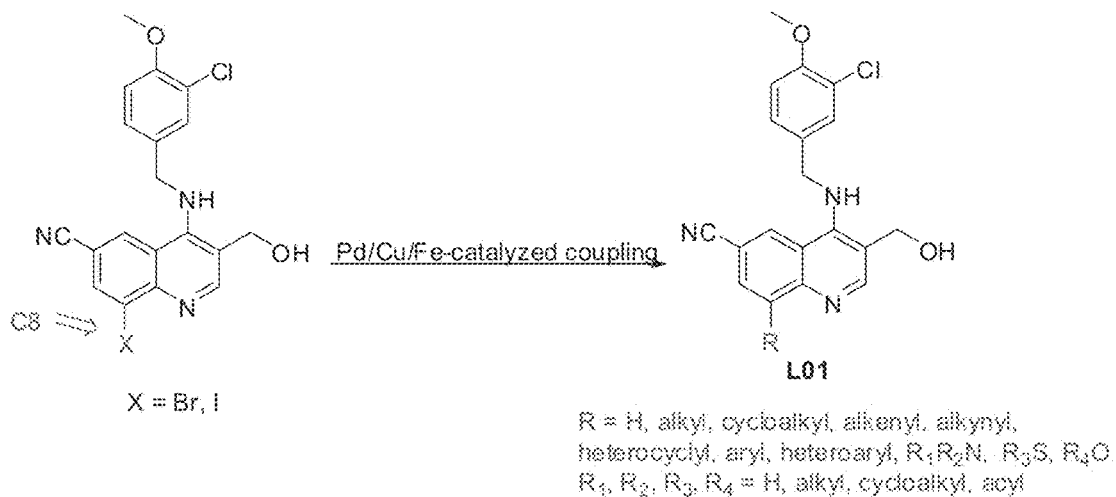

FIG. 50 is a schematic showing modifications at C8 of YF012403.

Figure 51:
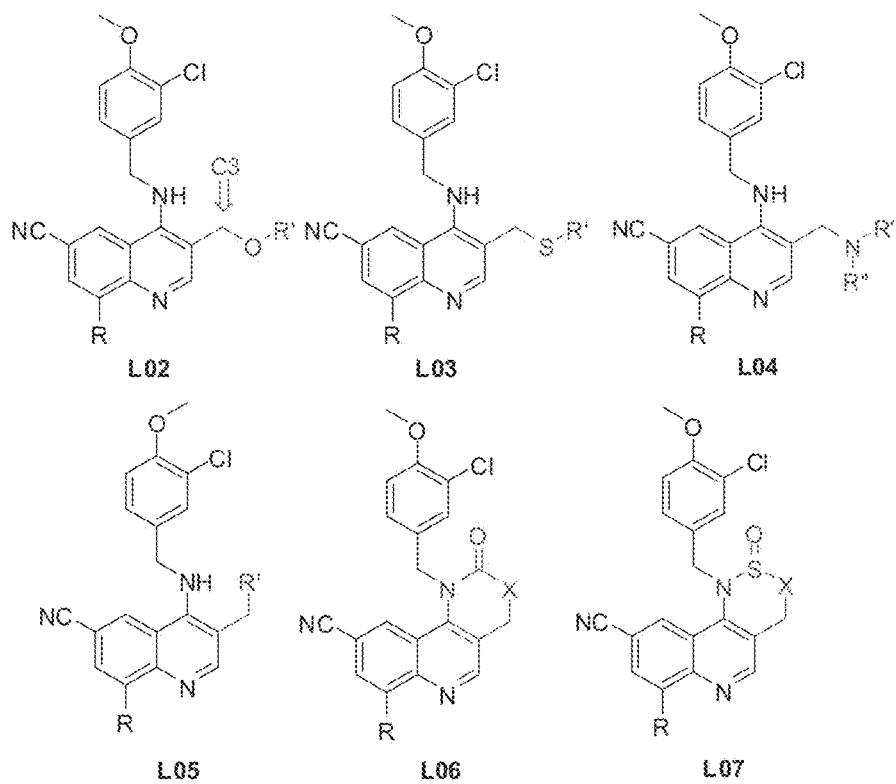

FIG. 51 is a schematic showing modifications at C3 of YF012403.

Figure 52:
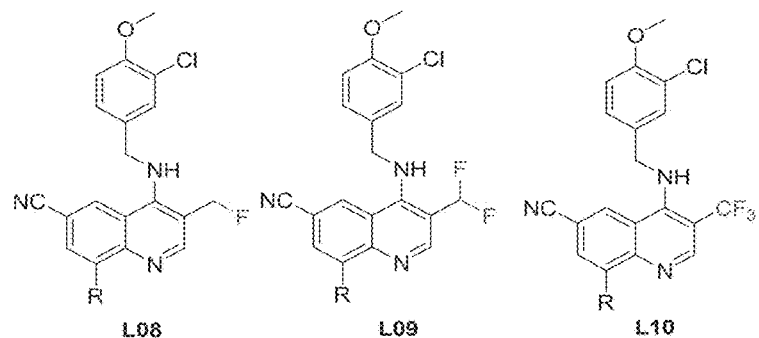

FIG. 52 is a schematic showing modifications at C3 of YF012403.

Figure 53:
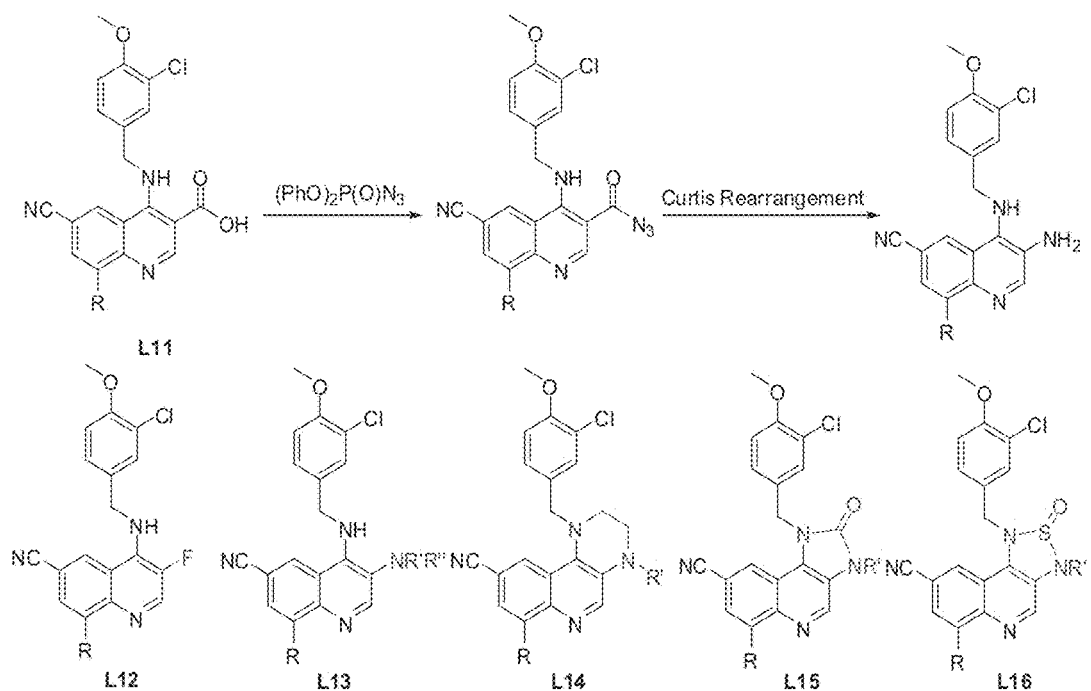

FIG. 53 is a schematic showing modifications at C3 of YF012403.

Figure 54:
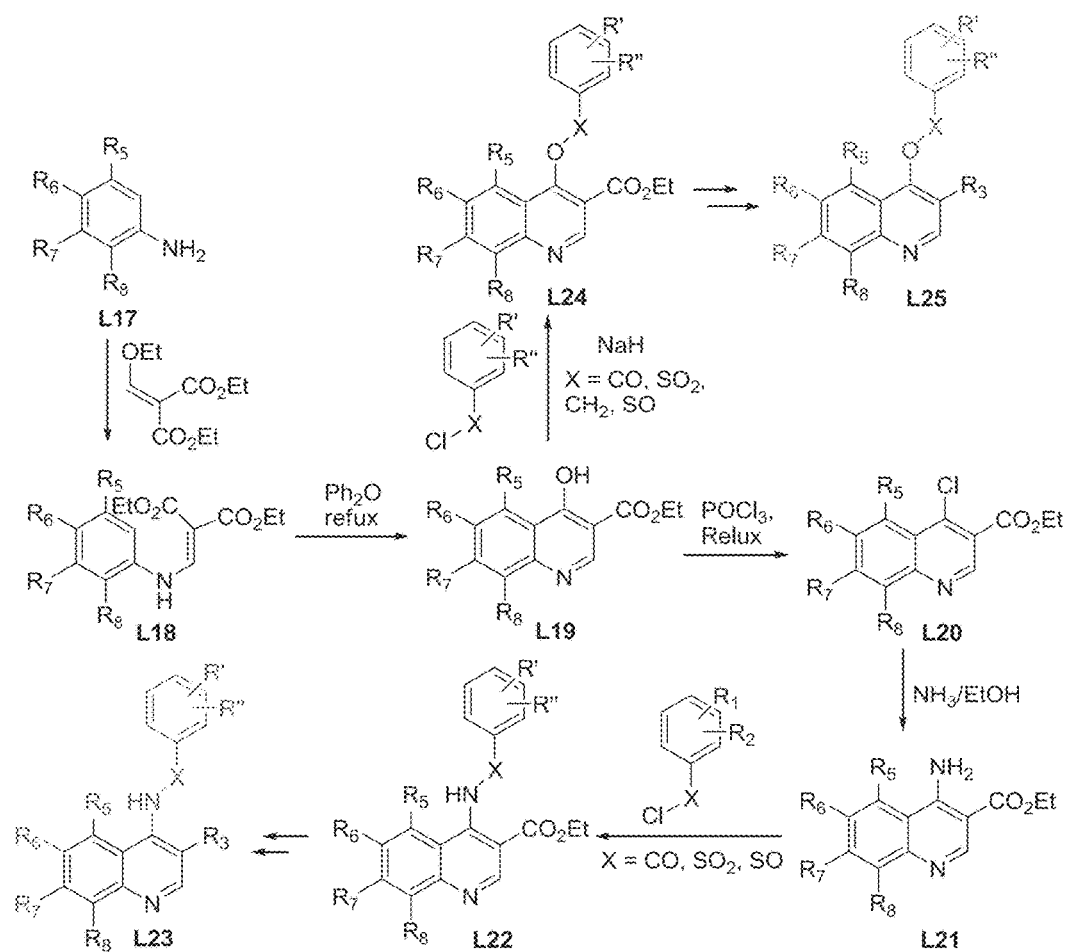

FIG. 54 is a schematic showing modifications at other positions of YF012403.

Figure 55A:
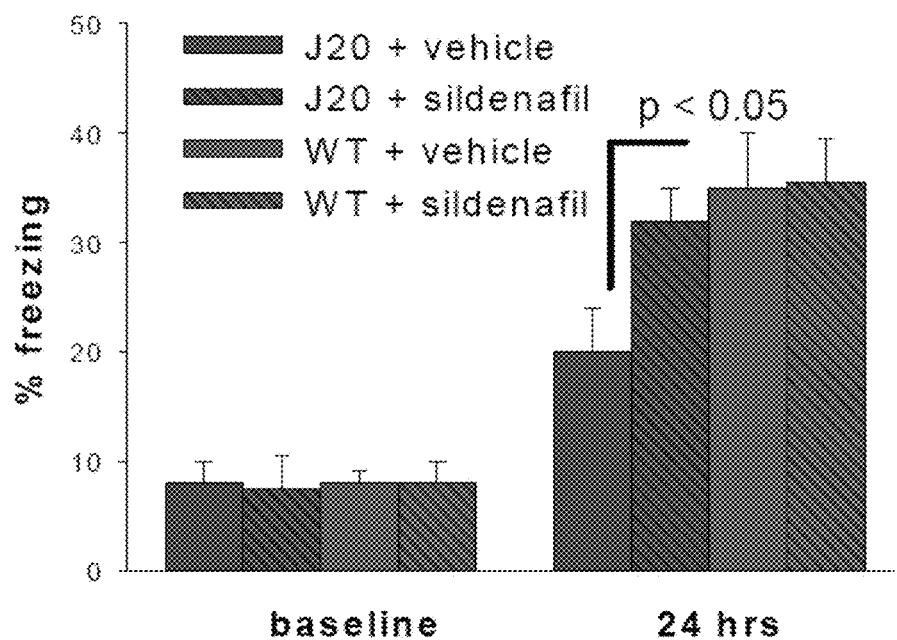
Figure 55B:
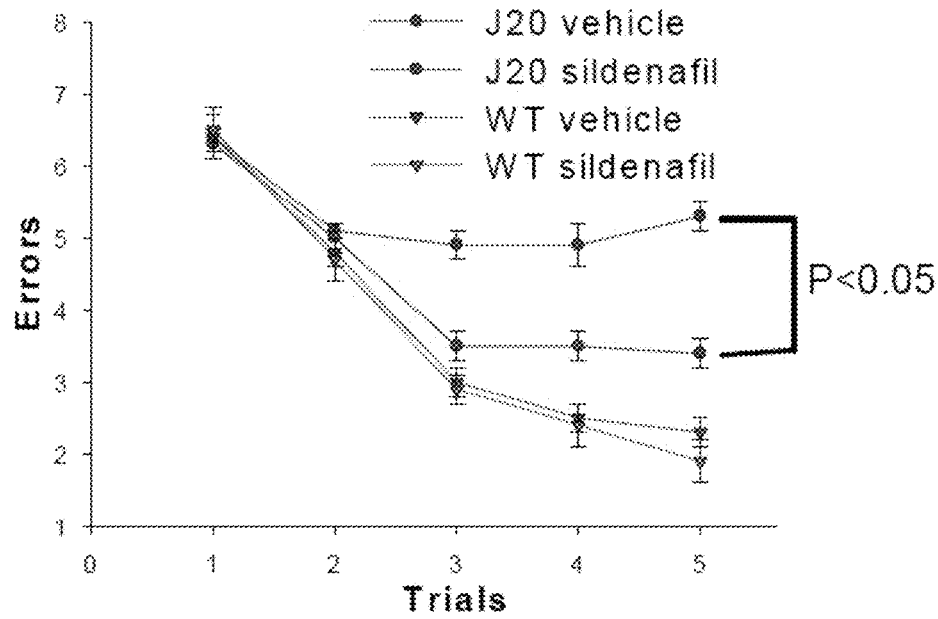

FIGS. 55A-B are graphs that show the acute beneficial effects of sildenafil on cognitive dysfunction of 5 month-old J20 mice during contextual fear conditioning (FC) (FIG. 55A) and RAWM (FIG. 55B) testing.

Figure 56A:
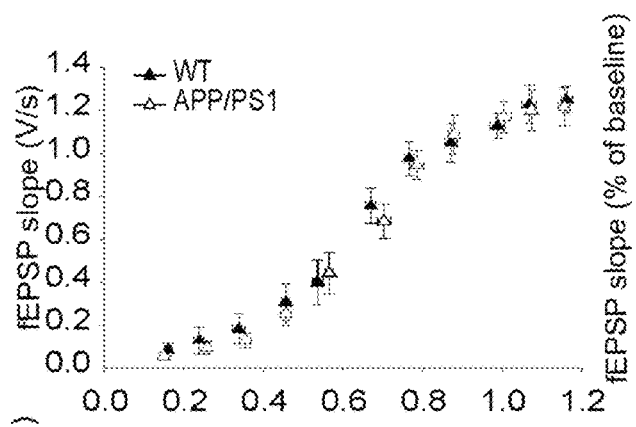
Figure 56B:
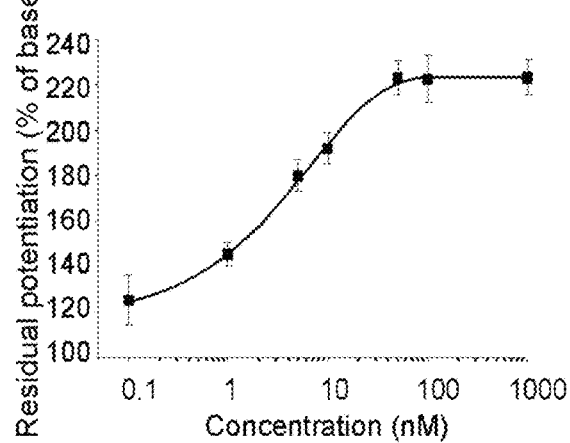
Figure 56C:
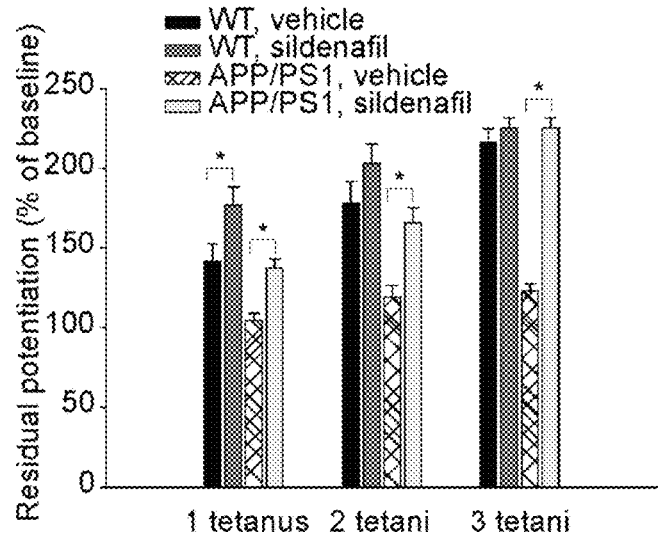

FIGS. 56A-C are graphs showing that a brief perfusion of hippocampal slices with sildenafil reverses CA1-LTP impairment in 3-month-old APP/PS1 mice. The graph in FIG. 56A shows that BST is similar in 3-month-old APP/PS1 animals and WT littermates. Summary graph of EPSP slopes versus fiber volley amplitudes for different stimulation intensities ranging from 5 to 35 V [35 V: ~97% of WT littermates in APP/PS1 mice, n=7 slices from 6 males vs. n=7 slices from 6 males in WT slices; two-way ANOVA: $F_{(1,12)}$=0.05, P=0.81]. There is not difference in fiber volley between WT and transgenic animals ($F_{(1,12)}$=3.97, P=0.06). FIG. 56B is a dose-response curve that shows the effect of different concentrations of sildenafil on synaptic plasticity in slices from transgenic animals. The minimum effective dose that completely rescues synaptic plasticity is 50 nM (n=6 slices from 6 males for each group). FIG. 56C is a graph showing that sildenafil (50 nM) ameliorates LTP in slices from APP/PS1 mice that were potentiated through 1 or 2 series of theta-burst stimulations (1 tetanus: $t_{(1,10)}$=3.38, P=0.007 compared to vehicle-treated APP/PS1 slices; 2 tetani: $t_{(1,10)}$=3.92, P=0.003; 3 tetani: $t_{(1,10)}$=13.47, P<0.001; n=6 slices from 6 males for each group). Slices from WT mice that received one theta-burst stimulation showed a significant increase in LTP when they were perfused with 50 nM sildenafil compared to vehicle-treated WT slices (1 tetanus: $t_{(1,10)}$=2.25, P=0.048; 2 tetani: $t_{(1,10)}$=1.37, P=0.200; 3 tetani: $t_{(1,10)}$=1.26, P=0.236; n=6 slices from 6 males for each group).

Figure 57A:
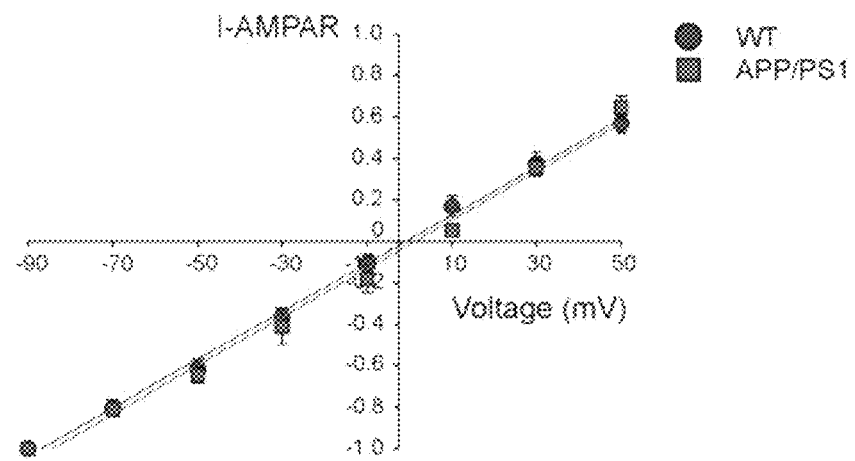
Figure 57B:
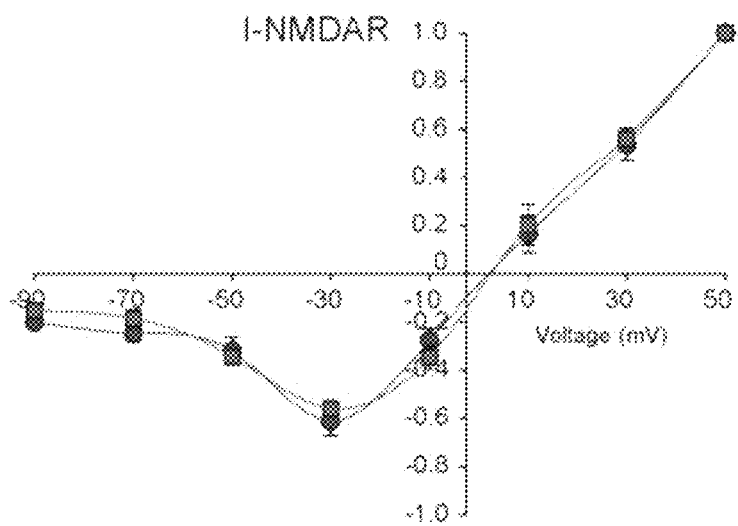
Figure 57C:
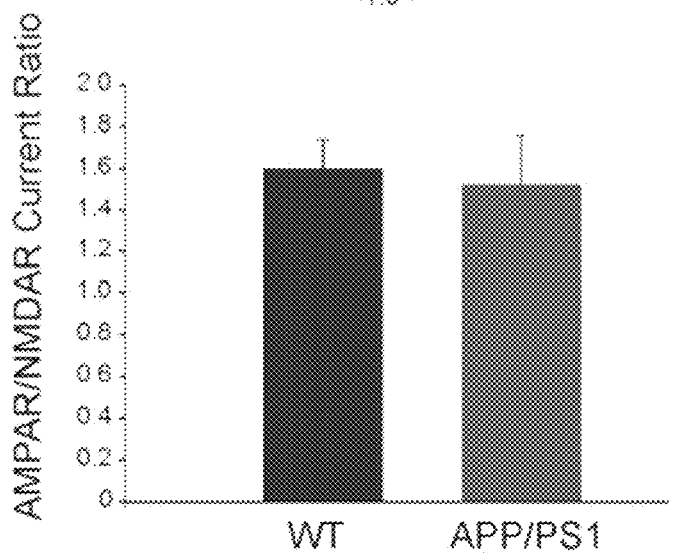

FIGS. 57A-C are graphs that show three month old APP/PS1 mice have normal BST associated with no changes in AMPA- and NMDA-receptor currents. FIGS. 57A-57B show normalized current-voltage plots of AMPA receptor (AMPAR) (FIG. 57A) and NMDA receptor (NMDAR) (FIG. 57B) currents from adult WT (n=3 cells) and APP/PS1 (n=3 cells) CA1 pyramidal cells. AMPAR-mediated EPSCs were normalized to the EPSC at −90 mV. NMDAR-mediated EPSCs were normalized to the NMDA response at +50 mV. FIG. 57C is a comparison of AMPAR to NMDAR current ratio in the WT and APP/PS1 pyramidal cells. The ratio was calculated by dividing the amplitude of the AMPAR current measured at −70 mV by the NMDAR current measured 50 ms after the peak at +50 mV.

Figure 58A:
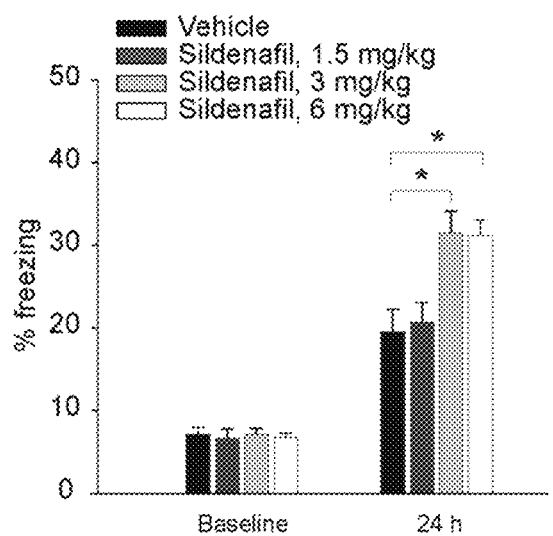
Figure 58B:
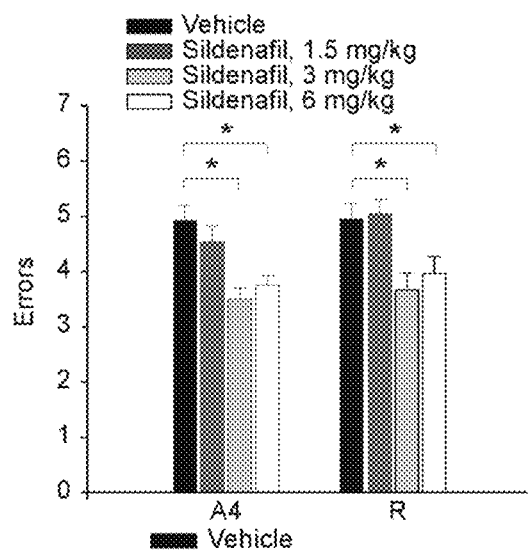
Figure 58C:
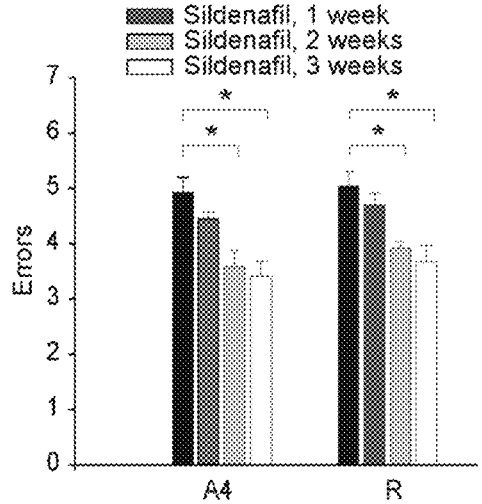

FIGS. 58A-C are graphs showing that sildenafil ameliorates cognitive function in 3-month-old APP/PS1 mice. FIG. 58A shows that the minimum concentration of sildenafil needed to improve contextual fear memory in APP/PS1 mice is 3 mg/kg. A concentration of 1.5 mg/kg does not improve freezing, whereas 6 mg/kg has the same effect as 3 mg/kg [1.5 mg/kg sildenafil: n=8 (4 males, 4 females) vs. vehicle treated animals n=14 (7 males, 7 females), $F_{(1,20)}$=0.82, P=0.375; 3 mg/kg sildenafil: n=8 (4 males, 4 females), $F_{(1,20)}$=11.58, P=0.003; 6 mg/kg sildenafil: n=8 (4 males, 4 females), $F_{(1,20)}$=8.48, P=0.009. FIG. 58B shows that the minimum concentration of sildenafil needed to improve spatial working memory in APP/PS1 mice is 3 mg/kg for 3 weeks. A concentration of 1.5 mg/kg does not improve RAWM performance, whereas 6 mg/kg has the same effect as 3 mg/kg [1.5 mg/kg sildenafil: n=8 (4 males, 4 females) vs. vehicle treated animals n=14 (7 males, 7 females), $F_{(1,20)}$=0.82, P=0.375 and $F_{(1,20)}$=0.05, P=0.824 for A4 and R, respectively; 3 mg/kg sildenafil: n=8 (4 males, 4 females), $F_{(1,20)}$=11.58, P=0.003 and $F_{(1,20)}$=11.36, P=0.003; 6 mg/kg sildenafil: n=8 (4 males, 4 females), $F_{(1,20)}$=8.48, P=0.009 and $F_{(1,20)}$=7.12, P=0.015]. FIG. 58C is a summary graph showing that the minimum time needed for sildenafil to have a positive effect on spatial working memory in APP/PS1 mice is 2 weeks with a concentration of 3 mg/kg [1 week: $F_{(1,20)}$=1.81, P=0.19 and $F_{(1,20)}$=0.82, P=0.386 for A4 and R, respectively; 2 weeks: $F_{(1,20)}$=9.69, P=0.005 and $F_{(1,20)}$=10.35, P=0.004; 3 weeks: $F_{(1,20)}$=13.19, P=0.002 and $F_{(1,20)}$=11.36, P=0.003; n=8 (4 males, 4 females) for each condition].

Figure 59:
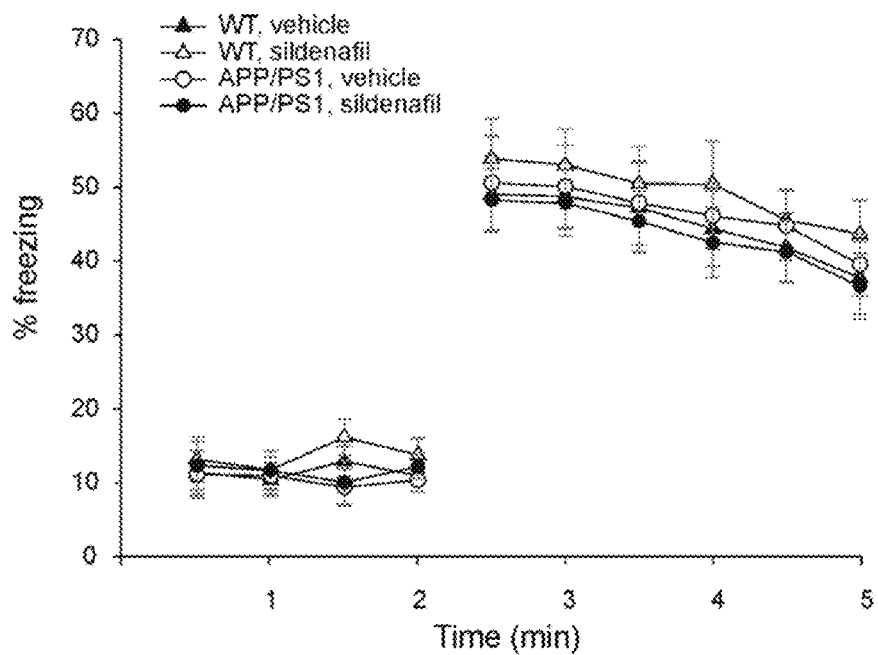

FIG. 59 is a graph that shows that sildenafil does not modify cued conditioning in 3 months old mice. Vehicle-treated APP/PS1 mice have similar performance as vehicle-treated WT littermates ($F_{(1,39)}$=0.16, P=0.691). Injections of sildenafil (3 mg/kg) do not affect freezing during cued conditioning in APP/PS1 mice and WT littermates ($F_{(1,38)}$=1.2, P=0.279 and $F_{(1,40)}$=0.08, P=0.773 compared to vehicle-treated WT mice, respectively).

Figure 60:
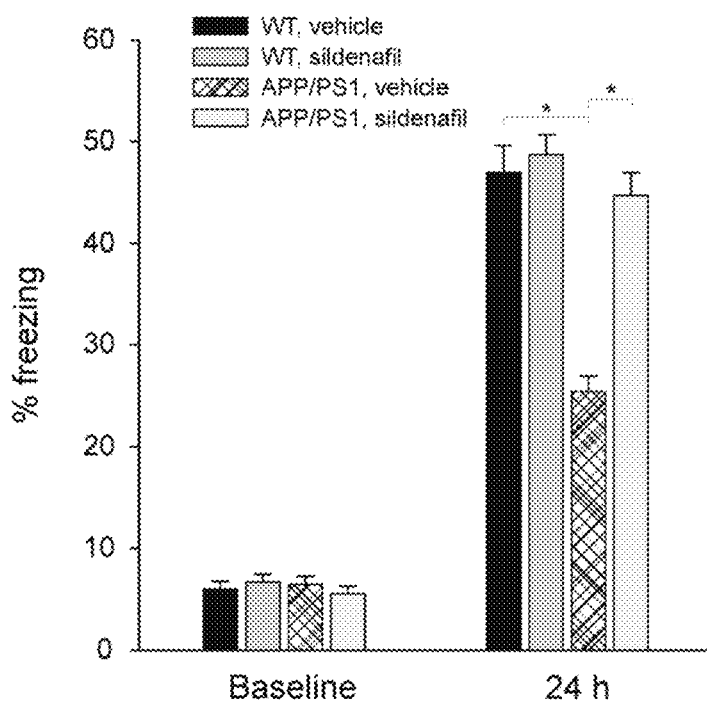

FIG. 60 is a graph that shows rescue by sildenafil of contextual fear memory impairment in APP/PS1 mice is complete with a high intensity foot shock eliciting high amounts of freezing [F(1,26)=52.24; P=0.001].

FIGS. 61A-C are graphs showing that tadalafil does not ameliorate cognition in 3-month-old APP/PS1 mice. FIG. 61A shows that tadalafil (1 mg/Kg, i.p.) does not modify contextual fear conditioning in 3 month-old APP/PS1 mice. APP/PS1 and WT littermates treated with tadalafil or vehicle show no difference in freezing prior to training [F(3,39)=0.26, P=0.853]. Fear conditioning performed 24 hrs after training shows a reduction of freezing responses in APP/PS1 mice treated with vehicle compared to vehicle-treated WT littermates [freezing time in vehicle-treated APP/PS1 mice is ~47% of vehicle-treated WT mice; n=12 (6 males, 6 females), vs. n=10 (5 males, 5 females) for WT littermates, F(1,20)=8.19, P=0.011]. Treatment with tadalafil does not rescue freezing behavior in APP/PS1 mice compared to vehicle-treated APP/PS1 animals [freezing time of tadalafil-treated APP/PS1 mice is ~122% of vehicle-treated APP/PS1 mice: n=8 (4 males, 4 females), F(1,18)=0.08, P=0.778]. Tadalafil does not affect the freezing responses of WT mice [~85% of vehicle-treated WT mice: n=13 (7 males, 6 females), F(1,21)=0.58, P=0.453]. FIG. 61B shows that cued fear conditioning is similar among the four groups [F(3,34)=1.42, P=0.253]. FIG. 61C shows that tadalafil does not improve spatial working memory in 3 month-old APP/PS1 mice. APP/PS1 mice treated with tadalafil do not learn the position of the hidden platform compared to vehicle-treated APP/PS1 [APP/PS1+ tadalafil: n=8 (4 males and females); APP/PS1+ vehicle: n=8 (5 males and females); F(1,14)=0.71, P=0.736 and F(1,14)=2.46, P=0.139 for A4 and R, respectively]. Tadalafil does not affect the performance of WT mice compared to vehicle-treated WT mice [WT+tadalafil: n=8 (4 males and females); WT+vehicle: n=8 (4 males and females); F(1,14)=0.32, P=0.579 and F(1,14)=0.09, P=0.763 for A4 and R, respectively].

FIGS. 62A-62H shows graphs that demonstrate the minimum concentration and duration of treatment with sildenafil needed in 3-month-old APP/PS1 mice to improve both associative and spatial memory in 6- to 8-month-old APP/PS1 mice. FIG. 62A is a summary graph showing that the minimum concentration of sildenafil needed to improve contextual fear memory is 3 mg/kg [n=8 (4 males, 4 females) for each condition in this and the following panels; F(1,14)=6.5, P=0.023 at 3 mg/kg sildenafil]. FIG. 62B is a summary graph showing that the minimum time needed for sildenafil to have a positive effect on contextual fear memory is 2 weeks with a concentration of 3 mg/kg [F(1,14)=13.9, P=0.002 at 2 weeks]. FIG. 62C is a summary graph showing that the minimum concentration of sildenafil needed to improve spatial working memory is 3 mg/kg [A4: $F(1,14)=12.7$, $P=0.001$ and R: $F(1,14)=13.6$, $P=0.002$ at 3 mg/kg sildenafil]. FIG. 62D is a summary graph showing that the minimum time needed for sildenafil to have a positive effect on spatial working memory is 2 weeks with a concentration of 3 mg/kg [A4: $F(1,14)=12.9$, $P=0.001$ and R: $F(1,14)=9.6$, $P=0.008$ at 2 weeks]. FIG. 62E is a summary graph showing that the minimum concentration of sildenafil needed to improve the performance with the MWM is 3 mg/kg (the graph shows the time needed to reach the platform in the last trial of the hidden platform) [$F(1,14)=16.9$, $P=0.001$ with 3 mg/kg sildenafil]. FIG. 62F is a summary graph showing that the minimum concentration of sildenafil needed to improve the performance with the probe trial is 3 mg/kg (the graph shows the percentage of time spent in the target quadrant—TQ) [$F(1,14)=18.3$, $P=0.001$ at 3 mg/kg sildenafil]. FIG. 62G is a summary graph showing that the minimum time needed for sildenafil to improve the performance with the MWM is 2 weeks with a concentration of 3 mg/kg [$F(1,14)=16.8$, $P=0.001$ at 2 weeks]. FIG. 62H is a summary graph showing that the minimum time needed for sildenafil to improve the performance with the probe trial is 2 weeks with a concentration of 3 mg/kg [$F(1,14)=19.8$, $P=0.001$ at 2 weeks].

Figure 63A:
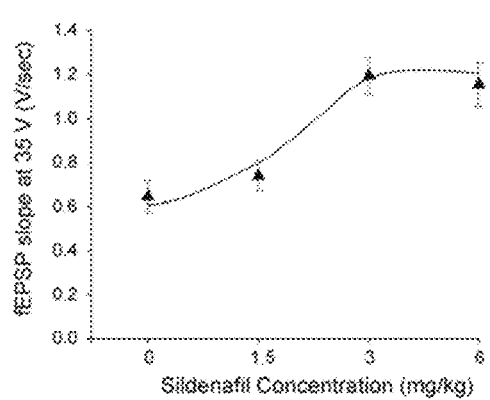
Figure 63B:
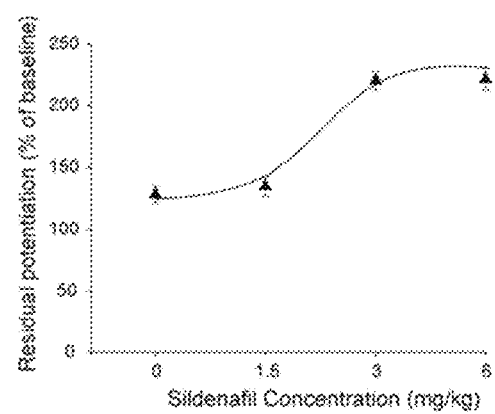
Figure 63C:
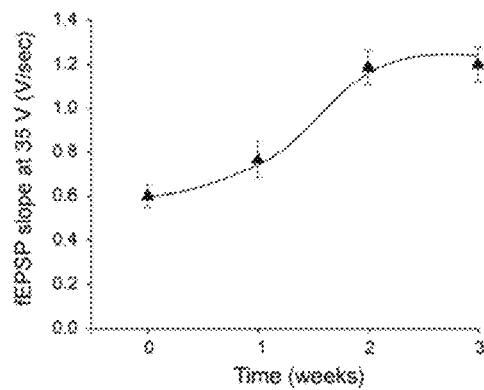
Figure 63D:
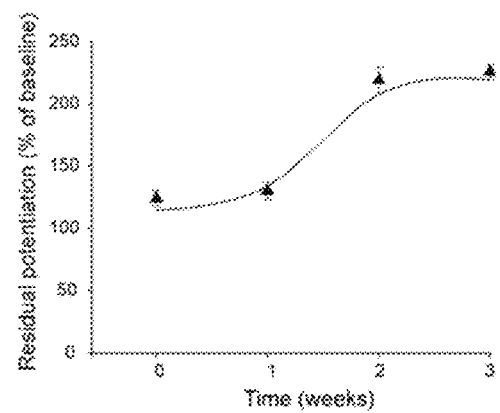

FIGS. 63A-D shows graphs that demonstrate the minimum concentration and duration of treatment with sildenafil needed in 3-month-old APP/PS1 mice to improve BST and LTP as they reach 6- to 8-months of age. FIG. 63A is a summary graph showing that the minimum concentration of sildenafil needed to improve BST is 3 mg/kg [n=8 males for each condition in this and following panels; $F(1,14)=23.32$, $P<0.001$ at 3 mg/kg sildenafil]. FIG. 63B is a summary graph showing that the minimum concentration of sildenafil needed to improve LTP is 3 mg/kg [$F(1,14)=70.3$, $P<0.001$ at 3 mg/kg sildenafil]. FIG. 63C is a summary graph showing that the minimum time needed for sildenafil to have a positive effect on BST is 2 weeks with a concentration of 3 mg/kg [$F(1,14)=39.4$, $P<0.001$ at 2 weeks]. FIG. 63D is a summary graph showing that the minimum time needed for sildenafil to have a positive effect on LTP is 2 weeks with a concentration of 3 mg/kg [$F(1,14)=64.5$, $P<0.001$ at 2 weeks].

Figure 64A:
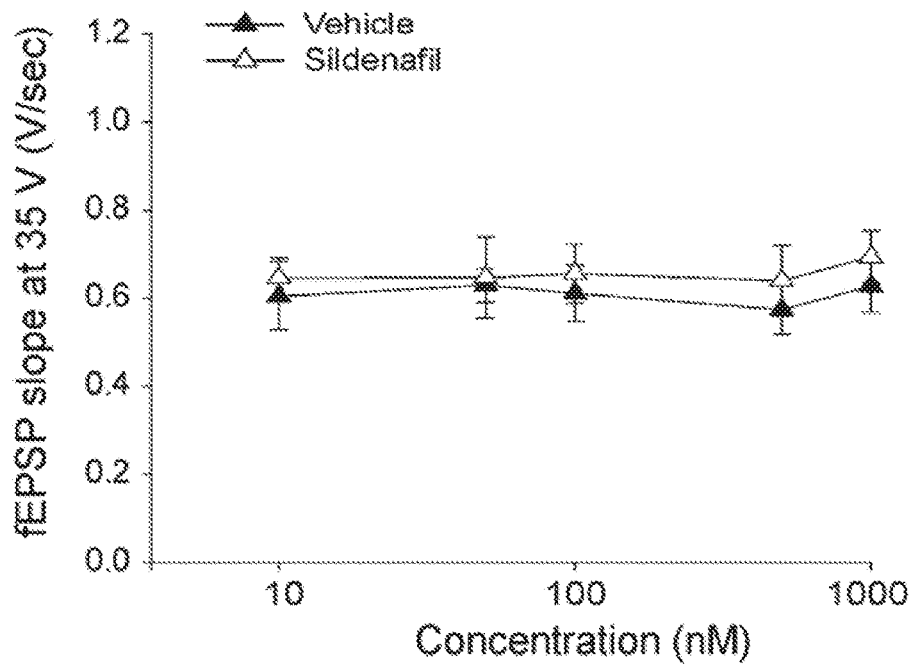
Figure 64B:
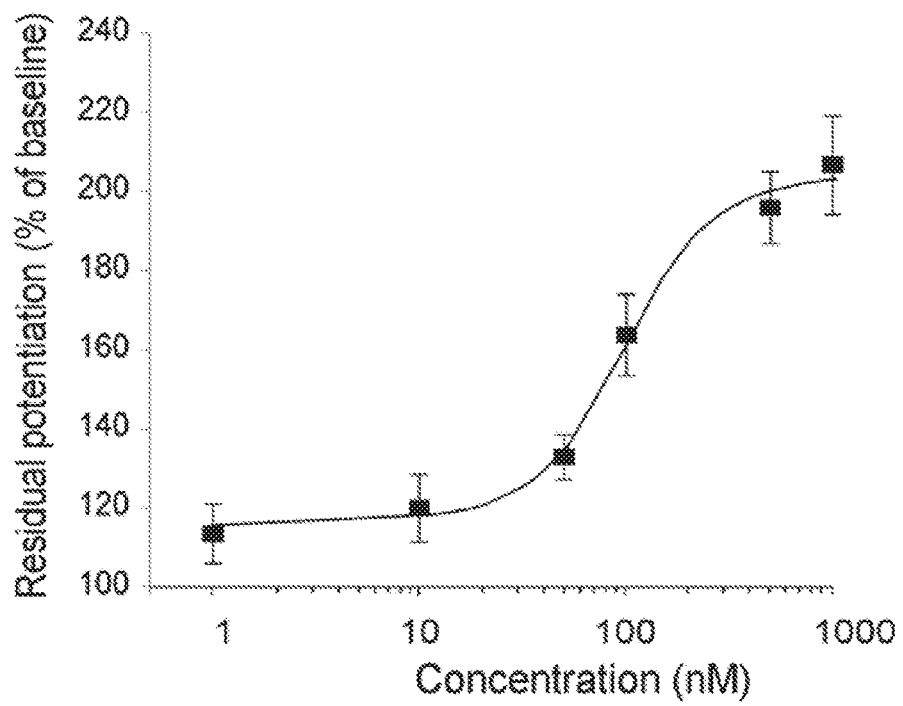

FIGS. 64A-B is a dose-response curve showing the effect of different concentrations of sildenafil, applied for 10 min through the bath solution, on BST and LTP in slices from 6 month old APP/PS1 animals. FIG. 64A is a graph that shows different concentrations of sildenafil do not change fEPSP slope ($F(4,30)=0.09$, $P=0.985$). FIG. 64B is a graph that shows the minimum effective dose of inhibitor that completely rescues LTP is 500 nM (93% of vehicle-treated WT slices; $t(1,11)=7.04$, $P<0.001$, n=7/4 for various groups).

FIGS. 65A-65D are graphs showing that sildenafil decreases Aβ levels in APP/PS1 mice. FIG. 65A shows that sildenafil decreases $A\beta_{40}$ and $A\beta_{42}$ levels in 3-month-old transgenic mice with a minimum effective dose of 3 mg/kg ($t_{(12)}=2.32$, $P=0.039$ and $t_{(12)}=2.30$, $P=0.04$ for $A\beta_{40}$ and $A\beta_{42}$, respectively; n=7 for various groups). FIG. 65B shows that daily injections of sildenafil for 3 weeks in 3-month-old APP/PS1 mice reduce Aβ levels in the same mice at 7-10 months of age. The minimum effective dose that decreases $A\beta_{40}$ and $A\beta_{42}$ levels is 3 mg/kg ($t_{(12)}=2.22$, $P=0.04$ and $t_{(12)}=2.85$, $P=0.01$ for $A\beta_{40}$ and $A\beta_{42}$, respectively; n=7 for various groups). FIG. 65C shows that the minimum time needed for 3 mg/kg sildenafil to have a positive effect on $A\beta_{40}$ is 2 weeks ($t_{(12)}=2.43$, $P=0.03$) whereas values of $A\beta_{42}$ levels did not reach significance at this time (2 weeks: $t_{(12)}=2.22$, $P=0.04$; 3 weeks: $t_{(12)}=2.85$, $P=0.01$; n=7 for various groups). FIG. 65D shows that the minimum time needed for 3 mg/kg sildenafil, administered at 3 months of age, to have a positive effect on $A\beta_{40}$ levels in the same mice at 7-8 months of age is 3 weeks ($t_{(12)}=2.33$, $P=0.03$) whereas levels of $A\beta_{42}$ at 2 weeks are slightly above significance (2 weeks: $t_{(12)}=2.02$, $P=0.06$; 3 weeks: $t_{(12)}=2.95$, $P=0.01$; n=7 for various groups).

Figure 66:
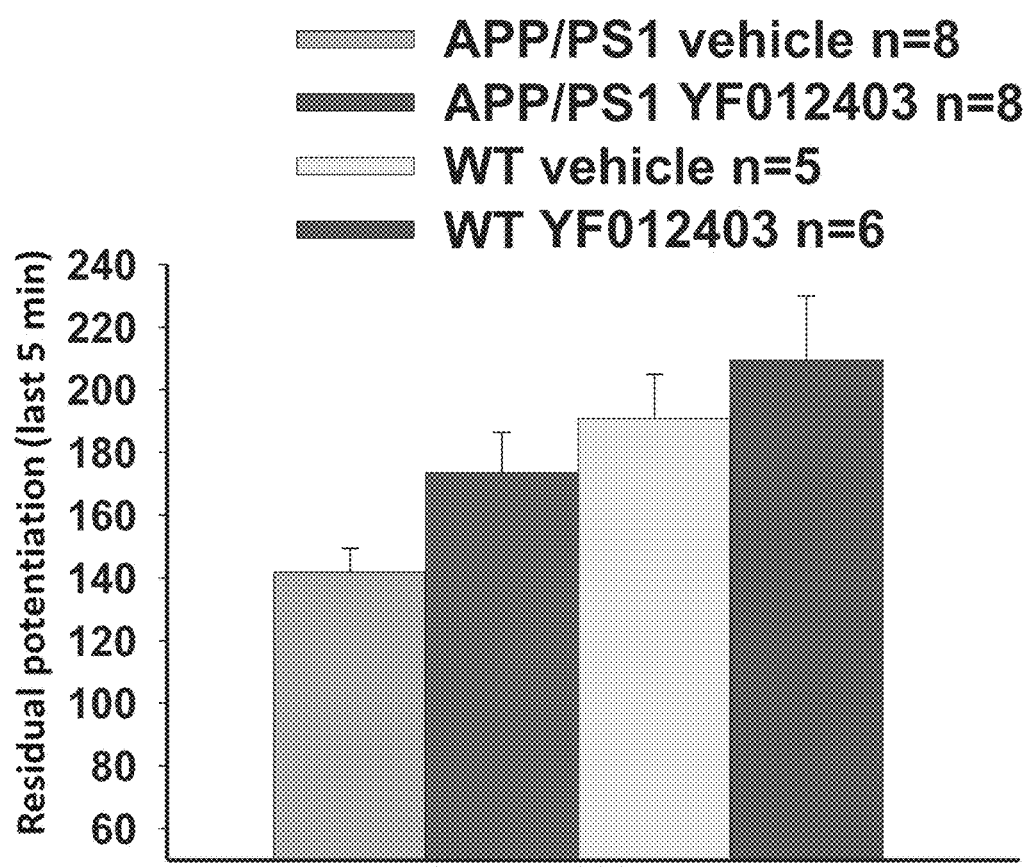

FIG. 66 shows that YF012403 (10 min prior to tetanus) rescues the defect in LTP in slices from transgenic mice.

Figure 67:
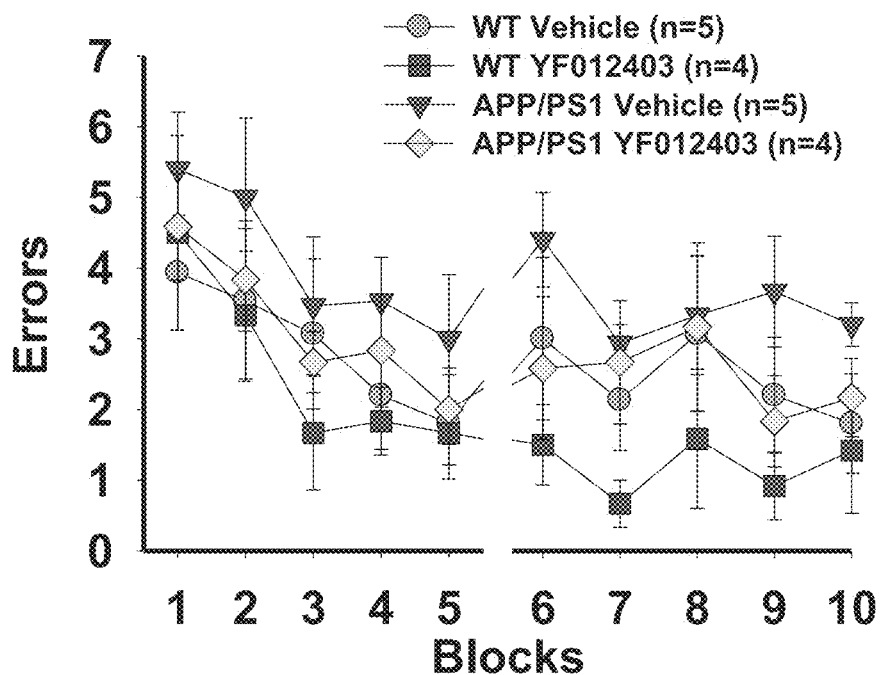
Figure 68:
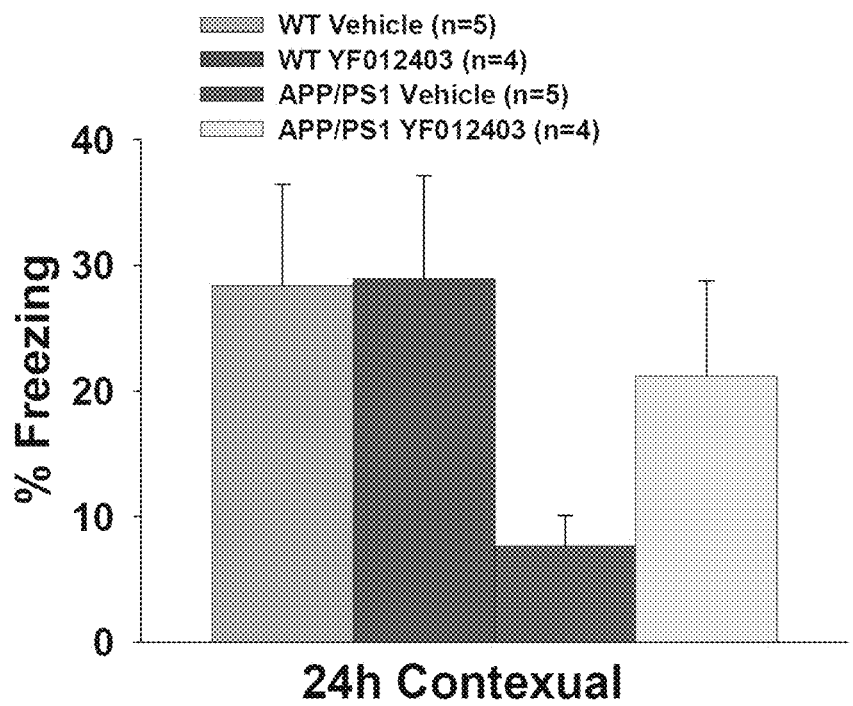

FIG. 67 and FIG. 68 show the effects of YF012403 in a transgenic mouse model of Alzheimer's disease. The graphs show that behavioral defects for 2 day radial arm water maze, as well as contextual fear memory are attenuated by treatment with the inhibitor. This is a transgenic mouse model of amyloid beta elevation.

DETAILED DESCRIPTION OF THE INVENTION

The invention provides for a class of quinoline-containing compounds which have excellent PDE5 inhibitory potency, high selectivity, reasonable pharmacokinetics and good permeability across the blood-brain-barrier (BBB). These compounds may be used to minimize the side effects for AD patients, the third most costly disease in the U.S. The compounds of the invention may also be used to treat erectile dysfunction (ED), pulmonary hypertension, cardiovascular disorder, diabetes, and GI disorders.

In some embodiments, the invention provides methods for identifying PDE5 inhibitors that can cause a sustained or long-term decrease in β-secretase activity or expression in a subject. In one embodiment, the invention provides methods that select for PDE5 inhibitors that can cause a decrease in β-secretase activity or expression in a subject well after administration of the PDE5 inhibitor has ended. For example, PDE5 inhibitors can be screened or selected based on their ability to cause a decrease in β-secretase activity or expression in an animal model of Aβ accumulation (such as APP/PS1 mice) for at least 1 month, 2 months, 3 months, 4 months, 5 months, 6 months, or more.

To shrink the candidate pool of PDE5 inhibitor compounds to be tested in Aβ accumulation animal models, PDE5 inhibitors can first be screened or selected based on their possession of certain characteristics, such as having one or more of: an $IC_{50}$ no greater than about 100 nM; a selectivity that is at least 50-fold greater for PDE5 than for other PDEs; a PDE5 inhibitory activity in vitro that has an $IC_{50}$ no greater than about 50 nM, the ability to penetrate the BBB; the ability to hydrolyze cGMP by at least about 20% (or at least about 80%); an interaction between the compound and PDE5 that comprises a second bridging ligand that is a hydroxyl group; and an interaction between the compound and PDE5 that comprises contacts with PDE5 at amino acid residues F787, L804, I813, M816, or a combination thereof (including contacts at all four residues).

In some embodiments, the candidate pool of PDE5 inhibitors to be tested in Aβ accumulation animal models can first be screened or selected based on "medicinal chemistry" strategies described herein (see Examples). For example, based on the structure analysis of reported PDE5 inhibitors and known SAR data (FIG. 12, four class of structurally related, but nevertheless formally independent scaffolds I-IV (see FIG. 13), are deemed as PDE5 inhibitor candidates. Compounds derived from these scaffolds can first be screened and optimized on computational models. Compounds with highest score will be synthesized and tested for potency. At this stage, the synthetic effort will be guided by the testing results of potency/selectivity. Compounds with satisfactory potency and selectivity (lead compounds) will be further studied for PK, bioavailability/brain penetration and off-target activities (safety). Selected compounds can be tested in the Aβ accumulation animal models to determine whether they cause a sustained a sustained or long-term decrease in β-secretase activity or expression. As used herein, a PDE5 inhibitor compound does not necessarily preclude the possibility that the compound may also be able to inhibit other PDEs.

Thus, the disclosure provides for the discovery that PDE5 inhibitor compounds display a prolonged and protective effect against synaptic dysfunction and memory loss that persists beyond the administration of the inhibitor. In some embodiments, PDE5 inhibitor compounds are desired and screened or selected for that have a prolonged inhibitory affect on β-secretase while having a prolonged enhancing effect on α-secretase. In some embodiments, methods of screening for therapeutic agents (for conditions associated with amyloid-β-peptide accumulation, such as AD) involve testing whether an agent exerts a prolonged inhibitory affect on β-secretase activity or expression and/or a prolonged stimulatory affect α-secretase activity or expression.

In some embodiments, the invention is directed at identifying and using agents that interact with Aβ targets that lead to neuronal dysfunction. The invention also provides for compounds that modulate PDE5 protein expression or activity, or that modulate activity or expression of secretases (for example, α- and β-secretase). For example, the compounds can be PDE5 inhibitors, a class of compounds that counteract the progression of neurodegenerative diseases, such as AD (Puzzo et al [12]). Currently used AD therapies (such as acetylcholinesterase inhibitors or NMDA antagonists) have limited efficacy.

Alzheimer's Disease

Alzheimer's disease (AD) is characterized by neuronal loss, extracellular senile plaques and intracellular neurofibrillary tangles, leading to memory loss. AD purportedly begins as a synaptic disorder produced at least in part, by Aβ (Selkoe, D. J. Alzheimer's disease is a synaptic failure. *Science* (New York, N. Y 298, 789-791 (2002)). Aβ-induced reduction in long-term-potentiation (LTP), a physiological correlate of synaptic plasticity that is thought to underlie learning and memory, and phosphorylation of the memory transcription factor CREB, are ameliorated by nitric oxide (NO) donors and cGMP-analogs (Puzzo, D., et al. Amyloid-beta peptide inhibits activation of the nitric oxide/cGMP/cAMP-responsive element-binding protein pathway during hippocampal synaptic plasticity. *J Neurosci* 25, 6887-6897 (2005)). Vice-versa, genetic ablation of NO-synthase 2 (NOS2) results in worsening of the AD phenotype in mice expressing mutated amyloid precursor protein (APP) (Colton, C. A., et al. NO synthase 2 (NOS2) deletion promotes multiple pathologies in a mouse model of Alzheimer's disease. *Proceedings of the National Academy of Sciences of the United States of America* 103, 12867-12872 (2006)). Taken together, these findings show that up-regulation of the NO pathway can be protective in AD.

AD is characterized neuropathologically by neuronal loss, extracellular senile plaques (SPs) and intracellular neurofibrillary tangles (NFTs). SPs are chiefly comprised of Aβ aggregates. The major component of NFTs is the microtubule binding protein tau. Clinically, AD is characterized by cognitive dysfunction and begins as a synaptic disorder that involves progressively larger areas of the brain over time [1]. An emerging view of the processes involved in synaptic impairment shows that the subtlety and variability of the earliest amnesic symptoms, occurring in the absence of any other clinical signs of brain injury, can be due to discrete changes in the function of a single synapse, produced at least in part, by Aβ [5, 7, 10, 11].

One of the important targets for developing a causal therapy for Alzheimer's disease is represented by synapses. Synaptic alterations are highly correlated with the severity of clinical dementia [1, 2], whereas other important variables such as senile plaques and neurofibrillary tangles are involved to a lesser extent [1]. The importance of synaptic alterations in AD has been confirmed by studies of transgenic (Tg) mouse models of AD [3] as well as of long-term potentiation (LTP), a widely studied cellular model of learning and memory (L&M) [4], which is impaired following application of amyloid-β (Aβ) both in slices and in vivo [3, 5-12]. Aβ has been found to markedly inhibit LTP. Electrophysiological studies using Tg, human Aβ producing mice have often revealed significant deficits in basal synaptic transmission and/or LTP in the hippocampus [23-30].

NO is a central molecule in cellular biochemical processes. The gas has been established as an important messenger molecule in various steps of brain physiology, from development to synaptic plasticity and learning and memory. In AD research, NO has been found to have a protective effect on Aβ-induced damage of the nervous system [38-40]. Studies performed on PC12 cells, sympathetic neurons and hippocampal neurons, have shown that treatment with the NO generator S-nitroso penicillamine exerts a neuroprotective effect due to the inhibition of the pro-apoptotic factor caspase-2 by nitrosylation [39], whereas inhibition of NO synthesis by N-nitro-L-arginine methyl ester does not protect against Aβ-induced neurotoxicity. Aβ has been found to impair NO generation by decreasing NMDA receptor signal transduction [38], by subtracting NADPH availability to NO-synthase (NOS) [41], or by inhibiting the phosphorylation of the serine-threonine kinase Akt [42]. Moreover, i-NOS deletion enhances AD pathology in the APP mice [43]. Thus, drugs enhancing the NO-cascade have a beneficial effect against AD [44].

Despite the neuroprotective function of NO is clear and indisputable, the gas has also been viewed as a major agent of neuropathology and cell death when it is produced in high quantity. High amounts of NO lead to generation of significant quantity of peroxinitrites that are responsible for oxidative and nitrosative stress in Aβ-induced cell death [45-51]. In fact, release of low amounts of NO by the constitutive forms of NOS that include both the neuronal and the endothelial isoforms, n-NOS and e-NOS, promotes synaptic plasticity and learning, whereas uncontrolled production of high amounts of the gas by the inducible form of NOS (i-NOS) can promote oxidative and nitrosative stress via production of peroxinitrite [45-51]. Thus, both Aβ-induced downregulation of the NO cascade which blocks plasticity and memory and generation of peroxinitrites leading to cell death, can play roles in AD. The current status of drug research exploiting these discoveries is focused both on finding ways to upregulate the NO cascade and therefore elicit neuroprotection, as well as on finding ways to block peroxinitrite toxic effects in order to limit neuropathology [52].

PDE5 Inhibition

Herein, therapeutic strategies can bypass NO production by focusing on steps at the downstream level of NO generation. PDE5, the enzyme that degrades cGMP, is such a downstream target of the disclosure's therapies aimed at treating Aβ deposits in subjects in need thereof. PDE5 is part of a superfamily of enzymes including 11 types/families of PDE (PDE1 to PDE11), some of which play a critical role in memory and behavior in diverse organisms ranging from the fruit fly, Drosophila melanogaster, to humans [53]. PDEs are multi-domain proteins, wherein about 270 amino acids localized towards the C-terminus is highly conserved between the 11 families. This domain contains the PDEs' catalytic function. Non-homologous amino acid segments have regulatory function or confer specific binding properties. PDE2, PDE5, PDE6 and PDE10 contain putative GAF domains within their regulatory amino terminal portion, which have been shown to bind cGMP.

PDE5, a cGMP specific PDE, is found in varying concentrations in various tissues such as vascular and visceral smooth muscle, platelets, and skeletal muscle. The cGMP-specific PDE is ubiquitously expressed, and can be found in several brain regions associated with cognitive function, including the hippocampus, cortex and cerebellum [17, 18]. PDE5 is comprised of the conserved C-terminal, zinc containing, catalytic domain, and an N-terminal regulatory domain. The C-terminus of PDE5 catalyses the cleavage of cGMP, while the N terminus contains two GAF domain repeats, which each contains a cGMP-binding site (one of high affinity and the other of lower affinity). Regulation of PDE5 activity occurs through binding of cGMP to the high and low affinity cGMP binding sites, subsequently followed by phosphorylation, which occurs only when both sites are occupied. Inhibition of PDE5 decreases cGMP breakdown, thus allows for maintenance of cGMP levels. Sildenafil, for example, is a potent inhibitor of PDE5 and is the active ingredient of Viagra™

Some clinically useful drugs have been developed as family-selective inhibitors of PDEs. However, none have been shown to exert long-lasting inhibitory effects on β-secretase expression or activity, as well as long-lasting excitatory effects on t-secretase expression or activity. Preclinical studies have shown that the selective PDE5 inhibitors sildenafil and vardenafil raise hippocampal cGMP levels and improve memory in aged rats (Prickaerts et al, 2002) and mice (Baratti & Boccia, 2001). In human studies sildenafil was found to enhance selective retention and verbal recognition memory in humans (Schultheiss et al, 2001). Because sildenafil (Viagra by Pfizer, pyrazol-[4,3-d]-pyrimidinone derivative) is reported to cross the blood brain barrier (BBB), it represents a good candidate for CNS studies. But evidence for vardenafil is indirect (Prickaerts, J., et al. Neurochem Int 45, 915-928 (2004)), and tadalafil is unlikely to cross it. Sildenafil has an $IC_{50}$ against PDE5 of 6.0 nM and an in vivo half-life of 0.4 hrs in rodents (~4 hrs in humans) (Walker, D. K., et al. Xenobiotica 29, 297-310 (1999); Daugan, A., et al. J Med Chem 46, 4533-4542 (2003)). In addition, it is very selective for PDE5 over all of the other PDE iso-enzymes, including PDE1, which is expressed in myocardium and blood vessels besides the brain and can result in vasodilatation and tachycardia (selectivity ratio 180) (Daugan, A., eta. J Med Chem 46, 4533-4542 (2003)), and PDE6, which is expressed only in retina and can transiently disturb vision (selectivity ratio 12) (Daugan, A., et al. J Med Chem 46, 4533-4542 (2003)).

A variety of physiological processes in the nervous, cardiovascular, and immune systems are controlled by the NO/cGMP signaling pathway. For example, in smooth muscle, NO and natriuretic peptides regulate vascular tone by stimulating relaxation through cGMP. Degradation of cGMP is controlled by cyclic nucleotide PDEs, and PDE5 is the most highly expressed PDE that hydrolyzes cGMP in these cells. One effective way to up-regulate the NO pathway is by increasing cGMP levels through inhibitors of phosphodiesterase 5 (PDE5), a member of a superfamily of enzymes including 11 types of PDE, some of which play a critical role in memory and behavior in diverse organisms ranging from the fruit fly, Drosophila melanogaster to humans (Davis, 1996; Barad et al, 1998; Zhang et al, 2004). These drugs are widely used to treat erectile dysfunction and pulmonary hypertension. Thus, their side effects are known and have not precluded their use in humans. Interestingly, PDE5 is expressed in several brain regions associated with cognitive function, such as the hippocampus, cortex and cerebellum (van Staveren, W. C., Steinbusch, H. W., Markerink-van Ittersum, M., Behrends, S. & de Vente, J. Eur J Neurosci 19, 2155-2168 (2004); Van Staveren, W. C., et al. J Comp Neurol 467, 566-580 (2003)).

Cyclic GMP, which phosphorylates the transcription factor CREB and activates cGMP dependent protein kinases (PKGs) has been implicated in the modulation of neurotransmission, LTP and memory [13-16]. Elevation of the cGMP levels through the inhibition of the cGMP-degrading enzyme phosphodiesterase-5 (PDE5), an enzyme expressed in several brain regions associated with cognitive function such as the hippocampus and cortex [17, 18], improves memory in aged rats [14] and mice [16]. Elevation of cGMP through the PDE5 inhibitor sildenafil (Viagra) also enhances selective retention and verbal recognition memory in humans [19]. The effects of cGMP on L&M are mediated by intra and extracellular nitric oxide (NO), a molecule whose production is stimulated by soluble guanylyl cyclase (sGC) [20-22]. Preclinical studies have shown that the selective PDE5 inhibitors sildenafil and vardenafil raise hippocampal cGMP levels and improve memory in aged rats (Prickaerts, J., de Vente, J., Honig, W., Steinbusch, H. W. & Blokland, A. Eur J Pharmacol 436, 83-87 (2002)) and mice (Baratti, C. M. & Boccia, M. M. Behav Pharmacol 10, 731-737 (1999)). Further studies using Tg Aβ-producing mice have revealed an age-dependent decrease in the phosphorylation of CREB protein, these studies have provided a clue as to the mechanisms underlying the Aβ-mediated changes in LTP [31-33]. CREB phosphorylation is required for memory formation and is regulated by cAMP levels and activated cAMP-dependent-protein kinase (PKA) [34-36] as well as by cGMP levels and activated cGMP-dependent-protein kinase (PKG) [37]. Importantly, in vitro studies report that Aβ inactivates PKA and PKG, thereby reducing cAMP, phospho-CREB and LTP [10, 12, 33]. These observations show that agents that enhance the CREB-signaling pathway and act through the NO-activated cascade have potential for the treatment of AD.

PDE5 Inhibitors Optimized for CNS Diseases

None of the commercially available PDE5 inhibitors were developed to have the characteristics required for administration in a chronic disease of the CNS, such as AD. Thus, in some embodiments, the invention provides methods for identifying an agent or compound for the treatment of AD (or other Aβ-accumulation related conditions) that comprise selecting the agent or compound on the basis of having one or more characteristics that make the compound optimized for treating CNS diseases. For example, the characteristics can comprise: an $IC_{50}$ no greater than about 100 nM; a selectivity that is at least 50-fold greater for PDE5 than for other PDEs; a PDE5 inhibitory activity in vitro that has an $IC_{50}$ no greater than about 50 nM, the ability to penetrate the BBB; the ability to hydrolyze cGMP by at least about 20% (or at least about 80%); an interaction between the compound and PDE5 that comprises a second bridging ligand that is a hydroxyl group; and an interaction between the compound and PDE5 that comprises contacts with PDE5 at amino acid residues F787, L804, I813, M816, or a combination thereof.

In some embodiments, the invention provides methods for identifying or designing agents or compounds for the treatment of conditions associated with Aβ accumulation, where computer aided-medicinal chemistry methods are used to identify and/or design agents or compounds tailored to satisfy one or more of the characteristics mentioned above and/or to suit the strengths of various bioassays described herein.

In some embodiments, the invention provides for PDE5 inhibitor compounds based on four scaffold structures identified through a thorough analysis of Structure-Activity Relationship (SAR) characteristics of existing PDE5 inhibitors. The scaffold structures served and will continue to serve as leads for development of future compounds [See EXAMPLE 3]. Compounds based on the four scaffold structures can be screened for having one or more characteristics, such as: an IC50 no greater than about 100 nM; a selectivity that is at least 50-fold greater for PDE5 than for other PDEs; a PDE5 inhibitory activity in vitro that has an IC50 no greater than about 50 nM, the ability to penetrate the BBB; the ability to hydrolyze cGMP by at least about 20% for at least about 80%), an interaction between the compound and PDE5 that comprises a second bridging ligand that is a hydroxyl group; and an interaction between the compound and PDE5 that comprises contacts with PDE5 al amino acid residues F787, L804, I813, M816, or a combination thereof, and/or for having the ability to cause a prolonged or sustained decrease in β-secretase activity or expression in an animal model of Aβ accumulation (such as the APP/PS1 mouse).

The invention provides methods for identifying compounds which can be used for treating subjects that exhibit abnormally elevated amyloid beta plaques. In addition, the invention provides methods for identifying compounds which can be used for the treatment of Alzheimer's disease, Lewy body dementia, inclusion body myositis, or cerebral amyloid angiopathy, hypertension, and erectile dysfunction. The methods can comprise the identification of test compounds or agents (e.g., peptides (such as antibodies or fragments thereof), small molecules, nucleic acids (such as siRNA or antisense RNA), or other agents) that can bind to a PDE5 polypeptide molecule and/or have an inhibitory effect on the biological activity of PDE5 or its expression, and subsequently determining whether these compounds can modulate secretase activity and/or decrease Aβ deposits. In one embodiment, the compound is a PDE5 inhibitor.

The term "modulate", as it appears herein, refers to a change in the activity or expression of a protein molecule. For example, modulation can cause an increase or a decrease in protein activity, binding characteristics, or any other biological, functional, or immunological properties of a secretase protein molecule.

In one embodiment, a PDE5 inhibitor compound can be a peptide fragment of a PDE5 protein that binds to the phosphodiesterase protein. For example, the PDE5 molecule can encompass any portion of at least about 8 consecutive amino acids of SEQ ID NO: 1 or SEQ ID NO: 2. The fragment can comprise at least about 10 amino acids, a least about 20 amino acids, at least about 30 amino acids, at least about 40 amino acids, a least about 50 amino acids, at least about 60 amino acids, or at least about 75 amino acids of SEQ ID NO: 1 or SEQ ID NO: 2.

SEQ ID NO: 1 is the human wild type amino acid sequence corresponding to the PDE5 enzyme (residues 1-875; Genbank Accession No. AAI26234):
MERAGPSFGQQRQQQQPQQQKQQQRDQDSVEAWLDDHWDFTFSYFVRKAT

REMVNAWFAERVHTIPVCKEGIRGHTESCSCPLQQSPRADNSAPGTPTRK

ISASEFDRPLRPIVVKDSEGTVSFLSDSEKKEQMPLTPPRFDHDEGDQCS

RLLELVKDISSHLDVTALCHKIFLHIHGLISADRYSLFLVCEDSSNDKFL

ISRLFDVAEGSTLEEVSNNCIRLEWNKGIVGHVAALGEPLNIKDAYEDPR

FNAEVDQITGYKTQSILCMPIKNHREEVVGVAQAINKKSGNGGTFTEKDE

KDFAAYLAFCGIVLHNAQLYETSLLENKRNQVLLDLASLIFEEQQSLEVI

LKKIAATIISFMQVQKCTIFIVDEDCSDSFSSVFHMECEELEKSSDTLTR

EHDANKINYMYAQYVKNTMEPLNIPDVSKDKRFPWTTENTGNVNQQCIRS

LLCTPIKNGKKNKVIGVCQLVNKMEENTGKVKPFNRNDEQFLEAFVIFCG

LGIQNTQMYEAVERAMAKQMVTLEVLSYHASAAEEETRELQSLAAAVVPS

AQTLKITDFSFSDFELSDLETALCTIRMFTDLNLVQNFQMKHEVLCRWIL

SVKKNYRKNVAYHNWRHAFNTAQCMFAALKAGKIQNKLTDLEILALLIAA

LSHDLDHRGVNNSYIQRSEHPLAQLYCHSIMEHEIHFDQCLMILNSPGNQ

ILSGLSIEEYKTTLKIIKQAILATDLALYIKRRGEFFELIRKNQFNLEDP

HQKELFLAMLMTACDLSAITKPWPIQQRIAELVATEFFDQGDRERKELNI

EPTDLMNREKKNKIPSMQVGFIDAICLQLYEALTHVSEDCFPLLDGCRKN

RQKWQALAEQQEKMLINGESGQAKRN

SEQ ID NO: 2 is the mouse wild type amino acid sequence corresponding to the PDE5 enzyme (residues 1-865; Genbank Accession No. NP_700471):
MERAGPNSVRSQQQRDPDWVEAWLDDHRDFTFSYFIRKATRDMVNAWFSE

RVHNIPVCKEGIRAHTESCSCSLQQSPHADNTTPGAPARKISASEFDRPL

RPIVVKDSEGTVSFLSDSGKKEQMPLTPPRFDSDEGDQCSRLLELVKDIS

SHLDVTALCHKIFLHIHGLISADRYTLFLVCEDSSKDKFLISRLFDVAEG

STLEEASNNCIRLEWNKGIVGHVAAFGEPLNIKDAYEDPRFNAEVDQITG

YKTQSILCMPIKNHREEVVGVAQAINKKSGNGGTFTEKDEKDFAAYLAFC

GIVLHNAQLYETSLLENKRNQVLLDLASLIFEEQQSLEVILKKIAATIIS

FMQVQKCTIFIVDEDCPDSFSRVFHMECEEVGKPSDPLTREQDANKINYM

YAQYVKNTMEPLNIPDVTKDKRFPWTNENMGHVNTPCIGSLLCTPIKNGK

KNKVIGVCQLVNKMEENTGKIKAFNQNDEQFLEAFVIFCGLGIQNTQMYE

AVERAMAKQMVTLEVLSYHASAAEEETRELQALSAAVVPSAQTLKITDFS

FSDFELSDLETALCTIRMFTDLNLVQNFQMKHEVLCRWILSVKKNYRKNV

AYHNWRHAFNTAQCMFAALKAGKIQNKLTDLETLALLIAALSHDLDHRGV

NNSYIQRSEHPLAQLYCHSIMEHRHFDQCLMILNSPGNQILSGLSIDEYK

TTLKIIKQAILATDLALYIKRRGEFFELIRKNQFSFEDPLQKELFLAMLM

TACDLSAITKPWPIQQRIAELVAAEFFDQGDRERKELNMEPADLMNREKK

NKIPSMQVGFIDAICLQLYEALTHVSEDCLPLLDGCRKNRQKWQALAEQQ

EKMLLNGESSQGKRD

Fragments include all possible amino acid lengths between and including about 8 and 100 about amino acids, for example, lengths between about 10 and 100 amino acids, between about 15 and 100 amino acids, between about 20 and 100 amino acids, between about 35 and 100 amino acids, between about 40 and 100 amino acids, between about 50 and 100 amino acids, between about 70 and 100 amino acids, between about 75 and 100 amino acids, or between about 80 and 100 amino acids. These peptide fragments can be obtained commercially or synthesized via liquid phase or solid phase synthesis methods (Atherton et al., (1989) *Solid Phase Peptide Synthesis: a Practical Approach.* IRL Press, Oxford, England). The PDE5 peptide fragments can be isolated from a natural source, genetically engineered, or chemically prepared. These methods are well known in the art.

A PDE5 inhibitor compound can also be a protein, such as an antibody (monoclonal, polyclonal, humanized, and the like), or a binding fragment thereof, directed against the phosphodiesterase enzyme, PDE5. An antibody fragment can be a form of an antibody other than the full-length form and includes portions or components that exist within full-length antibodies, in addition to antibody fragments that have been engineered. Antibody fragments can include, but are not limited to, single chain Fv (scFv), diabodies, Fv, and (Fab')$_2$, triabodies, Fc, Fab, CDR1, CDR2, CDR3, combinations of CDR's, variable regions, tetrabodies, bifunctional hybrid antibodies, framework regions, constant regions, and the like (see, Maynard et al., (2000) *Ann. Rev. Biomed. Eng.* 2:339-76; Hudson (1998) *Curr. Opin. Biotechnol.* 9:395-402). Antibodies can be obtained commercially, custom generated, or synthesized against an antigen of interest according to methods established in the art (Janeway et al., (2001) *Immunobiology,* 5th ed., Garland Publishing).

Inhibition of RNA encoding a PDE5 protein can effectively modulate the expression of the PDE5 gene from which the RNA is transcribed. Inhibitors are selected from the group comprising: siRNA, interfering RNA or RNAi; dsRNA; RNA Polymerase III transcribed DNAs; ribozymes; and antisense nucleic acid, which can be RNA, DNA, or artificial nucleic acid.

Antisense oligonucleotides, including antisense DNA, RNA, and DNA/RNA molecules, act to directly block the translation of mRNA by binding to targeted mRNA and preventing protein translation. For example, antisense oligonucleotides of at least about 15 bases and complementary to unique regions of the DNA sequence encoding a PDE5 polypeptide can be synthesized, e.g., by conventional phosphodiester techniques (Dallas et al., (2006) *Med. Sci. Monit.* 12(4):RA67-74; Kalota et al., (2006) *Handb. Exp. Pharmacol.* 173:173-96; Lutzelburger et al., (2006) *Handb. Exp. Pharmacol.* 173:243-59).

siRNA comprises a double stranded structure containing from about 15 to about 50 base pairs, for example from about 21 to about 25 base pairs, and having a nucleotide sequence identical or nearly identical to an expressed target gene or RNA within the cell. Antisense nucleotide sequences include, but are not limited to: morpholinos, 2'-O-methyl polynucleotides, DNA, RNA and the like. RNA polymerase III transcribed DNAs contain promoters, such as the U6 promoter. These DNAs can be transcribed to produce small hairpin RNAs in the cell that can function as siRNA or linear RNAs that can function as antisense RNA. The PDE5 inhibitor compound can contain ribonucleotides, deoxyribonucleotides, synthetic nucleotides, or any suitable combination such that the target RNA and/or gene is inhibited. In addition, these forms of nucleic acid can be single, double, triple, or quadruple stranded. (see for example Bass (2001) *Nature,* 411, 428 429; Elbashir et al., (2001) *Nature,* 411, 494 498; and PCT Publication Nos. WO 00/44895, WO 01/36646, WO 99/32619, WO 00/01846, WO 01/29058, WO 99/07409, WO 00/44914).

In some embodiments, a PDE5 inhibitor can be a small molecule that binds to a phosphodiesterase protein (for example a PDE5 protein) and disrupts its function. Small molecules are a diverse group of synthetic and natural substances generally having low molecular weights. They can be isolated from natural sources (for example, plants, fungi, microbes and the like), are obtained commercially and/or available as libraries or collections, or synthesized. Candidate small molecules that inhibit PDE5 can be identified via in silico screening or high-through-put (HTP) screening of combinatorial libraries. Most conventional pharmaceuticals, such as aspirin, penicillin, and many chemotherapeutics, are small molecules, can be obtained commercially, can be chemically synthesized, or can be obtained from random or combinatorial libraries as described below (Werner et al., (2006) *Brief Funct. Genomic Proteomic* 5(1):32-6).

Knowledge of the primary sequence of a molecule of interest, such as a PDE5 polypeptide, and the similarity of that sequence with other proteins of the same PDE family (such as PDE1, PDE2, PDE3, PDE4, PDE6, PDE7, PDE8, PDE9, PDE10, or PDE11), can provide information as to the inhibitors or antagonists of the protein of interest. Identification and screening antagonists can be further facilitated by determining structural features of the protein, e.g., using X-ray crystallography, neutron diffraction, nuclear magnetic resonance spectrometry, and other techniques for structure determination. These techniques provide for the rational design or identification of antagonists, in addition to protein agonists.

The invention provides methods for screening and identifying compounds used to treat conditions associated with accumulated amyloid-beta peptide deposits, such AD. In one embodiment, the method comprises selecting a PDE5 inhibitor compound that can modulate secretase activity for at least 1 month after completion of administration of the PDE5 inhibitor compound in an animal model of amyloid-beta peptide deposit accumulation. In another embodiment, the method comprises selecting a PDE5 inhibitor compound that comprises one or both of the following features: (a) the compound interacts with two or more amino acid residues of a phosphodiesterase protein, wherein the amino acid residues comprise F787, L804, I813, M816, or a combination thereof, or (b) the $2^{nd}$ bridging ligand (BL2) between the compound and a phosphodiesterase protein is OH—. In another embodiment, the method can comprise selecting a PDE5 inhibitor compound having one or more of the following features: (a) the IC$_{50}$ of the compound is no more than about 1000 nM; (b) the selectivity of the compound is at least a 50 fold greater potency towards PDE5 relative to PDE1, PDE2, PDE3, PDE4, PDE6, PDE7, PDE8, PDE9, PDE10, or PDE11; (c) the PDE5 inhibitory activity in vitro has an IC$_{50}$ no more than about 50 nM; (d) the compound penetrates the blood brain barrier; (e) the compound hydrolyzes cGMP by about 20% to about 80%; (f) the $2^{nd}$ bridging ligand (BL2) between the compound and a phosphodiesterase protein is OH—; or (g) the compound interacts with two or more amino acid residues of a phosphodiesterase protein, wherein the amino acid residues comprise F787, L804, I813, M816, or a combination thereof. In a further embodiment, the compound, for example the PDE5 inhibitor, has an IC$_{50}$ of at least about 0.1 nM, at least about 1 nM, at least about 5 nM, at least about 10 nM, at least about 25 nM, at least about 50 nM, at least about 100 nM, at least about 200 nM, at least about 300 nM, at least about 400 nM, at least about 500 nM, at least about 600 nM, at least about 700 nM, at least about 800 nM, or at least about 900 nM. In another embodiment, PDE5 inhibitory activity in vitro has an $IC_{50}$ of at least about 0.1 nM, at least about 1 nM, at least about 5 nM, at least about 10 nM, at least about 15 nM, at least about 20 nM, at least about 25 nM, at least about 30 nM, at least about 35 nM, at least about 40 nM, of at least about 45 nM, but no more than about 50 nM. In some embodiments, the PDE5 inhibitor compound can have a molecular mass less than about 500 Da in order to penetrate the blood brain barrier. In other embodiments, the PDE5 inhibitor compound can have a polar surface area less than about 90 $Å^2$ and should have 8 or fewer hydrogen bonds in order to penetrate the blood brain barrier. The screening and identifying of the compound can comprise in silico screening, molecular docking, in vivo screening, in vitro screening, or a combination thereof.

Test compounds, such as PDE5 inhibitor compounds, can be screened from large libraries of synthetic or natural compounds (see Wang et al., (2007) *Curr Med Chem*, 14(2):133-55; Mannhold (2006) *Curr Top Med Chem*, 6 (10):1031-47; and Hensen (2006) *Curr Med Chem* 13(4): 361-76). Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., (1996) *Tib Tech* 14:60).

Methods for preparing libraries of molecules are well known in the art and many libraries are commercially available. Libraries of interest in the invention include peptide libraries, randomized oligonucleotide libraries, synthetic organic combinatorial libraries, and the like. Degenerate peptide libraries can be readily prepared in solution, in immobilized form as bacterial flagella peptide displaying libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include for example but are not limited to peptide-on-plasmid libraries, polysome libraries, aptamer libraries, synthetic peptide libraries, synthetic small molecule libraries, neurotransmitter libraries, and chemical libraries. The libraries can also comprise cyclic carbon or heterocyclic structure and/or aromatic or polyaromatic structures substituted with one or more of the functional groups described herein.

Small molecule combinatorial libraries can also be generated and screened. A combinatorial library of small organic compounds is a collection of closely related analogs that differ from each other in one or more points of diversity and are synthesized by organic techniques using multi-step processes. Combinatorial libraries include a vast number of small organic compounds. One type of combinatorial library is prepared by means of parallel synthesis methods to produce a compound array. A compound array can be a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in U.S. Ser. No. 08/177,497, filed Jan. 5, 1994 and its corresponding PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

Examples of chemically synthesized libraries are described in Fodor et al., (1991) *Science* 251:767-773; Houghten et al., (1991) *Nature* 354:84-86; Lam et al., (1991) *Nature* 354:82-84; Medynski, (1994) *BioTechnology* 12:709-710; Gallop et al., (1994) *J. Medicinal Chemistry* 37(9):1233-1251; Ohlmeyer et al., (1993) *Proc. Natl. Acad. Sci. USA* 90:10922-10926; Erb et al., (1994) *Proc. Natl. Acad. Sci. USA* 91:11422-11426; Houghten et al., (1992) *Biotechniques* 13:412; Jayawickreme et al., (1994) *Proc. Natl. Acad. Sci. USA* 91:1614-1618; Salmon et al., (1993) *Proc. Natl. Acad. Sci. USA* 90:11708-11712; PCT Publication No. WO 93/20242, dated Oct. 14, 1993; and Brenner et al., (1992) *Proc. Natl. Acad. Sci. USA* 89:5381-5383.

Examples of phage display libraries are described in Scott et al., (1990) *Science* 249:386-390; Devlin et al., (1990) *Science*, 249:404-406; Christian, et al., (1992) *J. Mol. Biol.* 227:711-718; Lenstra, (1992) *J. Immunol. Meth.* 152:149-157; Kay et al., (1993) *Gene* 128:59-65; and PCT Publication No. WO 94/18318.

In vitro translation-based libraries include but are not limited to those described in PCT Publication No. WO 91/05058; and Mattheakis et al., (1994) *Proc. Natl. Acad. Sci. USA* 91:9022-9026.

In one non-limiting example, non-peptide libraries, such as a benzodiazepine library (see e.g., Bunin et al., (1994) *Proc. Natl. Acad. Sci. USA* 91:4708-4712), can be screened. Peptoid libraries, such as that described by Simon et al., (1992) *Proc. Natl. Acad. Sci. USA* 89:9367-9371, can also be used. Another example of a library that can be used, in which the amide functionalities in peptides have been permethylated to generate a chemically transformed combinatorial library, is described by Ostresh et al. (1994), *Proc. Natl. Acad. Sci. USA* 91:11138-11142.

The three dimensional geometric structure of an active site, for example that of a PDE5 polypeptide can be determined by known methods in the art, such as X-ray crystallography, which can determine a complete molecular structure. Solid or liquid phase NMR can be used to determine certain intramolecular distances. Any other experimental method of structure determination can be used to obtain partial or complete geometric structures. The geometric structures can be measured with a complexed ligand, natural or artificial, which can increase the accuracy of the active site structure determined. In one embodiment, a compound that binds to a PDE5 protein can be identified via: (1) providing an electronic library of test compounds; (2) providing atomic coordinates listed in Table 1 for at least 20 amino acid residues for the active site of PDE5 (see PDB Entry No. 1RKP), wherein the coordinates have a root mean square deviation therefrom, with respect to at least 50% of $C\alpha$ atoms, of not greater than about 2 Å, in a computer readable format; (3) converting the atomic coordinates into electrical signals readable by a computer processor to generate a three dimensional model of the PDE5 protein; (4) performing a data processing method, wherein electronic test compounds from the library are docked onto the three dimensional model of the PDE5 protein; and determining which test compound fits into the active site of the three dimensional model of the PDE5 protein, thereby identifying which compound would bind to PDE5. In another embodiment, the method can further comprise: synthesizing or obtaining the compound determined to dock to the active site of the PDE5 protein; contacting the PDE5 protein with the compound under a condition suitable for binding; and determining whether the compound modulates PDE5 protein expression or mRNA expression, or PDE5 protein activity using a diagnostic assay.

TABLE 1

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 | |
|---|---|---|---|---|---|---|---|---|---|---|---|
| ATOM | 1 | N | GLU | A | 535 | 62.379 | 7.919 | 74.219 | 1.00 | 64.07 | N |
| ATOM | 2 | CA | GLU | A | 535 | 61.655 | 7.334 | 75.386 | 1.00 | 64.13 | C |
| ATOM | 3 | C | GLU | A | 535 | 60.151 | 7.585 | 75.248 | 1.00 | 63.42 | C |
| ATOM | 4 | O | GLU | A | 535 | 59.719 | 8.722 | 75.040 | 1.00 | 63.16 | O |
| ATOM | 5 | CB | GLU | A | 535 | 62.164 | 7.961 | 76.686 | 1.00 | 64.66 | C |
| ATOM | 6 | CG | GLU | A | 535 | 61.856 | 7.150 | 77.938 | 1.00 | 65.75 | C |
| ATOM | 7 | CD | GLU | A | 535 | 63.045 | 6.329 | 78.407 | 1.00 | 66.70 | C |
| ATOM | 8 | OE1 | GLU | A | 535 | 64.082 | 6.932 | 78.763 | 1.00 | 66.73 | O |
| ATOM | 9 | OE2 | GLU | A | 535 | 62.945 | 5.083 | 78.421 | 1.00 | 67.31 | O |
| ATOM | 10 | N | GLU | A | 536 | 59.361 | 6.521 | 75.369 | 1.00 | 62.64 | N |
| ATOM | 11 | CA | GLU | A | 536 | 57.907 | 6.617 | 75.248 | 1.00 | 61.52 | C |
| ATOM | 12 | C | GLU | A | 536 | 57.196 | 6.915 | 76.564 | 1.00 | 60.16 | C |
| ATOM | 13 | O | GLU | A | 536 | 56.375 | 7.833 | 76.636 | 1.00 | 59.78 | O |
| ATOM | 14 | CB | GLU | A | 536 | 57.339 | 5.329 | 74.643 | 1.00 | 62.35 | C |
| ATOM | 15 | CG | GLU | A | 536 | 57.611 | 5.170 | 73.154 | 1.00 | 63.55 | C |
| ATOM | 16 | CD | GLU | A | 536 | 57.015 | 3.896 | 72.584 | 1.00 | 64.28 | C |
| ATOM | 17 | OE1 | GLU | A | 536 | 55.799 | 3.669 | 72.770 | 1.00 | 64.70 | O |
| ATOM | 18 | OE2 | GLU | A | 536 | 57.761 | 3.124 | 71.946 | 1.00 | 64.83 | O |
| ATOM | 19 | N | THR | A | 537 | 57.499 | 6.139 | 77.601 | 1.00 | 58.22 | N |
| ATOM | 20 | CA | THR | A | 537 | 56.868 | 6.353 | 78.895 | 1.00 | 56.36 | C |
| ATOM | 21 | C | THR | A | 537 | 57.251 | 7.740 | 79.400 | 1.00 | 54.93 | C |
| ATOM | 22 | O | THR | A | 537 | 56.556 | 8.322 | 80.227 | 1.00 | 55.10 | O |
| ATOM | 23 | CB | THR | A | 537 | 57.303 | 5.291 | 79.924 | 1.00 | 56.64 | C |
| ATOM | 24 | OG1 | THR | A | 537 | 56.388 | 5.291 | 81.027 | 1.00 | 56.74 | O |
| ATOM | 25 | CG2 | THR | A | 537 | 58.704 | 5.584 | 80.436 | 1.00 | 56.58 | C |
| ATOM | 26 | N | ARG | A | 538 | 58.360 | 8.268 | 78.892 | 1.00 | 53.09 | N |
| ATOM | 27 | CA | ARG | A | 538 | 58.813 | 9.594 | 79.287 | 1.00 | 51.19 | C |
| ATOM | 28 | C | ARG | A | 538 | 57.880 | 10.610 | 78.643 | 1.00 | 48.94 | C |
| ATOM | 29 | O | ARG | A | 538 | 57.497 | 11.602 | 79.264 | 1.00 | 48.50 | O |
| ATOM | 30 | CB | ARG | A | 538 | 60.247 | 9.836 | 78.816 | 1.00 | 53.02 | C |
| ATOM | 31 | CG | ARG | A | 538 | 60.906 | 11.044 | 79.458 | 1.00 | 55.21 | C |
| ATOM | 32 | CD | ARG | A | 538 | 62.339 | 11.222 | 78.983 | 1.00 | 57.48 | C |
| ATOM | 33 | NE | ARG | A | 538 | 63.018 | 12.282 | 79.722 | 1.00 | 59.89 | N |
| ATOM | 34 | CZ | ARG | A | 538 | 64.205 | 12.785 | 79.395 | 1.00 | 60.96 | C |
| ATOM | 35 | NH1 | ARG | A | 538 | 64.853 | 12.324 | 78.332 | 1.00 | 61.46 | N |
| ATOM | 36 | NH2 | ARG | A | 538 | 64.743 | 13.750 | 80.131 | 1.00 | 61.65 | N |
| ATOM | 37 | N | GLU | A | 539 | 57.518 | 10.357 | 77.388 | 1.00 | 45.81 | N |
| ATOM | 38 | CA | GLU | A | 539 | 56.609 | 11.242 | 76.679 | 1.00 | 42.68 | C |
| ATOM | 39 | C | GLU | A | 539 | 55.251 | 11.195 | 77.377 | 1.00 | 40.37 | C |
| ATOM | 40 | O | GLU | A | 539 | 54.585 | 12.214 | 77.519 | 1.00 | 39.22 | O |
| ATOM | 41 | CB | GLU | A | 539 | 56.460 | 10.808 | 75.215 | 1.00 | 43.02 | C |
| ATOM | 42 | CG | GLU | A | 539 | 55.432 | 11.626 | 74.449 | 1.00 | 43.19 | C |
| ATOM | 43 | CD | GLU | A | 539 | 55.298 | 11.213 | 72.995 | 1.00 | 44.20 | C |
| ATOM | 44 | OE1 | GLU | A | 539 | 55.160 | 10.000 | 72.723 | 1.00 | 45.03 | O |
| ATOM | 45 | OE2 | GLU | A | 539 | 55.317 | 12.106 | 72.125 | 1.00 | 43.70 | O |
| ATOM | 46 | N | LEU | A | 540 | 54.849 | 10.005 | 77.811 | 1.00 | 38.56 | N |
| ATOM | 47 | CA | LEU | A | 540 | 53.576 | 9.835 | 78.503 | 1.00 | 37.86 | C |
| ATOM | 48 | C | LEU | A | 540 | 53.597 | 10.591 | 79.829 | 1.00 | 37.30 | C |
| ATOM | 49 | O | LEU | A | 540 | 52.619 | 11.232 | 80.210 | 1.00 | 36.88 | O |
| ATOM | 50 | CB | LEU | A | 540 | 53.310 | 8.351 | 78.766 | 1.00 | 37.38 | C |
| ATOM | 51 | CG | LEU | A | 540 | 52.109 | 8.025 | 79.659 | 1.00 | 37.39 | C |
| ATOM | 52 | CD1 | LEU | A | 540 | 50.830 | 8.560 | 79.034 | 1.00 | 36.69 | C |
| ATOM | 53 | CD2 | LEU | A | 540 | 52.023 | 6.516 | 79.857 | 1.00 | 37.22 | C |
| ATOM | 54 | N | GLN | A | 541 | 54.720 | 10.498 | 80.532 | 1.00 | 36.78 | N |
| ATOM | 55 | CA | GLN | A | 541 | 54.882 | 11.179 | 81.807 | 1.00 | 36.28 | C |
| ATOM | 56 | C | GLN | A | 541 | 54.701 | 12.681 | 81.603 | 1.00 | 35.16 | C |
| ATOM | 57 | O | GLN | A | 541 | 53.961 | 13.335 | 82.343 | 1.00 | 34.46 | O |
| ATOM | 58 | CB | GLN | A | 541 | 56.271 | 10.886 | 82.382 | 1.00 | 37.39 | C |
| ATOM | 59 | CG | GLN | A | 541 | 56.571 | 11.610 | 83.685 | 1.00 | 39.02 | C |
| ATOM | 60 | CD | GLN | A | 541 | 57.923 | 11.232 | 84.260 | 1.00 | 40.18 | C |
| ATOM | 61 | OE1 | GLN | A | 541 | 58.950 | 11.337 | 83.585 | 1.00 | 41.02 | O |
| ATOM | 62 | NE2 | GLN | A | 541 | 57.930 | 10.790 | 85.512 | 1.00 | 40.34 | N |
| ATOM | 63 | N | SER | A | 542 | 55.363 | 13.216 | 80.579 | 1.00 | 33.84 | N |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 | |
|---|---|---|---|---|---|---|---|---|---|---|---|
| ATOM | 64 | CA | SER | A | 542 | 55.282 | 14.643 | 80.269 | 1.00 | 32.54 | C |
| ATOM | 65 | C | SER | A | 542 | 53.883 | 15.091 | 79.858 | 1.00 | 31.82 | C |
| ATOM | 66 | O | SER | A | 542 | 53.407 | 16.139 | 80.299 | 1.00 | 31.56 | O |
| ATOM | 67 | CB | SER | A | 542 | 56.265 | 14.991 | 79.151 | 1.00 | 33.33 | C |
| ATOM | 68 | OG | SER | A | 542 | 57.577 | 14.582 | 79.496 | 1.00 | 35.00 | O |
| ATOM | 69 | N | LEU | A | 543 | 53.225 | 14.310 | 79.006 | 1.00 | 30.20 | N |
| ATOM | 70 | CA | LEU | A | 543 | 51.887 | 14.674 | 78.558 | 1.00 | 29.51 | C |
| ATOM | 71 | C | LEU | A | 543 | 50.901 | 14.617 | 79.721 | 1.00 | 29.02 | C |
| ATOM | 72 | O | LEU | A | 543 | 50.123 | 15.542 | 79.924 | 1.00 | 28.83 | O |
| ATOM | 73 | CB | LEU | A | 543 | 51.423 | 13.738 | 77.435 | 1.00 | 29.76 | C |
| ATOM | 74 | CG | LEU | A | 543 | 49.958 | 13.851 | 76.997 | 1.00 | 28.65 | C |
| ATOM | 75 | CD1 | LEU | A | 543 | 49.697 | 15.223 | 76.399 | 1.00 | 28.64 | C |
| ATOM | 76 | CD2 | LEU | A | 543 | 49.644 | 12.751 | 75.989 | 1.00 | 29.19 | C |
| ATOM | 77 | N | ALA | A | 544 | 50.946 | 13.530 | 80.489 | 1.00 | 28.94 | N |
| ATOM | 78 | CA | ALA | A | 544 | 50.036 | 13.351 | 81.617 | 1.00 | 29.97 | C |
| ATOM | 79 | C | ALA | A | 544 | 50.184 | 14.418 | 82.704 | 1.00 | 30.89 | C |
| ATOM | 80 | O | ALA | A | 544 | 49.209 | 14.770 | 83.366 | 1.00 | 30.59 | O |
| ATOM | 81 | CB | ALA | A | 544 | 50.225 | 11.956 | 82.225 | 1.00 | 29.71 | C |
| ATOM | 82 | N | ALA | A | 545 | 51.395 | 14.935 | 82.879 | 1.00 | 31.85 | N |
| ATOM | 83 | CA | ALA | A | 545 | 51.657 | 15.949 | 83.898 | 1.00 | 33.51 | C |
| ATOM | 84 | C | ALA | A | 545 | 51.448 | 17.378 | 83.401 | 1.00 | 35.05 | C |
| ATOM | 85 | O | ALA | A | 545 | 51.354 | 18.315 | 84.199 | 1.00 | 36.04 | O |
| ATOM | 86 | CB | ALA | A | 545 | 53.076 | 15.795 | 84.416 | 1.00 | 33.74 | C |
| ATOM | 87 | N | ALA | A | 546 | 51.374 | 17.549 | 82.086 | 1.00 | 35.09 | N |
| ATOM | 88 | CA | ALA | A | 546 | 51.201 | 18.874 | 81.515 | 1.00 | 35.61 | C |
| ATOM | 89 | C | ALA | A | 546 | 49.813 | 19.438 | 81.763 | 1.00 | 35.63 | C |
| ATOM | 90 | O | ALA | A | 546 | 48.836 | 18.707 | 81.877 | 1.00 | 35.97 | O |
| ATOM | 91 | CB | ALA | A | 546 | 51.487 | 18.838 | 80.015 | 1.00 | 36.50 | C |
| ATOM | 92 | N | VAL | A | 547 | 49.733 | 20.756 | 81.847 | 1.00 | 35.36 | N |
| ATOM | 93 | CA | VAL | A | 547 | 48.461 | 21.416 | 82.059 | 1.00 | 35.33 | C |
| ATOM | 94 | C | VAL | A | 547 | 47.841 | 21.577 | 80.665 | 1.00 | 34.74 | C |
| ATOM | 95 | O | VAL | A | 547 | 48.558 | 21.821 | 79.694 | 1.00 | 33.97 | O |
| ATOM | 96 | CB | VAL | A | 547 | 48.679 | 22.785 | 82.745 | 1.00 | 36.26 | C |
| ATOM | 97 | CG1 | VAL | A | 547 | 49.003 | 23.844 | 81.721 | 1.00 | 36.87 | C |
| ATOM | 98 | CG2 | VAL | A | 547 | 47.470 | 23.147 | 83.570 | 1.00 | 36.92 | C |
| ATOM | 99 | N | VAL | A | 548 | 46.523 | 21.414 | 80.568 | 1.00 | 33.98 | N |
| ATOM | 100 | CA | VAL | A | 548 | 45.818 | 21.511 | 79.285 | 1.00 | 33.32 | C |
| ATOM | 101 | C | VAL | A | 548 | 45.177 | 22.876 | 79.070 | 1.00 | 33.04 | C |
| ATOM | 102 | O | VAL | A | 548 | 44.125 | 23.169 | 79.621 | 1.00 | 33.68 | O |
| ATOM | 103 | CB | VAL | A | 548 | 44.700 | 20.438 | 79.174 | 1.00 | 32.34 | C |
| ATOM | 104 | CG1 | VAL | A | 548 | 44.086 | 20.460 | 77.776 | 1.00 | 31.44 | C |
| ATOM | 105 | CG2 | VAL | A | 548 | 45.261 | 19.058 | 79.494 | 1.00 | 32.61 | C |
| ATOM | 106 | N | PRO | A | 549 | 45.795 | 23.724 | 78.243 | 1.00 | 33.67 | N |
| ATOM | 107 | CA | PRO | A | 549 | 45.221 | 25.051 | 78.002 | 1.00 | 33.42 | C |
| ATOM | 108 | C | PRO | A | 549 | 43.829 | 25.004 | 77.368 | 1.00 | 33.26 | C |
| ATOM | 109 | O | PRO | A | 549 | 43.436 | 24.002 | 76.759 | 1.00 | 33.22 | O |
| ATOM | 110 | CB | PRO | A | 549 | 46.274 | 25.728 | 77.126 | 1.00 | 33.75 | C |
| ATOM | 111 | CG | PRO | A | 549 | 46.905 | 24.588 | 76.413 | 1.00 | 34.40 | C |
| ATOM | 112 | CD | PRO | A | 549 | 47.031 | 23.529 | 77.471 | 1.00 | 33.46 | C |
| ATOM | 113 | N | SER | A | 550 | 43.083 | 26.090 | 77.537 | 1.00 | 32.37 | N |
| ATOM | 114 | CA | SER | A | 550 | 41.721 | 26.199 | 77.023 | 1.00 | 32.42 | C |
| ATOM | 115 | C | SER | A | 550 | 41.629 | 26.072 | 75.510 | 1.00 | 32.15 | C |
| ATOM | 116 | O | SER | A | 550 | 42.619 | 26.223 | 74.802 | 1.00 | 32.01 | O |
| ATOM | 117 | CB | SER | A | 550 | 41.116 | 27.541 | 77.421 | 1.00 | 32.10 | C |
| ATOM | 118 | OG | SER | A | 550 | 41.756 | 28.591 | 76.718 | 1.00 | 33.62 | O |
| ATOM | 119 | N | ALA | A | 551 | 40.418 | 25.801 | 75.032 | 1.00 | 32.30 | N |
| ATOM | 120 | CA | ALA | A | 551 | 40.150 | 25.667 | 73.608 | 1.00 | 32.75 | C |
| ATOM | 121 | C | ALA | A | 551 | 40.486 | 26.982 | 72.903 | 1.00 | 33.76 | C |
| ATOM | 122 | O | ALA | A | 551 | 41.063 | 26.986 | 71.809 | 1.00 | 32.78 | O |
| ATOM | 123 | CB | ALA | A | 551 | 38.688 | 25.323 | 73.389 | 1.00 | 31.08 | C |
| ATOM | 124 | N | GLN | A | 552 | 40.112 | 28.093 | 73.533 | 1.00 | 35.12 | N |
| ATOM | 125 | CA | GLN | A | 552 | 40.373 | 29.419 | 72.977 | 1.00 | 36.28 | C |
| ATOM | 126 | C | GLN | A | 552 | 41.872 | 29.640 | 72.816 | 1.00 | 35.40 | C |
| ATOM | 127 | O | GLN | A | 552 | 42.327 | 30.095 | 71.772 | 1.00 | 35.68 | O |
| ATOM | 128 | CB | GLN | A | 552 | 39.787 | 30.508 | 73.887 | 1.00 | 38.28 | C |
| ATOM | 129 | CG | GLN | A | 552 | 40.175 | 31.927 | 73.474 | 1.00 | 41.97 | C |
| ATOM | 130 | CD | GLN | A | 552 | 39.584 | 32.998 | 74.381 | 1.00 | 44.31 | C |
| ATOM | 131 | OE1 | GLN | A | 552 | 39.738 | 32.952 | 75.604 | 1.00 | 45.94 | O |
| ATOM | 132 | NE2 | GLN | A | 552 | 38.912 | 33.977 | 73.780 | 1.00 | 45.25 | N |
| ATOM | 133 | N | THR | A | 553 | 42.634 | 29.313 | 73.854 | 1.00 | 35.24 | N |
| ATOM | 134 | CA | THR | A | 553 | 44.084 | 29.479 | 73.815 | 1.00 | 35.13 | C |
| ATOM | 135 | C | THR | A | 553 | 44.719 | 28.630 | 72.709 | 1.00 | 34.63 | C |
| ATOM | 136 | O | THR | A | 553 | 45.675 | 29.057 | 72.059 | 1.00 | 34.04 | O |
| ATOM | 137 | CB | THR | A | 553 | 44.727 | 29.081 | 75.166 | 1.00 | 35.91 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | 74.456 | 130.132 | 90.00 | 90.00 | 120.00 | P 31 2 1 6 | |
|---|---|---|---|---|---|---|---|---|---|---|
| ATOM | 138 | OG1 | THR | A | 553 | 44.289 | 29.978 | 76.193 | 1.00 | 36.78 | O |
| ATOM | 139 | CG2 | THR | A | 553 | 46.246 | 29.119 | 75.073 | 1.00 | 36.40 | C |
| ATOM | 140 | N | LEU | A | 554 | 44.177 | 27.432 | 72.497 | 1.00 | 33.49 | N |
| ATOM | 141 | CA | LEU | A | 554 | 44.707 | 26.510 | 71.492 | 1.00 | 32.20 | C |
| ATOM | 142 | C | LEU | A | 554 | 44.226 | 26.770 | 70.066 | 1.00 | 31.50 | C |
| ATOM | 143 | O | LEU | A | 554 | 44.740 | 26.175 | 69.114 | 1.00 | 30.62 | O |
| ATOM | 144 | CB | LEU | A | 554 | 44.380 | 25.071 | 71.901 | 1.00 | 31.79 | C |
| ATOM | 145 | CG | LEU | A | 554 | 44.996 | 24.657 | 73.238 | 1.00 | 32.19 | C |
| ATOM | 146 | CD1 | LEU | A | 554 | 44.540 | 23.259 | 73.623 | 1.00 | 31.66 | C |
| ATOM | 147 | CD2 | LEU | A | 554 | 46.521 | 24.722 | 73.124 | 1.00 | 31.58 | C |
| ATOM | 148 | N | LYS | A | 555 | 43.243 | 27.657 | 69.925 | 1.00 | 30.33 | N |
| ATOM | 149 | CA | LYS | A | 555 | 42.692 | 28.018 | 68.623 | 1.00 | 30.16 | C |
| ATOM | 150 | C | LYS | A | 555 | 41.999 | 26.865 | 67.903 | 1.00 | 29.96 | C |
| ATOM | 151 | O | LYS | A | 555 | 41.728 | 26.970 | 66.703 | 1.00 | 29.11 | O |
| ATOM | 152 | CB | LYS | A | 555 | 43.801 | 28.544 | 67.708 | 1.00 | 31.51 | C |
| ATOM | 153 | CG | LYS | A | 555 | 44.678 | 29.622 | 68.306 | 1.00 | 32.51 | C |
| ATOM | 154 | CD | LYS | A | 555 | 45.948 | 29.766 | 67.480 | 1.00 | 34.45 | C |
| ATOM | 155 | CE | LYS | A | 555 | 47.010 | 30.567 | 68.213 | 1.00 | 35.84 | C |
| ATOM | 156 | NZ | LYS | A | 555 | 48.314 | 30.485 | 67.485 | 1.00 | 37.56 | N |
| ATOM | 157 | N | ILE | A | 556 | 41.695 | 25.781 | 68.615 | 1.00 | 28.78 | N |
| ATOM | 158 | CA | ILE | A | 556 | 41.076 | 24.624 | 67.971 | 1.00 | 28.91 | C |
| ATOM | 159 | C | ILE | A | 556 | 39.622 | 24.779 | 67.543 | 1.00 | 29.19 | C |
| ATOM | 160 | O | ILE | A | 556 | 39.063 | 23.879 | 66.917 | 1.00 | 29.06 | O |
| ATOM | 161 | CB | ILE | A | 556 | 41.202 | 23.345 | 68.841 | 1.00 | 28.80 | C |
| ATOM | 162 | CG1 | ILE | A | 556 | 40.496 | 23.536 | 70.183 | 1.00 | 28.62 | C |
| ATOM | 163 | CG2 | ILE | A | 556 | 42.671 | 23.010 | 69.044 | 1.00 | 27.87 | C |
| ATOM | 164 | CD1 | ILE | A | 556 | 40.373 | 22.258 | 70.988 | 1.00 | 28.38 | C |
| ATOM | 165 | N | THR | A | 557 | 39.009 | 25.912 | 67.866 | 1.00 | 29.50 | N |
| ATOM | 166 | CA | THR | A | 557 | 37.628 | 26.149 | 67.466 | 1.00 | 30.59 | C |
| ATOM | 167 | C | THR | A | 557 | 37.590 | 26.846 | 66.102 | 1.00 | 30.62 | C |
| ATOM | 168 | O | THR | A | 557 | 36.543 | 26.918 | 65.464 | 1.00 | 30.24 | O |
| ATOM | 169 | CB | THR | A | 557 | 36.883 | 27.031 | 68.495 | 1.00 | 32.28 | C |
| ATOM | 170 | OG1 | THR | A | 557 | 37.071 | 26.494 | 69.811 | 1.00 | 32.94 | O |
| ATOM | 171 | CG2 | THR | A | 557 | 35.387 | 27.063 | 68.186 | 1.00 | 32.13 | C |
| ATOM | 172 | N | ASP | A | 558 | 38.745 | 27.341 | 65.656 | 1.00 | 30.86 | N |
| ATOM | 173 | CA | ASP | A | 558 | 38.852 | 28.040 | 64.374 | 1.00 | 30.19 | C |
| ATOM | 174 | C | ASP | A | 558 | 38.948 | 27.094 | 63.171 | 1.00 | 29.95 | C |
| ATOM | 175 | O | ASP | A | 558 | 39.790 | 26.195 | 63.144 | 1.00 | 29.77 | O |
| ATOM | 176 | CB | ASP | A | 558 | 40.098 | 28.942 | 64.337 | 1.00 | 31.32 | C |
| ATOM | 177 | CG | ASP | A | 558 | 40.227 | 29.844 | 65.553 | 1.00 | 33.65 | C |
| ATOM | 178 | OD1 | ASP | A | 558 | 39.214 | 30.102 | 66.247 | 1.00 | 35.70 | O |
| ATOM | 179 | OD2 | ASP | A | 558 | 41.358 | 30.315 | 65.803 | 1.00 | 33.50 | O |
| ATOM | 180 | N | PHE | A | 559 | 38.108 | 27.309 | 62.164 | 1.00 | 28.55 | N |
| ATOM | 181 | CA | PHE | A | 559 | 38.176 | 26.478 | 60.974 | 1.00 | 28.88 | C |
| ATOM | 182 | C | PHE | A | 559 | 39.515 | 26.708 | 60.270 | 1.00 | 28.34 | C |
| ATOM | 183 | O | PHE | A | 559 | 40.006 | 25.839 | 59.553 | 1.00 | 27.56 | O |
| ATOM | 184 | CB | PHE | A | 559 | 37.028 | 26.800 | 60.012 | 1.00 | 29.35 | C |
| ATOM | 185 | CG | PHE | A | 559 | 35.697 | 26.246 | 60.443 | 1.00 | 30.27 | C |
| ATOM | 186 | CD1 | PHE | A | 559 | 34.686 | 27.091 | 60.889 | 1.00 | 31.00 | C |
| ATOM | 187 | CD2 | PHE | A | 559 | 35.453 | 24.874 | 60.392 | 1.00 | 30.91 | C |
| ATOM | 188 | CE1 | PHE | A | 559 | 33.443 | 26.579 | 61.282 | 1.00 | 31.39 | C |
| ATOM | 189 | CE2 | PHE | A | 559 | 34.223 | 24.349 | 60.779 | 1.00 | 30.09 | C |
| ATOM | 190 | CZ | PHE | A | 559 | 33.212 | 25.206 | 61.226 | 1.00 | 31.43 | C |
| ATOM | 191 | N | SER | A | 560 | 40.111 | 27.876 | 60.497 | 1.00 | 27.63 | N |
| ATOM | 192 | CA | SER | A | 560 | 41.388 | 28.226 | 59.877 | 1.00 | 27.38 | C |
| ATOM | 193 | C | SER | A | 560 | 42.605 | 27.663 | 60.605 | 1.00 | 26.39 | C |
| ATOM | 194 | O | SER | A | 560 | 43.742 | 27.952 | 60.233 | 1.00 | 26.83 | O |
| ATOM | 195 | CB | SER | A | 560 | 41.525 | 29.751 | 59.779 | 1.00 | 28.09 | C |
| ATOM | 196 | OG | SER | A | 560 | 40.526 | 30.291 | 58.929 | 1.00 | 31.03 | O |
| ATOM | 197 | N | PHE | A | 561 | 42.361 | 26.860 | 61.635 | 1.00 | 24.77 | N |
| ATOM | 198 | CA | PHE | A | 561 | 43.424 | 26.255 | 62.430 | 1.00 | 23.76 | C |
| ATOM | 199 | C | PHE | A | 561 | 44.554 | 25.643 | 61.607 | 1.00 | 23.00 | C |
| ATOM | 200 | O | PHE | A | 561 | 44.324 | 25.035 | 60.561 | 1.00 | 21.56 | O |
| ATOM | 201 | CB | PHE | A | 561 | 42.826 | 25.174 | 63.338 | 1.00 | 24.56 | C |
| ATOM | 202 | CG | PHE | A | 561 | 43.837 | 24.450 | 64.180 | 1.00 | 24.58 | C |
| ATOM | 203 | CD1 | PHE | A | 561 | 44.259 | 24.980 | 65.401 | 1.00 | 24.44 | C |
| ATOM | 204 | CD2 | PHE | A | 561 | 44.343 | 23.215 | 63.772 | 1.00 | 25.19 | C |
| ATOM | 205 | CE1 | PHE | A | 561 | 45.165 | 24.288 | 66.207 | 1.00 | 24.36 | C |
| ATOM | 206 | CE2 | PHE | A | 561 | 45.251 | 22.512 | 64.571 | 1.00 | 25.59 | C |
| ATOM | 207 | CZ | PHE | A | 561 | 45.663 | 23.049 | 65.794 | 1.00 | 25.48 | C |
| ATOM | 208 | N | SER | A | 562 | 45.774 | 25.796 | 62.111 | 1.00 | 22.34 | N |
| ATOM | 209 | CA | SER | A | 562 | 46.965 | 25.250 | 61.475 | 1.00 | 22.82 | C |
| ATOM | 210 | C | SER | A | 562 | 47.840 | 24.661 | 62.574 | 1.00 | 22.93 | C |
| ATOM | 211 | O | SER | A | 562 | 47.844 | 25.169 | 63.699 | 1.00 | 23.69 | O |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 | 6 |
|---|---|---|---|---|---|---|---|---|---|---|---|
| ATOM | 212 | CB | SER | A | 562 | 47.739 | 26.344 | 60.737 | 1.00 | 22.99 | C |
| ATOM | 213 | OG | SER | A | 562 | 48.934 | 25.814 | 60.195 | 1.00 | 23.71 | O |
| ATOM | 214 | N | ASP | A | 563 | 48.596 | 23.614 | 62.249 | 1.00 | 22.12 | N |
| ATOM | 215 | CA | ASP | A | 563 | 49.447 | 22.940 | 63.233 | 1.00 | 22.41 | C |
| ATOM | 216 | C | ASP | A | 563 | 50.950 | 23.082 | 62.994 | 1.00 | 22.50 | C |
| ATOM | 217 | O | ASP | A | 563 | 51.749 | 22.540 | 63.761 | 1.00 | 21.60 | O |
| ATOM | 218 | CB | ASP | A | 563 | 49.139 | 21.445 | 63.238 | 1.00 | 22.28 | C |
| ATOM | 219 | CG | ASP | A | 563 | 49.639 | 20.761 | 61.982 | 1.00 | 22.77 | C |
| ATOM | 220 | OD1 | ASP | A | 563 | 49.156 | 21.113 | 60.884 | 1.00 | 22.58 | O |
| ATOM | 221 | OD2 | ASP | A | 563 | 50.524 | 19.884 | 62.087 | 1.00 | 24.62 | O |
| ATOM | 222 | N | PHE | A | 564 | 51.338 | 23.780 | 61.935 | 1.00 | 22.69 | N |
| ATOM | 223 | CA | PHE | A | 564 | 52.758 | 23.931 | 61.614 | 1.00 | 24.24 | C |
| ATOM | 224 | C | PHE | A | 564 | 53.661 | 24.395 | 62.754 | 1.00 | 24.20 | C |
| ATOM | 225 | O | PHE | A | 564 | 54.798 | 23.938 | 62.867 | 1.00 | 24.07 | O |
| ATOM | 226 | CB | PHE | A | 564 | 52.949 | 24.876 | 60.428 | 1.00 | 23.91 | C |
| ATOM | 227 | CG | PHE | A | 564 | 52.302 | 24.403 | 59.164 | 1.00 | 25.67 | C |
| ATOM | 228 | CD1 | PHE | A | 564 | 52.254 | 23.044 | 58.852 | 1.00 | 25.98 | C |
| ATOM | 229 | CD2 | PHE | A | 564 | 51.773 | 25.320 | 58.259 | 1.00 | 25.83 | C |
| ATOM | 230 | CE1 | PHE | A | 564 | 51.688 | 22.610 | 57.653 | 1.00 | 26.86 | C |
| ATOM | 231 | CE2 | PHE | A | 564 | 51.208 | 24.894 | 57.059 | 1.00 | 26.23 | C |
| ATOM | 232 | CZ | PHE | A | 564 | 51.166 | 23.538 | 56.757 | 1.00 | 26.71 | C |
| ATOM | 233 | N | GLU | A | 565 | 53.160 | 25.289 | 63.596 | 1.00 | 25.20 | N |
| ATOM | 234 | CA | GLU | A | 565 | 53.958 | 25.813 | 64.709 | 1.00 | 26.01 | C |
| ATOM | 235 | C | GLU | A | 565 | 53.905 | 24.956 | 65.974 | 1.00 | 26.25 | C |
| ATOM | 236 | O | GLU | A | 565 | 54.545 | 25.291 | 66.975 | 1.00 | 27.06 | O |
| ATOM | 237 | CB | GLU | A | 565 | 53.493 | 27.229 | 65.065 | 1.00 | 26.43 | C |
| ATOM | 238 | CG | GLU | A | 565 | 52.112 | 27.273 | 65.704 | 1.00 | 27.48 | C |
| ATOM | 239 | CD | GLU | A | 565 | 51.007 | 27.612 | 64.719 | 1.00 | 29.85 | C |
| ATOM | 240 | OE1 | GLU | A | 565 | 51.069 | 27.161 | 63.547 | 1.00 | 29.74 | O |
| ATOM | 241 | OE2 | GLU | A | 565 | 50.062 | 28.322 | 65.128 | 1.00 | 29.41 | O |
| ATOM | 242 | N | LEU | A | 566 | 53.157 | 23.856 | 65.932 | 1.00 | 25.62 | N |
| ATOM | 243 | CA | LEU | A | 566 | 53.002 | 22.986 | 67.098 | 1.00 | 25.15 | C |
| ATOM | 244 | C | LEU | A | 566 | 53.899 | 21.754 | 67.148 | 1.00 | 24.78 | C |
| ATOM | 245 | O | LEU | A | 566 | 54.209 | 21.150 | 66.123 | 1.00 | 23.05 | O |
| ATOM | 246 | CB | LEU | A | 566 | 51.543 | 22.518 | 67.214 | 1.00 | 25.60 | C |
| ATOM | 247 | CG | LEU | A | 566 | 50.441 | 23.576 | 67.189 | 1.00 | 25.20 | C |
| ATOM | 248 | CD1 | LEU | A | 566 | 49.075 | 22.889 | 67.203 | 1.00 | 25.03 | C |
| ATOM | 249 | CD2 | LEU | A | 566 | 50.591 | 24.512 | 68.379 | 1.00 | 25.68 | C |
| ATOM | 250 | N | SER | A | 567 | 54.298 | 21.382 | 68.363 | 1.00 | 24.50 | N |
| ATOM | 251 | CA | SER | A | 567 | 55.127 | 20.198 | 68.577 | 1.00 | 24.64 | C |
| ATOM | 252 | C | SER | A | 567 | 54.156 | 19.029 | 68.756 | 1.00 | 24.67 | C |
| ATOM | 253 | O | SER | A | 567 | 52.952 | 19.238 | 68.906 | 1.00 | 22.93 | O |
| ATOM | 254 | CB | SER | A | 567 | 55.948 | 20.348 | 69.857 | 1.00 | 24.05 | C |
| ATOM | 255 | OG | SER | A | 567 | 55.087 | 20.298 | 70.982 | 1.00 | 22.98 | O |
| ATOM | 256 | N | ASP | A | 568 | 54.668 | 17.805 | 68.747 | 1.00 | 25.45 | N |
| ATOM | 257 | CA | ASP | A | 568 | 53.785 | 16.658 | 68.934 | 1.00 | 27.39 | C |
| ATOM | 258 | C | ASP | A | 568 | 53.066 | 16.788 | 70.275 | 1.00 | 26.88 | C |
| ATOM | 259 | O | ASP | A | 568 | 51.856 | 16.593 | 70.357 | 1.00 | 26.09 | O |
| ATOM | 260 | CB | ASP | A | 568 | 54.570 | 15.343 | 68.888 | 1.00 | 28.31 | C |
| ATOM | 261 | CG | ASP | A | 568 | 55.002 | 14.974 | 67.484 | 1.00 | 30.28 | C |
| ATOM | 262 | OD1 | ASP | A | 568 | 54.551 | 15.634 | 66.525 | 1.00 | 31.20 | O |
| ATOM | 263 | OD2 | ASP | A | 568 | 55.787 | 14.015 | 67.334 | 1.00 | 32.48 | O |
| ATOM | 264 | N | LEU | A | 569 | 53.814 | 17.136 | 71.320 | 1.00 | 26.83 | N |
| ATOM | 265 | CA | LEU | A | 569 | 53.221 | 17.292 | 72.645 | 1.00 | 27.03 | C |
| ATOM | 266 | C | LEU | A | 569 | 52.036 | 18.245 | 72.612 | 1.00 | 26.05 | C |
| ATOM | 267 | O | LEU | A | 569 | 50.993 | 17.966 | 73.198 | 1.00 | 25.43 | O |
| ATOM | 268 | CB | LEU | A | 569 | 54.261 | 17.807 | 73.645 | 1.00 | 28.18 | C |
| ATOM | 269 | CG | LEU | A | 569 | 53.750 | 18.206 | 75.037 | 1.00 | 29.46 | C |
| ATOM | 270 | CD1 | LEU | A | 569 | 52.985 | 17.050 | 75.686 | 1.00 | 28.67 | C |
| ATOM | 271 | CD2 | LEU | A | 569 | 54.944 | 18.608 | 75.907 | 1.00 | 30.57 | C |
| ATOM | 272 | N | GLU | A | 570 | 52.196 | 19.365 | 71.915 | 1.00 | 25.43 | N |
| ATOM | 273 | CA | GLU | A | 570 | 51.128 | 20.356 | 71.812 | 1.00 | 24.71 | C |
| ATOM | 274 | C | GLU | A | 570 | 49.896 | 19.826 | 71.081 | 1.00 | 23.37 | C |
| ATOM | 275 | O | GLU | A | 570 | 48.767 | 20.187 | 71.425 | 1.00 | 23.26 | O |
| ATOM | 276 | CB | GLU | A | 570 | 51.636 | 21.628 | 71.115 | 1.00 | 25.60 | C |
| ATOM | 277 | CG | GLU | A | 570 | 52.525 | 22.514 | 71.987 | 1.00 | 28.27 | C |
| ATOM | 278 | CD | GLU | A | 570 | 53.057 | 23.728 | 71.244 | 1.00 | 28.00 | C |
| ATOM | 279 | OE1 | GLU | A | 570 | 53.797 | 23.548 | 70.258 | 1.00 | 28.59 | O |
| ATOM | 280 | OE2 | GLU | A | 570 | 52.734 | 24.864 | 71.642 | 1.00 | 30.03 | O |
| ATOM | 281 | N | THR | A | 571 | 50.096 | 18.988 | 70.068 | 1.00 | 22.80 | N |
| ATOM | 282 | CA | THR | A | 571 | 48.947 | 18.441 | 69.344 | 1.00 | 22.18 | C |
| ATOM | 283 | C | THR | A | 571 | 48.197 | 17.480 | 70.261 | 1.00 | 22.78 | C |
| ATOM | 284 | O | THR | A | 571 | 46.969 | 17.406 | 70.226 | 1.00 | 23.51 | O |
| ATOM | 285 | CB | THR | A | 571 | 49.360 | 17.699 | 68.046 | 1.00 | 22.43 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | 74.456 | 130.132 | 90.00 | 90.00 | 120.00 | P 31 2 1 6 | |
|---|---|---|---|---|---|---|---|---|---|---|
| ATOM | 286 | OG1 | THR | A | 571 | 50.197 | 16.577 | 68.362 | 1.00 | 22.41 | O |
| ATOM | 287 | CG2 | THR | A | 571 | 50.090 | 18.646 | 67.100 | 1.00 | 18.66 | C |
| ATOM | 288 | N | ALA | A | 572 | 48.944 | 16.747 | 71.081 | 1.00 | 22.45 | N |
| ATOM | 289 | CA | ALA | A | 572 | 48.350 | 15.811 | 72.035 | 1.00 | 23.41 | C |
| ATOM | 290 | C | ALA | A | 572 | 47.502 | 16.580 | 73.055 | 1.00 | 23.81 | C |
| ATOM | 291 | O | ALA | A | 572 | 46.420 | 16.138 | 73.434 | 1.00 | 24.50 | O |
| ATOM | 292 | CB | ALA | A | 572 | 49.448 | 15.032 | 72.745 | 1.00 | 22.55 | C |
| ATOM | 293 | N | LEU | A | 573 | 47.996 | 17.735 | 73.501 | 1.00 | 23.91 | N |
| ATOM | 294 | CA | LEU | A | 573 | 47.242 | 18.551 | 74.453 | 1.00 | 23.75 | C |
| ATOM | 295 | C | LEU | A | 573 | 45.977 | 19.077 | 73.792 | 1.00 | 22.73 | C |
| ATOM | 296 | O | LEU | A | 573 | 44.933 | 19.164 | 74.430 | 1.00 | 23.52 | O |
| ATOM | 297 | CB | LEU | A | 573 | 48.096 | 19.719 | 74.970 | 1.00 | 24.06 | C |
| ATOM | 298 | CG | LEU | A | 573 | 49.316 | 19.301 | 75.805 | 1.00 | 25.24 | C |
| ATOM | 299 | CD1 | LEU | A | 573 | 50.149 | 20.531 | 76.163 | 1.00 | 26.24 | C |
| ATOM | 300 | CD2 | LEU | A | 573 | 48.850 | 18.587 | 77.074 | 1.00 | 25.62 | C |
| ATOM | 301 | N | CYS | A | 574 | 46.069 | 19.428 | 72.510 | 1.00 | 22.65 | N |
| ATOM | 302 | CA | CYS | A | 574 | 44.906 | 19.914 | 71.770 | 1.00 | 21.72 | C |
| ATOM | 303 | C | CYS | A | 574 | 43.872 | 18.785 | 71.655 | 1.00 | 22.09 | C |
| ATOM | 304 | O | CYS | A | 574 | 42.662 | 19.023 | 71.715 | 1.00 | 20.93 | O |
| ATOM | 305 | CB | CYS | A | 574 | 45.302 | 20.353 | 70.356 | 1.00 | 22.58 | C |
| ATOM | 306 | SG | CYS | A | 574 | 46.275 | 21.890 | 70.227 | 1.00 | 22.89 | S |
| ATOM | 307 | N | THR | A | 575 | 44.352 | 17.564 | 71.462 | 1.00 | 21.45 | N |
| ATOM | 308 | CA | THR | A | 575 | 43.451 | 16.413 | 71.333 | 1.00 | 22.28 | C |
| ATOM | 309 | C | THR | A | 575 | 42.738 | 16.154 | 72.662 | 1.00 | 22.10 | C |
| ATOM | 310 | O | THR | A | 575 | 41.563 | 15.809 | 72.681 | 1.00 | 24.22 | O |
| ATOM | 311 | CB | THR | A | 575 | 44.225 | 15.153 | 70.884 | 1.00 | 21.93 | C |
| ATOM | 312 | OG1 | THR | A | 575 | 44.863 | 15.422 | 69.629 | 1.00 | 20.68 | O |
| ATOM | 313 | CG2 | THR | A | 575 | 43.265 | 13.951 | 70.709 | 1.00 | 21.15 | C |
| ATOM | 314 | N | ILE | A | 576 | 43.443 | 16.322 | 73.775 | 1.00 | 23.78 | N |
| ATOM | 315 | CA | ILE | A | 576 | 42.816 | 16.137 | 75.081 | 1.00 | 24.23 | C |
| ATOM | 316 | C | ILE | A | 576 | 41.725 | 17.197 | 75.246 | 1.00 | 24.62 | C |
| ATOM | 317 | O | ILE | A | 576 | 40.621 | 16.902 | 75.713 | 1.00 | 24.61 | O |
| ATOM | 318 | CB | ILE | A | 576 | 43.837 | 16.283 | 76.238 | 1.00 | 24.90 | C |
| ATOM | 319 | CG1 | ILE | A | 576 | 44.827 | 15.116 | 76.217 | 1.00 | 24.63 | C |
| ATOM | 320 | CG2 | ILE | A | 576 | 43.110 | 16.307 | 77.580 | 1.00 | 24.33 | C |
| ATOM | 321 | CD1 | ILE | A | 576 | 45.998 | 15.296 | 77.176 | 1.00 | 25.31 | C |
| ATOM | 322 | N | ARG | A | 577 | 42.031 | 18.431 | 74.842 | 1.00 | 24.91 | N |
| ATOM | 323 | CA | ARG | A | 577 | 41.068 | 19.521 | 74.959 | 1.00 | 24.32 | C |
| ATOM | 324 | C | ARG | A | 577 | 39.808 | 19.243 | 74.156 | 1.00 | 24.61 | C |
| ATOM | 325 | O | ARG | A | 577 | 38.702 | 19.601 | 74.575 | 1.00 | 24.50 | O |
| ATOM | 326 | CB | ARG | A | 577 | 41.691 | 20.846 | 74.507 | 1.00 | 24.24 | C |
| ATOM | 327 | CG | ARG | A | 577 | 40.707 | 22.007 | 74.481 | 1.00 | 25.24 | C |
| ATOM | 328 | CD | ARG | A | 577 | 39.968 | 22.152 | 75.814 | 1.00 | 25.38 | C |
| ATOM | 329 | NE | ARG | A | 577 | 40.892 | 22.368 | 76.923 | 1.00 | 26.44 | N |
| ATOM | 330 | CZ | ARG | A | 577 | 40.524 | 22.480 | 78.196 | 1.00 | 26.97 | C |
| ATOM | 331 | NH1 | ARG | A | 577 | 39.244 | 22.394 | 78.531 | 1.00 | 27.02 | N |
| ATOM | 332 | NH2 | ARG | A | 577 | 41.440 | 22.686 | 79.134 | 1.00 | 27.69 | N |
| ATOM | 333 | N | MET | A | 578 | 39.974 | 18.608 | 72.998 | 1.00 | 24.65 | N |
| ATOM | 334 | CA | MET | A | 578 | 38.835 | 18.266 | 72.155 | 1.00 | 24.75 | C |
| ATOM | 335 | C | MET | A | 578 | 37.923 | 17.305 | 72.920 | 1.00 | 24.47 | C |
| ATOM | 336 | O | MET | A | 578 | 36.722 | 17.530 | 73.010 | 1.00 | 25.88 | O |
| ATOM | 337 | CB | MET | A | 578 | 39.304 | 17.601 | 70.848 | 1.00 | 25.09 | C |
| ATOM | 338 | CG | MET | A | 578 | 39.984 | 18.535 | 69.855 | 1.00 | 24.86 | C |
| ATOM | 339 | SD | MET | A | 578 | 40.615 | 17.664 | 68.395 | 1.00 | 26.22 | S |
| ATOM | 340 | CE | MET | A | 578 | 42.033 | 18.702 | 67.961 | 1.00 | 24.19 | C |
| ATOM | 341 | N | PHE | A | 579 | 38.495 | 16.234 | 73.463 | 1.00 | 24.40 | N |
| ATOM | 342 | CA | PHE | A | 579 | 37.713 | 15.253 | 74.222 | 1.00 | 25.06 | C |
| ATOM | 343 | C | PHE | A | 579 | 37.057 | 15.896 | 75.437 | 1.00 | 25.72 | C |
| ATOM | 344 | O | PHE | A | 579 | 35.903 | 15.613 | 75.770 | 1.00 | 26.35 | O |
| ATOM | 345 | CB | PHE | A | 579 | 38.599 | 14.110 | 74.721 | 1.00 | 23.56 | C |
| ATOM | 346 | CG | PHE | A | 579 | 38.871 | 13.051 | 73.693 | 1.00 | 24.34 | C |
| ATOM | 347 | CD1 | PHE | A | 579 | 39.867 | 13.224 | 72.734 | 1.00 | 23.82 | C |
| ATOM | 348 | CD2 | PHE | A | 579 | 38.128 | 11.875 | 73.686 | 1.00 | 23.12 | C |
| ATOM | 349 | CE1 | PHE | A | 579 | 40.116 | 12.243 | 71.787 | 1.00 | 23.30 | C |
| ATOM | 350 | CE2 | PHE | A | 579 | 38.369 | 10.889 | 72.743 | 1.00 | 22.91 | C |
| ATOM | 351 | CZ | PHE | A | 579 | 39.365 | 11.071 | 71.793 | 1.00 | 23.86 | C |
| ATOM | 352 | N | THR | A | 580 | 37.816 | 16.755 | 76.104 | 1.00 | 26.95 | N |
| ATOM | 353 | CA | THR | A | 580 | 37.339 | 17.439 | 77.299 | 1.00 | 27.41 | C |
| ATOM | 354 | C | THR | A | 580 | 36.173 | 18.376 | 77.029 | 1.00 | 28.05 | C |
| ATOM | 355 | O | THR | A | 580 | 35.131 | 18.281 | 77.676 | 1.00 | 28.33 | O |
| ATOM | 356 | CB | THR | A | 580 | 38.462 | 18.258 | 77.941 | 1.00 | 26.84 | C |
| ATOM | 357 | OG1 | THR | A | 580 | 39.551 | 17.391 | 78.262 | 1.00 | 25.94 | O |
| ATOM | 358 | CG2 | THR | A | 580 | 37.965 | 18.948 | 79.212 | 1.00 | 27.30 | C |
| ATOM | 359 | N | ASP | A | 581 | 36.348 | 19.283 | 76.075 | 1.00 | 28.86 | N |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | 74.456 | | 130.132 | 90.00 | 90.00 | 120.00 | P 31 2 1 6 | |
|---|---|---|---|---|---|---|---|---|---|---|---|
| ATOM | 360 | CA | ASP | A | 581 | 35.303 | 20.249 | 75.768 | 1.00 | 29.73 | C |
| ATOM | 361 | C | ASP | A | 581 | 34.059 | 19.656 | 75.129 | 1.00 | 30.39 | C |
| ATOM | 362 | O | ASP | A | 581 | 32.982 | 20.253 | 75.205 | 1.00 | 30.81 | O |
| ATOM | 363 | CB | ASP | A | 581 | 35.875 | 21.388 | 74.925 | 1.00 | 29.02 | C |
| ATOM | 364 | CG | ASP | A | 581 | 36.610 | 22.419 | 75.775 | 1.00 | 30.46 | C |
| ATOM | 365 | OD1 | ASP | A | 581 | 37.064 | 22.065 | 76.885 | 1.00 | 30.23 | O |
| ATOM | 366 | OD2 | ASP | A | 581 | 36.740 | 23.579 | 75.336 | 1.00 | 30.07 | O |
| ATOM | 367 | N | LEU | A | 582 | 34.193 | 18.489 | 74.503 | 1.00 | 30.71 | N |
| ATOM | 368 | CA | LEU | A | 582 | 33.033 | 17.826 | 73.910 | 1.00 | 31.03 | C |
| ATOM | 369 | C | LEU | A | 582 | 32.371 | 16.976 | 75.007 | 1.00 | 31.44 | C |
| ATOM | 370 | O | LEU | A | 582 | 31.475 | 16.176 | 74.742 | 1.00 | 31.49 | O |
| ATOM | 371 | CB | LEU | A | 582 | 33.451 | 16.942 | 72.726 | 1.00 | 30.86 | C |
| ATOM | 372 | CG | LEU | A | 582 | 33.930 | 17.664 | 71.458 | 1.00 | 31.01 | C |
| ATOM | 373 | CD1 | LEU | A | 582 | 34.478 | 16.654 | 70.461 | 1.00 | 29.77 | C |
| ATOM | 374 | CD2 | LEU | A | 582 | 32.778 | 18.446 | 70.848 | 1.00 | 30.34 | C |
| ATOM | 375 | N | ASN | A | 583 | 32.838 | 17.161 | 76.240 | 1.00 | 31.70 | N |
| ATOM | 376 | CA | ASN | A | 583 | 32.312 | 16.458 | 77.408 | 1.00 | 32.47 | C |
| ATOM | 377 | C | ASN | A | 583 | 32.455 | 14.938 | 77.385 | 1.00 | 32.09 | C |
| ATOM | 378 | O | ASN | A | 583 | 31.783 | 14.238 | 78.146 | 1.00 | 32.03 | O |
| ATOM | 379 | CB | ASN | A | 583 | 30.838 | 16.819 | 77.609 | 1.00 | 33.00 | C |
| ATOM | 380 | CG | ASN | A | 583 | 30.625 | 18.307 | 77.749 | 1.00 | 34.05 | C |
| ATOM | 381 | OD1 | ASN | A | 583 | 31.237 | 18.951 | 78.602 | 1.00 | 35.42 | O |
| ATOM | 382 | ND2 | ASN | A | 583 | 29.758 | 18.865 | 76.913 | 1.00 | 33.48 | N |
| ATOM | 383 | N | LEU | A | 584 | 33.337 | 14.432 | 76.531 | 1.00 | 31.46 | N |
| ATOM | 384 | CA | LEU | A | 584 | 33.545 | 12.994 | 76.414 | 1.00 | 30.77 | C |
| ATOM | 385 | C | LEU | A | 584 | 34.286 | 12.430 | 77.622 | 1.00 | 30.91 | C |
| ATOM | 386 | O | LEU | A | 584 | 34.030 | 11.303 | 78.047 | 1.00 | 30.53 | O |
| ATOM | 387 | CB | LEU | A | 584 | 34.306 | 12.686 | 75.122 | 1.00 | 30.25 | C |
| ATOM | 388 | CG | LEU | A | 584 | 33.668 | 13.319 | 73.879 | 1.00 | 30.05 | C |
| ATOM | 389 | CD1 | LEU | A | 584 | 34.515 | 13.021 | 72.639 | 1.00 | 28.59 | C |
| ATOM | 390 | CD2 | LEU | A | 584 | 32.247 | 12.786 | 73.705 | 1.00 | 29.62 | C |
| ATOM | 391 | N | VAL | A | 585 | 35.201 | 13.213 | 78.180 | 1.00 | 30.54 | N |
| ATOM | 392 | CA | VAL | A | 585 | 35.948 | 12.766 | 79.346 | 1.00 | 31.44 | C |
| ATOM | 393 | C | VAL | A | 585 | 35.009 | 12.619 | 80.543 | 1.00 | 32.33 | C |
| ATOM | 394 | O | VAL | A | 585 | 35.147 | 11.686 | 81.328 | 1.00 | 31.86 | O |
| ATOM | 395 | CB | VAL | A | 585 | 37.082 | 13.749 | 79.697 | 1.00 | 30.86 | C |
| ATOM | 396 | CG1 | VAL | A | 585 | 37.716 | 13.371 | 81.033 | 1.00 | 31.14 | C |
| ATOM | 397 | CG2 | VAL | A | 585 | 38.134 | 13.727 | 78.595 | 1.00 | 30.70 | C |
| ATOM | 398 | N | GLN | A | 586 | 34.050 | 13.534 | 80.667 | 1.00 | 33.63 | N |
| ATOM | 399 | CA | GLN | A | 586 | 33.081 | 13.496 | 81.764 | 1.00 | 35.21 | C |
| ATOM | 400 | C | GLN | A | 586 | 31.989 | 12.457 | 81.530 | 1.00 | 34.88 | C |
| ATOM | 401 | O | GLN | A | 586 | 31.774 | 11.577 | 82.359 | 1.00 | 35.41 | O |
| ATOM | 402 | CB | GLN | A | 586 | 32.407 | 14.864 | 81.949 | 1.00 | 37.53 | C |
| ATOM | 403 | CG | GLN | A | 586 | 31.369 | 14.893 | 83.083 | 1.00 | 41.13 | C |
| ATOM | 404 | CD | GLN | A | 586 | 30.398 | 16.065 | 82.978 | 1.00 | 43.71 | C |
| ATOM | 405 | OE1 | GLN | A | 586 | 29.729 | 16.237 | 81.954 | 1.00 | 45.81 | O |
| ATOM | 406 | NE2 | GLN | A | 586 | 30.308 | 16.872 | 84.041 | 1.00 | 44.18 | N |
| ATOM | 407 | N | ASN | A | 587 | 31.300 | 12.570 | 80.398 | 1.00 | 34.50 | N |
| ATOM | 408 | CA | ASN | A | 587 | 30.204 | 11.669 | 80.075 | 1.00 | 34.82 | C |
| ATOM | 409 | C | ASN | A | 587 | 30.551 | 10.189 | 79.998 | 1.00 | 34.80 | C |
| ATOM | 410 | O | ASN | A | 587 | 29.670 | 9.345 | 80.135 | 1.00 | 34.47 | O |
| ATOM | 411 | CB | ASN | A | 587 | 29.527 | 12.094 | 78.768 | 1.00 | 35.34 | C |
| ATOM | 412 | CG | ASN | A | 587 | 28.727 | 13.379 | 78.917 | 1.00 | 36.34 | C |
| ATOM | 413 | OD1 | ASN | A | 587 | 28.496 | 13.855 | 80.028 | 1.00 | 36.84 | O |
| ATOM | 414 | ND2 | ASN | A | 587 | 28.292 | 13.937 | 77.798 | 1.00 | 35.75 | N |
| ATOM | 415 | N | PHE | A | 588 | 31.822 | 9.866 | 79.789 | 1.00 | 33.94 | N |
| ATOM | 416 | CA | PHE | A | 588 | 32.217 | 8.468 | 79.692 | 1.00 | 33.99 | C |
| ATOM | 417 | C | PHE | A | 588 | 33.326 | 8.100 | 80.656 | 1.00 | 33.96 | C |
| ATOM | 418 | O | PHE | A | 588 | 34.027 | 7.104 | 80.479 | 1.00 | 33.81 | O |
| ATOM | 419 | CB | PHE | A | 588 | 32.589 | 8.157 | 78.244 | 1.00 | 32.61 | C |
| ATOM | 420 | CG | PHE | A | 588 | 31.454 | 8.387 | 77.292 | 1.00 | 32.74 | C |
| ATOM | 421 | CD1 | PHE | A | 588 | 30.308 | 7.596 | 77.363 | 1.00 | 31.91 | C |
| ATOM | 422 | CD2 | PHE | A | 588 | 31.490 | 9.432 | 76.376 | 1.00 | 31.91 | C |
| ATOM | 423 | CE1 | PHE | A | 588 | 29.216 | 7.844 | 76.539 | 1.00 | 31.46 | C |
| ATOM | 424 | CE2 | PHE | A | 588 | 30.397 | 9.689 | 75.545 | 1.00 | 32.32 | C |
| ATOM | 425 | CZ | PHE | A | 588 | 29.259 | 8.893 | 75.630 | 1.00 | 32.13 | C |
| ATOM | 426 | N | GLN | A | 589 | 33.459 | 8.927 | 81.686 | 1.00 | 35.48 | N |
| ATOM | 427 | CA | GLN | A | 589 | 34.435 | 8.742 | 82.754 | 1.00 | 36.24 | C |
| ATOM | 428 | C | GLN | A | 589 | 35.788 | 8.208 | 82.305 | 1.00 | 35.50 | C |
| ATOM | 429 | O | GLN | A | 589 | 36.230 | 7.153 | 82.766 | 1.00 | 35.43 | O |
| ATOM | 430 | CB | GLN | A | 589 | 33.848 | 7.807 | 83.814 | 1.00 | 38.75 | C |
| ATOM | 431 | CG | GLN | A | 589 | 32.329 | 7.870 | 83.898 | 1.00 | 42.30 | C |
| ATOM | 432 | CD | GLN | A | 589 | 31.752 | 6.903 | 84.911 | 1.00 | 45.65 | C |
| ATOM | 433 | OE1 | GLN | A | 589 | 30.561 | 6.583 | 84.868 | 1.00 | 47.58 | O |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 | 6 |
|---|---|---|---|---|---|---|---|---|---|---|---|
| ATOM | 434 | NE2 | GLN | A | 589 | 32.589 | 6.437 | 85.840 | 1.00 | 46.23 | N |
| ATOM | 435 | N | MET | A | 590 | 36.461 | 8.934 | 81.421 | 1.00 | 34.15 | N |
| ATOM | 436 | CA | MET | A | 590 | 37.769 | 8.491 | 80.958 | 1.00 | 33.36 | C |
| ATOM | 437 | C | MET | A | 590 | 38.833 | 8.905 | 81.966 | 1.00 | 33.32 | C |
| ATOM | 438 | O | MET | A | 590 | 38.819 | 10.032 | 82.465 | 1.00 | 33.23 | O |
| ATOM | 439 | CB | MET | A | 590 | 38.109 | 9.116 | 79.601 | 1.00 | 33.37 | C |
| ATOM | 440 | CG | MET | A | 590 | 37.144 | 8.793 | 78.476 | 1.00 | 33.12 | C |
| ATOM | 441 | SD | MET | A | 590 | 37.616 | 9.632 | 76.950 | 1.00 | 31.44 | S |
| ATOM | 442 | CE | MET | A | 590 | 36.284 | 9.164 | 75.875 | 1.00 | 31.30 | C |
| ATOM | 443 | N | LYS | A | 591 | 39.753 | 8.001 | 82.274 | 1.00 | 32.69 | N |
| ATOM | 444 | CA | LYS | A | 591 | 40.823 | 8.342 | 83.196 | 1.00 | 33.22 | C |
| ATOM | 445 | C | LYS | A | 591 | 41.882 | 9.104 | 82.403 | 1.00 | 32.29 | C |
| ATOM | 446 | O | LYS | A | 591 | 42.205 | 8.736 | 81.267 | 1.00 | 31.27 | O |
| ATOM | 447 | CB | LYS | A | 591 | 41.417 | 7.084 | 83.827 | 1.00 | 34.29 | C |
| ATOM | 448 | CG | LYS | A | 591 | 40.457 | 6.387 | 84.784 | 1.00 | 36.87 | C |
| ATOM | 449 | CD | LYS | A | 591 | 41.173 | 5.355 | 85.641 | 1.00 | 38.65 | C |
| ATOM | 450 | CE | LYS | A | 591 | 40.225 | 4.741 | 86.660 | 1.00 | 39.80 | C |
| ATOM | 451 | NZ | LYS | A | 591 | 40.936 | 3.829 | 87.597 | 1.00 | 40.74 | N |
| ATOM | 452 | N | HIS | A | 592 | 42.419 | 10.161 | 83.002 | 1.00 | 31.35 | N |
| ATOM | 453 | CA | HIS | A | 592 | 43.409 | 10.995 | 82.331 | 1.00 | 30.69 | C |
| ATOM | 454 | C | HIS | A | 592 | 44.564 | 10.231 | 81.713 | 1.00 | 30.36 | C |
| ATOM | 455 | O | HIS | A | 592 | 44.873 | 10.419 | 80.536 | 1.00 | 30.09 | O |
| ATOM | 456 | CB | HIS | A | 592 | 43.974 | 12.040 | 83.293 | 1.00 | 31.16 | C |
| ATOM | 457 | CG | HIS | A | 592 | 44.789 | 13.100 | 82.618 | 1.00 | 31.18 | C |
| ATOM | 458 | ND1 | HIS | A | 592 | 44.241 | 14.009 | 81.738 | 1.00 | 31.30 | N |
| ATOM | 459 | CD2 | HIS | A | 592 | 46.108 | 13.399 | 82.695 | 1.00 | 31.66 | C |
| ATOM | 460 | CE1 | HIS | A | 592 | 45.186 | 14.825 | 81.304 | 1.00 | 32.27 | C |
| ATOM | 461 | NE2 | HIS | A | 592 | 46.329 | 14.477 | 81.869 | 1.00 | 32.22 | N |
| ATOM | 462 | N | GLU | A | 593 | 45.205 | 9.374 | 82.502 | 1.00 | 30.02 | N |
| ATOM | 463 | CA | GLU | A | 593 | 46.349 | 8.617 | 82.013 | 1.00 | 29.94 | C |
| ATOM | 464 | C | GLU | A | 593 | 45.999 | 7.690 | 80.855 | 1.00 | 28.34 | C |
| ATOM | 465 | O | GLU | A | 593 | 46.826 | 7.458 | 79.981 | 1.00 | 27.62 | O |
| ATOM | 466 | CB | GLU | A | 593 | 46.990 | 7.806 | 83.148 | 1.00 | 31.81 | C |
| ATOM | 467 | CG | GLU | A | 593 | 46.037 | 6.850 | 83.839 | 1.00 | 35.34 | C |
| ATOM | 468 | CD | GLU | A | 593 | 45.399 | 7.452 | 85.080 | 1.00 | 37.30 | C |
| ATOM | 469 | OE1 | GLU | A | 593 | 45.005 | 8.641 | 85.051 | 1.00 | 37.55 | O |
| ATOM | 470 | OE2 | GLU | A | 593 | 45.284 | 6.723 | 86.087 | 1.00 | 39.65 | O |
| ATOM | 471 | N | VAL | A | 594 | 44.779 | 7.156 | 80.857 | 1.00 | 27.30 | N |
| ATOM | 472 | CA | VAL | A | 594 | 44.329 | 6.256 | 79.793 | 1.00 | 25.58 | C |
| ATOM | 473 | C | VAL | A | 594 | 44.148 | 7.025 | 78.480 | 1.00 | 25.20 | C |
| ATOM | 474 | O | VAL | A | 594 | 44.601 | 6.588 | 77.418 | 1.00 | 24.16 | O |
| ATOM | 475 | CB | VAL | A | 594 | 42.990 | 5.576 | 80.169 | 1.00 | 26.28 | C |
| ATOM | 476 | CG1 | VAL | A | 594 | 42.499 | 4.703 | 79.016 | 1.00 | 25.68 | C |
| ATOM | 477 | CG2 | VAL | A | 594 | 43.174 | 4.733 | 81.440 | 1.00 | 25.44 | C |
| ATOM | 478 | N | LEU | A | 595 | 43.478 | 8.168 | 78.558 | 1.00 | 24.80 | N |
| ATOM | 479 | CA | LEU | A | 595 | 43.259 | 9.003 | 77.385 | 1.00 | 25.06 | C |
| ATOM | 480 | C | LEU | A | 595 | 44.602 | 9.449 | 76.802 | 1.00 | 25.24 | C |
| ATOM | 481 | O | LEU | A | 595 | 44.793 | 9.448 | 75.584 | 1.00 | 25.32 | O |
| ATOM | 482 | CB | LEU | A | 595 | 42.413 | 10.225 | 77.759 | 1.00 | 24.44 | C |
| ATOM | 483 | CG | LEU | A | 595 | 42.164 | 11.235 | 76.633 | 1.00 | 24.77 | C |
| ATOM | 484 | CD1 | LEU | A | 595 | 41.654 | 10.515 | 75.395 | 1.00 | 24.53 | C |
| ATOM | 485 | CD2 | LEU | A | 595 | 41.162 | 12.279 | 77.093 | 1.00 | 23.71 | C |
| ATOM | 486 | N | CYS | A | 596 | 45.532 | 9.822 | 77.680 | 1.00 | 25.65 | N |
| ATOM | 487 | CA | CYS | A | 596 | 46.866 | 10.258 | 77.264 | 1.00 | 26.25 | C |
| ATOM | 488 | C | CYS | A | 596 | 47.615 | 9.144 | 76.543 | 1.00 | 27.05 | C |
| ATOM | 489 | O | CYS | A | 596 | 48.216 | 9.358 | 75.481 | 1.00 | 26.85 | O |
| ATOM | 490 | CB | CYS | A | 596 | 47.696 | 10.698 | 78.478 | 1.00 | 25.96 | C |
| ATOM | 491 | SG | CYS | A | 596 | 47.267 | 12.320 | 79.167 | 1.00 | 26.65 | S |
| ATOM | 492 | N | ARG | A | 597 | 47.597 | 7.959 | 77.144 | 1.00 | 26.45 | N |
| ATOM | 493 | CA | ARG | A | 597 | 48.269 | 6.804 | 76.572 | 1.00 | 26.81 | C |
| ATOM | 494 | C | ARG | A | 597 | 47.652 | 6.487 | 75.207 | 1.00 | 25.59 | C |
| ATOM | 495 | O | ARG | A | 597 | 48.368 | 6.245 | 74.242 | 1.00 | 25.07 | O |
| ATOM | 496 | CB | ARG | A | 597 | 48.128 | 5.607 | 77.520 | 1.00 | 28.07 | C |
| ATOM | 497 | CG | ARG | A | 597 | 49.129 | 4.498 | 77.292 | 1.00 | 33.12 | C |
| ATOM | 498 | CD | ARG | A | 597 | 49.106 | 3.508 | 78.452 | 1.00 | 36.48 | C |
| ATOM | 499 | NE | ARG | A | 597 | 49.348 | 4.178 | 79.727 | 1.00 | 40.06 | N |
| ATOM | 500 | CZ | ARG | A | 597 | 49.240 | 3.594 | 80.917 | 1.00 | 41.68 | C |
| ATOM | 501 | NH1 | ARG | A | 597 | 48.893 | 2.319 | 81.002 | 1.00 | 43.80 | N |
| ATOM | 502 | NH2 | ARG | A | 597 | 49.475 | 4.284 | 82.025 | 1.00 | 42.94 | N |
| ATOM | 503 | N | TRP | A | 598 | 46.323 | 6.508 | 75.134 | 1.00 | 24.05 | N |
| ATOM | 504 | CA | TRP | A | 598 | 45.611 | 6.229 | 73.891 | 1.00 | 23.45 | C |
| ATOM | 505 | C | TRP | A | 598 | 46.018 | 7.206 | 72.784 | 1.00 | 23.31 | C |
| ATOM | 506 | O | TRP | A | 598 | 46.324 | 6.800 | 71.665 | 1.00 | 23.07 | O |
| ATOM | 507 | CB | TRP | A | 598 | 44.097 | 6.327 | 74.109 | 1.00 | 23.98 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 | |
|---|---|---|---|---|---|---|---|---|---|---|---|
| ATOM | 508 | CG | TRP | A | 598 | 43.306 | 6.013 | 72.866 | 1.00 | 24.18 | C |
| ATOM | 509 | CD1 | TRP | A | 598 | 43.022 | 4.776 | 72.362 | 1.00 | 24.39 | C |
| ATOM | 510 | CD2 | TRP | A | 598 | 42.763 | 6.957 | 71.937 | 1.00 | 24.15 | C |
| ATOM | 511 | NE1 | TRP | A | 598 | 42.339 | 4.892 | 71.175 | 1.00 | 24.43 | N |
| ATOM | 512 | CE2 | TRP | A | 598 | 42.170 | 6.222 | 70.891 | 1.00 | 24.35 | C |
| ATOM | 513 | CE3 | TRP | A | 598 | 42.726 | 8.358 | 71.888 | 1.00 | 23.61 | C |
| ATOM | 514 | CZ2 | TRP | A | 598 | 41.547 | 6.838 | 69.802 | 1.00 | 24.16 | C |
| ATOM | 515 | CZ3 | TRP | A | 598 | 42.106 | 8.968 | 70.806 | 1.00 | 24.29 | C |
| ATOM | 516 | CH2 | TRP | A | 598 | 41.525 | 8.206 | 69.779 | 1.00 | 24.39 | C |
| ATOM | 517 | N | ILE | A | 599 | 46.013 | 8.496 | 73.103 | 1.00 | 23.06 | N |
| ATOM | 518 | CA | ILE | A | 599 | 46.386 | 9.515 | 72.135 | 1.00 | 22.60 | C |
| ATOM | 519 | C | ILE | A | 599 | 47.799 | 9.254 | 71.630 | 1.00 | 22.84 | C |
| ATOM | 520 | O | ILE | A | 599 | 48.060 | 9.337 | 70.429 | 1.00 | 21.66 | O |
| ATOM | 521 | CB | ILE | A | 599 | 46.311 | 10.926 | 72.763 | 1.00 | 22.65 | C |
| ATOM | 522 | CG1 | ILE | A | 599 | 44.849 | 11.266 | 73.063 | 1.00 | 22.83 | C |
| ATOM | 523 | CG2 | ILE | A | 599 | 46.948 | 11.960 | 71.826 | 1.00 | 23.20 | C |
| ATOM | 524 | CD1 | ILE | A | 599 | 44.645 | 12.548 | 73.848 | 1.00 | 21.99 | C |
| ATOM | 525 | N | LEU | A | 600 | 48.707 | 8.919 | 72.545 | 1.00 | 21.91 | N |
| ATOM | 526 | CA | LEU | A | 600 | 50.085 | 8.653 | 72.152 | 1.00 | 21.71 | C |
| ATOM | 527 | C | LEU | A | 600 | 50.233 | 7.379 | 71.319 | 1.00 | 21.76 | C |
| ATOM | 528 | O | LEU | A | 600 | 51.101 | 7.315 | 70.448 | 1.00 | 20.96 | O |
| ATOM | 529 | CB | LEU | A | 600 | 50.994 | 8.598 | 73.385 | 1.00 | 23.21 | C |
| ATOM | 530 | CG | LEU | A | 600 | 51.138 | 9.936 | 74.130 | 1.00 | 23.86 | C |
| ATOM | 531 | CD1 | LEU | A | 600 | 52.034 | 9.746 | 75.343 | 1.00 | 25.69 | C |
| ATOM | 532 | CD2 | LEU | A | 600 | 51.709 | 11.012 | 73.207 | 1.00 | 23.50 | C |
| ATOM | 533 | N | SER | A | 601 | 49.406 | 6.365 | 71.584 | 1.00 | 20.67 | N |
| ATOM | 534 | CA | SER | A | 601 | 49.469 | 5.134 | 70.789 | 1.00 | 21.19 | C |
| ATOM | 535 | C | SER | A | 601 | 48.963 | 5.466 | 69.383 | 1.00 | 20.71 | C |
| ATOM | 536 | O | SER | A | 601 | 49.533 | 5.030 | 68.384 | 1.00 | 21.98 | O |
| ATOM | 537 | CB | SER | A | 601 | 48.591 | 4.024 | 71.398 | 1.00 | 20.80 | C |
| ATOM | 538 | OG | SER | A | 601 | 49.078 | 3.606 | 72.659 | 1.00 | 21.54 | O |
| ATOM | 539 | N | VAL | A | 602 | 47.889 | 6.245 | 69.306 | 1.00 | 20.80 | N |
| ATOM | 540 | CA | VAL | A | 602 | 47.344 | 6.633 | 68.009 | 1.00 | 20.64 | C |
| ATOM | 541 | C | VAL | A | 602 | 48.426 | 7.366 | 67.224 | 1.00 | 20.78 | C |
| ATOM | 542 | O | VAL | A | 602 | 48.758 | 6.983 | 66.103 | 1.00 | 20.16 | O |
| ATOM | 543 | CB | VAL | A | 602 | 46.107 | 7.548 | 68.165 | 1.00 | 20.34 | C |
| ATOM | 544 | CG1 | VAL | A | 602 | 45.777 | 8.210 | 66.829 | 1.00 | 19.39 | C |
| ATOM | 545 | CG2 | VAL | A | 602 | 44.908 | 6.723 | 68.655 | 1.00 | 19.68 | C |
| ATOM | 546 | N | LYS | A | 603 | 48.991 | 8.412 | 67.819 | 1.00 | 21.10 | N |
| ATOM | 547 | CA | LYS | A | 603 | 50.037 | 9.178 | 67.148 | 1.00 | 22.43 | C |
| ATOM | 548 | C | LYS | A | 603 | 51.185 | 8.275 | 66.690 | 1.00 | 22.67 | C |
| ATOM | 549 | O | LYS | A | 603 | 51.657 | 8.366 | 65.560 | 1.00 | 22.58 | O |
| ATOM | 550 | CB | LYS | A | 603 | 50.587 | 10.266 | 68.082 | 1.00 | 23.15 | C |
| ATOM | 551 | CG | LYS | A | 603 | 51.634 | 11.158 | 67.415 | 1.00 | 24.97 | C |
| ATOM | 552 | CD | LYS | A | 603 | 52.306 | 12.107 | 68.392 | 1.00 | 27.74 | C |
| ATOM | 553 | CE | LYS | A | 603 | 53.136 | 11.321 | 69.391 | 1.00 | 28.43 | C |
| ATOM | 554 | NZ | LYS | A | 603 | 54.282 | 12.075 | 69.918 | 1.00 | 30.45 | N |
| ATOM | 555 | N | LYS | A | 604 | 51.633 | 7.404 | 67.582 | 1.00 | 24.48 | N |
| ATOM | 556 | CA | LYS | A | 604 | 52.731 | 6.492 | 67.278 | 1.00 | 26.81 | C |
| ATOM | 557 | C | LYS | A | 604 | 52.446 | 5.564 | 66.092 | 1.00 | 26.73 | C |
| ATOM | 558 | O | LYS | A | 604 | 53.370 | 5.100 | 65.420 | 1.00 | 26.36 | O |
| ATOM | 559 | CB | LYS | A | 604 | 53.048 | 5.652 | 68.520 | 1.00 | 28.66 | C |
| ATOM | 560 | CG | LYS | A | 604 | 54.159 | 4.644 | 68.337 | 1.00 | 32.77 | C |
| ATOM | 561 | CD | LYS | A | 604 | 54.322 | 3.789 | 69.587 | 1.00 | 34.54 | C |
| ATOM | 562 | CE | LYS | A | 604 | 55.359 | 2.691 | 69.371 | 1.00 | 37.21 | C |
| ATOM | 563 | NZ | LYS | A | 604 | 55.588 | 1.902 | 70.618 | 1.00 | 38.86 | N |
| ATOM | 564 | N | ASN | A | 605 | 51.172 | 5.303 | 65.818 | 1.00 | 26.83 | N |
| ATOM | 565 | CA | ASN | A | 605 | 50.841 | 4.401 | 64.727 | 1.00 | 27.59 | C |
| ATOM | 566 | C | ASN | A | 605 | 50.622 | 5.007 | 63.342 | 1.00 | 27.35 | C |
| ATOM | 567 | O | ASN | A | 605 | 50.079 | 4.360 | 62.440 | 1.00 | 27.36 | O |
| ATOM | 568 | CB | ASN | A | 605 | 49.681 | 3.496 | 65.145 | 1.00 | 28.86 | C |
| ATOM | 569 | CG | ASN | A | 605 | 50.163 | 2.321 | 65.987 | 1.00 | 31.06 | C |
| ATOM | 570 | OD1 | ASN | A | 605 | 50.746 | 1.369 | 65.462 | 1.00 | 31.33 | O |
| ATOM | 571 | ND2 | ASN | A | 605 | 49.960 | 2.403 | 67.301 | 1.00 | 32.35 | N |
| ATOM | 572 | N | TYR | A | 606 | 51.048 | 6.255 | 63.183 | 1.00 | 25.91 | N |
| ATOM | 573 | CA | TYR | A | 606 | 51.013 | 6.910 | 61.885 | 1.00 | 25.27 | C |
| ATOM | 574 | C | TYR | A | 606 | 52.502 | 6.944 | 61.535 | 1.00 | 26.48 | C |
| ATOM | 575 | O | TYR | A | 606 | 53.342 | 6.924 | 62.437 | 1.00 | 25.39 | O |
| ATOM | 576 | CB | TYR | A | 606 | 50.448 | 8.332 | 61.974 | 1.00 | 22.38 | C |
| ATOM | 577 | CG | TYR | A | 606 | 48.933 | 8.374 | 61.938 | 1.00 | 21.11 | C |
| ATOM | 578 | CD1 | TYR | A | 606 | 48.183 | 8.394 | 63.113 | 1.00 | 19.86 | C |
| ATOM | 579 | CD2 | TYR | A | 606 | 48.249 | 8.340 | 60.721 | 1.00 | 20.07 | C |
| ATOM | 580 | CE1 | TYR | A | 606 | 46.785 | 8.375 | 63.077 | 1.00 | 19.67 | C |
| ATOM | 581 | CE2 | TYR | A | 606 | 46.861 | 8.318 | 60.672 | 1.00 | 18.50 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 |
|---|---|---|---|---|---|---|---|---|---|---|
| ATOM | 582 | CZ | TYR | A | 606 | 46.132 | 8.335 | 61.849 | 1.00 | 20.00 | C |
| ATOM | 583 | OH | TYR | A | 606 | 44.750 | 8.319 | 61.789 | 1.00 | 19.86 | O |
| ATOM | 584 | N | ARG | A | 607 | 52.836 | 6.969 | 60.249 | 1.00 | 27.83 | N |
| ATOM | 585 | CA | ARG | A | 607 | 54.238 | 6.991 | 59.839 | 1.00 | 30.73 | C |
| ATOM | 586 | C | ARG | A | 607 | 54.640 | 8.401 | 59.414 | 1.00 | 31.88 | C |
| ATOM | 587 | O | ARG | A | 607 | 54.146 | 8.931 | 58.417 | 1.00 | 32.06 | O |
| ATOM | 588 | CB | ARG | A | 607 | 54.458 | 5.995 | 58.703 | 1.00 | 31.85 | C |
| ATOM | 589 | CG | ARG | A | 607 | 54.226 | 4.551 | 59.130 | 1.00 | 33.74 | C |
| ATOM | 590 | CD | ARG | A | 607 | 53.840 | 3.673 | 57.957 | 1.00 | 35.36 | C |
| ATOM | 591 | NE | ARG | A | 607 | 53.511 | 2.317 | 58.386 | 1.00 | 36.57 | N |
| ATOM | 592 | CZ | ARG | A | 607 | 54.409 | 1.413 | 58.760 | 1.00 | 37.51 | C |
| ATOM | 593 | NH1 | ARG | A | 607 | 55.702 | 1.712 | 58.751 | 1.00 | 38.76 | N |
| ATOM | 594 | NH2 | ARG | A | 607 | 54.013 | 0.212 | 59.158 | 1.00 | 37.98 | N |
| ATOM | 595 | N | LYS | A | 608 | 55.542 | 9.003 | 60.176 | 1.00 | 33.30 | N |
| ATOM | 596 | CA | LYS | A | 608 | 55.976 | 10.364 | 59.892 | 1.00 | 35.64 | C |
| ATOM | 597 | C | LYS | A | 608 | 56.750 | 10.502 | 58.586 | 1.00 | 35.56 | C |
| ATOM | 598 | O | LYS | A | 608 | 56.875 | 11.605 | 58.052 | 1.00 | 36.10 | O |
| ATOM | 599 | CB | LYS | A | 608 | 56.801 | 10.912 | 61.064 | 1.00 | 37.50 | C |
| ATOM | 600 | CG | LYS | A | 608 | 57.010 | 12.427 | 61.007 | 1.00 | 40.44 | C |
| ATOM | 601 | CD | LYS | A | 608 | 57.539 | 12.989 | 62.329 | 1.00 | 41.67 | C |
| ATOM | 602 | CE | LYS | A | 608 | 57.666 | 14.512 | 62.256 | 1.00 | 43.01 | C |
| ATOM | 603 | NZ | LYS | A | 608 | 58.129 | 15.120 | 63.542 | 1.00 | 44.18 | N |
| ATOM | 604 | N | ASN | A | 609 | 57.262 | 9.391 | 58.064 | 1.00 | 35.19 | N |
| ATOM | 605 | CA | ASN | A | 609 | 58.003 | 9.431 | 56.809 | 1.00 | 34.61 | C |
| ATOM | 606 | C | ASN | A | 609 | 57.044 | 9.651 | 55.635 | 1.00 | 33.47 | C |
| ATOM | 607 | O | ASN | A | 609 | 57.474 | 10.023 | 54.548 | 1.00 | 33.88 | O |
| ATOM | 608 | CB | ASN | A | 609 | 58.792 | 8.129 | 56.599 | 1.00 | 36.07 | C |
| ATOM | 609 | CG | ASN | A | 609 | 57.889 | 6.934 | 56.353 | 1.00 | 37.51 | C |
| ATOM | 610 | OD1 | ASN | A | 609 | 56.994 | 6.655 | 57.142 | 1.00 | 38.35 | O |
| ATOM | 611 | ND2 | ASN | A | 609 | 58.122 | 6.225 | 55.252 | 1.00 | 38.24 | N |
| ATOM | 612 | N | VAL | A | 610 | 55.750 | 9.418 | 55.851 | 1.00 | 31.24 | N |
| ATOM | 613 | CA | VAL | A | 610 | 54.755 | 9.619 | 54.795 | 1.00 | 29.70 | C |
| ATOM | 614 | C | VAL | A | 610 | 54.379 | 11.105 | 54.765 | 1.00 | 29.34 | C |
| ATOM | 615 | O | VAL | A | 610 | 53.872 | 11.648 | 55.751 | 1.00 | 28.89 | O |
| ATOM | 616 | CB | VAL | A | 610 | 53.499 | 8.749 | 55.043 | 1.00 | 29.17 | C |
| ATOM | 617 | CG1 | VAL | A | 610 | 52.449 | 9.031 | 53.991 | 1.00 | 27.99 | C |
| ATOM | 618 | CG2 | VAL | A | 610 | 53.886 | 7.276 | 55.021 | 1.00 | 28.13 | C |
| ATOM | 619 | N | ALA | A | 611 | 54.633 | 11.750 | 53.626 | 1.00 | 28.19 | N |
| ATOM | 620 | CA | ALA | A | 611 | 54.396 | 13.186 | 53.448 | 1.00 | 26.86 | C |
| ATOM | 621 | C | ALA | A | 611 | 53.063 | 13.772 | 53.900 | 1.00 | 25.97 | C |
| ATOM | 622 | O | ALA | A | 611 | 53.042 | 14.786 | 54.605 | 1.00 | 26.34 | O |
| ATOM | 623 | CB | ALA | A | 611 | 54.654 | 13.573 | 51.995 | 1.00 | 26.87 | C |
| ATOM | 624 | N | TYR | A | 612 | 51.951 | 13.171 | 53.492 | 1.00 | 24.90 | N |
| ATOM | 625 | CA | TYR | A | 612 | 50.654 | 13.704 | 53.887 | 1.00 | 24.31 | C |
| ATOM | 626 | C | TYR | A | 612 | 49.854 | 12.833 | 54.845 | 1.00 | 23.26 | C |
| ATOM | 627 | O | TYR | A | 612 | 49.371 | 13.318 | 55.863 | 1.00 | 22.10 | O |
| ATOM | 628 | CB | TYR | A | 612 | 49.782 | 14.010 | 52.666 | 1.00 | 24.87 | C |
| ATOM | 629 | CG | TYR | A | 612 | 48.521 | 14.742 | 53.060 | 1.00 | 26.36 | C |
| ATOM | 630 | CD1 | TYR | A | 612 | 48.593 | 15.991 | 53.675 | 1.00 | 26.89 | C |
| ATOM | 631 | CD2 | TYR | A | 612 | 47.265 | 14.159 | 52.898 | 1.00 | 27.39 | C |
| ATOM | 632 | CE1 | TYR | A | 612 | 47.450 | 16.640 | 54.130 | 1.00 | 27.55 | C |
| ATOM | 633 | CE2 | TYR | A | 612 | 46.111 | 14.802 | 53.351 | 1.00 | 28.71 | C |
| ATOM | 634 | CZ | TYR | A | 612 | 46.217 | 16.042 | 53.970 | 1.00 | 28.91 | C |
| ATOM | 635 | OH | TYR | A | 612 | 45.093 | 16.678 | 54.455 | 1.00 | 31.34 | O |
| ATOM | 636 | N | HIS | A | 613 | 49.691 | 11.555 | 54.518 | 1.00 | 23.09 | N |
| ATOM | 637 | CA | HIS | A | 613 | 48.933 | 10.667 | 55.395 | 1.00 | 22.38 | C |
| ATOM | 638 | C | HIS | A | 613 | 49.753 | 10.310 | 56.631 | 1.00 | 22.61 | C |
| ATOM | 639 | O | HIS | A | 613 | 50.366 | 9.249 | 56.708 | 1.00 | 22.98 | O |
| ATOM | 640 | CB | HIS | A | 613 | 48.511 | 9.404 | 54.641 | 1.00 | 21.97 | C |
| ATOM | 641 | CG | HIS | A | 613 | 47.416 | 9.640 | 53.646 | 1.00 | 22.49 | C |
| ATOM | 642 | ND1 | HIS | A | 613 | 47.626 | 9.621 | 52.284 | 1.00 | 21.52 | N |
| ATOM | 643 | CD2 | HIS | A | 613 | 46.108 | 9.948 | 53.819 | 1.00 | 22.36 | C |
| ATOM | 644 | CE1 | HIS | A | 613 | 46.498 | 9.910 | 51.661 | 1.00 | 22.32 | C |
| ATOM | 645 | NE2 | HIS | A | 613 | 45.560 | 10.112 | 52.569 | 1.00 | 23.90 | N |
| ATOM | 646 | N | ASN | A | 614 | 49.753 | 11.218 | 57.601 | 1.00 | 21.77 | N |
| ATOM | 647 | CA | ASN | A | 614 | 50.501 | 11.030 | 58.839 | 1.00 | 21.48 | C |
| ATOM | 648 | C | ASN | A | 614 | 49.682 | 11.561 | 60.015 | 1.00 | 20.79 | C |
| ATOM | 649 | O | ASN | A | 614 | 48.537 | 11.981 | 59.840 | 1.00 | 21.10 | O |
| ATOM | 650 | CB | ASN | A | 614 | 51.846 | 11.764 | 58.743 | 1.00 | 21.40 | C |
| ATOM | 651 | CG | ASN | A | 614 | 51.696 | 13.202 | 58.276 | 1.00 | 22.32 | C |
| ATOM | 652 | OD1 | ASN | A | 614 | 50.932 | 13.971 | 58.850 | 1.00 | 23.24 | O |
| ATOM | 653 | ND2 | ASN | A | 614 | 52.431 | 13.571 | 57.228 | 1.00 | 22.85 | N |
| ATOM | 654 | N | TRP | A | 615 | 50.269 | 11.551 | 61.204 | 1.00 | 19.62 | N |
| ATOM | 655 | CA | TRP | A | 615 | 49.573 | 12.021 | 62.393 | 1.00 | 19.39 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 | |
|---|---|---|---|---|---|---|---|---|---|---|---|
| ATOM | 656 | C | TRP | A | 615 | 48.991 | 13.432 | 62.268 | 1.00 | 19.87 | C |
| ATOM | 657 | O | TRP | A | 615 | 47.849 | 13.676 | 62.676 | 1.00 | 19.30 | O |
| ATOM | 658 | CB | TRP | A | 615 | 50.510 | 11.961 | 63.602 | 1.00 | 20.53 | C |
| ATOM | 659 | CG | TRP | A | 615 | 50.076 | 12.824 | 64.757 | 1.00 | 21.49 | C |
| ATOM | 660 | CD1 | TRP | A | 615 | 50.721 | 13.932 | 65.240 | 1.00 | 21.63 | C |
| ATOM | 661 | CD2 | TRP | A | 615 | 48.897 | 12.667 | 65.556 | 1.00 | 21.69 | C |
| ATOM | 662 | NE1 | TRP | A | 615 | 50.016 | 14.470 | 66.289 | 1.00 | 21.68 | N |
| ATOM | 663 | CE2 | TRP | A | 615 | 48.893 | 13.714 | 66.504 | 1.00 | 22.41 | C |
| ATOM | 664 | CE3 | TRP | A | 615 | 47.844 | 11.746 | 65.564 | 1.00 | 22.46 | C |
| ATOM | 665 | CZ2 | TRP | A | 615 | 47.873 | 13.862 | 67.452 | 1.00 | 21.99 | C |
| ATOM | 666 | CZ3 | TRP | A | 615 | 46.830 | 11.896 | 66.507 | 1.00 | 22.69 | C |
| ATOM | 667 | CH2 | TRP | A | 615 | 46.854 | 12.946 | 67.436 | 1.00 | 21.31 | C |
| ATOM | 668 | N | ARG | A | 616 | 49.765 | 14.360 | 61.712 | 1.00 | 19.16 | N |
| ATOM | 669 | CA | ARG | A | 616 | 49.279 | 15.732 | 61.583 | 1.00 | 19.38 | C |
| ATOM | 670 | C | ARG | A | 616 | 48.003 | 15.815 | 60.750 | 1.00 | 18.88 | C |
| ATOM | 671 | O | ARG | A | 616 | 47.126 | 16.626 | 61.035 | 1.00 | 20.14 | O |
| ATOM | 672 | CB | ARG | A | 616 | 50.372 | 16.636 | 61.006 | 1.00 | 19.58 | C |
| ATOM | 673 | CG | ARG | A | 616 | 51.601 | 16.777 | 61.939 | 1.00 | 19.33 | C |
| ATOM | 674 | CD | ARG | A | 616 | 51.205 | 17.143 | 63.382 | 1.00 | 19.19 | C |
| ATOM | 675 | NE | ARG | A | 616 | 52.370 | 17.272 | 64.264 | 1.00 | 20.83 | N |
| ATOM | 676 | CZ | ARG | A | 616 | 52.864 | 18.429 | 64.708 | 1.00 | 21.16 | C |
| ATOM | 677 | NH1 | ARG | A | 616 | 52.295 | 19.579 | 64.363 | 1.00 | 20.72 | N |
| ATOM | 678 | NH2 | ARG | A | 616 | 53.943 | 18.437 | 65.481 | 1.00 | 20.65 | N |
| ATOM | 679 | N | HIS | A | 617 | 47.891 | 14.978 | 59.726 | 1.00 | 19.11 | N |
| ATOM | 680 | CA | HIS | A | 617 | 46.680 | 14.973 | 58.914 | 1.00 | 18.93 | C |
| ATOM | 681 | C | HIS | A | 617 | 45.513 | 14.494 | 59.778 | 1.00 | 18.83 | C |
| ATOM | 682 | O | HIS | A | 617 | 44.438 | 15.093 | 59.775 | 1.00 | 19.75 | O |
| ATOM | 683 | CB | HIS | A | 617 | 46.836 | 14.050 | 57.699 | 1.00 | 18.84 | C |
| ATOM | 684 | CG | HIS | A | 617 | 45.531 | 13.665 | 57.077 | 1.00 | 19.13 | C |
| ATOM | 685 | ND1 | HIS | A | 617 | 44.626 | 14.595 | 56.614 | 1.00 | 18.00 | N |
| ATOM | 686 | CD2 | HIS | A | 617 | 44.960 | 12.453 | 56.891 | 1.00 | 19.38 | C |
| ATOM | 687 | CE1 | HIS | A | 617 | 43.549 | 13.971 | 56.172 | 1.00 | 19.86 | C |
| ATOM | 688 | NE2 | HIS | A | 617 | 43.727 | 12.671 | 56.330 | 1.00 | 19.30 | N |
| ATOM | 689 | N | ALA | A | 618 | 45.732 | 13.412 | 60.520 | 1.00 | 19.43 | N |
| ATOM | 690 | CA | ALA | A | 618 | 44.693 | 12.849 | 61.378 | 1.00 | 19.60 | C |
| ATOM | 691 | C | ALA | A | 618 | 44.286 | 13.857 | 62.448 | 1.00 | 19.42 | C |
| ATOM | 692 | O | ALA | A | 618 | 43.102 | 14.058 | 62.716 | 1.00 | 18.64 | O |
| ATOM | 693 | CB | ALA | A | 618 | 45.192 | 11.566 | 62.027 | 1.00 | 20.51 | C |
| ATOM | 694 | N | PHE | A | 619 | 45.282 | 14.482 | 63.063 | 1.00 | 19.50 | N |
| ATOM | 695 | CA | PHE | A | 619 | 45.045 | 15.487 | 64.088 | 1.00 | 20.02 | C |
| ATOM | 696 | C | PHE | A | 619 | 44.228 | 16.632 | 63.489 | 1.00 | 20.28 | C |
| ATOM | 697 | O | PHE | A | 619 | 43.252 | 17.081 | 64.076 | 1.00 | 21.04 | O |
| ATOM | 698 | CB | PHE | A | 619 | 46.385 | 16.016 | 64.620 | 1.00 | 20.99 | C |
| ATOM | 699 | CG | PHE | A | 619 | 46.247 | 17.208 | 65.522 | 1.00 | 20.46 | C |
| ATOM | 700 | CD1 | PHE | A | 619 | 45.570 | 17.105 | 66.735 | 1.00 | 20.41 | C |
| ATOM | 701 | CD2 | PHE | A | 619 | 46.781 | 18.442 | 65.152 | 1.00 | 20.31 | C |
| ATOM | 702 | CE1 | PHE | A | 619 | 45.423 | 18.215 | 67.573 | 1.00 | 20.49 | C |
| ATOM | 703 | CE2 | PHE | A | 619 | 46.640 | 19.560 | 65.980 | 1.00 | 20.02 | C |
| ATOM | 704 | CZ | PHE | A | 619 | 45.960 | 19.447 | 67.193 | 1.00 | 19.64 | C |
| ATOM | 705 | N | ASN | A | 620 | 44.627 | 17.099 | 62.311 | 1.00 | 20.76 | N |
| ATOM | 706 | CA | ASN | A | 620 | 43.901 | 18.172 | 61.644 | 1.00 | 21.16 | C |
| ATOM | 707 | C | ASN | A | 620 | 42.464 | 17.770 | 61.301 | 1.00 | 21.75 | C |
| ATOM | 708 | O | ASN | A | 620 | 41.541 | 18.580 | 61.407 | 1.00 | 21.18 | O |
| ATOM | 709 | CB | ASN | A | 620 | 44.652 | 18.605 | 60.382 | 1.00 | 21.66 | C |
| ATOM | 710 | CG | ASN | A | 620 | 45.707 | 19.659 | 60.678 | 1.00 | 22.26 | C |
| ATOM | 711 | OD1 | ASN | A | 620 | 45.397 | 20.698 | 61.256 | 1.00 | 23.57 | O |
| ATOM | 712 | ND2 | ASN | A | 620 | 46.947 | 19.396 | 60.296 | 1.00 | 22.73 | N |
| ATOM | 713 | N | THR | A | 621 | 42.273 | 16.517 | 60.898 | 1.00 | 21.37 | N |
| ATOM | 714 | CA | THR | A | 621 | 40.932 | 16.031 | 60.562 | 1.00 | 21.07 | C |
| ATOM | 715 | C | THR | A | 621 | 40.039 | 16.095 | 61.799 | 1.00 | 20.78 | C |
| ATOM | 716 | O | THR | A | 621 | 38.871 | 16.485 | 61.717 | 1.00 | 21.07 | O |
| ATOM | 717 | CB | THR | A | 621 | 40.978 | 14.573 | 60.043 | 1.00 | 21.12 | C |
| ATOM | 718 | OG1 | THR | A | 621 | 41.777 | 14.522 | 58.857 | 1.00 | 21.30 | O |
| ATOM | 719 | CG2 | THR | A | 621 | 39.564 | 14.063 | 59.705 | 1.00 | 20.92 | C |
| ATOM | 720 | N | ALA | A | 622 | 40.596 | 15.719 | 62.945 | 1.00 | 20.37 | N |
| ATOM | 721 | CA | ALA | A | 622 | 39.858 | 15.740 | 64.204 | 1.00 | 20.73 | C |
| ATOM | 722 | C | ALA | A | 622 | 39.576 | 17.180 | 64.637 | 1.00 | 21.19 | C |
| ATOM | 723 | O | ALA | A | 622 | 38.494 | 17.495 | 65.122 | 1.00 | 20.84 | O |
| ATOM | 724 | CB | ALA | A | 622 | 40.651 | 15.015 | 65.281 | 1.00 | 19.81 | C |
| ATOM | 725 | N | GLN | A | 623 | 40.556 | 18.057 | 64.461 | 1.00 | 21.37 | N |
| ATOM | 726 | CA | GLN | A | 623 | 40.366 | 19.454 | 64.829 | 1.00 | 21.92 | C |
| ATOM | 727 | C | GLN | A | 623 | 39.200 | 20.020 | 64.017 | 1.00 | 21.79 | C |
| ATOM | 728 | O | GLN | A | 623 | 38.322 | 20.694 | 64.563 | 1.00 | 21.48 | O |
| ATOM | 729 | CB | GLN | A | 623 | 41.655 | 20.244 | 64.570 | 1.00 | 22.41 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 | |
|---|---|---|---|---|---|---|---|---|---|---|---|
| ATOM | 730 | CG | GLN | A | 623 | 41.589 | 21.723 | 64.946 | 1.00 | 23.04 | C |
| ATOM | 731 | CD | GLN | A | 623 | 40.895 | 22.547 | 63.888 | 1.00 | 23.30 | C |
| ATOM | 732 | OE1 | GLN | A | 623 | 41.096 | 22.326 | 62.698 | 1.00 | 23.16 | O |
| ATOM | 733 | NE2 | GLN | A | 623 | 40.088 | 23.510 | 64.312 | 1.00 | 21.67 | N |
| ATOM | 734 | N | CYS | A | 624 | 39.172 | 19.721 | 62.722 | 1.00 | 21.83 | N |
| ATOM | 735 | CA | CYS | A | 624 | 38.091 | 20.207 | 61.877 | 1.00 | 23.04 | C |
| ATOM | 736 | C | CYS | A | 624 | 36.755 | 19.633 | 62.376 | 1.00 | 23.65 | C |
| ATOM | 737 | O | CYS | A | 624 | 35.738 | 20.316 | 62.363 | 1.00 | 23.51 | O |
| ATOM | 738 | CB | CYS | A | 624 | 38.333 | 19.813 | 60.419 | 1.00 | 22.98 | C |
| ATOM | 739 | SG | CYS | A | 624 | 37.111 | 20.472 | 59.244 | 1.00 | 23.32 | S |
| ATOM | 740 | N | MET | A | 625 | 36.760 | 18.381 | 62.827 | 1.00 | 24.06 | N |
| ATOM | 741 | CA | MET | A | 625 | 35.529 | 17.772 | 63.335 | 1.00 | 24.37 | C |
| ATOM | 742 | C | MET | A | 625 | 35.079 | 18.569 | 64.559 | 1.00 | 24.89 | C |
| ATOM | 743 | O | MET | A | 625 | 33.901 | 18.894 | 64.713 | 1.00 | 24.29 | O |
| ATOM | 744 | CB | MET | A | 625 | 35.775 | 16.307 | 63.728 | 1.00 | 24.65 | C |
| ATOM | 745 | CG | MET | A | 625 | 34.537 | 15.552 | 64.236 | 1.00 | 23.88 | C |
| ATOM | 746 | SD | MET | A | 625 | 33.241 | 15.329 | 62.988 | 1.00 | 24.24 | S |
| ATOM | 747 | CE | MET | A | 625 | 34.043 | 14.138 | 61.870 | 1.00 | 23.38 | C |
| ATOM | 748 | N | PHE | A | 626 | 36.035 | 18.882 | 65.426 | 1.00 | 25.12 | N |
| ATOM | 749 | CA | PHE | A | 626 | 35.755 | 19.642 | 66.635 | 1.00 | 25.63 | C |
| ATOM | 750 | C | PHE | A | 626 | 35.176 | 21.006 | 66.269 | 1.00 | 25.87 | C |
| ATOM | 751 | O | PHE | A | 626 | 34.162 | 21.429 | 66.829 | 1.00 | 25.20 | O |
| ATOM | 752 | CB | PHE | A | 626 | 37.038 | 19.817 | 67.449 | 1.00 | 25.83 | C |
| ATOM | 753 | CG | PHE | A | 626 | 36.848 | 20.587 | 68.723 | 1.00 | 27.11 | C |
| ATOM | 754 | CD1 | PHE | A | 626 | 36.312 | 19.971 | 69.851 | 1.00 | 26.38 | C |
| ATOM | 755 | CD2 | PHE | A | 626 | 37.199 | 21.936 | 68.793 | 1.00 | 26.52 | C |
| ATOM | 756 | CE1 | PHE | A | 626 | 36.125 | 20.688 | 71.037 | 1.00 | 27.69 | C |
| ATOM | 757 | CE2 | PHE | A | 626 | 37.017 | 22.664 | 69.975 | 1.00 | 28.07 | C |
| ATOM | 758 | CZ | PHE | A | 626 | 36.478 | 22.037 | 71.099 | 1.00 | 27.37 | C |
| ATOM | 759 | N | ALA | A | 627 | 35.819 | 21.683 | 65.319 | 1.00 | 25.94 | N |
| ATOM | 760 | CA | ALA | A | 627 | 35.365 | 22.997 | 64.870 | 1.00 | 26.64 | C |
| ATOM | 761 | C | ALA | A | 627 | 33.977 | 22.916 | 64.242 | 1.00 | 27.82 | C |
| ATOM | 762 | O | ALA | A | 627 | 33.135 | 23.788 | 64.462 | 1.00 | 27.51 | O |
| ATOM | 763 | CB | ALA | A | 627 | 36.360 | 23.587 | 63.869 | 1.00 | 27.41 | C |
| ATOM | 764 | N | ALA | A | 628 | 33.729 | 21.870 | 63.461 | 1.00 | 28.11 | N |
| ATOM | 765 | CA | ALA | A | 628 | 32.427 | 21.726 | 62.827 | 1.00 | 28.84 | C |
| ATOM | 766 | C | ALA | A | 628 | 31.352 | 21.491 | 63.893 | 1.00 | 30.25 | C |
| ATOM | 767 | O | ALA | A | 628 | 30.215 | 21.954 | 63.752 | 1.00 | 30.53 | O |
| ATOM | 768 | CB | ALA | A | 628 | 32.454 | 20.583 | 61.822 | 1.00 | 29.11 | C |
| ATOM | 769 | N | LEU | A | 629 | 31.720 | 20.790 | 64.965 | 1.00 | 31.21 | N |
| ATOM | 770 | CA | LEU | A | 629 | 30.797 | 20.514 | 66.065 | 1.00 | 31.99 | C |
| ATOM | 771 | C | LEU | A | 629 | 30.530 | 21.770 | 66.892 | 1.00 | 32.80 | C |
| ATOM | 772 | O | LEU | A | 629 | 29.388 | 22.052 | 67.251 | 1.00 | 32.42 | O |
| ATOM | 773 | CB | LEU | A | 629 | 31.361 | 19.429 | 66.988 | 1.00 | 31.44 | C |
| ATOM | 774 | CG | LEU | A | 629 | 31.436 | 17.993 | 66.462 | 1.00 | 32.76 | C |
| ATOM | 775 | CD1 | LEU | A | 629 | 32.178 | 17.119 | 67.464 | 1.00 | 31.09 | C |
| ATOM | 776 | CD2 | LEU | A | 629 | 30.031 | 17.462 | 66.224 | 1.00 | 32.65 | C |
| ATOM | 777 | N | LYS | A | 630 | 31.592 | 22.505 | 67.210 | 1.00 | 32.93 | N |
| ATOM | 778 | CA | LYS | A | 630 | 31.476 | 23.732 | 67.994 | 1.00 | 34.28 | C |
| ATOM | 779 | C | LYS | A | 630 | 31.076 | 24.911 | 67.112 | 1.00 | 34.39 | C |
| ATOM | 780 | O | LYS | A | 630 | 29.894 | 25.213 | 66.964 | 1.00 | 34.34 | O |
| ATOM | 781 | CB | LYS | A | 630 | 32.802 | 24.051 | 68.690 | 1.00 | 34.70 | C |
| ATOM | 782 | CG | LYS | A | 630 | 33.190 | 23.064 | 69.767 | 1.00 | 35.41 | C |
| ATOM | 783 | CD | LYS | A | 630 | 32.153 | 23.027 | 70.875 | 1.00 | 36.36 | C |
| ATOM | 784 | CE | LYS | A | 630 | 32.603 | 22.114 | 71.996 | 1.00 | 37.50 | C |
| ATOM | 785 | NZ | LYS | A | 630 | 31.620 | 22.046 | 73.113 | 1.00 | 39.26 | N |
| ATOM | 786 | N | ALA | A | 631 | 32.071 | 25.563 | 66.520 | 1.00 | 34.00 | N |
| ATOM | 787 | CA | ALA | A | 631 | 31.828 | 26.708 | 65.655 | 1.00 | 34.98 | C |
| ATOM | 788 | C | ALA | A | 631 | 30.745 | 26.411 | 64.615 | 1.00 | 35.56 | C |
| ATOM | 789 | O | ALA | A | 631 | 29.884 | 27.250 | 64.350 | 1.00 | 35.81 | O |
| ATOM | 790 | CB | ALA | A | 631 | 33.127 | 27.124 | 64.967 | 1.00 | 34.27 | C |
| ATOM | 791 | N | GLY | A | 632 | 30.784 | 25.216 | 64.034 | 1.00 | 35.65 | N |
| ATOM | 792 | CA | GLY | A | 632 | 29.795 | 24.848 | 63.036 | 1.00 | 36.45 | C |
| ATOM | 793 | C | GLY | A | 632 | 28.444 | 24.454 | 63.614 | 1.00 | 37.05 | C |
| ATOM | 794 | O | GLY | A | 632 | 27.514 | 24.153 | 62.870 | 1.00 | 36.87 | O |
| ATOM | 795 | N | LYS | A | 633 | 28.343 | 24.443 | 64.939 | 1.00 | 38.34 | N |
| ATOM | 796 | CA | LYS | A | 633 | 27.104 | 24.101 | 65.640 | 1.00 | 40.04 | C |
| ATOM | 797 | C | LYS | A | 633 | 26.452 | 22.772 | 65.245 | 1.00 | 40.79 | C |
| ATOM | 798 | O | LYS | A | 633 | 25.233 | 22.623 | 65.335 | 1.00 | 41.41 | O |
| ATOM | 799 | CB | LYS | A | 633 | 26.080 | 25.233 | 65.479 | 1.00 | 40.46 | C |
| ATOM | 800 | CG | LYS | A | 633 | 26.502 | 26.549 | 66.117 | 1.00 | 41.28 | C |
| ATOM | 801 | CD | LYS | A | 633 | 25.437 | 27.622 | 65.921 | 1.00 | 43.26 | C |
| ATOM | 802 | CE | LYS | A | 633 | 25.892 | 28.975 | 66.458 | 1.00 | 43.46 | C |
| ATOM | 803 | NZ | LYS | A | 633 | 24.948 | 30.064 | 66.056 | 1.00 | 45.08 | N |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | | 130.132 | 90.00 | 90.00 | 120.00 | P 31 2 1 | 6 |
|---|---|---|---|---|---|---|---|---|---|---|---|---|
| ATOM | 804 | N | ILE | A | 634 | 27.258 | 21.807 | 64.818 | 1.00 | 40.89 | N | |
| ATOM | 805 | CA | ILE | A | 634 | 26.743 | 20.500 | 64.431 | 1.00 | 41.48 | C | |
| ATOM | 806 | C | ILE | A | 634 | 26.514 | 19.648 | 65.678 | 1.00 | 42.34 | C | |
| ATOM | 807 | O | ILE | A | 634 | 25.709 | 18.718 | 65.677 | 1.00 | 42.84 | O | |
| ATOM | 808 | CB | ILE | A | 634 | 27.742 | 19.775 | 63.501 | 1.00 | 41.22 | C | |
| ATOM | 809 | CG1 | ILE | A | 634 | 27.818 | 20.510 | 62.163 | 1.00 | 41.52 | C | |
| ATOM | 810 | CG2 | ILE | A | 634 | 27.334 | 18.320 | 63.313 | 1.00 | 40.18 | C | |
| ATOM | 811 | CD1 | ILE | A | 634 | 28.950 | 20.044 | 61.268 | 1.00 | 42.19 | C | |
| ATOM | 812 | N | GLN | A | 635 | 27.231 | 19.981 | 66.742 | 1.00 | 42.86 | N | |
| ATOM | 813 | CA | GLN | A | 635 | 27.145 | 19.261 | 68.005 | 1.00 | 43.96 | C | |
| ATOM | 814 | C | GLN | A | 635 | 25.717 | 18.979 | 68.483 | 1.00 | 44.80 | C | |
| ATOM | 815 | O | GLN | A | 635 | 25.414 | 17.871 | 68.926 | 1.00 | 45.06 | O | |
| ATOM | 816 | CB | GLN | A | 635 | 27.911 | 20.045 | 69.070 | 1.00 | 44.10 | C | |
| ATOM | 817 | CG | GLN | A | 635 | 27.835 | 19.486 | 70.471 | 1.00 | 45.22 | C | |
| ATOM | 818 | CD | GLN | A | 635 | 28.758 | 20.226 | 71.419 | 1.00 | 45.45 | C | |
| ATOM | 819 | OE1 | GLN | A | 635 | 28.811 | 21.456 | 71.415 | 1.00 | 46.41 | O | |
| ATOM | 820 | NE2 | GLN | A | 635 | 29.488 | 19.481 | 72.237 | 1.00 | 45.04 | N | |
| ATOM | 821 | N | ASN | A | 636 | 24.842 | 19.976 | 68.382 | 1.00 | 45.32 | N | |
| ATOM | 822 | CA | ASN | A | 636 | 23.456 | 19.839 | 68.829 | 1.00 | 45.41 | C | |
| ATOM | 823 | C | ASN | A | 636 | 22.628 | 18.866 | 68.001 | 1.00 | 44.87 | C | |
| ATOM | 824 | O | ASN | A | 636 | 21.577 | 18.406 | 68.443 | 1.00 | 44.79 | O | |
| ATOM | 825 | CB | ASN | A | 636 | 22.761 | 21.206 | 68.822 | 1.00 | 46.54 | C | |
| ATOM | 826 | CG | ASN | A | 636 | 23.479 | 22.230 | 69.676 | 1.00 | 48.24 | C | |
| ATOM | 827 | OD1 | ASN | A | 636 | 23.661 | 22.037 | 70.881 | 1.00 | 48.35 | O | |
| ATOM | 828 | ND2 | ASN | A | 636 | 23.896 | 23.331 | 69.054 | 1.00 | 49.31 | N | |
| ATOM | 829 | N | LYS | A | 637 | 23.095 | 18.551 | 66.801 | 1.00 | 44.14 | N | |
| ATOM | 830 | CA | LYS | A | 637 | 22.356 | 17.650 | 65.932 | 1.00 | 43.64 | C | |
| ATOM | 831 | C | LYS | A | 637 | 22.744 | 16.183 | 66.074 | 1.00 | 42.68 | C | |
| ATOM | 832 | O | LYS | A | 637 | 22.204 | 15.331 | 65.370 | 1.00 | 42.44 | O | |
| ATOM | 833 | CB | LYS | A | 637 | 22.532 | 18.087 | 64.477 | 1.00 | 44.85 | C | |
| ATOM | 834 | CG | LYS | A | 637 | 22.133 | 19.532 | 64.233 | 1.00 | 47.07 | C | |
| ATOM | 835 | CD | LYS | A | 637 | 22.184 | 19.891 | 62.759 | 1.00 | 48.61 | C | |
| ATOM | 836 | CE | LYS | A | 637 | 21.603 | 21.274 | 62.524 | 1.00 | 49.01 | C | |
| ATOM | 837 | NZ | LYS | A | 637 | 21.367 | 21.524 | 61.079 | 1.00 | 50.60 | N | |
| ATOM | 838 | N | LEU | A | 638 | 23.661 | 15.883 | 66.990 | 1.00 | 41.27 | N | |
| ATOM | 839 | CA | LEU | A | 638 | 24.117 | 14.508 | 67.179 | 1.00 | 40.07 | C | |
| ATOM | 840 | C | LEU | A | 638 | 24.068 | 14.083 | 68.638 | 1.00 | 39.23 | C | |
| ATOM | 841 | O | LEU | A | 638 | 23.930 | 14.916 | 69.530 | 1.00 | 39.72 | O | |
| ATOM | 842 | CB | LEU | A | 638 | 25.552 | 14.360 | 66.662 | 1.00 | 39.45 | C | |
| ATOM | 843 | CG | LEU | A | 638 | 25.827 | 14.860 | 65.244 | 1.00 | 39.08 | C | |
| ATOM | 844 | CD1 | LEU | A | 638 | 27.300 | 14.669 | 64.902 | 1.00 | 38.86 | C | |
| ATOM | 845 | CD2 | LEU | A | 638 | 24.949 | 14.113 | 64.266 | 1.00 | 38.98 | C | |
| ATOM | 846 | N | THR | A | 639 | 24.186 | 12.782 | 68.877 | 1.00 | 38.25 | N | |
| ATOM | 847 | CA | THR | A | 639 | 24.165 | 12.259 | 70.240 | 1.00 | 37.28 | C | |
| ATOM | 848 | C | THR | A | 639 | 25.589 | 12.195 | 70.771 | 1.00 | 36.75 | C | |
| ATOM | 849 | O | THR | A | 639 | 26.548 | 12.351 | 70.011 | 1.00 | 36.05 | O | |
| ATOM | 850 | CB | THR | A | 639 | 23.581 | 10.836 | 70.302 | 1.00 | 37.19 | C | |
| ATOM | 851 | OG1 | THR | A | 639 | 24.478 | 9.923 | 69.656 | 1.00 | 36.69 | O | |
| ATOM | 852 | CG2 | THR | A | 639 | 22.220 | 10.781 | 69.614 | 1.00 | 36.32 | C | |
| ATOM | 853 | N | ASP | A | 640 | 25.729 | 11.961 | 72.073 | 1.00 | 36.26 | N | |
| ATOM | 854 | CA | ASP | A | 640 | 27.052 | 11.867 | 72.672 | 1.00 | 36.32 | C | |
| ATOM | 855 | C | ASP | A | 640 | 27.850 | 10.697 | 72.099 | 1.00 | 35.02 | C | |
| ATOM | 856 | O | ASP | A | 640 | 29.059 | 10.816 | 71.884 | 1.00 | 34.76 | O | |
| ATOM | 857 | CB | ASP | A | 640 | 26.955 | 11.723 | 74.193 | 1.00 | 38.26 | C | |
| ATOM | 858 | CG | ASP | A | 640 | 26.662 | 13.039 | 74.887 | 1.00 | 39.96 | C | |
| ATOM | 859 | OD1 | ASP | A | 640 | 26.725 | 14.087 | 74.217 | 1.00 | 40.78 | O | |
| ATOM | 860 | OD2 | ASP | A | 640 | 26.381 | 13.027 | 76.105 | 1.00 | 42.06 | O | |
| ATOM | 861 | N | LEU | A | 641 | 27.182 | 9.571 | 71.854 | 1.00 | 33.08 | N | |
| ATOM | 862 | CA | LEU | A | 641 | 27.868 | 8.406 | 71.308 | 1.00 | 32.34 | C | |
| ATOM | 863 | C | LEU | A | 641 | 28.357 | 8.663 | 69.890 | 1.00 | 31.96 | C | |
| ATOM | 864 | O | LEU | A | 641 | 29.424 | 8.185 | 69.504 | 1.00 | 31.71 | O | |
| ATOM | 865 | CB | LEU | A | 641 | 26.959 | 7.172 | 71.332 | 1.00 | 31.19 | C | |
| ATOM | 866 | CG | LEU | A | 641 | 26.635 | 6.602 | 72.720 | 1.00 | 30.69 | C | |
| ATOM | 867 | CD1 | LEU | A | 641 | 25.708 | 5.397 | 72.577 | 1.00 | 29.71 | C | |
| ATOM | 868 | CD2 | LEU | A | 641 | 27.915 | 6.201 | 73.427 | 1.00 | 28.60 | C | |
| ATOM | 869 | N | GLU | A | 642 | 27.578 | 9.418 | 69.118 | 1.00 | 31.24 | N | |
| ATOM | 870 | CA | GLU | A | 642 | 27.955 | 9.735 | 67.747 | 1.00 | 30.84 | C | |
| ATOM | 871 | C | GLU | A | 642 | 29.158 | 10.675 | 67.742 | 1.00 | 29.56 | C | |
| ATOM | 872 | O | GLU | A | 642 | 30.075 | 10.506 | 66.943 | 1.00 | 28.91 | O | |
| ATOM | 873 | CB | GLU | A | 642 | 26.772 | 10.363 | 67.003 | 1.00 | 31.18 | C | |
| ATOM | 874 | CG | GLU | A | 642 | 25.542 | 9.454 | 66.983 | 1.00 | 31.88 | C | |
| ATOM | 875 | CD | GLU | A | 642 | 24.388 | 10.020 | 66.184 | 1.00 | 32.73 | C | |
| ATOM | 876 | OE1 | GLU | A | 642 | 24.076 | 11.221 | 66.340 | 1.00 | 32.27 | O | |
| ATOM | 877 | OE2 | GLU | A | 642 | 23.786 | 9.255 | 65.405 | 1.00 | 32.80 | O | |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 6 | |
|---|---|---|---|---|---|---|---|---|---|---|---|
| ATOM | 878 | N | ILE | A | 643 | 29.153 | 11.645 | 68.652 | 1.00 | 28.48 | N |
| ATOM | 879 | CA | ILE | A | 643 | 30.249 | 12.607 | 68.771 | 1.00 | 27.88 | C |
| ATOM | 880 | C | ILE | A | 643 | 31.525 | 11.900 | 69.224 | 1.00 | 26.94 | C |
| ATOM | 881 | O | ILE | A | 643 | 32.612 | 12.190 | 68.728 | 1.00 | 25.90 | O |
| ATOM | 882 | CB | ILE | A | 643 | 29.892 | 13.731 | 69.777 | 1.00 | 28.36 | C |
| ATOM | 883 | CG1 | ILE | A | 643 | 28.781 | 14.610 | 69.186 | 1.00 | 28.88 | C |
| ATOM | 884 | CG2 | ILE | A | 643 | 31.132 | 14.562 | 70.107 | 1.00 | 28.38 | C |
| ATOM | 885 | CD1 | ILE | A | 643 | 28.190 | 15.609 | 70.155 | 1.00 | 30.17 | C |
| ATOM | 886 | N | LEU | A | 644 | 31.379 | 10.966 | 70.160 | 1.00 | 26.15 | N |
| ATOM | 887 | CA | LEU | A | 644 | 32.507 | 10.191 | 70.670 | 1.00 | 25.82 | C |
| ATOM | 888 | C | LEU | A | 644 | 33.118 | 9.369 | 69.535 | 1.00 | 25.67 | C |
| ATOM | 889 | O | LEU | A | 644 | 34.334 | 9.338 | 69.359 | 1.00 | 24.76 | O |
| ATOM | 890 | CB | LEU | A | 644 | 32.026 | 9.253 | 71.783 | 1.00 | 27.00 | C |
| ATOM | 891 | CG | LEU | A | 644 | 32.975 | 8.165 | 72.294 | 1.00 | 27.02 | C |
| ATOM | 892 | CD1 | LEU | A | 644 | 34.141 | 8.798 | 73.026 | 1.00 | 27.74 | C |
| ATOM | 893 | CD2 | LEU | A | 644 | 32.219 | 7.227 | 73.226 | 1.00 | 28.47 | C |
| ATOM | 894 | N | ALA | A | 645 | 32.257 | 8.700 | 68.770 | 1.00 | 25.19 | N |
| ATOM | 895 | CA | ALA | A | 645 | 32.691 | 7.863 | 67.659 | 1.00 | 24.40 | C |
| ATOM | 896 | C | ALA | A | 645 | 33.376 | 8.669 | 66.555 | 1.00 | 23.83 | C |
| ATOM | 897 | O | ALA | A | 645 | 34.407 | 8.254 | 66.020 | 1.00 | 22.94 | O |
| ATOM | 898 | CB | ALA | A | 645 | 31.496 | 7.106 | 67.088 | 1.00 | 24.19 | C |
| ATOM | 899 | N | LEU | A | 646 | 32.794 | 9.817 | 66.218 | 1.00 | 22.61 | N |
| ATOM | 900 | CA | LEU | A | 646 | 33.338 | 10.689 | 65.181 | 1.00 | 23.41 | C |
| ATOM | 901 | C | LEU | A | 646 | 34.742 | 11.182 | 65.521 | 1.00 | 22.68 | C |
| ATOM | 902 | O | LEU | A | 646 | 35.642 | 11.141 | 64.678 | 1.00 | 23.43 | O |
| ATOM | 903 | CB | LEU | A | 646 | 32.423 | 11.901 | 64.966 | 1.00 | 23.21 | C |
| ATOM | 904 | CG | LEU | A | 646 | 31.104 | 11.691 | 64.214 | 1.00 | 24.57 | C |
| ATOM | 905 | CD1 | LEU | A | 646 | 30.240 | 12.953 | 64.327 | 1.00 | 24.83 | C |
| ATOM | 906 | CD2 | LEU | A | 646 | 31.389 | 11.369 | 62.759 | 1.00 | 23.27 | C |
| ATOM | 907 | N | LEU | A | 647 | 34.927 | 11.645 | 66.754 | 1.00 | 21.87 | N |
| ATOM | 908 | CA | LEU | A | 647 | 36.226 | 12.159 | 67.175 | 1.00 | 21.96 | C |
| ATOM | 909 | C | LEU | A | 647 | 37.288 | 11.077 | 67.088 | 1.00 | 21.42 | C |
| ATOM | 910 | O | LEU | A | 647 | 38.385 | 11.311 | 66.570 | 1.00 | 21.70 | O |
| ATOM | 911 | CB | LEU | A | 647 | 36.159 | 12.713 | 68.603 | 1.00 | 21.42 | C |
| ATOM | 912 | CG | LEU | A | 647 | 37.450 | 13.388 | 69.094 | 1.00 | 20.22 | C |
| ATOM | 913 | CD1 | LEU | A | 647 | 37.841 | 14.506 | 68.160 | 1.00 | 20.73 | C |
| ATOM | 914 | CD2 | LEU | A | 647 | 37.238 | 13.934 | 70.497 | 1.00 | 21.29 | C |
| ATOM | 915 | N | ILE | A | 648 | 36.964 | 9.894 | 67.602 | 1.00 | 21.60 | N |
| ATOM | 916 | CA | ILE | A | 648 | 37.883 | 8.760 | 67.560 | 1.00 | 20.41 | C |
| ATOM | 917 | C | ILE | A | 648 | 38.162 | 8.363 | 66.108 | 1.00 | 20.06 | C |
| ATOM | 918 | O | ILE | A | 648 | 39.311 | 8.114 | 65.729 | 1.00 | 19.99 | O |
| ATOM | 919 | CB | ILE | A | 648 | 37.299 | 7.543 | 68.325 | 1.00 | 21.47 | C |
| ATOM | 920 | CG1 | ILE | A | 648 | 37.280 | 7.838 | 69.828 | 1.00 | 21.87 | C |
| ATOM | 921 | CG2 | ILE | A | 648 | 38.137 | 6.292 | 68.049 | 1.00 | 21.57 | C |
| ATOM | 922 | CD1 | ILE | A | 648 | 36.453 | 6.853 | 70.655 | 1.00 | 22.97 | C |
| ATOM | 923 | N | ALA | A | 649 | 37.110 | 8.300 | 65.297 | 1.00 | 19.50 | N |
| ATOM | 924 | CA | ALA | A | 649 | 37.246 | 7.944 | 63.880 | 1.00 | 19.34 | C |
| ATOM | 925 | C | ALA | A | 649 | 38.146 | 8.955 | 63.157 | 1.00 | 19.12 | C |
| ATOM | 926 | O | ALA | A | 649 | 39.080 | 8.585 | 62.439 | 1.00 | 20.17 | O |
| ATOM | 927 | CB | ALA | A | 649 | 35.863 | 7.911 | 63.214 | 1.00 | 18.41 | C |
| ATOM | 928 | N | ALA | A | 650 | 37.860 | 10.236 | 63.340 | 1.00 | 18.82 | N |
| ATOM | 929 | CA | ALA | A | 650 | 38.666 | 11.276 | 62.694 | 1.00 | 19.02 | C |
| ATOM | 930 | C | ALA | A | 650 | 40.144 | 11.053 | 63.009 | 1.00 | 18.08 | C |
| ATOM | 931 | O | ALA | A | 650 | 40.977 | 11.025 | 62.111 | 1.00 | 19.28 | O |
| ATOM | 932 | CB | ALA | A | 650 | 38.223 | 12.661 | 63.175 | 1.00 | 18.68 | C |
| ATOM | 933 | N | LEU | A | 651 | 40.458 | 10.871 | 64.287 | 1.00 | 18.24 | N |
| ATOM | 934 | CA | LEU | A | 651 | 41.835 | 10.659 | 64.722 | 1.00 | 18.02 | C |
| ATOM | 935 | C | LEU | A | 651 | 42.427 | 9.332 | 64.229 | 1.00 | 18.25 | C |
| ATOM | 936 | O | LEU | A | 651 | 43.638 | 9.228 | 64.006 | 1.00 | 16.91 | O |
| ATOM | 937 | CB | LEU | A | 651 | 41.909 | 10.695 | 66.260 | 1.00 | 19.00 | C |
| ATOM | 938 | CG | LEU | A | 651 | 41.688 | 12.022 | 66.998 | 1.00 | 19.68 | C |
| ATOM | 939 | CD1 | LEU | A | 651 | 41.356 | 11.761 | 68.457 | 1.00 | 19.96 | C |
| ATOM | 940 | CD2 | LEU | A | 651 | 42.942 | 12.893 | 66.883 | 1.00 | 20.84 | C |
| ATOM | 941 | N | SER | A | 652 | 41.575 | 8.323 | 64.054 | 1.00 | 17.83 | N |
| ATOM | 942 | CA | SER | A | 652 | 42.040 | 6.990 | 63.655 | 1.00 | 19.00 | C |
| ATOM | 943 | C | SER | A | 652 | 41.872 | 6.594 | 62.193 | 1.00 | 19.23 | C |
| ATOM | 944 | O | SER | A | 652 | 42.416 | 5.579 | 61.773 | 1.00 | 19.98 | O |
| ATOM | 945 | CB | SER | A | 652 | 41.311 | 5.918 | 64.483 | 1.00 | 19.45 | C |
| ATOM | 946 | OG | SER | A | 652 | 41.370 | 6.180 | 65.871 | 1.00 | 21.36 | O |
| ATOM | 947 | N | HIS | A | 653 | 41.139 | 7.385 | 61.421 | 1.00 | 19.68 | N |
| ATOM | 948 | CA | HIS | A | 653 | 40.833 | 7.008 | 60.046 | 1.00 | 19.43 | C |
| ATOM | 949 | C | HIS | A | 653 | 41.941 | 6.658 | 59.063 | 1.00 | 20.17 | C |
| ATOM | 950 | O | HIS | A | 653 | 41.654 | 6.011 | 58.064 | 1.00 | 20.39 | O |
| ATOM | 951 | CB | HIS | A | 653 | 39.887 | 8.040 | 59.414 | 1.00 | 18.92 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | | 130.132 | 90.00 | 90.00 | 120.00 | P 31 2 1 | 6 |
|---|---|---|---|---|---|---|---|---|---|---|
| ATOM | 952 | CG | HIS | A | 653 | 40.586 | 9.209 | 58.789 | 1.00 | 18.98 | C |
| ATOM | 953 | ND1 | HIS | A | 653 | 41.019 | 10.296 | 59.519 | 1.00 | 19.24 | N |
| ATOM | 954 | CD2 | HIS | A | 653 | 40.923 | 9.452 | 57.503 | 1.00 | 17.63 | C |
| ATOM | 955 | CE1 | HIS | A | 653 | 41.590 | 11.163 | 58.700 | 1.00 | 17.52 | C |
| ATOM | 956 | NE2 | HIS | A | 653 | 41.543 | 10.675 | 57.472 | 1.00 | 17.34 | N |
| ATOM | 957 | N | ASP | A | 654 | 43.185 | 7.078 | 59.301 | 1.00 | 19.61 | N |
| ATOM | 958 | CA | ASP | A | 654 | 44.278 | 6.740 | 58.379 | 1.00 | 20.03 | C |
| ATOM | 959 | C | ASP | A | 654 | 45.429 | 5.997 | 59.049 | 1.00 | 20.31 | C |
| ATOM | 960 | O | ASP | A | 654 | 46.558 | 6.012 | 58.546 | 1.00 | 20.95 | O |
| ATOM | 961 | CB | ASP | A | 654 | 44.834 | 7.998 | 57.722 | 1.00 | 19.88 | C |
| ATOM | 962 | CG | ASP | A | 654 | 44.038 | 8.416 | 56.506 | 1.00 | 20.74 | C |
| ATOM | 963 | OD1 | ASP | A | 654 | 43.609 | 7.511 | 55.752 | 1.00 | 21.43 | O |
| ATOM | 964 | OD2 | ASP | A | 654 | 43.859 | 9.632 | 56.255 | 1.00 | 20.20 | O |
| ATOM | 965 | N | LEU | A | 655 | 45.160 | 5.387 | 60.200 | 1.00 | 19.89 | N |
| ATOM | 966 | CA | LEU | A | 655 | 46.183 | 4.669 | 60.937 | 1.00 | 20.36 | C |
| ATOM | 967 | C | LEU | A | 655 | 47.025 | 3.704 | 60.097 | 1.00 | 20.84 | C |
| ATOM | 968 | O | LEU | A | 655 | 46.496 | 2.945 | 59.273 | 1.00 | 20.21 | O |
| ATOM | 969 | CB | LEU | A | 655 | 45.550 | 3.903 | 62.107 | 1.00 | 20.08 | C |
| ATOM | 970 | CG | LEU | A | 655 | 45.222 | 4.666 | 63.390 | 1.00 | 21.11 | C |
| ATOM | 971 | CD1 | LEU | A | 655 | 44.266 | 3.835 | 64.250 | 1.00 | 20.20 | C |
| ATOM | 972 | CD2 | LEU | A | 655 | 46.503 | 4.957 | 64.148 | 1.00 | 21.02 | C |
| ATOM | 973 | N | ASP | A | 656 | 48.340 | 3.774 | 60.302 | 1.00 | 21.70 | N |
| ATOM | 974 | CA | ASP | A | 656 | 49.314 | 2.917 | 59.638 | 1.00 | 23.38 | C |
| ATOM | 975 | C | ASP | A | 656 | 49.397 | 3.104 | 58.126 | 1.00 | 24.19 | C |
| ATOM | 976 | O | ASP | A | 656 | 49.942 | 2.262 | 57.426 | 1.00 | 23.92 | O |
| ATOM | 977 | CB | ASP | A | 656 | 49.005 | 1.454 | 59.992 | 1.00 | 24.45 | C |
| ATOM | 978 | CG | ASP | A | 656 | 50.169 | 0.514 | 59.698 | 1.00 | 25.59 | C |
| ATOM | 979 | OD1 | ASP | A | 656 | 51.328 | 0.865 | 60.015 | 1.00 | 25.86 | O |
| ATOM | 980 | OD2 | ASP | A | 656 | 49.924 | −0.588 | 59.166 | 1.00 | 26.82 | O |
| ATOM | 981 | N | HIS | A | 657 | 48.865 | 4.215 | 57.626 | 1.00 | 25.15 | N |
| ATOM | 982 | CA | HIS | A | 657 | 48.905 | 4.508 | 56.189 | 1.00 | 25.34 | C |
| ATOM | 983 | C | HIS | A | 657 | 50.365 | 4.555 | 55.728 | 1.00 | 26.06 | C |
| ATOM | 984 | O | HIS | A | 657 | 51.219 | 5.137 | 56.397 | 1.00 | 25.14 | O |
| ATOM | 985 | CB | HIS | A | 657 | 48.231 | 5.854 | 55.921 | 1.00 | 24.46 | C |
| ATOM | 986 | CG | HIS | A | 657 | 47.716 | 6.012 | 54.524 | 1.00 | 24.00 | C |
| ATOM | 987 | ND1 | HIS | A | 657 | 48.542 | 6.066 | 53.422 | 1.00 | 22.91 | N |
| ATOM | 988 | CD2 | HIS | A | 657 | 46.453 | 6.146 | 54.056 | 1.00 | 23.03 | C |
| ATOM | 989 | CE1 | HIS | A | 657 | 47.809 | 6.230 | 52.335 | 1.00 | 24.09 | C |
| ATOM | 990 | NE2 | HIS | A | 657 | 46.538 | 6.281 | 52.694 | 1.00 | 22.84 | N |
| ATOM | 991 | N | ARG | A | 658 | 50.656 | 3.947 | 54.583 | 1.00 | 27.49 | N |
| ATOM | 992 | CA | ARG | A | 658 | 52.026 | 3.935 | 54.081 | 1.00 | 29.96 | C |
| ATOM | 993 | C | ARG | A | 658 | 52.238 | 4.827 | 52.861 | 1.00 | 30.06 | C |
| ATOM | 994 | O | ARG | A | 658 | 53.321 | 4.846 | 52.285 | 1.00 | 29.63 | O |
| ATOM | 995 | CB | ARG | A | 658 | 52.446 | 2.497 | 53.758 | 1.00 | 32.14 | C |
| ATOM | 996 | CG | ARG | A | 658 | 52.573 | 1.591 | 54.989 | 1.00 | 35.42 | C |
| ATOM | 997 | CD | ARG | A | 658 | 52.639 | 0.118 | 54.582 | 1.00 | 39.58 | C |
| ATOM | 998 | NE | ARG | A | 658 | 53.007 | −0.760 | 55.694 | 1.00 | 42.66 | N |
| ATOM | 999 | CZ | ARG | A | 658 | 54.221 | −0.807 | 56.235 | 1.00 | 43.93 | C |
| ATOM | 1000 | NH1 | ARG | A | 658 | 55.190 | −0.027 | 55.767 | 1.00 | 45.35 | N |
| ATOM | 1001 | NH2 | ARG | A | 658 | 54.472 | −1.632 | 57.241 | 1.00 | 44.87 | N |
| ATOM | 1002 | N | GLY | A | 659 | 51.210 | 5.573 | 52.474 | 1.00 | 30.34 | N |
| ATOM | 1003 | CA | GLY | A | 659 | 51.335 | 6.442 | 51.318 | 1.00 | 31.78 | C |
| ATOM | 1004 | C | GLY | A | 659 | 50.508 | 5.932 | 50.155 | 1.00 | 32.86 | C |
| ATOM | 1005 | O | GLY | A | 659 | 50.460 | 4.726 | 49.903 | 1.00 | 32.41 | O |
| ATOM | 1006 | N | VAL | A | 660 | 49.854 | 6.844 | 49.444 | 1.00 | 34.47 | N |
| ATOM | 1007 | CA | VAL | A | 660 | 49.015 | 6.460 | 48.315 | 1.00 | 37.07 | C |
| ATOM | 1008 | C | VAL | A | 660 | 49.716 | 5.555 | 47.301 | 1.00 | 38.55 | C |
| ATOM | 1009 | O | VAL | A | 660 | 49.075 | 4.704 | 46.687 | 1.00 | 39.62 | O |
| ATOM | 1010 | CB | VAL | A | 660 | 48.467 | 7.697 | 47.570 | 1.00 | 37.04 | C |
| ATOM | 1011 | CG1 | VAL | A | 660 | 47.547 | 8.489 | 48.483 | 1.00 | 37.23 | C |
| ATOM | 1012 | CG2 | VAL | A | 660 | 49.622 | 8.568 | 47.084 | 1.00 | 37.36 | C |
| ATOM | 1013 | N | ASN | A | 661 | 51.024 | 5.726 | 47.131 | 1.00 | 40.07 | N |
| ATOM | 1014 | CA | ASN | A | 661 | 51.766 | 4.908 | 46.171 | 1.00 | 42.63 | C |
| ATOM | 1015 | C | ASN | A | 661 | 52.388 | 3.644 | 46.746 | 1.00 | 44.42 | C |
| ATOM | 1016 | O | ASN | A | 661 | 53.207 | 2.991 | 46.092 | 1.00 | 44.01 | O |
| ATOM | 1017 | CB | ASN | A | 661 | 52.849 | 5.735 | 45.481 | 1.00 | 41.27 | C |
| ATOM | 1018 | CG | ASN | A | 661 | 52.270 | 6.828 | 44.615 | 1.00 | 41.09 | C |
| ATOM | 1019 | OD1 | ASN | A | 661 | 51.226 | 6.644 | 43.993 | 1.00 | 40.35 | O |
| ATOM | 1020 | ND2 | ASN | A | 661 | 52.947 | 7.970 | 44.560 | 1.00 | 40.87 | N |
| ATOM | 1021 | N | ASN | A | 662 | 52.004 | 3.300 | 47.968 | 1.00 | 46.67 | N |
| ATOM | 1022 | CA | ASN | A | 662 | 52.520 | 2.099 | 48.596 | 1.00 | 49.44 | C |
| ATOM | 1023 | C | ASN | A | 662 | 51.453 | 1.007 | 48.483 | 1.00 | 51.35 | C |
| ATOM | 1024 | O | ASN | A | 662 | 50.285 | 1.227 | 48.808 | 1.00 | 50.63 | O |
| ATOM | 1025 | CB | ASN | A | 662 | 52.877 | 2.380 | 50.055 | 1.00 | 50.07 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 1026 | CG | ASN | A | 662 | 53.501 | 1.186 | 50.736 | 1.00 | 50.69 | C |
| ATOM | 1027 | OD1 | ASN | A | 662 | 52.844 | 0.165 | 50.939 | 1.00 | 50.93 | O |
| ATOM | 1028 | ND2 | ASN | A | 662 | 54.779 | 1.302 | 51.089 | 1.00 | 50.91 | N |
| ATOM | 1029 | N | SER | A | 663 | 51.872 | −0.162 | 48.004 | 1.00 | 54.13 | N |
| ATOM | 1030 | CA | SER | A | 663 | 50.990 | −1.311 | 47.792 | 1.00 | 57.21 | C |
| ATOM | 1031 | C | SER | A | 663 | 51.130 | −2.385 | 48.872 | 1.00 | 59.09 | C |
| ATOM | 1032 | O | SER | A | 663 | 50.423 | −3.394 | 48.846 | 1.00 | 59.12 | O |
| ATOM | 1033 | CB | SER | A | 663 | 51.299 | −1.949 | 46.430 | 1.00 | 57.27 | C |
| ATOM | 1034 | OG | SER | A | 663 | 51.323 | −0.992 | 45.384 | 1.00 | 58.78 | O |
| ATOM | 1035 | N | TYR | A | 664 | 52.038 | −2.171 | 49.816 | 1.00 | 61.54 | N |
| ATOM | 1036 | CA | TYR | A | 664 | 52.280 | −3.143 | 50.874 | 1.00 | 64.28 | C |
| ATOM | 1037 | C | TYR | A | 664 | 51.029 | −3.686 | 51.565 | 1.00 | 65.88 | C |
| ATOM | 1038 | O | TYR | A | 664 | 50.698 | −4.863 | 51.420 | 1.00 | 66.03 | O |
| ATOM | 1039 | CB | TYR | A | 664 | 53.224 | −2.552 | 51.918 | 1.00 | 64.85 | C |
| ATOM | 1040 | CG | TYR | A | 664 | 53.771 | −3.590 | 52.855 | 1.00 | 65.69 | C |
| ATOM | 1041 | CD1 | TYR | A | 664 | 53.082 | −3.952 | 54.012 | 1.00 | 66.10 | C |
| ATOM | 1042 | CD2 | TYR | A | 664 | 54.963 | −4.246 | 52.562 | 1.00 | 66.20 | C |
| ATOM | 1043 | CE1 | TYR | A | 664 | 53.573 | −4.948 | 54.855 | 1.00 | 66.66 | C |
| ATOM | 1044 | CE2 | TYR | A | 664 | 55.460 | −5.238 | 53.389 | 1.00 | 66.43 | C |
| ATOM | 1045 | CZ | TYR | A | 664 | 54.765 | −5.586 | 54.535 | 1.00 | 66.77 | C |
| ATOM | 1046 | OH | TYR | A | 664 | 55.277 | −6.563 | 55.357 | 1.00 | 66.80 | O |
| ATOM | 1047 | N | ILE | A | 665 | 50.336 | −2.834 | 52.312 | 1.00 | 67.73 | N |
| ATOM | 1048 | CA | ILE | A | 665 | 49.137 | −3.260 | 53.033 | 1.00 | 69.76 | C |
| ATOM | 1049 | C | ILE | A | 665 | 48.178 | −4.107 | 52.206 | 1.00 | 71.22 | C |
| ATOM | 1050 | O | ILE | A | 665 | 47.630 | −5.094 | 52.696 | 1.00 | 71.40 | O |
| ATOM | 1051 | CB | ILE | A | 665 | 48.342 | −2.058 | 53.581 | 1.00 | 69.70 | C |
| ATOM | 1052 | CG1 | ILE | A | 665 | 49.233 | −1.230 | 54.507 | 1.00 | 69.76 | C |
| ATOM | 1053 | CG2 | ILE | A | 665 | 47.104 | −2.553 | 54.334 | 1.00 | 69.55 | C |
| ATOM | 1054 | CD1 | ILE | A | 665 | 48.601 | 0.060 | 54.979 | 1.00 | 69.31 | C |
| ATOM | 1055 | N | GLN | A | 666 | 47.976 | −3.720 | 50.954 | 1.00 | 72.97 | N |
| ATOM | 1056 | CA | GLN | A | 666 | 47.063 | −4.436 | 50.075 | 1.00 | 74.96 | C |
| ATOM | 1057 | C | GLN | A | 666 | 47.620 | −5.773 | 49.582 | 1.00 | 76.03 | C |
| ATOM | 1058 | O | GLN | A | 666 | 46.895 | −6.764 | 49.510 | 1.00 | 76.08 | O |
| ATOM | 1059 | CB | GLN | A | 666 | 46.711 | −3.540 | 48.889 | 1.00 | 75.43 | C |
| ATOM | 1060 | CG | GLN | A | 666 | 46.253 | −2.154 | 49.314 | 1.00 | 76.40 | C |
| ATOM | 1061 | CD | GLN | A | 666 | 46.411 | −1.128 | 48.215 | 1.00 | 77.09 | C |
| ATOM | 1062 | OE1 | GLN | A | 666 | 45.698 | −1.156 | 47.211 | 1.00 | 77.79 | O |
| ATOM | 1063 | NE2 | GLN | A | 666 | 47.362 | −0.216 | 48.395 | 1.00 | 77.18 | N |
| ATOM | 1064 | N | ARG | A | 667 | 48.907 | −5.799 | 49.251 | 1.00 | 77.41 | N |
| ATOM | 1065 | CA | ARG | A | 667 | 49.549 | −7.015 | 48.761 | 1.00 | 78.95 | C |
| ATOM | 1066 | C | ARG | A | 667 | 49.920 | −7.987 | 49.877 | 1.00 | 79.77 | C |
| ATOM | 1067 | O | ARG | A | 667 | 50.309 | −9.124 | 49.613 | 1.00 | 79.73 | O |
| ATOM | 1068 | CB | ARG | A | 667 | 50.797 | −6.654 | 47.947 | 1.00 | 79.33 | C |
| ATOM | 1069 | CG | ARG | A | 667 | 50.479 | −6.078 | 46.575 | 1.00 | 79.99 | C |
| ATOM | 1070 | CD | ARG | A | 667 | 51.651 | −5.305 | 45.989 | 1.00 | 80.54 | C |
| ATOM | 1071 | NE | ARG | A | 667 | 51.369 | −4.805 | 44.642 | 1.00 | 81.26 | N |
| ATOM | 1072 | CZ | ARG | A | 667 | 50.286 | −4.109 | 44.302 | 1.00 | 81.68 | C |
| ATOM | 1073 | NH1 | ARG | A | 667 | 49.359 | −3.820 | 45.207 | 1.00 | 81.97 | N |
| ATOM | 1074 | NH2 | ARG | A | 667 | 50.127 | −3.696 | 43.052 | 1.00 | 81.83 | N |
| ATOM | 1075 | N | SER | A | 668 | 49.800 | −7.543 | 51.124 | 1.00 | 80.94 | N |
| ATOM | 1076 | CA | SER | A | 668 | 50.121 | −8.402 | 52.256 | 1.00 | 82.25 | C |
| ATOM | 1077 | C | SER | A | 668 | 48.904 | −9.235 | 52.651 | 1.00 | 83.15 | C |
| ATOM | 1078 | O | SER | A | 668 | 48.996 | −10.114 | 53.509 | 1.00 | 83.20 | O |
| ATOM | 1079 | CB | SER | A | 668 | 50.599 | −7.570 | 53.451 | 1.00 | 82.24 | C |
| ATOM | 1080 | OG | SER | A | 668 | 49.583 | −6.700 | 53.915 | 1.00 | 82.67 | O |
| ATOM | 1081 | N | GLU | A | 669 | 47.765 | −8.953 | 52.022 | 1.00 | 84.18 | N |
| ATOM | 1082 | CA | GLU | A | 669 | 46.535 | −9.689 | 52.291 | 1.00 | 85.37 | C |
| ATOM | 1083 | C | GLU | A | 669 | 46.329 | −10.706 | 51.162 | 1.00 | 85.83 | C |
| ATOM | 1084 | O | GLU | A | 669 | 47.111 | −10.746 | 50.217 | 1.00 | 85.97 | O |
| ATOM | 1085 | CB | GLU | A | 669 | 45.344 | −8.721 | 52.379 | 1.00 | 85.95 | C |
| ATOM | 1086 | CG | GLU | A | 669 | 44.101 | −9.308 | 53.047 | 1.00 | 86.88 | C |
| ATOM | 1087 | CD | GLU | A | 669 | 43.094 | −8.245 | 53.468 | 1.00 | 87.30 | C |
| ATOM | 1088 | OE1 | GLU | A | 669 | 42.505 | −7.581 | 52.588 | 1.00 | 87.69 | O |
| ATOM | 1089 | OE2 | GLU | A | 669 | 42.893 | −8.071 | 54.690 | 1.00 | 87.62 | O |
| ATOM | 1090 | N | HIS | A | 670 | 45.275 | −11.509 | 51.272 | 1.00 | 86.43 | N |
| ATOM | 1091 | CA | HIS | A | 670 | 44.924 | −12.570 | 50.315 | 1.00 | 86.94 | C |
| ATOM | 1092 | C | HIS | A | 670 | 44.807 | −12.183 | 48.825 | 1.00 | 87.14 | C |
| ATOM | 1093 | O | HIS | A | 670 | 43.702 | −12.129 | 48.278 | 1.00 | 87.16 | O |
| ATOM | 1094 | CB | HIS | A | 670 | 43.617 | −13.217 | 50.784 | 1.00 | 87.12 | C |
| ATOM | 1095 | CG | HIS | A | 670 | 43.594 | −14.707 | 50.655 | 1.00 | 87.37 | C |
| ATOM | 1096 | ND1 | HIS | A | 670 | 43.201 | −15.354 | 49.503 | 1.00 | 87.40 | N |
| ATOM | 1097 | CD2 | HIS | A | 670 | 43.940 | −15.679 | 51.533 | 1.00 | 87.48 | C |
| ATOM | 1098 | CE1 | HIS | A | 670 | 43.307 | −16.658 | 49.676 | 1.00 | 87.52 | C |
| ATOM | 1099 | NE2 | HIS | A | 670 | 43.753 | −16.883 | 50.898 | 1.00 | 87.57 | N |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | | 130.132 | 90.00 | 90.00 | 120.00 | P 31 2 1 6 | |
|---|---|---|---|---|---|---|---|---|---|---|
| ATOM | 1100 | N | PRO | A | 671 | 45.954 | −11.992 | 48.141 | 1.00 | 87.32 | N |
| ATOM | 1101 | CA | PRO | A | 671 | 46.158 | −11.621 | 46.733 | 1.00 | 87.30 | C |
| ATOM | 1102 | C | PRO | A | 671 | 44.974 | −10.913 | 46.064 | 1.00 | 87.21 | C |
| ATOM | 1103 | O | PRO | A | 671 | 44.912 | −9.678 | 46.034 | 1.00 | 87.39 | O |
| ATOM | 1104 | CB | PRO | A | 671 | 46.543 | −12.953 | 46.124 | 1.00 | 87.35 | C |
| ATOM | 1105 | CG | PRO | A | 671 | 47.608 | −13.414 | 47.203 | 1.00 | 87.49 | C |
| ATOM | 1106 | CD | PRO | A | 671 | 47.052 | −12.889 | 48.558 | 1.00 | 87.38 | C |
| ATOM | 1107 | N | LEU | A | 672 | 44.040 | −11.689 | 45.526 | 1.00 | 87.03 | N |
| ATOM | 1108 | CA | LEU | A | 672 | 42.849 | −11.111 | 44.916 | 1.00 | 86.85 | C |
| ATOM | 1109 | C | LEU | A | 672 | 41.986 | −10.568 | 46.058 | 1.00 | 86.61 | C |
| ATOM | 1110 | O | LEU | A | 672 | 40.759 | −10.500 | 45.964 | 1.00 | 86.38 | O |
| ATOM | 1111 | CB | LEU | A | 672 | 42.074 | −12.173 | 44.134 | 1.00 | 86.85 | C |
| ATOM | 1112 | CG | LEU | A | 672 | 42.616 | −12.629 | 42.778 | 1.00 | 86.78 | C |
| ATOM | 1113 | CD1 | LEU | A | 672 | 41.449 | −13.223 | 42.016 | 1.00 | 86.88 | C |
| ATOM | 1114 | CD2 | LEU | A | 672 | 43.209 | −11.467 | 41.980 | 1.00 | 86.69 | C |
| ATOM | 1115 | N | ALA | A | 673 | 42.666 | −10.184 | 47.134 | 1.00 | 86.38 | N |
| ATOM | 1116 | CA | ALA | A | 673 | 42.056 | −9.649 | 48.342 | 1.00 | 85.97 | C |
| ATOM | 1117 | C | ALA | A | 673 | 41.396 | −8.294 | 48.112 | 1.00 | 85.67 | C |
| ATOM | 1118 | O | ALA | A | 673 | 40.617 | −7.836 | 48.946 | 1.00 | 85.70 | O |
| ATOM | 1119 | CB | ALA | A | 673 | 43.120 | −9.536 | 49.440 | 1.00 | 85.94 | C |
| ATOM | 1120 | N | GLN | A | 674 | 41.703 | −7.660 | 46.984 | 1.00 | 85.15 | N |
| ATOM | 1121 | CA | GLN | A | 674 | 41.135 | −6.351 | 46.661 | 1.00 | 84.67 | C |
| ATOM | 1122 | C | GLN | A | 674 | 39.613 | −6.349 | 46.446 | 1.00 | 83.76 | C |
| ATOM | 1123 | O | GLN | A | 674 | 38.920 | −5.432 | 46.892 | 1.00 | 83.70 | O |
| ATOM | 1124 | CB | GLN | A | 674 | 41.820 | −5.767 | 45.409 | 1.00 | 85.59 | C |
| ATOM | 1125 | CG | GLN | A | 674 | 43.283 | −5.362 | 45.596 | 1.00 | 86.53 | C |
| ATOM | 1126 | CD | GLN | A | 674 | 43.928 | −4.836 | 44.318 | 1.00 | 87.08 | C |
| ATOM | 1127 | OE1 | GLN | A | 674 | 44.249 | −5.603 | 43.409 | 1.00 | 87.49 | O |
| ATOM | 1128 | NE2 | GLN | A | 674 | 44.117 | −3.520 | 44.246 | 1.00 | 87.54 | N |
| ATOM | 1129 | N | LEU | A | 675 | 39.087 | −7.379 | 45.791 | 1.00 | 82.61 | N |
| ATOM | 1130 | CA | LEU | A | 675 | 37.659 | −7.418 | 45.488 | 1.00 | 81.28 | C |
| ATOM | 1131 | C | LEU | A | 675 | 36.731 | −8.045 | 46.530 | 1.00 | 80.23 | C |
| ATOM | 1132 | O | LEU | A | 675 | 35.535 | −7.748 | 46.559 | 1.00 | 80.12 | O |
| ATOM | 1133 | CB | LEU | A | 675 | 37.476 | −8.074 | 44.121 | 1.00 | 81.47 | C |
| ATOM | 1134 | CG | LEU | A | 675 | 38.479 | −7.486 | 43.117 | 1.00 | 81.42 | C |
| ATOM | 1135 | CD1 | LEU | A | 675 | 38.302 | −8.152 | 41.783 | 1.00 | 81.50 | C |
| ATOM | 1136 | CD2 | LEU | A | 675 | 38.300 | −5.976 | 42.991 | 1.00 | 81.40 | C |
| ATOM | 1137 | N | TYR | A | 676 | 37.278 | −8.902 | 47.387 | 1.00 | 78.95 | N |
| ATOM | 1138 | CA | TYR | A | 676 | 36.504 | −9.539 | 48.449 | 1.00 | 77.57 | C |
| ATOM | 1139 | C | TYR | A | 676 | 36.194 | −8.482 | 49.503 | 1.00 | 75.67 | C |
| ATOM | 1140 | O | TYR | A | 676 | 35.105 | −7.894 | 49.509 | 1.00 | 75.94 | O |
| ATOM | 1141 | CB | TYR | A | 676 | 37.312 | −10.705 | 49.026 | 1.00 | 79.09 | C |
| ATOM | 1142 | CG | TYR | A | 676 | 37.402 | −11.814 | 48.013 | 1.00 | 80.54 | C |
| ATOM | 1143 | CD1 | TYR | A | 676 | 36.295 | −12.616 | 47.761 | 1.00 | 81.23 | C |
| ATOM | 1144 | CD2 | TYR | A | 676 | 38.525 | −11.963 | 47.197 | 1.00 | 81.05 | C |
| ATOM | 1145 | CE1 | TYR | A | 676 | 36.285 | −13.513 | 46.717 | 1.00 | 82.14 | C |
| ATOM | 1146 | CE2 | TYR | A | 676 | 38.528 | −12.871 | 46.138 | 1.00 | 81.83 | C |
| ATOM | 1147 | CZ | TYR | A | 676 | 37.398 | −13.641 | 45.905 | 1.00 | 82.47 | C |
| ATOM | 1148 | OH | TYR | A | 676 | 37.351 | −14.519 | 44.847 | 1.00 | 83.12 | O |
| ATOM | 1149 | N | CYS | A | 677 | 37.156 | −8.242 | 50.388 | 1.00 | 72.77 | N |
| ATOM | 1150 | CA | CYS | A | 677 | 37.015 | −7.217 | 51.416 | 1.00 | 69.74 | C |
| ATOM | 1151 | C | CYS | A | 677 | 37.345 | −5.878 | 50.748 | 1.00 | 67.28 | C |
| ATOM | 1152 | O | CYS | A | 677 | 38.502 | −5.461 | 50.740 | 1.00 | 67.18 | O |
| ATOM | 1153 | CB | CYS | A | 677 | 38.004 | −7.471 | 52.554 | 1.00 | 69.91 | C |
| ATOM | 1154 | SG | CYS | A | 677 | 38.281 | −6.031 | 53.600 | 1.00 | 69.81 | S |
| ATOM | 1155 | N | HIS | A | 678 | 36.343 | −5.206 | 50.185 | 1.00 | 64.08 | N |
| ATOM | 1156 | CA | HIS | A | 678 | 36.585 | −3.929 | 49.514 | 1.00 | 60.63 | C |
| ATOM | 1157 | C | HIS | A | 678 | 36.845 | −2.795 | 50.514 | 1.00 | 57.06 | C |
| ATOM | 1158 | O | HIS | A | 678 | 36.557 | −2.937 | 51.704 | 1.00 | 56.42 | O |
| ATOM | 1159 | CB | HIS | A | 678 | 35.418 | −3.583 | 48.584 | 1.00 | 62.54 | C |
| ATOM | 1160 | CG | HIS | A | 678 | 35.740 | −2.513 | 47.586 | 1.00 | 64.43 | C |
| ATOM | 1161 | ND1 | HIS | A | 678 | 35.900 | −1.191 | 47.941 | 1.00 | 65.61 | N |
| ATOM | 1162 | CD2 | HIS | A | 678 | 35.957 | −2.573 | 46.250 | 1.00 | 65.04 | C |
| ATOM | 1163 | CE1 | HIS | A | 678 | 36.200 | −0.481 | 46.868 | 1.00 | 65.84 | C |
| ATOM | 1164 | NE2 | HIS | A | 678 | 36.242 | −1.296 | 45.828 | 1.00 | 66.00 | N |
| ATOM | 1165 | N | SER | A | 679 | 37.375 | −1.672 | 50.024 | 1.00 | 52.71 | N |
| ATOM | 1166 | CA | SER | A | 679 | 37.738 | −0.546 | 50.886 | 1.00 | 48.04 | C |
| ATOM | 1167 | C | SER | A | 679 | 38.777 | −1.164 | 51.807 | 1.00 | 45.31 | C |
| ATOM | 1168 | O | SER | A | 679 | 38.749 | −0.987 | 53.024 | 1.00 | 44.54 | O |
| ATOM | 1169 | CB | SER | A | 679 | 36.543 | −0.054 | 51.710 | 1.00 | 47.68 | C |
| ATOM | 1170 | OG | SER | A | 679 | 35.600 | 0.620 | 50.902 | 1.00 | 46.88 | O |
| ATOM | 1171 | N | ILE | A | 680 | 39.692 | −1.908 | 51.195 | 1.00 | 41.93 | N |
| ATOM | 1172 | CA | ILE | A | 680 | 40.732 | −2.618 | 51.917 | 1.00 | 39.16 | C |
| ATOM | 1173 | C | ILE | A | 680 | 41.550 | −1.767 | 52.888 | 1.00 | 36.30 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 | 6 |
|---|---|---|---|---|---|---|---|---|---|---|---|
| ATOM | 1174 | O | ILE | A | 680 | 41.776 | −2.177 | 54.017 | 1.00 | 34.33 | O |
| ATOM | 1175 | CB | ILE | A | 680 | 41.667 | −3.345 | 50.923 | 1.00 | 39.71 | C |
| ATOM | 1176 | CG1 | ILE | A | 680 | 42.631 | −4.257 | 51.682 | 1.00 | 39.57 | C |
| ATOM | 1177 | CG2 | ILE | A | 680 | 42.410 | −2.331 | 50.072 | 1.00 | 40.14 | C |
| ATOM | 1178 | CD1 | ILE | A | 680 | 43.426 | −5.178 | 50.777 | 1.00 | 41.19 | C |
| ATOM | 1179 | N | MET | A | 681 | 41.989 | −0.591 | 52.453 | 1.00 | 34.80 | N |
| ATOM | 1180 | CA | MET | A | 681 | 42.769 | 0.291 | 53.315 | 1.00 | 33.59 | C |
| ATOM | 1181 | C | MET | A | 681 | 41.961 | 0.715 | 54.538 | 1.00 | 31.42 | C |
| ATOM | 1182 | O | MET | A | 681 | 42.434 | 0.617 | 55.666 | 1.00 | 32.21 | O |
| ATOM | 1183 | CB | MET | A | 681 | 43.218 | 1.538 | 52.545 | 1.00 | 34.53 | C |
| ATOM | 1184 | CG | MET | A | 681 | 44.359 | 1.299 | 51.576 | 1.00 | 37.45 | C |
| ATOM | 1185 | SD | MET | A | 681 | 45.861 | 0.792 | 52.439 | 1.00 | 40.06 | S |
| ATOM | 1186 | CE | MET | A | 681 | 46.370 | 2.359 | 53.165 | 1.00 | 39.76 | C |
| ATOM | 1187 | N | GLU | A | 682 | 40.738 | 1.178 | 54.312 | 1.00 | 29.63 | N |
| ATOM | 1188 | CA | GLU | A | 682 | 39.886 | 1.620 | 55.409 | 1.00 | 27.83 | C |
| ATOM | 1189 | C | GLU | A | 682 | 39.612 | 0.519 | 56.436 | 1.00 | 27.23 | C |
| ATOM | 1190 | O | GLU | A | 682 | 39.533 | 0.796 | 57.634 | 1.00 | 25.93 | O |
| ATOM | 1191 | CB | GLU | A | 682 | 38.571 | 2.183 | 54.867 | 1.00 | 27.59 | C |
| ATOM | 1192 | CG | GLU | A | 682 | 38.720 | 3.476 | 54.048 | 1.00 | 28.02 | C |
| ATOM | 1193 | CD | GLU | A | 682 | 39.481 | 3.279 | 52.739 | 1.00 | 29.28 | C |
| ATOM | 1194 | OE1 | GLU | A | 682 | 39.379 | 2.186 | 52.145 | 1.00 | 27.32 | O |
| ATOM | 1195 | OE2 | GLU | A | 682 | 40.169 | 4.224 | 52.294 | 1.00 | 28.60 | O |
| ATOM | 1196 | N | HIS | A | 683 | 39.469 | −0.726 | 55.981 | 1.00 | 26.34 | N |
| ATOM | 1197 | CA | HIS | A | 683 | 39.233 | −1.826 | 56.914 | 1.00 | 25.90 | C |
| ATOM | 1198 | C | HIS | A | 683 | 40.477 | −1.990 | 57.769 | 1.00 | 25.31 | C |
| ATOM | 1199 | O | HIS | A | 683 | 40.389 | −2.259 | 58.968 | 1.00 | 25.62 | O |
| ATOM | 1200 | CB | HIS | A | 683 | 38.930 | −3.129 | 56.165 | 1.00 | 26.85 | C |
| ATOM | 1201 | CG | HIS | A | 683 | 37.492 | −3.274 | 55.775 | 1.00 | 26.92 | C |
| ATOM | 1202 | ND1 | HIS | A | 683 | 36.504 | −3.580 | 56.685 | 1.00 | 26.84 | N |
| ATOM | 1203 | CD2 | HIS | A | 683 | 36.868 | −3.103 | 54.586 | 1.00 | 26.72 | C |
| ATOM | 1204 | CE1 | HIS | A | 683 | 35.332 | −3.588 | 56.075 | 1.00 | 27.20 | C |
| ATOM | 1205 | NE2 | HIS | A | 683 | 35.526 | −3.301 | 54.800 | 1.00 | 27.36 | N |
| ATOM | 1206 | N | HIS | A | 684 | 41.634 | −1.815 | 57.142 | 1.00 | 24.66 | N |
| ATOM | 1207 | CA | HIS | A | 684 | 42.908 | −1.919 | 57.839 | 1.00 | 24.73 | C |
| ATOM | 1208 | C | HIS | A | 684 | 42.977 | −0.803 | 58.880 | 1.00 | 24.18 | C |
| ATOM | 1209 | O | HIS | A | 684 | 43.317 | −1.045 | 60.032 | 1.00 | 23.63 | O |
| ATOM | 1210 | CB | HIS | A | 684 | 44.068 | −1.786 | 56.843 | 1.00 | 25.27 | C |
| ATOM | 1211 | CG | HIS | A | 684 | 45.424 | −1.777 | 57.484 | 1.00 | 26.02 | C |
| ATOM | 1212 | ND1 | HIS | A | 684 | 45.952 | −2.873 | 58.134 | 1.00 | 25.96 | N |
| ATOM | 1213 | CD2 | HIS | A | 684 | 46.347 | −0.792 | 57.600 | 1.00 | 25.92 | C |
| ATOM | 1214 | CE1 | HIS | A | 684 | 47.138 | −2.563 | 58.625 | 1.00 | 26.23 | C |
| ATOM | 1215 | NE2 | HIS | A | 684 | 47.401 | −1.305 | 58.316 | 1.00 | 26.02 | N |
| ATOM | 1216 | N | HIS | A | 685 | 42.645 | 0.423 | 58.476 | 1.00 | 24.00 | N |
| ATOM | 1217 | CA | HIS | A | 685 | 42.688 | 1.539 | 59.416 | 1.00 | 22.79 | C |
| ATOM | 1218 | C | HIS | A | 685 | 41.791 | 1.247 | 60.615 | 1.00 | 22.55 | C |
| ATOM | 1219 | O | HIS | A | 685 | 42.163 | 1.510 | 61.758 | 1.00 | 21.67 | O |
| ATOM | 1220 | CB | HIS | A | 685 | 42.245 | 2.847 | 58.747 | 1.00 | 21.96 | C |
| ATOM | 1221 | CG | HIS | A | 685 | 43.073 | 3.228 | 57.561 | 1.00 | 21.33 | C |
| ATOM | 1222 | ND1 | HIS | A | 685 | 44.451 | 3.190 | 57.570 | 1.00 | 21.52 | N |
| ATOM | 1223 | CD2 | HIS | A | 685 | 42.718 | 3.676 | 56.332 | 1.00 | 21.14 | C |
| ATOM | 1224 | CE1 | HIS | A | 685 | 44.910 | 3.597 | 56.399 | 1.00 | 20.01 | C |
| ATOM | 1225 | NE2 | HIS | A | 685 | 43.878 | 3.898 | 55.631 | 1.00 | 20.93 | N |
| ATOM | 1226 | N | PHE | A | 686 | 40.607 | 0.707 | 60.356 | 1.00 | 23.14 | N |
| ATOM | 1227 | CA | PHE | A | 686 | 39.703 | 0.384 | 61.446 | 1.00 | 24.54 | C |
| ATOM | 1228 | C | PHE | A | 686 | 40.293 | −0.691 | 62.359 | 1.00 | 25.13 | C |
| ATOM | 1229 | O | PHE | A | 686 | 40.228 | −0.575 | 63.585 | 1.00 | 25.48 | O |
| ATOM | 1230 | CB | PHE | A | 686 | 38.353 | −0.103 | 60.934 | 1.00 | 25.17 | C |
| ATOM | 1231 | CG | PHE | A | 686 | 37.445 | −0.552 | 62.032 | 1.00 | 26.21 | C |
| ATOM | 1232 | CD1 | PHE | A | 686 | 36.893 | 0.376 | 62.913 | 1.00 | 26.80 | C |
| ATOM | 1233 | CD2 | PHE | A | 686 | 37.220 | −1.902 | 62.253 | 1.00 | 27.27 | C |
| ATOM | 1234 | CE1 | PHE | A | 686 | 36.134 | −0.033 | 63.998 | 1.00 | 27.27 | C |
| ATOM | 1235 | CE2 | PHE | A | 686 | 36.458 | −2.326 | 63.345 | 1.00 | 27.89 | C |
| ATOM | 1236 | CZ | PHE | A | 686 | 35.918 | −1.390 | 64.217 | 1.00 | 27.93 | C |
| ATOM | 1237 | N | ASP | A | 687 | 40.858 | −1.739 | 61.768 | 1.00 | 25.65 | N |
| ATOM | 1238 | CA | ASP | A | 687 | 41.454 | −2.802 | 62.566 | 1.00 | 26.17 | C |
| ATOM | 1239 | C | ASP | A | 687 | 42.517 | −2.207 | 63.481 | 1.00 | 24.82 | C |
| ATOM | 1240 | O | ASP | A | 687 | 42.629 | −2.585 | 64.642 | 1.00 | 22.98 | O |
| ATOM | 1241 | CB | ASP | A | 687 | 42.085 | −3.880 | 61.677 | 1.00 | 29.27 | C |
| ATOM | 1242 | CG | ASP | A | 687 | 41.052 | −4.792 | 61.046 | 1.00 | 33.31 | C |
| ATOM | 1243 | OD1 | ASP | A | 687 | 40.054 | −5.123 | 61.729 | 1.00 | 36.16 | O |
| ATOM | 1244 | OD2 | ASP | A | 687 | 41.240 | −5.193 | 59.874 | 1.00 | 35.83 | O |
| ATOM | 1245 | N | GLN | A | 688 | 43.295 | −1.272 | 62.946 | 1.00 | 24.28 | N |
| ATOM | 1246 | CA | GLN | A | 688 | 44.340 | −0.610 | 63.724 | 1.00 | 24.28 | C |
| ATOM | 1247 | C | GLN | A | 688 | 43.691 | 0.160 | 64.871 | 1.00 | 22.95 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | 130.132 | 90.00 | 90.00 | 120.00 | P 31 2 1 6 | |
|---|---|---|---|---|---|---|---|---|---|---|
| ATOM | 1248 | O | GLN | A | 688 | 44.133 | 0.081 | 66.015 | 1.00 | 23.59 | O |
| ATOM | 1249 | CB | GLN | A | 688 | 45.135 | 0.347 | 62.831 | 1.00 | 24.61 | C |
| ATOM | 1250 | CG | GLN | A | 688 | 46.039 | −0.360 | 61.836 | 1.00 | 27.56 | C |
| ATOM | 1251 | CD | GLN | A | 688 | 47.204 | −1.066 | 62.509 | 1.00 | 29.57 | C |
| ATOM | 1252 | OE1 | GLN | A | 688 | 48.056 | −0.427 | 63.126 | 1.00 | 29.65 | O |
| ATOM | 1253 | NE2 | GLN | A | 688 | 47.246 | −2.391 | 62.394 | 1.00 | 29.57 | N |
| ATOM | 1254 | N | CYS | A | 689 | 42.632 | 0.896 | 64.551 | 1.00 | 22.05 | N |
| ATOM | 1255 | CA | CYS | A | 689 | 41.897 | 1.674 | 65.540 | 1.00 | 20.99 | C |
| ATOM | 1256 | C | CYS | A | 689 | 41.416 | 0.758 | 66.667 | 1.00 | 21.59 | C |
| ATOM | 1257 | O | CYS | A | 689 | 41.630 | 1.047 | 67.844 | 1.00 | 20.81 | O |
| ATOM | 1258 | CB | CYS | A | 689 | 40.696 | 2.350 | 64.875 | 1.00 | 20.11 | C |
| ATOM | 1259 | SG | CYS | A | 689 | 39.584 | 3.219 | 65.998 | 1.00 | 22.22 | S |
| ATOM | 1260 | N | LEU | A | 690 | 40.782 | −0.353 | 66.292 | 1.00 | 21.89 | N |
| ATOM | 1261 | CA | LEU | A | 690 | 40.256 | −1.308 | 67.261 | 1.00 | 23.02 | C |
| ATOM | 1262 | C | LEU | A | 690 | 41.340 | −1.925 | 68.150 | 1.00 | 23.78 | C |
| ATOM | 1263 | O | LEU | A | 690 | 41.143 | −2.073 | 69.359 | 1.00 | 23.96 | O |
| ATOM | 1264 | CB | LEU | A | 690 | 39.483 | −2.421 | 66.538 | 1.00 | 23.05 | C |
| ATOM | 1265 | CG | LEU | A | 690 | 38.736 | −3.419 | 67.428 | 1.00 | 24.22 | C |
| ATOM | 1266 | CD1 | LEU | A | 690 | 37.698 | −2.680 | 68.262 | 1.00 | 25.51 | C |
| ATOM | 1267 | CD2 | LEU | A | 690 | 38.069 | −4.484 | 66.568 | 1.00 | 23.71 | C |
| ATOM | 1268 | N | MET | A | 691 | 42.476 | −2.291 | 67.561 | 1.00 | 24.50 | N |
| ATOM | 1269 | CA | MET | A | 691 | 43.561 | −2.887 | 68.339 | 1.00 | 25.97 | C |
| ATOM | 1270 | C | MET | A | 691 | 44.051 | −1.904 | 69.408 | 1.00 | 25.62 | C |
| ATOM | 1271 | O | MET | A | 691 | 44.337 | −2.290 | 70.540 | 1.00 | 24.15 | O |
| ATOM | 1272 | CB | MET | A | 691 | 44.731 | −3.279 | 67.432 | 1.00 | 29.30 | C |
| ATOM | 1273 | CG | MET | A | 691 | 44.359 | −4.233 | 66.302 | 1.00 | 35.33 | C |
| ATOM | 1274 | SD | MET | A | 691 | 45.786 | −4.814 | 65.321 | 1.00 | 42.12 | S |
| ATOM | 1275 | CE | MET | A | 691 | 45.364 | −6.545 | 65.127 | 1.00 | 39.80 | C |
| ATOM | 1276 | N | ILE | A | 692 | 44.158 | −0.631 | 69.042 | 1.00 | 24.96 | N |
| ATOM | 1277 | CA | ILE | A | 692 | 44.602 | 0.375 | 69.992 | 1.00 | 24.69 | C |
| ATOM | 1278 | C | ILE | A | 692 | 43.562 | 0.536 | 71.097 | 1.00 | 24.93 | C |
| ATOM | 1279 | O | ILE | A | 692 | 43.910 | 0.640 | 72.276 | 1.00 | 25.24 | O |
| ATOM | 1280 | CB | ILE | A | 692 | 44.848 | 1.739 | 69.297 | 1.00 | 25.05 | C |
| ATOM | 1281 | CG1 | ILE | A | 692 | 46.037 | 1.615 | 68.335 | 1.00 | 24.23 | C |
| ATOM | 1282 | CG2 | ILE | A | 692 | 45.133 | 2.815 | 70.346 | 1.00 | 24.86 | C |
| ATOM | 1283 | CD1 | ILE | A | 692 | 46.287 | 2.869 | 67.477 | 1.00 | 25.03 | C |
| ATOM | 1284 | N | LEU | A | 693 | 42.287 | 0.539 | 70.715 | 1.00 | 24.89 | N |
| ATOM | 1285 | CA | LEU | A | 693 | 41.191 | 0.670 | 71.677 | 1.00 | 25.65 | C |
| ATOM | 1286 | C | LEU | A | 693 | 41.132 | −0.478 | 72.680 | 1.00 | 25.72 | C |
| ATOM | 1287 | O | LEU | A | 693 | 40.566 | −0.325 | 73.760 | 1.00 | 26.68 | O |
| ATOM | 1288 | CB | LEU | A | 693 | 39.843 | 0.745 | 70.952 | 1.00 | 24.67 | C |
| ATOM | 1289 | CG | LEU | A | 693 | 39.479 | 2.080 | 70.301 | 1.00 | 24.93 | C |
| ATOM | 1290 | CD1 | LEU | A | 693 | 38.165 | 1.929 | 69.516 | 1.00 | 21.93 | C |
| ATOM | 1291 | CD2 | LEU | A | 693 | 39.365 | 3.153 | 71.387 | 1.00 | 23.04 | C |
| ATOM | 1292 | N | ASN | A | 694 | 41.700 | −1.625 | 72.317 | 1.00 | 26.40 | N |
| ATOM | 1293 | CA | ASN | A | 694 | 41.693 | −2.792 | 73.194 | 1.00 | 27.39 | C |
| ATOM | 1294 | C | ASN | A | 694 | 43.034 | −3.051 | 73.873 | 1.00 | 27.89 | C |
| ATOM | 1295 | O | ASN | A | 694 | 43.151 | −3.975 | 74.671 | 1.00 | 28.05 | O |
| ATOM | 1296 | CB | ASN | A | 694 | 41.272 | −4.050 | 72.421 | 1.00 | 28.45 | C |
| ATOM | 1297 | CG | ASN | A | 694 | 39.790 | −4.065 | 72.095 | 1.00 | 30.82 | C |
| ATOM | 1298 | OD1 | ASN | A | 694 | 38.957 | −3.787 | 72.955 | 1.00 | 34.31 | O |
| ATOM | 1299 | ND2 | ASN | A | 694 | 39.454 | −4.393 | 70.856 | 1.00 | 31.56 | N |
| ATOM | 1300 | N | SER | A | 695 | 44.041 | −2.241 | 73.556 | 1.00 | 27.21 | N |
| ATOM | 1301 | CA | SER | A | 695 | 45.363 | −2.397 | 74.152 | 1.00 | 27.57 | C |
| ATOM | 1302 | C | SER | A | 695 | 45.307 | −2.062 | 75.637 | 1.00 | 27.38 | C |
| ATOM | 1303 | O | SER | A | 695 | 44.589 | −1.157 | 76.049 | 1.00 | 26.73 | O |
| ATOM | 1304 | CB | SER | A | 695 | 46.376 | −1.468 | 73.471 | 1.00 | 28.21 | C |
| ATOM | 1305 | OG | SER | A | 695 | 46.624 | −1.866 | 72.138 | 1.00 | 30.28 | O |
| ATOM | 1306 | N | PRO | A | 696 | 46.065 | −2.793 | 76.464 | 1.00 | 28.12 | N |
| ATOM | 1307 | CA | PRO | A | 696 | 46.041 | −2.500 | 77.898 | 1.00 | 27.96 | C |
| ATOM | 1308 | C | PRO | A | 696 | 46.466 | −1.062 | 78.197 | 1.00 | 27.75 | C |
| ATOM | 1309 | O | PRO | A | 696 | 47.410 | −0.538 | 77.591 | 1.00 | 26.30 | O |
| ATOM | 1310 | CB | PRO | A | 696 | 46.997 | −3.540 | 78.488 | 1.00 | 29.31 | C |
| ATOM | 1311 | CG | PRO | A | 696 | 47.902 | −3.884 | 77.353 | 1.00 | 30.80 | C |
| ATOM | 1312 | CD | PRO | A | 696 | 46.967 | −3.918 | 76.167 | 1.00 | 29.71 | C |
| ATOM | 1313 | N | GLY | A | 697 | 45.741 | −0.429 | 79.115 | 1.00 | 26.84 | N |
| ATOM | 1314 | CA | GLY | A | 697 | 46.035 | 0.939 | 79.497 | 1.00 | 26.60 | C |
| ATOM | 1315 | C | GLY | A | 697 | 45.593 | 1.991 | 78.495 | 1.00 | 26.28 | C |
| ATOM | 1316 | O | GLY | A | 697 | 45.784 | 3.187 | 78.735 | 1.00 | 25.78 | O |
| ATOM | 1317 | N | ASN | A | 698 | 44.996 | 1.556 | 77.387 | 1.00 | 25.57 | N |
| ATOM | 1318 | CA | ASN | A | 698 | 44.532 | 2.462 | 76.334 | 1.00 | 25.23 | C |
| ATOM | 1319 | C | ASN | A | 698 | 43.022 | 2.423 | 76.119 | 1.00 | 25.16 | C |
| ATOM | 1320 | O | ASN | A | 698 | 42.506 | 3.074 | 75.207 | 1.00 | 23.86 | O |
| ATOM | 1321 | CB | ASN | A | 698 | 45.196 | 2.101 | 75.003 | 1.00 | 25.93 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | | 130.132 | 90.00 | 90.00 | 120.00 | P 31 2 1 6 | |
|---|---|---|---|---|---|---|---|---|---|---|
| ATOM | 1322 | CG | ASN | A | 698 | 46.678 | 2.402 | 74.983 | 1.00 | 26.87 | C |
| ATOM | 1323 | OD1 | ASN | A | 698 | 47.109 | 3.406 | 74.423 | 1.00 | 27.03 | O |
| ATOM | 1324 | ND2 | ASN | A | 698 | 47.468 | 1.530 | 75.596 | 1.00 | 27.99 | N |
| ATOM | 1325 | N | GLN | A | 699 | 42.307 | 1.676 | 76.952 | 1.00 | 24.20 | N |
| ATOM | 1326 | CA | GLN | A | 699 | 40.866 | 1.531 | 76.769 | 1.00 | 24.34 | C |
| ATOM | 1327 | C | GLN | A | 699 | 39.974 | 2.697 | 77.176 | 1.00 | 24.77 | C |
| ATOM | 1328 | O | GLN | A | 699 | 39.279 | 2.637 | 78.199 | 1.00 | 24.40 | O |
| ATOM | 1329 | CB | GLN | A | 699 | 40.419 | 0.241 | 77.453 | 1.00 | 24.44 | C |
| ATOM | 1330 | CG | GLN | A | 699 | 41.034 | −0.982 | 76.796 | 1.00 | 25.18 | C |
| ATOM | 1331 | CD | GLN | A | 699 | 41.109 | −2.174 | 77.716 | 1.00 | 27.03 | C |
| ATOM | 1332 | OE1 | GLN | A | 699 | 40.108 | −2.590 | 78.293 | 1.00 | 27.20 | O |
| ATOM | 1333 | NE2 | GLN | A | 699 | 42.306 | −2.731 | 77.861 | 1.00 | 27.83 | N |
| ATOM | 1334 | N | ILE | A | 700 | 39.964 | 3.746 | 76.350 | 1.00 | 24.07 | N |
| ATOM | 1335 | CA | ILE | A | 700 | 39.158 | 4.924 | 76.645 | 1.00 | 24.94 | C |
| ATOM | 1336 | C | ILE | A | 700 | 37.656 | 4.679 | 76.571 | 1.00 | 25.08 | C |
| ATOM | 1337 | O | ILE | A | 700 | 36.880 | 5.540 | 76.956 | 1.00 | 24.59 | O |
| ATOM | 1338 | CB | ILE | A | 700 | 39.504 | 6.125 | 75.718 | 1.00 | 25.34 | C |
| ATOM | 1339 | CG1 | ILE | A | 700 | 39.326 | 5.732 | 74.248 | 1.00 | 24.79 | C |
| ATOM | 1340 | CG2 | ILE | A | 700 | 40.926 | 6.605 | 75.998 | 1.00 | 25.16 | C |
| ATOM | 1341 | CD1 | ILE | A | 700 | 39.398 | 6.922 | 73.294 | 1.00 | 25.40 | C |
| ATOM | 1342 | N | LEU | A | 701 | 37.244 | 3.514 | 76.078 | 1.00 | 25.70 | N |
| ATOM | 1343 | CA | LEU | A | 701 | 35.821 | 3.193 | 76.011 | 1.00 | 25.97 | C |
| ATOM | 1344 | C | LEU | A | 701 | 35.387 | 2.188 | 77.101 | 1.00 | 27.21 | C |
| ATOM | 1345 | O | LEU | A | 701 | 34.256 | 1.692 | 77.093 | 1.00 | 26.42 | O |
| ATOM | 1346 | CB | LEU | A | 701 | 35.472 | 2.646 | 74.625 | 1.00 | 25.82 | C |
| ATOM | 1347 | CG | LEU | A | 701 | 35.635 | 3.626 | 73.458 | 1.00 | 25.35 | C |
| ATOM | 1348 | CD1 | LEU | A | 701 | 35.220 | 2.952 | 72.170 | 1.00 | 26.35 | C |
| ATOM | 1349 | CD2 | LEU | A | 701 | 34.786 | 4.867 | 73.696 | 1.00 | 26.20 | C |
| ATOM | 1350 | N | SER | A | 702 | 36.277 | 1.901 | 78.046 | 1.00 | 28.19 | N |
| ATOM | 1351 | CA | SER | A | 702 | 35.958 | 0.948 | 79.109 | 1.00 | 29.27 | C |
| ATOM | 1352 | C | SER | A | 702 | 34.778 | 1.417 | 79.958 | 1.00 | 30.38 | C |
| ATOM | 1353 | O | SER | A | 702 | 34.119 | 0.611 | 80.612 | 1.00 | 30.51 | O |
| ATOM | 1354 | CB | SER | A | 702 | 37.175 | 0.724 | 80.013 | 1.00 | 28.94 | C |
| ATOM | 1355 | OG | SER | A | 702 | 37.434 | 1.859 | 80.828 | 1.00 | 28.49 | O |
| ATOM | 1356 | N | GLY | A | 703 | 34.516 | 2.722 | 79.943 | 1.00 | 30.20 | N |
| ATOM | 1357 | CA | GLY | A | 703 | 33.427 | 3.271 | 80.728 | 1.00 | 30.06 | C |
| ATOM | 1358 | C | GLY | A | 703 | 32.039 | 3.030 | 80.165 | 1.00 | 30.10 | C |
| ATOM | 1359 | O | GLY | A | 703 | 31.047 | 3.122 | 80.893 | 1.00 | 30.40 | O |
| ATOM | 1360 | N | LEU | A | 704 | 31.958 | 2.729 | 78.873 | 1.00 | 28.97 | N |
| ATOM | 1361 | CA | LEU | A | 704 | 30.675 | 2.482 | 78.228 | 1.00 | 28.63 | C |
| ATOM | 1362 | C | LEU | A | 704 | 30.137 | 1.102 | 78.589 | 1.00 | 29.50 | C |
| ATOM | 1363 | O | LEU | A | 704 | 30.897 | 0.205 | 78.935 | 1.00 | 28.98 | O |
| ATOM | 1364 | CB | LEU | A | 704 | 30.820 | 2.565 | 76.703 | 1.00 | 27.31 | C |
| ATOM | 1365 | CG | LEU | A | 704 | 30.928 | 3.920 | 75.991 | 1.00 | 27.53 | C |
| ATOM | 1366 | CD1 | LEU | A | 704 | 32.024 | 4.768 | 76.610 | 1.00 | 25.43 | C |
| ATOM | 1367 | CD2 | LEU | A | 704 | 31.202 | 3.678 | 74.512 | 1.00 | 25.52 | C |
| ATOM | 1368 | N | SER | A | 705 | 28.822 | 0.937 | 78.510 | 1.00 | 30.52 | N |
| ATOM | 1369 | CA | SER | A | 705 | 28.214 | −0.363 | 78.783 | 1.00 | 31.09 | C |
| ATOM | 1370 | C | SER | A | 705 | 28.422 | −1.158 | 77.498 | 1.00 | 31.45 | C |
| ATOM | 1371 | O | SER | A | 705 | 28.741 | −0.578 | 76.458 | 1.00 | 30.33 | O |
| ATOM | 1372 | CB | SER | A | 705 | 26.717 | −0.213 | 79.054 | 1.00 | 30.76 | C |
| ATOM | 1373 | OG | SER | A | 705 | 26.054 | 0.320 | 77.920 | 1.00 | 30.72 | O |
| ATOM | 1374 | N | ILE | A | 706 | 28.246 | −2.474 | 77.561 | 1.00 | 31.49 | N |
| ATOM | 1375 | CA | ILE | A | 706 | 28.431 | −3.303 | 76.379 | 1.00 | 31.58 | C |
| ATOM | 1376 | C | ILE | A | 706 | 27.570 | −2.841 | 75.206 | 1.00 | 31.39 | C |
| ATOM | 1377 | O | ILE | A | 706 | 28.012 | −2.872 | 74.053 | 1.00 | 31.47 | O |
| ATOM | 1378 | CB | ILE | A | 706 | 28.135 | −4.801 | 76.681 | 1.00 | 32.51 | C |
| ATOM | 1379 | CG1 | ILE | A | 706 | 28.449 | −5.650 | 75.447 | 1.00 | 32.96 | C |
| ATOM | 1380 | CG2 | ILE | A | 706 | 26.673 | −4.990 | 77.069 | 1.00 | 31.23 | C |
| ATOM | 1381 | CD1 | ILE | A | 706 | 29.853 | −5.469 | 74.922 | 1.00 | 34.07 | C |
| ATOM | 1382 | N | GLU | A | 707 | 26.348 | −2.400 | 75.484 | 1.00 | 31.64 | N |
| ATOM | 1383 | CA | GLU | A | 707 | 25.476 | −1.944 | 74.405 | 1.00 | 32.73 | C |
| ATOM | 1384 | C | GLU | A | 707 | 25.951 | −0.609 | 73.833 | 1.00 | 32.15 | C |
| ATOM | 1385 | O | GLU | A | 707 | 25.903 | −0.391 | 72.623 | 1.00 | 31.17 | O |
| ATOM | 1386 | CB | GLU | A | 707 | 24.029 | −1.826 | 74.892 | 1.00 | 34.95 | C |
| ATOM | 1387 | CG | GLU | A | 707 | 23.401 | −3.164 | 75.291 | 1.00 | 38.64 | C |
| ATOM | 1388 | CD | GLU | A | 707 | 23.431 | −4.194 | 74.164 | 1.00 | 41.39 | C |
| ATOM | 1389 | OE1 | GLU | A | 707 | 22.881 | −3.910 | 73.074 | 1.00 | 41.69 | O |
| ATOM | 1390 | OE2 | GLU | A | 707 | 24.003 | −5.292 | 74.373 | 1.00 | 43.16 | O |
| ATOM | 1391 | N | GLU | A | 708 | 26.406 | 0.287 | 74.703 | 1.00 | 31.80 | N |
| ATOM | 1392 | CA | GLU | A | 708 | 26.906 | 1.582 | 74.253 | 1.00 | 31.35 | C |
| ATOM | 1393 | C | GLU | A | 708 | 28.138 | 1.339 | 73.385 | 1.00 | 30.77 | C |
| ATOM | 1394 | O | GLU | A | 708 | 28.323 | 1.970 | 72.341 | 1.00 | 29.85 | O |
| ATOM | 1395 | CB | GLU | A | 708 | 27.285 | 2.448 | 75.453 | 1.00 | 31.93 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 1396 | CG | GLU | A | 708 | 26.091 | 3.064 | 76.174 | 1.00 | 34.14 | C |
| ATOM | 1397 | CD | GLU | A | 708 | 26.489 | 3.793 | 77.441 | 1.00 | 35.02 | C |
| ATOM | 1398 | OE1 | GLU | A | 708 | 25.709 | 4.654 | 77.900 | 1.00 | 37.29 | O |
| ATOM | 1399 | OE2 | GLU | A | 708 | 27.573 | 3.501 | 77.987 | 1.00 | 34.33 | O |
| ATOM | 1400 | N | TYR | A | 709 | 28.963 | 0.397 | 73.829 | 1.00 | 29.79 | N |
| ATOM | 1401 | CA | TYR | A | 709 | 30.194 | 0.042 | 73.142 | 1.00 | 29.26 | C |
| ATOM | 1402 | C | TYR | A | 709 | 29.956 | −0.492 | 71.728 | 1.00 | 29.67 | C |
| ATOM | 1403 | O | TYR | A | 709 | 30.575 | −0.024 | 70.771 | 1.00 | 29.38 | O |
| ATOM | 1404 | CB | TYR | A | 709 | 30.955 | −0.992 | 73.972 | 1.00 | 27.77 | C |
| ATOM | 1405 | CG | TYR | A | 709 | 32.288 | −1.396 | 73.390 | 1.00 | 27.67 | C |
| ATOM | 1406 | CD1 | TYR | A | 709 | 33.355 | −0.492 | 73.327 | 1.00 | 26.72 | C |
| ATOM | 1407 | CD2 | TYR | A | 709 | 32.486 | −2.685 | 72.898 | 1.00 | 26.83 | C |
| ATOM | 1408 | CE1 | TYR | A | 709 | 34.587 | −0.871 | 72.785 | 1.00 | 26.23 | C |
| ATOM | 1409 | CE2 | TYR | A | 709 | 33.705 | −3.074 | 72.357 | 1.00 | 26.97 | C |
| ATOM | 1410 | CZ | TYR | A | 709 | 34.750 | −2.168 | 72.302 | 1.00 | 26.95 | C |
| ATOM | 1411 | OH | TYR | A | 709 | 35.947 | −2.572 | 71.758 | 1.00 | 26.33 | O |
| ATOM | 1412 | N | LYS | A | 710 | 29.067 | −1.471 | 71.590 | 1.00 | 29.83 | N |
| ATOM | 1413 | CA | LYS | A | 710 | 28.794 | −2.033 | 70.275 | 1.00 | 30.53 | C |
| ATOM | 1414 | C | LYS | A | 710 | 28.268 | −0.963 | 69.311 | 1.00 | 30.43 | C |
| ATOM | 1415 | O | LYS | A | 710 | 28.594 | −0.968 | 68.123 | 1.00 | 29.85 | O |
| ATOM | 1416 | CB | LYS | A | 710 | 27.793 | −3.186 | 70.388 | 1.00 | 31.48 | C |
| ATOM | 1417 | CG | LYS | A | 710 | 28.287 | −4.342 | 71.264 | 1.00 | 33.54 | C |
| ATOM | 1418 | CD | LYS | A | 710 | 27.442 | −5.608 | 71.092 | 1.00 | 34.58 | C |
| ATOM | 1419 | CE | LYS | A | 710 | 25.971 | −5.366 | 71.399 | 1.00 | 36.04 | C |
| ATOM | 1420 | NZ | LYS | A | 710 | 25.156 | −6.623 | 71.310 | 1.00 | 37.04 | N |
| ATOM | 1421 | N | THR | A | 711 | 27.456 | −0.048 | 69.826 | 1.00 | 29.80 | N |
| ATOM | 1422 | CA | THR | A | 711 | 26.905 | 1.021 | 69.003 | 1.00 | 29.96 | C |
| ATOM | 1423 | C | THR | A | 711 | 28.018 | 1.978 | 68.568 | 1.00 | 29.26 | C |
| ATOM | 1424 | O | THR | A | 711 | 28.100 | 2.364 | 67.398 | 1.00 | 29.58 | O |
| ATOM | 1425 | CB | THR | A | 711 | 25.822 | 1.808 | 69.774 | 1.00 | 30.83 | C |
| ATOM | 1426 | OG1 | THR | A | 711 | 24.729 | 0.932 | 70.087 | 1.00 | 31.30 | O |
| ATOM | 1427 | CG2 | THR | A | 711 | 25.307 | 2.972 | 68.936 | 1.00 | 31.90 | C |
| ATOM | 1428 | N | THR | A | 712 | 28.881 | 2.346 | 69.507 | 1.00 | 28.32 | N |
| ATOM | 1429 | CA | THR | A | 712 | 29.976 | 3.254 | 69.195 | 1.00 | 27.69 | C |
| ATOM | 1430 | C | THR | A | 712 | 30.919 | 2.610 | 68.184 | 1.00 | 27.19 | C |
| ATOM | 1431 | O | THR | A | 712 | 31.237 | 3.220 | 67.167 | 1.00 | 26.50 | O |
| ATOM | 1432 | CB | THR | A | 712 | 30.738 | 3.658 | 70.469 | 1.00 | 27.67 | C |
| ATOM | 1433 | OG1 | THR | A | 712 | 29.834 | 4.319 | 71.368 | 1.00 | 28.26 | O |
| ATOM | 1434 | CG2 | THR | A | 712 | 31.882 | 4.615 | 70.129 | 1.00 | 26.58 | C |
| ATOM | 1435 | N | LEU | A | 713 | 31.351 | 1.375 | 68.444 | 1.00 | 26.56 | N |
| ATOM | 1436 | CA | LEU | A | 713 | 32.234 | 0.679 | 67.506 | 1.00 | 26.61 | C |
| ATOM | 1437 | C | LEU | A | 713 | 31.649 | 0.662 | 66.100 | 1.00 | 26.37 | C |
| ATOM | 1438 | O | LEU | A | 713 | 32.368 | 0.857 | 65.128 | 1.00 | 26.97 | O |
| ATOM | 1439 | CB | LEU | A | 713 | 32.485 | −0.772 | 67.931 | 1.00 | 26.07 | C |
| ATOM | 1440 | CG | LEU | A | 713 | 33.630 | −1.105 | 68.881 | 1.00 | 27.61 | C |
| ATOM | 1441 | CD1 | LEU | A | 713 | 33.852 | −2.629 | 68.863 | 1.00 | 27.54 | C |
| ATOM | 1442 | CD2 | LEU | A | 713 | 34.906 | −0.382 | 68.447 | 1.00 | 27.62 | C |
| ATOM | 1443 | N | LYS | A | 714 | 30.347 | 0.415 | 65.998 | 1.00 | 27.41 | N |
| ATOM | 1444 | CA | LYS | A | 714 | 29.667 | 0.370 | 64.703 | 1.00 | 28.02 | C |
| ATOM | 1445 | C | LYS | A | 714 | 29.737 | 1.716 | 63.988 | 1.00 | 27.75 | C |
| ATOM | 1446 | O | LYS | A | 714 | 30.006 | 1.776 | 62.788 | 1.00 | 27.18 | O |
| ATOM | 1447 | CB | LYS | A | 714 | 28.201 | −0.033 | 64.887 | 1.00 | 30.89 | C |
| ATOM | 1448 | CG | LYS | A | 714 | 27.346 | 0.108 | 63.624 | 1.00 | 33.65 | C |
| ATOM | 1449 | CD | LYS | A | 714 | 25.906 | −0.340 | 63.874 | 1.00 | 35.22 | C |
| ATOM | 1450 | CE | LYS | A | 714 | 25.070 | −0.245 | 62.608 | 1.00 | 36.34 | C |
| ATOM | 1451 | NZ | LYS | A | 714 | 23.723 | −0.861 | 62.793 | 1.00 | 38.97 | N |
| ATOM | 1452 | N | ILE | A | 715 | 29.475 | 2.792 | 64.727 | 1.00 | 26.60 | N |
| ATOM | 1453 | CA | ILE | A | 715 | 29.529 | 4.127 | 64.152 | 1.00 | 25.95 | C |
| ATOM | 1454 | C | ILE | A | 715 | 30.964 | 4.457 | 63.748 | 1.00 | 25.38 | C |
| ATOM | 1455 | O | ILE | A | 715 | 31.192 | 5.057 | 62.697 | 1.00 | 25.14 | O |
| ATOM | 1456 | CB | ILE | A | 715 | 29.014 | 5.185 | 65.152 | 1.00 | 26.71 | C |
| ATOM | 1457 | CG1 | ILE | A | 715 | 27.520 | 4.953 | 65.430 | 1.00 | 26.93 | C |
| ATOM | 1458 | CG2 | ILE | A | 715 | 29.237 | 6.582 | 64.592 | 1.00 | 26.26 | C |
| ATOM | 1459 | CD1 | ILE | A | 715 | 26.961 | 5.780 | 66.588 | 1.00 | 27.42 | C |
| ATOM | 1460 | N | ILE | A | 716 | 31.925 | 4.054 | 64.577 | 1.00 | 24.12 | N |
| ATOM | 1461 | CA | ILE | A | 716 | 33.338 | 4.309 | 64.288 | 1.00 | 24.37 | C |
| ATOM | 1462 | C | ILE | A | 716 | 33.757 | 3.588 | 63.021 | 1.00 | 24.11 | C |
| ATOM | 1463 | O | ILE | A | 716 | 34.477 | 4.138 | 62.192 | 1.00 | 24.32 | O |
| ATOM | 1464 | CB | ILE | A | 716 | 34.266 | 3.804 | 65.412 | 1.00 | 22.91 | C |
| ATOM | 1465 | CG1 | ILE | A | 716 | 34.063 | 4.627 | 66.681 | 1.00 | 22.79 | C |
| ATOM | 1466 | CG2 | ILE | A | 716 | 35.725 | 3.859 | 64.945 | 1.00 | 21.65 | C |
| ATOM | 1467 | CD1 | ILE | A | 716 | 34.854 | 4.109 | 67.872 | 1.00 | 21.67 | C |
| ATOM | 1468 | N | LYS | A | 717 | 33.325 | 2.338 | 62.887 | 1.00 | 24.40 | N |
| ATOM | 1469 | CA | LYS | A | 717 | 33.672 | 1.550 | 61.713 | 1.00 | 25.22 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | | 130.132 | 90.00 | 90.00 | 120.00 | P 31 2 1 6 | |
|---|---|---|---|---|---|---|---|---|---|---|
| ATOM | 1470 | C | LYS | A | 717 | 33.091 | 2.172 | 60.445 | 1.00 | 25.70 | C |
| ATOM | 1471 | O | LYS | A | 717 | 33.791 | 2.312 | 59.445 | 1.00 | 25.83 | O |
| ATOM | 1472 | CB | LYS | A | 717 | 33.166 | 0.116 | 61.870 | 1.00 | 25.53 | C |
| ATOM | 1473 | CG | LYS | A | 717 | 33.576 | −0.814 | 60.750 | 1.00 | 26.18 | C |
| ATOM | 1474 | CD | LYS | A | 717 | 33.242 | −2.257 | 61.120 | 1.00 | 27.27 | C |
| ATOM | 1475 | CE | LYS | A | 717 | 33.568 | −3.222 | 60.001 | 1.00 | 26.85 | C |
| ATOM | 1476 | NZ | LYS | A | 717 | 33.342 | −4.627 | 60.436 | 1.00 | 27.16 | N |
| ATOM | 1477 | N | GLN | A | 718 | 31.812 | 2.540 | 60.488 | 1.00 | 25.97 | N |
| ATOM | 1478 | CA | GLN | A | 718 | 31.157 | 3.156 | 59.337 | 1.00 | 27.02 | C |
| ATOM | 1479 | C | GLN | A | 718 | 31.836 | 4.495 | 59.029 | 1.00 | 26.67 | C |
| ATOM | 1480 | O | GLN | A | 718 | 32.057 | 4.847 | 57.869 | 1.00 | 26.29 | O |
| ATOM | 1481 | CB | GLN | A | 718 | 29.666 | 3.390 | 59.632 | 1.00 | 28.70 | C |
| ATOM | 1482 | CG | GLN | A | 718 | 28.898 | 2.112 | 60.008 | 1.00 | 32.94 | C |
| ATOM | 1483 | CD | GLN | A | 718 | 27.441 | 2.374 | 60.380 | 1.00 | 35.85 | C |
| ATOM | 1484 | OE1 | GLN | A | 718 | 27.144 | 3.163 | 61.285 | 1.00 | 37.30 | O |
| ATOM | 1485 | NE2 | GLN | A | 718 | 26.525 | 1.704 | 59.684 | 1.00 | 37.21 | N |
| ATOM | 1486 | N | ALA | A | 719 | 32.168 | 5.234 | 60.082 | 1.00 | 25.30 | N |
| ATOM | 1487 | CA | ALA | A | 719 | 32.811 | 6.532 | 59.918 | 1.00 | 25.10 | C |
| ATOM | 1488 | C | ALA | A | 719 | 34.138 | 6.380 | 59.182 | 1.00 | 24.15 | C |
| ATOM | 1489 | O | ALA | A | 719 | 34.433 | 7.137 | 58.263 | 1.00 | 25.50 | O |
| ATOM | 1490 | CB | ALA | A | 719 | 33.032 | 7.186 | 61.287 | 1.00 | 24.05 | C |
| ATOM | 1491 | N | ILE | A | 720 | 34.935 | 5.396 | 59.582 | 1.00 | 23.09 | N |
| ATOM | 1492 | CA | ILE | A | 720 | 36.219 | 5.176 | 58.942 | 1.00 | 22.38 | C |
| ATOM | 1493 | C | ILE | A | 720 | 36.061 | 4.641 | 57.519 | 1.00 | 22.35 | C |
| ATOM | 1494 | O | ILE | A | 720 | 36.779 | 5.065 | 56.617 | 1.00 | 22.16 | O |
| ATOM | 1495 | CB | ILE | A | 720 | 37.114 | 4.232 | 59.810 | 1.00 | 21.78 | C |
| ATOM | 1496 | CG1 | ILE | A | 720 | 37.439 | 4.936 | 61.136 | 1.00 | 22.04 | C |
| ATOM | 1497 | CG2 | ILE | A | 720 | 38.388 | 3.862 | 59.067 | 1.00 | 20.92 | C |
| ATOM | 1498 | CD1 | ILE | A | 720 | 38.437 | 4.223 | 62.031 | 1.00 | 21.45 | C |
| ATOM | 1499 | N | LEU | A | 721 | 35.118 | 3.723 | 57.303 | 1.00 | 22.70 | N |
| ATOM | 1500 | CA | LEU | A | 721 | 34.913 | 3.186 | 55.959 | 1.00 | 22.52 | C |
| ATOM | 1501 | C | LEU | A | 721 | 34.489 | 4.317 | 55.037 | 1.00 | 23.02 | C |
| ATOM | 1502 | O | LEU | A | 721 | 34.854 | 4.344 | 53.866 | 1.00 | 24.19 | O |
| ATOM | 1503 | CB | LEU | A | 721 | 33.843 | 2.079 | 55.960 | 1.00 | 23.25 | C |
| ATOM | 1504 | CG | LEU | A | 721 | 34.195 | 0.786 | 56.709 | 1.00 | 24.15 | C |
| ATOM | 1505 | CD1 | LEU | A | 721 | 33.127 | −0.289 | 56.430 | 1.00 | 24.76 | C |
| ATOM | 1506 | CD2 | LEU | A | 721 | 35.552 | 0.292 | 56.256 | 1.00 | 22.86 | C |
| ATOM | 1507 | N | ALA | A | 722 | 33.729 | 5.260 | 55.581 | 1.00 | 23.48 | N |
| ATOM | 1508 | CA | ALA | A | 722 | 33.253 | 6.406 | 54.815 | 1.00 | 23.24 | C |
| ATOM | 1509 | C | ALA | A | 722 | 34.389 | 7.249 | 54.236 | 1.00 | 23.40 | C |
| ATOM | 1510 | O | ALA | A | 722 | 34.203 | 7.946 | 53.234 | 1.00 | 22.99 | O |
| ATOM | 1511 | CB | ALA | A | 722 | 32.364 | 7.276 | 55.694 | 1.00 | 23.42 | C |
| ATOM | 1512 | N | THR | A | 723 | 35.564 | 7.198 | 54.855 | 1.00 | 23.00 | N |
| ATOM | 1513 | CA | THR | A | 723 | 36.681 | 7.994 | 54.357 | 1.00 | 23.00 | C |
| ATOM | 1514 | C | THR | A | 723 | 37.261 | 7.439 | 53.058 | 1.00 | 23.73 | C |
| ATOM | 1515 | O | THR | A | 723 | 38.224 | 7.984 | 52.517 | 1.00 | 22.86 | O |
| ATOM | 1516 | CB | THR | A | 723 | 37.787 | 8.145 | 55.424 | 1.00 | 22.33 | C |
| ATOM | 1517 | OG1 | THR | A | 723 | 38.344 | 6.864 | 55.749 | 1.00 | 21.17 | O |
| ATOM | 1518 | CG2 | THR | A | 723 | 37.195 | 8.773 | 56.683 | 1.00 | 23.62 | C |
| ATOM | 1519 | N | ASP | A | 724 | 36.673 | 6.348 | 52.569 | 1.00 | 24.32 | N |
| ATOM | 1520 | CA | ASP | A | 724 | 37.084 | 5.760 | 51.297 | 1.00 | 25.97 | C |
| ATOM | 1521 | C | ASP | A | 724 | 36.369 | 6.636 | 50.270 | 1.00 | 26.42 | C |
| ATOM | 1522 | O | ASP | A | 724 | 35.144 | 6.594 | 50.171 | 1.00 | 26.39 | O |
| ATOM | 1523 | CB | ASP | A | 724 | 36.580 | 4.315 | 51.177 | 1.00 | 27.17 | C |
| ATOM | 1524 | CG | ASP | A | 724 | 36.796 | 3.725 | 49.787 | 1.00 | 27.66 | C |
| ATOM | 1525 | OD1 | ASP | A | 724 | 37.278 | 4.440 | 48.890 | 1.00 | 28.01 | O |
| ATOM | 1526 | OD2 | ASP | A | 724 | 36.478 | 2.535 | 49.587 | 1.00 | 29.76 | O |
| ATOM | 1527 | N | LEU | A | 725 | 37.117 | 7.438 | 49.521 | 1.00 | 27.06 | N |
| ATOM | 1528 | CA | LEU | A | 725 | 36.487 | 8.319 | 48.537 | 1.00 | 29.11 | C |
| ATOM | 1529 | C | LEU | A | 725 | 35.582 | 7.571 | 47.561 | 1.00 | 29.87 | C |
| ATOM | 1530 | O | LEU | A | 725 | 34.623 | 8.138 | 47.042 | 1.00 | 30.24 | O |
| ATOM | 1531 | CB | LEU | A | 725 | 37.545 | 9.114 | 47.771 | 1.00 | 29.36 | C |
| ATOM | 1532 | CG | LEU | A | 725 | 38.197 | 10.261 | 48.549 | 1.00 | 28.95 | C |
| ATOM | 1533 | CD1 | LEU | A | 725 | 39.389 | 10.798 | 47.777 | 1.00 | 29.96 | C |
| ATOM | 1534 | CD2 | LEU | A | 725 | 37.169 | 11.356 | 48.795 | 1.00 | 29.37 | C |
| ATOM | 1535 | N | ALA | A | 726 | 35.881 | 6.300 | 47.313 | 1.00 | 30.76 | N |
| ATOM | 1536 | CA | ALA | A | 726 | 35.048 | 5.513 | 46.409 | 1.00 | 31.28 | C |
| ATOM | 1537 | C | ALA | A | 726 | 33.642 | 5.442 | 46.997 | 1.00 | 31.31 | C |
| ATOM | 1538 | O | ALA | A | 726 | 32.652 | 5.522 | 46.270 | 1.00 | 32.05 | O |
| ATOM | 1539 | CB | ALA | A | 726 | 35.625 | 4.113 | 46.236 | 1.00 | 31.66 | C |
| ATOM | 1540 | N | LEU | A | 727 | 33.548 | 5.311 | 48.318 | 1.00 | 31.27 | N |
| ATOM | 1541 | CA | LEU | A | 727 | 32.244 | 5.246 | 48.961 | 1.00 | 30.98 | C |
| ATOM | 1542 | C | LEU | A | 727 | 31.576 | 6.616 | 48.991 | 1.00 | 31.58 | C |
| ATOM | 1543 | O | LEU | A | 727 | 30.349 | 6.720 | 48.899 | 1.00 | 31.00 | O |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | | 130.132 | 90.00 | 90.00 | 120.00 | P 31 2 1 | 6 |
|---|---|---|---|---|---|---|---|---|---|---|
| ATOM | 1544 | CB | LEU | A | 727 | 32.358 | 4.687 | 50.382 | 1.00 | 30.98 | C |
| ATOM | 1545 | CG | LEU | A | 727 | 32.819 | 3.234 | 50.537 | 1.00 | 31.73 | C |
| ATOM | 1546 | CD1 | LEU | A | 727 | 32.570 | 2.784 | 51.981 | 1.00 | 32.31 | C |
| ATOM | 1547 | CD2 | LEU | A | 727 | 32.058 | 2.323 | 49.570 | 1.00 | 32.38 | C |
| ATOM | 1548 | N | TYR | A | 728 | 32.381 | 7.667 | 49.124 | 1.00 | 31.57 | N |
| ATOM | 1549 | CA | TYR | A | 728 | 31.849 | 9.027 | 49.138 | 1.00 | 32.42 | C |
| ATOM | 1550 | C | TYR | A | 728 | 31.173 | 9.333 | 47.798 | 1.00 | 33.23 | C |
| ATOM | 1551 | O | TYR | A | 728 | 30.047 | 9.823 | 47.754 | 1.00 | 33.29 | O |
| ATOM | 1552 | CB | TYR | A | 728 | 32.972 | 10.041 | 49.383 | 1.00 | 31.75 | C |
| ATOM | 1553 | CG | TYR | A | 728 | 32.617 | 11.453 | 48.960 | 1.00 | 31.60 | C |
| ATOM | 1554 | CD1 | TYR | A | 728 | 31.603 | 12.159 | 49.602 | 1.00 | 31.22 | C |
| ATOM | 1555 | CD2 | TYR | A | 728 | 33.265 | 12.063 | 47.886 | 1.00 | 31.32 | C |
| ATOM | 1556 | CE1 | TYR | A | 728 | 31.235 | 13.433 | 49.185 | 1.00 | 31.91 | C |
| ATOM | 1557 | CE2 | TYR | A | 728 | 32.905 | 13.340 | 47.459 | 1.00 | 32.61 | C |
| ATOM | 1558 | CZ | TYR | A | 728 | 31.886 | 14.017 | 48.115 | 1.00 | 32.46 | C |
| ATOM | 1559 | OH | TYR | A | 728 | 31.513 | 15.272 | 47.700 | 1.00 | 34.08 | O |
| ATOM | 1560 | N | ILE | A | 729 | 31.876 | 9.048 | 46.710 | 1.00 | 34.82 | N |
| ATOM | 1561 | CA | ILE | A | 729 | 31.348 | 9.296 | 45.374 | 1.00 | 37.06 | C |
| ATOM | 1562 | C | ILE | A | 729 | 30.113 | 8.451 | 45.083 | 1.00 | 38.48 | C |
| ATOM | 1563 | O | ILE | A | 729 | 29.237 | 8.851 | 44.320 | 1.00 | 38.62 | O |
| ATOM | 1564 | CB | ILE | A | 729 | 32.423 | 9.025 | 44.306 | 1.00 | 37.19 | C |
| ATOM | 1565 | CG1 | ILE | A | 729 | 33.463 | 10.148 | 44.342 | 1.00 | 37.45 | C |
| ATOM | 1566 | CG2 | ILE | A | 729 | 31.784 | 8.908 | 42.926 | 1.00 | 38.11 | C |
| ATOM | 1567 | CD1 | ILE | A | 729 | 34.567 | 10.002 | 43.325 | 1.00 | 39.16 | C |
| ATOM | 1568 | N | LYS | A | 730 | 30.040 | 7.288 | 45.714 | 1.00 | 40.06 | N |
| ATOM | 1569 | CA | LYS | A | 730 | 28.918 | 6.381 | 45.518 | 1.00 | 41.63 | C |
| ATOM | 1570 | C | LYS | A | 730 | 27.660 | 6.838 | 46.249 | 1.00 | 41.67 | C |
| ATOM | 1571 | O | LYS | A | 730 | 26.557 | 6.685 | 45.735 | 1.00 | 42.26 | O |
| ATOM | 1572 | CB | LYS | A | 730 | 29.310 | 4.978 | 45.989 | 1.00 | 42.71 | C |
| ATOM | 1573 | CG | LYS | A | 730 | 28.238 | 3.912 | 45.819 | 1.00 | 45.29 | C |
| ATOM | 1574 | CD | LYS | A | 730 | 28.723 | 2.583 | 46.401 | 1.00 | 46.43 | C |
| ATOM | 1575 | CE | LYS | A | 730 | 27.695 | 1.470 | 46.235 | 1.00 | 47.25 | C |
| ATOM | 1576 | NZ | LYS | A | 730 | 28.195 | 0.178 | 46.795 | 1.00 | 47.44 | N |
| ATOM | 1577 | N | ARG | A | 731 | 27.820 | 7.421 | 47.433 | 1.00 | 41.53 | N |
| ATOM | 1578 | CA | ARG | A | 731 | 26.665 | 7.850 | 48.219 | 1.00 | 41.43 | C |
| ATOM | 1579 | C | ARG | A | 731 | 26.349 | 9.342 | 48.247 | 1.00 | 41.16 | C |
| ATOM | 1580 | O | ARG | A | 731 | 25.269 | 9.733 | 48.690 | 1.00 | 40.19 | O |
| ATOM | 1581 | CB | ARG | A | 731 | 26.816 | 7.363 | 49.662 | 1.00 | 42.53 | C |
| ATOM | 1582 | CG | ARG | A | 731 | 26.993 | 5.858 | 49.796 | 1.00 | 44.52 | C |
| ATOM | 1583 | CD | ARG | A | 731 | 27.032 | 5.454 | 51.260 | 1.00 | 46.07 | C |
| ATOM | 1584 | NE | ARG | A | 731 | 25.791 | 5.793 | 51.950 | 1.00 | 47.44 | N |
| ATOM | 1585 | CZ | ARG | A | 731 | 25.610 | 5.673 | 53.262 | 1.00 | 47.85 | C |
| ATOM | 1586 | NH1 | ARG | A | 731 | 26.593 | 5.219 | 54.030 | 1.00 | 48.63 | N |
| ATOM | 1587 | NH2 | ARG | A | 731 | 24.449 | 6.009 | 53.807 | 1.00 | 48.65 | N |
| ATOM | 1588 | N | ARG | A | 732 | 27.274 | 10.178 | 47.787 | 1.00 | 41.06 | N |
| ATOM | 1589 | CA | ARG | A | 732 | 27.041 | 11.619 | 47.810 | 1.00 | 41.36 | C |
| ATOM | 1590 | C | ARG | A | 732 | 25.812 | 12.035 | 47.003 | 1.00 | 41.66 | C |
| ATOM | 1591 | O | ARG | A | 732 | 25.085 | 12.953 | 47.391 | 1.00 | 40.90 | O |
| ATOM | 1592 | CB | ARG | A | 732 | 28.274 | 12.371 | 47.300 | 1.00 | 40.99 | C |
| ATOM | 1593 | CG | ARG | A | 732 | 28.540 | 12.254 | 45.816 | 1.00 | 41.09 | C |
| ATOM | 1594 | CD | ARG | A | 732 | 29.749 | 13.096 | 45.458 | 1.00 | 41.63 | C |
| ATOM | 1595 | NE | ARG | A | 732 | 30.009 | 13.148 | 44.023 | 1.00 | 41.54 | N |
| ATOM | 1596 | CZ | ARG | A | 732 | 30.923 | 13.941 | 43.470 | 1.00 | 41.70 | C |
| ATOM | 1597 | NH1 | ARG | A | 732 | 31.651 | 14.738 | 44.237 | 1.00 | 40.94 | N |
| ATOM | 1598 | NH2 | ARG | A | 732 | 31.106 | 13.943 | 42.155 | 1.00 | 42.34 | N |
| ATOM | 1599 | N | GLY | A | 733 | 25.581 | 11.353 | 45.886 | 1.00 | 41.99 | N |
| ATOM | 1600 | CA | GLY | A | 733 | 24.436 | 11.674 | 45.054 | 1.00 | 43.20 | C |
| ATOM | 1601 | C | GLY | A | 733 | 23.132 | 11.684 | 45.829 | 1.00 | 43.42 | C |
| ATOM | 1602 | O | GLY | A | 733 | 22.310 | 12.582 | 45.663 | 1.00 | 43.61 | O |
| ATOM | 1603 | N | GLU | A | 734 | 22.940 | 10.684 | 46.683 | 1.00 | 43.75 | N |
| ATOM | 1604 | CA | GLU | A | 734 | 21.722 | 10.586 | 47.479 | 1.00 | 43.80 | C |
| ATOM | 1605 | C | GLU | A | 734 | 21.604 | 11.764 | 48.439 | 1.00 | 43.62 | C |
| ATOM | 1606 | O | GLU | A | 734 | 20.520 | 12.321 | 48.620 | 1.00 | 43.36 | O |
| ATOM | 1607 | CB | GLU | A | 734 | 21.714 | 9.282 | 48.278 | 1.00 | 44.36 | C |
| ATOM | 1608 | CG | GLU | A | 734 | 20.369 | 8.969 | 48.915 | 1.00 | 45.73 | C |
| ATOM | 1609 | CD | GLU | A | 734 | 20.459 | 7.910 | 49.995 | 1.00 | 46.03 | C |
| ATOM | 1610 | OE1 | GLU | A | 734 | 21.223 | 6.936 | 49.821 | 1.00 | 46.17 | O |
| ATOM | 1611 | OE2 | GLU | A | 734 | 19.754 | 8.051 | 51.016 | 1.00 | 47.16 | O |
| ATOM | 1612 | N | PHE | A | 735 | 22.726 | 12.125 | 49.059 | 1.00 | 43.39 | N |
| ATOM | 1613 | CA | PHE | A | 735 | 22.785 | 13.237 | 50.010 | 1.00 | 43.06 | C |
| ATOM | 1614 | C | PHE | A | 735 | 22.430 | 14.542 | 49.305 | 1.00 | 43.37 | C |
| ATOM | 1615 | O | PHE | A | 735 | 21.651 | 15.345 | 49.816 | 1.00 | 42.91 | O |
| ATOM | 1616 | CB | PHE | A | 735 | 24.197 | 13.321 | 50.618 | 1.00 | 42.33 | C |
| ATOM | 1617 | CG | PHE | A | 735 | 24.370 | 14.412 | 51.647 | 1.00 | 41.76 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | 130.132 | 90.00 | 90.00 | 120.00 | P 31 2 1 6 | |
|---|---|---|---|---|---|---|---|---|---|---|
| ATOM | 1618 | CD1 | PHE | A | 735 | 23.483 | 14.539 | 52.708 | 1.00 | 41.33 | C |
| ATOM | 1619 | CD2 | PHE | A | 735 | 25.447 | 15.293 | 51.569 | 1.00 | 41.57 | C |
| ATOM | 1620 | CE1 | PHE | A | 735 | 23.666 | 15.525 | 53.678 | 1.00 | 41.65 | C |
| ATOM | 1621 | CE2 | PHE | A | 735 | 25.639 | 16.280 | 52.533 | 1.00 | 40.91 | C |
| ATOM | 1622 | CZ | PHE | A | 735 | 24.749 | 16.397 | 53.590 | 1.00 | 40.90 | C |
| ATOM | 1623 | N | PHE | A | 736 | 23.005 | 14.739 | 48.124 | 1.00 | 44.18 | N |
| ATOM | 1624 | CA | PHE | A | 736 | 22.755 | 15.935 | 47.335 | 1.00 | 45.75 | C |
| ATOM | 1625 | C | PHE | A | 736 | 21.302 | 15.948 | 46.871 | 1.00 | 47.41 | C |
| ATOM | 1626 | O | PHE | A | 736 | 20.627 | 16.975 | 46.941 | 1.00 | 47.33 | O |
| ATOM | 1627 | CB | PHE | A | 736 | 23.692 | 15.958 | 46.125 | 1.00 | 45.63 | C |
| ATOM | 1628 | CG | PHE | A | 736 | 25.150 | 16.063 | 46.488 | 1.00 | 44.55 | C |
| ATOM | 1629 | CD1 | PHE | A | 736 | 26.131 | 15.644 | 45.597 | 1.00 | 44.33 | C |
| ATOM | 1630 | CD2 | PHE | A | 736 | 25.541 | 16.605 | 47.710 | 1.00 | 44.32 | C |
| ATOM | 1631 | CE1 | PHE | A | 736 | 27.484 | 15.759 | 45.915 | 1.00 | 44.21 | C |
| ATOM | 1632 | CE2 | PHE | A | 736 | 26.891 | 16.726 | 48.039 | 1.00 | 44.19 | C |
| ATOM | 1633 | CZ | PHE | A | 736 | 27.863 | 16.303 | 47.138 | 1.00 | 44.12 | C |
| ATOM | 1634 | N | GLU | A | 737 | 20.829 | 14.793 | 46.413 | 1.00 | 48.92 | N |
| ATOM | 1635 | CA | GLU | A | 737 | 19.459 | 14.645 | 45.934 | 1.00 | 51.07 | C |
| ATOM | 1636 | C | GLU | A | 737 | 18.456 | 14.976 | 47.038 | 1.00 | 51.84 | C |
| ATOM | 1637 | O | GLU | A | 737 | 17.473 | 15.683 | 46.807 | 1.00 | 51.75 | O |
| ATOM | 1638 | CB | GLU | A | 737 | 19.232 | 13.211 | 45.449 | 1.00 | 51.73 | C |
| ATOM | 1639 | CG | GLU | A | 737 | 17.941 | 13.001 | 44.678 | 1.00 | 53.05 | C |
| ATOM | 1640 | CD | GLU | A | 737 | 17.632 | 11.533 | 44.464 | 1.00 | 53.37 | C |
| ATOM | 1641 | OE1 | GLU | A | 737 | 18.546 | 10.783 | 44.058 | 1.00 | 53.50 | O |
| ATOM | 1642 | OE2 | GLU | A | 737 | 16.474 | 11.129 | 44.697 | 1.00 | 54.22 | O |
| ATOM | 1643 | N | LEU | A | 738 | 18.709 | 14.460 | 48.238 | 1.00 | 53.21 | N |
| ATOM | 1644 | CA | LEU | A | 738 | 17.830 | 14.697 | 49.378 | 1.00 | 54.70 | C |
| ATOM | 1645 | C | LEU | A | 738 | 17.785 | 16.170 | 49.764 | 1.00 | 55.83 | C |
| ATOM | 1646 | O | LEU | A | 738 | 16.793 | 16.644 | 50.312 | 1.00 | 56.02 | O |
| ATOM | 1647 | CB | LEU | A | 738 | 18.286 | 13.868 | 50.584 | 1.00 | 54.83 | C |
| ATOM | 1648 | CG | LEU | A | 738 | 18.146 | 12.344 | 50.484 | 1.00 | 55.40 | C |
| ATOM | 1649 | CD1 | LEU | A | 738 | 18.818 | 11.684 | 51.683 | 1.00 | 55.13 | C |
| ATOM | 1650 | CD2 | LEU | A | 738 | 16.673 | 11.967 | 50.422 | 1.00 | 55.07 | C |
| ATOM | 1651 | N | ILE | A | 739 | 18.859 | 16.895 | 49.476 | 1.00 | 57.19 | N |
| ATOM | 1652 | CA | ILE | A | 739 | 18.913 | 18.311 | 49.816 | 1.00 | 58.82 | C |
| ATOM | 1653 | C | ILE | A | 739 | 18.197 | 19.188 | 48.793 | 1.00 | 59.61 | C |
| ATOM | 1654 | O | ILE | A | 739 | 17.574 | 20.182 | 49.161 | 1.00 | 59.57 | O |
| ATOM | 1655 | CB | ILE | A | 739 | 20.372 | 18.789 | 49.978 | 1.00 | 58.96 | C |
| ATOM | 1656 | CG1 | ILE | A | 739 | 21.044 | 18.005 | 51.109 | 1.00 | 59.35 | C |
| ATOM | 1657 | CG2 | ILE | A | 739 | 20.404 | 20.282 | 50.289 | 1.00 | 59.06 | C |
| ATOM | 1658 | CD1 | ILE | A | 739 | 22.496 | 18.371 | 51.344 | 1.00 | 59.59 | C |
| ATOM | 1659 | N | ARG | A | 740 | 18.280 | 18.823 | 47.515 | 1.00 | 60.85 | N |
| ATOM | 1660 | CA | ARG | A | 740 | 17.616 | 19.596 | 46.466 | 1.00 | 62.31 | C |
| ATOM | 1661 | C | ARG | A | 740 | 16.124 | 19.642 | 46.767 | 1.00 | 62.97 | C |
| ATOM | 1662 | O | ARG | A | 740 | 15.529 | 20.712 | 46.893 | 1.00 | 63.07 | O |
| ATOM | 1663 | CB | ARG | A | 740 | 17.777 | 18.936 | 45.094 | 1.00 | 62.90 | C |
| ATOM | 1664 | CG | ARG | A | 740 | 19.155 | 18.431 | 44.744 | 1.00 | 63.79 | C |
| ATOM | 1665 | CD | ARG | A | 740 | 19.056 | 17.559 | 43.501 | 1.00 | 64.14 | C |
| ATOM | 1666 | NE | ARG | A | 740 | 20.250 | 16.750 | 43.290 | 1.00 | 64.41 | N |
| ATOM | 1667 | CZ | ARG | A | 740 | 20.304 | 15.704 | 42.472 | 1.00 | 64.58 | C |
| ATOM | 1668 | NH1 | ARG | A | 740 | 19.228 | 15.338 | 41.786 | 1.00 | 64.12 | N |
| ATOM | 1669 | NH2 | ARG | A | 740 | 21.431 | 15.018 | 42.348 | 1.00 | 64.86 | N |
| ATOM | 1670 | N | LYS | A | 741 | 15.538 | 18.453 | 46.874 | 1.00 | 63.77 | N |
| ATOM | 1671 | CA | LYS | A | 741 | 14.112 | 18.275 | 47.130 | 1.00 | 64.50 | C |
| ATOM | 1672 | C | LYS | A | 741 | 13.686 | 18.654 | 48.543 | 1.00 | 64.84 | C |
| ATOM | 1673 | O | LYS | A | 741 | 12.519 | 18.502 | 48.903 | 1.00 | 64.95 | O |
| ATOM | 1674 | CB | LYS | A | 741 | 13.726 | 16.818 | 46.854 | 1.00 | 64.52 | C |
| ATOM | 1675 | CG | LYS | A | 741 | 14.141 | 16.323 | 45.473 | 1.00 | 64.82 | C |
| ATOM | 1676 | CD | LYS | A | 741 | 13.930 | 14.824 | 45.330 | 1.00 | 65.17 | C |
| ATOM | 1677 | CE | LYS | A | 741 | 14.418 | 14.321 | 43.980 | 1.00 | 65.79 | C |
| ATOM | 1678 | NZ | LYS | A | 741 | 14.302 | 12.837 | 43.858 | 1.00 | 65.91 | N |
| ATOM | 1679 | N | ASN | A | 742 | 14.628 | 19.143 | 49.342 | 1.00 | 65.28 | N |
| ATOM | 1680 | CA | ASN | A | 742 | 14.334 | 19.540 | 50.717 | 1.00 | 65.79 | C |
| ATOM | 1681 | C | ASN | A | 742 | 13.693 | 18.401 | 51.502 | 1.00 | 65.61 | C |
| ATOM | 1682 | O | ASN | A | 742 | 12.707 | 18.608 | 52.210 | 1.00 | 65.80 | O |
| ATOM | 1683 | CB | ASN | A | 742 | 13.390 | 20.744 | 50.734 | 1.00 | 66.71 | C |
| ATOM | 1684 | CG | ASN | A | 742 | 13.937 | 21.930 | 49.969 | 1.00 | 67.73 | C |
| ATOM | 1685 | OD1 | ASN | A | 742 | 13.301 | 22.981 | 49.903 | 1.00 | 68.51 | O |
| ATOM | 1686 | ND2 | ASN | A | 742 | 15.119 | 21.768 | 49.383 | 1.00 | 68.31 | N |
| ATOM | 1687 | N | GLN | A | 743 | 14.255 | 17.202 | 51.380 | 1.00 | 65.23 | N |
| ATOM | 1688 | CA | GLN | A | 743 | 13.723 | 16.040 | 52.082 | 1.00 | 64.72 | C |
| ATOM | 1689 | C | GLN | A | 743 | 14.699 | 15.506 | 53.126 | 1.00 | 64.19 | C |
| ATOM | 1690 | O | GLN | A | 743 | 14.475 | 14.445 | 53.706 | 1.00 | 64.01 | O |
| ATOM | 1691 | CB | GLN | A | 743 | 13.394 | 14.927 | 51.086 | 1.00 | 65.26 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | 130.132 | 90.00 | 90.00 | 120.00 | P 31 2 1 6 | |
|---|---|---|---|---|---|---|---|---|---|---|
| ATOM | 1692 | CG | GLN | A | 743 | 12.493 | 15.361 | 49.947 | 1.00 | 66.07 | C |
| ATOM | 1693 | CD | GLN | A | 743 | 12.051 | 14.197 | 49.089 | 1.00 | 66.52 | C |
| ATOM | 1694 | OE1 | GLN | A | 743 | 11.312 | 13.325 | 49.542 | 1.00 | 67.13 | O |
| ATOM | 1695 | NE2 | GLN | A | 743 | 12.504 | 14.173 | 47.843 | 1.00 | 66.88 | N |
| ATOM | 1696 | N | PHE | A | 744 | 15.781 | 16.240 | 53.362 | 1.00 | 63.55 | N |
| ATOM | 1697 | CA | PHE | A | 744 | 16.777 | 15.815 | 54.340 | 1.00 | 62.76 | C |
| ATOM | 1698 | C | PHE | A | 744 | 16.184 | 15.823 | 55.746 | 1.00 | 62.15 | C |
| ATOM | 1699 | O | PHE | A | 744 | 15.602 | 16.816 | 56.178 | 1.00 | 62.08 | O |
| ATOM | 1700 | CB | PHE | A | 744 | 18.003 | 16.732 | 54.286 | 1.00 | 62.47 | C |
| ATOM | 1701 | CG | PHE | A | 744 | 19.163 | 16.237 | 55.105 | 1.00 | 61.73 | C |
| ATOM | 1702 | CD1 | PHE | A | 744 | 19.779 | 15.027 | 54.799 | 1.00 | 61.32 | C |
| ATOM | 1703 | CD2 | PHE | A | 744 | 19.638 | 16.977 | 56.182 | 1.00 | 61.30 | C |
| ATOM | 1704 | CE1 | PHE | A | 744 | 20.851 | 14.562 | 55.554 | 1.00 | 61.16 | C |
| ATOM | 1705 | CE2 | PHE | A | 744 | 20.709 | 16.521 | 56.944 | 1.00 | 61.11 | C |
| ATOM | 1706 | CZ | PHE | A | 744 | 21.316 | 15.311 | 56.628 | 1.00 | 61.06 | C |
| ATOM | 1707 | N | ASN | A | 745 | 16.340 | 14.705 | 56.450 | 1.00 | 61.64 | N |
| ATOM | 1708 | CA | ASN | A | 745 | 15.820 | 14.554 | 57.806 | 1.00 | 61.08 | C |
| ATOM | 1709 | C | ASN | A | 745 | 16.813 | 13.754 | 58.649 | 1.00 | 60.61 | C |
| ATOM | 1710 | O | ASN | A | 745 | 17.014 | 12.562 | 58.416 | 1.00 | 60.41 | O |
| ATOM | 1711 | CB | ASN | A | 745 | 14.471 | 13.827 | 57.762 | 1.00 | 61.23 | C |
| ATOM | 1712 | CG | ASN | A | 745 | 13.856 | 13.634 | 59.140 | 1.00 | 61.42 | C |
| ATOM | 1713 | OD1 | ASN | A | 745 | 12.857 | 12.930 | 59.284 | 1.00 | 61.89 | O |
| ATOM | 1714 | ND2 | ASN | A | 745 | 14.441 | 14.263 | 60.154 | 1.00 | 61.19 | N |
| ATOM | 1715 | N | LEU | A | 746 | 17.431 | 14.413 | 59.623 | 1.00 | 60.11 | N |
| ATOM | 1716 | CA | LEU | A | 746 | 18.404 | 13.757 | 60.490 | 1.00 | 59.73 | C |
| ATOM | 1717 | C | LEU | A | 746 | 17.748 | 12.868 | 61.532 | 1.00 | 59.63 | C |
| ATOM | 1718 | O | LEU | A | 746 | 18.430 | 12.128 | 62.242 | 1.00 | 59.52 | O |
| ATOM | 1719 | CB | LEU | A | 746 | 19.273 | 14.797 | 61.200 | 1.00 | 59.50 | C |
| ATOM | 1720 | CG | LEU | A | 746 | 20.359 | 15.491 | 60.377 | 1.00 | 59.37 | C |
| ATOM | 1721 | CD1 | LEU | A | 746 | 21.074 | 16.515 | 61.243 | 1.00 | 59.01 | C |
| ATOM | 1722 | CD2 | LEU | A | 746 | 21.341 | 14.454 | 59.852 | 1.00 | 59.19 | C |
| ATOM | 1723 | N | GLU | A | 747 | 16.425 | 12.937 | 61.625 | 1.00 | 59.72 | N |
| ATOM | 1724 | CA | GLU | A | 747 | 15.707 | 12.138 | 62.606 | 1.00 | 59.66 | C |
| ATOM | 1725 | C | GLU | A | 747 | 15.665 | 10.662 | 62.230 | 1.00 | 59.07 | C |
| ATOM | 1726 | O | GLU | A | 747 | 15.595 | 9.800 | 63.107 | 1.00 | 59.19 | O |
| ATOM | 1727 | CB | GLU | A | 747 | 14.285 | 12.672 | 62.791 | 1.00 | 60.71 | C |
| ATOM | 1728 | CG | GLU | A | 747 | 13.560 | 12.068 | 63.987 | 1.00 | 62.29 | C |
| ATOM | 1729 | CD | GLU | A | 747 | 12.212 | 12.714 | 64.248 | 1.00 | 63.13 | C |
| ATOM | 1730 | OE1 | GLU | A | 747 | 12.172 | 13.948 | 64.453 | 1.00 | 63.74 | O |
| ATOM | 1731 | OE2 | GLU | A | 747 | 11.194 | 11.988 | 64.251 | 1.00 | 63.51 | O |
| ATOM | 1732 | N | ASP | A | 748 | 15.708 | 10.359 | 60.937 | 1.00 | 58.42 | N |
| ATOM | 1733 | CA | ASP | A | 748 | 15.685 | 8.962 | 60.521 | 1.00 | 58.07 | C |
| ATOM | 1734 | C | ASP | A | 748 | 17.118 | 8.444 | 60.407 | 1.00 | 57.21 | C |
| ATOM | 1735 | O | ASP | A | 748 | 17.982 | 9.090 | 59.813 | 1.00 | 57.21 | O |
| ATOM | 1736 | CB | ASP | A | 748 | 14.941 | 8.796 | 59.191 | 1.00 | 58.46 | C |
| ATOM | 1737 | CG | ASP | A | 748 | 15.845 | 8.938 | 57.993 | 1.00 | 59.25 | C |
| ATOM | 1738 | OD1 | ASP | A | 748 | 16.432 | 10.026 | 57.821 | 1.00 | 60.50 | O |
| ATOM | 1739 | OD2 | ASP | A | 748 | 15.968 | 7.958 | 57.224 | 1.00 | 58.99 | O |
| ATOM | 1740 | N | PRO | A | 749 | 17.383 | 7.262 | 60.980 | 1.00 | 56.22 | N |
| ATOM | 1741 | CA | PRO | A | 749 | 18.696 | 6.610 | 60.983 | 1.00 | 55.20 | C |
| ATOM | 1742 | C | PRO | A | 749 | 19.442 | 6.530 | 59.652 | 1.00 | 54.35 | C |
| ATOM | 1743 | O | PRO | A | 749 | 20.660 | 6.705 | 59.616 | 1.00 | 54.19 | O |
| ATOM | 1744 | CB | PRO | A | 749 | 18.392 | 5.227 | 61.562 | 1.00 | 55.53 | C |
| ATOM | 1745 | CG | PRO | A | 749 | 16.966 | 4.998 | 61.164 | 1.00 | 55.80 | C |
| ATOM | 1746 | CD | PRO | A | 749 | 16.348 | 6.335 | 61.468 | 1.00 | 55.99 | C |
| ATOM | 1747 | N | HIS | A | 750 | 18.730 | 6.263 | 58.562 | 1.00 | 53.15 | N |
| ATOM | 1748 | CA | HIS | A | 750 | 19.396 | 6.160 | 57.269 | 1.00 | 52.03 | C |
| ATOM | 1749 | C | HIS | A | 750 | 20.139 | 7.435 | 56.894 | 1.00 | 51.09 | C |
| ATOM | 1750 | O | HIS | A | 750 | 21.318 | 7.396 | 56.538 | 1.00 | 50.70 | O |
| ATOM | 1751 | CB | HIS | A | 750 | 18.400 | 5.836 | 56.156 | 1.00 | 51.99 | C |
| ATOM | 1752 | CG | HIS | A | 750 | 19.023 | 5.800 | 54.795 | 1.00 | 52.21 | C |
| ATOM | 1753 | ND1 | HIS | A | 750 | 19.925 | 4.829 | 54.416 | 1.00 | 52.27 | N |
| ATOM | 1754 | CD2 | HIS | A | 750 | 18.913 | 6.643 | 53.740 | 1.00 | 52.07 | C |
| ATOM | 1755 | CE1 | HIS | A | 750 | 20.344 | 5.075 | 53.187 | 1.00 | 51.95 | C |
| ATOM | 1756 | NE2 | HIS | A | 750 | 19.746 | 6.171 | 52.755 | 1.00 | 51.32 | N |
| ATOM | 1757 | N | GLN | A | 751 | 19.441 | 8.563 | 56.966 | 1.00 | 49.77 | N |
| ATOM | 1758 | CA | GLN | A | 751 | 20.033 | 9.839 | 56.610 | 1.00 | 48.68 | C |
| ATOM | 1759 | C | GLN | A | 751 | 21.048 | 10.326 | 57.636 | 1.00 | 47.88 | C |
| ATOM | 1760 | O | GLN | A | 751 | 21.986 | 11.044 | 57.287 | 1.00 | 47.20 | O |
| ATOM | 1761 | CB | GLN | A | 751 | 18.934 | 10.884 | 56.385 | 1.00 | 49.16 | C |
| ATOM | 1762 | CG | GLN | A | 751 | 18.065 | 10.577 | 55.164 | 1.00 | 49.50 | C |
| ATOM | 1763 | CD | GLN | A | 751 | 17.060 | 11.672 | 54.853 | 1.00 | 50.36 | C |
| ATOM | 1764 | OE1 | GLN | A | 751 | 17.425 | 12.831 | 54.651 | 1.00 | 50.58 | O |
| ATOM | 1765 | NE2 | GLN | A | 751 | 15.784 | 11.306 | 54.804 | 1.00 | 50.55 | N |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | | 74.456 | | | 74.456 | 130.132 | 90.00 | 90.00 | 120.00 | P 31 2 1 | 6 |
|---|---|---|---|---|---|---|---|---|---|---|---|
| ATOM | 1766 | N | LYS | A | 752 | 20.872 | 9.943 | 58.897 | 1.00 | 46.53 | N |
| ATOM | 1767 | CA | LYS | A | 752 | 21.830 | 10.352 | 59.912 | 1.00 | 45.81 | C |
| ATOM | 1768 | C | LYS | A | 752 | 23.161 | 9.676 | 59.605 | 1.00 | 45.05 | C |
| ATOM | 1769 | O | LYS | A | 752 | 24.215 | 10.306 | 59.658 | 1.00 | 44.62 | O |
| ATOM | 1770 | CB | LYS | A | 752 | 21.363 | 9.964 | 61.315 | 1.00 | 45.78 | C |
| ATOM | 1771 | CG | LYS | A | 752 | 22.471 | 10.084 | 62.358 | 1.00 | 46.32 | C |
| ATOM | 1772 | CD | LYS | A | 752 | 21.947 | 10.449 | 63.739 | 1.00 | 47.16 | C |
| ATOM | 1773 | CE | LYS | A | 752 | 21.585 | 11.924 | 63.832 | 1.00 | 46.71 | C |
| ATOM | 1774 | NZ | LYS | A | 752 | 21.360 | 12.335 | 65.248 | 1.00 | 46.77 | N |
| ATOM | 1775 | N | GLU | A | 753 | 23.103 | 8.389 | 59.276 | 1.00 | 44.15 | N |
| ATOM | 1776 | CA | GLU | A | 753 | 24.307 | 7.640 | 58.944 | 1.00 | 43.53 | C |
| ATOM | 1777 | C | GLU | A | 753 | 24.951 | 8.228 | 57.691 | 1.00 | 41.84 | C |
| ATOM | 1778 | O | GLU | A | 753 | 26.175 | 8.333 | 57.599 | 1.00 | 41.15 | O |
| ATOM | 1779 | CB | GLU | A | 753 | 23.972 | 6.171 | 58.687 | 1.00 | 45.13 | C |
| ATOM | 1780 | CG | GLU | A | 753 | 25.189 | 5.337 | 58.331 | 1.00 | 47.89 | C |
| ATOM | 1781 | CD | GLU | A | 753 | 24.826 | 4.013 | 57.692 | 1.00 | 50.08 | C |
| ATOM | 1782 | OE1 | GLU | A | 753 | 24.329 | 4.016 | 56.543 | 1.00 | 51.71 | O |
| ATOM | 1783 | OE2 | GLU | A | 753 | 25.033 | 2.969 | 58.339 | 1.00 | 51.01 | O |
| ATOM | 1784 | N | LEU | A | 754 | 24.116 | 8.599 | 56.722 | 1.00 | 40.36 | N |
| ATOM | 1785 | CA | LEU | A | 754 | 24.606 | 9.180 | 55.478 | 1.00 | 38.78 | C |
| ATOM | 1786 | C | LEU | A | 754 | 25.283 | 10.512 | 55.775 | 1.00 | 37.61 | C |
| ATOM | 1787 | O | LEU | A | 754 | 26.301 | 10.843 | 55.173 | 1.00 | 37.43 | O |
| ATOM | 1788 | CB | LEU | A | 754 | 23.454 | 9.394 | 54.491 | 1.00 | 38.76 | C |
| ATOM | 1789 | CG | LEU | A | 754 | 23.816 | 10.079 | 53.167 | 1.00 | 38.96 | C |
| ATOM | 1790 | CD1 | LEU | A | 754 | 24.800 | 9.220 | 52.387 | 1.00 | 39.08 | C |
| ATOM | 1791 | CD2 | LEU | A | 754 | 22.556 | 10.317 | 52.348 | 1.00 | 39.05 | C |
| ATOM | 1792 | N | PHE | A | 755 | 24.718 | 11.269 | 56.711 | 1.00 | 36.81 | N |
| ATOM | 1793 | CA | PHE | A | 755 | 25.286 | 12.560 | 57.081 | 1.00 | 35.66 | C |
| ATOM | 1794 | C | PHE | A | 755 | 26.645 | 12.382 | 57.745 | 1.00 | 35.44 | C |
| ATOM | 1795 | O | PHE | A | 755 | 27.606 | 13.069 | 57.391 | 1.00 | 35.00 | O |
| ATOM | 1796 | CB | PHE | A | 755 | 24.356 | 13.315 | 58.030 | 1.00 | 34.78 | C |
| ATOM | 1797 | CG | PHE | A | 755 | 24.930 | 14.610 | 58.529 | 1.00 | 34.38 | C |
| ATOM | 1798 | CD1 | PHE | A | 755 | 25.197 | 15.653 | 57.647 | 1.00 | 34.47 | C |
| ATOM | 1799 | CD2 | PHE | A | 755 | 25.226 | 14.780 | 59.876 | 1.00 | 33.95 | C |
| ATOM | 1800 | CE1 | PHE | A | 755 | 25.755 | 16.849 | 58.104 | 1.00 | 34.35 | C |
| ATOM | 1801 | CE2 | PHE | A | 755 | 25.783 | 15.968 | 60.345 | 1.00 | 34.47 | C |
| ATOM | 1802 | CZ | PHE | A | 755 | 26.049 | 17.005 | 59.459 | 1.00 | 34.37 | C |
| ATOM | 1803 | N | LEU | A | 756 | 26.720 | 11.469 | 58.713 | 1.00 | 34.29 | N |
| ATOM | 1804 | CA | LEU | A | 756 | 27.976 | 11.211 | 59.412 | 1.00 | 33.74 | C |
| ATOM | 1805 | C | LEU | A | 756 | 29.073 | 10.850 | 58.410 | 1.00 | 32.83 | C |
| ATOM | 1806 | O | LEU | A | 756 | 30.223 | 11.241 | 58.572 | 1.00 | 33.03 | O |
| ATOM | 1807 | CB | LEU | A | 756 | 27.805 | 10.076 | 60.435 | 1.00 | 34.02 | C |
| ATOM | 1808 | CG | LEU | A | 756 | 26.907 | 10.349 | 61.651 | 1.00 | 34.36 | C |
| ATOM | 1809 | CD1 | LEU | A | 756 | 26.909 | 9.135 | 62.583 | 1.00 | 34.63 | C |
| ATOM | 1810 | CD2 | LEU | A | 756 | 27.414 | 11.575 | 62.401 | 1.00 | 34.55 | C |
| ATOM | 1811 | N | ALA | A | 757 | 28.709 | 10.107 | 57.370 | 1.00 | 31.88 | N |
| ATOM | 1812 | CA | ALA | A | 757 | 29.665 | 9.714 | 56.344 | 1.00 | 30.86 | C |
| ATOM | 1813 | C | ALA | A | 757 | 30.117 | 10.945 | 55.555 | 1.00 | 30.52 | C |
| ATOM | 1814 | O | ALA | A | 757 | 31.300 | 11.103 | 55.252 | 1.00 | 29.30 | O |
| ATOM | 1815 | CB | ALA | A | 757 | 29.034 | 8.696 | 55.409 | 1.00 | 30.67 | C |
| ATOM | 1816 | N | MET | A | 758 | 29.165 | 11.815 | 55.228 | 1.00 | 29.75 | N |
| ATOM | 1817 | CA | MET | A | 758 | 29.472 | 13.030 | 54.480 | 1.00 | 29.58 | C |
| ATOM | 1818 | C | MET | A | 758 | 30.338 | 13.972 | 55.316 | 1.00 | 28.32 | C |
| ATOM | 1819 | O | MET | A | 758 | 31.271 | 14.588 | 54.799 | 1.00 | 27.59 | O |
| ATOM | 1820 | CB | MET | A | 758 | 28.178 | 13.736 | 54.059 | 1.00 | 30.87 | C |
| ATOM | 1821 | CG | MET | A | 758 | 27.353 | 12.960 | 53.035 | 1.00 | 31.88 | C |
| ATOM | 1822 | SD | MET | A | 758 | 28.337 | 12.469 | 51.611 | 1.00 | 34.89 | S |
| ATOM | 1823 | CE | MET | A | 758 | 28.144 | 13.836 | 50.553 | 1.00 | 37.46 | C |
| ATOM | 1824 | N | LEU | A | 759 | 30.028 | 14.063 | 56.609 | 1.00 | 26.74 | N |
| ATOM | 1825 | CA | LEU | A | 759 | 30.765 | 14.916 | 57.536 | 1.00 | 26.28 | C |
| ATOM | 1826 | C | LEU | A | 759 | 32.212 | 14.446 | 57.665 | 1.00 | 25.07 | C |
| ATOM | 1827 | O | LEU | A | 759 | 33.137 | 15.256 | 57.633 | 1.00 | 24.51 | O |
| ATOM | 1828 | CB | LEU | A | 759 | 30.087 | 14.916 | 58.914 | 1.00 | 25.35 | C |
| ATOM | 1829 | CG | LEU | A | 759 | 30.770 | 15.719 | 60.024 | 1.00 | 26.66 | C |
| ATOM | 1830 | CD1 | LEU | A | 759 | 30.903 | 17.173 | 59.608 | 1.00 | 27.86 | C |
| ATOM | 1831 | CD2 | LEU | A | 759 | 29.966 | 15.601 | 61.311 | 1.00 | 27.35 | C |
| ATOM | 1832 | N | MET | A | 760 | 32.402 | 13.137 | 57.811 | 1.00 | 23.76 | N |
| ATOM | 1833 | CA | MET | A | 760 | 33.745 | 12.582 | 57.923 | 1.00 | 22.68 | C |
| ATOM | 1834 | C | MET | A | 760 | 34.556 | 12.989 | 56.706 | 1.00 | 22.10 | C |
| ATOM | 1835 | O | MET | A | 760 | 35.694 | 13.425 | 56.835 | 1.00 | 21.70 | O |
| ATOM | 1836 | CB | MET | A | 760 | 33.696 | 11.054 | 58.019 | 1.00 | 22.55 | C |
| ATOM | 1837 | CG | MET | A | 760 | 33.357 | 10.521 | 59.404 | 1.00 | 21.17 | C |
| ATOM | 1838 | SD | MET | A | 760 | 34.662 | 10.880 | 60.626 | 1.00 | 22.97 | S |
| ATOM | 1839 | CE | MET | A | 760 | 36.068 | 9.954 | 59.967 | 1.00 | 21.20 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 |  | 74.456 |  | 130.132 | 90.00 | 90.00 | 120.00 | P 31 2 1 6 | |
|---|---|---|---|---|---|---|---|---|---|---|
| ATOM | 1840 | N | THR | A | 761 | 33.967 | 12.848 | 55.522 | 1.00 | 21.82 | N |
| ATOM | 1841 | CA | THR | A | 761 | 34.658 | 13.212 | 54.290 | 1.00 | 22.25 | C |
| ATOM | 1842 | C | THR | A | 761 | 35.010 | 14.698 | 54.295 | 1.00 | 22.43 | C |
| ATOM | 1843 | O | THR | A | 761 | 36.110 | 15.090 | 53.900 | 1.00 | 22.77 | O |
| ATOM | 1844 | CB | THR | A | 761 | 33.791 | 12.907 | 53.043 | 1.00 | 22.27 | C |
| ATOM | 1845 | OG1 | THR | A | 761 | 33.520 | 11.498 | 52.983 | 1.00 | 22.04 | O |
| ATOM | 1846 | CG2 | THR | A | 761 | 34.519 | 13.319 | 51.778 | 1.00 | 21.95 | C |
| ATOM | 1847 | N | ALA | A | 762 | 34.073 | 15.519 | 54.748 | 1.00 | 21.79 | N |
| ATOM | 1848 | CA | ALA | A | 762 | 34.296 | 16.959 | 54.793 | 1.00 | 22.62 | C |
| ATOM | 1849 | C | ALA | A | 762 | 35.512 | 17.317 | 55.649 | 1.00 | 22.58 | C |
| ATOM | 1850 | O | ALA | A | 762 | 36.273 | 18.217 | 55.300 | 1.00 | 22.27 | O |
| ATOM | 1851 | CB | ALA | A | 762 | 33.047 | 17.670 | 55.319 | 1.00 | 20.62 | C |
| ATOM | 1852 | N | CYS | A | 763 | 35.691 | 16.615 | 56.767 | 1.00 | 22.42 | N |
| ATOM | 1853 | CA | CYS | A | 763 | 36.823 | 16.879 | 57.649 | 1.00 | 22.05 | C |
| ATOM | 1854 | C | CYS | A | 763 | 38.119 | 16.319 | 57.076 | 1.00 | 22.14 | C |
| ATOM | 1855 | O | CYS | A | 763 | 39.185 | 16.927 | 57.216 | 1.00 | 20.72 | O |
| ATOM | 1856 | CB | CYS | A | 763 | 36.568 | 16.278 | 59.035 | 1.00 | 22.36 | C |
| ATOM | 1857 | SG | CYS | A | 763 | 35.197 | 17.050 | 59.958 | 1.00 | 23.87 | S |
| ATOM | 1858 | N | ASP | A | 764 | 38.011 | 15.173 | 56.409 | 1.00 | 21.35 | N |
| ATOM | 1859 | CA | ASP | A | 764 | 39.152 | 14.490 | 55.810 | 1.00 | 21.95 | C |
| ATOM | 1860 | C | ASP | A | 764 | 39.784 | 15.317 | 54.693 | 1.00 | 22.80 | C |
| ATOM | 1861 | O | ASP | A | 764 | 40.992 | 15.241 | 54.448 | 1.00 | 22.34 | O |
| ATOM | 1862 | CB | ASP | A | 764 | 38.680 | 13.157 | 55.232 | 1.00 | 21.79 | C |
| ATOM | 1863 | CG | ASP | A | 764 | 39.803 | 12.134 | 55.049 | 1.00 | 23.38 | C |
| ATOM | 1864 | OD1 | ASP | A | 764 | 40.994 | 12.439 | 55.300 | 1.00 | 21.60 | O |
| ATOM | 1865 | OD2 | ASP | A | 764 | 39.459 | 10.997 | 54.646 | 1.00 | 22.81 | O |
| ATOM | 1866 | N | LEU | A | 765 | 38.958 | 16.106 | 54.016 | 1.00 | 23.09 | N |
| ATOM | 1867 | CA | LEU | A | 765 | 39.423 | 16.924 | 52.903 | 1.00 | 23.90 | C |
| ATOM | 1868 | C | LEU | A | 765 | 39.593 | 18.396 | 53.274 | 1.00 | 23.81 | C |
| ATOM | 1869 | O | LEU | A | 765 | 39.971 | 19.210 | 52.429 | 1.00 | 24.79 | O |
| ATOM | 1870 | CB | LEU | A | 765 | 38.428 | 16.824 | 51.735 | 1.00 | 24.84 | C |
| ATOM | 1871 | CG | LEU | A | 765 | 37.966 | 15.430 | 51.313 | 1.00 | 24.92 | C |
| ATOM | 1872 | CD1 | LEU | A | 765 | 36.919 | 15.552 | 50.218 | 1.00 | 26.17 | C |
| ATOM | 1873 | CD2 | LEU | A | 765 | 39.147 | 14.616 | 50.842 | 1.00 | 24.09 | C |
| ATOM | 1874 | N | SER | A | 766 | 39.335 | 18.735 | 54.531 | 1.00 | 23.43 | N |
| ATOM | 1875 | CA | SER | A | 766 | 39.394 | 20.128 | 54.974 | 1.00 | 23.76 | C |
| ATOM | 1876 | C | SER | A | 766 | 40.687 | 20.928 | 54.744 | 1.00 | 23.80 | C |
| ATOM | 1877 | O | SER | A | 766 | 40.668 | 22.150 | 54.836 | 1.00 | 23.46 | O |
| ATOM | 1878 | CB | SER | A | 766 | 38.980 | 20.232 | 56.446 | 1.00 | 23.41 | C |
| ATOM | 1879 | OG | SER | A | 766 | 39.903 | 19.578 | 57.289 | 1.00 | 25.01 | O |
| ATOM | 1880 | N | ALA | A | 767 | 41.800 | 20.268 | 54.442 | 1.00 | 22.76 | N |
| ATOM | 1881 | CA | ALA | A | 767 | 43.032 | 21.020 | 54.186 | 1.00 | 23.49 | C |
| ATOM | 1882 | C | ALA | A | 767 | 42.794 | 21.927 | 52.983 | 1.00 | 23.36 | C |
| ATOM | 1883 | O | ALA | A | 767 | 43.441 | 22.962 | 52.831 | 1.00 | 23.54 | O |
| ATOM | 1884 | CB | ALA | A | 767 | 44.192 | 20.075 | 53.892 | 1.00 | 22.25 | C |
| ATOM | 1885 | N | ILE | A | 768 | 41.849 | 21.526 | 52.134 | 1.00 | 23.21 | N |
| ATOM | 1886 | CA | ILE | A | 768 | 41.523 | 22.268 | 50.923 | 1.00 | 23.09 | C |
| ATOM | 1887 | C | ILE | A | 768 | 40.799 | 23.585 | 51.208 | 1.00 | 23.40 | C |
| ATOM | 1888 | O | ILE | A | 768 | 40.676 | 24.437 | 50.323 | 1.00 | 24.42 | O |
| ATOM | 1889 | CB | ILE | A | 768 | 40.645 | 21.396 | 49.967 | 1.00 | 23.10 | C |
| ATOM | 1890 | CG1 | ILE | A | 768 | 40.699 | 21.951 | 48.544 | 1.00 | 22.94 | C |
| ATOM | 1891 | CG2 | ILE | A | 768 | 39.189 | 21.386 | 50.438 | 1.00 | 22.45 | C |
| ATOM | 1892 | CD1 | ILE | A | 768 | 42.063 | 21.858 | 47.892 | 1.00 | 22.32 | C |
| ATOM | 1893 | N | THR | A | 769 | 40.348 | 23.765 | 52.447 | 1.00 | 23.44 | N |
| ATOM | 1894 | CA | THR | A | 769 | 39.606 | 24.964 | 52.836 | 1.00 | 23.84 | C |
| ATOM | 1895 | C | THR | A | 769 | 40.414 | 26.014 | 53.600 | 1.00 | 24.61 | C |
| ATOM | 1896 | O | THR | A | 769 | 39.916 | 27.109 | 53.881 | 1.00 | 24.77 | O |
| ATOM | 1897 | CB | THR | A | 769 | 38.429 | 24.593 | 53.741 | 1.00 | 23.54 | C |
| ATOM | 1898 | OG1 | THR | A | 769 | 38.927 | 24.293 | 55.053 | 1.00 | 23.45 | O |
| ATOM | 1899 | CG2 | THR | A | 769 | 37.696 | 23.368 | 53.194 | 1.00 | 24.03 | C |
| ATOM | 1900 | N | LYS | A | 770 | 41.650 | 25.680 | 53.947 | 1.00 | 24.82 | N |
| ATOM | 1901 | CA | LYS | A | 770 | 42.495 | 26.578 | 54.731 | 1.00 | 23.96 | C |
| ATOM | 1902 | C | LYS | A | 770 | 42.933 | 27.878 | 54.053 | 1.00 | 24.59 | C |
| ATOM | 1903 | O | LYS | A | 770 | 42.857 | 28.020 | 52.830 | 1.00 | 24.15 | O |
| ATOM | 1904 | CB | LYS | A | 770 | 43.745 | 25.816 | 55.188 | 1.00 | 24.10 | C |
| ATOM | 1905 | CG | LYS | A | 770 | 43.456 | 24.575 | 56.028 | 1.00 | 22.84 | C |
| ATOM | 1906 | CD | LYS | A | 770 | 42.815 | 24.936 | 57.359 | 1.00 | 22.59 | C |
| ATOM | 1907 | CE | LYS | A | 770 | 42.421 | 23.679 | 58.134 | 1.00 | 22.33 | C |
| ATOM | 1908 | NZ | LYS | A | 770 | 42.054 | 23.970 | 59.543 | 1.00 | 19.86 | N |
| ATOM | 1909 | N | PRO | A | 771 | 43.389 | 28.856 | 54.856 | 1.00 | 24.70 | N |
| ATOM | 1910 | CA | PRO | A | 771 | 43.851 | 30.132 | 54.306 | 1.00 | 25.27 | C |
| ATOM | 1911 | C | PRO | A | 771 | 44.907 | 29.845 | 53.244 | 1.00 | 25.72 | C |
| ATOM | 1912 | O | PRO | A | 771 | 45.697 | 28.906 | 53.376 | 1.00 | 26.69 | O |
| ATOM | 1913 | CB | PRO | A | 771 | 44.434 | 30.835 | 55.528 | 1.00 | 25.87 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 1914 | CG | PRO | A | 771 | 43.486 | 30.411 | 56.613 | 1.00 | 25.42 | C |
| ATOM | 1915 | CD | PRO | A | 771 | 43.289 | 28.922 | 56.327 | 1.00 | 24.17 | C |
| ATOM | 1916 | N | TRP | A | 772 | 44.920 | 30.660 | 52.198 | 1.00 | 26.14 | N |
| ATOM | 1917 | CA | TRP | A | 772 | 45.853 | 30.497 | 51.091 | 1.00 | 26.83 | C |
| ATOM | 1918 | C | TRP | A | 772 | 47.285 | 30.095 | 51.458 | 1.00 | 27.31 | C |
| ATOM | 1919 | O | TRP | A | 772 | 47.818 | 29.132 | 50.913 | 1.00 | 27.44 | O |
| ATOM | 1920 | CB | TRP | A | 772 | 45.876 | 31.776 | 50.254 | 1.00 | 27.19 | C |
| ATOM | 1921 | CG | TRP | A | 772 | 46.790 | 31.719 | 49.065 | 1.00 | 28.34 | C |
| ATOM | 1922 | CD1 | TRP | A | 772 | 47.695 | 32.668 | 48.686 | 1.00 | 28.69 | C |
| ATOM | 1923 | CD2 | TRP | A | 772 | 46.851 | 30.685 | 48.077 | 1.00 | 28.48 | C |
| ATOM | 1924 | NE1 | TRP | A | 772 | 48.316 | 32.291 | 47.518 | 1.00 | 29.86 | N |
| ATOM | 1925 | CE2 | TRP | A | 772 | 47.815 | 31.079 | 47.120 | 1.00 | 28.99 | C |
| ATOM | 1926 | CE3 | TRP | A | 772 | 46.182 | 29.465 | 47.899 | 1.00 | 28.49 | C |
| ATOM | 1927 | CZ2 | TRP | A | 772 | 48.133 | 30.293 | 46.006 | 1.00 | 28.84 | C |
| ATOM | 1928 | CZ3 | TRP | A | 772 | 46.497 | 28.682 | 46.789 | 1.00 | 28.20 | C |
| ATOM | 1929 | CH2 | TRP | A | 772 | 47.462 | 29.102 | 45.857 | 1.00 | 28.53 | C |
| ATOM | 1930 | N | PRO | A | 773 | 47.942 | 30.833 | 52.369 | 1.00 | 28.12 | N |
| ATOM | 1931 | CA | PRO | A | 773 | 49.310 | 30.405 | 52.681 | 1.00 | 27.93 | C |
| ATOM | 1932 | C | PRO | A | 773 | 49.380 | 28.998 | 53.272 | 1.00 | 27.54 | C |
| ATOM | 1933 | O | PRO | A | 773 | 50.331 | 28.261 | 53.011 | 1.00 | 28.71 | O |
| ATOM | 1934 | CB | PRO | A | 773 | 49.817 | 31.499 | 53.630 | 1.00 | 28.56 | C |
| ATOM | 1935 | CG | PRO | A | 773 | 48.569 | 32.048 | 54.246 | 1.00 | 29.60 | C |
| ATOM | 1936 | CD | PRO | A | 773 | 47.585 | 32.063 | 53.099 | 1.00 | 28.63 | C |
| ATOM | 1937 | N | ILE | A | 774 | 48.372 | 28.617 | 54.050 | 1.00 | 26.28 | N |
| ATOM | 1938 | CA | ILE | A | 774 | 48.354 | 27.283 | 54.641 | 1.00 | 25.88 | C |
| ATOM | 1939 | C | ILE | A | 774 | 48.061 | 26.240 | 53.560 | 1.00 | 25.68 | C |
| ATOM | 1940 | O | ILE | A | 774 | 48.796 | 25.266 | 53.422 | 1.00 | 26.17 | O |
| ATOM | 1941 | CB | ILE | A | 774 | 47.300 | 27.173 | 55.765 | 1.00 | 25.43 | C |
| ATOM | 1942 | CG1 | ILE | A | 774 | 47.580 | 28.225 | 56.844 | 1.00 | 26.53 | C |
| ATOM | 1943 | CG2 | ILE | A | 774 | 47.328 | 25.771 | 56.383 | 1.00 | 26.22 | C |
| ATOM | 1944 | CD1 | ILE | A | 774 | 49.002 | 28.193 | 57.366 | 1.00 | 26.44 | C |
| ATOM | 1945 | N | GLN | A | 775 | 47.003 | 26.451 | 52.781 | 1.00 | 24.76 | N |
| ATOM | 1946 | CA | GLN | A | 775 | 46.655 | 25.505 | 51.718 | 1.00 | 24.63 | C |
| ATOM | 1947 | C | GLN | A | 775 | 47.818 | 25.287 | 50.744 | 1.00 | 24.83 | C |
| ATOM | 1948 | O | GLN | A | 775 | 48.084 | 24.159 | 50.341 | 1.00 | 25.04 | O |
| ATOM | 1949 | CB | GLN | A | 775 | 45.395 | 25.978 | 50.973 | 1.00 | 23.00 | C |
| ATOM | 1950 | CG | GLN | A | 775 | 45.254 | 25.480 | 49.528 | 1.00 | 23.61 | C |
| ATOM | 1951 | CD | GLN | A | 775 | 45.246 | 23.960 | 49.380 | 1.00 | 23.19 | C |
| ATOM | 1952 | OE1 | GLN | A | 775 | 45.396 | 23.442 | 48.270 | 1.00 | 24.48 | O |
| ATOM | 1953 | NE2 | GLN | A | 775 | 45.068 | 23.245 | 50.486 | 1.00 | 23.08 | N |
| ATOM | 1954 | N | GLN | A | 776 | 48.519 | 26.354 | 50.367 | 1.00 | 24.83 | N |
| ATOM | 1955 | CA | GLN | A | 776 | 49.661 | 26.198 | 49.462 | 1.00 | 25.79 | C |
| ATOM | 1956 | C | GLN | A | 776 | 50.624 | 25.148 | 50.009 | 1.00 | 25.59 | C |
| ATOM | 1957 | O | GLN | A | 776 | 51.164 | 24.340 | 49.256 | 1.00 | 26.19 | O |
| ATOM | 1958 | CB | GLN | A | 776 | 50.429 | 27.519 | 49.300 | 1.00 | 27.64 | C |
| ATOM | 1959 | CG | GLN | A | 776 | 49.844 | 28.494 | 48.290 | 1.00 | 29.97 | C |
| ATOM | 1960 | CD | GLN | A | 776 | 50.691 | 29.758 | 48.154 | 1.00 | 32.05 | C |
| ATOM | 1961 | OE1 | GLN | A | 776 | 50.765 | 30.570 | 49.075 | 1.00 | 32.82 | O |
| ATOM | 1962 | NE2 | GLN | A | 776 | 51.341 | 29.918 | 47.006 | 1.00 | 32.20 | N |
| ATOM | 1963 | N | ARG | A | 777 | 50.833 | 25.177 | 51.323 | 1.00 | 25.10 | N |
| ATOM | 1964 | CA | ARG | A | 777 | 51.730 | 24.242 | 51.999 | 1.00 | 25.97 | C |
| ATOM | 1965 | C | ARG | A | 777 | 51.163 | 22.827 | 52.052 | 1.00 | 25.04 | C |
| ATOM | 1966 | O | ARG | A | 777 | 51.861 | 21.857 | 51.763 | 1.00 | 24.81 | O |
| ATOM | 1967 | CB | ARG | A | 777 | 52.004 | 24.715 | 53.430 | 1.00 | 26.87 | C |
| ATOM | 1968 | CG | ARG | A | 777 | 52.721 | 26.059 | 53.525 | 1.00 | 29.79 | C |
| ATOM | 1969 | CD | ARG | A | 777 | 54.098 | 25.974 | 52.908 | 1.00 | 31.69 | C |
| ATOM | 1970 | NE | ARG | A | 777 | 54.945 | 27.103 | 53.292 | 1.00 | 33.06 | N |
| ATOM | 1971 | CZ | ARG | A | 777 | 56.180 | 27.279 | 52.836 | 1.00 | 34.14 | C |
| ATOM | 1972 | NH1 | ARG | A | 777 | 56.695 | 26.399 | 51.986 | 1.00 | 33.83 | N |
| ATOM | 1973 | NH2 | ARG | A | 777 | 56.899 | 28.327 | 53.224 | 1.00 | 34.38 | N |
| ATOM | 1974 | N | LEU | A | 778 | 49.899 | 22.706 | 52.438 | 1.00 | 25.14 | N |
| ATOM | 1975 | CA | LEU | A | 778 | 49.287 | 21.384 | 52.514 | 1.00 | 25.15 | C |
| ATOM | 1976 | C | LEU | A | 778 | 49.233 | 20.733 | 51.130 | 1.00 | 25.09 | C |
| ATOM | 1977 | O | LEU | A | 778 | 49.294 | 19.513 | 51.018 | 1.00 | 25.32 | O |
| ATOM | 1978 | CB | LEU | A | 778 | 47.898 | 21.491 | 53.138 | 1.00 | 25.35 | C |
| ATOM | 1979 | CG | LEU | A | 778 | 47.949 | 22.043 | 54.572 | 1.00 | 24.73 | C |
| ATOM | 1980 | CD1 | LEU | A | 778 | 46.541 | 22.299 | 55.083 | 1.00 | 23.82 | C |
| ATOM | 1981 | CD2 | LEU | A | 778 | 48.692 | 21.061 | 55.484 | 1.00 | 24.45 | C |
| ATOM | 1982 | N | ALA | A | 779 | 49.128 | 21.545 | 50.079 | 1.00 | 25.66 | N |
| ATOM | 1983 | CA | ALA | A | 779 | 49.104 | 21.015 | 48.718 | 1.00 | 26.21 | C |
| ATOM | 1984 | C | ALA | A | 779 | 50.495 | 20.454 | 48.385 | 1.00 | 26.90 | C |
| ATOM | 1985 | O | ALA | A | 779 | 50.605 | 19.458 | 47.675 | 1.00 | 27.42 | O |
| ATOM | 1986 | CB | ALA | A | 779 | 48.706 | 22.112 | 47.716 | 1.00 | 25.68 | C |
| ATOM | 1987 | N | GLU | A | 780 | 51.548 | 21.090 | 48.904 | 1.00 | 27.64 | N |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 1988 | CA | GLU | A | 780 | 52.926 | 20.619 | 48.691 | 1.00 | 28.52 | C |
| ATOM | 1989 | C | GLU | A | 780 | 53.046 | 19.188 | 49.220 | 1.00 | 28.83 | C |
| ATOM | 1990 | O | GLU | A | 780 | 53.605 | 18.310 | 48.565 | 1.00 | 28.91 | O |
| ATOM | 1991 | CB | GLU | A | 780 | 53.942 | 21.455 | 49.481 | 1.00 | 30.08 | C |
| ATOM | 1992 | CG | GLU | A | 780 | 54.454 | 22.748 | 48.866 | 1.00 | 32.45 | C |
| ATOM | 1993 | CD | GLU | A | 780 | 55.577 | 23.365 | 49.717 | 1.00 | 32.89 | C |
| ATOM | 1994 | OE1 | GLU | A | 780 | 56.720 | 22.851 | 49.685 | 1.00 | 33.15 | O |
| ATOM | 1995 | OE2 | GLU | A | 780 | 55.310 | 24.353 | 50.433 | 1.00 | 33.06 | O |
| ATOM | 1996 | N | LEU | A | 781 | 52.545 | 18.980 | 50.435 | 1.00 | 28.04 | N |
| ATOM | 1997 | CA | LEU | A | 781 | 52.591 | 17.671 | 51.072 | 1.00 | 28.52 | C |
| ATOM | 1998 | C | LEU | A | 781 | 51.865 | 16.628 | 50.234 | 1.00 | 28.15 | C |
| ATOM | 1999 | O | LEU | A | 781 | 52.397 | 15.547 | 49.985 | 1.00 | 29.64 | O |
| ATOM | 2000 | CB | LEU | A | 781 | 51.981 | 17.740 | 52.482 | 1.00 | 27.20 | C |
| ATOM | 2001 | CG | LEU | A | 781 | 52.760 | 18.567 | 53.513 | 1.00 | 27.06 | C |
| ATOM | 2002 | CD1 | LEU | A | 781 | 52.082 | 18.489 | 54.878 | 1.00 | 26.98 | C |
| ATOM | 2003 | CD2 | LEU | A | 781 | 54.187 | 18.049 | 53.603 | 1.00 | 27.19 | C |
| ATOM | 2004 | N | VAL | A | 782 | 50.653 | 16.951 | 49.798 | 1.00 | 28.45 | N |
| ATOM | 2005 | CA | VAL | A | 782 | 49.882 | 16.026 | 48.978 | 1.00 | 28.00 | C |
| ATOM | 2006 | C | VAL | A | 782 | 50.636 | 15.698 | 47.697 | 1.00 | 28.90 | C |
| ATOM | 2007 | O | VAL | A | 782 | 50.710 | 14.535 | 47.288 | 1.00 | 28.29 | O |
| ATOM | 2008 | CB | VAL | A | 782 | 48.514 | 16.607 | 48.616 | 1.00 | 28.09 | C |
| ATOM | 2009 | CG1 | VAL | A | 782 | 47.821 | 15.703 | 47.599 | 1.00 | 28.37 | C |
| ATOM | 2010 | CG2 | VAL | A | 782 | 47.665 | 16.742 | 49.868 | 1.00 | 27.74 | C |
| ATOM | 2011 | N | ALA | A | 783 | 51.199 | 16.724 | 47.065 | 1.00 | 29.36 | N |
| ATOM | 2012 | CA | ALA | A | 783 | 51.955 | 16.531 | 45.834 | 1.00 | 29.79 | C |
| ATOM | 2013 | C | ALA | A | 783 | 53.180 | 15.650 | 46.079 | 1.00 | 29.89 | C |
| ATOM | 2014 | O | ALA | A | 783 | 53.519 | 14.816 | 45.251 | 1.00 | 29.22 | O |
| ATOM | 2015 | CB | ALA | A | 783 | 52.382 | 17.879 | 45.261 | 1.00 | 30.24 | C |
| ATOM | 2016 | N | THR | A | 784 | 53.846 | 15.835 | 47.214 | 1.00 | 30.89 | N |
| ATOM | 2017 | CA | THR | A | 784 | 55.024 | 15.028 | 47.523 | 1.00 | 32.31 | C |
| ATOM | 2018 | C | THR | A | 784 | 54.656 | 13.552 | 47.623 | 1.00 | 32.78 | C |
| ATOM | 2019 | O | THR | A | 784 | 55.307 | 12.702 | 47.018 | 1.00 | 32.20 | O |
| ATOM | 2020 | CB | THR | A | 784 | 55.683 | 15.466 | 48.846 | 1.00 | 32.85 | C |
| ATOM | 2021 | OG1 | THR | A | 784 | 56.255 | 16.767 | 48.686 | 1.00 | 34.10 | O |
| ATOM | 2022 | CG2 | THR | A | 784 | 56.778 | 14.487 | 49.255 | 1.00 | 33.26 | C |
| ATOM | 2023 | N | GLU | A | 785 | 53.605 | 13.251 | 48.377 | 1.00 | 33.35 | N |
| ATOM | 2024 | CA | GLU | A | 785 | 53.175 | 11.869 | 48.541 | 1.00 | 35.30 | C |
| ATOM | 2025 | C | GLU | A | 785 | 52.725 | 11.257 | 47.216 | 1.00 | 36.57 | C |
| ATOM | 2026 | O | GLU | A | 785 | 52.991 | 10.088 | 46.950 | 1.00 | 36.40 | O |
| ATOM | 2027 | CB | GLU | A | 785 | 52.033 | 11.775 | 49.561 | 1.00 | 34.05 | C |
| ATOM | 2028 | CG | GLU | A | 785 | 51.800 | 10.361 | 50.080 | 1.00 | 34.14 | C |
| ATOM | 2029 | CD | GLU | A | 785 | 50.639 | 10.265 | 51.062 | 1.00 | 32.63 | C |
| ATOM | 2030 | OE1 | GLU | A | 785 | 50.602 | 11.044 | 52.036 | 1.00 | 32.13 | O |
| ATOM | 2031 | OE2 | GLU | A | 785 | 49.769 | 9.397 | 50.860 | 1.00 | 33.18 | O |
| ATOM | 2032 | N | PHE | A | 786 | 52.054 | 12.055 | 46.390 | 1.00 | 38.52 | N |
| ATOM | 2033 | CA | PHE | A | 786 | 51.554 | 11.591 | 45.096 | 1.00 | 41.56 | C |
| ATOM | 2034 | C | PHE | A | 786 | 52.621 | 11.341 | 44.034 | 1.00 | 43.37 | C |
| ATOM | 2035 | O | PHE | A | 786 | 52.622 | 10.303 | 43.375 | 1.00 | 43.15 | O |
| ATOM | 2036 | CB | PHE | A | 786 | 50.559 | 12.598 | 44.510 | 1.00 | 42.76 | C |
| ATOM | 2037 | CG | PHE | A | 786 | 49.157 | 12.462 | 45.029 | 1.00 | 44.06 | C |
| ATOM | 2038 | CD1 | PHE | A | 786 | 48.105 | 13.080 | 44.361 | 1.00 | 44.13 | C |
| ATOM | 2039 | CD2 | PHE | A | 786 | 48.881 | 11.722 | 46.175 | 1.00 | 44.64 | C |
| ATOM | 2040 | CE1 | PHE | A | 786 | 46.798 | 12.958 | 44.819 | 1.00 | 45.22 | C |
| ATOM | 2041 | CE2 | PHE | A | 786 | 47.575 | 11.594 | 46.642 | 1.00 | 45.06 | C |
| ATOM | 2042 | CZ | PHE | A | 786 | 46.533 | 12.213 | 45.965 | 1.00 | 45.01 | C |
| ATOM | 2043 | N | PHE | A | 787 | 53.522 | 12.301 | 43.868 | 1.00 | 45.60 | N |
| ATOM | 2044 | CA | PHE | A | 787 | 54.548 | 12.211 | 42.840 | 1.00 | 48.34 | C |
| ATOM | 2045 | C | PHE | A | 787 | 55.933 | 11.742 | 43.276 | 1.00 | 50.87 | C |
| ATOM | 2046 | O | PHE | A | 787 | 56.554 | 10.928 | 42.596 | 1.00 | 51.41 | O |
| ATOM | 2047 | CB | PHE | A | 787 | 54.664 | 13.570 | 42.143 | 1.00 | 47.52 | C |
| ATOM | 2048 | CG | PHE | A | 787 | 53.347 | 14.119 | 41.661 | 1.00 | 47.05 | C |
| ATOM | 2049 | CD1 | PHE | A | 787 | 52.628 | 13.467 | 40.662 | 1.00 | 47.18 | C |
| ATOM | 2050 | CD2 | PHE | A | 787 | 52.814 | 15.276 | 42.220 | 1.00 | 46.89 | C |
| ATOM | 2051 | CE1 | PHE | A | 787 | 51.396 | 13.961 | 40.227 | 1.00 | 46.97 | C |
| ATOM | 2052 | CE2 | PHE | A | 787 | 51.584 | 15.779 | 41.794 | 1.00 | 46.60 | C |
| ATOM | 2053 | CZ | PHE | A | 787 | 50.874 | 15.121 | 40.795 | 1.00 | 46.57 | C |
| ATOM | 2054 | N | ASP | A | 788 | 56.421 | 12.246 | 44.403 | 1.00 | 54.06 | N |
| ATOM | 2055 | CA | ASP | A | 788 | 57.754 | 11.884 | 44.870 | 1.00 | 57.14 | C |
| ATOM | 2056 | C | ASP | A | 788 | 57.852 | 10.610 | 45.702 | 1.00 | 59.28 | C |
| ATOM | 2057 | O | ASP | A | 788 | 58.806 | 9.842 | 45.559 | 1.00 | 59.70 | O |
| ATOM | 2058 | CB | ASP | A | 788 | 58.364 | 13.052 | 45.648 | 1.00 | 57.69 | C |
| ATOM | 2059 | CG | ASP | A | 788 | 58.480 | 14.309 | 44.805 | 1.00 | 58.54 | C |
| ATOM | 2060 | OD1 | ASP | A | 788 | 58.917 | 14.205 | 43.640 | 1.00 | 59.09 | O |
| ATOM | 2061 | OD2 | ASP | A | 788 | 58.142 | 15.400 | 45.306 | 1.00 | 58.96 | O |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 2062 | N | GLN | A | 789 | 56.879 | 10.383 | 46.575 | 1.00 | 61.34 | N |
| ATOM | 2063 | CA | GLN | A | 789 | 56.902 | 9.190 | 47.404 | 1.00 | 63.39 | C |
| ATOM | 2064 | C | GLN | A | 789 | 56.356 | 7.990 | 46.646 | 1.00 | 65.20 | C |
| ATOM | 2065 | O | GLN | A | 789 | 55.672 | 8.136 | 45.633 | 1.00 | 65.25 | O |
| ATOM | 2066 | CB | GLN | A | 789 | 56.098 | 9.410 | 48.684 | 1.00 | 62.76 | C |
| ATOM | 2067 | CG | GLN | A | 789 | 56.694 | 10.450 | 49.614 | 1.00 | 62.27 | C |
| ATOM | 2068 | CD | GLN | A | 789 | 56.000 | 10.481 | 50.959 | 1.00 | 61.76 | C |
| ATOM | 2069 | OE1 | GLN | A | 789 | 54.795 | 10.708 | 51.044 | 1.00 | 61.40 | O |
| ATOM | 2070 | NE2 | GLN | A | 789 | 56.759 | 10.247 | 52.019 | 1.00 | 61.93 | N |
| ATOM | 2071 | N | GLY | A | 790 | 56.664 | 6.803 | 47.150 | 1.00 | 67.54 | N |
| ATOM | 2072 | CA | GLY | A | 790 | 56.218 | 5.580 | 46.512 | 1.00 | 70.84 | C |
| ATOM | 2073 | C | GLY | A | 790 | 57.389 | 4.626 | 46.449 | 1.00 | 73.06 | C |
| ATOM | 2074 | O | GLY | A | 790 | 57.303 | 3.547 | 45.863 | 1.00 | 73.36 | O |
| ATOM | 2075 | N | ASP | A | 791 | 58.489 | 5.049 | 47.068 | 1.00 | 75.27 | N |
| ATOM | 2076 | CA | ASP | A | 791 | 59.732 | 4.286 | 47.132 | 1.00 | 77.61 | C |
| ATOM | 2077 | C | ASP | A | 791 | 60.847 | 5.284 | 47.436 | 1.00 | 79.03 | C |
| ATOM | 2078 | O | ASP | A | 791 | 62.018 | 5.044 | 47.136 | 1.00 | 79.33 | O |
| ATOM | 2079 | CB | ASP | A | 791 | 60.009 | 3.590 | 45.795 | 1.00 | 78.12 | C |
| ATOM | 2080 | CG | ASP | A | 791 | 60.995 | 2.445 | 45.925 | 1.00 | 78.59 | C |
| ATOM | 2081 | OD1 | ASP | A | 791 | 62.162 | 2.696 | 46.292 | 1.00 | 78.93 | O |
| ATOM | 2082 | OD2 | ASP | A | 791 | 60.599 | 1.289 | 45.662 | 1.00 | 78.84 | O |
| ATOM | 2083 | N | ARG | A | 792 | 60.467 | 6.410 | 48.035 | 1.00 | 80.51 | N |
| ATOM | 2084 | CA | ARG | A | 792 | 61.416 | 7.464 | 48.373 | 1.00 | 81.86 | C |
| ATOM | 2085 | C | ARG | A | 792 | 61.651 | 7.520 | 49.880 | 1.00 | 82.34 | C |
| ATOM | 2086 | O | ARG | A | 792 | 61.064 | 6.680 | 50.597 | 1.00 | 82.64 | O |
| ATOM | 2087 | CB | ARG | A | 792 | 60.886 | 8.815 | 47.881 | 1.00 | 82.55 | C |
| ATOM | 2088 | CG | ARG | A | 792 | 61.955 | 9.879 | 47.687 | 1.00 | 83.72 | C |
| ATOM | 2089 | CD | ARG | A | 792 | 61.346 | 11.189 | 47.200 | 1.00 | 84.60 | C |
| ATOM | 2090 | NE | ARG | A | 792 | 62.355 | 12.121 | 46.700 | 1.00 | 85.24 | N |
| ATOM | 2091 | CZ | ARG | A | 792 | 63.378 | 12.581 | 47.415 | 1.00 | 85.49 | C |
| ATOM | 2092 | NH1 | ARG | A | 792 | 63.541 | 12.198 | 48.676 | 1.00 | 85.43 | N |
| ATOM | 2093 | NH2 | ARG | A | 792 | 64.242 | 13.426 | 46.868 | 1.00 | 85.64 | N |
| ATOM | 2094 | N | GLU | A | 808 | 58.424 | 19.870 | 35.550 | 1.00 | 68.21 | N |
| ATOM | 2095 | CA | GLU | A | 808 | 58.478 | 20.251 | 36.990 | 1.00 | 68.12 | C |
| ATOM | 2096 | C | GLU | A | 808 | 57.266 | 19.712 | 37.747 | 1.00 | 67.56 | C |
| ATOM | 2097 | O | GLU | A | 808 | 56.231 | 19.407 | 37.152 | 1.00 | 67.80 | O |
| ATOM | 2098 | CB | GLU | A | 808 | 58.542 | 21.777 | 37.126 | 1.00 | 68.77 | C |
| ATOM | 2099 | CG | GLU | A | 808 | 58.544 | 22.291 | 38.561 | 1.00 | 69.54 | C |
| ATOM | 2100 | CD | GLU | A | 808 | 59.771 | 21.857 | 39.344 | 1.00 | 69.98 | C |
| ATOM | 2101 | OE1 | GLU | A | 808 | 59.975 | 20.636 | 39.517 | 1.00 | 70.30 | O |
| ATOM | 2102 | OE2 | GLU | A | 808 | 60.532 | 22.743 | 39.787 | 1.00 | 70.46 | O |
| ATOM | 2103 | N | LYS | A | 809 | 57.408 | 19.600 | 39.063 | 1.00 | 66.63 | N |
| ATOM | 2104 | CA | LYS | A | 809 | 56.345 | 19.096 | 39.922 | 1.00 | 65.43 | C |
| ATOM | 2105 | C | LYS | A | 809 | 55.273 | 20.151 | 40.185 | 1.00 | 64.30 | C |
| ATOM | 2106 | O | LYS | A | 809 | 54.095 | 19.932 | 39.903 | 1.00 | 64.32 | O |
| ATOM | 2107 | CB | LYS | A | 809 | 56.944 | 18.629 | 41.247 | 1.00 | 66.00 | C |
| ATOM | 2108 | CG | LYS | A | 809 | 55.944 | 18.060 | 42.230 | 1.00 | 66.61 | C |
| ATOM | 2109 | CD | LYS | A | 809 | 56.626 | 17.784 | 43.553 | 1.00 | 67.03 | C |
| ATOM | 2110 | CE | LYS | A | 809 | 55.665 | 17.211 | 44.569 | 1.00 | 67.48 | C |
| ATOM | 2111 | NZ | LYS | A | 809 | 56.328 | 17.090 | 45.896 | 1.00 | 68.14 | N |
| ATOM | 2112 | N | LYS | A | 810 | 55.690 | 21.293 | 40.725 | 1.00 | 62.99 | N |
| ATOM | 2113 | CA | LYS | A | 810 | 54.778 | 22.391 | 41.037 | 1.00 | 61.43 | C |
| ATOM | 2114 | C | LYS | A | 810 | 53.679 | 22.606 | 40.004 | 1.00 | 59.84 | C |
| ATOM | 2115 | O | LYS | A | 810 | 52.496 | 22.601 | 40.339 | 1.00 | 59.74 | O |
| ATOM | 2116 | CB | LYS | A | 810 | 55.551 | 23.705 | 41.197 | 1.00 | 62.32 | C |
| ATOM | 2117 | CG | LYS | A | 810 | 56.206 | 23.916 | 42.552 | 1.00 | 62.82 | C |
| ATOM | 2118 | CD | LYS | A | 810 | 56.710 | 25.349 | 42.673 | 1.00 | 63.50 | C |
| ATOM | 2119 | CE | LYS | A | 810 | 57.278 | 25.645 | 44.053 | 1.00 | 63.79 | C |
| ATOM | 2120 | NZ | LYS | A | 810 | 57.709 | 27.068 | 44.170 | 1.00 | 63.81 | N |
| ATOM | 2121 | N | ASN | A | 811 | 54.081 | 22.801 | 38.752 | 1.00 | 57.79 | N |
| ATOM | 2122 | CA | ASN | A | 811 | 53.145 | 23.048 | 37.658 | 1.00 | 55.64 | C |
| ATOM | 2123 | C | ASN | A | 811 | 51.922 | 22.137 | 37.662 | 1.00 | 53.52 | C |
| ATOM | 2124 | O | ASN | A | 811 | 50.825 | 22.555 | 37.289 | 1.00 | 53.28 | O |
| ATOM | 2125 | CB | ASN | A | 811 | 53.870 | 22.918 | 36.320 | 1.00 | 56.32 | C |
| ATOM | 2126 | CG | ASN | A | 811 | 55.196 | 23.644 | 36.311 | 1.00 | 57.26 | C |
| ATOM | 2127 | OD1 | ASN | A | 811 | 55.287 | 24.807 | 36.713 | 1.00 | 57.51 | O |
| ATOM | 2128 | ND2 | ASN | A | 811 | 56.237 | 22.964 | 35.848 | 1.00 | 57.93 | N |
| ATOM | 2129 | N | LYS | A | 812 | 52.112 | 20.893 | 38.084 | 1.00 | 51.40 | N |
| ATOM | 2130 | CA | LYS | A | 812 | 51.017 | 19.932 | 38.126 | 1.00 | 48.95 | C |
| ATOM | 2131 | C | LYS | A | 812 | 50.053 | 20.236 | 39.269 | 1.00 | 46.54 | C |
| ATOM | 2132 | O | LYS | A | 812 | 48.877 | 19.888 | 39.213 | 1.00 | 46.09 | O |
| ATOM | 2133 | CB | LYS | A | 812 | 51.566 | 18.514 | 38.308 | 1.00 | 49.74 | C |
| ATOM | 2134 | CG | LYS | A | 812 | 52.766 | 18.189 | 37.440 | 1.00 | 50.45 | C |
| ATOM | 2135 | CD | LYS | A | 812 | 53.125 | 16.714 | 37.518 | 1.00 | 51.26 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 2136 | CE | LYS | A | 812 | 52.016 | 15.848 | 36.939 | 1.00 | 51.82 | C |
| ATOM | 2137 | NZ | LYS | A | 812 | 52.389 | 14.407 | 36.923 | 1.00 | 52.77 | N |
| ATOM | 2138 | N | ILE | A | 813 | 50.555 | 20.905 | 40.299 | 1.00 | 43.60 | N |
| ATOM | 2139 | CA | ILE | A | 813 | 49.745 | 21.211 | 41.470 | 1.00 | 40.82 | C |
| ATOM | 2140 | C | ILE | A | 813 | 48.517 | 22.104 | 41.281 | 1.00 | 39.20 | C |
| ATOM | 2141 | O | ILE | A | 813 | 47.415 | 21.730 | 41.675 | 1.00 | 37.95 | O |
| ATOM | 2142 | CB | ILE | A | 813 | 50.633 | 21.793 | 42.594 | 1.00 | 40.12 | C |
| ATOM | 2143 | CG1 | ILE | A | 813 | 51.661 | 20.736 | 43.015 | 1.00 | 39.09 | C |
| ATOM | 2144 | CG2 | ILE | A | 813 | 49.773 | 22.236 | 43.771 | 1.00 | 38.50 | C |
| ATOM | 2145 | CD1 | ILE | A | 813 | 52.609 | 21.180 | 44.101 | 1.00 | 40.56 | C |
| ATOM | 2146 | N | PRO | A | 814 | 48.680 | 23.287 | 40.669 | 1.00 | 38.45 | N |
| ATOM | 2147 | CA | PRO | A | 814 | 47.507 | 24.150 | 40.493 | 1.00 | 37.62 | C |
| ATOM | 2148 | C | PRO | A | 814 | 46.319 | 23.508 | 39.777 | 1.00 | 36.63 | C |
| ATOM | 2149 | O | PRO | A | 814 | 45.187 | 23.603 | 40.250 | 1.00 | 36.40 | O |
| ATOM | 2150 | CB | PRO | A | 814 | 48.076 | 25.373 | 39.761 | 1.00 | 38.21 | C |
| ATOM | 2151 | CG | PRO | A | 814 | 49.284 | 24.834 | 39.061 | 1.00 | 38.72 | C |
| ATOM | 2152 | CD | PRO | A | 814 | 49.881 | 23.890 | 40.067 | 1.00 | 38.23 | C |
| ATOM | 2153 | N | SER | A | 815 | 46.563 | 22.846 | 38.653 | 1.00 | 36.02 | N |
| ATOM | 2154 | CA | SER | A | 815 | 45.466 | 22.207 | 37.935 | 1.00 | 36.04 | C |
| ATOM | 2155 | C | SER | A | 815 | 44.908 | 21.029 | 38.748 | 1.00 | 34.95 | C |
| ATOM | 2156 | O | SER | A | 815 | 43.703 | 20.782 | 38.744 | 1.00 | 34.97 | O |
| ATOM | 2157 | CB | SER | A | 815 | 45.926 | 21.739 | 36.549 | 1.00 | 36.34 | C |
| ATOM | 2158 | OG | SER | A | 815 | 46.955 | 20.773 | 36.643 | 1.00 | 38.30 | O |
| ATOM | 2159 | N | MET | A | 816 | 45.782 | 20.318 | 39.456 | 1.00 | 33.91 | N |
| ATOM | 2160 | CA | MET | A | 816 | 45.354 | 19.189 | 40.279 | 1.00 | 32.25 | C |
| ATOM | 2161 | C | MET | A | 816 | 44.401 | 19.658 | 41.367 | 1.00 | 31.26 | C |
| ATOM | 2162 | O | MET | A | 816 | 43.357 | 19.041 | 41.596 | 1.00 | 30.42 | O |
| ATOM | 2163 | CB | MET | A | 816 | 46.550 | 18.494 | 40.935 | 1.00 | 32.87 | C |
| ATOM | 2164 | CG | MET | A | 816 | 46.141 | 17.454 | 41.986 | 1.00 | 34.57 | C |
| ATOM | 2165 | SD | MET | A | 816 | 47.517 | 16.558 | 42.741 | 1.00 | 36.00 | S |
| ATOM | 2166 | CE | MET | A | 816 | 48.033 | 17.707 | 43.994 | 1.00 | 34.52 | C |
| ATOM | 2167 | N | GLN | A | 817 | 44.758 | 20.754 | 42.035 | 1.00 | 29.69 | N |
| ATOM | 2168 | CA | GLN | A | 817 | 43.922 | 21.289 | 43.101 | 1.00 | 28.59 | C |
| ATOM | 2169 | C | GLN | A | 817 | 42.593 | 21.847 | 42.593 | 1.00 | 28.57 | C |
| ATOM | 2170 | O | GLN | A | 817 | 41.581 | 21.779 | 43.290 | 1.00 | 28.10 | O |
| ATOM | 2171 | CB | GLN | A | 817 | 44.674 | 22.374 | 43.881 | 1.00 | 28.02 | C |
| ATOM | 2172 | CG | GLN | A | 817 | 45.871 | 21.865 | 44.677 | 1.00 | 27.10 | C |
| ATOM | 2173 | CD | GLN | A | 817 | 45.533 | 20.672 | 45.557 | 1.00 | 27.36 | C |
| ATOM | 2174 | OE1 | GLN | A | 817 | 45.470 | 19.532 | 45.085 | 1.00 | 26.66 | O |
| ATOM | 2175 | NE2 | GLN | A | 817 | 45.304 | 20.929 | 46.843 | 1.00 | 26.57 | N |
| ATOM | 2176 | N | VAL | A | 818 | 42.589 | 22.413 | 41.388 | 1.00 | 28.47 | N |
| ATOM | 2177 | CA | VAL | A | 818 | 41.343 | 22.945 | 40.839 | 1.00 | 28.28 | C |
| ATOM | 2178 | C | VAL | A | 818 | 40.435 | 21.775 | 40.468 | 1.00 | 27.80 | C |
| ATOM | 2179 | O | VAL | A | 818 | 39.237 | 21.809 | 40.717 | 1.00 | 28.18 | O |
| ATOM | 2180 | CB | VAL | A | 818 | 41.586 | 23.815 | 39.576 | 1.00 | 28.11 | C |
| ATOM | 2181 | CG1 | VAL | A | 818 | 40.251 | 24.302 | 39.020 | 1.00 | 28.07 | C |
| ATOM | 2182 | CG2 | VAL | A | 818 | 42.476 | 25.021 | 39.925 | 1.00 | 26.93 | C |
| ATOM | 2183 | N | GLY | A | 819 | 41.018 | 20.737 | 39.877 | 1.00 | 28.19 | N |
| ATOM | 2184 | CA | GLY | A | 819 | 40.239 | 19.574 | 39.494 | 1.00 | 28.11 | C |
| ATOM | 2185 | C | GLY | A | 819 | 39.664 | 18.902 | 40.727 | 1.00 | 28.42 | C |
| ATOM | 2186 | O | GLY | A | 819 | 38.498 | 18.497 | 40.742 | 1.00 | 26.66 | O |
| ATOM | 2187 | N | PHE | A | 820 | 40.490 | 18.799 | 41.769 | 1.00 | 28.31 | N |
| ATOM | 2188 | CA | PHE | A | 820 | 40.075 | 18.188 | 43.028 | 1.00 | 28.49 | C |
| ATOM | 2189 | C | PHE | A | 820 | 38.898 | 18.947 | 43.615 | 1.00 | 28.60 | C |
| ATOM | 2190 | O | PHE | A | 820 | 37.899 | 18.349 | 44.019 | 1.00 | 28.01 | O |
| ATOM | 2191 | CB | PHE | A | 820 | 41.238 | 18.189 | 44.028 | 1.00 | 29.06 | C |
| ATOM | 2192 | CG | PHE | A | 820 | 40.879 | 17.643 | 45.386 | 1.00 | 29.18 | C |
| ATOM | 2193 | CD1 | PHE | A | 820 | 40.457 | 16.325 | 45.532 | 1.00 | 29.38 | C |
| ATOM | 2194 | CD2 | PHE | A | 820 | 40.982 | 18.442 | 46.521 | 1.00 | 29.72 | C |
| ATOM | 2195 | CE1 | PHE | A | 820 | 40.141 | 15.803 | 46.793 | 1.00 | 29.10 | C |
| ATOM | 2196 | CE2 | PHE | A | 820 | 40.671 | 17.932 | 47.788 | 1.00 | 30.75 | C |
| ATOM | 2197 | CZ | PHE | A | 820 | 40.248 | 16.605 | 47.918 | 1.00 | 29.62 | C |
| ATOM | 2198 | N | ILE | A | 821 | 39.011 | 20.273 | 43.652 | 1.00 | 29.21 | N |
| ATOM | 2199 | CA | ILE | A | 821 | 37.948 | 21.107 | 44.195 | 1.00 | 29.50 | C |
| ATOM | 2200 | C | ILE | A | 821 | 36.635 | 21.011 | 43.414 | 1.00 | 30.03 | C |
| ATOM | 2201 | O | ILE | A | 821 | 35.573 | 20.837 | 44.000 | 1.00 | 30.31 | O |
| ATOM | 2202 | CB | ILE | A | 821 | 38.384 | 22.592 | 44.256 | 1.00 | 29.95 | C |
| ATOM | 2203 | CG1 | ILE | A | 821 | 39.488 | 22.765 | 45.305 | 1.00 | 30.09 | C |
| ATOM | 2204 | CG2 | ILE | A | 821 | 37.190 | 23.478 | 44.612 | 1.00 | 29.13 | C |
| ATOM | 2205 | CD1 | ILE | A | 821 | 40.056 | 24.164 | 45.371 | 1.00 | 30.52 | C |
| ATOM | 2206 | N | ASP | A | 822 | 36.702 | 21.126 | 42.094 | 1.00 | 31.42 | N |
| ATOM | 2207 | CA | ASP | A | 822 | 35.487 | 21.057 | 41.282 | 1.00 | 32.40 | C |
| ATOM | 2208 | C | ASP | A | 822 | 34.789 | 19.713 | 41.406 | 1.00 | 32.69 | C |
| ATOM | 2209 | O | ASP | A | 822 | 33.620 | 19.624 | 41.782 | 1.00 | 33.09 | O |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | 130.132 | 90.00 | 90.00 | 120.00 | P 31 2 1 6 | |
|---|---|---|---|---|---|---|---|---|---|---|
| ATOM | 2210 | CB | ASP | A | 822 | 35.805 | 21.299 | 39.804 | 1.00 | 33.16 | C |
| ATOM | 2211 | CG | ASP | A | 822 | 36.085 | 22.753 | 39.497 | 1.00 | 33.88 | C |
| ATOM | 2212 | OD1 | ASP | A | 822 | 35.416 | 23.619 | 40.097 | 1.00 | 34.43 | O |
| ATOM | 2213 | OD2 | ASP | A | 822 | 36.958 | 23.026 | 38.647 | 1.00 | 35.03 | O |
| ATOM | 2214 | N | ALA | A | 823 | 35.538 | 18.666 | 41.099 | 1.00 | 32.10 | N |
| ATOM | 2215 | CA | ALA | A | 823 | 35.020 | 17.315 | 41.113 | 1.00 | 32.83 | C |
| ATOM | 2216 | C | ALA | A | 823 | 34.624 | 16.703 | 42.457 | 1.00 | 32.44 | C |
| ATOM | 2217 | O | ALA | A | 823 | 33.644 | 15.963 | 42.521 | 1.00 | 32.63 | O |
| ATOM | 2218 | CB | ALA | A | 823 | 36.008 | 16.422 | 40.413 | 1.00 | 32.28 | C |
| ATOM | 2219 | N | ILE | A | 824 | 35.351 | 17.020 | 43.527 | 1.00 | 32.23 | N |
| ATOM | 2220 | CA | ILE | A | 824 | 35.068 | 16.430 | 44.841 | 1.00 | 32.19 | C |
| ATOM | 2221 | C | ILE | A | 824 | 34.624 | 17.331 | 45.996 | 1.00 | 32.32 | C |
| ATOM | 2222 | O | ILE | A | 824 | 33.722 | 16.966 | 46.760 | 1.00 | 31.86 | O |
| ATOM | 2223 | CB | ILE | A | 824 | 36.305 | 15.630 | 45.352 | 1.00 | 32.99 | C |
| ATOM | 2224 | CG1 | ILE | A | 824 | 36.510 | 14.375 | 44.507 | 1.00 | 34.20 | C |
| ATOM | 2225 | CG2 | ILE | A | 824 | 36.114 | 15.224 | 46.819 | 1.00 | 33.64 | C |
| ATOM | 2226 | CD1 | ILE | A | 824 | 35.409 | 13.338 | 44.676 | 1.00 | 34.79 | C |
| ATOM | 2227 | N | CYS | A | 825 | 35.248 | 18.498 | 46.127 | 1.00 | 31.92 | N |
| ATOM | 2228 | CA | CYS | A | 825 | 34.973 | 19.397 | 47.248 | 1.00 | 31.49 | C |
| ATOM | 2229 | C | CYS | A | 825 | 33.821 | 20.403 | 47.228 | 1.00 | 32.05 | C |
| ATOM | 2230 | O | CYS | A | 825 | 33.062 | 20.493 | 48.196 | 1.00 | 31.20 | O |
| ATOM | 2231 | CB | CYS | A | 825 | 36.263 | 20.148 | 47.585 | 1.00 | 31.20 | C |
| ATOM | 2232 | SG | CYS | A | 825 | 37.694 | 19.058 | 47.751 | 1.00 | 30.53 | S |
| ATOM | 2233 | N | LEU | A | 826 | 33.700 | 21.179 | 46.157 | 1.00 | 32.58 | N |
| ATOM | 2234 | CA | LEU | A | 826 | 32.656 | 22.198 | 46.103 | 1.00 | 33.94 | C |
| ATOM | 2235 | C | LEU | A | 826 | 31.258 | 21.751 | 46.534 | 1.00 | 34.41 | C |
| ATOM | 2236 | O | LEU | A | 826 | 30.671 | 22.337 | 47.447 | 1.00 | 34.06 | O |
| ATOM | 2237 | CB | LEU | A | 826 | 32.612 | 22.826 | 44.708 | 1.00 | 34.32 | C |
| ATOM | 2238 | CG | LEU | A | 826 | 33.841 | 23.707 | 44.432 | 1.00 | 35.28 | C |
| ATOM | 2239 | CD1 | LEU | A | 826 | 33.755 | 24.311 | 43.032 | 1.00 | 34.77 | C |
| ATOM | 2240 | CD2 | LEU | A | 826 | 33.920 | 24.816 | 45.488 | 1.00 | 35.22 | C |
| ATOM | 2241 | N | GLN | A | 827 | 30.726 | 20.715 | 45.897 | 1.00 | 34.80 | N |
| ATOM | 2242 | CA | GLN | A | 827 | 29.393 | 20.241 | 46.247 | 1.00 | 35.63 | C |
| ATOM | 2243 | C | GLN | A | 827 | 29.253 | 19.800 | 47.702 | 1.00 | 34.41 | C |
| ATOM | 2244 | O | GLN | A | 827 | 28.238 | 20.079 | 48.343 | 1.00 | 34.18 | O |
| ATOM | 2245 | CB | GLN | A | 827 | 28.978 | 19.094 | 45.328 | 1.00 | 37.53 | C |
| ATOM | 2246 | CG | GLN | A | 827 | 28.538 | 19.540 | 43.949 | 1.00 | 41.26 | C |
| ATOM | 2247 | CD | GLN | A | 827 | 27.842 | 18.433 | 43.193 | 1.00 | 43.28 | C |
| ATOM | 2248 | OE1 | GLN | A | 827 | 28.469 | 17.449 | 42.795 | 1.00 | 45.48 | O |
| ATOM | 2249 | NE2 | GLN | A | 827 | 26.531 | 18.575 | 43.007 | 1.00 | 44.13 | N |
| ATOM | 2250 | N | LEU | A | 828 | 30.267 | 19.116 | 48.223 | 1.00 | 32.81 | N |
| ATOM | 2251 | CA | LEU | A | 828 | 30.221 | 18.644 | 49.603 | 1.00 | 31.56 | C |
| ATOM | 2252 | C | LEU | A | 828 | 30.097 | 19.785 | 50.604 | 1.00 | 30.95 | C |
| ATOM | 2253 | O | LEU | A | 828 | 29.214 | 19.769 | 51.462 | 1.00 | 30.78 | O |
| ATOM | 2254 | CB | LEU | A | 828 | 31.463 | 17.807 | 49.929 | 1.00 | 30.85 | C |
| ATOM | 2255 | CG | LEU | A | 828 | 31.561 | 17.294 | 51.372 | 1.00 | 31.10 | C |
| ATOM | 2256 | CD1 | LEU | A | 828 | 30.290 | 16.548 | 51.761 | 1.00 | 28.71 | C |
| ATOM | 2257 | CD2 | LEU | A | 828 | 32.780 | 16.393 | 51.502 | 1.00 | 29.84 | C |
| ATOM | 2258 | N | TYR | A | 829 | 30.976 | 20.780 | 50.502 | 1.00 | 30.25 | N |
| ATOM | 2259 | CA | TYR | A | 829 | 30.915 | 21.903 | 51.428 | 1.00 | 29.63 | C |
| ATOM | 2260 | C | TYR | A | 829 | 29.656 | 22.746 | 51.229 | 1.00 | 31.03 | C |
| ATOM | 2261 | O | TYR | A | 829 | 29.161 | 23.365 | 52.173 | 1.00 | 30.36 | O |
| ATOM | 2262 | CB | TYR | A | 829 | 32.184 | 22.750 | 51.313 | 1.00 | 27.51 | C |
| ATOM | 2263 | CG | TYR | A | 829 | 33.395 | 22.000 | 51.817 | 1.00 | 25.67 | C |
| ATOM | 2264 | CD1 | TYR | A | 829 | 34.406 | 21.599 | 50.949 | 1.00 | 25.70 | C |
| ATOM | 2265 | CD2 | TYR | A | 829 | 33.500 | 21.638 | 53.162 | 1.00 | 25.11 | C |
| ATOM | 2266 | CE1 | TYR | A | 829 | 35.497 | 20.847 | 51.410 | 1.00 | 25.99 | C |
| ATOM | 2267 | CE2 | TYR | A | 829 | 34.586 | 20.887 | 53.630 | 1.00 | 24.96 | C |
| ATOM | 2268 | CZ | TYR | A | 829 | 35.575 | 20.499 | 52.751 | 1.00 | 24.77 | C |
| ATOM | 2269 | OH | TYR | A | 829 | 36.652 | 19.779 | 53.211 | 1.00 | 26.34 | O |
| ATOM | 2270 | N | GLU | A | 830 | 29.135 | 22.764 | 50.005 | 1.00 | 33.02 | N |
| ATOM | 2271 | CA | GLU | A | 830 | 27.908 | 23.501 | 49.739 | 1.00 | 35.24 | C |
| ATOM | 2272 | C | GLU | A | 830 | 26.801 | 22.760 | 50.473 | 1.00 | 35.34 | C |
| ATOM | 2273 | O | GLU | A | 830 | 26.015 | 23.358 | 51.202 | 1.00 | 35.24 | O |
| ATOM | 2274 | CB | GLU | A | 830 | 27.603 | 23.544 | 48.238 | 1.00 | 36.80 | C |
| ATOM | 2275 | CG | GLU | A | 830 | 28.574 | 24.397 | 47.437 | 1.00 | 40.01 | C |
| ATOM | 2276 | CD | GLU | A | 830 | 28.138 | 24.594 | 45.997 | 1.00 | 42.51 | C |
| ATOM | 2277 | OE1 | GLU | A | 830 | 28.949 | 25.113 | 45.200 | 1.00 | 44.05 | O |
| ATOM | 2278 | OE2 | GLU | A | 830 | 26.986 | 24.237 | 45.660 | 1.00 | 44.51 | O |
| ATOM | 2279 | N | ALA | A | 831 | 26.763 | 21.445 | 50.291 | 1.00 | 36.58 | N |
| ATOM | 2280 | CA | ALA | A | 831 | 25.757 | 20.612 | 50.944 | 1.00 | 37.09 | C |
| ATOM | 2281 | C | ALA | A | 831 | 25.815 | 20.773 | 52.463 | 1.00 | 37.54 | C |
| ATOM | 2282 | O | ALA | A | 831 | 24.784 | 20.939 | 53.121 | 1.00 | 38.03 | O |
| ATOM | 2283 | CB | ALA | A | 831 | 25.967 | 19.152 | 50.563 | 1.00 | 36.98 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | 130.132 | 90.00 | 90.00 | 120.00 | P 31 2 1 6 | |
|---|---|---|---|---|---|---|---|---|---|---|
| ATOM | 2284 | N | LEU | A | 832 | 27.024 | 20.728 | 53.015 | 1.00 | 37.39 | N |
| ATOM | 2285 | CA | LEU | A | 832 | 27.213 | 20.866 | 54.454 | 1.00 | 37.92 | C |
| ATOM | 2286 | C | LEU | A | 832 | 26.704 | 22.209 | 54.973 | 1.00 | 38.41 | C |
| ATOM | 2287 | O | LEU | A | 832 | 26.106 | 22.285 | 56.048 | 1.00 | 37.66 | O |
| ATOM | 2288 | CB | LEU | A | 832 | 28.695 | 20.718 | 54.798 | 1.00 | 37.33 | C |
| ATOM | 2289 | CG | LEU | A | 832 | 29.120 | 20.913 | 56.256 | 1.00 | 37.07 | C |
| ATOM | 2290 | CD1 | LEU | A | 832 | 28.400 | 19.920 | 57.163 | 1.00 | 36.76 | C |
| ATOM | 2291 | CD2 | LEU | A | 832 | 30.629 | 20.727 | 56.354 | 1.00 | 36.13 | C |
| ATOM | 2292 | N | THR | A | 833 | 26.952 | 23.267 | 54.210 | 1.00 | 39.40 | N |
| ATOM | 2293 | CA | THR | A | 833 | 26.521 | 24.604 | 54.600 | 1.00 | 40.43 | C |
| ATOM | 2294 | C | THR | A | 833 | 24.999 | 24.687 | 54.715 | 1.00 | 41.58 | C |
| ATOM | 2295 | O | THR | A | 833 | 24.475 | 25.383 | 55.585 | 1.00 | 41.44 | O |
| ATOM | 2296 | CB | THR | A | 833 | 27.016 | 25.655 | 53.591 | 1.00 | 40.43 | C |
| ATOM | 2297 | OG1 | THR | A | 833 | 28.445 | 25.594 | 53.508 | 1.00 | 40.08 | O |
| ATOM | 2298 | CG2 | THR | A | 833 | 26.605 | 27.054 | 54.029 | 1.00 | 40.30 | C |
| ATOM | 2299 | N | HIS | A | 834 | 24.294 | 23.977 | 53.839 | 1.00 | 42.83 | N |
| ATOM | 2300 | CA | HIS | A | 834 | 22.836 | 23.971 | 53.871 | 1.00 | 44.18 | C |
| ATOM | 2301 | C | HIS | A | 834 | 22.361 | 23.317 | 55.164 | 1.00 | 44.18 | C |
| ATOM | 2302 | O | HIS | A | 834 | 21.443 | 23.810 | 55.816 | 1.00 | 44.11 | O |
| ATOM | 2303 | CB | HIS | A | 834 | 22.272 | 23.210 | 52.667 | 1.00 | 45.90 | C |
| ATOM | 2304 | CG | HIS | A | 834 | 22.606 | 23.835 | 51.348 | 1.00 | 47.87 | C |
| ATOM | 2305 | ND1 | HIS | A | 834 | 22.382 | 25.169 | 51.078 | 1.00 | 48.91 | N |
| ATOM | 2306 | CD2 | HIS | A | 834 | 23.132 | 23.306 | 50.217 | 1.00 | 49.09 | C |
| ATOM | 2307 | CE1 | HIS | A | 834 | 22.756 | 25.434 | 49.839 | 1.00 | 49.44 | C |
| ATOM | 2308 | NE2 | HIS | A | 834 | 23.215 | 24.322 | 49.294 | 1.00 | 49.70 | N |
| ATOM | 2309 | N | VAL | A | 835 | 22.995 | 22.208 | 55.534 | 1.00 | 44.13 | N |
| ATOM | 2310 | CA | VAL | A | 835 | 22.634 | 21.509 | 56.761 | 1.00 | 44.29 | C |
| ATOM | 2311 | C | VAL | A | 835 | 22.879 | 22.428 | 57.953 | 1.00 | 44.77 | C |
| ATOM | 2312 | O | VAL | A | 835 | 22.083 | 22.469 | 58.891 | 1.00 | 44.61 | O |
| ATOM | 2313 | CB | VAL | A | 835 | 23.459 | 20.212 | 56.941 | 1.00 | 43.91 | C |
| ATOM | 2314 | CG1 | VAL | A | 835 | 23.153 | 19.586 | 58.287 | 1.00 | 43.92 | C |
| ATOM | 2315 | CG2 | VAL | A | 835 | 23.130 | 19.227 | 55.832 | 1.00 | 43.83 | C |
| ATOM | 2316 | N | SER | A | 836 | 23.986 | 23.164 | 57.909 | 1.00 | 45.46 | N |
| ATOM | 2317 | CA | SER | A | 836 | 24.328 | 24.091 | 58.979 | 1.00 | 45.41 | C |
| ATOM | 2318 | C | SER | A | 836 | 24.998 | 25.344 | 58.426 | 1.00 | 45.70 | C |
| ATOM | 2319 | O | SER | A | 836 | 26.135 | 25.301 | 57.949 | 1.00 | 45.42 | O |
| ATOM | 2320 | CB | SER | A | 836 | 25.254 | 23.426 | 59.992 | 1.00 | 45.69 | C |
| ATOM | 2321 | OG | SER | A | 836 | 25.536 | 24.312 | 61.061 | 1.00 | 46.80 | O |
| ATOM | 2322 | N | GLU | A | 837 | 24.278 | 26.459 | 58.501 | 1.00 | 45.48 | N |
| ATOM | 2323 | CA | GLU | A | 837 | 24.761 | 27.745 | 58.012 | 1.00 | 45.20 | C |
| ATOM | 2324 | C | GLU | A | 837 | 26.150 | 28.072 | 58.544 | 1.00 | 43.35 | C |
| ATOM | 2325 | O | GLU | A | 837 | 26.976 | 28.643 | 57.840 | 1.00 | 43.07 | O |
| ATOM | 2326 | CB | GLU | A | 837 | 23.805 | 28.863 | 58.445 | 1.00 | 47.25 | C |
| ATOM | 2327 | CG | GLU | A | 837 | 22.344 | 28.658 | 58.069 | 1.00 | 50.33 | C |
| ATOM | 2328 | CD | GLU | A | 837 | 22.094 | 28.781 | 56.579 | 1.00 | 51.93 | C |
| ATOM | 2329 | OE1 | GLU | A | 837 | 22.450 | 27.842 | 55.830 | 1.00 | 52.30 | O |
| ATOM | 2330 | OE2 | GLU | A | 837 | 21.546 | 29.826 | 56.159 | 1.00 | 52.90 | O |
| ATOM | 2331 | N | ASP | A | 838 | 26.394 | 27.697 | 59.792 | 1.00 | 42.24 | N |
| ATOM | 2332 | CA | ASP | A | 838 | 27.655 | 27.979 | 60.462 | 1.00 | 41.10 | C |
| ATOM | 2333 | C | ASP | A | 838 | 28.909 | 27.278 | 59.930 | 1.00 | 39.59 | C |
| ATOM | 2334 | O | ASP | A | 838 | 30.019 | 27.568 | 60.380 | 1.00 | 39.40 | O |
| ATOM | 2335 | CB | ASP | A | 838 | 27.488 | 27.714 | 61.959 | 1.00 | 42.20 | C |
| ATOM | 2336 | CG | ASP | A | 838 | 26.456 | 28.636 | 62.599 | 1.00 | 43.60 | C |
| ATOM | 2337 | OD1 | ASP | A | 838 | 26.705 | 29.861 | 62.660 | 1.00 | 43.79 | O |
| ATOM | 2338 | OD2 | ASP | A | 838 | 25.394 | 28.139 | 63.035 | 1.00 | 43.97 | O |
| ATOM | 2339 | N | CYS | A | 839 | 28.740 | 26.366 | 58.978 | 1.00 | 37.72 | N |
| ATOM | 2340 | CA | CYS | A | 839 | 29.877 | 25.665 | 58.385 | 1.00 | 35.85 | C |
| ATOM | 2341 | C | CYS | A | 839 | 30.321 | 26.349 | 57.099 | 1.00 | 35.52 | C |
| ATOM | 2342 | O | CYS | A | 839 | 31.191 | 25.852 | 56.382 | 1.00 | 34.97 | O |
| ATOM | 2343 | CB | CYS | A | 839 | 29.519 | 24.209 | 58.094 | 1.00 | 35.29 | C |
| ATOM | 2344 | SG | CYS | A | 839 | 29.469 | 23.164 | 59.566 | 1.00 | 32.68 | S |
| ATOM | 2345 | N | PHE | A | 840 | 29.727 | 27.506 | 56.826 | 1.00 | 35.34 | N |
| ATOM | 2346 | CA | PHE | A | 840 | 30.033 | 28.284 | 55.631 | 1.00 | 34.86 | C |
| ATOM | 2347 | C | PHE | A | 840 | 31.526 | 28.541 | 55.402 | 1.00 | 33.81 | C |
| ATOM | 2348 | O | PHE | A | 840 | 32.014 | 28.410 | 54.280 | 1.00 | 34.50 | O |
| ATOM | 2349 | CB | PHE | A | 840 | 29.292 | 29.626 | 55.681 | 1.00 | 36.35 | C |
| ATOM | 2350 | CG | PHE | A | 840 | 29.591 | 30.530 | 54.518 | 1.00 | 37.35 | C |
| ATOM | 2351 | CD1 | PHE | A | 840 | 29.199 | 30.180 | 53.230 | 1.00 | 37.68 | C |
| ATOM | 2352 | CD2 | PHE | A | 840 | 30.276 | 31.727 | 54.710 | 1.00 | 38.31 | C |
| ATOM | 2353 | CE1 | PHE | A | 840 | 29.484 | 31.011 | 52.140 | 1.00 | 38.62 | C |
| ATOM | 2354 | CE2 | PHE | A | 840 | 30.568 | 32.566 | 53.628 | 1.00 | 38.81 | C |
| ATOM | 2355 | CZ | PHE | A | 840 | 30.170 | 32.205 | 52.340 | 1.00 | 38.43 | C |
| ATOM | 2356 | N | PRO | A | 841 | 32.268 | 28.922 | 56.457 | 1.00 | 32.73 | N |
| ATOM | 2357 | CA | PRO | A | 841 | 33.698 | 29.181 | 56.262 | 1.00 | 32.14 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | 130.132 | 90.00 | 90.00 | 120.00 | P 31 2 1 6 | |
|---|---|---|---|---|---|---|---|---|---|---|
| ATOM | 2358 | C | PRO | A | 841 | 34.476 | 28.072 | 55.562 | 1.00 | 31.60 | C |
| ATOM | 2359 | O | PRO | A | 841 | 35.456 | 28.349 | 54.867 | 1.00 | 31.70 | O |
| ATOM | 2360 | CB | PRO | A | 841 | 34.210 | 29.491 | 57.677 | 1.00 | 32.17 | C |
| ATOM | 2361 | CG | PRO | A | 841 | 33.108 | 29.027 | 58.597 | 1.00 | 33.53 | C |
| ATOM | 2362 | CD | PRO | A | 841 | 31.853 | 29.270 | 57.824 | 1.00 | 33.24 | C |
| ATOM | 2363 | N | LEU | A | 842 | 34.048 | 26.822 | 55.731 | 1.00 | 30.04 | N |
| ATOM | 2364 | CA | LEU | A | 842 | 34.722 | 25.718 | 55.059 | 1.00 | 28.62 | C |
| ATOM | 2365 | C | LEU | A | 842 | 34.519 | 25.912 | 53.559 | 1.00 | 28.71 | C |
| ATOM | 2366 | O | LEU | A | 842 | 35.456 | 25.805 | 52.771 | 1.00 | 28.43 | O |
| ATOM | 2367 | CB | LEU | A | 842 | 34.136 | 24.371 | 55.504 | 1.00 | 27.39 | C |
| ATOM | 2368 | CG | LEU | A | 842 | 34.498 | 23.915 | 56.924 | 1.00 | 27.17 | C |
| ATOM | 2369 | CD1 | LEU | A | 842 | 33.683 | 22.676 | 57.309 | 1.00 | 26.91 | C |
| ATOM | 2370 | CD2 | LEU | A | 842 | 35.985 | 23.618 | 56.996 | 1.00 | 26.62 | C |
| ATOM | 2371 | N | LEU | A | 843 | 33.281 | 26.210 | 53.176 | 1.00 | 29.02 | N |
| ATOM | 2372 | CA | LEU | A | 843 | 32.936 | 26.433 | 51.778 | 1.00 | 28.68 | C |
| ATOM | 2373 | C | LEU | A | 843 | 33.623 | 27.688 | 51.250 | 1.00 | 28.97 | C |
| ATOM | 2374 | O | LEU | A | 843 | 34.201 | 27.682 | 50.170 | 1.00 | 29.07 | O |
| ATOM | 2375 | CB | LEU | A | 843 | 31.422 | 26.579 | 51.637 | 1.00 | 28.84 | C |
| ATOM | 2376 | CG | LEU | A | 843 | 30.910 | 27.102 | 50.295 | 1.00 | 28.49 | C |
| ATOM | 2377 | CD1 | LEU | A | 843 | 31.326 | 26.158 | 49.181 | 1.00 | 29.41 | C |
| ATOM | 2378 | CD2 | LEU | A | 843 | 29.389 | 27.236 | 50.356 | 1.00 | 29.84 | C |
| ATOM | 2379 | N | ASP | A | 844 | 33.556 | 28.767 | 52.021 | 1.00 | 30.01 | N |
| ATOM | 2380 | CA | ASP | A | 844 | 34.191 | 30.020 | 51.618 | 1.00 | 30.34 | C |
| ATOM | 2381 | C | ASP | A | 844 | 35.678 | 29.760 | 51.370 | 1.00 | 29.94 | C |
| ATOM | 2382 | O | ASP | A | 844 | 36.226 | 30.115 | 50.324 | 1.00 | 29.66 | O |
| ATOM | 2383 | CB | ASP | A | 844 | 34.038 | 31.064 | 52.722 | 1.00 | 31.63 | C |
| ATOM | 2384 | CG | ASP | A | 844 | 34.342 | 32.468 | 52.242 | 1.00 | 32.55 | C |
| ATOM | 2385 | OD1 | ASP | A | 844 | 34.808 | 33.282 | 53.060 | 1.00 | 34.10 | O |
| ATOM | 2386 | OD2 | ASP | A | 844 | 34.103 | 32.759 | 51.051 | 1.00 | 34.53 | O |
| ATOM | 2387 | N | GLY | A | 845 | 36.322 | 29.121 | 52.340 | 1.00 | 29.14 | N |
| ATOM | 2388 | CA | GLY | A | 845 | 37.734 | 28.830 | 52.211 | 1.00 | 28.15 | C |
| ATOM | 2389 | C | GLY | A | 845 | 38.049 | 28.013 | 50.978 | 1.00 | 28.60 | C |
| ATOM | 2390 | O | GLY | A | 845 | 39.054 | 28.252 | 50.310 | 1.00 | 28.66 | O |
| ATOM | 2391 | N | CYS | A | 846 | 37.191 | 27.045 | 50.671 | 1.00 | 29.05 | N |
| ATOM | 2392 | CA | CYS | A | 846 | 37.399 | 26.180 | 49.517 | 1.00 | 29.85 | C |
| ATOM | 2393 | C | CYS | A | 846 | 37.319 | 26.979 | 48.225 | 1.00 | 30.11 | C |
| ATOM | 2394 | O | CYS | A | 846 | 38.080 | 26.747 | 47.286 | 1.00 | 29.65 | O |
| ATOM | 2395 | CB | CYS | A | 846 | 36.349 | 25.068 | 49.501 | 1.00 | 29.98 | C |
| ATOM | 2396 | SG | CYS | A | 846 | 36.585 | 23.867 | 48.186 | 1.00 | 30.84 | S |
| ATOM | 2397 | N | ARG | A | 847 | 36.379 | 27.913 | 48.184 | 1.00 | 30.81 | N |
| ATOM | 2398 | CA | ARG | A | 847 | 36.193 | 28.760 | 47.012 | 1.00 | 32.54 | C |
| ATOM | 2399 | C | ARG | A | 847 | 37.374 | 29.701 | 46.814 | 1.00 | 31.90 | C |
| ATOM | 2400 | O | ARG | A | 847 | 37.880 | 29.843 | 45.706 | 1.00 | 33.42 | O |
| ATOM | 2401 | CB | ARG | A | 847 | 34.912 | 29.569 | 47.157 | 1.00 | 32.77 | C |
| ATOM | 2402 | CG | ARG | A | 847 | 33.653 | 28.752 | 46.957 | 1.00 | 34.36 | C |
| ATOM | 2403 | CD | ARG | A | 847 | 32.442 | 29.582 | 47.332 | 1.00 | 35.13 | C |
| ATOM | 2404 | NE | ARG | A | 847 | 31.186 | 28.936 | 46.970 | 1.00 | 36.07 | N |
| ATOM | 2405 | CZ | ARG | A | 847 | 30.002 | 29.342 | 47.412 | 1.00 | 36.29 | C |
| ATOM | 2406 | NH1 | ARG | A | 847 | 29.933 | 30.385 | 48.229 | 1.00 | 35.79 | N |
| ATOM | 2407 | NH2 | ARG | A | 847 | 28.893 | 28.719 | 47.032 | 1.00 | 35.82 | N |
| ATOM | 2408 | N | LYS | A | 848 | 37.812 | 30.344 | 47.888 | 1.00 | 32.70 | N |
| ATOM | 2409 | CA | LYS | A | 848 | 38.942 | 31.258 | 47.791 | 1.00 | 32.02 | C |
| ATOM | 2410 | C | LYS | A | 848 | 40.143 | 30.514 | 47.222 | 1.00 | 31.83 | C |
| ATOM | 2411 | O | LYS | A | 848 | 40.835 | 31.024 | 46.341 | 1.00 | 31.51 | O |
| ATOM | 2412 | CB | LYS | A | 848 | 39.266 | 31.849 | 49.164 | 1.00 | 33.25 | C |
| ATOM | 2413 | CG | LYS | A | 848 | 38.220 | 32.852 | 49.643 | 1.00 | 34.64 | C |
| ATOM | 2414 | CD | LYS | A | 848 | 38.535 | 33.386 | 51.026 | 1.00 | 36.03 | C |
| ATOM | 2415 | CE | LYS | A | 848 | 37.464 | 34.366 | 51.479 | 1.00 | 36.82 | C |
| ATOM | 2416 | NZ | LYS | A | 848 | 37.723 | 34.905 | 52.846 | 1.00 | 37.75 | N |
| ATOM | 2417 | N | ASN | A | 849 | 40.374 | 29.294 | 47.705 | 1.00 | 30.48 | N |
| ATOM | 2418 | CA | ASN | A | 849 | 41.489 | 28.501 | 47.206 | 1.00 | 29.64 | C |
| ATOM | 2419 | C | ASN | A | 849 | 41.335 | 28.116 | 45.732 | 1.00 | 28.95 | C |
| ATOM | 2420 | O | ASN | A | 849 | 42.325 | 28.051 | 45.000 | 1.00 | 27.78 | O |
| ATOM | 2421 | CB | ASN | A | 849 | 41.685 | 27.242 | 48.061 | 1.00 | 29.24 | C |
| ATOM | 2422 | CG | ASN | A | 849 | 42.384 | 27.540 | 49.385 | 1.00 | 29.87 | C |
| ATOM | 2423 | OD1 | ASN | A | 849 | 43.260 | 28.403 | 49.449 | 1.00 | 27.60 | O |
| ATOM | 2424 | ND2 | ASN | A | 849 | 42.012 | 26.814 | 50.438 | 1.00 | 28.16 | N |
| ATOM | 2425 | N | ARG | A | 850 | 40.110 | 27.854 | 45.284 | 1.00 | 29.49 | N |
| ATOM | 2426 | CA | ARG | A | 850 | 39.922 | 27.496 | 43.875 | 1.00 | 30.82 | C |
| ATOM | 2427 | C | ARG | A | 850 | 40.374 | 28.679 | 43.026 | 1.00 | 31.76 | C |
| ATOM | 2428 | O | ARG | A | 850 | 41.099 | 28.525 | 42.046 | 1.00 | 31.56 | O |
| ATOM | 2429 | CB | ARG | A | 850 | 38.455 | 27.190 | 43.552 | 1.00 | 31.11 | C |
| ATOM | 2430 | CG | ARG | A | 850 | 38.278 | 26.728 | 42.112 | 1.00 | 32.12 | C |
| ATOM | 2431 | CD | ARG | A | 850 | 36.822 | 26.576 | 41.689 | 1.00 | 33.80 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | 74.456 | 130.132 | 90.00 | 90.00 | 120.00 | P 31 2 1 6 | |
|---|---|---|---|---|---|---|---|---|---|
| ATOM | 2432 | NE | ARG | A | 850 | 36.725 | 25.949 | 40.372 | 1.00 | 33.21 | N |
| ATOM | 2433 | CZ | ARG | A | 850 | 37.117 | 26.510 | 39.229 | 1.00 | 33.14 | C |
| ATOM | 2434 | NH1 | ARG | A | 850 | 37.638 | 27.731 | 39.218 | 1.00 | 33.01 | N |
| ATOM | 2435 | NH2 | ARG | A | 850 | 36.992 | 25.844 | 38.090 | 1.00 | 32.02 | N |
| ATOM | 2436 | N | GLN | A | 851 | 39.929 | 29.862 | 43.429 | 1.00 | 34.17 | N |
| ATOM | 2437 | CA | GLN | A | 851 | 40.259 | 31.109 | 42.754 | 1.00 | 36.68 | C |
| ATOM | 2438 | C | GLN | A | 851 | 41.778 | 31.283 | 42.669 | 1.00 | 36.44 | C |
| ATOM | 2439 | O | GLN | A | 851 | 42.323 | 31.534 | 41.595 | 1.00 | 36.01 | O |
| ATOM | 2440 | CB | GLN | A | 851 | 39.609 | 32.260 | 43.527 | 1.00 | 38.87 | C |
| ATOM | 2441 | CG | GLN | A | 851 | 39.871 | 33.652 | 43.001 | 1.00 | 43.28 | C |
| ATOM | 2442 | CD | GLN | A | 851 | 39.024 | 34.687 | 43.723 | 1.00 | 46.06 | C |
| ATOM | 2443 | OE1 | GLN | A | 851 | 39.063 | 34.794 | 44.954 | 1.00 | 48.08 | O |
| ATOM | 2444 | NE2 | GLN | A | 851 | 38.245 | 35.449 | 42.961 | 1.00 | 47.71 | N |
| ATOM | 2445 | N | LYS | A | 852 | 42.459 | 31.123 | 43.802 | 1.00 | 36.45 | N |
| ATOM | 2446 | CA | LYS | A | 852 | 43.913 | 31.255 | 43.853 | 1.00 | 36.02 | C |
| ATOM | 2447 | C | LYS | A | 852 | 44.643 | 30.257 | 42.954 | 1.00 | 35.56 | C |
| ATOM | 2448 | O | LYS | A | 852 | 45.530 | 30.633 | 42.191 | 1.00 | 34.56 | O |
| ATOM | 2449 | CB | LYS | A | 852 | 44.407 | 31.088 | 45.293 | 1.00 | 37.15 | C |
| ATOM | 2450 | CG | LYS | A | 852 | 44.115 | 32.270 | 46.211 | 1.00 | 37.95 | C |
| ATOM | 2451 | CD | LYS | A | 852 | 44.966 | 33.474 | 45.836 | 1.00 | 39.41 | C |
| ATOM | 2452 | CE | LYS | A | 852 | 44.877 | 34.569 | 46.887 | 1.00 | 39.50 | C |
| ATOM | 2453 | NZ | LYS | A | 852 | 45.703 | 35.750 | 46.511 | 1.00 | 39.99 | N |
| ATOM | 2454 | N | TRP | A | 853 | 44.280 | 28.981 | 43.050 | 1.00 | 35.24 | N |
| ATOM | 2455 | CA | TRP | A | 853 | 44.927 | 27.954 | 42.239 | 1.00 | 34.88 | C |
| ATOM | 2456 | C | TRP | A | 853 | 44.650 | 28.134 | 40.746 | 1.00 | 36.31 | C |
| ATOM | 2457 | O | TRP | A | 853 | 45.529 | 27.908 | 39.911 | 1.00 | 35.72 | O |
| ATOM | 2458 | CB | TRP | A | 853 | 44.470 | 26.557 | 42.676 | 1.00 | 33.38 | C |
| ATOM | 2459 | CG | TRP | A | 853 | 45.115 | 26.052 | 43.947 | 1.00 | 31.36 | C |
| ATOM | 2460 | CD1 | TRP | A | 853 | 44.476 | 25.616 | 45.077 | 1.00 | 30.70 | C |
| ATOM | 2461 | CD2 | TRP | A | 853 | 46.518 | 25.890 | 44.196 | 1.00 | 30.28 | C |
| ATOM | 2462 | NE1 | TRP | A | 853 | 45.394 | 25.190 | 46.010 | 1.00 | 29.39 | N |
| ATOM | 2463 | CE2 | TRP | A | 853 | 46.653 | 25.347 | 45.497 | 1.00 | 30.18 | C |
| ATOM | 2464 | CE3 | TRP | A | 853 | 47.673 | 26.149 | 43.448 | 1.00 | 30.35 | C |
| ATOM | 2465 | CZ2 | TRP | A | 853 | 47.901 | 25.059 | 46.065 | 1.00 | 29.91 | C |
| ATOM | 2466 | CZ3 | TRP | A | 853 | 48.918 | 25.862 | 44.015 | 1.00 | 30.78 | C |
| ATOM | 2467 | CH2 | TRP | A | 853 | 49.017 | 25.323 | 45.313 | 1.00 | 30.50 | C |
| ATOM | 2468 | N | GLN | A | 854 | 43.425 | 28.534 | 40.416 | 1.00 | 37.83 | N |
| ATOM | 2469 | CA | GLN | A | 854 | 43.036 | 28.735 | 39.023 | 1.00 | 39.72 | C |
| ATOM | 2470 | C | GLN | A | 854 | 43.851 | 29.874 | 38.406 | 1.00 | 40.20 | C |
| ATOM | 2471 | O | GLN | A | 854 | 44.315 | 29.776 | 37.271 | 1.00 | 39.40 | O |
| ATOM | 2472 | CB | GLN | A | 854 | 41.536 | 29.038 | 38.943 | 1.00 | 41.25 | C |
| ATOM | 2473 | CG | GLN | A | 854 | 40.818 | 28.324 | 37.800 | 1.00 | 44.10 | C |
| ATOM | 2474 | CD | GLN | A | 854 | 40.919 | 29.068 | 36.490 | 1.00 | 45.46 | C |
| ATOM | 2475 | OE1 | GLN | A | 854 | 40.357 | 30.154 | 36.335 | 1.00 | 47.15 | O |
| ATOM | 2476 | NE2 | GLN | A | 854 | 41.639 | 28.491 | 35.538 | 1.00 | 46.05 | N |
| ATOM | 2477 | N | ALA | A | 855 | 44.026 | 30.950 | 39.166 | 1.00 | 41.09 | N |
| ATOM | 2478 | CA | ALA | A | 855 | 44.802 | 32.086 | 38.696 | 1.00 | 42.40 | C |
| ATOM | 2479 | C | ALA | A | 855 | 46.216 | 31.607 | 38.372 | 1.00 | 43.59 | C |
| ATOM | 2480 | O | ALA | A | 855 | 46.811 | 32.033 | 37.386 | 1.00 | 43.48 | O |
| ATOM | 2481 | CB | ALA | A | 855 | 44.841 | 33.169 | 39.762 | 1.00 | 42.50 | C |
| ATOM | 2482 | N | LEU | A | 856 | 46.749 | 30.714 | 39.202 | 1.00 | 44.56 | N |
| ATOM | 2483 | CA | LEU | A | 856 | 48.088 | 30.178 | 38.974 | 1.00 | 45.85 | C |
| ATOM | 2484 | C | LEU | A | 856 | 48.080 | 29.248 | 37.767 | 1.00 | 47.27 | C |
| ATOM | 2485 | O | LEU | A | 856 | 49.035 | 29.217 | 36.990 | 1.00 | 47.18 | O |
| ATOM | 2486 | CB | LEU | A | 856 | 48.579 | 29.406 | 40.201 | 1.00 | 45.30 | C |
| ATOM | 2487 | CG | LEU | A | 856 | 48.934 | 30.208 | 41.454 | 1.00 | 45.32 | C |
| ATOM | 2488 | CD1 | LEU | A | 856 | 49.354 | 29.251 | 42.559 | 1.00 | 45.02 | C |
| ATOM | 2489 | CD2 | LEU | A | 856 | 50.056 | 31.190 | 41.145 | 1.00 | 45.53 | C |
| ATOM | 2490 | N | ALA | A | 857 | 46.999 | 28.486 | 37.622 | 1.00 | 49.11 | N |
| ATOM | 2491 | CA | ALA | A | 857 | 46.854 | 27.552 | 36.513 | 1.00 | 51.82 | C |
| ATOM | 2492 | C | ALA | A | 857 | 46.979 | 28.287 | 35.180 | 1.00 | 53.77 | C |
| ATOM | 2493 | O | ALA | A | 857 | 47.632 | 27.808 | 34.253 | 1.00 | 53.77 | O |
| ATOM | 2494 | CB | ALA | A | 857 | 45.505 | 26.848 | 36.597 | 1.00 | 51.72 | C |
| ATOM | 2495 | N | GLU | A | 858 | 46.347 | 29.454 | 35.095 | 1.00 | 55.97 | N |
| ATOM | 2496 | CA | GLU | A | 858 | 46.393 | 30.264 | 33.882 | 1.00 | 58.82 | C |
| ATOM | 2497 | C | GLU | A | 858 | 47.754 | 30.949 | 33.811 | 1.00 | 60.62 | C |
| ATOM | 2498 | O | GLU | A | 858 | 48.073 | 31.623 | 32.831 | 1.00 | 60.99 | O |
| ATOM | 2499 | CB | GLU | A | 858 | 45.285 | 31.317 | 33.913 | 1.00 | 58.29 | C |
| ATOM | 2500 | CG | GLU | A | 858 | 43.945 | 30.772 | 34.377 | 1.00 | 58.53 | C |
| ATOM | 2501 | CD | GLU | A | 858 | 42.893 | 31.848 | 34.540 | 1.00 | 58.51 | C |
| ATOM | 2502 | OE1 | GLU | A | 858 | 43.238 | 32.960 | 34.998 | 1.00 | 58.59 | O |
| ATOM | 2503 | OE2 | GLU | A | 858 | 41.716 | 31.576 | 34.226 | 1.00 | 58.36 | O |
| ATOM | 2504 | N | GLN | A | 859 | 48.545 | 30.765 | 34.866 | 1.00 | 62.94 | N |
| ATOM | 2505 | CA | GLN | A | 859 | 49.881 | 31.342 | 34.974 | 1.00 | 65.25 | C |

TABLE 1-continued

Atomic Coordinates for Residues of a Phosphodiesterase Type V Crystal
(see http://www.rcsb.org/pdb/explore/explore.do?structureId=1RKP).
Table 1 discloses SEQ ID NOS: 9 and 10, respectively.

| CRYST1 | 74.456 | | | 74.456 | | 130.132 | 90.00 | 90.00 | 120.00 | P 31 2 1 6 | |
|---|---|---|---|---|---|---|---|---|---|---|---|
| ATOM | 2506 | C | GLN | A | 859 | 49.836 | 32.821 | 35.342 | 1.00 | 66.53 | C |
| ATOM | 2507 | O | GLN | A | 859 | 49.409 | 33.659 | 34.547 | 1.00 | 67.06 | O |
| ATOM | 2508 | CB | GLN | A | 859 | 50.649 | 31.146 | 33.665 | 1.00 | 65.62 | C |
| ATOM | 2509 | CG | GLN | A | 859 | 50.925 | 29.689 | 33.340 | 1.00 | 66.74 | C |
| ATOM | 2510 | CD | GLN | A | 859 | 51.310 | 29.478 | 31.890 | 1.00 | 67.56 | C |
| ATOM | 2511 | OE1 | GLN | A | 859 | 52.220 | 30.128 | 31.373 | 1.00 | 68.15 | O |
| ATOM | 2512 | NE2 | GLN | A | 859 | 50.616 | 28.560 | 31.224 | 1.00 | 67.40 | N |
| ATOM | 2513 | N | GLN | A | 860 | 50.278 | 33.127 | 36.560 | 1.00 | 67.86 | N |
| ATOM | 2514 | CA | GLN | A | 860 | 50.305 | 34.495 | 37.068 | 1.00 | 69.17 | C |
| ATOM | 2515 | C | GLN | A | 860 | 51.602 | 35.221 | 36.709 | 1.00 | 69.76 | C |
| ATOM | 2516 | O | GLN | A | 860 | 52.558 | 35.146 | 37.512 | 1.00 | 70.12 | O |
| ATOM | 2517 | CB | GLN | A | 860 | 50.121 | 34.497 | 38.589 | 1.00 | 69.65 | C |
| ATOM | 2518 | CG | GLN | A | 860 | 48.673 | 34.392 | 39.049 | 1.00 | 70.61 | C |
| ATOM | 2519 | CD | GLN | A | 860 | 48.545 | 34.436 | 40.561 | 1.00 | 70.97 | C |
| ATOM | 2520 | OE1 | GLN | A | 860 | 49.263 | 35.179 | 41.231 | 1.00 | 71.16 | O |
| ATOM | 2521 | NE2 | GLN | A | 860 | 47.620 | 33.649 | 41.103 | 1.00 | 71.34 | N |
| ATOM | 2522 | OXT | GLN | A | 860 | 51.653 | 35.845 | 35.626 | 1.00 | 70.21 | O |

Methods for predicting the effect on protein conformation of a change in protein sequence, are known in the art, and the skilled artisan can thus design a variant which functions as an antagonist according to known methods. One example of such a method is described by Dahiyat and Mayo in *Science* (1997) 278:82 87, which describes the design of proteins de novo. The method can be applied to a known protein to vary only a portion of the polypeptide sequence. Similarly, Blake (U.S. Pat. No. 5,565,325) teaches the use of known ligand structures to predict and synthesize variants with similar or modified function.

Other methods for preparing or identifying peptides that bind to a target are known in the art. Molecular imprinting, for instance, can be used for the de novo construction of macromolecular structures such as peptides that bind to a molecule. See, for example, Kenneth J. Shea, *Molecular Imprinting of Synthetic Network Polymers: The De Novo synthesis of Macromolecular Binding and Catalytic Sites*, TRIP Vol. 2, No. 5, May 1994; Mosbach, (1994) *Trends in Biochem. Sci.*, 19(9); and Wulff, G., in *Polymeric Reagents and Catalysts* (Ford, W. T., Ed.) ACS Symposium Series No. 308, pp 186-230, American Chemical Society (1986). One method for preparing mimics of a PDE5 inhibitor involves the steps of: (i) polymerization of functional monomers around a known substrate (the template) that exhibits a desired activity; (ii) removal of the template molecule; and then (iii) polymerization of a second class of monomers in, the void left by the template, to provide a new molecule which exhibits one or more desired properties which are similar to that of the template. Other binding molecules such as polysaccharides, nucleosides, drugs, nucleoproteins, lipoproteins, carbohydrates, glycoproteins, steroids, lipids, and other biologically active materials can also be prepared. This method is useful for designing various biological mimics that are more stable than their natural counterparts, because they are prepared by the free radical polymerization of functional monomers, resulting in a compound with a non-biodegradable backbone. Other methods for designing such molecules include, e.g., drug design based on structure activity relationships, which require the synthesis and evaluation of a number of compounds and molecular modeling.

The invention also provides in vivo and in vitro methods for identifying a compound that binds to a PDE5 protein. In one embodiment, the method comprises: (a) obtaining a tissue and/or cells that express the PDE5 protein; (b) contacting the tissue and/or cell with a ligand source for an effective period of time; (c) measuring a secondary messenger response, wherein the response is indicative of a ligand binding to PDE5 protein; (d) isolating the ligand from the ligand source; and (e) identifying the structure of the ligand that binds PDE5 protein, thereby identifying which compound would bind to PDE5 protein. As used herein, the term "ligand source" can be any compound library described herein, or a library of neurotransmitters that can be used to screen for compounds that would act as an agonist or antagonist of PDE5. Screening compound libraries listed herein [also see U.S. Patent Application Publication No. 2005/0009163, which is hereby incorporated by reference in its entirety], in combination with in vivo animal studies and functional and signaling assays can be used to identify PDE5 inhibitor compounds that can be used to treat subjects afflicted with abnormal Aβ deposits, such as AD.

A PDE5 inhibitor compound can be a compound that decreases the activity and/or expression of a PDE5 molecule in vivo and/or in vitro. PDE5 inhibitor compounds can be compounds that exert their effect on the activity of PDE5 via the expression, via post-translational modifications, or by other means. In one embodiment, a PDE5 inhibitor can decrease PDE5 protein or mRNA expression, or PDE5 activity by at least about 10%, at least about 20%, at least about 30%, at least about 40%, at least about 50%, at least about 60%, at least about 70%, at least about 75%, at least about 80%, at least about 85%, at least about 90%, at least about 95%, at least about 97%, at least about 99%, or 100%.

Test compounds or agents which bind to a PDE5 molecule, and/or have a stimulatory or inhibitory effect on the activity or the expression of a PDE5 molecule, can be identified by various assays. The assay can be a binding assay comprising direct or indirect measurement of the binding of a test compound or a known PDE5 ligand to the active site of a PDE5 protein. The assay can also be an activity assay comprising direct or indirect measurement of the activity of a PDE5 molecule. The assay can also be an expression assay comprising direct or indirect measurement of the expression of PDE5 mRNA or protein. The various screening assays can be combined with an in vivo assay comprising measuring the effect of the test compound on cognitive and synaptic function in an animal model for neurodegenerative disorders, such as AD. The activity of a PDE5 inhibitor can be measured in various ways, such as detecting an alteration in a downstream secondary messengers of the NO pathway [see FIG. 19]. The alteration can be in intracellular cyclic guanosine monophosphate (cGMP) concentration, in intracellular GTP concentration, in the intracellular protein kinase G (PKG) concentration, in the intracellular phosphorylation of CREB, or a combination thereof. For example, if an increase in cGMP levels is observed following administration of a PDE inhibitor and the inhibitor is detected or its metabolites in a dialysate, the test compound will be deemed active and thus a PDE5 inhibitor.

The diagnostic assay of the screening methods of the invention can also involve monitoring the expression of a PDE5 molecule. For example, inhibitors of the expression of a PDE5 molecule can be identified via contacting a PDE5-positive cell or tissue with a test compound and determining the expression of PDE5 protein or PDE5 mRNA in the cell. The protein or mRNA expression level of PDE5 in the presence of the test compound is compared to the protein or mRNA expression level of PDE5 in the absence of the test compound. The test compound can then be identified as an inhibitor of PDE5 expression based on this comparison. For example, when expression of PDE5 protein or mRNA is statistically or significantly less in the presence of the test compound than in its absence, the compound is identified as an inhibitor of the expression of PDE5 protein or mRNA. In other words, the test compound can also be said to be a PDE5 inhibitor compound (such as an antagonist). The expression level of PDE5 protein or mRNA in cells can be determined by methods described herein.

Determining the ability of a test compound to bind to a PDE5 molecule or a variant thereof, such as a PDE5 mutant described herein, can be accomplished using real-time Bimolecular Interaction Analysis (BIA) [McConnell, (1992); Sjolander, (1991)]. BIA is a technology for studying biospecific interactions in real time, without labeling any of the interactants (e.g., BIA-Core™). Changes in optical phenomenon surface plasmon resonance (SPR) can be used as an indication of real-time reactions between biological molecules.

Structure-Activity Relationship (SAR) of Known PDE5 Inhibitors

An analysis of the chemical structures of existing PDE5 inhibitors reveals that they can be divided into the following classes: 1) cGMP-based molecules, represented by sildenafil and vardenafil; 2) β-carbolines-derived molecules, represented by tadalafil; 3) pyrazolopyridine, phthalazine and quinoline derivatives; 4) isoquinazolinone and isoquinolinone derivatives.

As exemplified by sildenafil and vardenafil (Levitra, by Bayer), the cGMP-based PDE5 inhibitors are simple analogs of cGMP and differ only in the number and position of hetero-atoms such as nitrogen on the purine ring of cGMP (FIG. 43). These early PDE5 inhibitors show good potency but have poor selectivity over PDE1 and PDE6. For example, the $IC_{50}$ for PDE5 is 10 nM and 5 nM for sildenafil and vardenafil, respectively, but the PDE6/PDE5 selectivity ratios are only 12 for sildenafil and 3.5 for vardenafil [Boschelli et al., *J Med Chem,* 2001. 44(5): p. 822-33; Wang et al., Bioorg Med Chem Lett, 2000. 10(21): p. 2477-80]. Although sildenafil and vardenafil represent completely different classes of chemical structures based on the differences between their polycyclic cores, these two compounds share significant structural similarity, which explains the fact that both of them have poor selectivity. With the success of launching sildenafil and vardenafil, numerous efforts have been made to develop new PDE5 inhibitors based on pyrazolopryrimidinone core structure (for instance Udenafil by Dong-A Pharm). Unfortunately, most of the newly designed compounds inherited the poor selectivity over PDE6 from sildenafil even if they turned to be excellent PDE5 inhibitors. To improve the selectivity, several groups investigated modification on the phenyl ring of sildenafil. By changing the substitution pattern of the pyrazolo moiety of sildenafil combined with the transformation of phenyl to pyridine, selectivity was improved. This class of compounds also featured a nitrogen- or oxygen-containing substituent introduced on the nitrogen at the 6-position of the pyrazolopryrimidinone, which have high PDE5 potency and selectivity versus PDE6 up to 2482-fold [Barrios Sosa et al., *Bioorg Med Chem Lett,* 2004. 14(9): p. 2155-8] (see Pf-1 in FIG. 43, as well as, for example, WO 2002074774, WO 2002074312, EP 995750, WO 9849166, EP 995751, WO 9307149; EP 636626; U.S. Pat. No. 5,294,612, EP 1092718, WO 9924433; US 2003199693). It should be noted, however, that selectivity for remaining PDEs, as well as PK, BBB penetration, and toxicity profiles of this class of compounds are not known.

Molecules featuring β-carbolines constitute the basis for a 2nd class of PDE5 inhibitors. Ethyl beta-carboline-3-carboxylate (beta-CCE) was a weak, non-selective PDE5 inhibitor that led to the modestly selective hydantoin and, ultimately, to tadalafil (Cialis, by Lilly; FIG. 44). Tadalafil is a highly potent ($IC_{50}$=5 nM) and highly selective PDE5 inhibitor with selectivity of PDE5/PDE1-4 and PDE5/PDE6 over 1000, but poor selectivity for PDE11 (~5) that can alter spermatogenesis and fertilization potential [Graham et al., *Bioorg Med Chem Lett,* 2007. 17(21): p. 5886-93; Masliah, *Histol Histopathol,* 1995. 10(2): p. 509-19]. If for an AD drug, fertility dysfunction is unlikely to represent a major problem, another side effect of tadalafil, back pain, can be a bigger problem for chronic use in a senile population [Selkoe et al., Science, 2002. 298(5594): p. 789-91; Sant'Angelo et al., Neurochem Res, 2003. 28(7): p. 1009-15; Bliss et al., Nature, 1993. 361(6407): p. 31-9; Cullen et al., Neuroreport, 1997. 8(15): p. 3213-7] (incidentally, it is not clear whether this side effect is due to inhibition of PDE11 or other off target molecules). SAR studies have indicated that the NH group is essential. Alkylation of the nitrogen or replacement of nitrogen by sulfur abolishes activity is consistent with the role NH as an essential H-bond donor. SAR also indicated the hydrophobic aromatic ring (3,4-methylenedioxyphenyl) is necessary for high potency. PDE5 tolerates a wide range of substituents on the imide nitrogen of the hydantoin as well as the free piperazinedione nitrogen of tadalafil. At least one carbonyl group is important. Deletion of both markedly decreases potency, whereas removal of either one is only marginally deleterious [Wang et al., Bioorg Med Chem Lett, 2000. 10(21): p. 2477-80]. Nonetheless, because of the poor selectivity problems related to PDE11 (which was not overcome), back pain, and its inability to cross the BBB (clog P=1.43; the NH group, which is quite acidic, is essential to its activity, but can make the compounds polar and consequently difficult to penetrate the BBB), it is unlikely that this compound can serve as a base for developing an AD drug.

A series of pyrimidinylpyrroloquinolones was also recently developed by Johnson & Johnson (JJ), as potent and selective PDE5 inhibitors. During the synthesis of JJ1 (FIG. 44), pyrroloquinolone JJ2 was formed as a minor byproduct. The potency of JJ2 against PDE5 exceeded the β-carboline and JJ1, because the high NH acidity (pKa~9) increases its propensity for hydrogen-bond with PDE5 ([Freir et al., *J Neurophysiol*, 2001. 85(2): p. 708-13], WO 2001087882). Although JJ2 showed very good potency, superior selectivity and in vivo efficacy in a dog model for ED, poor solubility precluded further use of this compound. Similar to the SAR for tadalafil and analogs, a tolerance for a wide range of substituents on the pyrole nitrogen made it possible to develop desirable physical and chemical properties such as solubility and absorption while retaining potency and selectivity. As a consequence, JJ3 was developed and showed oral bioavailability of more than 30% in male rats, as well as good in vivo efficacy in a dog model of ED [Itoh et al., Eur J Pharmacol, 1999. 382(3): p. 167-75; Kim et al., J Neurosci, 2001. 21(4): p. 1327-33]. Additional features (full PDE selectivity profile, PK, BBB penetration) are not known.

In yet another series of structures, BMS1 was reported as a potent PDE5 inhibitor ($IC_{50}$=1 nM, FIG. 45). Using BMS1 as a template, Bristol-Myers Squibb (BMS) identified BMS2 (FIG. 3) as a PDE5 inhibitor with improved potency and selectivity compared to sildenafil ($IC_{50}$<0.8 nM) ((Stephan et al., *J Neurosci*, 2001. 21(15): p. 5703-14), WO 2000015222). The X-ray structure of BMS2 showed that the benzylic amine —NH— formed a hydrogen bond with the amide carbonyl. This observation, coupled with the structure of Eisai's potent PDE5 inhibitor E1 (FIG. 45, $IC_{50}$=0.56 nM), $EC_{50}$=13 nM) (Vitolo et al., Proc Natl Acad Sci USA, 2002. 99(20): p. 13217-21; WO 9807430), led the scientists at BMS to design compounds with constrained conformation and the pyrazolopyrido-pyridazine scaffold yielding the potent PDE5 inhibitor BMS3 ($IC_{50}$=0.3 nM, $EC_{50}$=13 nM, FIG. 45) with PDE1 and PDE6 isozyme selectivities superior to those of sildenafil. Of note, BMS3 had a desirable PK profile in two animal species with fewer PDE-related side effects such as visual disturbances (Walsh et al., *Nature*, 2002. 416(6880): p. 535-9). More recently, BMS and a Japanese company independently reported that a combination of the important features of BMS2 and E1 led to a quinoline series of derivatives illustrated by BMS4. BMS4 is the most potent and selective PDE5 inhibitor to date, 30-fold more potent than sildenafil and significantly more selective than sildenafil against other PDE isozymes ($IC_{50}$=0.05 nM, >7800 selective versus PDE1-6) (Selig et al., Learn Mem, 1996. 3(1): p. 42-8; WO 0112608, 2001). However, BMS4 lacks a complete PDE specificity profile, PK profile and in vivo efficacy against AD. In addition, the presence of benzylic alcohol causes concerns on off target side effects. Therefore, YF012403 has been developed as discussed herein.

Incorporation of an additional ring into cGMP-based PDE5 inhibitors generated a new class of structures. The fused 3-ring system, N-3 substituted imidazoquinazolinones, shows improved potency and selectivity compared to sildenafil (BMS5, $IC_{50}$=0.5 nM, PDE1-3/PDE5>10,000, PDE6/PDE5 60, FIG. 46). Incorporation of another nitrogen and a benzyl group into the middle ring forms another family of potent and selective PDE5 inhibitors represented by BMS6 ($IC_{50}$=0.31 nM, >10,000 fold selective vs. PDE1 and 160 fold vs. PDE6) (US 2002133008). Based on the reported in vitro properties, this scaffold may be of interest in terms of developing new PDE5 inhibitors because the value of PDE5/PDE6 reached 160, however, it needs to be pointed out that the compounds derived from this scaffold may also cause some off-target toxicity since the $IC_{50}$ of BMS6 for PDE6 is around 50 nM, indicating that these derivatives may still be good PDE6 inhibitors.

The naphthalene analog TS1 was discovered by a Japanese company as a potent and selective PDE5 inhibitor ($IC_{50}$=6.2 nM, PDE1-4/PDE5>16000; FIG. 46). Superimposition of TS1 with cGMP shows that the naphthalene ring in TS1 significantly overlaps the purine nucleus in cGMP and the pendant phenyl group at the 1-position of TS1 fills a space occupied by the cyclic phosphate group in cGMP. Based on this observation, a class of potent and selective PDE5 inhibitors was identified as illustrated by T1032 ($IC_{50}$<1.0 nM, PDE1/PDE5, 1300, PDE2/PDE5>10 000, PDE3/PDE5>10 000, PDE4/PDE5 4700, PDE6/PDE5 28; FIG. 46). T1032 displays the most potent relaxant effect on isolated rabbit corpus cavernosum ($EC_{50}$ 7.9 nM) (Prickaerts et al., Eur J Pharmacol, 2002, 436(1-2): p. 83-7; WO 9838168; JP 2000072675). Introduction of a nitrogen atom into the phenyl ring of T1032 led to yet another new structural class of potent and specific PDE5 inhibitors illustrated by T1056 (FIG. 46) with potent PDE5 inhibition ($IC_{50}$=0.23 nM) and excellent PDE5 selectivity against other PDEs1-4,6 (>100,000-fold selective versus PDE1-4, 240-fold selective vs. PDE6). This compound showed more potent relaxant effects on isolated rabbit corpus cavernosum ($EC_{50}$=5.0 nM) than sildenafil ($EC_{50}$=8.7 nM) [Ukita et al., Bioorg Med Chem Lett, 2003. 13(14): p. 2341-5.]. However, since T1056 has an $IC_{50}$ of 56 nM against PDE6, it raises the same concern as BMS6.

Currently used AD therapies (acetylcholinesterase inhibitors or NMDA antagonists) have limited efficacy. Major efforts are underway to inhibit tangle formation, to combat inflammation and oxidative damage, and to decrease Aβ load in the brain either by the use of agents that inhibit β and γ secretases or increase secretase, by the use of drugs that inhibit Aβ oligomerization [Nakagami et al, Br J Pharmacol, 2002. 137(5): p. 676-82; Walsh et al., J Neurosci, 2005. 25(10): p. 2455-62], or by the use of treatments such as immunization with Aβ that appear to augment the removal of A from the brain [Schenk et al., Nature, 1999. 400(6740): p. 173-7]. However, the role of APP, Aβ 40, and the secretases in normal physiological function [Wu et al., Eur J Pharmacol, 1995. 284(3): p. R1-3; Kowalska et al., Biochem Biophys Res Commun, 1994. 205(3): p. 1829-35; Mattson et al., J Neurochem, 1999. 73(2): p. 532-7] can present a problem in providing effective and safe approaches to AD therapy.

Exemplary PDE5 Inhibitor Compounds Optimized for CNS Disorders

The invention provides for compounds that bind to PDE5. These compounds can be identified by the screening methods and assays described herein, and inhibit the activity or expression of PDE5 proteins. In one embodiment, the invention encompasses compounds of the following formulae:

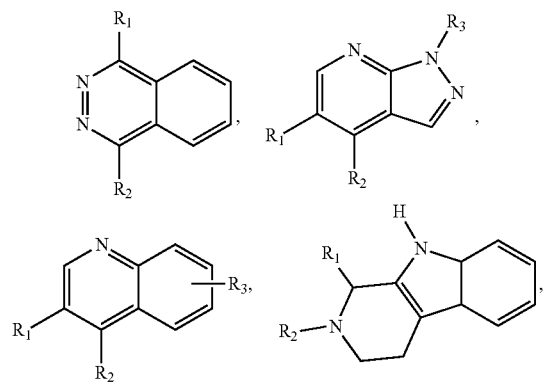

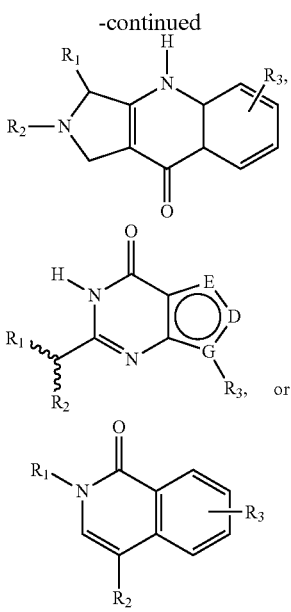

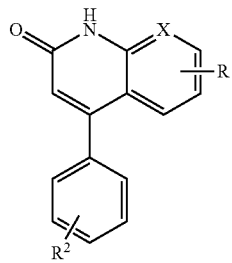

wherein $R^1$, $R^2$, and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In one embodiment, the invention encompasses compounds of Formula Ia:

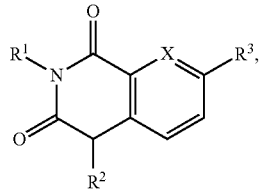

Formula Ia, wherein:
X is CR or N;
each R is independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen, at the 2, 3, or 4 position on the ring, relative to X; and
$R^2$ is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen, at the 2, 3, 4, 5, or 6 position on the ring.

In one embodiment, R is —H.

In another embodiment, R is —O—$C_1$-$C_6$ alkyl, such as —$OCH_3$.

In yet another embodiment, R is —$C_1$-$C_6$ alkyl-$C_6$-$C_{10}$ aryl, such as benzyl.

In one embodiment, the R of X and the R on the ring are different.

In another embodiment, $R^2$ is —H.

In one embodiment, the invention encompasses compounds of Formula Ib:

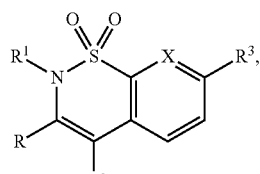

wherein:
X is CR or N;
R is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen;
$R^1$ is —H, —$C_1$-$C_6$ alkyl, —$C_1$-$C_6$ alkyl-$C_6$-$C_{10}$ aryl, or —$C_6$-$C_{10}$ aryl; and
$R^2$ and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In an embodiment, R is —H.

In one embodiment, the invention encompasses compounds of Formula Ic:

Formula Ic

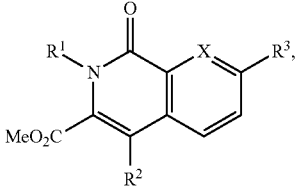

wherein:
X is CR, or N;
R is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen;
$R^1$ is —H, —$C_1$-$C_6$ alkyl, —$C_1$-$C_6$ alkyl-$C_6$-$C_{10}$ aryl, or —$C_6$-$C_{10}$ aryl; and
$R^2$ and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In an embodiment, R is —H.

In one embodiment, the invention encompasses compounds of Formula Id:

Formula Id wherein:
X is CR, or N;
R is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen;
$R^1$ is —H, —$C_1$-$C_6$ alkyl, —$C_1$-$C_6$ alkyl-$C_6$-$C_{10}$ aryl, or —$C_6$-$C_{10}$ aryl; and $R^2$ and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In an embodiment, R is —H.

In one embodiment, the invention encompasses compounds of Formula Ie:

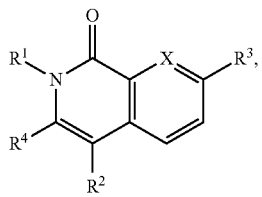

Formula Ie wherein:
- X is CR, or N;
- R is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen;
- $R^1$ is —H, —$C_1$-$C_6$ alkyl, —$C_1$-$C_6$ alkyl-$C_6$-$C_{10}$ aryl, or —$C_6$-$C_{10}$ aryl;
- $R^2$ and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen; and
- $R^4$ is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, halogen, or —$CO_2$—$C_1$-$C_6$ alkyl.

In one embodiment, R is —H.

In another embodiment, $R^2$ is —OH.

In a further embodiment, $R^2$ is a halogen, such as —Cl.

In an embodiment, $R^3$ is —H.

In another embodiment, $R^4$ is —$CO_2$—$C_1$-$C_6$ alkyl, such as —$CO_2$Me.

In yet another embodiment, $R^4$ is —H.

In one embodiment, the invention encompasses compounds of Formula IIa:

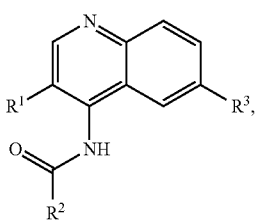

Formula IIa wherein:
- $R^1$, $R^2$, and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In an embodiment, $R^2$ is aryl, such as phenyl.

In another embodiment, $R^1$ is —H.

In yet another embodiment, $R^3$ is —H.

In one embodiment, the invention encompasses compounds of Formula IIb:

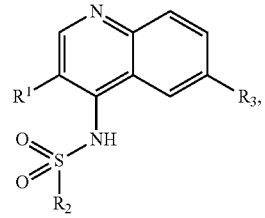

Formula IIb wherein:
- $R^1$, $R^2$, and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In an embodiment, the $C_6$-$C_{10}$ aryl is substituted with one or more of —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In an embodiment, $R^2$ is aryl, such as phenyl.

In another embodiment, $R_2$ is —$C_6$-$C_{10}$ aryl substituted with —$C_1$-$C_6$ alkyl, such as toluyl.

In one embodiment, $R^1$ is —H.

In an embodiment, $R^3$ is —H.

In another embodiment, $R^3$ is —$C_1$-$C_6$ alkyl, such as isopropyl.

In one embodiment, the invention encompasses compounds of Formula IIc:

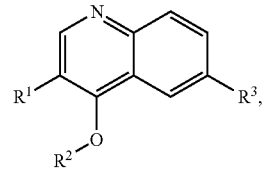

Formula IIc wherein:
- $R^1$ and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen; and $R^2$ is —H, —$C_1$-$C_6$ alkyl, —$C_1$-$C_6$ alkyl-$C_6$-$C_{10}$ aryl, or —$C_6$-$C_{10}$ aryl.

In an embodiment, $R^1$ is —H.

In one embodiment, $R^2$ is —H.

In another embodiment, $R^2$ is —$C_1$-$C_6$ alkyl-$C_6$-$C_{10}$ aryl, such as benzyl.

In still another embodiment, $R^3$ is —H.

In one embodiment, the invention encompasses compounds of Formula IId:

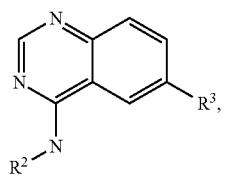

Formula IId wherein:
- $R^2$ is —H, —$C_1$-$C_6$ alkyl, —$C_1$-$C_6$ alkyl-$C_6$-$C_{10}$ aryl, —C(O)—$C_1$-$C_6$ alkyl, or —$C_6$-$C_{10}$ aryl; and R$^3$ is —H, —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen.

In one embodiment, C$_6$-C$_{10}$ aryl is substituted with one or more of —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen.

In an embodiment, R$^2$ is —C$_1$-C$_6$ alkyl-C$_6$-C$_{10}$ aryl, such as benzyl.

In another embodiment, R$^2$ is —C$_1$-C$_6$ alkyl-C$_6$-C$_{10}$ aryl, wherein the —C$_6$-C$_{10}$ aryl group is substituted with one or more of —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, or halogen.

In a specific embodiment, R$^2$ is —C$_1$-C$_6$ alkyl-C$_6$-C$_{10}$ aryl, wherein the —C$_6$-C$_{10}$ aryl group is substituted with —O—C$_1$-C$_6$ alkyl, such as —OMe.

In another specific embodiment, R$^2$ is —C$_1$-C$_6$ alkyl-C$_6$-C$_{10}$ aryl, wherein the —C$_6$-C$_{10}$ aryl group is substituted with halogen, such as —Cl.

In an embodiment, R$^3$ is —H.

In a specific embodiment, R$^3$ is halogen, such as —Cl.

In one embodiment, the invention encompasses compounds of Formula IIe:

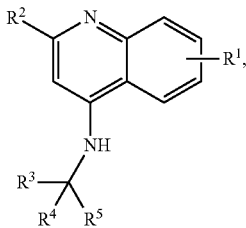

Formula IIe wherein:
R$^1$ and R$^2$ are each independently —H, —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen, and R$^1$ can be on the 5, 6, 7, or 8 position of the quinoline ring; and R$^3$, R$^4$, and R$^5$ are each independently —H, —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen.

In one embodiment, C$_6$-C$_{10}$ aryl is substituted with one or more of —H, —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen.

In an embodiment, R$^1$ is halogen, such as —Cl.

In one embodiment, the invention encompasses compounds of Formula IIIa:

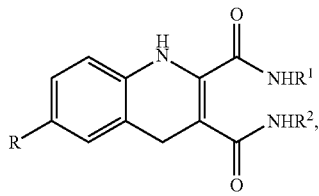

Formula IIIa wherein:
R is —H, —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen;

R$^1$ and R$_2$ are each independently —H, —C$_1$-C$_6$ alkyl, —C$_1$-C$_6$ alkyl-C$_6$-C$_{10}$ aryl, or —C$_6$-C$_{10}$ aryl.

In one embodiment, the invention encompasses compounds of Formula IIIa-1:

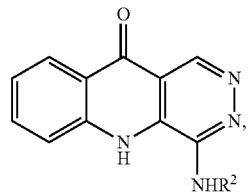

Formula IIIa-1 wherein:
R$^2$ is —H, —C$_1$-C$_6$ alkyl, —C$_1$-C$_6$ alkyl-C$_6$-C$_{10}$ aryl, or —C$_6$-C$_{10}$ aryl.

In one embodiment, the compound comprises Formula IIIb:

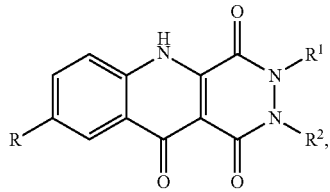

Formula IIIb wherein:
R is —H, —OH, —C$_1$-C$_6$ alkyl, —O—C$_1$-C$_6$ alkyl, —C$_1$-C$_6$ alkyl-C$_6$-C$_{10}$ aryl, —C$_6$-C$_{10}$ aryl, —O—C$_6$-C$_{10}$ aryl, or halogen; and R$^1$ and R$^2$ are each independently —H, —C$_1$-C$_6$ alkyl, —C$_1$-C$_6$ alkyl-C$_6$-C$_{10}$ aryl, or —C$_6$-C$_{10}$ aryl.

In an embodiment, R is —H.

In an embodiment, R$^1$ is —H.

In an embodiment, R$^2$ is —H.

In one embodiment, the compound of Formula IIIb is a compound of Formula IIIb-1:

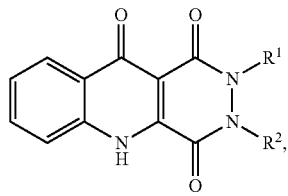

Formula IIIb-1 wherein:
R$^1$ and R$^2$ are as defined for Formula IIIb.

In one embodiment, the invention encompasses compounds of Formula IIIc:

Formula IIIc

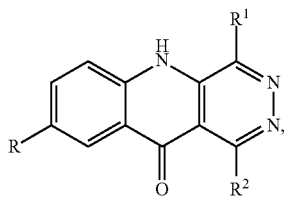

wherein:
R, $R^1$, and $R^2$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In one embodiment, R is —H.
In an embodiment, $R^1$ is halogen, such as —Cl.
In an embodiment, $R^2$ is halogen, such as —Cl.

In one embodiment, the invention encompasses compounds of Formula IIIc-1:

Formula IIIc-1

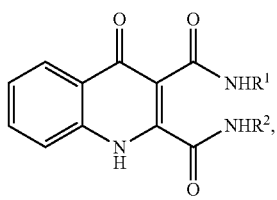

wherein:
$R^1$ and $R^2$ are as defined for Formula IIIa.

In one embodiment, the invention encompasses compounds of Formula IIId:

Formula IIId

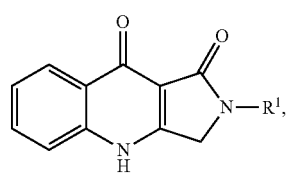

wherein:
$R^1$ is —H, —$C_1$-$C_6$ alkyl, —$C_1$-$C_6$ alkyl-$C_6$-$C_{10}$ aryl, or —$C_6$-$C_{10}$ aryl.

In one embodiment, the invention encompasses compounds of Formula IIIe:

Formula IIIe

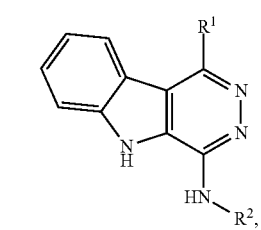

wherein:
$R^1$ is —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen; and $R^2$ is —H, —$C_1$-$C_6$ alkyl, —$C_1$-$C_6$ alkyl-$C_6$-$C_{10}$ aryl, or —$C_6$-$C_{10}$ aryl.

In one embodiment, the invention encompasses compounds of Formula IIIf:

Formula IIIf

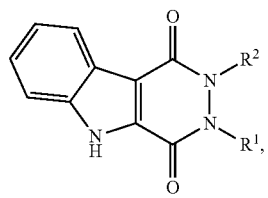

wherein:
$R^1$ and $R^2$ are each independently —H, —$C_1$-$C_6$ alkyl, —$C_1$-$C_6$ alkyl-$C_6$-$C_{10}$ aryl, or —$C_6$-$C_{10}$ aryl.

In one embodiment, the invention encompasses compounds of Formula IVa:

Formula IVa

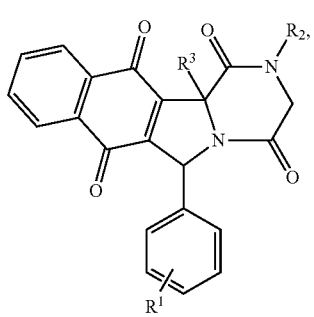

wherein:
$R^1$ and $R^3$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen; and
$R^2$ is —H, —$C_1$-$C_6$ alkyl, —$C_1$-$C_6$ alkyl-$C_6$-$C_{10}$ aryl, or —$C_6$-$C_{10}$ aryl.

In one embodiment, $R^1$ is —H.
In one embodiment, $R^2$ is —$C_1$-$C_6$ alkyl, such as methyl.
In one embodiment, $R^3$ is —H.
In another embodiment, $R^3$ is —$C_1$-$C_6$ alkyl or —$C_1$-$C_6$ alkyl-$C_6$-$C_{10}$ aryl.

In one embodiment, the invention encompasses compounds of Formula IVb:

Formula IVb

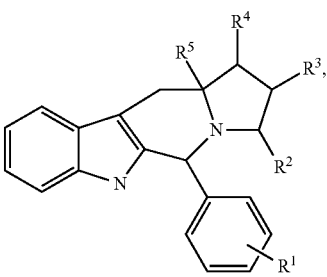

wherein:
$R^1$, $R^2$, $R^3$, $R^4$, and $R^5$ are each independently —H, —OH, —$C_1$-$C_6$ alkyl, —O—$C_1$-$C_6$ alkyl, —$C_1$-$C_6$ alkyl-$C_6$-$C_{10}$ aryl, —$C_6$-$C_{10}$ aryl, —O—$C_6$-$C_{10}$ aryl, or halogen.

In one embodiment, $R^1$ is —H.
In one embodiment, $R^2$ is —H.
In one embodiment, $R^3$ is —H.
In one embodiment, $R^4$ is —H.
In one embodiment, $R^5$ is —H. In another embodiment, $R^5$ is —$C_1$-$C_6$ alkyl or —$C_1$-$C_6$ alkyl-$C_6$-$C_{10}$ aryl.

In one embodiment, the compounds contain a fused planar ring system, and this ring system contains: (1) a hydrogen bond acceptor (e.g. N on pyrimidyl ring and C=O on sildenafil) or (2) an H-bond donor (NH) or H-bond acceptor (C=O) or both (amide NH—C=O).

In another embodiment, the compounds contain a fused planar ring system with 3 hydrophobic groups ($R^1$, $R^2$, and $R^3$). The optimal size and nature of these 3 hydrophobic groups for tight binding to PDE5 seems to depend on the strength of hydrogen bonding between the enzyme and the H bond acceptor or donor. For inhibitors with a H bond acceptor (C=O, N:) on the fused planar ring system, a bulky aromatic $R^2$ group helps to achieve optimal fit at the site occupied by the phosphate of cGMP. For inhibitors with a H bond donor (i.e. NH of tadalafil) on the fused planar ring system, a bulky aromatic $R^1$ group helps to achieve optimal fit at the hydrophobic Q2 pocket. $R^3$ can be small, and it appears to be less significant than $R^1$ and $R^2$. These observations comport with insights from the X-ray structures of the PDE5-inhibitor complexes. By modification of $R^1$, $R^2$, $R^3$, the potency, selectivity and PK properties such as oral bioavailability, cellular penetration, and blood-brain barrier penetration can be fine-tuned.

In one embodiment, the invention encompasses compounds of Formula (V):

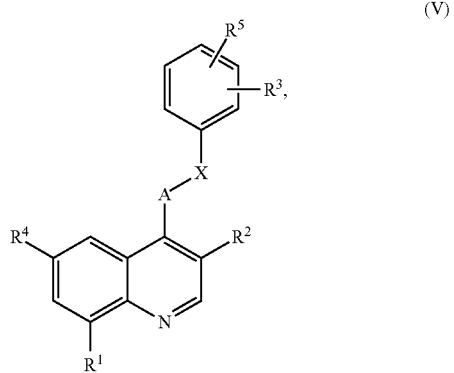

(V)

wherein:
A is O or N;
X is —$(CH_2)_n$-, C(O), S(O), or S(O)$_2$;
$R^1$ is hydrogen, $C_1$-$C_6$ alkyl, $C_3$-$C_8$ cycloalkyl, —$NR^7R^8$, —$SR^7$, or heterocyclyl;
$R^2$ is —$CH_2OR^6$ or —$CO_2R^8$;
$R^3$ is hydrogen or halogen;
$R^4$ is —CN or halogen;
$R^5$ is hydrogen or —$OR^6$;
$R^6$ is hydrogen, —$C_1$-$C_6$ alkyl, —$C_3$-$C_8$ cycloalkyl, or —$C(O)R^9$;
$R^7$ and $R^8$ are each independently hydrogen, —$C_1$-$C_6$ alkyl, —$C_3$-$C_8$ cycloalkyl, or —$C(O)R^9$, wherein the $C_1$-$C_6$ alkyl or $C_3$-$C_8$ cycloalkyl are optionally substituted with —$C_1$-$C_6$ alkyl, —$C_3$-$C_8$ cycloalkyl, —$NR^9R^{10}$, —$SR^9$, or heterocyclyl; or, $R^7$ and $R^8$ together with the nitrogen atom to which they are attached form a 3 to 8-membered heterocycle, wherein any one of the ring carbon atoms is optionally replaced with a heteroatom, and wherein the heterocycle is optionally substituted with $C_1$-$C_6$ alkyl; and
$R^9$ and $R^{10}$ are each independently hydrogen, $C_1$-$C_6$ alkyl, or $C_3$-$C_8$ cycloalkyl; and n is 1, 2, or 3,
or a pharmaceutically acceptable salt or tautomer thereof.

In one embodiment, A is N.
In one embodiment, X is —$(CH_2)_n$-, where n is 1, 2, or 3.
In one embodiment, $R^1$ is hydrogen. In another embodiment, $R^1$ is cycloalkyl.
In one embodiment, $R^1$ is $C_3$-$C_8$ cycloalkyl, —$NR^7R^8$, or —$SR^7$. In another embodiment, $R^1$ is $C_3$-$C_8$ cycloalkyl or —$NR^7R^8$. In still another embodiment, $R^1$ is $C_3$-$C_8$ cycloalkyl. In yet another embodiment, $R^1$ is —$NR^7R^8$. In still another embodiment, $R^7$ and $R^8$ are each independently hydrogen, —$C_1$-$C_6$ alkyl, —$C_3$-$C_8$ cycloalkyl, or —$C(O)R^9$, wherein the $C_1$-$C_6$ alkyl or $C_3$-$C_8$ cycloalkyl are optionally substituted with —$C_1$-$C_6$ alkyl, —$C_3$-$C_8$ cycloalkyl, or —$NR^9R^{10}$; or, $R^7$ and $R^8$ together with the nitrogen atom to which they are attached form a 3 to 8-membered heterocycle, wherein any one of the ring carbon atoms is optionally replaced with O, $NR^9$ or N—$C(O)R^9$. In still another embodiment, $R^1$ is —$SR^7$. In yet another embodiment, $R^1$ is —S—($C_1$-$C_6$)-alkyl. In a specific embodiment, $R^1$ is cyclopropyl, while in another particular embodiment $R^1$ is dimethylamino.

In one embodiment, $R^2$ is $CH_2$—OH.
In one embodiment, $R^3$ is H. In a specific embodiment, $R^3$ is a halogen, such as chloro.
In one embodiment, $R^4$ is —CN. In another embodiment, $R^4$ is a halogen (for example, fluorine).
In one embodiment, $R^5$ is hydrogen. In another embodiment, $R^5$ is —$OR^6$, where $R^6$ is —$C_1$-$C_6$ alkyl, or —$C_3$-$C_8$ cycloalkyl. In a specific embodiment, $R^5$ is —$OCH_3$.

In another embodiment, the compound is of formula (V-1):

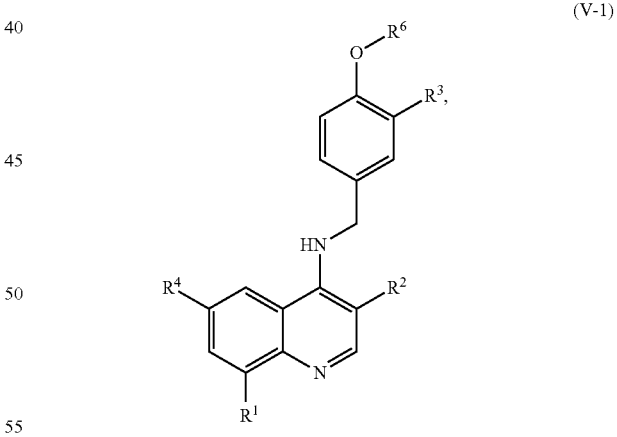

(V-1)

wherein:
$R^1$ is hydrogen, $C_1$-$C_6$ alkyl, $C_3$-$C_8$ cycloalkyl, —$NR^7R^8$, —$SR^7$, or heterocyclyl;
$R^2$ is —$CH_2OR^6$ or —$CO_2R^8$;
$R^3$ is hydrogen or halogen;
$R^4$ is —CN or halogen;
$R^6$ is hydrogen, —$C_1$-$C_6$ alkyl, —$C_3$-$C_8$ cycloalkyl, or —$C(O)R^9$;
$R^7$ and $R^8$ are each independently hydrogen, —$C_1$-$C_6$ alkyl, —$C_3$-$C_8$ cycloalkyl, or —$C(O)R^9$, wherein the $C_1$-$C_6$ alkyl or $C_3$-$C_8$ cycloalkyl are optionally substituted with —C$_1$-C$_6$ alkyl, —C$_3$-C$_8$ cycloalkyl, —NR$^9$R$^{10}$, —SR$^9$, or heterocyclyl; or, R$^7$ and R$^8$ together with the nitrogen atom to which they are attached form a 3 to 8-membered heterocycle, wherein any one of the ring carbon atoms is optionally replaced with a heteroatom, and wherein the heterocycle is optionally substituted with C$_1$-C$_6$ alkyl; and R$^9$ and R$^{10}$ are each independently hydrogen, C$_1$-C$_6$ alkyl, or C$_3$-C$_8$ cycloalkyl, or a pharmaceutically acceptable salt or tautomer thereof.

In one embodiment, R$^1$ is hydrogen. In another embodiment, R$^1$ is cycloalkyl.

In one embodiment, R$^1$ is C$_3$-C$_8$ cycloalkyl, —NR$^7$R$^8$, or —SR$^7$. In another embodiment, R$^1$ is C$_3$-C$_8$ cycloalkyl or —NR$^7$R$^8$. In still another embodiment, R$^1$ is C$_3$-C$_8$ cycloalkyl. In yet another embodiment, R$^1$ is —NR$^7$R$^8$. In still another embodiment, R$^7$ and R$^8$ are each independently hydrogen, —C$_1$-C$_6$ alkyl, —C$_3$-C$_8$ cycloalkyl, or —C(O)R$^9$, wherein the C$_1$-C$_6$ alkyl or C$_3$-C$_8$ cycloalkyl are optionally substituted with —C$_1$-C$_6$ alkyl, —C$_3$-C$_8$ cycloalkyl, or —NR$^9$R$^{10}$; or, R$^7$ and R$^8$ together with the nitrogen atom to which they are attached form a 3 to 8-membered heterocycle, wherein any one of the ring carbon atoms is optionally replaced with O, NR$^9$ or N—C(O)R$^9$. In still another embodiment, R$^1$ is —SR$^7$. In yet another embodiment, R$^1$ is —S—(C$_1$-C$_6$)-alkyl. In a specific embodiment, R$^1$ is cyclopropyl, while in another particular embodiment R$^1$ is dimethylamino.

In one embodiment, R$^2$ is CH$_2$—OH.

In one embodiment, R$^3$ is H. In a specific embodiment, R$^3$ is a halogen, such as chloro.

In one embodiment, R$^4$ is —CN. In another embodiment, R$^4$ is a halogen (for example, fluorine).

In one embodiment, R$^6$ is C.

In another embodiment, the compound is of formula (V-1a):

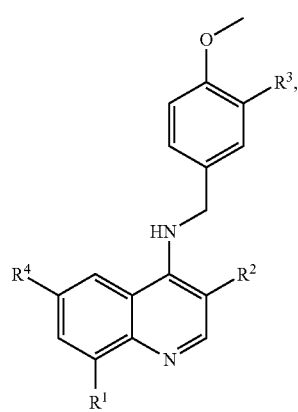

(V-1a)

wherein:
R$^1$ is hydrogen, C$_1$-C$_6$ alkyl, C$_3$-C$_8$ cycloalkyl, —NR$^7$R$^8$, —SR$^7$, or heterocyclyl;
R$^2$ is —CH$_2$OR$^6$ or —CO$_2$R$^8$;
R$^3$ is hydrogen or halogen;
R$^4$ is —CN or halogen;
R$^7$ and R$^8$ are each independently hydrogen, —C$_1$-C$_6$ alkyl, —C$_3$-C$_8$ cycloalkyl, or —C(O)R$^9$, wherein the C$_1$-C$_6$ alkyl or C$_3$-C$_8$ cycloalkyl are optionally substituted with —C$_1$-C$_6$ alkyl, —C$_3$-C$_8$ cycloalkyl, —NR$^9$R$^{10}$, —SR$^9$, or heterocyclyl or, R$^7$ and R$^8$ together with the nitrogen atom to which they are attached form a 3 to 8-membered heterocycle, wherein any one of the ring carbon atoms is optionally replaced with a heteroatom, and wherein the heterocycle is optionally substituted with C$_1$-C$_6$ alkyl; and R$^9$ and R$^{10}$ are each independently hydrogen, C$_1$-C$_6$ alkyl, or C$_3$-C$_8$ cycloalkyl, or a pharmaceutically acceptable salt or tautomer thereof.

In one embodiment, R$^1$ is hydrogen. In another embodiment, R$^1$ is cycloalkyl.

In one embodiment, R$^1$ is C$_3$-C$_8$ cycloalkyl, —NR$^7$R$^8$, or —SR$^7$. In another embodiment, R$^1$ is C$_3$-C$_8$ cycloalkyl or —NR$^7$R$^8$. In still another embodiment, R$^1$ is C$_3$-C$_8$ cycloalkyl. In yet another embodiment, R$^1$ is —NR$^7$R$^8$. In still another embodiment, R$^7$ and R$^8$ are each independently hydrogen, —C$_1$-C$_6$ alkyl, —C$_3$-C$_8$ cycloalkyl, or —C(O)R$^9$, wherein the C$_1$-C$_6$ alkyl or C$_3$-C$_8$ cycloalkyl are optionally substituted with —C$_1$-C$_6$ alkyl, —C$_3$-C$_8$ cycloalkyl, or —NR$^9$R$^{10}$; or, R$^7$ and R$^8$ together with the nitrogen atom to which they are attached form a 3 to 8-membered heterocycle, wherein any one of the ring carbon atoms is optionally replaced with O, NR$^9$ or N—C(O)R$^9$. In still another embodiment, R$^1$ is —SR$^7$. In yet another embodiment, R$^1$ is —S—(C$_1$-C$_6$)-alkyl. In a specific embodiment, R$^1$ is cyclopropyl, while in another particular embodiment R$^1$ is dimethylamino.

In one embodiment, R$^2$ is CH$_2$—OH.

In one embodiment, R$^3$ is H. In a specific embodiment, R$^3$ is a halogen, such as chloro.

In one embodiment, R$^4$ is —CN. In another embodiment, R$^4$ is a halogen (for example, fluorine).

In another embodiment, the compound is of formula (V-1a1):

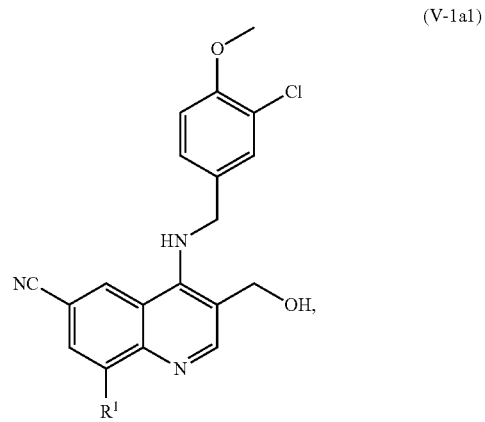

(V-1a1)

wherein:
R$^1$ is hydrogen, C$_1$-C$_6$ alkyl, C$_3$-C$_8$ cycloalkyl, —NR$^7$R$^8$, —SR$^7$, or heterocyclyl;
R$^7$ and R$^8$ are each independently hydrogen, —C$_1$-C$_6$ alkyl, —C$_3$-C$_8$ cycloalkyl, or —C(O)R$^9$, wherein the C$_1$-C$_6$ alkyl or C$_3$-C$_8$ cycloalkyl are optionally substituted with —C$_1$-C$_6$ alkyl, —C$_3$-C$_8$ cycloalkyl, —NR$^9$R$^{10}$, —SR$^9$, or heterocyclyl; or, R$^7$ and R$^8$ together with the nitrogen atom to which they are attached form a 3 to 8-membered heterocycle, wherein any one of the ring carbon atoms is optionally replaced with a heteroatom, and wherein the heterocycle is optionally substituted with $C_1$-$C_6$ alkyl; and $R^9$ and $R^{10}$ are each independently hydrogen, $C_1$-$C_6$ alkyl, or $C_3$-$C_8$ cycloalkyl, or a pharmaceutically acceptable salt or tautomer thereof.

In one embodiment, $R^1$ is hydrogen. In another embodiment, $R^1$ is cycloalkyl.

In one embodiment, $R^1$ is $C_3$-$C_8$ cycloalkyl, —$NR^7R^8$, or —$SR^7$. In another embodiment, $R^1$ is $C_3$-$C_8$ cycloalkyl or —$NR^7R^8$. In still another embodiment, $R^1$ is $C_3$-$C_8$ cycloalkyl. In yet another embodiment, $R^1$ is —$NR^7R^8$. In still another embodiment, $R^7$ and $R^8$ are each independently hydrogen, —$C_1$-$C_6$ alkyl, —$C_3$-$C_8$ cycloalkyl, or —$C(O)R^9$, wherein the $C_1$-$C_6$ alkyl or $C_3$-$C_8$ cycloalkyl are optionally substituted with —$C_1$-$C_6$ alkyl, —$C_3$-$C_8$ cycloalkyl, or —$NR^9R^{10}$; or, $R^7$ and $R^8$ together with the nitrogen atom to which they are attached form a 3 to 8-membered heterocycle, wherein any one of the ring carbon atoms is optionally replaced with O, $NR^9$ or N—$C(O)R^9$. In still another embodiment, $R^1$ is —$SR^7$. In yet another embodiment, $R^1$ is —S—$(C_1$-$C_6)$-alkyl. In a specific embodiment, $R^1$ is cyclopropyl, while in another particular embodiment $R^1$ is dimethylamino.

In particular embodiments, the compound is:

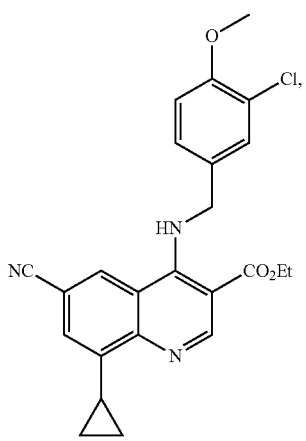

1

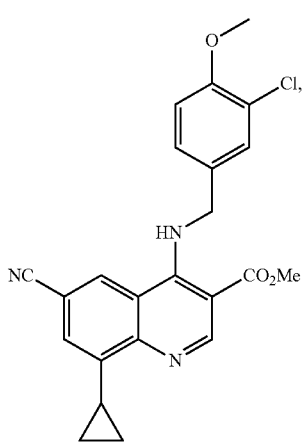

2

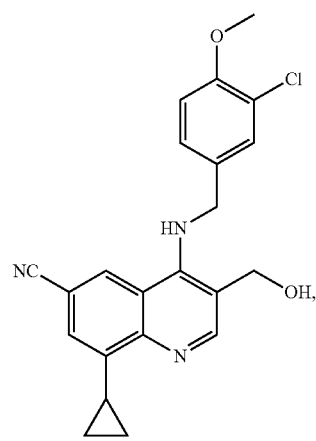

3

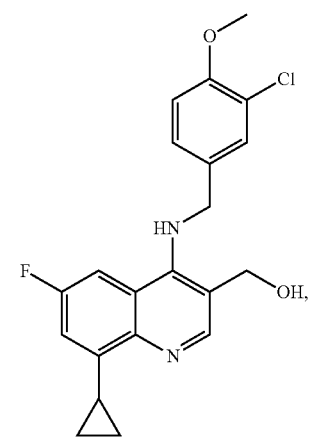

4

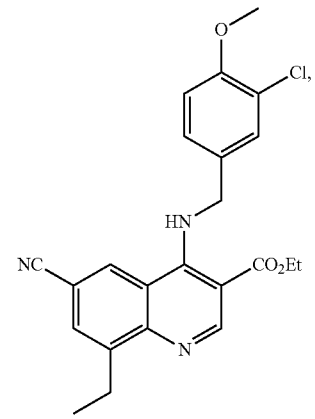

5

6
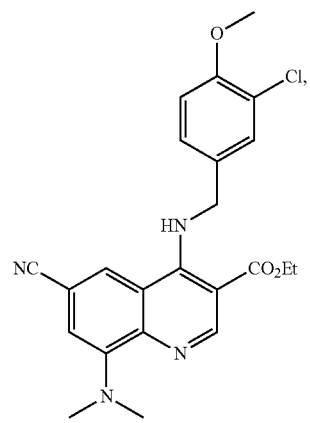
7
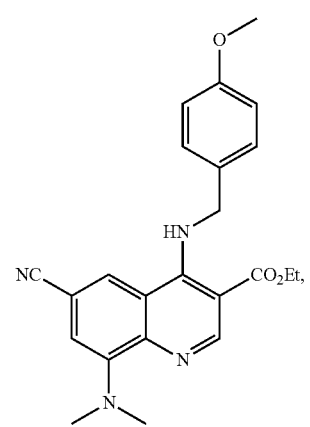
8
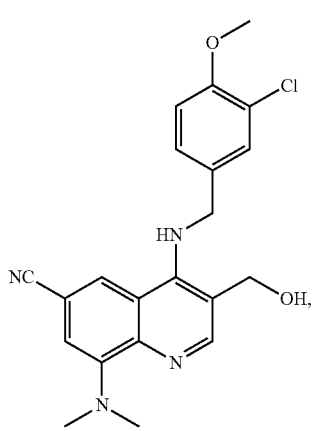
9
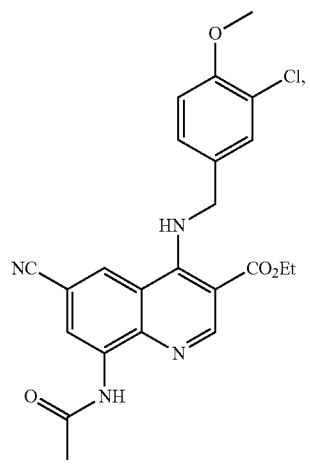
10
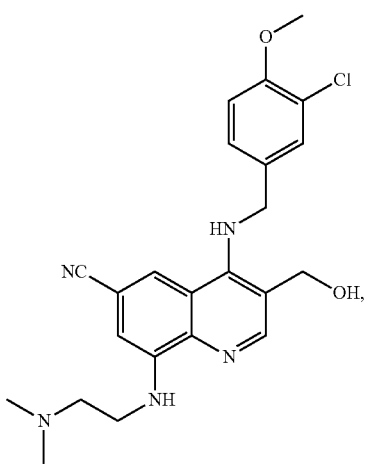
11
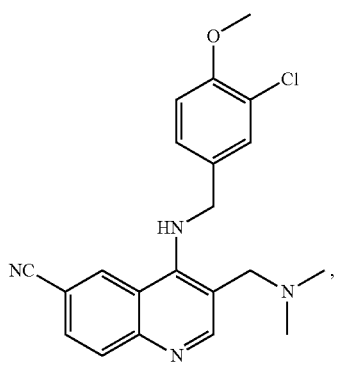

12
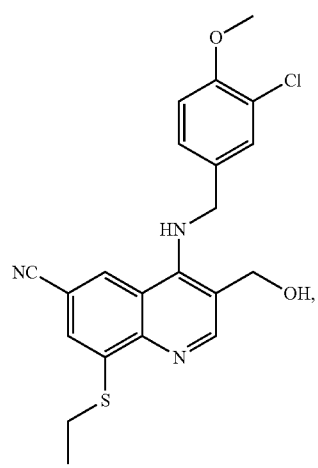
13
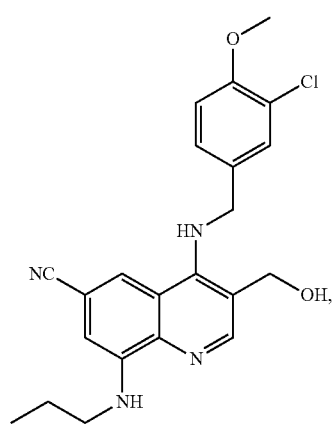
14
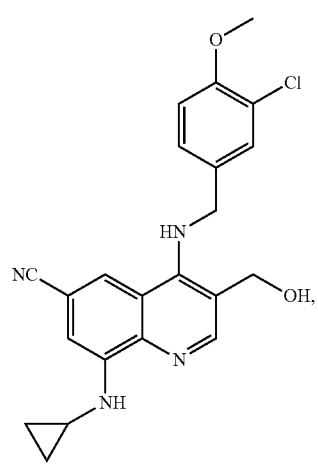
15
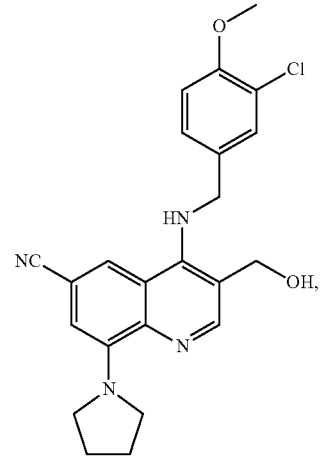
16
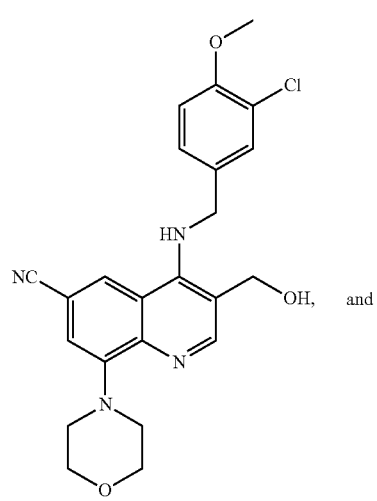
and
17
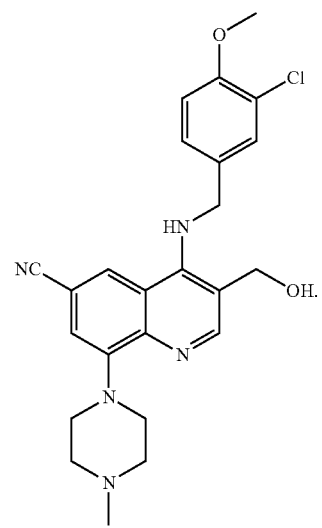

In other embodiments, the compound is
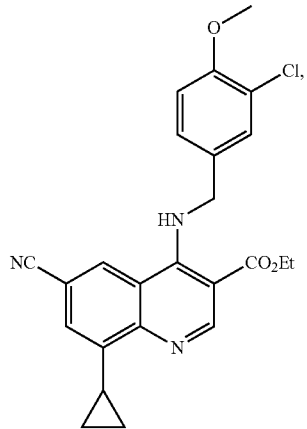
1
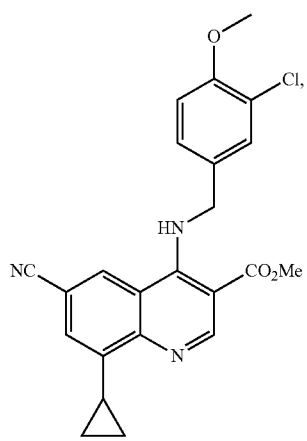
2
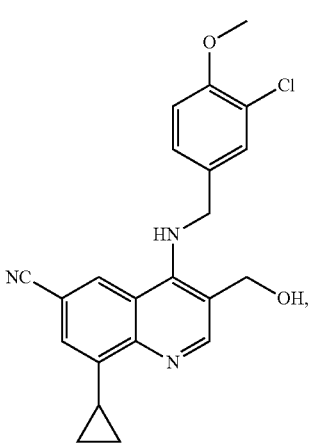
3
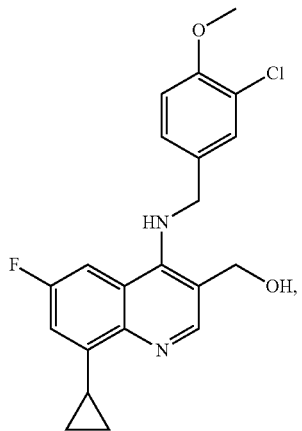
4
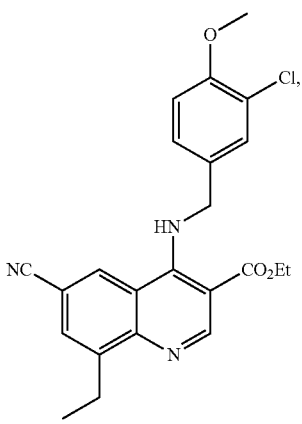
5
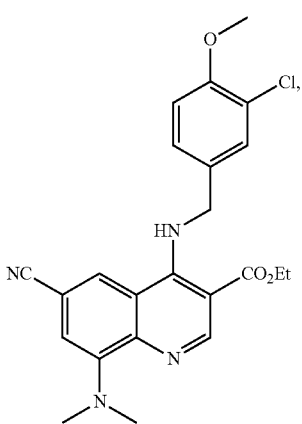
6

-continued
7
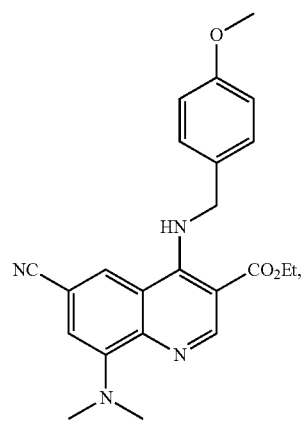
8
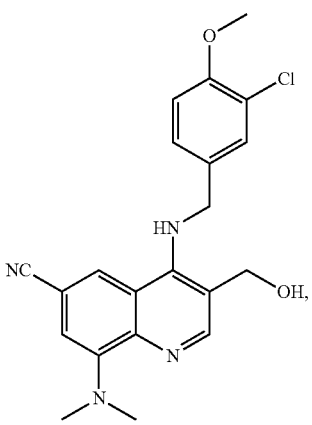
9
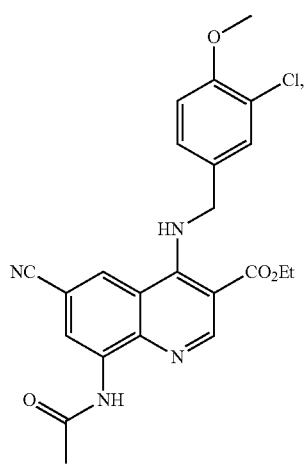
-continued
10
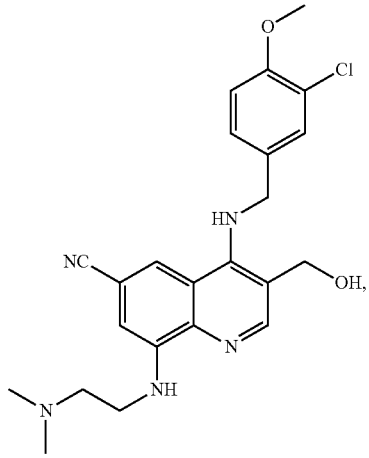
12
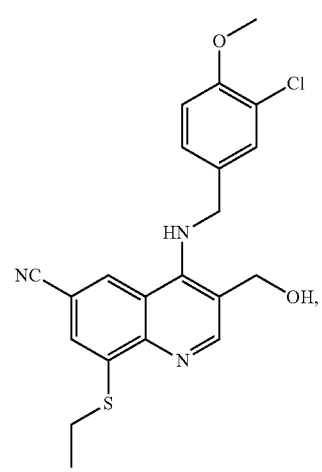
13
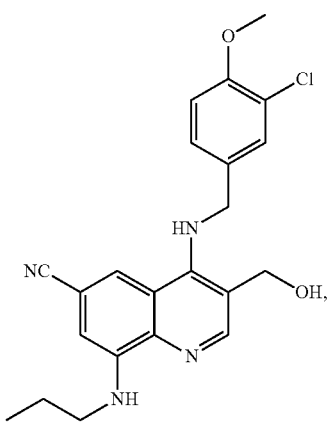

14
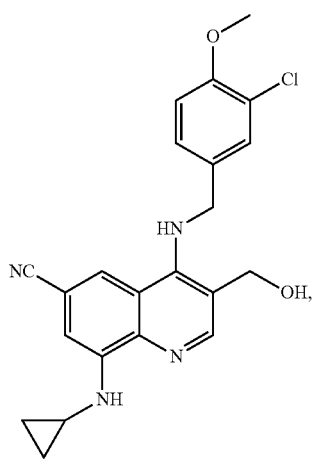
15
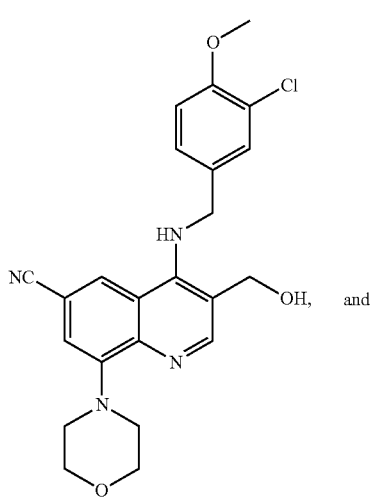
16
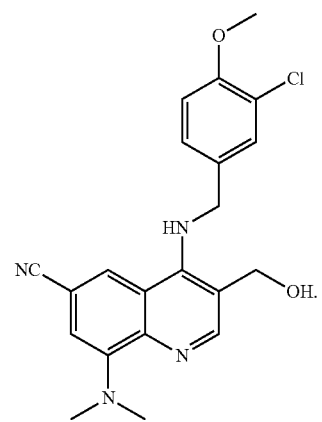
5
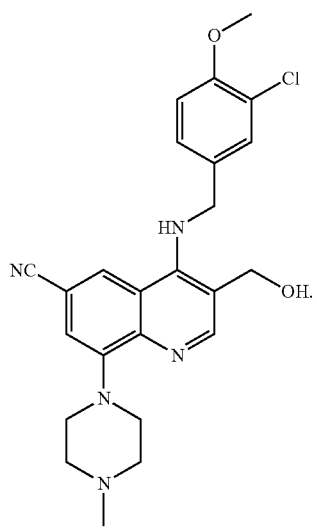
In specific embodiments, the compound is
3
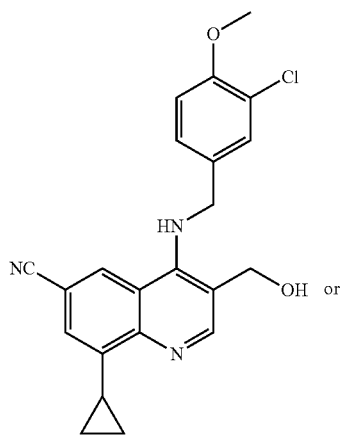  or
8

In one specific embodiment, the compound is:

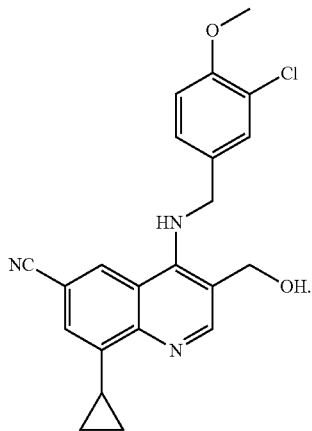

In another specific embodiment, the compound is:

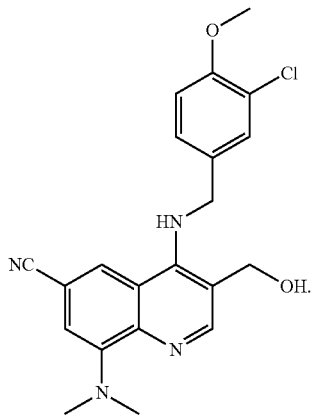

In one embodiment, the compounds of the invention do not include compounds of formula X:

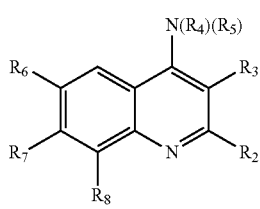

wherein:
$R^2$, $R^6$, $R^7$ and $R^8$ are independently hydrogen, halogen, alkyl, substituted alkyl, alkoxy, nitro, cyano, aryl, heteroaryl, or heterocyclo;
$R^3$ is —$(CH_2)_z$, Y, wherein z is 0, 1, 2, or 3;
$R^4$ and $R^5$ (i) are independently hydrogen, alkyl, substituted alkyl, cycloalykl, substituted cycloalkyl, aryl, or heteroaryl, with the proviso that $R^4$ and $R^5$ are not both hydrogen; (ii) taken together form a heterocyclo ring; or (iii) one of $R^4$ and $R^5$ together with Y forms a heterocyclo ring;

Y is (i) independently selected from —$OR^9$, —$CO_2R^9$, —$CH(CO_2R^9)_2$, —$O(C=O)NR^{10}R^{11}$, —$NR^{10}R^{11}$, —$NR^{10}(C=O)NR^{11}R^{12}$, —$CH[(C=O)NR^{10}R^{11}]_2$, —$(C=O)$ $NRO^{10}R^{11}$, —$NR^{10}(C=O)R^{12}$, —$S(O)_mR^9$, —$SO_2NR^{10}R^{11}$, imidazole, substituted imidazole, triazole, substituted triazole, or cyano, or (ii) together with $R^4$ or $R^5$ forms a heterocylo ring; and
m is 0, 1, or 2;
$R^9$ is hydrogen, alkyl, substituted alkyl, hydroxy, alkoxy, cycloalkyl, substituted cycloalkyl, heterocyclo, aryl, heteroaryl, or pentafluorophenyl; and
$R^{10}$, $R^{11}$, and $R^{12}$ are (i) independently selected from hydrogen, alkyl, substituted alkyl, alkoxy, cycloalkyl, substituted cycloalkyl, aryl, heterocyclo, and heteroaryl; or (ii) taken together, wherein $R^{10}$ forms a three-to seven-membered heterocyclo ring with $R^{11}$ or $R^{12}$, or $R^{11}$ forms a three-to seven-membered heterocyclo ring with $R^{12}$.

The invention also provides methods for increasing α-secretase protein activity or expression in a subject by administering any one of the compounds having Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18) above. The invention also provides a method for decreasing β-secretase protein activity or expression in a subject by administering any one of the compounds having Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18) above. In addition, the invention provides methods for reducing amyloid beta (Aβ) protein deposits in a subject by administering any one of the compounds having Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18) above.

In some embodiments, compounds having Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18) are first screened for their ability to satisfy one or more of the following characteristics: an $IC_{50}$ no greater than about 100 nM; a selectivity that is at least 50-fold greater for PDE5 than for other PDEs; a PDE5 inhibitory activity in vitro that has an $IC_{50}$ no greater than about 50 nM, the ability to penetrate the BBB; the ability to hydrolyze cGMP by at least about 20% (or at least about 80%); an interaction between the compound and PDE5 that comprises a second bridging ligand that is a hydroxyl group; and an interaction between the compound and PDE5 that comprises contacts with PDE5 at amino acid residues F787, L804, I813, M816, or a combination thereof. Thereafter or independently, the compounds can be tested for their ability to provide long-lasting effects on inhibiting β-secretase activity or expression and/or on activating α-secretase activity or expression (such as in the mouse APP transgenic model).

In one embodiment, the method comprises administering to the subject an effective amount of a composition comprising a PDE5 inhibitor compound. In another embodiment, the subject exhibits abnormally elevated amyloid beta plaques. In a further embodiment, the subject is afflicted with Alzheimer's disease, Lewy body dementia, inclusion body myositis, or cerebral amyloid angiopathy. In some embodiments, the Aβ protein deposit comprises an $A\beta_{40}$ isomer, an $A\beta_{42}$ isomer, or a combination thereof. In further embodiments, α-secretase protein activity or expression is increased up to 3 months post-treatment, up to 4 months post-treatment, up to 5 months post-treatment, or up to 6 months post-treatment. In other embodiments, β-secretase protein activity or expression is decreased up to 3 months post-treatment, up to 4 months post-treatment, up to 5 months post-treatment, or up to 6 months post-treatment.

PDE5 inhibitor compounds of the invention can be incorporated into pharmaceutical compositions suitable for administration. Such compositions can comprise a PDE5 inhibitor compound (such as sildenafil, tadalafil, vardenafil, or a compound comprising Formula Ia, Formula Ib, Formula Ic, Formula Id, Formula Ie, Formula IIa, Formula IIb, Formula IIc, Formula IId, Formula IIe, Formula IIIa, Formula IIIb, Formula IIIc, Formula IIIa-1, Formula IIIb-1, Formula IIIc-1, Formula IIId, Formula IIIe, Formula IIIf; Formula IVa, Formula IVb, Formula V, Formula V-1, Formula V-1-a, or Formula V-a-1 (such as any one of compounds 1-18) and a pharmaceutically acceptable carrier. The compositions can be administered alone or in combination with at least one other agent, such as a stabilizing compound, which can be administered in any sterile, biocompatible pharmaceutical carrier including, but not limited to, saline, buffered saline, dextrose, and water. The compositions can be administered to a patient alone, or in combination with other agents, drugs or hormones. In one embodiment, the effective amount of a PDE5 inhibitor compound can be at least about 3 mg/kg body weight. In another embodiment, the composition is administered at least once daily for up to 18 days, up to 19 days, up to 20 days, up to 21 days, up to 22 days, up to 23 days, up to 24 days, or up to 25 days.

Non-limiting examples of additional PDE5 inhibitors include: 5-[2-ethoxy-5-(4-methyl-1-piperazinylsulphonyl) phenyl]-1-methyl-3-n-propyl-1,6-dihydro-7H-pyrazolo[4,3-d]pyrimidin-7-one (sildenafil) also known as 1-[[3-(6,7-dihydro-1-methyl-7-oxo-3-propyl-1H-pyrazolo[4,3-d]pyrimidin-5-yl)-4-ethoxyphenyl]sulphonyl]-4-methylpiperazine (see EP-A-0463756); 5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyrid-in-2-yl)methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d]pyrimidin-7-one (see WO99/54333); 6-benzo[1,3]dioxol-5-yl-2-methyl-2,3,6,7,12,12a-hexahydro-pyrazino[1',2':1,6]pyrido[3,4-b]indole-1,4-dione (cialis); (+)-3-ethyl-5-[5-(4-ethylpiperazin-1-ylsulphonyl)-2-(2-methoxy-1(R)-methy-1 ethoxy)pyridin-3-yl]-2-methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methyl-ethyl]oxy)pyridin-3-yl}-2-methyl-2,6-dihydro-7H-pyrazolo[4,3-d]pyrimidin-7-one (see WO99/54333); 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazol-o[4,3-d]pyrimidin-5-yl]-3-pyridylsulphonyl}-4-ethylpiperazine (see WOO 1/27113, Example 8); 5-[2-iso-butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO01/27113, Example 15); 5-[2-ethoxy-5-(4-ethylpiperazin-1-ylsulphonyl)pyridin-3-yl]-3-ethyl-2-phe-nyl-2,6-dihydro-7H-pyrazolo[4,3-d]pyrimidin-7-one (see WO01/27113, Example 66); 5-(5-acetyl-2-propoxy-3-pyridinyl)-3-ethyl-2-(1-isopropyl-3-azetidin-yl)-2,6-dihydro-7H-pyrazolo[4,3-d]pyrimidin-7-one (see WO01/27112, Example 124); 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one (see WO01/27112, Example 132); (6R,12aR)-2,3,6,7,12,12a-hexahydro-2-methyl-6-(3,4-methylenedioxyph-enyl)-pyrazino[2',1':6,1]pyrido[3,4-b]indole-1,4-dione (IC-351), i.e. the compound of examples 78 and 95 of published international application WO95/19978, as well as the compound of examples 1, 3, 7 and 8; 2-[2-ethoxy-5-(4-ethylpiperazin-1-yl-1-sulphonyl)-phenyl]-5-methyl-7-pro-pyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; the compound of example 11 in WO93/07124 (EISAI); and compounds 3 and 14 from Rotella D P, J. Med. Chem., 2000, 43, 1257.

According to the invention, a pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions.

Any of the therapeutic applications described herein can be applied to any subject in need of such therapy, including, for example, a mammal such as a dog, a cat, a cow, a horse, a rabbit, a monkey, a pig, a sheep, a goat, or a human.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the PDE5 inhibitor compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1—Sildenafil (Viagra) Leads to an Immediate and Persistent Improvement of Hippocampal Synaptic Plasticity, Memory and Aβ Load in an Alzheimer Mouse Model This example discusses whether sildenafil can exert beneficial effects against synaptic dysfunction and memory loss of mice carrying both the mutant amyloid precursor protein (APP; K670N,M671L) and presenilin-1 (PS1; M146L) (termed APP/PS1 mice). The PDE5 inhibitor sildenafil (Viagra) was tested to see whether it was beneficial against the AD phenotype in a mouse model of amyloid deposition. The inhibitor produces an immediate and long-lasting amelioration of synaptic function, CREB phosphorylation and memory. This effect was associated with a reduction of Aβ levels. Thus, PDE5 inhibitors have potential for the treatment of AD and other diseases associated with elevated Aβ levels.

Previous studies show that a) NO protects against Aβ-induced LTP block; b) sGC is involved in NO-protection against Aβ-induced LTP block; c) cGMP and activation of its downstream target, PKG, have a beneficial effect against Aβ-induced LTP block; d) increase in NO and cGMP levels can protect against Aβ suppression of phospho-CREB increase during LTP; e) sGC is involved in NO protection against Aβ-induced block of increase in phospho-CREB during LTP; f) PKG is involved in the effect of cGMP analogs on CREB phosphorylation during Aβ treatment; g) Aβ-induced suppression of LTP is associated with block of the increase in cGMP levels (Puzzo, D., et al., J Neurosci, 2005. 25(29): p. 6887-97). Various explanations support these findings: a) given that the cofactor NADPH strongly complexes soluble Aβ, which results in its diminished availability for NOS functioning [Colton, C. A., et al., Proc Natl Acad Sci USA, 2006. 103(34): p. 12867-72], Aβ can function as a sink for NADPH, preventing the production of NO by NOS and consequently halting the resulting cascade of events that includes cGMP production and ends with CREB phosphorylation; b) an increase of PDE activity following Aβ application [Wirtz-Brugger, F. and A. Giovanni, Neuroscience, 2000. 99(4): p. 737-50]; c and d) a decrease of sGC activity and/or expression [Baltrons, M. A., et al., Neurobiol Dis, 2002. 10(2): p. 139-49] (i.e. PDE activity increase has been demonstrated on both isolated blood vessels and cultured microglia in which PDE5 inhibition re-establishes normal vasoactivity and blocks inflammatory response due to Aβ [Paris, D., et al., Exp Neurol, 1999. 157(1): p. 211-21]); and f) a reduction of NOS expression. Although identifying the link between the NO cascade and Aβ-induced synaptic dysfunction would constitute an important research subject, new PDE5 inhibitor drugs will be developed.

Acute Effects of Sildenafil on Synaptic Function in Hippocampal Slices of APP/PS1 Mice.

Figure 1A:
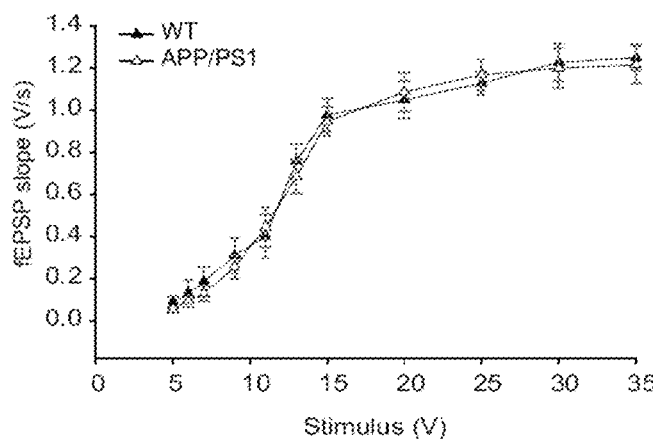
FIG. 1A is a graph of field input-output relationship for different stimulation intensities (5-35 V) that shows that BST is similar in 3-month-old APP/PS1 animals and WT littermates. The slope of the input-output curve at stimulation intensity equal to 35 V was ~97% of WT littermates in APP/PS1 mice (APP/PS1 mice: 1.21±0.08 V/sec., n=7 slices from 6 males; WT mice: 1.25±0.06 V/sec., n=7 slices from 6 males). A two-way ANOVA showed no difference between double transgenic mice and their littermate controls [$F_{(1,12)}$=0.05, P=0.81]. Similar results were observed when plotting the fEPSP slope versus the amplitude of the fiber afferent volley.
Figure 1B:
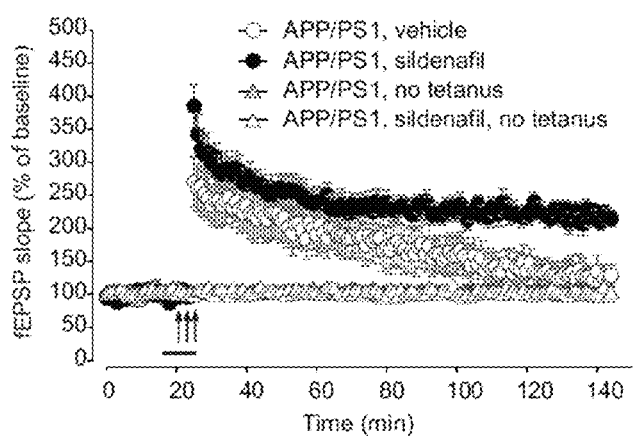
FIG. 1B is a graph representing that ten minutes perfusion with sildenafil (50 nM) reverses LTP impairment in APP/PS1 mice (sildenafil-treated APP/PS1 mice equal to ~100% of vehicle-treated WT littermates at 120 min. after tetanus, vs. ~65% in vehicle-treated APP/PS1 mice; sildenafil-treated APP/PS1 mice: 215.08±11.85% at 120 min. after tetanus, n=8 slices from 7 males; vehicle-treated APP/PS1 mice: 128.47±16.79%, n=9 slices from 7 males, [$F_{(1,15)}$=4.98, P=0.041]). The inhibitor has no effect on basal neurotransmission either during its application or 120 minutes after the end of the application in experiments where no tetanic stimulation is applied (~96% of vehicle-treated WT slices in sildenafil-treated APP/PS1 slices, vs. ~97% in vehicle-treated transgenic slices; APP/PS1: 99.99±3.71% in sildenafil-treated slices, n=4 slices from 4 males, vs. 100.88±1.02% in vehicle-treated slices, n=5 slices from 4 males, [$F_{(1,7)}$=1.15, P=0.31]). Arrows indicate time and pattern of the tetani in this and the following figures. Bars represent the time of the application of the drug or vehicle in this and the following figures. Sildenafil reverses the impairment of LTP in the CA1 region of slices from 3-month-old APP/PS1 mice.
Figure 1C:
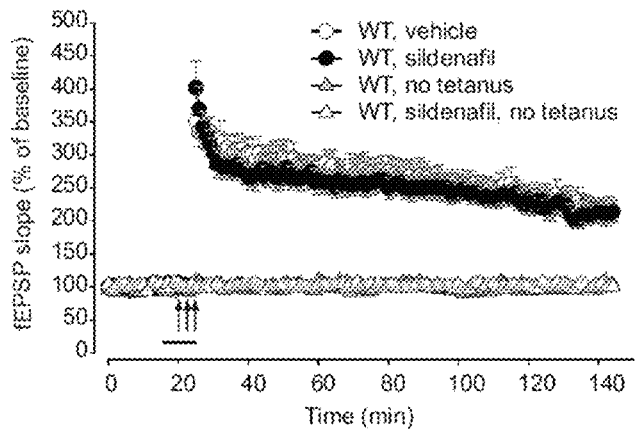
FIG. 1C is a graph showing that sildenafil (50 nM) does not affect LTP in WT mice. Levels of LTP at 120 min. after tetanus were ~99% of vehicle-treated WT slices (vehicle-treated WT mice: 214.28±17.49%, n=10 slices from 8 males, sildenafil-treated WT mice: 213.26±13.66%, n=9 slices from 8 males, [$F_{(1,17)}$=0.23, P=0.63]). The inhibitor has no effect on basal synaptic responses either during its application or 120 minutes after the end of the application in experiments where no tetanic stimulation is applied (~97% of vehicle-treated WT slices; 100.51±2.34% in sildenafil-treated slices, n=5 slices from 4 males, vs. 103.72±3.86% in vehicle-treated slices, n=4 slices from 4 males, [$F_{(1,7)}$=0.26, P=0.62]). These experiments were interleaved with those of APP/PS1 mice.

A brief application of sildenafil was tested to see whether it rescued the defect in LTP of slices derived from 3 month-old APP/PS1 mice, when synaptic plasticity impairment is just starting whereas basal synaptic transmission (BST) is normal[412]. BST was determined by measuring the slope of the field excitatory postsynaptic potential (fEPSPs) at increasing stimulus intensity in APP/PS1 and wild-type (WT) mice. No difference in BST among the different groups was observed (FIG. 1A). Hippocampal slices were then perfused with sildenafil (50 nM) for 10 min before inducing LTP through tetanic stimulation of the Schaeffer collateral pathway. Potentiation in sildenafil treated APP/PS1 slices was far greater than in vehicle-treated APP/PS1 slices (FIG. 1B). On the other hand, sildenafil did not change the amplitude of LTP in slices of WT mice compared to WT slices treated with vehicle alone (FIG. 1C). Sildenafil had no effect on basal synaptic responses either during its application or 120 minutes after the end of the application in experiments where no tetanus was applied either in slices from APP/PS1 mice or WT littermates (FIGS. 1B-1C).

As a control for PDE5 specificity of the sildenafil effect onto synaptic dysfunction, a more specific PDE5 inhibitor, tadalafil, was used. Differently than sildenafil and vardenafil which are cGMP based inhibitors, tadalafil is a β-carbolines-derived drug with no effect on PDE1 (selectivity ratio >2000) and on PDE6 (selectivity ratio 1000), and an $IC_{50}$ against PDE5 of 5.0 nM[411]. In these experiments slices were bathed in 50 nM tadalafil for 10 min prior to tetanus. Potentiation in tadalafil-treated APP/PS1 slices was far greater than in vehicle-treated APP/PS1 slices (FIGS. 8A-8B). Tadalafil did not change the amplitude of baseline and LTP in WT mice (FIGS. 8A-8B).

As an additional control for PDE5 specificity, IC354 was also used a PDE1 inhibitor. It is the HCl salt of IC224[413], a highly selective PDE1 inhibitor ($IC_{50}$ against PDE1 of 80 nM; ratio of $IC_{50}$ value for the next most sensitive PDE to $IC_{50}$ value for PDE1 equal to 127). In these experiments slices were bathed in 1 μM IC354 for 10 min prior to tetanus. Differently than sildenafil or tadalafil, the treatment did not augment LTP. Potentiation in IC354 treated APP/PS1 slices was similar to vehicle-treated APP/PS1 slices (FIGS. 8C-8D) and IC354 did not change the amplitude of LTP in hippocampal slices of WT mice (FIGS. 8C-8D). Thus, these results taken together with the experiments with sildenafil and tadalafil demonstrate that inhibition of PDE5 (but not PDE1) protects AD-like animal models against synaptic dysfunction, supporting that inhibition of PDE5 can be beneficial against synaptic dysfunction in AD.

Acute Effects of Sildenafil on the Cognitive Function of APP/PS1 Mice.

Given that sildenafil reversed LTP deficits in 3-month-old APP/PS1, it was then tested whether the inhibitor reversed the cognitive defects in these animals. As reported above sildenafil offers the advantage of crossing the BBB and therefore it can be easily utilized in behavioural experiments. Three-month-old mice were divided into 4 groups: APP/PS1 with sildenafil, APP/PS1 with vehicle, WT with sildenafil and WT with vehicle. Sildenafil and vehicle control solutions were administered i.p. at a concentration of 3 mg/kg. This concentration was chosen based on previous studies showing that these amounts of sildenafil raise hippocampal cGMP levels and improve memory in aged rats[46] and mice[47] independent of vascular effects[46]. The effects of acute administration of sildenafil was first examined on fear-conditioning learning, a type of learning that is impaired in several AD mouse models[414] and depends on hippocampus and amygdala. The hippocampus is indispensable for contextual fear conditioning[415], a form of associative learning in which mice must associate a neutral stimulus with an aversive one. Mice were trained to associate neutral stimuli with an aversive one. They were placed in a new context (fear conditioning box), exposed to a white noise cue (CS) paired with a mild foot shock (US), and injected with sildenafil immediately after the training. Fear learning was assessed twenty-four hours later by measuring freezing behaviour—the absence of all movement except for that necessitated by breathing—in response to representation of the context or of the auditory cue within a completely different context. No difference was found in the freezing behaviour among the four groups of mice before the training phase (FIG. 2A). Twenty-four hours later, a decrease in the freezing behaviour of vehicle-treated APP/PS1 mice compared with that of vehicle-treated WT littermates in the analysis of the contextual learning was observed (FIG. 2A). Sildenafil treatment improved contextual learning in the transgenic animals (FIG. 2A) whereas sildenafil-treated WT animals did not show a significant increase in freezing (FIG. 2A), probably because maximal levels of memory are already induced in vehicle-treated WT mice after the training session, as has been found both in *Drosophila* and in mice[416, 417]. Fear conditioning, a hippocampus-independent task A[15], was next tested and no difference in freezing among the 4 groups was found, as APP/PS1 mice are known to have a selective hippocampus-dependent impairment in associative learning[414].

To exclude the possibility that sildenafil produced its behavioural effect through a peripheral vascular action, the study of fear memory was repeated using tadalafil which is unable to cross the BBB (cLogP=1.43 and information from its manufacturer). Tadalafil and vehicle control solutions were administered i.p. at a concentration of 1 mg/kg. Tadalafil did not improve associative learning in APP/PS1 mice. Thus, the effect of sildenafil cannot be due to inhibition of PDE5 in the vascular compartment (FIG. 9).

Next, the effect of treatment with sildenafil was examined on spatial working memory, a type of short-term memory that can be studied with the radial-arm water maze test. This task has already demonstrated memory deficits in other transgenic models of AD[412, 418] and has been shown to depend upon hippocampal function[419]. Mice were required to learn and memorize the location of a hidden platform in one of the arms of a maze with respect to spatial cues. APP/PS1 injected with vehicle showed severe abnormalities in spatial memory for platform location during both acquisition and retention of the task compared to vehicle-injected WT littermates (FIG. 2B). However, daily injections of sildenafil for 3 weeks immediately after the $4^{th}$ acquisition trial ameliorated the behavioural performance of APP/PS1 mice (FIG. 2B). Treatment with sildenafil did not affect the performance of WT mice compared to vehicle-injected WT littermates (FIG. 2B). The four groups of mice showed no difference in the time needed to find the platform in the visible platform task, as well as in swimming speed (FIG. 10). Thus, vision, motor coordination, or motivation were not affected in the four groups of mice and did not influence the radial-arm water maze test results.

Persistent Effects of Sildenafil on Cognitive and Synaptic Functions in APP/PS1 Mice.

Sildenafil was tested to determine whether a brief course of treatment can provide long term benefits. The PDE5 inhibitor was examined to see if it maintains its protective effect against synaptic dysfunction and memory loss. In these experiments, both APP/PS1 and WT mice of 3 months of age were injected intraperitoneally with 3 mg/kg/day sildenafil for 3 weeks, then the treatment was stopped for 9-12 weeks prior to testing. The mice were next subjected to training for contextual learning. As in the acute experiments, when the animals were reintroduced into the same context in which they had been trained 9-12 weeks before, the freezing time was greatly increased in APP/PS1 mice that had been previously treated with sildenafil compared to vehicle-treated APP/PS1 littermates (FIG. 3A). Sildenafil did not increase the freezing time in WT littermates compared to WT mice treated with vehicle (FIG. 3A). There were no differences between the 4 groups in the cued conditioning test. These data indicate that inhibition of PDE5 protects fear contextual learning in APP/PS1 mice for an extended time beyond the duration of drug administration.

The effects of one course of 3-week treatment with sildenafil on spatial working memory were next tested using the radial-arm water-maze task. There was a difference between the number of errors made by vehicle-treated APP/PS1 and WT mice (FIG. 3B)[412]. Administration of sildenafil for 3 weeks, 9-12 weeks prior to the testing, reduced the gap between the two groups without affecting performance of the WT animals (FIG. 3B). These data indicate that one course of long-term treatment with the PDE5 inhibitor protects spatial working memory in APP/PS1 mice.

To investigate sildenafil effect on long-term memory, reference memory was tested with a Morris water maze task that is known to require hippocampal function[420] and is impaired after 6 months of age in the APP/PS1 mice[412]. Vehicle-treated transgenic mice needed more time to find the hidden platform after six sessions compared to WT littermates (FIG. 3C). When APP/PS1 mice were treated previously with sildenafil they showed a marked improvement of their behavioural performance. Sildenafil did not affect the performance in WT littermates (FIG. 3C). Reference memory was also assessed with the probe trial, another test of spatial reference memory[420]. This task is performed after the sixth hidden-platform session. The platform is removed from the water and the animals are allowed to search for 60 seconds. A mouse, knowing that the platform was in a certain position, will trawl repeatedly over that position looking for it. The mouse is thus indicating that it knows the position independently of such tactile cues as hitting the platform. The amount of time spent in each quadrant of the maze can be used to evaluate the spatial bias of an animal's search pattern. Vehicle-treated WT mice spent more time in the target quadrant (TQ), where the platform had been located during training than in other quadrants, than in the adjacent quadrant to the right (AR), in the adjacent quadrant to the left (AL), or in the opposite quadrant (OQ) (FIG. 3D). Also, sildenafil improved the performance of the APP/PS1 mice which searched more in the quadrant where the platform had been located during training than in other quadrants (FIG. 3D). In contrast, vehicle-treated APP/PS1 mice did not retain the information and spent less time in the TQ compared to vehicle-treated WT littermates. Sildenafil-treated WT mice remembered where the platform was the previous days and spent about the same time as vehicle-treated WT littermates. A visible platform trial performed after the probe trials did not reveal any difference in the time to reach the platform and swimming speed among the 4 groups (FIGS. 11A-11B).

To add depth to the analysis of the functional changes that underlie the striking effects of sildenafil on APP/PS1 mice behavioral performance, synaptic function in hippocampi from the same mice was examined. In contrast to 3-month-old double transgenic mice, 8- to 9-month old APP/PS1 animals show a reduction of synaptic strength[412]. Previous treatment with sildenafil in APP/PS1 mice produced greater values of fEPSP slope in response to a 35V stimulus in slices from 8 to 9 month old then in vehicle-treated APP/PS1 littermates slices (FIG. 4A). On the other hand, sildenafil did not change responses in WT littermates. CA3-CA1 connections that had been tested for BST were also assessed for their capacity of undergoing potentiation. LTP values recorded from slices obtained from APP/PS1 that had been previously treated with sildenafil were similar to their sildenafil treated-WT littermates and far greater than those from vehicle-treated APP/PS1 littermates (FIGS. 4B-4C). Eight- to nine-month old WT mice showed similar amounts of potentiation whether treated with sildenafil or with vehicle (FIG. 4C). No differences were noted in the baseline transmission of the four groups of mice in the absence of tetanus (FIGS. 4B-4C). Taken together, these data indicate that one course of treatment with sildenafil is protects APP/PS1 mice against synaptic dysfunction for a long time.

Effects of Sildenafil on CREB Phosphorylation in APP/PS1 Mice.

Given that the duration of action of sildenafil is relatively short, a direct effect of the PDE5 inhibitor cannot be held responsible for its long-term effects. CREB has been implicated in the regulation of genes whose expression results in the formation and stabilization of long-term memory and CREB phosphorylation is required for CREB ability to bind to CREB binding protein (CBP) and to stimulate CRE dependent gene expression[421]. Aβ elevation is also known to block the tetanus-induced increase in phosphorylation of the memory molecule CREB (Puzzo, D., et al. Amyloid-beta peptide inhibits activation of the nitric oxide/cGMP/cAMP-responsive element-binding protein pathway during hippocampal synaptic plasticity. *J Neurosci* 25, 6887-6897 (2005)[422]. Thus, to gain insights into the mechanism by which the inhibitor produces the long-term changes in synaptic physiology and behaviour, levels of CREB phosphorylation were measured in sildenafil- and vehicle-treated transgenic and WT mice. Hippocampal slices were treated as described in the electrophysiological experiments, fixed 60 minutes after the treatment, stained with anti-phospho-CREB antibodies at Ser-133, and viewed on a confocal microscope. An increase in the intensity of immunofluorescence in CA1 cell body area of WT mice after application of the tetanus compared to control non-tetanized slices (FIGS. 5A-5B) was observed. APP/PS1 animals did not have the physiological increase of CA1 phospho-CREB immunofluorescence after tetanus (FIGS. 5A-5B), however, sildenafil re-established normal phospho-CREB increase in tetanized slices of the double transgenics (FIGS. 5A-5B). Sildenafil did not affect the tetanus-induced increase in immunofluorescence in WT animals (FIGS. 5A-5B).

Mice were injected with 3 mg/kg/day sildenafil or vehicle at the age of 3 months and then left without treatment for 9-12 weeks. An increase in immunofluorescence intensity in CA1 cell body area of WT mice after application of the tetanus compared to non-tetanized control slices was observed (FIG. 5C). APP/PS1 mice did not reveal the physiological increase of phospho-CREB after tetanus but previous treatment with sildenafil re-established it (FIG. 5C). Moreover, phospho-CREB immunofluorescence did not vary in slices from sildenafil-treated WT mice with tetanic stimulation (FIG. 5C). Thus, without being bound by theory, at the root of the long-term improvement in synaptic physiology and behaviour there is the re-establishment of the increase of CREB phosphorylation in APP/PS1 mice following tetanic stimulation of the Schaffer collateral-CA1 connection.

Effects of Sildenafil on Aβ Levels of APP/PS1 Mice.

Improvement in CREB phosphorylation in the APP/PS1 mice was examined with respect to whether the inhibitor also affected Aβ levels, a hallmark of AD. ELISA of extracts of cerebral cortices revealed a difference in human $A\beta_{40}$ and $A\beta_{42}$ levels both immediately after 1 course of 3 week treatment with sildenafil at the age of 3 months in APP/PS1 mice and in mice that were sacrificed after the second round of behavioural testing at 7-10 months (FIG. 6A, FIG. 7A). Thus, without being bound by theory, a reduction in Aβ levels is at the bases of the prolonged beneficial effect by sildenafil.

Aβ originates from APP through a proteolytic process catalyzed by secretases, producing different fragments with characteristic functions[424]. APP is first cleaved by α and β secretases that generate soluble extracellular fragments, named α-APPs and β-APPs, and three forms of carboxyterminal fragments (CTFs): C83 by α-secretase cleavage, C89 and C99 by β-secretase cleavage[425, 426]. CTFs are substrates of γ-secretase generating C-terminal peptides of 57-58 residues (APP intracellular domain, AID) and Aβ fragments from CTFβ[427]. To assess whether the decrease in Aβ levels was related to changes in APP processing [see FIG. 20], western blot analyses on mice brain cortex for full length APP and its fragments was performed. No differences in levels of full-length APP and sAPPα were observed in 3 months old APP/PS1 mice treated with vehicle or sildenafil (FIGS. 6B-6D), whereas a decrease in sAPPβ (FIGS. 6B, 6E) and an increase of the CTF fragment C83 and C99 were found in APP/PS1 after sildenafil treatment compared to vehicle-treated transgenics (FIGS. 6B, 6F).

APP levels were found unchanged also in 7-10 months old transgenic mice (FIGS. 7B-7C). They have been treated with daily injections of sildenafil for 3 weeks at age of 3 months. APP/PS1 mice treated with sildenafil showed an increase of sAPPα protein levels, showing that the treatment modifies α-secretase activity (FIGS. 7B, 7D). Moreover, a decrease in sAPPβ in transgenic mice treated with sildenafil was observed (FIGS. 7B, 7E) showing a down-regulation of BACE activity. Analysis of the levels of the CTF fragments C83 and C99 did not reveal any change due to the treatment (FIGS. 7B, 7F). Thus, without being bound by theory, the reduction in Aβ levels by sildenafil is due to an action of the inhibitor onto α- and β-secretase activity.

Discussion

It is shown that a treatment with the PDE5 inhibitor sildenafil rescues synaptic and memory deficits in a transgenic mouse model of amyloid deposition. Sildenafil also re-establishes the increase in phosphorylation of the transcription factor and memory molecule CREB. In addition, the inhibitor counteracts the negative effects of high levels of Aβ on synaptic function, memory and CREB phosphorylation not only immediately, but also for a prolonged period beyond the drug administration. Finally, sildenafil causes an immediate and long-lasting reduction in $A\beta_{40}$ and $A\beta_{42}$ levels. Sildenafil causes a prolonged reduction in Aβ levels which in turn re-establishes normal synaptic function and memory.

A relevant finding of the present study is the beneficial effect of sildenafil onto synaptic dysfunction in a mouse model of amyloid deposition. This finding is consistent with studies on slices showing that cGMP increase through the use of NO donors or cGMP analogs rescues the reduction of LTP and the inhibition of CREB phosphorylation induced by exogenous application of Aβ (Puzzo, D., et al. *J Neurosci* 25, 6887-6897 (2005)). Given that altered synaptic function is a fundamental aspect in the cognitive decline of AD[428], an advantage of using PDE5 inhibitors in AD can be that this class of compounds will counteract aspects of the disease linked to synaptic dysfunction that can be relevant to memory loss.

Another discovery reported in the study is the reversal of the memory impairment in an amyloid-depositing mouse model following PDE5 inhibition. These results are in agreement with the observation that NO-mimetic molecules can reverse the cognitive impairment caused by scopolamine[429], or by forebrain cholinergic depletion[430], showing that stimulating the NO/cGMP signal transduction system can provide new, effective treatments for cognitive disorders. With regard to the beneficial effect on memory, it is interesting to note that inhibition of PDE5 activity during a narrow time window immediately after training for fear learning or after acquisition of the spatial task (but not 5 min before training for fear learning or acquisition of the spatial task) improves learning in the transgenic animals. Considering that the in vivo half-life of sildenafil is 0.4 hrs in rodents[410], there can be a time-window during the first 20-25 min after the electric shock or the acquisition of the spatial task during which learning processes are susceptible of improvement by PDE5 inhibition. Moreover, given that the beneficial effect of sildenafil was observed with its injection after the training, inhibition of PDE5 acts on memory consolidation mechanisms, and not on aspects of performance, such as perception of pain or of the environment.

In the present studies a brief course of sildenafil was still beneficial after 3 to 5 months from the drug administration. Considering that sildenafil has a short half-life, this effect can be due to a long-lasting synaptic modification through an action on gene expression. CREB has been implicated in the regulation of genes whose expression results in the formation and stabilization of long-term memory probably through the formation of new synaptic connections[416]. When phospho-CREB binds to CREB binding protein (CBP), it stimulates CRE dependent gene expression. CBP functions as a co-activator that facilitates interactions with the basal transcription machinery by working as an acetyltransferase that catalyzes acetylation of the histone H3 of the chromatin, causing a loss in chromosomal repression and increase in the transcription of memory associated genes. Histone acetylation can be self-perpetuating, creating a functionally stable chromatin state and thus chronic changes in the rates of specific gene expression[431-433]. Thus, without being bound by theory, the prolonged beneficial effect of sildenafil is due to a permanent increase in histone acetylation. Inhibition of histone de-acetylation that is normally due to a group of enzymes with a reverse effect of CBP, re-establishes normal LTP and memory in APP/PS1 mice[434].

Decrease in Aβ levels by PDE5 inhibition in transgenic mice is another important finding of the present studies. Without being bound by theory, the beneficial effect of sildenafil is specific to PDE5 inhibition because tadalafil, a highly selective PDE5 inhibitor reproduced the effect of sildenafil on synaptic dysfunction, whereas IC354, a selective inhibitor of PDE1, another PDE that can be inhibited by sildenafil, did not re-establish normal LTP in slices from the double transgenic mice. Moreover, differently than rolipram which did not improve spatial working memory immediately after its administration, sildenafil immediately augmented spatial working memory. Most importantly, a striking difference between the effect of sildenafil and those of rolipram is that the former reduced Aβ levels in the brains of APP/PS1 mice, whereas the latter did not affect Aβ concentration.

When proposing a new class of drugs as therapeutic agents it is important to consider their side effects. This can have determined the failure of PDE4 inhibitors to enhance memory. An advantage of using PDE5 inhibitors is that their side effects are known as they have already been utilized for many years. Priapism has been reported to occur in a few cases following the intake of PDE5 inhibitors. However, the current view about the cause of priapism is that it is due to a dysregulation of PDE5 function following down-regulation of the NO pathway[440]—a phenomenon that is also caused by Aβ increase (Puzzo, D., et al. Amyloid-beta peptide inhibits activation of the nitric oxide/cGMP/cAMP-responsive element-binding protein pathway during hippocampal synaptic plasticity. *J Neurosci* 25, 6887-6897 (2005))—such that, paradoxically, PDE5 inhibitors have been proposed as therapeutic agents against priapism[441, 442]. Additional adverse events of the PDE5 inhibitors include mild vasodilatory effects such as headache, flushing, dyspepsia, and nasal congestion or rhinitis, which can warrant caution in proposing PDE5 inhibitors as AD agents. However, although Aβ is primarily accumulating in the CNS, Aβ is also present in the blood of patients affected by AD and other neurological disorders characterized by abnormal Aβ production[443, 444]. Intriguingly, systemic Aβ potentiates vasoconstriction not only in cerebral vasculature but also in other districts of the vascular system[445-451]. Moreover, hypertension is often associated with AD[446, 448, 449]. Thus, it is very appealing to think that PDE5 inhibitors can counteract not only memory loss and Aβ generation, but also vascular symptoms that often affect AD patients Drugs acting on the NO-cascade have vascular effects that can affect the cognitive performance. Thus, an alternative explanation for the beneficial effect of sildenafil is that the inhibitor works through a vascular effect instead of an intra-neuronal effect. This is unlikely as inhibition of PDE5 re-established normal LTP in slices directly exposed to PDE5 inhibitors. Moreover, although cAMP analogues have been shown to induce more dilatation of cerebral arterioles in the parietal cortex than cGMP analogues[455], only 8-Br-cGMP (but not 8-Br-cAMP) improved memory performance in rodents[46] showing that vascular mechanisms can not account for the cGMP effects. Most importantly, tadalafil that does not cross the BBB did not reproduce the behavioral effects of sildenafil.

The present findings are in agreement with reports showing that upregulation of the NO cascade has a protective effect on Aβ-induced damage in the CNS[456-458]. For instance, studies performed on PC12 cells, sympathetic neurons and hippocampal neurons, have shown that treatment with the NO generator S-nitroso penicillamine has a neuroprotective action through nitrosylation that inhibits the pro-apoptotic factor caspase-2[457]. Aβ has been found to impair NO generation by different mechanisms including a decrease in NMDA receptor signal transduction[456], subtraction of NADPH availability to NOS[459], and inhibition of the phosphorylation of the serine-threonine kinase Akt[451]. The superior temporal cortex of AD patients shows a reduction in soluble guanylyl cyclase activity[460]. Soluble guanylyl cyclase is decreased following Aβ exposure in brain astroglial cells[461]. PDE activity increase has been found on both isolated blood cells and cultured microglia, in which PDE5 inhibition re-establishes normal vasoactivity and blocks inflammatory response caused by Aβ[462]. However, NO has also been viewed as a major agent of neuropathology and cell death when it is produced in high quantity. High amounts of NO lead to generation of significant quantity of peroxinitrites that are responsible for oxidative and nitrosative stress in Aβ-induced cell death[463-469]. These opposite findings can be reconciled with the findings with the observation that release of low amounts of NO by the constitutive forms of NOS including both the neuronal and the endothelial isoforms, n-NOS and e-NOS, promotes synaptic plasticity and learning, whereas uncontrolled production of high amounts of the gas by the inducible form of NO-synthase (iNOS) can promote oxidative and nitrosative stress via production of peroxinitrite[463-469] [see FIG. 19 and FIG. 21]. The current status of drug research exploiting these discoveries is focused both on finding ways to upregulate the NO cascade and therefore elicit neuroprotection, as well as on finding ways to block peroxinitrite toxic effects in order to limit neuropathology[470]. The present therapeutic strategy intervening with PDE5 offers the advantage of bypassing NO production by focusing on steps at the downstream level of NO generation [see FIG. 19 and FIG. 21].

CONCLUSION

Sildenafil treatment ameliorates synaptic and cognitive dysfunction in AD mouse mode. Agents increasing cGMP levels rescue the reduction of L-LTP, Tetanus-induced increase of CREB phosphorylation, and Contextual learning in APP/PS1 mice. The beneficial effect of the increase in cGMP levels by sildenafil on cognition, synaptic transmission and CREB phosphorylation can be extended beyond the duration of its administration.

Methods

Animals:
Double transgenic mice expressing both the human APP (K670M:N671L) and PS1 (M146L) (line 6.2) mutations were compared to WT littermates. They were obtained by crossing APP with PS1 animals. To identify the genotype of the animals, the polymerase chain reaction was used on samples of the tail[412]. All experiments were performed using male mice. The animals were maintained on a 12-12 h light-dark cycle (with light onset at 06:00 hours) in temperature and humidity controlled rooms of the Columbia University Animal Facility. Food and water were available ad libitum.

Drug Preparation:
Sildenafil was synthesized in 6 steps according to reported procedures (Terrett et al., 1996) (U.S. Pat. No. 5,346,901. 1994). Briefly, commercially available 2-ethoxybenzoic acid was converted to 2-ethoxybenzoyl chloride with thionyl chloride. Reaction of 2-ethoxybenzoyl chloride with 4-amino-1-methyl-3-N-propylpyrazole-5-carboxamide yielded the amide in 90% yield. Cyclization of the amide using NaOH afforded pyrazolopyrimidinone in 77% yield. Chlorosulfonylation of the pyrazolopyrimidinone in chlorosulfonic acid, followed by reaction with N-methylpiperazine provided sildenafil in 90% yield. Tadalafil was also synthesized according to reported procedures (Daugan et al., 2003b). Briefly, D-tryptophan methyl ester reacted with piperonal under Pictet-Spengler reaction condition (TFA/CH2Cl2/MeOH) and the resulting product condensed with chloroacetyl chloride to provide acylated intermediate. Reaction of the intermediate with N-methyl amine provided tadalafil. Tadalafil was diluted in 0.1% DMSO.

Drug Administration:

Three-month-old APP/PS1 and WT mice were separated into 4 groups: APP/PS1 mice treated with vehicle, APP/PS1 mice treated with PDE inhibitor, WT mice treated with vehicle, and WT mice treated with PDE inhibitor. In the experiments assessing the acute effects of PDE inhibition on synaptic dysfunction sildenafil (50 nM) or tadalafil (50 nM) or IC354 (1 μM) were directly given to the hippocampal slices through the perfusion system for 10 min prior to the theta burst [see FIG. 23]. In the remaining experiments, sildenafil was injected via i.p. The drug was administered either acutely or for 1 course of 3 week treatment. For assessment of the short-term effects of sildenafil, the drug was given at a concentration of 3 mg/kg immediately after the training. This dose yields concentrations of ~2.5 μM cGMP in the hippocampus[453]. For assessment of long-term effects, sildenafil was given daily by i.p. injection at a concentration of 3 mg/kg for 3 weeks and then treatment was stopped for 9-12 weeks prior to behavioral testing. Contextual and cued fear conditioning was performed for 3 days. Radial-arm water-maze (RAWM) was performed for 3 weeks. Then, the animals were sacrificed for electrophysiological recordings. To decide the time of administration of sildenafil in the acute experiments, a series of studies was performed in which the inhibitor was injected i.p. at 5 min before the electric shock or at 5 min before the first acquisition trial with the radial arm water maze. No beneficial effect was observed both on the freezing time and the number of errors in sildenafil-injected APP/PS1 mice (sildenafil-treated APP/PS1 mice demonstrated a freezing time equal to ~90% that of vehicle-treated APP/PS1 mice; n=7 males for sildenafil-treated transgenics and 6 males for vehicle-treated transgenics, P>0.05; ~5 errors in the retention trial for both sildenafil- and vehicle-treated transgenics, n=6 males for sildenafil-treated transgenics and 5 males for vehicle-treated transgenics, P>0.05, sildenafil did not affect the behavioral performance of WT mice in both tasks, n=5 males for all the conditions). Thus, all the behavioral experiments on the acute effects of sildenafil reported in the result section were performed with injection after the training.

Electrophysiological Analysis:

Animals were sacrificed by cervical dislocation followed by decapitation. Hippocampi were quickly removed. Transverse hippocampal slices (400 μm) were cut and recorded according to standard procedures[454]. For example, following cutting hippocampal slices were transferred to a recording chamber where they were maintained at 29° C. and perfused with artificial cerebrospinal fluid (ACSF) continuously bubbled with 95% $O_2$ and 5% $CO_2$. The ACSF composition in mM was: 124.0 NaCl, 4.4 KCl, 1.0 $Na_2HPO_4$, 25.0 $NaHCO_3$, 2.0 $CaCl_2$, 2.0 $MgSO_4$, 10.0 glucose. CA1 fEPSPs were recorded by placing both the stimulating and the recording electrodes in CA1 stratum radiatum. BST was assayed either by plotting the peak amplitude of the fiber volley against the slope of the fEPSP, or by plotting the stimulus voltages against slopes of fEPSP. For LTP experiments, a 15 min baseline was recorded every min at an intensity that evokes a response ~35% of the maximum evoked response. LTP was induced using θ-burst stimulation (4 pulses at 100 Hz, with the bursts repeated at 5 Hz and each tetanus including 3 ten-burst trains separated by 15 sec). In a set of experiments LTP was induced with 1 or 2 ten-burst trains to assess the effect of sildenafil on LTP induced with a different strength of the tetanus. Responses were recorded for 2 hrs after tetanization and measured as field-excitatory-post-synaptic potential (fEPSP) slope expressed as percentage of baseline. The results were expressed as mean±Standard Error Mean (SEM).

Behavioral Studies—Fear Conditioning:

This type of cognitive test is much faster than other behavioral tasks that require multiple days of training and testing[414, 417]. The conditioning chamber was in a sound-attenuating box. A clear Plexiglas window allowed the experimenter to film the mouse performance with a camera placed on a tripod and connected to the Freezeframe software (MED Ass. Inc.). To provide background white noise (72 dB), a single computer fan was installed in one of the sides of the sound-attenuating chamber. The conditioning chamber had a 36-bar insulated shock grid floor. The floor was removable, and after each experimental subject, the floor was cleaned with 75% ethanol and then with water. Only one animal at a time was present in the experimentation room. For the cued and contextual conditioning experiments, mice were placed in the conditioning chamber for 2 min before the onset of a discrete tone (CS) (a sound that lasted 30 sec at 2800 Hz and 85 dB). In the last 2 sec of the CS, mice were given a foot shock (US) of 0.50 mA for 2 sec through the bars of the floor. After the CS/US pairing, the mice were left in the conditioning chamber for another 30 sec and were then placed back in their home cages. Freezing behavior, defined as the absence of all movement except for that necessitated by breathing, was scored using the Freezeview software.

To evaluate contextual fear learning, freezing was measured for 5 min (consecutive) in the chamber in which the mice was trained 24 hr after training. To evaluate cued fear learning, following contextual testing, the mice were placed in a new context (triangular cage with smooth flat floor and with vanilla odorant) for 2 min (pre-CS test), after which they were exposed to the CS for 3 min (CS test), and freezing will be measured. Sensory perception of the shock was determined through threshold assessment. A sequence of single foot shocks was delivered to animals placed on the same electrified grid used for fear conditioning. Initially, a 0.1 mV shock was delivered for 1 sec, and the animal behavior was evaluated for flinching, jumping, and vocalization. At 30 sec intervals the shock intensity was increased by 0.1 mV to 0.7 mV and then returned to 0 mV in 0.1 mV increments at 30 sec intervals. Threshold to vocalization, flinching, and then jumping was quantified for each animal by averaging the shock intensity at which each animal manifests a behavioral response to the foot shock. No difference was observed among different groups of mice in the experiments in which fear conditioning was tested in the presence of sildenafil or vehicle.

Behavioral Studies—Spatial Working Memory:

This is a type of short-term memory that can be studied with the RAWM test[12]. Briefly, the RAWM consisted of a white tank (120 cm diameter) filled with water (24-25° C.) and made opaque by the addition of non-toxic white paint. Within the tank walls were positioned so as to produce six arms, radiating from a central area. Spatial cues were presented on the walls of the testing room. At the end of one of the arms was positioned a clear 10 cm submerged (1.5 cm) platform that remained in the same location for every trial in one day, but was moved about randomly from day to day. On each trial the mouse started the task from a different randomly chosen arm. The mouse did not use its long-term memory of the location of the platform on previous days, but relied on the short-term memory of its location on the day in question based on spatial cues that were present in the room. Each trial lasted 1 min and errors were counted each time the mouse entered the wrong arm or needed more than 20 sec to reach the platform. After each error the mouse was pulled back to the start arm for that trial. After 4 consecutive acquisition trials, the mouse was placed in its home cage for 30 min, then returned to the maze and administered a $5^{th}$ retention trial. Testing was considered completed as the WT mice made the same number of errors at the $4^{th}$ and $5^{th}$ trial. The scores for each mouse on the last three days of testing were averaged and used for statistical analysis.

Behavioral Studies—Reference Memory: The task studied with the Morris water maze has been previously described[12]. Briefly, mice were trained in 2 daily sessions (4 hours apart), each consisting of 3 trials (1 minute each), for 3 days. Time required to reach the hidden platform was recorded. To test the retention of the spatial memory, 4 probe trials were performed after the training with the platform moved. The maze was divided into 4 quadrants. The percent of time spent in the quadrant that previously contained the platform was recorded and analyzed with a video tracking system (HVS 2020; HVS Image).

Behavioral Studies—Visible Platform Testing:

Visible-platform training to test visual and motor deficits was performed in the same pool as in the Morris water maze, with the platform marked with a black flag and positioned randomly from trial to trial. Time to reach the platform and speed was recorded and analyzed with a video-tracking system (HVS 2020, HVS Image, UK).

Immunocytochemical Experiments:

Immunocytochemical measurements of phospho-CREB were performed as previously described (Puzzo, D., et al. Amyloid-beta peptide inhibits activation of the nitric oxide/cGMP/cAMP-responsive element-binding protein pathway during hippocampal synaptic plasticity. *J Neurosci* 25, 6887-6897 (2005)). Briefly, hippocampal slices were fixed in ice-cold 4% paraformaldehyde at 1 minute after the treatment. Slices were washed three times in phosphate-buffered saline (PBS), treated with 0.3% Triton X-100 for 60 minutes, washed three times in PBS again, treated with 50 mM ammonium chloride for 20 minutes and incubated in 10% goat serum for 60 minutes. Slices were incubated with the primary antibody (rabbit polyclonal anti-phospo-CREB from Upstate Biotechnology diluted 1:100 in 10% goat serum) for 36 hours at 4° C. Slices were washed in PBS (6 times, 2 hours each time), incubated with the secondary antibody (goat anti-rabbit antibody labelled with Alexa Fluor 488, from Molecular Probes), diluted 1:100 in 10% goat serum, for 12 hours at 4° C. and washed in PBS again (6 times, 2 hours each time). Slices were examined by confocal microscopy (Nikon D-Eclipse Cl) using a 4× and a 16× objective. Kalman averages of 4 scans were collected for each image. The analysis was performed using the NIH image software by an observer who was blind to the experimental treatment. The mean fluorescence intensity that exceeded a threshold set above background was determined for each slice in CA1 cell body area. The values were normalized to the values from untreated control slices from the same animal and expressed as mean percent of control±SEM. The specificity of the immunofluorescence was confirmed by omitting the primary antibody, which resulted in a significant reduction in fluorescence intensity.

Determination of Aβ Levels:

Frozen hemi-brains were weighed and homogenized in 5 M guanidine HCL/50 mM Tris HCL solution. $A\beta_{40}$ and $A\beta_{42}$ were measured using human β amyloid ELISA kits (Biosource, CA), according to the manufacturer's protocol. ELISA signals were reported as the mean+s.e.m. in nanograms of Aβ per milligram of cortex. For example, hippocampal slices were fixed in ice-cold 4% paraformaldehyde at 1 minute after the treatment. Slices were washed three times in phosphate-buffered saline (PBS), treated with 0.3% Triton X-100 for 60 minutes, washed three times in PBS again, treated with 50 mM ammonium chloride for 20 minutes and incubated in 10% goat serum for 60 minutes. Slices were incubated with the primary antibody (rabbit polyclonal anti-phospo-CREB from Upstate Biotechnology diluted 1:100 in 10% goat serum) for 36 hours at 4° C. Slices were washed in PBS (6 times, 2 hours each time), incubated with the secondary antibody (goat anti-rabbit antibody labelled with Alexa Fluor 488, from Molecular Probes), diluted 1:100 in 10% goat serum, for 12 hours at 4° C. and washed in PBS again (6 times, 2 hours each time). Slices were examined by confocal microscopy (Nikon D-Eclipse Cl) using a 4× and a 16× objective. Kalman averages of 4 scans were collected for each image. The analysis was performed using the NIH image software by an observer who was blind to the experimental treatment. The mean fluorescence intensity that exceeded a threshold set above background was determined for each slice in CA1 cell body area. The values were normalized to the values from untreated control slices from the same animal and expressed as mean percent of control±SEM. The specificity of the immunofluorescence was confirmed by omitting the primary antibody, which resulted in a significant reduction in fluorescence intensity.

Western Blot:

Mice brains were homogenized in buffer (20 mM tris base, 1 mM EDTA, 1 mM EGTA, 250 mM sucrose) containing protease inhibitors. Part of the homogenates was ultracentrifugated at 100,000 g for 1 h and the supernatants were used to analyze the sAPPα and the sAPPβ fragments. The protein concentration in each homogenate was quantified to analyze the equal amounts of protein from each sample. Samples were loaded into the wells of a 4-12% Bis-Tris precast gel, electrophoresed and transferred according to manufacturer's protocol. After Ponceau S staining, membranes were washed and incubated in 5% non-fat milk powder in PBS for 1 h at room temperature. Then, they were incubated overnight at 4° C. with the following primary antibodies, diluted in goat serum 5% in PBS: mouse 22C11 for APP full length detection (1:4000, Sigma); mouse sAPPα and Swedish sAPPβ (1:4000 and 1:1000, IBL), rabbit AbD for CTFs (1:250, Zymed), mouse Tubulin as control (1:20.000, Sigma). After overnight incubation, membranes were washed 3 times in PBS for 30 minutes and incubated with goat anti-mouse or goat-anti-rabbit antibody, diluted in 5% non-fat milk powder in PBS (1:4000 and 1:2000). After 30 minutes washing in PBS, radiographic detection was performed after exposure to ECL (Pierce). The analysis was performed using the NIH image software by an observer who was blind to the experimental treatment. The mean intensity that was determined for each samples and the values were normalized to the values from tubulin and expressed as mean percent of control±SEM.

Statistical Analyses:

For all experiments mice were coded to "blind" investigators with respect to genotype and treatment. Data were expressed as mean±SEM. Results were analyzed with student t-test (pairwise comparisons) or ANOVA with post-hoc correction (multiple comparisons). The level of significance was set for P<0.05.

REFERENCES FOR EXAMPLE 1

A1. Selkoe, D. J. Alzheimer's disease is a synaptic failure. *Science* (New York, N. Y 298, 789-791 (2002).
A2. Puzzo, D., et al. Amyloid-beta peptide inhibits activation of the nitric oxide/cGMP/cAMP-responsive element-binding protein pathway during hippocampal synaptic plasticity. *J Neurosci* 25, 6887-6897 (2005).
A3. Colton, C. A., et al. NO synthase 2 (NOS2) deletion promotes multiple pathologies in a mouse model of Alzheimer's disease. *Proceedings of the National Academy of Sciences of the United States of America* 103, 12867-12872 (2006).
A4. van Staveren, W. C., Steinbusch, H. W., Markerink-van Ittersum, M., Behrends, S. & de Vente, J. Species differences in the localization of cGMP-producing and NO-responsive elements in the mouse and rat hippocampus using cGMP immunocytochemistry. *Eur J Neurosci* 19, 2155-2168 (2004).
A5. Van Staveren, W. C., et al. mRNA expression patterns of the cGMP-hydrolyzing phosphodiesterases types 2, 5, and 9 during development of the rat brain. *J Comp Neurol* 467, 566-580 (2003).
A6. Prickaerts, J., de Vente, J., Honig, W., Steinbusch, H. W. & Blokland, A. cGMP, but not cAMP, in rat hippocampus is involved in early stages of object memory consolidation. *Eur J Pharmacol* 436, 83-87 (2002).
A7. Baratti, C. M. & Boccia, M. M. Effects of sildenafil on long-term retention of an inhibitory avoidance response in mice. *Behav Pharmacol* 10, 731-737 (1999).
A8. FDA. Viagra tablets (sildenafil citrate). Review and evaluation of pharmacology and toxicology data. Report from the Division of Cardio-renal Drug Products (HFD-10). Center for Drug Evaluation and Research. in *Food and Drug Administration* 121-122 (Washington, D C, 1998).
A9. Prickaerts, J., et al. Phosphodiesterase type 5 inhibition improves early memory consolidation of object information. *Neurochem Int* 45, 915-928 (2004).
A10. Walker, D. K., et al. Pharmacokinetics and metabolism of sildenafil in mouse, rat, rabbit, dog and man. *Xenobiotica* 29, 297-310 (1999).
A11. Daugan, A., et al. The discovery of tadalafil: a novel and highly selective PDE5 inhibitor. 2: 2,3,6,7,12,12a-hexahydropyrazino[1',2':1,6]pyrido[3,4-b]indole-1,4-dione analogues. *J. Med Chem* 46, 4533-4542 (2003).
A12. Trinchese, F., et al. Progressive age-related development of Alzheimer-like pathology in APP/PS1 mice. *Ann Neurol* 55, 801-814 (2004).
A13. Snyder, P. B., Esselstyn, J. M., Loughney, K., Wolda, S. L. & Florio, V. A. The role of cyclic nucleotide phosphodiesterases in the regulation of adipocyte lipolysis. *Journal of lipid research* 46, 494-503 (2005).
A14. Gong, B., et al. Persistent improvement in synaptic and cognitive functions in an Alzheimer mouse model following rolipram treatment. *J. Clin. Invest.* 114, 1624-1634 (2004).
A15. Phillips, R. G. & LeDoux, J. E. Differential contribution of amygdala and hippocampus to cued and contextual fear conditioning. *Behav Neurosci* 106, 274-285 (1992).
A16. Tully, T., Bourtchouladze, R., Scott, R. & Tallman, J. Targeting the CREB pathway for memory enhancers. *Nat Rev Drug Discov* 2, 267-277 (2003).
A17. Gong, B., et al. Persistent improvement in synaptic and cognitive functions in an Alzheimer mouse model after rolipram treatment. *J Clin Invest* 114, 1624-1634 (2004).
A18. Morgan, D., et al. A beta peptide vaccination prevents memory loss in an animal model of Alzheimer's disease. *Nature* 408, 982-985 (2000).
A19. Diamond, D. M., Park, C. R., Heman, K. L. & Rose, G. M. Exposing rats to a predator impairs spatial working memory in the radial arm water maze. *Hippocampus* 9, 542-552 (1999).
A20. Schenk, F. & Morris, R. G. Dissociation between components of spatial memory in rats after recovery from the effects of retrohippocampal lesions. *Exp Brain Res* 58, 11-28 (1985).
A21. Silva, A. J., Kogan, J. H., Frankland, P. W. & Kida, S. CREB and memory. *Annu Rev Neurosci* 21, 127-148 (1998).
A22. Gong, B., et al. Ubiquitin Hydrolase Uch-L1 Rescues beta-Amyloid-Induced Decreases in Synaptic Function and Contextual Memory. *Cell* 126, 775-788 (2006).
A23. Lu, Y. F., Kandel, E. R. & Hawkins, R. D. Nitric oxide signaling contributes to late-phase LTP and CREB phosphorylation in the hippocampus. *J Neurosci* 19, 10250-10261 (1999).
A24. Mattson, M. P. Cellular actions of beta-amyloid precursor protein and its soluble and fibrillogenic derivatives. *Physiol Rev* 77, 1081-1132 (1997).
A25. Russo, C., et al. Signal transduction through tyrosine-phosphorylated C-terminal fragments of amyloid precursor protein via an enhanced interaction with Shc/Grb2 adaptor proteins in reactive astrocytes of Alzheimer's disease brain. *The Journal of biological chemistry* 277, 35282-35288 (2002).
A26. Simons, M., et al. Amyloidogenic processing of the human amyloid precursor protein in primary cultures of rat hippocampal neurons. *J Neurosci* 16, 899-908 (1996).
A27. Passer, B., et al. Generation of an apoptotic intracellular peptide by gamma-secretase cleavage of Alzheimer's amyloid beta protein precursor. *J Alzheimers Dis* 2, 289-301 (2000).
A28. Masliah, E. Mechanisms of synaptic dysfunction in Alzheimer's disease. *Histol Histopathol* 10, 509-519 (1995).
A29. Thatcher, G. R., Bennett, B. M., Dringenberg, H. C. & Reynolds, J. N. Novel nitrates as NO mimetics directed at Alzheimer's disease. *J Alzheimers Dis* 6, S75-84 (2004).
A30. Bennett, B. M., et al. Cognitive deficits in rats after forebrain cholinergic depletion are reversed by a novel NO mimetic nitrate ester. *Neuropsychopharmacology* 32, 505-513 (2007).
A31. Turner, B. M. Cellular memory and the histone code. *Cell* 111, 285-291 (2002).
A32. Battaglioli, E., et al. REST repression of neuronal genes requires components of the hSWI.SNF complex. *The Journal of biological chemistry* 277, 41038-41045 (2002).
A33. Lunyak, V. V., et al. Corepressor-dependent silencing of chromosomal regions encoding neuronal genes. *Science* (New York, N.Y. 298, 1747-1752 (2002).
A34. Francis, Y. I., et al. Beneficial effect of the histone deacetylase inhibitor TSA in a mouse model of Alzheimer's disease. in *Soc Neurosci. Abstr.* 548.545 (San Diego, 2007).
A35. Jantzen, P. T., et al. Microglial activation and beta-amyloid deposit reduction caused by a nitric oxide-releasing nonsteroidal anti-inflammatory drug in amyloid precursor protein plus presenilin-1 transgenic mice. *J Neurosci* 22, 2246-2254 (2002).

A36. Nicholson, C. D. Pharmacology of nootropics and metabolically active compounds in relation to their use in dementia. *Psychopharmacology (Berl)* 101, 147-159 (1990).

A37. Nehlig, A., Daval, J. L. & Debry, G. Caffeine and the central nervous system: mechanisms of action, biochemical, metabolic and psychostimulant effects. *Brain Res Brain Res Rev* 17, 139-170 (1992).

A38. Randt, C. T., Judge, M. E., Bonnet, K. A. & Quartermain, D. Brain cyclic AMP and memory in mice. *Pharmacology, biochemistry, and behavior* 17, 677-680 (1982).

A39. Villiger, J. W. & Dunn, A. J. Phosphodiesterase inhibitors facilitate memory for passive avoidance conditioning. *Behavioral and neural biology* 31, 354-359 (1981).

A40. Champion, H. C., Bivalacqua, T. J., Takimoto, E., Kass, D. A. & Burnett, A. L. Phosphodiesterase-5A dysregulation in penile erectile tissue is a mechanism of priapism. *Proceedings of the National Academy of Sciences of the United States of America* 102, 1661-1666 (2005).

A41. Burnett, A. L., Bivalacqua, T. J., Champion, H. C. & Musicki, B. Long-term oral phosphodiesterase 5 inhibitor therapy alleviates recurrent priapism. *Urology* 67, 1043-1048 (2006).

A42. Rajfer, J., Gore, J. L., Kaufman, J. & Gonzalez-Cadavid, N. Case report: Avoidance of palpable corporal fibrosis due to priapism with upregulators of nitric oxide. *J Sex Med* 3, 173-176 (2006).

A43. Basun, H., Nilsberth, C., Eckman, C., Lannfelt, L. & Younkin, S. Plasma levels of Abeta42 and Abeta40 in Alzheimer patients during treatment with the acetylcholinesterase inhibitor tacrine. *Dement Geriatr Cogn Disord* 14, 156-160 (2002).

A44. Andreasen, N., Sjogren, M. & Blennow, K. CSF markers for Alzheimer's disease: total tau, phospho-tau and Abeta42. *World J Biol Psychiatry* 4, 147-155 (2003).

A45. Kalaria, R. N. Vascular factors in Alzheimer's disease. *Int Psychogeriatr* 15 Suppl 1, 47-52 (2003).

A46. Gentile, M. T., et al. Mechanisms of soluble beta-amyloid impairment of endothelial function. *The Journal of biological chemistry* 279, 48135-48142 (2004).

A47. Smith, C. C., Stanyer, L. & Betteridge, D. J. Soluble beta-amyloid (A beta) 40 causes attenuation or potentiation of noradrenaline-induced vasoconstriction in rats depending upon the concentration employed. *Neuroscience letters* 367, 129-132 (2004).

A48. Price, J. M., Hellermann, A., Hellermann, G. & Sutton, E. T. Aging enhances vascular dysfunction induced by the Alzheimer's peptide beta-amyloid. *Neurol Res* 26, 305-311 (2004).

A49. Pasquier, F. & Leys, D. [Blood pressure and Alzheimer's disease]. *Rev Neurol (Paris)* 154, 743-751 (1998).

A50. Khalil, Z., et al. Mechanisms of peripheral microvascular dysfunction in transgenic mice overexpressing the Alzheimer's disease amyloid Abeta protein. *J Alzheimers Dis* 4, 467-478 (2002).

A51. Suhara, T., et al. Abeta42 generation is toxic to endothelial cells and inhibits eNOS function through an Akt/GSK-3beta signaling-dependent mechanism. *Neurobiol Aging* 24, 437-451 (2003).

A52. Terrett, N. K., Bell, A. S., Brown, D. & Ellis, P. Sildenafil (VIAGRA™), a potent and selective inhibitor of type 5 cGMP phosphodiesterase with utility for the treatment of male erectile dysfunction. *Bioorg Med Chem Lett* 6, 1819-1824 (1996).

A53. Prickaerts, J., et al. Effects of two selective phosphodiesterase type 5 inhibitors, sildenafil and vardenafil, on object recognition memory and hippocampal cyclic GMP levels in the rat. *Neuroscience* 113, 351-361 (2002).

A54. Vitolo, O. V., et al. Amyloid beta-peptide inhibition of the PKA/CREB pathway and long-term potentiation: reversibility by drugs that enhance cAMP signaling. *Proceedings of the National Academy of Sciences of the United States of America* 99, 13217-13221 (2002).

A55. Paterno, R., Faraci, F. M. & Heistad, D. D. Role of Ca(2+)-dependent K+ channels in cerebral vasodilatation induced by increases in cyclic GMP and cyclic AMP in the rat. *Stroke* 27, 1603-1607; discussion 1607-1608 (1996).

A56. McCarty, M. F. Vascular nitric oxide may lessen Alzheimer's risk. *Med Hypotheses* 51, 465-476 (1998).

A57. Troy, C. M., et al. Caspase-2 mediates neuronal cell death induced by beta-amyloid. *J Neurosci* 20, 1386-1392 (2000).

A58. Wirtz-Brugger, F. & Giovanni, A. Guanosine 3',5'-cyclic monophosphate mediated inhibition of cell death induced by nerve growth factor withdrawal and beta-amyloid: protective effects of propentofylline. *Neuroscience* 99, 737-750 (2000).

A59. Venturini, G., et al. Beta-amyloid inhibits NOS activity by subtracting NADPH availability. *Faseb J* 16, 1970-1972 (2002).

A60. Bonkale, W. L., Winblad, B., Ravid, R. & Cowburn, R. F. Reduced nitric oxide responsive soluble guanylyl cyclase activity in the superior temporal cortex of patients with Alzheimer's disease. *Neuroscience letters* 187, 5-8 (1995).

A61. Baltrons, M. A., Pedraza, C. E., Heneka, M. T. & Garcia, A. Beta-amyloid peptides decrease soluble guanylyl cyclase expression in astroglial cells. *Neurobiol Dis* 10, 139-149 (2002).

A62. Paris, D., et al. Inhibition of Alzheimer's beta-amyloid induced vasoactivity and proinflammatory response in microglia by a cGMP-dependent mechanism. *Exp Neurol* 157, 211-221 (1999).

A63. Haas, J., Storch-Hagenlocher, B., Biessmann, A. & Wildemann, B. Inducible nitric oxide synthase and argininosuccinate synthetase: co-induction in brain tissue of patients with Alzheimer's dementia and following stimulation with beta-amyloid 1-42 in vitro. *Neuroscience letters* 322, 121-125 (2002).

A64. Tran, M. H., et al. Amyloid beta-peptide induces nitric oxide production in rat hippocampus: association with cholinergic dysfunction and amelioration by inducible nitric oxide synthase inhibitors. *Faseb J* 15, 1407-1409 (2001).

A65. McCann, S. M. The nitric oxide hypothesis of brain aging. *Exp Gerontol* 32, 431-440 (1997).

A66. Xie, Z., et al. Peroxynitrite mediates neurotoxicity of amyloid beta-peptide 1-42- and lipopolysaccharide-activated microglia. *J Neurosci* 22, 3484-3492 (2002).

A67. Wong, A., et al. Advanced glycation endproducts co-localize with inducible nitric oxide synthase in Alzheimer's disease. *Brain Res* 920, 32-40 (2001).

A68. Wang, Q., Rowan, M. J. & Anwyl, R. Beta-amyloid-mediated inhibition of NMDA receptor-dependent long-term potentiation induction involves activation of microglia and stimulation of inducible nitric oxide synthase and superoxide. *J Neurosci* 24, 6049-6056 (2004).

A69. Monsonego, A., Imitola, J., Zota, V., Oida, T. & Weiner, H. L. Microglia-mediated nitric oxide cytotoxicity of T cells following amyloid beta-peptide presentation to Th1 cells. *J Immunol* 171, 2216-2224 (2003).

A70. Contestabile, A., Monti, B., Contestabile, A. & Ciani, E. Brain nitric oxide and its dual role in neurodegeneration/neuroprotection: understanding molecular mechanisms to devise drug approaches. *Curr Med Chem* 10, 2147-2174 (2003).

Example 2—Identification of PDE5 Inhibitors which are Optimized for AD—Compounds with High Affinity for PDE5 and Good Selectivity Relative to Other PDEs Synaptic transmission and cognition are altered in double Tg (transgenic) mice expressing both the human amyloid precursor protein (APP) mutation (K670M:N671L) and the human presenilin-1 (PS1) mutation (M146L), termed APP/PS1 mice [23]. None of the existing PDE5 inhibitors has been developed to counteract diseases of the CNS and at the same time possesses the selectivity required for chronic administration to an elderly population with comorbid conditions such as AD patients. PDE5 inhibitors that are tailored to be used in AD patients can be screened, and can be tested to see whether these compounds can re-establish normal cognition in Tg AD models.

Enhancement of the NO/sGC/cGMP/PKG/CREB pathway through inhibition of PDE5 counteracts Aβ-induced synaptic and cognitive abnormalities. Drugs that both act on the NO/sGC/cGMP/PKG/CREB pathway and are optimized for the CNS are lacking. New drugs will be identified with a) high specificity and potency, b) good PK, bioavailability and CNS penetration, c) safety. None of the existing drugs is known to fit all of these criteria. Sildenafil is reported to cross the BBB [72] and has an $IC_{50}$ against PDE5 of 6.0 nM and an in vivo half-life of 0.4 hrs in rodents (~4 hrs in humans) [70, 74]. However, the selectivity ratio for PDE1, which is expressed in myocardium and blood vessels besides the brain and can result in mild vasodilatatory effects is 180, and that for PDE6, which is expressed only in retina and can transiently disturb vision is equal to 12 [67, 86]. Evidence for Vardenafil ability to cross the BBB is indirect [87] ($IC_{50}$ against PDE5 0.17 nM, selectivity ratio for PDE1>1000 and PDE6=3.5) [88, 89], and Tadalafil does not cross it (tadalafil also does not improve cognitive performance in APP/PS1 mice) ($IC_{50}$ against PDE5 5 nM, selectivity ratio for PDE1>2000 and PDE6=1000) [86]. A Structure-Activity Relationship (SAR) analysis of reported PDE5 inhibitors will be conducted and then a Computer-Aided MedChem Strategy will be employed to develop compounds that can fit all of these criteria.

Medicinal Chemistry Strategy.

The strength of this proposal lies in the intensive use of functional assays at every stage of the project and the parallel use of a validated in vivo disease model. The medicinal chemistry approach must be tailored to suit the strengths of the bioassays and the reality that the resources for medicinal chemistry are an order of magnitude lower than can be found in industry. Existing PDE5 inhibitors are used as treatment of ED. Based on the structure analysis of reported PDE5 inhibitors and known SAR data (FIG. 12), four class of structurally related, but nevertheless formally independent scaffolds I-IV (see FIG. 13), are deemed as PDE5 inhibitor candidates. Compounds derived from these scaffolds will be screened and optimized on the computational models. Compounds with highest score will be synthesized and for potency. At this stage, the synthetic effort will be guided by the testing results of potency/selectivity. Compounds with satisfactory potency and selectivity (lead compounds) will be further studied for PK, bioavailability/brain penetration and off-target activities (safety).

Structure-Activity Relationship (SAR) of Known PDE5 Inhibitors:

Although the design of early PDE5 inhibitors relied on mimicking the structure of cGMP, now a broad array of SAR data and very recent high resolution X-ray structures of PDE5 complexed with sildenafil, vardenafil and tadalafil are available and will provide a great basis to develop PDE5 inhibitors with the desired properties. After a survey of multiple distinct scaffold structures for PDE5 inhibitors and careful analysis of the SAR data from published reports, the scaffolds share a very common and important feature: all structures contain a fused planar ring system, and this ring system contains: (1) a hydrogen bond acceptor (e.g. N on pyrimidyl ring and C=O on sildenafil) or (2) an H-bond donor (NH) or H-bond acceptor (C=O) or both (amide NH—C=O). These observations comport with insights from the X-ray structures of the PDE5-inhibitor complexes. In addition to this planar ring system, all of the PDE5 inhibitors contain 3 hydrophobic groups ($R^1$, $R^2$, $R^3$). The size and nature of these 3 hydrophobic groups seems to depend on the strength of H bonding between the enzyme and the H bond acceptor or donor. For inhibitors with a H bond acceptor (C=O, N:) on the fused planar ring system, a bulky aromatic $R^2$ group achieves optimal fit at the site occupied by the phosphate of cGMP. For inhibitors with a H bond donor (i.e. NH of tadalafil) on the ring system, a bulky aromatic R1 group achieves optimal fit at the hydrophobic Q2 pocket. $R^3$ seems to be small and less significant compared with $R^1$ and $R^2$. By modification of $R^1$, $R^2$, $R^3$, the potency, selectivity and other PK properties such as oral bioavailability and cellular penetration can be optimized. The fused planar ring systems in thus far reported PDE5 inhibitors are listed in FIG. 12.

Scaffolds to Be Synthesized:

Based on the SAR analysis above, four sets of scaffolds (FIG. 13) are presented: 1) cGMP-based, represented by sildenafil (Viagra) and vardenafil (Levitra) (Pfizer, Bayer, Sheering-Plough), 2) β-carbolines-derived, represented by tadalafil (Cialis) (Lilly, Johnson & Johnson (J&J), 3) quinazoline and isoquinolinone derivatives (Bristol-Myers-Squibb (BMS), Japan), 4) phthalazine derivatives (BMS, Japan). These compound classes meet the following criteria: 1) a fused ring system with an H-bond acceptor or donor; 2) readily synthesized from readily available starting materials; 3) sufficient sites modifiable to generate a relatively large number of compounds for screening.

The design of scaffolds Ia-Ic is based on the known structures T1056 (shown in FIG. 13) with potent PDE5 inhibition ($IC_{50}$=0.23 nM) and excellent PDE5 selectivity against other PDEs1-4,6 (>100,000-fold selectivity versus PDE1-4, 240-fold vs. PDE6) (WO 9838168; JP 2000072675). In scaffold Ia, $R^2$ hydrophobic groups, to fit the site of phosphate of cGMP, can be introduced readily by Suzuki cross-coupling reaction with a versatile intermediate 5 (scheme Ia). If another $R^1$ group is required for Q2 pocket, the NH of the amide can be the site for substitution. In scaffold Ib, the enamine moiety is replaced with an amide. In scaffold Ic, the S=O will function as an H-bond acceptor.

Scaffolds were also based on the quinoline structure (IIa-IId) listed in FIG. 13. Two patents report quinoline derivatives as PDE5 inhibitors with general structure IIe (WO 2001012608, JP 2002308877). The quinoline-based PDE5 inhibitors reported by BMS is 120-fold more potent than sildenafil and significantly more selective than sildenafil against other PDE isozymes ($IC_{50}$=0.05 nM, PDE1-4/PDE5>7800, and PDE6/PDE5=160). From this compound, new compounds will be developed. For example the nitrogen can be replaced by O, C or S, or hetero atom can be introduced at various positions of either ring to generate new classes of compounds. Little SAR information is available on the quinolines, but a series of molecules, which can be synthesized in 2-3 steps and are generally isosteric with structure IIe, would guide predicted derivatives for in silico screening (see synthesis of scaffold IIa-IIc).

Scaffold IIIa-c and IIIa-1-IIIc-1 illustrated in FIG. 13 are designed based mainly on the observation that all reported PDE5 inhibitors possess a planar fused ring system with a H-bond acceptor or donor. Hydrophobic interactions are the predominant force in tadalafil binding, and related scaffolds are illustrated by IVa and IVb (FIG. 13).

Synthesis of Scaffold Ia:

The synthesis of target compound Ia is outlined in Scheme Ia (FIG. 14). The key intermediate quinolinone 3 can be obtained by cyclization of malonamide 2, which can be readily prepared from malonyl dichloride and substituted anilines, in the presence of commercially available Eaton's reagent. Quinolinone 3 is then converted to the 4-chloro derivative 5 through a straightforward two-step chlorination/hydrolysis sequence. Suzuki cross-coupling reaction allows compound 5 to couple with arylboronic acid, yielding the target compound Ia in good yield Synthesis of Scaffold IIa-IIc:

IIc will be synthesized by reaction of substituted aniline with ethoxymethylenemalonic ester at high temperature, followed by an alkylating reactant such as benzyl bromide, which would yield IIc-4. The intermediate 4-hydroxyquinoline (IIc-1) can be converted to 4-chloroquinoline IIc-2, a very versatile intermediate. The reaction of IIc-2 with different amines provides large number of compounds, e.g. 4-aminoquinoline IIc-3 can be obtained from 4-chloroquinoline by reaction with ammonia. IIc-3 can be readily converted to amide IIa-1 and sulphonamide IIb-1 (Scheme IIa-IIc; FIG. 15).

Synthesis of Scaffold Id:

IId can be synthesized as outlined in scheme IId (FIG. 16). Anthranilic acid is treated with excess formamidine acetate at high temperature to yield compound IId-1. The chloride product IId-2 is obtained by treatment of IId-1 with thionyl chloride at reflux. Coupling chloride IId-2 with 3-chloro-4-methoxybenzylamine provides IId-3.

Synthesis of scaffold III:

(see Scheme III; FIG. 17) Reaction of 2-aminobenzoic acid methyl ester with dimethyl acetylenedicarboxylate followed by a cyclization induced by t-BuOK provides product IIIc-1. Treatment of IIIc-1 with $NH_2NH_2$ yields the product IIIb-1 which is converted to IIIa-1. Reaction of IIIa-1 with amine provides IIIa. Reaction of IIIc-1 with amine provides IIIc. Alkylation of IIIb-1 provides IIIb.

Synthesis of Scaffold IVa:

As shown in Scheme IVa (FIG. 18), the target compounds IV can be prepared from the readily available amino acid methyl ester. Reaction with aromatic aldehydes provides the imine IVa-1. 1,3-dipolar cycloaddition of imine IVa-1 with naphthoquinone yields the key intermediate IVa-2. The target piperazinedione IVa can be obtained by acetylation of compound IVa-2, followed by ring closure in the presence of primary amines.

Evaluation of Drug Activity

In Vitro Tests:

Candidate compounds will be tested for PDE5 inhibitory activity first. If the activity is modest, the compounds will be tested against other PDEs to evaluate selectivity. The PDEs will be purchased or prepared according to the methods described in the literature. A PDE assay will be performed according to reported methods [90, 91] using Multiscreen plates (Millipore) and a vacuum manifold (Millipore), available in the lab, on which both the reaction and the subsequent separation of substrates and products can be achieved. The assay will use 50 mM Tris pH 7.5, 5 mM Mg acetate, 1 mM EGTA, and 250 µg/mL snake venom nucleotidase, 50 nM [8-$^3$H]-cGMP (15 Ci/mmol; Amersham) or [8-$^3$H]-cAMP (25 Ci/mmol; Amersham). Reactions are started by the addition of 25 µL of the diluted enzyme preparation. The assays will be incubated for 30 min at 30° C. Microcolumns will be prepared by aliquoting 300 µL per well of QAE Sephadex previously swollen for 2 hrs in water (12 mL/g). At the end of the incubation, the total volume of the assays will be loaded on microcolumn plate by filtration. The elution of free radioactivity will be obtained by 200 µL of water from which 50 µL aliquots will be analyzed by scintillation counting.

In addition to being potent inhibitors of PDE5, the candidate compounds must also be selective (some of the side-effects by known inhibitors are believed to be due, at least in part, to non-specific inhibition of other PDEs, such as PDE1 being found in heart and PDE6 primarily located in retina; see also [92] for a review). When assayed against other PDE families, they must show at least a 50 fold greater potency towards PDE5. These families include PDE1, Ca2+/calmodulin dependent; PDE2, cGMP-stimulated; PDE3, cGMP-inhibited; PDE4, cAMP-specific; PDE5, cGMP-specific; PDE6, photoreceptor cGMP-specific; PDE7, cAMP-specific; PDE8, cAMP-specific; PDE9, cGMP-specific; PDE10 and PDE11, hydrolyzing both cAMP and cGMP. In addition, these compounds have to be selective against kinases, such as PKG, PKA, PKC and PKB. Assays for these PDEs, as well as PKG and PKA, are well-established in the lab.

Tests in Primary Cultures and Adult Mice:

Compounds with sufficient PDE5 inhibitory activity in vitro ($IC_{50}$<50 nM) will be further tested in a functional assay to determine whether the compounds can increase cGMP in the neurons. Hippocampal neurons will be prepared as previously described [93] and seeded in 24-well culture dishes at a density of (1-2)×$10^5$ cells/well. Experiments will be performed after 10 days in culture when cells will reach confluence and form synaptic contacts. Media will be aspirated and replaced with 0.5 mL of PBS containing the PDE inhibitor. After 30 min at 37° C., soluble guanylyl cyclase will be stimulated by addition of 100 µM BAY 41-2272, a sGC stimulator with no effects on PDE activity [94], for 10 min at 37° C. At the end of the incubation, the medium will be removed and stored at −20° C. for extracellular cyclic nucleotides determinations. Intracellular cyclic nucleotides will be extracted by two ethanolic (65%) washes at 4° C. for 5 min. The ethanolic extracts will be pooled, evaporated to dryness and stored at −20° C. cGMP will be measured by scintillation proximity immunoassay (Amersham). All experiments will be performed in triplicate.

Compounds that pass the test in hippocampal cultures will also be tested in adult mice, following an assessment of acute toxicity to determine the dose of compound to be administered to the animal (see "toxicity tests" below). Animals will be treated with the PDE inhibitor, samples will be collected, homogenized immediately, and sonicated in the BIOTRAK cGMP enzyme immunoassay kit buffer containing 4 mM EDTA (Amersham, Ill.); samples will be centrifuged (12,000×g, for 5 min) to measure cGMP in the supernatant using the kit (results will normalized to the pellet protein levels with Lowry's procedure). If an increase in cGMP levels is found following PDE inhibitors and the inhibitor or its metabolites is detected in the dialysate, the candidate compound will be deemed as active.

Computational Strategy

General Studies.

To discover new drug candidates that bind to PDE5, medicinal chemistry efforts will be aided by computational modeling. A rational design approach, such as a structure-based virtual screening described in Xiong et al., ("Dynamic structures of phosphodiesterase-5 active site by combined molecular dynamics simulations and hybrid quantum mechanical/molecular mechanical calculations," Dec. 27, 2007, *J Comp Chem* [Epub ahead of print]), can help to maximize the chances of finding new drugs that associate with amino acid residues F787, L804, I813, M816, or a combination thereof of PDE5 (Card et al., 2004, *Structure*, 12:2233-47). The computation protocol can be used for preliminary docking studies using the structures represented by the 4 major classes of scaffolds shown on FIG. 13. The computational results can qualitatively show whether some of the structures or their structural variants fit the binding site of PDE5.

General ADMET Considerations

Optimization with respect to ADMET properties of the library members should be considered at the early stage of the drug discovery to guide synthetic efforts [167, 168]. For design purposes, med chem filters (MCF) will be used [169, 170] (e.g. presence of reactive, unstable, or toxicophore groups); compliance of the designed compounds will be controlled by the Lipinski "rule of five" [171, 172] [it states: 1) five or fewer hydrogen bond donors; 2) ten or fewer hydrogen bond acceptors; 3) molecular weight less than 500; 4) calculated log P less than or equal to 5]; polar and lipophilic surface areas will be kept optimal for solubility and cell-permeability properties [173], and optimal bioavailability score [174] of potential inhibitors utilizing ADMET Predictor [149].

ADMET Predictor [149], an advanced ADMET structure-property prediction program that includes additional ADME predictive models beyond the well known rule of five, can be used to predict potential ligands via flexible docking. The program predicts all of the important properties critical to oral absorption (including $pK_a$'s), as well as several pharmacokinetic properties and many aspects of toxicity [149]. The BBB penetration will also be theoretically estimated by calculating the polar surface area (PSA) and the oil/water partition coefficient (log P) of each candidate compound and using the well-established quantitative structure-activity relationship (QSAR) and artificial neural network (ANN) models [150, 151]. These QSAR and ANN models have demonstrated that the BBB penetration of a compound is determined by the PSA and log P (or PSA and molecular weight) of the compound, both of which can be calculated conveniently by ADMET Predictor. Usually, compounds that can cross the BBB should have a molecular mass less than 450 Da and a PSA smaller than 90 Å$^2$ [150].

Such considerations are relevant to ensuring the ability of compounds to penetrate the membrane thus allowing for studies at both the cellular and animal levels. It should be noted, though, that molecules computationally predicted to be drug-like are not "automatically drug-like" [175] as there are too many different mechanisms and parameters that affect the actual in vivo activity. To allow for further modifications that can be required to improve ADMET profile, a major emphasis on using "lead-likeness" [176, 177] criteria will be placed. The activity and ADMET profiles of the resulting "lead-like" compounds can be later improved via additional rounds of computer modeling and medicinal chemistry efforts, and a variety of cell-based assays for cellular and molecular pharmacology and in vitro and in vivo toxicology.

Example 3—Identification of PDE5 Inhibitors which are Optimized for AD—Determination of Whether Compounds have Good PK, Bioavailability, and Brain Penetration Pharmacokinetic assays that need to be performed when developing CNS drugs will include the measurement of a) bioavailability and b) brain uptake. They will be carried out in mice that will be i.p. injected with the candidate compounds (for final drug candidates PK tests will be also performed using p.o. and i.v. routes of administration). 5-6 mice/sex will be used for each time-point. For the assessment of bioavailability (concentration of compound in the blood as a function of time after administration), blood samples will be obtained from test animals following a single acute administration. The time course study after drug administration will include at least six points (5 minutes, 15 minutes, 1 hour, 2 hours, 5 hours, and 24 hours). The animals will be anesthetized with pentobarbital (50 mg/kg). Blood will be harvested by intracardiac puncture, collected in heparanized tubes, and plasma obtained by centrifugation. Samples will be analyzed by LC-MS to measure the amounts of the candidate compound and metabolites. An indication of brain uptake and blood brain barrier penetration will be obtained by tissue extraction of the candidate compound from brain following perfusion with PBS of the mice. Briefly, brain homogenates will be centrifuged 12,000×g for 10 min. The compound will be isolated by solid phase extraction, then analyzed by HPLC and measured using LC-MS. Pattern of time dependent changes in brain concentration will be compared with that of blood concentration. Similar patterns will be indicative of the fact that brain uptake reflects concentration of the blood. A peak brain/blood concentration ratio >1 will show that brain uptake for the compound is comparable with that of known CNS drugs in clinical use. For example, the brain/blood ratio for minaprine, a 6-phenylaminopyridazine CNS drug, is >2 [178].

General Considerations:

Of note, sildenafil has been shown to cross the BBB [179], and the efficacy of sildenafil on the AD animal models further demonstrates that PDE5 inhibitors can achieve brain penetration for a CNS target. While there is no "golden rule" for brain penetration, empiric correlations show the importance of a molecular mass under 400-500 Da, 8 or fewer hydrogen bonds, and the presence of basic amines rather than carboxylic acids. Also, a variety of methods including computational approaches (see "Stage #2" of "Computational design" above) have been developed to assess CNS penetration of drug candidates. Also, PDE5 is an intracellular enzyme; PDE5 inhibitors must cross the cell membrane to increase cGMP and thus cell based screening for PDE5 activity will also address the issue of absorbance. Finally, the structure of the candidate drug can support a chemistry-based approach to BBB penetration. For example, the polar functional groups on a water-soluble, non-CNS penetrating drug can be masked by introducing lipid-soluble moieties, or the water-soluble drug can be conjugated to a lipid-soluble drug carrier. Ideally, the new drug or the prodrug is metabolized within the brain and converted to the parent drug. This chemistry-based approach has been used successfully in solving the BBB drug-delivery problem in clinical practice [180]. In conjunction with the computational methods described at stage #2 it should provide reliable prediction of BBB access.

Ascertaining Whether Newly Identified Compounds are Safe

Before determining drug efficacy in the APP/PS1 mouse, but after synthesis of sufficient quantities of compound and a determination of a formulation for delivery, data addressing the rudimentary pharmacokinetic properties and toxicity of the compound will be generated. It has been estimated that over half of all drugs fail to reach the market because of problems with ADMET [181]. Therefore, before embarking on a course of costly animal toxicology, recent advances in in vitro ADMET testing will be utilized to screen compounds with a quick, inexpensive battery of assays performed by Charles River Laboratories. Two areas will be focused on that have resulted in the withdrawal of many drugs from the market and that can sometimes affect an entire chemical series: drug-drug interactions (liver metabolism), hERG channel blockage (cardiac dysfunction). To test for drug-drug interactions related to hepatotoxicity (the leading cause of drug withdrawal during the past 25 years and especially important for a heavily-medicated Alzheimer's population) [182], the Cytochrome P450 inhibition assay will be used. Cytochrome P450 is an important component of liver metabolism. Moreover, there are pharmacological interactions between PDE5 inhibitors and other medications metabolized by the cytochrome P450 (P3A4 isoform), such as the azole antifungals, erythromycin and the HIV protease inhibitors. Thus, the $IC_{50}$ data gathered from this ELISA assay will allow for the elimination of compounds that inhibit isozymes of CYP450. To test for hERG channel blockage, which impairs proper cardiac electrophysiology and can lead to Torsades-de-pointes and fatality, the rubidium flux method will be used to assess whether lead compounds affect ion flow through these important cardiac channels.

Next, acute toxicity will be evaluated. All clinical signs, time of onset, duration, reversibility of toxicity and mortalities will be recorded. Animals will be observed periodically during the first 24 hrs with continuous monitoring given to the first 4 hrs, then at least once a day for 14 days or until they die to check food and liquid intake, weight, as well as locomotion and exploratory behavior.

Maximum tolerated dose (MTD) and chronic toxicity will also be evaluated. MTD will be computed as the maximum administered dose that does not produce any toxicity effect in terms of malaise or death (body weight will be monitored over time). Chronic toxicity will assessed at the MTD. All clinical signs, time of onset, duration, reversibility of toxicity and mortalities will be recorded.

The occurrence of chronic toxicity signs will be assessed for at least 1 month after the end of the treatment. Gross necropsies will be performed in all animals, including those sacrificed moribund, found dead, or terminated at 14 days after the acute treatment or at the end of the chronic treatment over 30 days. Gross evaluation at necropsy will include weights and measurements of organs. The color of the organs will be noted to determine if there is fatty change, hemorrhage, pigment deposition or other changes. Organs will be palpated and directly visualized to examine for lesions and changes in consistency such as abnormal growths, fibrosis, necrosis, or fat deposition. Histopathologic evaluation of liver, kidney, brain and muscle will be performed.

Liver sections will be evaluated for portal and hepatocellular inflammation, bile ductular proliferation, hepatocellular injury including apoptosis and necrosis, fibrosis, steatosis, hypertrophy, pigment deposition (bile, iron, and copper) and oncocytic (mitochondrial proliferative) changes. Slides will be stained with hematoxylin and eosin and trichrome for initial review.

Renal sections will be examined with hematoxylin and eosin, trichrome and periodic acid Schiff (PAS). Glomeruli, vessels, tubules, collecting ducts and interstitium will be evaluated for cellularity, inflammation, collagen deposition/fibrosis/sclerosis. It will be determined if there is proximal tubular epithelial cell damage or renal papillary necrosis, some of the more common nephrotoxic effects.

Neurotoxicity will be evaluated in all regions of the brain, including neocortex, striatum, thalamus, hippocampus, cerebellum, brain stem and spinal cord. The brain will be examined for cytoarchitecture, neuronal loss (apoptosis and necrosis), inflammation, axonal degeneration, gliosis, and myelination. Hematoxylin and eosin stained slides will be used for general assessment and additional stains if needed will include Luxol fast blue-PAS for myelination, GFAP (glial fibrillary acidic protein) for astrocytic response, and CD68 for microglial response.

Muscle will be evaluated with hematoxylin and eosin to examine for neurogenic or myopathic atrophy, necrotic fibers, regenerative fibers, fat deposition, or inflammation. Trichrome stain will be used to determine fibrosis. If changes are determined during the initial screening, frozen sections will be made to evaluate fiber type distribution with ATPase stains. In vitro cytotoxicity assays will be carried out to evaluate cell viability after administration of the drug in primary neuronal cultures using fluorescein diacetate method. Motor, sensor, motivational and cognitive performances will be monitored during both acute and chronic toxicity evaluations using the visible and hidden platform testing, as well as gross behavioral evaluation (exploratory behavior, PICA, feeding, distress). To avoid causing excessive pain or tissue damage in the animal, pharmaceuticals with irritants or corrosive character will not be administered in concentration that can produce severe toxicity solely from local effects.

General Considerations:

Although in vivo toxicity is a very difficult property to predict, some general strategies will be followed. Functionality that can render a molecule electrophilic (i.e. alkyl halides or Michael acceptors) would be addressed immediately. Such functionality is commonly found to result in toxicity. For example, if a hit contained a bromomethyl group, derivatives would be prepared that eliminate the bromide, replacing it with an electron-withdrawing and/or hydrophobic group (but not a good leaving group), such as trifluoromethyl, or eliminating the methylene between the bromine and the other substituent attached to the methylene (i.e. transforming a benzyl bromide to a bromophenyl).

Metabolic stability is also difficult to predict a priori. However, functionality that is commonly known to be metabolically unstable (i.e. esters) would be replaced with known bioisosteres [183]. Another common pathway leading to lower metabolic stability is aromatic ring oxidation. Therefore, during the SAR studies aromatic and heterocyclic rings will be rendered less electron-rich by the strategic placement of electron-withdrawing groups (e.g. F or Cl) or by substitution (i.e. replacing a phenyl ring with a pyridine ring). In cases where this change does not result in decreased efficacy, a significant increase in metabolic stability can be realized. In addition, efforts would be made to eliminate functionality known to produce metabolites that are prone to bioconjugation [184]. Such metabolites can be hepatotoxic and limit the usefulness of the compound which will be discarded.

Compound Analysis.

All compounds synthesized and tested for biological activity will be fully characterized and purified to >95% as determined by HPLC and $^1$H NMR. Furthermore, additional analytical techniques (i.e. $^{13}$C NMR, IR, melting point, MS and/or elemental analysis) will be used to determine structure and purify. In the case of optically pure materials, the purity will be assessed by chiral stationary-phase HPLC. In certain cases where structural uncertainty remains other techniques (i.e. 2-D NMR, and x-ray crystallography) will be utilized.

Example 4—Screening of the New PDE5 Inhibitors by Selecting Compounds that Rescue Synaptic Dysfunction in APP/PS1 Mice Synaptic dysfunction is a major hallmark of AD [1]. Several animal models of AD have become available during the last 12 years. Since even in the fastest model, AD pathology does not start before the end of the $2^{nd}$ month, it has been necessary to wait at least until this age to inject drugs into the animal to assess whether they are beneficial to synaptic impairment, plaque formation and increase of Aβ levels. Such in vivo approaches can be labor intensive. An alternative approach is achieved by the use of cell cultures from Tg animals which provide a new, fast, efficient and reproducible in vitro method for the screening and testing of compounds for the treatment and therapy of AD or Aβ-associated diseases (see U.S. patent Ser. No. 10/980,922). These candidates will be examined to see whether they can rescue changes in basal number of active boutons and glutamate-induced long-lasting increase in active bouton number in APP/PS1 cultures. This method is relatively fast and easy to perform [93, 185].

The PDE5 inhibitors will be examined if they re-establish normal numbers of active boutons and glutamate-induced increases in active boutons in cultures from APP/PS1 mice. Next, these results will be validated in hippocampal slices to see if the enhancers re-establish normal LTP in the CA1 region of slices from APP/PS1 mice.

Based on a med/chem analysis of existing PDE5 inhibitors, four classes of scaffolds have been identified that can serve for the development of new PDE5 inhibitor candidates. These compounds are being screened and optimized using the computational models described herein. Thus, new PDE5 inhibitors will be identified with a) high specificity and potency, b) great CNS penetration, and c) safety. The following fundamental 3 endpoints will be focused on: a) identification of compounds with high affinity for PDE5 and good selectivity relative to other PDEs; b) determination of whether such compounds have good PK, bioavailability and brain penetration; c) ascertaining whether compounds that meet the aforementioned criteria are safe.

Experimental Design:

Based on the finding that APP/PS1 cultures show an increase in the basal number of functional presynaptic release sites (see FIG. 22B), the compounds will be screened as shown by MedChem studies to select those that can re-establish normal basal number of active boutons. The number of active boutons, with and without PDE5 inhibitor treatment, will be examined in cultures from double Tg- and WT-littermates. 10-day old cultures from APP/PS1 and WT littermates will be treated for 4 days to test whether the compounds can rescue the increase in active bouton number. 10-day old cultures from APP/PS1 and WT littermates will also be treated for 20 min to test whether a short treatment rescues the increase in functional active boutons. If there is no difference in basal active bouton number between compound-treated cultures from double Tg and WT animals, but cultures from double Tg mice treated with vehicle alone show increased basal active bouton number, compounds will be deemed blockers of the development of changes in basal number of functional boutons in cultures from AD animal models.

Lack of a glutamate-induced increase in the number of active boutons is another phenomenon that occurs in cultures from APP/PS1 mice (see FIG. 22C). The new compounds will be examined as to whether they can rescue the impairment of this plastic change. The same strategies will be used as for the basal number of active boutons. Briefly, cultures from APP/PS1 and WT littermates will be treated for 4 days from day 10, or for 20 min on day 10 before evoking the glutamate-induced increase in active bouton number. Re-establishment of the glutamate-induced increase in active bouton number will be examined. If this is observed, the compounds will be deemed to being able to rescue impairment of synaptic plasticity in cultures from APP/PS1 mice.

Methods

Double Tg mice will be obtained by crossing APP (K670M:N671L) with PS1(M146L) (line 6.2) animals. The genotype will be identified by PCR on tail samples [186-188]. Primary cultures will be prepared from one-day-old mouse pups as previously described (see Ninan et al [189]).

Vesicle Cycling studies will be done 7-21 days after plating (see detailed description in Ninan et al [189]). Briefly, loading of FM 1-43 will be induced by changing the perfusion medium from normal bath solution to hyperkalemic solution with 5 μM FM 1-43 for 45 sec. ADVASEP-7 (1 mM) will be introduced for 60 sec in the washing solution at 1 and 6 min of washing. Unloading will be performed with multiple 15 sec applications of hyperkalemic solution (without FM 1-43). The difference between the images before and after multiple exposures to hyperkalemic solution will give the measure of FM 1-43 stained vesicles [see FIG. 22A]. The number of active boutons per uniform length of randomly selected neurites (15×6.85 μm field) at 12 μM from the cell body will be measured in blind. Plasticity will be induced through glutamate (200 μM in $Mg^{2+}$ free bath solution for 30 sec). Staining and destaining procedures will be repeated 30 min after glutamate. All images will be acquired using Nikon D-Eclipse C1 confocal microscope. Total number of boutons from randomly selected fields (30.8×30.8 μm) will be blindly assessed using NIH Image (v. 1.61).

Electrophysiological Analysis will be performed on males (see detailed description in Gong et al, [83]). 400 μm slices will be cut with a tissue chopper and maintained in an interface chamber at 29° C. for 90 min prior to recording. Briefly, CA1 fEPSPs will be recorded by placing both the stimulating and the recording electrodes in CA1 stratum radiatum. BST will be assayed either by plotting the stimulus voltages against slopes of fEPSP, or by plotting the peak amplitude of the fiber volley against the slope of the fEPSP. For LTP experiments, a 15 min baseline will be recorded every min at an intensity that evokes a response ~35% of the maximum evoked response. LTP will be induced using θ-burst stimulation (4 pulses at 100 Hz, with the bursts repeated at 5 Hz and each tetanus including 3 ten-burst trains separated by 15 sec).

Statistical Analyses will be carried out as described herein.

Example 5—Screening of PDE5 Inhibitors Selected Through Tests on Synaptic Function to Examine Whether they Prevent Cognitive Abnormalities in APP/PS1 Mice Enhancers of the NO/sGC/cGMP/PKG/CREB pathway can rescue the cognitive deficits observed in APP/PS1 mice of 3 and 6 months of age. New PDE5 inhibitors screened in Tg cultures and slices will be determined as to whether they can protect APP/PS1 mice against impairments of spatial working memory, reference memory and contextual fear learning. Treatment with the new PDE5 inhibitors will be examined to see if they have beneficial effects on abnormal cognition in APP/PS1 mice.

Experimental Design:

In a first series of experiments, spatial working memory, a type of short term memory that is impaired at early stages in patients affected by AD and APP/PS1 mice, will be tested using the RAWM. Next, associative memory, a type of contextual memory that is tested with FC and is impaired at the age of 3 month in APP/PS1 mice, will be examined. Finally, reference memory, a type of long-term memory that is tested with the MWM and is impaired in APP/PS1 mice at the age of 6 months, will be assessed. In addition, controls will be conducted with the visible platform task, sensory threshold and cued conditioning tests. The treatment will be performed with the same timing as in the preliminary studies (i.e. immediately after training). Conditions to be tested include: APP/PS1 and WT treated with PDE5 inhibitors, APP/PS1 and WT treated with vehicle. After behavioral testing mice will be sacrificed and their blood and brains used for measurement of Aβ levels. As a control for effectiveness of PDE5 inhibition, hippocampal cGMP levels in APP/PS1 mice will be measured after administration of the compounds. If the compounds have a beneficial effect, there should be no difference or little difference in the RAWM, and/or MWM, and/or FC tasks between compound-treated Tgs and WT littermates, whereas vehicle-treated double Tgs should show abnormal L&M. Compound-treated WT mice should show normal learning. No difference is expected in speed and latency to the platform (visible platform test), as well as in the cued conditioning for the various groups of mice. No difference is also expected in sensory perception of the shock for the various groups of mice. These results will indicate that treatment with these compounds can prevent the development of cognitive abnormalities in AD animal models. There is also the possibility that the compounds can ameliorate one type of memory and not the other. The beneficial effect of the compounds is limited to that type of memory.

In these studies, the beneficial effect of sildenafil on RAWM and FC has been observed to last beyond the duration of the application of the drug. To address whether this prolonged effect on RAWM and FC is observed using the newly identified PDE5 inhibitors, one group of 3-month-old APP/PS1 mice will be used that will be divided into two subgroups that will be treated with the compounds and vehicle, respectively. The treatment will last for 3 weeks. WT littermates will serve as controls and receive the same treatment. As the animals will be 6 months old, they will perform the full battery of behavioral tests, including RAWM, MWM and contextual FC, as well as visible platform testing, sensory threshold testing and cued conditioning. Then the animals will be sacrificed for measurement of hippocampal cGMP levels, and blood and brain Aβ levels. If the compounds will re-establish normal cognition, the beneficial effect of these compounds will be deemed to act on the cognitive impairment of adult AD animal models that lasts beyond the drug application.

Methods

Animals to be used in these studies have been described herein.

Behavioral Studies:

Experiments will be performed in blind only on male animals to reduce variability.

Spatial Working Memory.

This type of short-term memory can be studied with the RAWM test. The task has proven informative in the analysis of other Tg models of AD [23, 33, 76, 211]. Briefly, the RAWM will consist of a tank filled with opaque water by powdered milk. Walls will positioned so as to produce six arms, radiating from a central area. Spatial cues will be present on the walls of the testing room. At the end of one of the arms will be a clear 10 cm submerged platform that will remain in the same location for every trial on a given day, but will be moved about randomly from day to day. For each trial the mouse will start the task from a different randomly chosen arm. The mouse cannot use its long-term memory of the location of the platform on previous days, but must rely on the short-term memory of its location on the day in question based on spatial cues that are present in the room. Each trial will last 1 min and errors will be counted each time the mouse will enter the wrong arm or will need more than 10 sec to reach the platform. After each error the mouse will be pulled back to the start arm for that trial. After 4 consecutive acquisition trials, the mouse will be placed in its home cage for 30 min, then returned to the maze and administered a $5^{th}$ retention trial. Testing will be considered completed when the WT mice make the same number of errors during the $4^{th}$ and $5^{th}$ trial. The scores for each mouse on the last 3 days of testing will be averaged and used for statistical analysis. Visible-platform training to test visual and motor deficits will be performed in the same pool but without arms, with the platform marked with a black flag and positioned randomly from trial to trial. Each animal will be allowed to swim for 1 min. Time to reach the platform and speed will be recorded.

Reference Memory.

This long-lasting type of memory will be tested with the MWM, as previously described [23]. Briefly, the test will be performed in the same pool as above but without arms. The pool will be divided into 4 sections. The mouse will start from one section and will have to find a hidden platform beneath the surface of the water. The location of the platform will remain constant throughout the different days. Time required to reach the hidden platform (latency) will be recorded. The training will be followed by 4 probe trials with the platform moved to test the retention of the spatial memory. The percent of time spent in the quadrant that used to contain the platform will be recorded and analyzed with a video-tracking system (HVS Image, UK).

FC.

This associative memory test is much faster than other behavioral tasks that require multiple days of training and testing [33]. The conditioning chamber will be in a sound-attenuating box. The conditioning chamber will have a 36-bar insulated shock grid removable floor. For the cued and contextual conditioning experiments, mice will be placed in the conditioning chamber for 2 min before the onset of a discrete tone (CS) (a sound that lasted 30 s at 2800 Hz and 85 dB). In the last 2 s of the CS, mice will be given a foot shock (US) of 0.50 mA for 2 s through the bars of the floor. After the CS/US pairing, the mice will be left in the conditioning chamber for another 30 s and will then be placed back in their home cages. Freezing behavior, defined as the absence of all movement except for that necessitated by breathing, will be scored using the Freezeview software (MED Ass. Inc.). To evaluate contextual fear learning, freezing will be measured for 5 min (consecutive) in the chamber in which the mice will be trained 24 hr after training. To evaluate cued fear learning, following contextual testing, the mice will be placed in a new context (triangular cage with smooth flat floor and with vanilla odorant) for 2 min (pre-CS test), after which they will be exposed to the CS for 3 min (CS test), and freezing will be measured. Sensory perception of the shock will be determined through threshold assessment, as described [33].

Determination of cGMP and cAMP:

The method has been described in the "Evaluation of drug activity" "tests in adult mice" section (for cAMP, BIOTRAK cAMP enzyme immunoassay kit buffer will be used).

Determination of Aβ levels will be performed on homogenates of frozen hemi-brains as previously described [23]. Homogenate will be mixed with formic acid, sonicated, and spun at 50,000 rpm at 4° C. Supernatant will be diluted in neutralization solution. The neutralized material will be stored at −80° C. before loading onto ELISA plates. Aβ will be trapped with either monoclonal antibody to Aβ40 (JRF/cAβ40/10) or Aβ42 (JRF/cAβ42/26) and then detected with horseradish peroxidase-conjugated JRF/Aβtot/17 [212]. ELISA signals will be reported as the mean+s.e.m. of two replica wells in fmol amyloid-β per mg protein (determined with the BCA Protein Assay Reagent Kit, PIERCE), based on standard curves using synthetic Aβ40 and Aβ42 peptide standards (American Peptide).

Blood will be harvested in a tube containing 10 mM EDTA, centrifuged at 4000 rpm for 5 min at 4° C. Plasma will be stored at −80° C. before loading onto ELISA plates.

Statistical Analyses: For all experiments mice will be coded to blind investigators with respect to genotype and treatment. Results will be expressed as Standard Error Mean (SEM). Level of significance will be set for p<0.05. Results will be analyzed with ANOVA with post-hoc correction with drug or genotype as main effect. Experiments will be designed in a balanced fashion, and mice will be trained and tested at each of the different conditions in 3 or 4 separate experiments. For probe trials, data will be analyzed with ANOVA for repeated measures for percent of time spent in the quadrant where the platform is located during training with respect to other quadrants, followed by planned comparisons to confirm if mice spend more time in the target than in adjacent quadrant to the right, left, or opposite from the target quadrant.

REFERENCES FOR EXAMPLES 2-5

1. Masliah, E., *Mechanisms of synaptic dysfunction in Alzheimer's disease*. Histol Histopathol, 1995. 10(2): p. 509-19.
2. Selkoe, D. J., *Alzheimer's disease is a synaptic failure*. Science, 2002. 298(5594): p. 789-91.
3. Sant'Angelo, A., F. Trinchese, and O. Arancio, *Usefulness of behavioral and electrophysiological studies in transgenic models of Alzheimer's disease*. Neurochem Res, 2003. 28(7): p. 1009-15.
4. Bliss, T. V. and G. L. Collingridge, *A synaptic model of memory: long-term potentiation in the hippocampus*. Nature, 1993. 361(6407): p. 31-9.
5. Cullen, W. K., et al., *Block of LTP in rat hippocampus in vivo by beta-amyloid precursor protein fragments*. Neuroreport, 1997. 8(15): p. 3213-7.
6. Freir, D. B., C. Holscher, and C. E. Herron, *Blockade of long-term potentiation by beta-amyloidpeptides in the CA1 region of the rat hippocampus in vivo*. J Neurophysiol, 2001. 85(2): p. 708-13.
7. Itoh, A., et al., *Impairments of long-term potentiation in hippocampal slices of beta-amyloid-infused rats*. Eur J Pharmacol, 1999. 382(3): p. 167-75.
8. Kim, J. H., et al., *Use-dependent effects of amyloidogenic fragments of (beta)-amyloid precursor protein on synaptic plasticity in rat hippocampus in vivo*. J Neurosci, 2001. 21(4): p. 1327-33.
9. Stephan, A., S. Laroche, and S. Davis, *Generation of aggregated beta-amyloid in the rat hippocampus impairs synaptic transmission and plasticity and causes memory deficits*. J Neurosci, 2001. 21(15): p. 5703-14.
10. Vitolo, O. V., et al., *Amyloid beta-peptide inhibition of the PKA/CREB pathway and long-term potentiation: reversibility by drugs that enhance cAMP signaling*. Proc Natl Acad Sci USA, 2002. 99(20): p. 13217-21.
11. Walsh, D. M., et al., *Naturally secreted oligomers of amyloid beta protein potently inhibit hippocampal long-term potentiation in vivo*. Nature, 2002. 416(6880): p. 535-9.
12. Puzzo, D., et al., *Amyloid-beta peptide inhibits activation of the nitric oxide/cGMP/cAMP-responsive element-binding protein pathway during hippocampal synaptic plasticity*. J Neurosci, 2005. 25(29): p. 6887-97.
13. Selig, D. K., et al., *Examination of the role of cGMP in long-term potentiation in the CA1 region of the hippocampus*. Learn Mem, 1996. 3(1): p. 42-8.
14. Prickaerts, J., et al., *cGMP, but not cAMP, in rat hippocampus is involved in early stages of object memory consolidation*. Eur J Pharmacol, 2002. 436(1-2): p. 83-7.
15. Paakkari, I. and P. Lindsberg, *Nitric oxide in the central nervous system*. Ann Med, 1995. 27(3): p. 369-77.
16. Baratti, C. M. and M. M. Boccia, *Effects of sildenafil on long-term retention of an inhibitory avoidance response in mice*. Behav Pharmacol, 1999. 10(8): p. 731-7.
17. van Staveren, W. C., et al., *Species differences in the localization of cGMP-producing and NO-responsive elements in the mouse and rat hippocampus using cGMP immunocytochemistry*. Eur J Neurosci, 2004. 19(8): p. 2155-68.
18. Van Staveren, W. C., et al., *mRNA expression patterns of the cGMP-hydrolyzing phosphodiesterases types 2, 5, and 9 during development of the rat brain*. J Comp Neurol, 2003. 467(4): p. 566-80.
19. Schultheiss, D., et al., *Central effects of sildenafil (Viagra) on auditory selective attention and verbal recognition memory in humans: a study with event-related brain potentials*. World J Urol, 2001. 19(1): p. 46-50.
20. Kemenes, I., et al., *Critical time-window for NO-cGMP-dependent long-term memory formation after one-trial appetitive conditioning*. J Neurosci, 2002. 22(4): p. 1414-25.
21. Baltrons, M. A., et al., *Regulation of NO-dependent cyclic GMP formation by inflammatory agents in neural cells*. Toxicol Lett, 2003. 139(2-3): p. 191-8.
22. Bon, C. L. and J. Garthwaite, *On the role of nitric oxide in hippocampal long-term potentiation*. J Neurosci, 2003. 23(5): p. 1941-8.

23. Trinchese, F., et al., *Progressive age-related development of Alzheimer-like pathology in APP/PS1 mice.* Ann Neurol, 2004. 55(6): p. 801-14.
24. Chapman, P. F., et al., *Impaired synaptic plasticity and learning in aged amyloid precursor protein transgenic mice.* Nat Neurosci, 1999. 2(3): p. 271-6.
25. Fitzjohn, S. M., et al., *Age-related impairment of synaptic transmission but normal long-term potentiation in transgenic mice that overexpress the human APP695SWE mutant form of amyloid precursor protein.* J Neurosci, 2001. 21(13): p. 4691-8.
26. Hsia, A. Y., et al., *Plaque-independent disruption of neural circuits in Alzheimer's disease mouse models.* Proc Natl Acad Sci USA, 1999. 96(6): p. 3228-33.
27. Jolas, T., et al., *Long-term potentiation is increased in the CA1 area of the hippocampus of APP(swe/ind) CRND8 mice.* Neurobiol Dis, 2002. 11(3): p. 394-409.
28. Larson, J., et al., *Alterations in synaptic transmission and long-term potentiation in hippocampal slices from young and aged PDAPP mice.* Brain Res, 1999. 840(1-2): p. 23-35.
29. Moechars, D., et al., *Early phenotypic changes in transgenic mice that overexpress different mutants of amyloid precursor protein in brain.* J Biol Chem, 1999. 274(10): p. 6483-92.
30. Nalbantoglu, J., et al., *Impaired learning and LTP in mice expressing the carboxy terminus of the Alzheimer amyloid precursor protein.* Nature, 1997. 387(6632): p. 500-5.
31. Dineley, K. T., et al., *Beta-amyloid activates the mitogen-activated protein kinase cascade via hippocampal alpha7 nicotinic acetylcholine receptors: In vitro and in vivo mechanisms related to Alzheimer's disease.* J Neurosci, 2001. 21(12): p. 4125-33.
32. Dineley, K. T., et al., *Accelerated plaque accumulation, associative learning deficits, and up-regulation of alpha 7 nicotinic receptor protein in transgenic mice co-expressing mutant human presenilin 1 and amyloid precursor proteins.* J Biol Chem, 2002. 277(25): p. 22768-80.
33. Gong, B., et al., *Persistent improvement in synaptic and cognitive functions in an Alzheimer mouse model following rolipram treatment.* J. Clin. Invest., 2004. 114: p. 1624-1634.
34. Yin, J. C., et al., *Induction of a dominant negative CREB transgene specifically blocks long-term memory in Drosophila.* Cell, 1994. 79(1): p. 49-58.
35. Bourtchuladze, R., et al., *Deficient long-term memory in mice with a targeted mutation of the cAMP-responsive element-binding protein.* Cell, 1994. 79(1): p. 59-68.
36. Bach, M. E., et al., *Age-related defects in spatial memory are correlated with defects in the late phase of hippocampal long-term potentiation in vitro and are attenuated by drugs that enhance the cAMP signaling pathway.* Proc Natl Acad Sci USA, 1999. 96(9): p. 5280-5.
37. Lu, Y. F., E. R. Kandel, and R. D. Hawkins, *Nitric oxide signaling contributes to late-phase LTP and CREB phosphorylation in the hippocampus.* J Neurosci, 1999. 19(23): p. 10250-61.
38. McCarty, M. F., *Vascular nitric oxide may lessen Alzheimer's risk.* Med Hypotheses, 1998. 51(6): p. 465-76.
39. Troy, C. M., et al., *Caspase-2 mediates neuronal cell death induced by beta-amyloid.* J Neurosci, 2000. 20(4): p. 1386-92.
40. Wirtz-Brugger, F. and A. Giovanni, *Guanosine 3',5'-cyclic monophosphate mediated inhibition of cell death induced by nerve growth factor withdrawal and beta-amyloid protective effects of propentofylline.* Neuroscience, 2000. 99(4): p. 737-50.
41. Venturini, G., et al., *Beta-amyloid inhibits NOS activity by subtracting NADPH availability.* Faseb J, 2002. 16(14): p. 1970-2.
42. Suhara, T., et al., *Abeta42 generation is toxic to endothelial cells and inhibits eNOS function through an Akt/GSK-3beta signaling-dependent mechanism.* Neurobiol Aging, 2003. 24(3): p. 437-51.
43. Colton, C. A., et al., *NO synthase 2 (NOS2) deletion promotes multiple pathologies in a mouse model of Alzheimer's disease.* Proc Natl Acad Sci USA, 2006. 103(34): p. 12867-72.
44. Thatcher, G. R., B. M. Bennett, and J. N. Reynolds, *Nitric oxide mimetic molecules as therapeutic agents in Alzheimer's disease.* Curr Alzheimer Res, 2005. 2(2): p. 171-82.
45. Haas, J., et al., *Inducible nitric oxide synthase and argininosuccinate synthetase. co-induction in brain tissue of patients with Alzheimer's dementia and following stimulation with beta-amyloid 1-42 in vitro.* Neurosci Lett, 2002. 322(2): p. 121-5.
46. Tran, M. H., et al., *Amyloid beta-peptide induces nitric oxide production in rat hippocampus: association with cholinergic dysfunction and amelioration by inducible nitric oxide synthase inhibitors.* Faseb J, 2001. 15(8): p. 1407-9.
47. McCann, S. M., *The nitric oxide hypothesis of brain aging.* Exp Gerontol, 1997. 32(4-5): p. 431-40.
48. Xie, Z., et al., *Peroxynitrite mediates neurotoxicity of amyloid beta-peptide1-42-and lipopolysaccharide-activated microglia.* J Neurosci, 2002. 22(9): p. 3484-92.
49. Wong, A., et al., *Advanced glycation endproducts co-localize with inducible nitric oxide synthase in Alzheimer's disease.* Brain Res, 2001. 920(1-2): p. 32-40.
50. Wang, Q., M. J. Rowan, and R. Anwyl, *Beta-amyloid-mediated inhibition of NMDA receptor-dependent long-term potentiation induction involves activation of microglia and stimulation of inducible nitric oxide synthase and superoxide.* J Neurosci, 2004. 24(27): p. 6049-56.
51. Monsonego, A., et al., *Microglia-mediated nitric oxide cytotoxicity of T cells following amyloid beta-peptide presentation to Th1 cells.* J Immunol, 2003. 171(5): p. 2216-24.
52. Contestabile, A., et al., *Brain nitric oxide and its dual role in neurodegeneration/neuroprotection: understanding molecular mechanisms to devise drug approaches.* Curr Med Chem, 2003. 10(20): p. 2147-74.
53. Davis, R. L., et al., *The cyclic AMP system and Drosophila learning.* Mol Cell Biochem, 1995. 149-150: p. 271-8.
54. Davis, R. L., *Physiology and biochemistry of Drosophila learning mutants.* Physiol Rev, 1996. 76(2): p. 299-317.
55. Lee, D. and D. K. O'Dowd, *cAMP-dependent plasticity at excitatory cholinergic synapses in Drosophila neurons: alterations in the memory mutant dunce.* J Neurosci, 2000. 20(6): p. 2104-11.
56. Barad, M., et al., *Rolipram, a type IV-specific phosphodiesterase inhibitor, facilitates the establishment of long-lasting long-term potentiation and improves memory.* Proc Natl Acad Sci USA, 1998. 95(25): p. 15020-5.
57. Zhang, H. T., et al., *Inhibition of cyclic AMP phosphodiesterase (PDE4) reverses memory deficits associated with NMDA receptor antagonism.* Neuropsychopharmacology, 2000. 23(2): p. 198-204.

58. Nakagami, Y., et al., *A novel beta-sheet breaker, RS-0406, reverses amyloid beta-induced cytotoxicity and impairment of long-term potentiation in vitro*. Br J Pharmacol, 2002. 137(5): p. 676-82.
59. Walsh, D. M., et al., *Certain inhibitors of synthetic amyloid beta-peptide (Abeta) fibrillogenesis block oligomerization of natural Abeta and thereby rescue long-term potentiation*. J Neurosci, 2005. 25(10): p. 2455-62.
60. Schenk, D., et al., *Immunization with amyloid-beta attenuates Alzheimer-disease-like pathology in the PDAPP mouse*. Nature, 1999. 400(6740): p. 173-7.
61. Wu, J., R. Anwyl, and M. J. Rowan, *beta-Amyloid-(1-40) increases long-term potentiation in rat hippocampus in vitro*. Eur J Pharmacol, 1995. 284(3): p. R1-3.
62. Kowalska, M. A. and K. Badellino, *beta-Amyloid protein induces platelet aggregation and supports platelet adhesion*. Biochem Biophys Res Commun, 1994. 205(3): p. 1829-35.
63. Mattson, M. P., Z. H. Guo, and J. D. Geiger, *Secreted form of amyloid precursor protein enhances basal glucose and glutamate transport and protects against oxidative impairment of glucose and glutamate transport in synaptosomes by a cyclic GMP-mediated mechanism*. J Neurochem, 1999. 73(2): p. 532-7.
64. Borchelt, D. R., et al., *Accelerated amyloid deposition in the brains of transgenic mice coexpressing mutant presenilin 1 and amyloid precursor proteins*. Neuron, 1997. 19(4): p. 939-45.
65. Baltrons, M. A., et al., *Beta-amyloid peptides decrease soluble guanylyl cyclase expression in astroglial cells*. Neurobiol Dis, 2002. 10(2): p. 139-49.
66. Paris, D., et al., *Inhibition of Alzheimer's beta-amyloid induced vasoactivity and proinflammatory response in microglia by a cGMP-dependent mechanism*. Exp Neurol, 1999. 157(1): p. 211-21.
67. Corbin, J. D. and S. H. Francis, *Pharmacology of phosphodiesterase-5 inhibitors*. Int J Clin Pract, 2002. 56(6): p. 453-9.
68. Terrett, N. K., et al., *Sildenafil (VIAGRA™), a potent and selective inhibitor of type 5 cGMP phosphodiesterase with utility for the treatment of male erectile dysfunction*. Bioorg Med Chem Lett, 1996. 6(15): p. 1819-1824.
69. Trinchese, F., et al., *Progressive age-related development of Alzheimer-like pathology in APP/PS1 mice: early impairment of long-term potentiation and short-term memory associated with amyloid-beta production and plaque deposition*. Ann Neurol, In press.
70. Daugan, A., et al., *The discovery of tadalafil: a novel and highly selective PDE5 inhibitor. 2. 2,3,6,7,12,12a-hexahydropyrazino[1',2':1,6]pyrido[3,4-b]indole-1, 4-dione analogues*. J Med Chem, 2003. 46(21): p. 4533-42.
71. Snyder, P. B., et al., *The role of cyclic nucleotide phosphodiesterases in the regulation of adipocyte lipolysis*. J Lipid Res, 2005. 46(3): p. 494-503.
72. FDA. *Viagra tablets (sildenafil citrate). Review and evaluation of pharmacology and toxicology data. Report from the Division of Cardio-renal Drug Products (HFD-10). Center for Drug Evaluation and Research. in Food and Drug Administration.* 1998. Washington, D.C.
73. Prickaerts, J., et al., *Effects of two selective phosphodiesterase type 5 inhibitors, sildenafil and vardenafil, on object recognition memory and hippocampal cyclic GMP levels in the rat*. Neuroscience, 2002. 113(2): p. 351-61.
74. Walker, D. K., et al., *Pharmacokinetics and metabolism of sildenafil in mouse, rat, rabbit, dog and man*. Xenobiotica, 1999. 29(3): p. 297-310.
75. Arancio, O., et al., *RAGE potentiates Abeta-induced perturbation of neuronal function in transgenic mice*. Embo J, 2004. 23(20): p. 4096-105.
76. Lustbader, J. W., et al., *ABAD directly links Abeta to mitochondrial toxicity in Alzheimer's disease*. Science, 2004. 304(5669): p. 448-52.
77. Takuma, K., et al., *ABAD enhances Abeta-induced cell stress via mitochondrial dysfunction*. Faseb J, 2005. 19(6): p. 597-8.
78. Tully, T., et al., *Targeting the CREB pathway for memory enhancers*. Nat Rev Drug Discov, 2003. 2(4): p. 267-77.
79. Turner, B. M., *Cellular memory and the histone code*. Cell, 2002. 111(3): p. 285-91.
80. Battaglioli, E., et al., *REST repression of neuronal genes requires components of the hSWI.SNF complex*. J Biol Chem, 2002. 277(43): p. 41038-45.
81. Lunyak, V. V., et al., *Corepressor-dependent silencing of chromosomal regions encoding neuronal genes*. Science, 2002. 298(5599): p. 1747-52.
82. Francis, Y. I., et al. *Beneficial effect of the histone deacetylase inhibitor TSA in a mouse model of Alzheimer's disease.* in Soc Neurosci. Abstr. 2007. San Diego.
83. Gong, B., et al., *Ubiquitin Hydrolase Uch-L1 Rescues beta-Amyloid-Induced Decreases in Synaptic Function and Contextual Memory*. Cell, 2006. 126(4): p. 775-88.
84. Trinchese, F., et al. *Alzheimer Aβ Increases Neurotransmitter Release and Blocks Synaptic Plasticity in Hippocampal Cultures.* in The 9th International Conference on Alzheimer's Disease and Related Disorders Abstr. 2004. Philadelphia.
85. Takahashi, R. H., et al., *Oligomerization of Alzheimer's beta-amyloid within processes and synapses of cultured neurons and brain*. The Journal of Neuroscience, 2004. 24(14): p. 3592-3599.
86. Daugan, A., et al., *The discovery of tadalafil: a novel and highly selective PDE5 inhibitor. 1: 5,6,11,11a-tetrahydro-1H-imidazo[1',5':1,6]pyrido[3,4-b]indole-1,3(2H)—dione analogues*. J Med Chem, 2003. 46(21): p. 4525-32.
87. Prickaerts, J., et al., *Phosphodiesterase type 5 inhibition improves early memory consolidation of object information*. Neurochem Int, 2004. 45(6): p. 915-28.
88. Saenz de Tejada, I., et al., *The phosphodiesterase inhibitory selectivity and the in vitro and in vivo potency of the new PDE5 inhibitor vardenafil*. Int J Impot Res, 2001. 13(5): p. 282-90.
89. Zhang, X., Q. Feng, and R. H. Cote, *Efficacy and selectivity of phosphodiesterase-targeted drugs in inhibiting photoreceptor phosphodiesterase (PDE6) in retinal photoreceptors*. Invest Ophthalmol Vis Sci, 2005. 46(9): p. 3060-6.
90. Coste, H. and P. Grondin, *Characterization of a novel potent and specific inhibitor of type V phosphodiesterase*. Biochem Pharmacol, 1995. 50(10): p. 1577-85.
91. Wells, J. N., C. E. Baird, and W. U. a. J. G. Hardman Y j, *Cyclic nucleotide phosphodiesterase activities of pig coronary arteries*. Biochim Biophys Acta, 1975. 384(2): p. 430-42.
92. Gresser, U. and C. H. Gleiter, *Erectile dysfunction: comparison of efficacy and side effects of the PDE-5 inhibitors sildenafil, vardenafil and tadalafil—review of the literature*. Eur J Med Res, 2002. 7(10): p. 435-46.
93. Ninan, I. and O. Arancio, *Presynaptic CaMKII Is Necessary for Synaptic Plasticity in Cultured Hippocampal Neurons*. Neuron, 2004. 42(1): p. 129-41.

94. Koglin, M., J. P. Stasch, and S. Behrends, *BAY 41-2272 activates two isoforms of nitric oxide-sensitive guanylyl cyclase.* Biochem Biophys Res Commun, 2002. 292(4): p. 1057-62.

95. Xiong, Y., et al., *Characterization of a catalytic ligand bridging metal ions in phosphodiesterases 4 and 5 by molecular dynamics simulations and hybrid quantum mechanical/molecular mechanical calculations.* Biophys J, 2006. 91(5): p. 1858-67.

96. Zhan, C. G. and F. Zheng, *First computational evidence for a catalytic bridging hydroxide ion in a phosphodiesterase active site.* J Am Chem Soc, 2001. 123(12): p. 2835-8.

97. Chen, X. and C.-G. Zhan, *Fundamental reaction pathways and free energy barriers for ester hydrolysis of intracellular second messenger 3¢,5¢-cyclic nucleotide.* J. Phys. Chem. B, 2004. 108: p. 3789-3797.

98. Chen, X. and C.-G. Zhan, *Theoretical determination of activation free energies for alkaline hydrolysis of cyclic and acyclic phosphodiesters in aqueous solution* J. Phys. Chem. B, 2004. 108: p. 6407-6413.

99. Yang, G. F., et al., *Understanding the structure-activity and structure-selectivity correlation of cyclic guanine derivatives as phosphodiesterase-5 inhibitors by molecular docking, CoMFA and CoMSIA analyses.* Bioorg Med Chem, 2006. 14(5): p. 1462-73.

100. Zhan, C.-G., J. Bentley, and D. M. Chipman, *Volume polarization in reaction field theory* J. Chem. Phys., 1998. 108: p. 177-192.

101. Huai, Q., et al., *Crystal structures of phosphodiesterases 4 and 5 in complex with inhibitor 3-isobutyl-1-methylxanthine suggest a conformation determinant of inhibitor selectivity.* J Biol Chem, 2004. 279(13): p. 13095-101.

102. Lee, M. E., et al., *Crystal structure of phosphodiesterase 4D and inhibitor complex(1).* FEBS Lett, 2002. 530(1-3): p. 53-8.

103. Sung, B. J., et al., *Structure of the catalytic domain of human phosphodiesterase 5 with bound drug molecules.* Nature, 2003. 425(6953): p. 98-102.

104. Card, G. L., et al., *Structural basis for the activity of drugs that inhibit phosphodiesterases.* Structure, 2004. 12(12): p. 2233-47.

105. Huai, Q., J. Colicelli, and H. Ke, *The crystal structure of AMP-bound PDE4 suggests a mechanism for phosphodiesterase catalysis.* Biochemistry, 2003. 42(45): p. 13220-6.

106. Scapin, G., et al., *Crystal structure of human phosphodiesterase 3B: atomic basis for substrate and inhibitor specificity.* Biochemistry, 2004. 43(20): p. 6091-100.

107. Zhang, K. Y., et al., *A glutamine switch mechanism for nucleotide selectivity by phosphodiesterases.* Mol Cell, 2004. 15(2): p. 279-86.

108. Huai, Q., et al., *Crystal structure of phosphodiesterase 9 shows orientation variation of inhibitor 3-isobutyl-1-methylxanthine binding.* Proc Natl Acad Sci USA, 2004. 101(26): p. 9624-9.

109. Cao, Q., et al., *Crystal structure of human PDE2 for structure-based drug design,* W.I.P.O.P. Int., Editor. 2005, Pfizer Inc.: USA. p. 169.

110. Zhan, C. G., et al., *Theoretical determination of chromophores in the chromogenic effects of aromatic neurotoxicants.* J Am Chem Soc, 2002. 124(11): p. 2744-52.

111. Zhan, C.-G., J. Bentley, and D. M. Chipman, *Volume polarization in reaction field theory.* J. Chem. Phys., 1998. 108: p. 177-192.

112. Zhan, C.-G. and D. M. Chipman, *Cavity size in reaction field theory.* J. Chem. Phys., 1998. 109: p. 10543-10558.

113. Zhan, C.-G. and D. M. Chipman, *Effect of hydrogen bonding on the vibrations of benzosemiquinone radical anion* J. Phys. Chem. A, 1998. 102: p. 1230-1235.

114. Zhan, C.-G., D. W. Landry, and R. L. Ornstein, *Energy barriers for alkaline hydrolysis of carboxylic acid esters in aqueous solution by reaction field calculations* J. Phys. Chem. A 2000 104: p. 7672-7678.

115. Zhan, C.-G. and D. A. Dixon, *Absolute hydration free energy of the proton from first-principles electronic structure calculations* J. Phys. Chem. A 2001. 105: p. 11534-11540.

116. Zhan, C.-G. and D. A. Dixon, *First-principles determination of absolute hydration free energy of hydroxide ion* J. Phys. Chem. A 2002 106: p. 9737-9744.

117. Dixon, D. A., et al., *Decomposition pathways of peroxynitrous acid: Gas-phase and solution energetics.* J. Phys. Chem. A 2002. 106: p. 3191-3196.

118. Zhan, C.-G., et al., *Theoretical determination of chromophores in the chromogenic effects of neurotoxicants* J. Am. Chem. Soc., 2002. 124: p. 2744-2752.

119. Dixon, D. A., et al., *Acidities of HNO, HOONO, HONO, and HONO2* Int. J. Mass Spectrom, 2003. 227: p. 421-438.

120. Zhan, C.-G., F. Zheng, and D. A. Dixon, *Theoretical studies of photoelectron spectra of SO42-(H2O)n clusters and the extrapolation to bulk solution* J. Chem. Phys., 2003. 119: p. 781-793.

121. Zhan, C.-G., D. A. Dixon, and P. S. Spencer, *Computational insights into the chemical structures and mechanisms of the chromogenic and neurotoxic effects of aromatic g-diketones.* J. Phys. Chem. B, 2003. 107: p. 2853-2861.

122. Zhan, C.-G., D. A. Dixon, and P. S. Spencer, *Chromogenic and neurotoxic effects of aliphatic-diketone: Computational insights into the molecular structures and mechanism.* J. Phys. Chem. B 2004. 108: p. 6098-6104.

123. Zhan, C.-G. and D. A. Dixon, *The nature and absolute hydration free energy of the solvated electron in water* J. Phys. Chem. B, 2003. 107: p. 4403-4417.

124. Zhan, C.-G. and D. A. Dixon, *Hydration of the fluoride anion: Structures and absolute hydration free energy from first-principles electronic structure calculations.* J. Phys. Chem. A, 2004. 108: p. 2020-2029.

125. Degerman, E., P. Belfrage, and V. C. Manganiello, *Structure, localization, and regulation of cGMP-inhibited phosphodiesterase (PDE3).* J Biol Chem, 1997. 272(11): p. 6823-6.

126. Soderling, S. H. and J. A. Beavo, *Regulation of cAMP and cGMP signaling: new phosphodiesterases and new functions.* Curr Opin Cell Biol, 2000. 12(2): p. 174-9.

127. Richter, W., et al., *Identification of inhibitor binding sites of the cAMP-specific phosphodiesterase 4.* Cell Signal, 2001. 13(4): p. 287-97.

128. Herman, S. B., et al., *Analysis of a mutation in phosphodiesterase type 4 that alters both inhibitor activity and nucleotide selectivity.* Mol Pharmacol, 2000. 57(5): p. 991-9.

129. Schudt, C., et al., *Zardaverine as a selective inhibitor of phosphodiesterase isozymes.* Biochem Pharmacol, 1991. 42(1): p. 153-62.

130. Turko, I. V., S. H. Francis, and J. D. Corbin, *Potential roles of conserved amino acids in the catalytic domain of the cGMP-binding cGMP-specific phosphodiesterase.* J Biol Chem, 1998. 273(11): p. 6460-6.

131. Park, K., et al., *Sildenafil inhibits phosphodiesterase type 5 in human clitoral corpus cavernosum smooth muscle.* Biochem Biophys Res Commun, 1998. 249(3): p. 612-7.
132. Choi, S., et al., *Efficacy of vardenafil and sildenafil in facilitating penile erection in an animal model.* J Androl, 2002. 23(3): p. 332-7.
133. Rotella, D. P., *Phosphodiesterase 5 inhibitors: current status and potential applications.* Nat Rev Drug Discov, 2002. 1(9): p. 674-82.
134. Karnam, S. M., Z. Huiping, and M. M. Gabriel, *PKA-dependent activation of PDE3A and PDE4 and inhibition of adenylyl cyclase V/VI in smooth muscle.* Am. J. Physiol. Cell Physiol., 2001. 282: p. C508-C517.
135. Xu, R. X., et al., *Atomic structure of PDE4: insights into phosphodiesterase mechanism and specificity.* Science, 2000. 288(5472): p. 1822-5.
136. Liu, S., et al., *Dissecting the cofactor-dependent and independent bindings of PDE4 inhibitors.* Biochemistry, 2001. 40(34): p. 10179-86.
137. Wang, P., et al., *Characterization of human, dog and rabbit corpus cavernosum type 5 phosphodiesterases.* Life Sci, 2001. 68(17): p. 1977-87.
138. Bohm, H. J., *The computer program LUDI: a new method for the de novo design of enzyme inhibitors.* J Comput Aided Mol Des, 1992. 6(1): p. 61-78.
139. Bohm, H. J., *LUDI: rule-based automatic design of new substituents for enzyme inhibitor leads.* J Comput Aided Mol Des, 1992. 6(6): p. 593-606.
140. Bohm, H. J., *On the use of LUDI to search the Fine Chemicals Directory for ligands of proteins of known three-dimensional structure.* J Comput Aided Mol Des, 1994. 8(5): p. 623-32.
141. Lawrence, M. C. and P. C. Davis, *CLIX: a search algorithm for finding novel ligands capable of binding proteins of known three-dimensional structure.* Proteins, 1992. 12(1): p. 31-41.
142. Ho, C. M. and G. R. Marshall, *FOUNDATION: a program to retrieve all possible structures containing a user-defined minimum number of matching query elements from three-dimensional databases.* J Comput Aided Mol Des, 1993. 7(1): p. 3-22.
143. Rotstein, S. H. and M. K. Murcko, *GroupBuild: A Fragment-Based Method for De NoVo Drug Design"*. J. Med. Chem., 1993. 36: p. 1700-1710.
144. Gillet, V., et al., *SPROUT: a program for structure generation.* J Comput Aided Mol Des, 1993. 7(2): p. 127-53.
145. Gillet, V. J., et al., *SPROUT: recent developments in the de novo design of molecules.* J Chem Inf Comput Sci, 1994. 34(1): p. 207-17.
146. Taylor, R. D., P. J. Jewsbury, and J. W. Essex, *A review of protein-small molecule docking methods.* J Comput Aided Mol Des, 2002. 16(3): p. 151-66.
147. Ewing, T. J., et al., *DOCK 4.0: search strategies for automated molecular docking of flexible molecule databases.* J Comput Aided Mol Des, 2001. 15(5): p. 411-28.
148. Irwin, J. J. and B. K. Shoichet, *ZINC—a free database of commercially available compounds for virtual screening.* J Chem Inf Model, 2005. 45(1): p. 177-82.
149. http www simulations-plus.com/products/predictor/what_is_predictor.html.
150. Bajorath, J., *Integration of virtual and high-throughput screening.* Nat Rev Drug Discov, 2002. 1(11): p. 882-94.
151. Osterberg, T. and U. Norinder, *Prediction of polar surface area and drug transport processes using simple parameters and PLS statistics.* J Chem Inf Comput Sci, 2000. 40(6): p. 1408-11.
152. Case, D. A., et al., *The Amber biomolecular simulation programs.* J Comput Chem, 2005. 26(16): p. 1668-88.
153. Cornell, W. D., et al., *A second generation force field for the simulation of proteins, nucleic acids, and organic molecules.* J. Am. Chem. Soc., 1995 117: p. 5179-5197.
154. Kale, L., et al., *NAMD2: greater scalability for parallel molecular dynamics.* 1999. 151: p. 283-312.
155. Zhan, C.-G., et al., *Determination of two structural forms of catalytic bridging ligand in zinc-phosphotriesterase by molecular dynamics simulation and quantum chemical calculation.* J. Am. Chem. Soc., 1999. 121: p. 7279-7282.
156. Koca, J., et al., *Mobility of the active site bound paraoxon and sarin in zinc-phosphotriesterase by molecular dynamics simulation and quantum chemical calculation.* J Am Chem Soc, 2001. 123(5): p. 817-26.
157. Gao, D., et al., *Computational design of a human butyrylcholinesterase mutant for accelerating cocaine hydrolysis based on the transition-state simulation.* Angew Chem Int Ed Engl, 2006. 45(4): p. 653-7.
158. Pan, Y., et al., *Computational redesign of human butyrylcholinesterase for anticocaine medication.* Proc Natl Acad Sci USA, 2005. 102(46): p. 16656-61.
159. Zhan, C. G. and D. Gao, *Catalytic mechanism and energy barriers for butyrylcholinesterase-catalyzed hydrolysis of cocaine.* Biophys J, 2005. 89(6): p. 3863-72.
160. Hamza, A. and C. G. Zhan, *How can (−)-epigallocatechin gallate from green tea prevent HIV-1 infection? Mechanistic insights from computational modeling and the implication for rational design of anti-HIV-1 entry inhibitors.* J Phys Chem B Condens Matter Mater Surf Interfaces Biophys, 2006. 110(6): p. 2910-7.
161. Huang, X., et al., *Structural and functional characterization of human microsomal prostaglandin E synthase-1 by computational modeling and site-directed mutagenesis.* Bioorg Med Chem, 2006. 14(10): p. 3553-62.
162. Hamza, A., et al., *Understanding human 15-hydroxyprostaglandin dehydrogenase binding with NAD+ and PGE2 by homology modeling, docking and molecular dynamics simulation.* Bioorg Med Chem, 2005. 13(14): p. 4544-51.
163. Hamza, A., et al., *Molecular dynamics simulation of cocaine binding with human butyrylcholinesterase and its mutants.* J Phys Chem B Condens Matter Mater Surf Interfaces Biophys, 2005. 109(10): p. 4776-82.
164. Fadrna, E., et al., *Molecular dynamics simulations of Guanine quadruplex loops: advances and force field limitations.* Biophys J, 2004. 87(1): p. 227-42.
165. Harris, D. L., et al., *Theoretical study of the ligand-CYP2B4 complexes: effect of structure on binding free energies and heme spin state.* Proteins, 2004. 55(4): p. 895-914.
166. AbdulHameed, M. D. M., A. Hamza, and C.-G. Zhan, *Microscopic modes and free energies of 3-phosphoinositide-dependent kinase-1 (PDK1) binding with celecoxib and other inhibitors.* J. Phys. Chem. B, 2006.
167. Schwardt, O., H. Kolb, and B. Ernst, *Drug discovery today.* Curr Top Med Chem, 2003. 3(1): p. 1-9.
168. van de Waterbeemd, H. and E. Gifford, *ADMET in silico modelling: towards prediction paradise?* Nat Rev Drug Discov, 2003. 2(3): p. 192-204.

169. Martin, E. J., et al., *Measuring diversity: experimental design of combinatorial libraries for drug discovery*. J Med Chem, 1995. 38(9): p. 1431-6.
170. Blaney, J. M. and E. J. Martin, *Computational approaches for combinatorial library design and molecular diversity analysis*. Curr Opin Chem Biol, 1997. 1(1): p. 54-9.
171. Lipinski, C. A., et al., *Experimental and Computational Approaches to Estimate Solubility and Permeability in Drug Discovery and Development Settings*. Adv. Drug Deliv. Rev., 1997. 23: p. 3-25.
172. Lipinski, C. A., *Drug-like properties and the causes of poor solubility and poor permeability*. J Pharmacol Toxicol Methods, 2000. 44(1): p. 235-49.
173. Ajay, *Predicting drug-likeness: why and how?* Curr Top Med Chem, 2002. 2(12): p. 1273-86.
174. Martin, Y. C., *A bioavailability score*. J Med Chem, 2005. 48(9): p. 3164-70.
175. Kubinyi, H., *Drug research: myths, hype and reality*. Nat Rev Drug Discov, 2003. 2(8): p. 665-8.
176. Teague, S. J., et al., *The Design of Leadlike Combinatorial Libraries*. Angew Chem Int Ed Engl, 1999. 38(24): p. 3743-3748.
177. Oprea, T. I., et al., *Is there a difference between leads and drugs? A historical perspective*. J Chem Inf Comput Sci, 2001. 41(5): p. 1308-15.
178. Caccia, S., T. Fossati, and A. Mancinelli, *Disposition and metabolism of minaprine in the rat*. Xenobiotica, 1985. 15(12): p. 1111-9.
179. Schiefer, J. and R. Sparing, *Transient global amnesia after intake of tadalafil, a PDE-5 inhibitor: a possible association?* Int J Impot Res, 2005. 17(4): p. 383-4.
180. Pardridge, W. M., *Blood-brain barrier drug targeting: the future of brain drug development*. Mol Interv, 2003. 3(2): p. 90-105, 51.
181. Hodgson, J., *ADMET—turning chemicals into drugs*. Nat Biotechnol, 2001. 19(8): p. 722-6.
182. Suter, W., *Predictive value of in vitro safety studies*. Curr Opin Chem Biol, 2006. 10(4): p. 362-6.
183. Chen, X. and W. Wang, *The Use of Bioisosteric Groups in Hit Optimization*. Ann. Reports Med. Chem., 2003. 38: p. 333-346.
184. Evans, D. C., et al., *Drug-Protein Adducts: An Industry Perspective on Minimizing the Potential for Drug Bioactivation in Drug Discovery and Develeopment*. Chem. Res. Toxicol., 2004. 17: p. 3-16.
185. Liu, S., et al., *alpha-Synuclein produces a long-lasting increase in neurotransmitter release*. Embo J, 2004. 23(22): p. 4506-16.
186. Duff, K., et al., *Increased amyloid-beta42(43) in brains of mice expressing mutant presenilin 1*. Nature, 1996. 383(6602): p. 710-3.
187. Hsiao, K., et al., *Correlative memory deficits, Abeta elevation, and amyloid plaques in transgenic mice*. Science, 1996. 274(5284): p. 99-102.
188. Di Rosa, G., et al., *Calpain inhibitors: a treatment for Alzheimer's disease*. J Mol Neurosci, 2002. 19(1-2): p. 135-41.
189. Arancio, O., E. R. Kandel, and R. D. Hawkins, *Activity-dependent long-term enhancement of transmitter release by presynaptic 3',5'-cyclic GMP in cultured hippocampal neurons*. Nature, 1995. 376(6535): p. 74-80.
190. Paterno, R., F. M. Faraci, and D. D. Heistad, *Role of Ca(2+)-dependent K+ channels in cerebral vasodilatation induced by increases in cyclic GMP and cyclic AMP in the rat*. Stroke, 1996. 27(9): p. 1603-7; discussion 1607-8.
191. Kloner, R. A., et al., *Cardiovascular safety update of Tadalafil: retrospective analysis of data from placebo-controlled and open-label clinical trials of Tadalafil with as needed, three times-per-week or once-a-day dosing*. Am J Cardiol, 2006. 97(12): p. 1778-84.
192. Basun, H., et al., *Plasma levels of Abeta42 and Abeta40 in Alzheimer patients during treatment with the acetylcholinesterase inhibitor tacrine*. Dement Geriatr Cogn Disord, 2002. 14(3): p. 156-60.
193. Andreasen, N., M. Sjogren, and K. Blennow, *CSF markers for Alzheimer's disease: total tau, phospho-tau and Abeta42*. World J Biol Psychiatry, 2003. 4(4): p. 147-55.
194. Kalaria, R. N., *Vascular factors in Alzheimer's disease*. Int Psychogeriatr, 2003. 15 Suppl 1: p. 47-52.
195. Gentile, M. T., et al., *Mechanisms of soluble beta-amyloid impairment of endothelial function*. J Biol Chem, 2004. 279(46): p. 48135-42.
196. Smith, C. C., L. Stanyer, and D. J. Betteridge, *Soluble beta-amyloid (A beta) 40 causes attenuation or potentiation of noradrenaline-induced vasoconstriction in rats depending upon the concentration employed*. Neurosci Lett, 2004. 367(1): p. 129-32.
197. Price, J. M., et al., *Aging enhances vascular dysfunction induced by the Alzheimer's peptide beta-amyloid*. Neurol Res, 2004. 26(3): p. 305-11.
198. Khalil, Z., et al., *Mechanisms of peripheral microvascular dysfunction in transgenic mice overexpressing the Alzheimer's disease amyloid Abeta protein*. J Alzheimers Dis, 2002. 4(6): p. 467-78.
199. Pasquier, F. and D. Leys, [*Blood pressure and Alzheimer's disease*]. Rev Neurol (Paris), 1998. 154(11): p. 743-51.
200. Champion, H. C., et al., *Phosphodiesterase-5A dysregulation in penile erectile tissue is a mechanism of priapism*. Proc Natl Acad Sci USA, 2005. 102(5): p. 1661-6.
201. Burnett, A. L., et al., *Long-term oral phosphodiesterase 5 inhibitor therapy alleviates recurrent priapism*. Urology, 2006. 67(5): p. 1043-8.
202. Rajfer, J., et al., *Case report: Avoidance of palpable corporal fibrosis due to priapism with upregulators of nitric oxide*. J Sex Med, 2006. 3(1): p. 173-6.
203. Moreno, H. W., et al. *Imaging Hippocampal Dysfunction in Transgenic Mice with MRI*. in The 9th International Conference on Alzheimer's Disease and Related Disorders Abstr. 2004. Philadelphia.
204. Moreno, H. W., et al. *Adapting fMRI so that normal and abnormal hippocampal circuits can be investigated in transgenic mice*. in Soc Neurosci. Abstr. 2004
205. Yu, R., et al. *The retromer and Alzheimer's disease: characterizing retromer knock-down mice with and without APP mutations*, in Soc Neurosci. Abstr. 2005.
206. Oddo, S., et al., *Triple-transgenic model of Alzheimer's disease with plaques and tangles: intracellular Abeta and synaptic dysfunction*. Neuron, 2003. 39(3): p. 409-21.
207. Billings, L. M., et al., *Intraneuronal Abeta causes the onset of early Alzheimer's disease-related cognitive deficits in transgenic mice*. Neuron, 2005. 45(5): p. 675-88.
208. Arendash, G. W., et al., *Progressive, age-related behavioral impairments in transgenic mice carrying both mutant amyloid precursor protein and presenilin-1 transgenes*. Brain Res, 2001. 891(1-2): p. 42-53.
209. Liu, L., et al., *Abeta levels in serum, CSF and brain, and cognitive deficits in APP+PS1 transgenic mice*. Neuroreport, 2003. 14(1): p. 163-6.

210. Puolivali, J., et al., *Hippocampal A beta 42 levels correlate with spatial memory deficit in APP and PS1 double transgenic mice.* Neurobiol Dis, 2002. 9(3): p. 339-47.
211. Morgan, D., et al., *A beta peptide vaccination prevents memory loss in an animal model of Alzheimer's disease.* Nature, 2000. 408(6815): p. 982-5.
212. Janus, C., et al., *A beta peptide immunization reduces behavioural impairment and plaques in a model of Alzheimer's disease.* Nature, 2000. 408(6815): p. 979-82.

Example 6—Quinoline Compounds and Pharmacology Studies

Electrophysiological Protocol

Following cutting hippocampal slices were transferred to a recording chamber where they were maintained at 29° C. and perfused with artificial cerebrospinal fluid (ACSF) continuously bubbled with 95% $O_2$ and 5% $CO_2$. The ACSF composition in mM was: 124.0 NaCl, 4.4 KCl, 1.0 $Na_2HPO_4$, 25.0 $NaHCO_3$, 2.0 $CaCl_2$, 2.0 $MgSO_4$, 10.0 glucose. CA1 fEPSPs were recorded by placing both the stimulating and the recording electrodes in CA1 stratum radiatum. BST was assayed either by plotting the stimulus voltages against slopes of fEPSP, or by plotting the peak amplitude of the fiber volley against the slope of the fEPSP. A 15 min baseline was recorded every min at an intensity that evokes a response ~35% of the maximum evoked response. LTP was induced using q-burst stimulation (4 pulses at 100 Hz, with the bursts repeated at 5 Hz and each tetanus including 3 ten-burst trains separated by 15 sec). Responses were recorded for 1 hr after tetanization and measured as field-excitatory-post-synaptic potential (fEPSP) slope expressed as percentage of baseline.

In these experiments YF012403 (the cyclopropyl lead compound) was directly given to the hippocampal slices through the perfusion system for 10 min prior to the theta burst. Aβ42 was given for 20 minutes prior to the theta burst. Oligomeric Aβ42 was prepared as described previously (Stine et al., 2003). Briefly, the lyophilized peptide (American Peptide) was resuspended in 100% 1,1,1,3,3,3-hexafluoro-2-propanol (HFIP; Sigma, St. Louis, Mo.) to 1 mM. The solution was aliquoted, and the HFIP was allowed to evaporate in the fume hood. The resulting clear peptide film was dried under vacuum in a SpeedVac and stored at −20° C. Twenty-four hours before use, the aliquots were added to dimethylsulfoxide (DMSO; Sigma) and sonicated for 10 min. Oligomeric Aβ-42 was obtained by diluting Aβ-42-DMSO into ACSF concentration, vortexed for 30 s, and incubated at 4° C. for 24 h. Before use, this compound was added to ACSF to obtain 200 nM.

Acute Toxicity Profile

Timeline: 24 h-7 days. In the timeline, no fatal effects were observed.

Dosage:
Single dose at 500 mg/kg, i.p.
Single dose at 1000 mg/kg, i.p.
Single dose at 2000 mg/kg, p.o.
Species: Mouse Compounds A new class of quinoline-containing compounds have been synthesized which have excellent PDE5 inhibitory potency, high selectivity, reasonable pharmacokinetics and good permeability to the blood-brain-barrier (BBB). These compounds may be used to minimize the side effects for AD patients, the third most costly disease in the U.S. The compounds of the invention may also be used to treat erectile dysfunction (ED), pulmonary hypertension, cardiovascular disorder, diabetes, and GI disorders.

The leading compounds are an 8-cyclopropyl quinoline derivative (YF012403) and an 8-dimethylaminoquinoline (YF016203) derivative. The $IC_{50}$ of these compounds to PDE5 are 1.2 nM and 4.5 nM, respectively. For example, in BABL/c mice, the YF012403 compound half-life is 1.04 h in the brain and 1.33 hr in the plasma as compared to Sildenafil (a known PDE5 inhibitor) which has a brain half-life of 0.84 h and a plasma half-life of 1.21 h. Distribution of YF012403 in brain tissue versus that in the plasma (non-protein-bound free form; $C_{Brain}/C_{Plasma}$) is 0.41, which indicates that the penetration of the compound to the BBB is acceptable with respect to druggability. Thus, the compounds are potential candidates for treatment of AD patients.

YF012403 has high potency ($IC_{50}$=0.27 nM), and excellent selectivity for PDE5 over other PDE isoforms (FIG. 27). In addition, it penetrates the BBB after p.o. administration with a $T_{max}$=0.5 hr and a $C_{max}$=385 ng/g at a dosage of 50 mg/kg. Furthermore, the compound is safe up to 2 g/kg (p.o.) in acute toxicity test. Most importantly, it shows both ex vivo and in vivo efficacy: it ameliorates LTP in hippocampal slices treated with Aβ42 and contextual fear memory in mice infused with Aβ42. YF012403 is biologically active in tests of synaptic and cognitive function following Aβ elevation.

Using YF012403 as a lead candidate, we will design and synthesize PDE5 inhibitors bearing different moieties at the C3 and the C8 positions, as well as other parts of the quinoline. It is noted that N, and S groups substituted at the C8 position of the quinoline (see also FIG. 50), have not been previously reported.

General Synthesis Method of Scheme A

The incentive compounds of formulas XIII' and XIV' can be prepared conveniently according to the synthetic sequence as shown in Scheme A (FIG. 38).

As shown in FIG. 38, starting from commercial available 4-amino-3-bromobenzonitrile (I'), the key intermediate, substituted 4-hydroxyquinoline III', is conveniently prepared by reaction of aniline I' with diethyl ethoxymethylenemalonate, followed by an intra-molecular cyclization reaction at a high temperature. The substituted 4-hydroxyquinoline III' is then allowed to react with arylalkyl halide, aroyl halide or arylsulfonyl halide to afford 8-bromoquinoline V'. Alternatively, by reaction with $POCl_3$, the 4-hydroxyquinoline is readily converted to the corresponding 4-chloroquinoline VI', which reacts either with arylalkylamine to afford key intermediate VIII', or with ammonia directly to yield 4-aminoquinoline IX'. The 4-aminoquinoline is then allowed to react with arylalkyl halide, aroyl halide or arylsulfonyl halide to give another key intermediate X'. Starting from the key intermediates V', VIII', X', which are represented by formula XI', the incentive formula XIII' is prepared by coupling of cycloalkylboronic acid or substituted amine with the 8-bromoquinoline XI', followed by reduction of the ethyl ester to provide the resulting intermediate XIII'. Through substitution by nucleophiles such as substituted amines, or reaction with electrophiles such as alkyl, acyl or sulfonyl halides, the incentive formula XIII' is conveniently converted to incentive formula XIV'.

Synthesis Examples of Compounds

The following examples are offered for illustrative purpose for the incentive compounds and intermediates, and are not intended to limit the scope of the claims in any manner. Those skill of the art will readily recognize a variety of noncritical parameters which can be changed or modified to yield essentially the same results.

Example 1

The synthesis of compound 9a within the invention is outlined in Scheme I, with the details of the individual steps given in FIG. 39.

Preparation of diethyl
2-((2-bromo-4-cyanophenylamino)methylene)malonate
(Intermediate 3a)

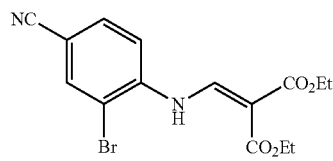 [SMILES: CCOC(=O)C(=CNc1ccc(C#N)cc1Br)C(=O)OCC]

To a solution of 5.00 g (25.4 mmol) 4-amino-3-bromobenzonitrile in 30 mL of toluene was added 8.23 g (38.1 mmol) of diethyl ethoxymethylenemalonate (2a). The mixture was then heated to reflux for overnight with a condenser open to the air. The resulting solution was cooled down to room temperature and poured into 100 mL of hexanes. The white precipitate was collected and washed with hexanes (30 mL×3) to yield 11.9 g of an off-while solid as the desired product. MS ESI (m/z) 367 (M+1)$^+$.

Preparation of ethyl
8-bromo-6-cyano-4-hydroxyquinoline-3-carboxylate
(Intermediate 4a)

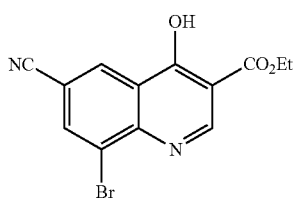 [SMILES: CCOC(=O)c1cnc2c(Br)cc(C#N)cc2c1O]

100 mL of diphenyl ether was heated to reflux followed by addition of 5.00 g (13.6 mmol) diethyl 2-((2-bromo-4-cyanophenylamino)methylene)malonate in portions in 30 minutes. The resulting brown solution was reflux for another hour and then cooled down to room temperature. The precipitate was collected and washed with hexanes (15 mL×3) to give 5.69 g of a light brown solid as the desired product. MS ESI (m/z) 321 (M+1)$^+$.

Preparation of ethyl
8-bromo-4-chloro-6-cyanoquinoline-3-carboxylate
(Intermediate 5a)

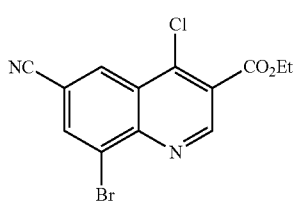 [SMILES: CCOC(=O)c1cnc2c(Br)cc(C#N)cc2c1Cl]

The mixture of 3.85 g (12 mmol) and 50 mL of POCl$_3$ was heated to reflux for 48 hours. The solvent was removed in vacuum and co-distilled with CHCl$_3$ (50 mL) and toluene (50 mL×2). The resulting dark brown syrup was dissolved in 50 mL of CH$_2$Cl$_2$ and treated with Et$_3$N until pH>10. The dark-red solution was then allowed to go through a silica gel pad (3 cm×4 cm). The silica pad was washed with 100 mL of CH$_2$Cl$_2$. The filtrates were collected and concentrated to yield a brown solid, which was used in the next step directly without further purification.

Preparation of ethyl
8-bromo-4-chloro-6-cyanoquinoline-3-carboxylate
(Intermediate 7a)

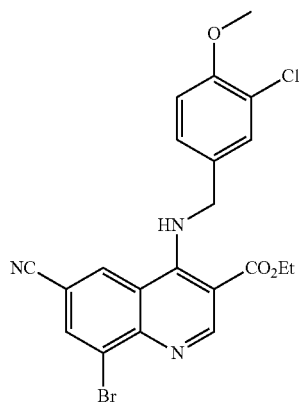 [SMILES: CCOC(=O)c1cnc2c(Br)cc(C#N)cc2c1NCc1ccc(OC)c(Cl)c1]

To the crude product of ethyl 8-bromo-4-chloro-6-cyanoquinoline-3-carboxylate obtained above was added 3.12 g (15 mmol) of (3-chloro-4-methoxyphenyl)methanamine hydrochloride (6a), 7.74 g of diisopropylethylamine and 50 mL of n-propanol. The resulting mixture was refluxed for 2.5 hours and then poured to 100 mL of ice-water. The precipitate was collected by filtration and washed by H$_2$O (30 mL×2) and ethanol (30 mL×3) to give 5.0 g of a yellow solid as the title compound. MS ESI (m/z) 474 (M+1)$^+$.

Preparation of ethyl 4-(3-chloro-4-methoxybenzylamino)-6-cyano-8-cyclopropy-quinoline-3-carboxylate (Intermediate 8a)

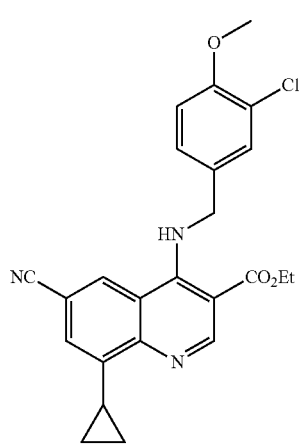 [SMILES: CCOC(=O)c1cnc2c(C3CC3)cc(C#N)cc2c1NCc1ccc(OC)c(Cl)c1]

Under nitrogen, to the solution of 475 mg (1 mmol) of 8-bromo-4-chloro-6-cyano-quinoline-3-carboxylate in 5 mL of dry toluene was added 129 mg (1.5 mmol) of cyclopropylboronic acid, 58 mg (0.05 mmol) of (tetrakis(triphenylphosphine) palladium (0) and 815 mg (2.5 mmol) of $Cs_2CO_3$. After the mixture was refluxed overnight, the precipitate in the solution was removed by filtration. The filtrate was concentrated and purified by flash chromatography (ethyl acetate:hexanes=1:4) to yield a 366 mg of a yellow solid as the desired compound. MS ESI (m/z) 436 $(M+1)^+$.

Preparation of 4-(3-chloro-4-methoxybenzylamino)-8-cyclopropyl-3-(hydroxymethyl)-quinoline-6-carbonitrile (Compound 9a)

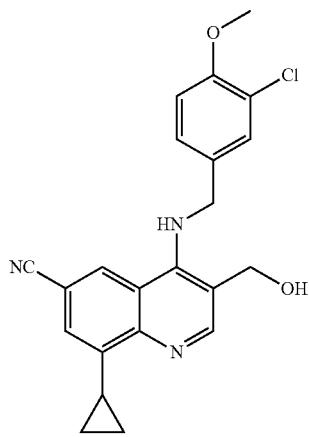 [SMILES: COc1ccc(CNc2c(CO)cnc3c(C4CC4)cc(C#N)cc23)cc1Cl]

Under nitrogen, to the solution of 180 mg (0.43 mmol) of intermediate 8 in 5 mL of dry THF was added 2.2 mL (2.2 mmol) of lithium tri(tert-butoxy)aluminum hydride (1 M in hexane). The resulting solution was refluxed overnight and then quenched with 1 mL of MeOH. 30 minutes later, the mixture was poured to a separatory funnel, followed by addition of 150 mL of $CH_2Cl_2$ and 50 mL of 1N NaOH. The organic layer was separated, washed with 1N NaOH (50 mL) and dried over $MgSO_4$. The solid was filtered off. Concentration of the filtrate gave 156 mg of a yellow solid as the incentive compound. $^1$H NMR (DMSO-$d_6$, 300 MHz): δ 8.69 (d, J=1.2 Hz, 1H), 8.48 (s, 1H), 7.42 (t, J=7 Hz, 1H), 7.37 (d, J=2.1 Hz, 1H), 7.33 (d, J=1.2 Hz, 1H), 7.21 (dd, $J_1$=8.4 Hz, $J_2$=2.1 Hz, 1H), 7.08 (d, J=8.4 Hz, 1H), 5.38 (t, J=5.1 Hz, 1H), 4.79 (d, J=7 Hz, 2H), 4.43 (d, J=5.1 Hz, 2H), 3.79 (s, 3H), 3.09-3.14 (m, 1H), 1.02-1.08 (m, 2H), 0.72-0.87 (m, 2H); MS ESI (m/z) 394 $(M+1)^+$.

Example 2

The synthesis of compound 11a within the invention is outlined in Scheme II, with the details of the individual steps given in FIG. 40.

Preparation of ethyl 4-(3-chloro-4-methoxybenzylamino)-6-cyano-8-(dimethylamino)-quinoline-3-carboxylate (Intermediate 10a)

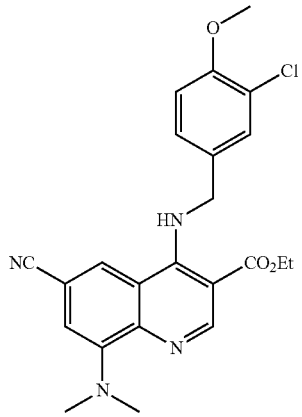 [SMILES: CCOC(=O)c1cnc2c(N(C)C)cc(C#N)cc2c1NCc1ccc(OC)c(Cl)c1]

Under nitrogen, to the solution of 475 mg (1 mmol) of 8-bromo-4-chloro-6-cyano-quinoline-3-carboxylate in 5 mL of dry toluene was added 11 mg (0.05 mmol) of palladium (II) acetate, 50 mg of (R)-BINAP, and 812 mg (2.5 mmol) of $Cs_2CO_3$, and 3 mL of the solution of dimethylamine in ethanol (5.6 M). After the mixture was refluxed overnight, the precipitate in the solution was removed by filtration. The filtrate was concentrated and purified by flash chromatography (ethyl acetate:hexanes=1:2) to yield a 140 mg of a yellow solid as the desired compound. MS ESI (m/z) 439 $(M+1)^+$.

Preparation of 4-(3-chloro-4-methoxybenzylamino)-8-(dimethylamino)-3-(hydroxymethyl)-quinoline-6-carbonitrile (Compound 11a)

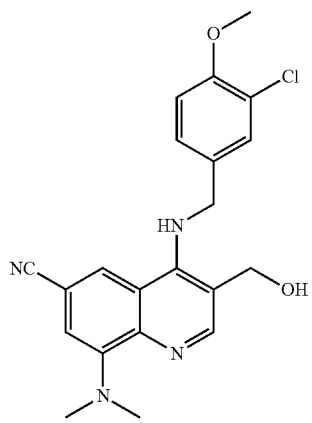 [SMILES: COc1ccc(CNc2c(CO)cnc3c(N(C)C)cc(C#N)cc23)cc1Cl]

Compound 11a was prepared by a method analogous to that described in the preparation of compound 9a starting from ethyl 4-(3-chloro-4-methoxybenzylamino)-6-cyano-8-(dimethylamino)-quinoline-3-carboxylate. $^1$H NMR (CDCl$_3$, 300 MHz): δ 8.37 (s, 1H), 7.90 (d, J=1 Hz, 1H), 7.31 (d, J=2 Hz, 1H), 7.16 (dd, $J_1$=8.7 Hz, $J_2$=2 Hz, 1H), 7.05 (d, J=1 Hz, 1H), 6.90 (d, J=8.7 Hz, 1H), 5.70 (t, J=4.2 Hz, 1H), 4.67 (s, 2H), 4.64 (d, J=4.2 Hz, 2H), 3.89 (s, 3H), 3.04 (s, 6H); MS ESI (m/z) 397 $(M+1)^+$.

Intermediate 10a within the invention is also synthesized through the synthetic route outlined in Scheme III-A1, with the details of the individual steps given in FIG. 41.

Preparation of 3-(dimethylamino)-4-nitrobenzonitrile (Intermediate 13a)

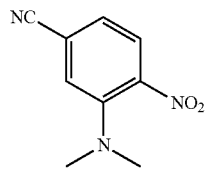

The mixture of 16.7 g (100 mmol) of 3-fluoro-4-nitrobenzonitrile and 100 mL of the solution of dimethylamine in ethanol (5 M) was refluxed overnight. The resulting dark red solution was then poured in to 100 mL of ice-water. The precipitate was collected by filtration and washed by $H_2O$ (50 mL×2) and ethanol (50 mL×2) to give 16.9 g of a organe needle crystal as the desired product. MS ESI (m/z) 192 (M+1)$^+$.

Preparation of 4-amino-3-(dimethylamino)benzonitrile (Intermediate 14a)

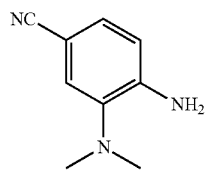

To 16 g (84 mmol) of 3-(dimethylamino)-4-nitrobenzonitrile was added 1 g of palladium on carbon (10%, w/w) and 100 mL of methanol. The mixture was saturated with hydrogen and stirred at room temperature overnight. The palladium on carbon was then filtered off. Concentration of the filtration gave 12.8 of a dark-red solid as the desired product. MS ESI (m/z) 162 (M+1)$^+$.

Preparation of diethyl 2-((4-cyano-2-(dimethylamino)phenylamino) methylene)malonate (Intermediate 15a)

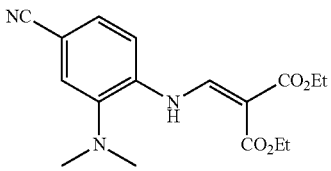 [SMILES: CCOC(=O)C(=CNc1ccc(C#N)cc1N(C)C)C(=O)OCC]

Intermediate 15a was prepared by a method analogous to that described in the preparation of intermediate 3a starting from 4-amino-3-(dimethylamino)benzonitrile. MS ESI (m/z) 332 (M+1)$^+$.

Preparation of ethyl 6-cyano-8-(dimethylamino)-4-hydroxyquinoline-3-carboxylate (Intermediate 16a)

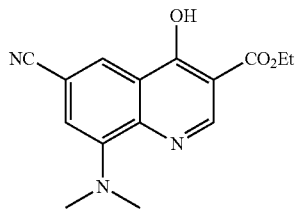 [SMILES: CCOC(=O)c1cnc2c(N(C)C)cc(C#N)cc2c1O]

Intermediate 16a was prepared by a method analogous to that described in the preparation of intermediate 4a starting from diethyl 2-((4-cyano-2-(dimethylamino)phenylamino)-methylene)malonate. MS ESI (m/z) 286 (M+1)$^+$.

Preparation of ethyl 4-chloro-6-cyano-8-(dimethylamino)quinoline-3-carboxylate (Intermediate 17a)

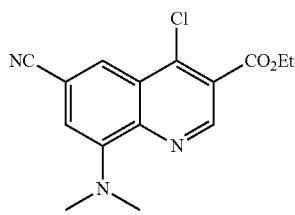 [SMILES: CCOC(=O)c1cnc2c(N(C)C)cc(C#N)cc2c1Cl]

Intermediate 17a was prepared by a method analogous to that described in the preparation of intermediate 5a starting from ethyl 6-cyano-8-(dimethylamino)-4-hydroxy-quinoline-3-carboxylate. MS ESI (m/z) 304 (M+1)$^+$.

Preparation of ethyl 4-(3-chloro-4-methoxybenzylamino)-6-cyano-8-(dimethylamino)-quinoline-3-carboxylate (Intermediate 10a)

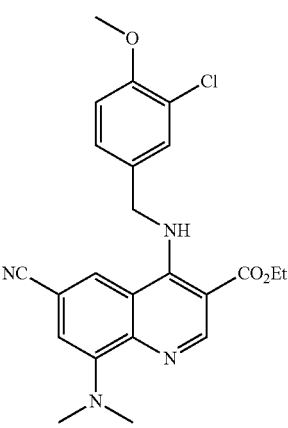 [SMILES: CCOC(=O)c1cnc2c(N(C)C)cc(C#N)cc2c1NCc1ccc(OC)c(Cl)c1]

Intermediate 10a was prepared by a method analogous to that described in the preparation of intermediate 7a starting from ethyl 6-cyano-8-(dimethylamino)-4-hydroxy-quinoline-3-carboxylate. MS ESI (m/z) 439 (M+1)$^+$.

Protocol of PDE Assay for Compound Screening

Materials: IMAP™ TR-FRET Screening Express with Progressive Binding Kit from Molecular Devices (R8160); FAM-Cyclic-3',5'-GMP from Molecular Devices (R7507); PDE5 inhibitors.

Methods

Step 1: A dilution series of the inhibitors ranging from 300 pM to 10 µM in 1× PDE Assay Buffer are made. Subsequently, FAM-cGMP is diluted to 200 nM in 1×PDE Assay Buffer. PDE5A1 enzymes are then diluted to 0.125 ng/µl in 1×PDE Assay Buffer.

Step 2: The following components are added to a low binding black plate: a) 25l of 200 nM FAM-cGMP (Final concentration will be 100 nM); b) 5 µl of the compounds (Final concentration=30 pM to 1 µM); c) 20 µl of PDE5A1 (0.125 ng/l) (Final amount=2.5 ng/reaction). The components are mixed and incubated at room temp. for 1 hour.

Step 3: A 1× reagent-binding buffer (75% 1× Binding Buffer A and 25% 1× Binding Buffer B) is then prepared followed by a Binding Solution that is prepared by diluting Binding Reagent with 1× reagent-binding Buffer (1:600). 120 µl of Binding Solution is then added to each well and the plate is incubated at room temperature for 1 hour.

Step 4: Fluorescence polarization is measured at excitation of 485 nm and emission of 520 nm in BioTek Synergy™ 2 microplate reader.

Protocol of Pharmacokinetics Testing

The pharmacokinetic studies were conducted in male BABL/c mice. The blood and brain samples were collected at predetermined times from three mice per time point. Six time points were measured for each compound: 0, 0.25, 0.5, 1.0, 2.0, and 4.0 hour. An LC-MS/MS method was developed to determine these compounds in plasma and brain samples.

Quantification was achieved by the internal standard method using peak area ratios of the analysis to the internal standard in plasma and brain. Concentrations were calculated using a weighted least-squares linear regression (W=1/×2). The major pharmacokinetic parameters were calculated and the brain-to-plasma distribution ratios were estimated.

Dose Preparation and Dose Administration:

The PDE5 inhibitor was prepared by dissolving the test article in 0.5% methyl cellulose to yield final concentrations at 5 mg/mL for PO administration. Sildenafil was prepared by dissolving the article in 0.2 M hydrochloric acid solution (pH=1) to yield final concentrations at 5 mg/mL. Dose volume for each test animal was determined based on the most recent body weight.

Sample Collection

Blood.

Blood (approximately 250 µL) was collected via retro-orbital puncture into tubes containing sodium heparin anti-coagulant at pre-dose (0 h) and 0.25, 0.5, 1.0, 2.0, and 4.0 hour from three mice per time point after administration. Mice were sacrificed by cervical dislocation after blood harvest. The plasma were separated via centrifugation (4° C., 3500 rpm, 10 min) and stored in −80° C. before analysis.

Preparation of Plasma Samples.

Frozen unknown plasma samples were thawed at room temperature and vortexed thoroughly. With a pipette, 25 µL of plasma was transferred into a 1.5 mL Eppendorf tube. To each sample, 25 µL of methanol and 25 µL of the internal standard were added, followed by the addition of 100-µL methanol. The sample mixture was vortexed for approximately 1 min. After centrifugation at 11000 g for 5 min, the upper organic layer was transferred to a glass tube and evaporated at 40° C. under a gentle stream of nitrogen. Residues were dissolved in 150 µL of the mobile phase, and mixed in a vortex mixer. A 20-µL aliquot of the resulting solution was injected onto the LC/MS/MS system for analysis.

Brain.

Brains were collected immediately after mice death. The brains were excised, weighed, and rinsed by cold saline and then frozen at −80° C. until further process for LC/MS/MS analysis.

Preparation of Brain Samples.

On the day of the assay, the frozen tissue samples were thawed unassisted at room temperature. When completely thawed, each tissue sample of 200 mg was weighed and placed into a plastic tube. Methanol (1.0 mL) was added to facilitate homogenization, which was conducted using a Fluko F6/10 superfine homogenizer for approximately 1 min. Then, the homogenized samples were vortexed for 1 min. A 25-µL aliquot of the homogenized samples was transferred into an Eppendorf tube. To each sample, 25 µL of methanol and 25 µL of the internal standard were added. The sample mixture centrifuged at 11000 g for 5 min. A 20-µL aliquot of the supernatants was diluted to 80 µL or 60 µL with the mobile phase and a 10-µL aliquot was injected onto the LC/MS/MS system for analysis.

Example 7—Quinoline Derivatives can be Developed as Potent and Selective PDE5 Inhibitors for the Treatment of AD Our findings support that inhibition of PDE5 can be beneficial against cognitive loss in AD. However, none of the existing commercially available inhibitors, including sildenafil, are optimized for the CNS. Moreover, even the non-commercially available synthesized inhibitors have not been fully characterized for CNS use. A good CNS drug should have high specificity and potency, as well as good PK, bioavailability and CNS penetration, and finally should be safe. For instance, sildenafil is reported to cross the BBB [S137] and has an $IC_{50}$ against PDE5 of 6.0 nM and an in vivo half-life of 0.4 hrs in rodents (~4 hrs in humans) [S135, S138]. However, the selectivity ratio for PDE1, which is expressed in myocardium and blood vessels besides the brain and may result in mild vasodilatatory effects is 180, and that for PDE6, which is expressed only in retina and can transiently disturb vision is equal to 12 [S106, S107]. Evidence for vardenafil ability to cross the BBB is indirect [150], and even if its IC50 against PDE5 is 0.17 nM, the selectivity ratio for PDE6 is equal to 3.5 [S151, S152]. Without being bound by theory, tadalafil, cannot cross the BBB. Thus, our laboratories have launched a program to develop new PDE5 inhibitors based on knowledge of structures of existing PDE5 inhibitors with a) high specificity and potency, b) great PK properties and CNS penetration, and c) safety, to be used in AD.

Many PDE5 inhibitors have been developed in the past decades and numerous potent compounds have been reported in the literature. Hence, we avoided wasting resources to develop an entirely new scaffold with high potency and excellent selectivity. Instead we focused on known inhibitors and performed a SAR analysis of the existing scaffolds to choose a structure that can lead to the discovery of a class of compounds that can be helpful in the treatment of AD. Rather than choosing cGMP-based molecules such as sildenafil and vardenafil, or β-carbolinesderived molecules such as tadalafil, we identified quinoline derivatives as the top candidates for the design and synthesis of PDE5 inhibitors to be optimized against AD, based on the high potency and selectivity of BMS4. This compound contains important features of two other potent inhibitors, BMS2 and E1 (FIG. 45). It was reported as the most potent and selective PDE5 inhibitor ever identified to date [S19]. Although the in vitro tests of this compound reached our criteria for potency and selectivity for PDE1-6, its selectivity for the remaining PDEs, in vivo efficacy in an AD model or other diseases, PK including BBB penetration, toxicity, and solubility remain unknown. In addition, only a few substituents on the quinoline ring were investigated and just one compound was dominant. Thus, we synthesized YF012403 (FIG. 24), to verify the potency and selectivity of this scaffold, as well as its effectiveness against synaptic and cognitive loss by Aβ, and also to explore the possibility of modifying the scaffold for lead optimization in view of developing a drug that can effectively counteract synaptic and memory loss in AD.

Starting from 2-bromo-4-cyanoaniline, YF012403 was prepared in six steps after reduction of the ester which was obtained by cross-coupling of cyclopropyl boronic acid with quinoline bromide 7 in the presence of Pd(PPh$_3$)4. The coupling precursor 7 can be synthesized using the procedure described in [S19]. Of note, the organometal catalyzed cross-coupling reaction leaves us with a great freedom for further modification of this scaffold. For example, by using Buchwald-Hartwig reaction conditions, the 8-dimethyl analog of YF012403, YF016203, was synthesized. In vitro assays showed that these two compounds have great inhibitory activity against PDE5 and selectivity against all other PDE isoforms (see FIG. 27). The IC$_{50}$'s of YF012403 and YF016203 for PDE5 are 0.27 nM (FIG. 47) and 0.4 nM, respectively. Neither one of these compounds inhibits any of the other PDEs (PDE5/PDE>1000).

We then investigated the PK and BBB penetration capability of YF012403. After p.o. administration at 50 mg/kg to BABL/c mice, plasma and brain concentrations were determined by the LC-MS/MS. The plasma and brain concentrations at each sampling time are shown in FIG. 48. The data in FIG. 28 indicate that YF012403 is rapidly absorbed as illustrated by the peak plasma concentration occurring at 0.5 h after dosing. Moreover, the T$_{max}$ values in the brain and plasma were similar, indicating that the distribution of YF012403 to the brain is also fast. Finally, the amount of YF012403 in the brain was lower than that in the plasma with an AUC$_{0-4}$ ratio of 0.41 and the elimination half-lives of YF012403 in the brain and plasma were 1.04 and 1.33, respectively.

Our next goal was to check if YF012403 can attenuate synaptic and cognitive dysfunction in APP/PS1 mice. We induced LTP or contextual fear memory in the presence of oligomeric Aβ$_{42}$, or vehicle [S18]. In the LTP experiments 200 nM Aβ$_{42}$ or vehicle were perfused through the bath solution for 20 min prior to the application of the θ-burst. In the behavioral experiments 200 nM Aβ$_{42}$ or vehicle were bilaterally infused 15 min prior to the foot shock into dorsal hippocampus of the animal that had been pre-implanted with a cannula the week before. Aβ reduced LTP and contextual fear memory (FIG. 49). However, YF012403 (50 nM, for 10 min prior to the θ-burst in the LTP experiments; 3 or 10 mg/Kg, p.o., immediately after training in the behavioral experiments) ameliorated the electrophysiological and behavioral deficits (FIG. 49). Taken together, these results indicate that YF012403 is a good compound for optimization.

Computational Modeling is Reliable for Predicting the PDE Inhibitor Activity and Selectivity.

Although X-ray crystal structures of PDE1 to PDE5, PDE7, and PDE9 [S27-S35] have been reported, the fine structure at the active site, for example, whether OH$^-$ (hydroxide anion), or a H$_2$O (water molecule) is the 2nd bridging ligand (BL2) is uncertain because hydrogen atoms can not be determined by X-ray diffraction technique. Using various state-of-the-art computational techniques: molecular dynamics (MD) [S21], first-principles quantum mechanics (QM) [S22], in-house developed first-principles QM-fully polarizable continuum model (QM/FPCM) method [S21, S2, S36-S50] and hybrid QM/molecular mechanics (QM/MM) [S21], HO (hydroxide anion), not H$_2$O [142-154] was discovered to be the BL2 in the reported PDE crystal structures. Since the hydroxide anion (HO$^-$) is expected to serve as the nucleophile that initiates the catalytic hydrolysis of the substrate [S21, S22], these findings provide a base to construct an accurate 3D structural model, which is critical for performing homology modeling for each of the other PDE families whose X-ray crystal structures are unknown. These newly determined fine 3D structures of PDE5 and other PDEs provide a unique opportunity to help finding selective PDE5 inhibitors that work for CNS.

Medicinal Chemistry Strategy to Design and Synthesize New PDE5 Inhibitors which are Optimized for AD.

Our data show that enhancement of the NO/sGC/cGMP/PKG/CREB pathway through inhibition of PDE5 counteracts Aβ-induced synaptic and cognitive abnormalities. Drugs that both act on the NO/sGC/cGMP/PKG/CREB pathway and are optimized for the CNS are lacking. We will obtain new drugs with a) high specificity and potency, b) good PK, bioavailability and CNS penetration, and c) safety. None of the existing drugs is known to fit all of these criteria. Thus, Computer-Aided MedChem Strategy is being used to develop compounds that fit the criteria described herein.

Functional assays will be used in testing PDE5 modulating compounds, such as PDE5 inhibitors, in addition to the parallel use of a validated in vivo disease model. Compounds will be selected according to the following criteria: high potency, excellent selectivity, a reasonable PK profile, and good BBB penetration. Based on the availability of high resolution X-ray structures of PDE5 complexed with sildenafil, vardenafil and tadalafil, in silico calculations will be used to determine druggability and permeability of the designed structures. The compounds with the highest scores will be synthesized. Compounds with satisfactory potency and selectivity will be studied further for PK, bioavailability/brain penetration, and other safety profiles.

Our research design will focus on modifications of YF012403 to optimize its druggability. YF012403 has a primary benzylic alcohol at the 3-position (C3), which can be oxidized by microsomes generating benzaldehyde and consequently causing first-pass metabolism problems and severe side effects due to subsequent conjugate addition to proteins. Its half-life may therefore also be dramatically limited. Thus, it is necessary to convert the benzylic alcohol into other more drug-friendly groups. Secondly, YF012403 bears a cyclopropyl group at the 8-position (C8) which may not be stable in vivo by undergoing ring opening, and thus representing an electrophilic liability. To avoid this problem, we will change the cyclopropyl to other substituents. Thirdly, the log BB of YF012403 is only −0.38, and therefore is not ideal for drugs against CNS diseases (a peak brain/blood concentration ratio >1 is comparable with that of known CNS drugs in clinical use). Finally, because some 3-cyanoquinoline derivatives have shown inhibitory activity against the NF-κB and other kinases (see for instance [S51-S56]) and replacing the 3-cyano group with an ester group or an alcohol has been found to eliminate these activities entirely [S53, S55], we will modify the group at C3 to minimize the off-target activity. Therefore, we describe structures focusing on modification of the moieties at both the C3 and the C8 positions. In addition, we will modify other parts of the quinoline to improve the pharmacological properties of the top candidates to avoid other ADMET problems.

Modifications at C8.

Previous work has indicated that the modifications at C8 are very critical for the inhibitory activity of the new compound [S19]. Although only hydrogen and an ethyl group at the C8 position of the quinoline were explored, given that the ethyl group gave the best result, a bulkier group at C8 would yield better activity. This allows us to pursue an even larger variation at this position, such as positioning cycloalkyl, heterocyclic groups, or alkylamino groups at the C8 position, in order to identify the best substituents at this position. Similar to the preparation of YF012403, these compounds can be synthesized by coupling reactions aided by organometallic catalysis in the presence of Pd, Cu or Fe, such as Heck coupling, Negishi coupling, and Buchwald-Hartwig coupling reactions, starting from the halides which are accessible using the reported procedure [S19] (FIG. 50).

Modifications at C3.

The reduction of the C3-ethyl ester to the corresponding alcohol lowers the $IC_{50}$ by one order of magnitude and increases the selectivity over PDE6 by 70-fold. It is unclear whether or not the improvement of activity is due to the fact that an electron-withdrawing group has been replaced by an electron-donating group on the aryl ring, or the hydrogen bond between the resulting alcohol and the 5-amine, or the necessity of an H-acceptor/donor supplied by the free hydroxyl group. However, as noted above, the benzylic alcohol and cyano group at the C3 position can cause potential problems. Thus, several strategies described herein can help to optimize the structure at the C3 position.

The ester/ether L02, thioether/thioester L03, amine/amide L04 can be easily obtained by reaction of the benzyl chloride or benzyl mesylate derived from the free alcohol L01 with alcohol/acid, thiol/thiolacid, or amine/amide in the presence of base, respectively. The above-mentioned benzyl chloride/mesylate can also be substituted by a heterocycle to afford L05. Reaction of alcohol L01 or thiol (L03, R'=H) or amine (L04, R'=H) with triphosgene/carbonyldiimidazole (CDI) or thionyl chloride will lead to the cyclic urea/carbamide (L06), and cyclic thiourea/sulfonamide (L07), respectively. These simple conversions will allow us to rapidly construct several compound libraries derived from the benzylic alcohol that will be able to improve the druggability of this scaffold. In addition, since these compounds may have lower tPSAs, they may have better BBB permeability than the polar alcohol (FIG. 51).

In another strategy, fluorine can be introduced at C3 because usually fluorinated compounds have good PK and an intra-molecular F—H bond can increase the lipophilicity, BBB penetration and bioavailability. Reaction of alcohol L01 with Deoxo-Fluor® affords the benzyl fluoride L08. Conversion of L01 to its corresponding aldehyde followed by reaction with Deoxo-Fluor® gives the difluoro derivative L09. The trifluoromethyl analog L10 is readily obtained by reaction of Deoxo-Fluor® with 3-carboxylic quinoline (FIG. 52).

Introduction of an amino group at the C3 position can be realized via a Curtis rearrangement from the azide derived from 3-carboxylic quinoline. With the 3-amino-quinoline L11 in hand, the 3-fluoro derivative can be prepared, employing Sandmeyer reaction conditions in the presence of $HBF_4$. Treatment of L11 with an alkyl halide, 1,2-dibromoethane, triphosgene/carbonyldiimidazole (CDI) or thionyl chloride yields other derivatives L13-L16 (FIG. 53).

Modifications at Other Parts.

As our studies proceed, our SAR database will be expanded further and the best substituents at C3 and C8 will be identified. To further improve the pharmacological properties and druggability of this scaffold, we can also modify other parts of this scaffold. Starting from the substituted aniline L17, 3-hydroxy quinoline L19 can be prepared by treatment of L17 with methylenemalonate followed by cyclization at elevated temperatures. Refluxing L19 with POCl3 would yield 3-chloroquinoline L20, which can then be converted to 3-amino derivative L21 by treatment with ammonia. Treatment of L19 and L21 with different electrophiles would give amide/sulfonamide L22 and ester/sulfonate/ether L24, respectively. Both L22 and L24 will then be converted to the desired derivatives (L23 and L25) based on the SAR studies at C3 described above in section b (FIG. 54).

The structures described herein cover numerous variations and some of them may not be good PDE5 inhibitors with improved selectivity, BBB permeability, PK, and/or other pharmacological properties. Thus, to avoid wasting limited resources before the actual synthesis is begun computational chemistry will be used to assist in prioritizing and identifying top-tier candidates based on docking and AMDET parameter (such as clog P, tPSA, clog BB) calculations. In addition to that, during the optimization process, attention must be given to the previously obtained data so that the subsequent investigations can be guided accordingly.

Computational Strategy to Design and Synthesize New PDE5 Inhibitors which are Optimized for AD.

PDE5 inhibitory properties will be optimized using a computational design consisting of several major stages. Stage 1 involves initial structure-based virtual screening (with a rigid enzyme structure) through de novo design or combinatorial library docking. The computational methods used in the Stage 1 are very fast and, therefore, useful for an automated screening of a large number of virtual molecules or molecular fragments. The highly ranked virtual compounds from Stage 1 will be further considered in Stage 2 for more sophisticated flexible docking. A limited number of virtual compounds (the top-100 or less) that pass Stage 2 will undergo more sophisticated MD simulations of microscopic binding of PDE5 in water and MM-PBSA binding free energy calculations (Stage #3). Next, the selectivity of the predicted PDE5 inhibitors will be evaluated in Stage 4. Among the structures described herein, those being shown by these computational studies will be synthesized and tested for enzymatic activity, so that we will employ a fully integrated approach including medicinal chemistry, computational studies and analysis of drug activity.

i. Stage #1. Initial Structure-Based Virtual Screening:

Two computational approaches will be used to perform automated large-scale virtual screening with a rigid enzyme structure: de novo design and combinatorial library docking. Both approaches, to be used in an automated way, have their own advantages and thus complement each other. The de novo ligand design is based on a detailed analysis of microscopic enzyme-ligand binding and considers the binding site of a known enzyme or receptor. The structure analysis of existing PDE5 inhibitors and our recently determined 3D structure of the binding site allow us to determine a class of pharmacophore/scaffold with high potency. This pharmacophore/scaffold can then be used as the basis for de novo design of ligands for the receptor. Given the 3D structure of the enzyme, one may identify the subsites of interaction that would ideally be fulfilled by a ligand. A computer program then compares fragments from a database to the interaction subsites, with hits proposed according to scoring rules that reflect real binding. This automated comparison predicts favorable combinations of fragments in different subsites of interaction. A number of computer programs can provide fragment combination methods, including LUDI [S183-S185], CLIX [S186], SPLICE [S187], GroupBuild [S188], and SPROUT [S189-S191]. We have chosen the LUDI program for this project. The program will be able to position molecular fragments into the interaction subsites in such a way that favorable interactions can be formed with the enzyme. Each combination of fragments will then be connected into a single virtual molecule whose ability to bind PDE5 will be scored.

In the combinatorial library docking approach, we will construct a virtual combinatorial library with a docking strategy (using the DOCK6.0 program [S192]), and then the docking of each of these virtual compounds with the PDE5 active site. A commonly used docking strategy is to dissect a ligand into a scaffold and rigid sub-structure fragments, and then to generate new molecular structures by probing many different fragments in a combinatorial fashion. After removing the original fragments (substituents) from the lead compound, we will screen the "fragment"-like compounds in the ZINC database [S193] by docking these fragments in multiple positions and orientations into the subsites of the PDE5 active site. The top fragments (e.g. 500) for each subsite will be ranked and used by the CombilibMaker™ program (Tripos, Inc.) to build a combinatorial library composed of $(500)^n$ virtual compounds. When only two subsites are considered for each round of computational design, we will have n=2 and $(500)^n$=250,000 compounds built from each lead compound. Finally, each virtual compound in the combinatorial library will be docked into the PDE5 active site and its binding scored by the automated flexible docking function of the DOCK6.0 program [S192]. Based on the relative values of the docking scores determined by using the DOCK6.0 program and also the docking geometries, the top-scored compounds will be selected for further evaluation in the next stage. These approaches allow us to investigate the possibility of further modification of the quinoline scaffold.

ii. Stage #2. Flexible Docking and BBB Penetration Prediction:

The binding structures predicted in Stage #1 for the top scored compounds with a rigid enzyme structure will be further refined and rescored by using the Amber score approach implemented in the DOCK6.0 program [S192]. During the Amber scoring calculation, the input coordinates and parameters of the enzyme-ligand complex will be read into the system. Then, energy minimization using the conjugate gradient method will be performed to optimize the enzyme-ligand contacts. The energy minimization will be followed by a (short-time) Langevin MD simulation at constant temperature and, finally, a short energy-minimization to obtain the final energetic results of the system. Compounds that have both the best docking scores and reasonable docking geometries will be selected for further evaluation in the next stage.

We will also theoretically estimate the BBB penetration by calculating the polar surface area (PSA) and the oil/water partition coefficient (log P) of each candidate compound and using the well-established quantitative structure-activity relationship (QSAR) and artificial neural network (ANN) models [S194, S195]. These QSAR and ANN models have demonstrated that the BBB penetration of a compound is determined by the PSA and log P (or PSA and molecular weight) of the compound, both of which can be calculated conveniently by commercially available software. Usually, compounds that can cross the BBB should have a molecular mass less than 450 Da and a PSA smaller than 90.2 Å$^2$ [S194].

iii. Stage #3. MD Simulation in Water and MM-PBSA Binding Free Energy Calculation:

For each of top scored compounds that pass both the flexible docking and BBB penetration tests in Stage #2, we will further perform MD simulation on the PDE5-ligand complex. The MD simulation will be performed in a water bath using Amber program suite [S196] with the new-generation force field developed by Cornell et al [S197]. NAMD program (using the same Amber force field or CHARMM force field) [S198] will also be used for massively parallel MD simulations [S199-S207]. Finally, the stable trajectories of MD simulations will be used to perform more sophisticated molecular mechanics-Poisson-Boltzmann surface area (MM-PBSA) [S208, S209] binding free energy calculations; the detailed MM-PBSA protocol to be used in this project and its high accuracy in predicting protein-ligand binding have been described and discussed in detail in our recently accomplished computational studies of the inhibitions of PDEs and other proteins [S204, S210]. The calculated binding free energy is a theoretical indicator of the binding affinity for a ligand binding with the enzyme (PDE5). Only compounds predicted to have higher binding affinity for PDE5 will be evaluated in Stage #4 for their selectivity.

iv. Stage #4. Computational Evaluation of the Selectivity of the Predicted PDE5 Inhibitors:

Based on the modeled 3D structures of all PDE families, a new PDE5 inhibitor with an improved selectivity may be designed in such a way that the inhibitor not only keeps the good interactions with the common residues of PDEs, but also has improved interactions with non-common residues (e.g. F787, L804, I813, and M816) of PDE5. Although these non-common residues are not unique for PDE5, no other PDE family has all of these non-common residues. A PDE5 inhibitor is expected to be selective, if it has favorable interactions with all of these non-common residues in addition to the common residues. We will model the binding of the compounds with a virtual library and with other PDEs to assess their selectivity. The results will indicate that some compounds in the virtual library are expected to have a significantly lower binding affinity with other PDEs.

We will use the 3D models of the PDE structures and repeat the flexible docking in Stage #2 (and, if necessary, MD and MM-PBSA calculations in Stage #3) for each of the predicted PDE5 inhibitors binding with other PDE families. The predicted new compounds that are potentially potent and selective for PDE5 (i.e. the predicted IC$_{50}$<50 nM and the predicted selectivity >100-fold) will be submitted for chemical synthesis and biochemical assays. The actual outcome of the wet experimental tests will be used to refine the computational design protocol and improve the rational basis for subsequent predictions.

Compound Analysis.

All compounds synthesized and tested for biological activity will be fully characterized and purified to >95% as determined by HPLC and 1H NMR. Furthermore, additional analytical techniques (i.e. $^{13}$C NMR, IR, melting point, MS and/or elemental analysis) will be used to determine structure and purify. In the case of optically pure materials, the purity will be assessed by chiral stationary-phase HPLC. In certain cases where structural uncertainty remains other techniques (i.e. 2-D NMR, and x-ray crystallography) will be utilized.

REFERENCES FOR EXAMPLE 7

S18. Walsh, D. M., I. Klyubin, J. V. Fadeeva, W. K. Cullen, R. Anwyl, M. S. Wolfe, M. J. Rowan, and D. J. Selkoe, *Naturally secreted oligomers of amyloid beta protein potently inhibit hippocampal long-term potentiation in vivo.* Nature, 2002. 416(6880): p. 535-9.

S19. Selig, D. K., M. R. Segal, D. Liao, R. C. Malenka, R. Malinow, R. A. Nicoll, and J. E. Lisman, *Examination of the role of cGMP in long-term potentiation in the CA1 region of the hippocampus.* Learn Mem, 1996. 3(1): p. 42-8.

S21. Paakkari, I. and P. Lindsberg, *Nitric oxide in the central nervous system.* Ann Med, 1995. 27(3): p. 369-77.

S22. Baratti, C. M. and M. M. Boccia, *Effects of sildenafil on long-term retention of an inhibitory avoidance response in mice.* Behav Pharmacol, 1999. 10(8): p. 731-7.

S27. Chapman, P. F., G. L. White, M. W. Jones, D. Cooper-Blacketer, V. J. Marshall, M. Irizarry, L. Younkin, M. A. Good, T. V. Bliss, B. T. Hyman, S. G. Younkin, and K. K. Hsiao, *Impaired synaptic plasticity and learning in aged amyloid precursor protein transgenic mice.* Nat Neurosci, 1999. 2(3): p. 271-6.

S28. Fitzjohn, S. M., R. A. Morton, F. Kuenzi, T. W. Rosahl, M. Shearman, H. Lewis, D. Smith, D. S. Reynolds, C. H. Davies, G. L. Collingridge, and G. R. Seabrook, *Age-related impairment of synaptic transmission but normal long-term potentiation in transgenic mice that overexpress the human APP695SWE mutant form of amyloid precursor protein.* J Neurosci, 2001. 21(13): p. 4691-8.

S29. Hsia, A. Y., E. Masliah, L. McConlogue, G. Q. Yu, G. Tatsuno, K. Hu, D. Kholodenko, R. C. Malenka, R. A. Nicoll, and L. Mucke, *Plaque-independent disruption of neural circuits in Alzheimer's disease mouse models.* Proc Natl Acad Sci USA, 1999. 96(6): p. 3228-33.

S30. Jolas, T., X. S. Zhang, Q. Zhang, G. Wong, R. Del Vecchio, L. Gold, and T. Priestley, *Long-term potentiation is increased in the CA1 area of the hippocampus of APP(swe/ind) CRND8 mice.* Neurobiol Dis, 2002. 11(3): p. 394-409.

S31. Larson, J., G. Lynch, D. Games, and P. Seubert, *Alterations in synaptic transmission and long-term potentiation in hippocampal slices from young and aged PDAPP mice.* Brain Res, 1999. 840(1-2): p. 23-35.

S32. Moechars, D., I. Dewachter, K. Lorent, D. Reverse, V. Baekelandt, A. Naidu, I. Tesseur, K. Spittaels, C. V. Haute, F. Checler, E. Godaux, B. Cordell, and F. Van Leuven, *Early phenotypic changes in transgenic mice that overexpress different mutants of amyloid precursor protein in brain.* J Biol Chem, 1999. 274(10): p. 6483-92.

S33. Nalbantoglu, J., G. Tirado-Santiago, A. Lahsaini, J. Poirier, O. Goncalves, G. Verge, F. Momoli, S. A. Welner, G. Massicotte, J. P. Julien, and M. L. Shapiro, *Impaired learning and LTP in mice expressing the carboxy terminus of the Alzheimer amyloid precursor protein.* Nature, 1997. 387(6632): p. 500-5.

S34. Dineley, K. T., M. Westerman, D. Bui, K. Bell, K. H. Ashe, and J. D. Sweatt, *Beta-amyloid activates the mitogen-activated protein kinase cascade via hippocampal alpha7 nicotinic acetylcholine receptors: In vitro and in vivo mechanisms related to Alzheimer's disease.* J Neurosci, 2001. 21(12): p. 4125-33.

S35. Dineley, K. T., X. Xia, D. Bui, J. D. Sweatt, and H. Zheng, *Accelerated plaque accumulation, associative learning deficits, and up-regulation of alpha 7 nicotinic receptor protein in transgenic mice co-expressing mutant human presenilin 1 and amyloid precursor proteins.* J Biol Chem, 2002. 277(25): p. 22768-80.

S36. Gong, B., O. V. Vitolo, F. Trinchese, S. Liu, M. Shelanski, and O. Arancio, *Persistent improvement in synaptic and cognitive functions in an Alzheimer mouse model following rolipram treatment.* J. Clin. Invest., 2004. 114: p. 1624-1634.

S37. Yin, J. C., J. S. Wallach, M. Del Vecchio, E. L. Wilder, H. Zhou, W. G. Quinn, and T. Tully, *Induction of a dominant negative CREB transgene specifically blocks long-term memory in Drosophila.* Cell, 1994. 79(1): p. 49-58.

S38. Bourtchuladze, R., B. Frenguelli, J. Blendy, D. Cioffi, G. Schutz, and A. J. Silva, *Deficient long-term memory in mice with a targeted mutation of the cAMP-responsive element-binding protein.* Cell, 1994. 79(1): p. 59-68.

S39. Bach, M. E., M. Barad, H. Son, M. Zhuo, Y. F. Lu, R. Shih, I. Mansuy, R. D. Hawkins, and E. R. Kandel, *Age-related defects in spatial memory are correlated with defects in the late phase of hippocampal long-term potentiation in vitro and are attenuated by drugs that enhance the cAMP signaling pathway.* Proc Natl Acad Sci USA, 1999. 96(9): p. 5280-5.

S40. Lu, Y. F., E. R. Kandel, and R. D. Hawkins, *Nitric oxide signaling contributes to late-phase LTP and CREB phosphorylation in the hippocampus.* J Neurosci, 1999. 19(23): p. 10250-61.

S41. McCarty, M. F., *Vascular nitric oxide may lessen Alzheimer's risk.* Med Hypotheses, 1998. 51(6): p. 465-76.

S42. Troy, C. M., S. A. Rabacchi, W. J. Friedman, T. F. Frappier, K. Brown, and M. L. Shelanski, *Caspase-2 mediates neuronal cell death induced by beta-amyloid.* J Neurosci, 2000. 20(4): p. 1386-92.

S43. Wirtz-Brugger, F. and A. Giovanni, *Guanosine 3',5'-cyclic monophosphate mediated inhibition of cell death induced by nerve growth factor withdrawal and beta-amyloid protective effects of propentofylline.* Neuroscience, 2000. 99(4): p. 737-50.

S44. Venturini, G., M. Colasanti, T. Persichini, E. Fioravanti, P. Ascenzi, L. Palomba, O. Cantoni, and G. Musci, *Beta-amyloid inhibits NOS activity by subtracting NADPH availability.* Faseb J, 2002. 16(14): p. 1970-2.

S45. Suhara, T., J. Magrane, K. Rosen, R. Christensen, H. S. Kim, B. Zheng, D. L. McPhie, K. Walsh, and H. Querfurth, *Abeta42 generation is toxic to endothelial cells and inhibits eNOS function through an Akt/GSK-3beta signaling-dependent mechanism.* Neurobiol Aging, 2003. 24(3): p. 437-51.

S46. Colton, C. A., M. P. Vitek, D. A. Wink, Q. Xu, V. Cantillana, M. L. Previti, W. E. Van Nostrand, J. B. Weinberg, and H. Dawson, *NO synthase 2 (NOS2) dele-* tion promotes multiple pathologies in a mouse model of Alzheimer's disease. Proc Natl Acad Sci USA, 2006. 103(34): p. 12867-72.

S47. Thatcher, G. R., B. M. Bennett, and J. N. Reynolds, Nitric oxide mimetic molecules as therapeutic agents in Alzheimer's disease. Curr Alzheimer Res, 2005. 2(2): p. 171-82.

S48. Haas, J., B. Storch-Hagenlocher, A. Biessmann, and B. Wildemann, Inducible nitric oxide synthase and argininosuccinate synthetase: co-induction in brain tissue of patients with Alzheimer's dementia and following stimulation with beta-amyloid 1-42 in vitro. Neurosci Lett, 2002. 322(2): p. 121-5.

S49. Tran, M. H., K. Yamada, A. Olariu, M. Mizuno, X. H. Ren, and T. Nabeshima, Amyloid beta-peptide induces nitric oxide production in rat hippocampus: association with cholinergic dysfunction and amelioration by inducible nitric oxide synthase inhibitors. Faseb J, 2001. 15(8): p. 1407-9.

S50. McCann, S. M., The nitric oxide hypothesis of brain aging. Exp Gerontol, 1997. 32(4-5): p. 431-40.

S106. Corbin, J. D. and S. H. Francis, Pharmacology of phosphodiesterase-5 inhibitors. Int J Clin Pract, 2002. 56(6): p. 453-9.

S107. Daugan, A., P. Grondin, C. Ruault, A. C. Le Monnier de Gouville, H. Coste, J. Kirilovsky, F. Hyafil, and R. Labaudiniere, The discovery of tadalafil: a novel and highly selective PDE5 inhibitor. 1: 5,6,11,11a-tetrahydro-1H-imidazo[1',5':1,6]pyrido[3,4-b]indole-1,3(2H)-dio ne analogues. J Med Chem, 2003. 46(21): p. 4525-32.

S135. Daugan, A., P. Grondin, C. Ruault, A. C. Le Monnier de Gouville, H. Coste, J. M. Linget, J. Kirilovsky, F. Hyafil, and R. Labaudiniere, The discovery of tadalafil: a novel and highly selective PDE5 inhibitor. 2: 2,3,6,7,12,12a-hexahydropyrazino-[1',2':1,6]pyrido[3,4-b]indole-1,4-dione analogues. J Med Chem, 2003. 46(21): p. 4533-42.

S137. FDA. Viagra tablets (sildenafil citrate). Review and evaluation of pharmacology and toxicology data. Report from the Division of Cardio-renal Drug Products (HFD-10). Center for Drug Evaluation and Research. in Food and Drug Administration. 1998. Washington, D.C.

S138. Walker, D. K., M. J. Ackland, G. C. James, G. J. Muirhead, D. J. Rance, P. Wastall, and P. A. Wright, Pharmacokinetics and metabolism of sildenafil in mouse, rat, rabbit, dog and man. Xenobiotica, 1999. 29(3): p. 297-310.

S142. Tully, T., R. Bourtchouladze, R. Scott, and J. Tallman, Targeting the CREB pathway for memory enhancers. Nat Rev Drug Discov, 2003. 2(4): p. 267-77.

S143. Turner, B. M., Cellular memory and the histone code. Cell, 2002. 111(3): p. 285-91.

S144. Battaglioli, E., M. E. Andres, D. W. Rose, J. G. Chenoweth, M. G. Rosenfeld, M. E. Anderson, and G. Mandel, REST repression of neuronal genes requires components of the hSWI.SNF complex. J Biol Chem, 2002. 277(43): p. 41038-45.

S145. Lunyak, V. V., R. Burgess, G. G. Prefontaine, C. Nelson, S. H. Sze, J. Chenoweth, P. Schwartz, P. A. Pevzner, C. Glass, G. Mandel, and M. G. Rosenfeld, Corepressor-dependent silencing of chromosomal regions encoding neuronal genes. Science, 2002. 298(5599): p. 1747-52.

S146. Francis, Y. I., M. Fa', H. Ashraf, H. Zhang, D. S. Latchman, and O. Arancio. Beneficial effect of the histone deacetylase inhibitor TSA in a mouse model of Alzheimer's disease. in Soc Neurosci. Abstr. 2007. San Diego.

S147. Gong, B., Z. Cao, P. Zheng, O. V. Vitolo, S. Liu, A. Staniszewski, D. Moolman, H. Zhang, M. Shelanski, and O. Arancio, Ubiquitin Hydrolase Uch-L1 Rescues beta-Amyloid-Induced Decreases in Synaptic Function and Contextual Memory. Cell, 2006. 126(4): p. 775-88.

S148. Trinchese, F., I. Ninan, S. Liu, and O. Arancio. Alzheimer Aβ Increases Neurotransmitter Release and Blocks Synaptic Plasticity in Hippocampal Cultures. in The 9th International Conference on Alzheimer's Disease and Related Disorders Abstr. 2004. Philadelphia.

S149. Takahashi, R. H., C. G. Almeida, P. F. Kearney, F. Yu, M. T. Lin, T. A. Milner, and G. K. Gouras, Oligomerization of Alzheimer's beta-amyloid within processes and synapses of cultured neurons and brain. The Journal of Neuroscience, 2004. 24(14): p. 3592-3599.

S150. Prickaerts, J., A. Sik, W. C. van Staveren, G. Koopmans, H. W. Steinbusch, F. J. van der Staay, J. de Vente, and A. Blokland, Phosphodiesterase type 5 inhibition improves early memory consolidation of object information. Neurochem Int, 2004. 45(6): p. 915-28.

S151. Saenz de Tejada, I., J. Angulo, P. Cuevas, A. Fernandez, I. Moncada, A. Allona, E. Lledo, H. G. Korschen, U. Niewohner, H. Haning, E. Pages, and E. Bischoff, The phosphodiesterase inhibitory selectivity and the in vitro and in vivo potency of the new PDE5 inhibitor vardenafil. Int J Impot Res, 2001. 13(5): p. 282-90.

S152. Zhang, X., Q. Feng, and R. H. Cote, Efficacy and selectivity of phosphodiesterase-targeted drugs in inhibiting photoreceptor phosphodiesterase (PDE6) in retinal photoreceptors. Invest Ophthalmol Vis Sci, 2005. 46(9): p. 3060-6.

S153. Xiong, Y., H. T. Lu, Y. Li, G. F. Yang, and C. G. Zhan, Characterization of a catalytic ligand bridging metal ions in phosphodiesterases 4 and 5 by molecular dynamics simulations and hybrid quantum mechanical/molecular mechanical calculations. Biophys J, 2006. 91(5): p. 1858-67.

S154. Zhan, C. G. and F. Zheng, First computational evidence for a catalytic bridging hydroxide ion in a phosphodiesterase active site. J Am Chem Soc, 2001. 123(12): p. 2835-8.

S183. Bohm, H. J., The computer program LUDI: a new method for the de novo design of enzyme inhibitors. J Comput Aided Mol Des, 1992. 6(1): p. 61-78.

S184. Bohm, H. J., LUDI. rule-based automatic design of new substituents for enzyme inhibitor leads. J Comput Aided Mol Des, 1992. 6(6): p. 593-606.

S185. Bohm, H. J., On the use of LUDI to search the Fine Chemicals Directory for ligands of proteins of known three-dimensional structure. J Comput Aided Mol Des, 1994. 8(5): p. 623-32.

S186. Lawrence, M. C. and P. C. Davis, CLIX: a search algorithm for finding novel ligands capable of binding proteins of known three-dimensional structure. Proteins, 1992. 12(1): p. 31-41.

S187. Ho, C. M. and G. R. Marshall, FOUNDATION: a program to retrieve all possible structures containing a user-defined minimum number of matching query elements from three-dimensional databases. J Comput Aided Mol Des, 1993. 7(1): p. 3-22.

S188. Rostein, S. H. and M. K. Murcko, GroupBuild: A Fragment-Based Method for De NoVo Drug Design". J. Med. Chem., 1993. 36: p. 1700-1710.

S189. Gillet, V., A. P. Johnson, P. Mata, S. Sike, and P. Williams, SPROUT: a program for structure generation. J Comput Aided Mol Des, 1993. 7(2): p. 127-53.

S190. Gillet, V. J., W. Newell, P. Mata, G. Myatt, S. Sike, Z. Zsoldos, and A. P. Johnson, *SPROUT: recent developments in the de novo design of molecules*. J Chem Inf Comput Sci, 1994. 34(1): p. 207-17.

S191. Taylor, R. D., P. J. Jewsbury, and J. W. Essex, *A review of protein-small molecule docking methods*. J Comput Aided Mol Des, 2002. 16(3): p. 151-66.

S192. Ewing, T. J., S. Makino, A. G. Skillman, and I. D. Kuntz, *DOCK 4.0: search strategies for automated molecular docking of flexible molecule databases*. J Comput Aided Mol Des, 2001. 15(5): p. 411-28.

S193. Irwin, J. J. and B. K. Shoichet, *ZINC—a free database of commercially available compounds for virtual screening*. J Chem Inf Model, 2005. 45(1): p. 177-82.

S194. Bajorath, J., *Integration of virtual and high-throughput screening*. Nat Rev Drug Discov, 2002. 1(11): p. 882-94.

S195. Osterberg, T. and U. Norinder, *Prediction of polar surface area and drug transport processes using simple parameters and PLS statistics*. J Chem Inf Comput Sci, 2000. 40(6): p. 1408-11.

S196. Case, D. A., T. E. Cheatham, 3rd, T. Darden, H. Gohlke, R. Luo, K. M. Merz, Jr., A. Onufriev, C. Simmerling, B. Wang, and R. J. Woods, *The Amber biomolecular simulation programs*. J Comput Chem, 2005. 26(16): p. 1668-88.

S197. Cornell, W. D., P. Cieplak, C. I. Bayly, I. R. Gould, J. K. M. Merz, D. M. Ferguson, D. C. Spellmeyer, T. Fox, J. W. Caldwell, and P. A. Kollman, *A second generation force field for the simulation of proteins, nucleic acids, and organic molecules*. J. Am. Chem. Soc., 1995 117: p. 5179-5197.

S198. Kalé, L., R. Skeel, M. Bhandarkar, R. Brunner, A. Gursoy, N. Krawetz, J. Phillips, A. Shinozaki, K. Varadarajan, and K. Schulten, J. Comput. Phys., *NAMD2: greater scalability for parallel molecular dynamics*. 1999. 151: p. 283-312.

S199. Zhan, C.-G., O. Norberto de Souza, R. Rittenhouse, and R. L. Ornstein, *Determination of two structural forms of catalytic bridging ligand in zinc-phosphotriesterase by molecular dynamics simulation and quantum chemical calculation*. J. Am. Chem. Soc., 1999. 121: p. 7279-7282.

S200. Koca, J., C. G. Zhan, R. C. Rittenhouse, and R. L. Ornstein, *Mobility of the active site bound paraoxon and sarin in zinc-phosphotriesterase by molecular dynamics simulation and quantum chemical calculation*. J Am Chem Soc, 2001. 123(5): p. 817-26.

SS201. Gao, D., H. Cho, W. Yang, Y. Pan, G. Yang, H. H. Tai, and C. G. Zhan, *Computational design of a human butyrylcholinesterase mutant for accelerating cocaine hydrolysis based on the transition-state simulation*. Angew Chem Int Ed Engl, 2006. 45(4): p. 653-7.

S202. Pan, Y., D. Gao, W. Yang, H. Cho, G. Yang, H. H. Tai, and C. G. Zhan, *Computational redesign of human butyrylcholinesterase for anticocaine medication*. Proc Natl Acad Sci USA, 2005. 102(46): p. 16656-61.

S203. Zhan, C. G. and D. Gao, *Catalytic mechanism and energy barriers for butyrylcholinesterase-catalyzed hydrolysis of cocaine*. Biophys J, 2005. 89(6): p. 3863-72.

S204. Hamza, A. and C. G. Zhan, *How can (−)-epigallocatechin gallate from green tea prevent HIV-1 infection? Mechanistic insights from computational modeling and the implication for rational design of anti-HIV-1 entry inhibitors*. J Phys Chem B Condens Matter Mater Surf Interfaces Biophys, 2006. 110(6): p. 2910-7.

S205. Huang, X., W. Yan, D. Gao, M. Tong, H. H. Tai, and C. G. Zhan, *Structural and functional characterization of human microsomal prostaglandin E synthase-1 by computational modeling and site-directed mutagenesis*. Bioorg Med Chem, 2006. 14(10): p. 3553-62.

S206. Hamza, A., H. Cho, H. H. Tai, and C. G. Zhan, *Understanding human 15-hydroxyprostaglandin dehydrogenase binding with NAD+ and PGE2 by homology modeling, docking and molecular dynamics simulation*. Bioorg Med Chem, 2005. 13(14): p. 4544-51.

S207. Hamza, A., H. Cho, H. H. Tai, and C. G. Zhan, *Molecular dynamics simulation of cocaine binding with human butyrylcholinesterase and its mutants*. J Phys Chem B Condens Matter Mater Surf Interfaces Biophys, 2005. 109(10): p. 4776-82.

S208. Fadrna, E., N. Spackova, R. Stefl, J. Koca, T. E. Cheatham, 3rd, and J. Sponer, *Molecular dynamics simulations of Guanine quadruplex loops: advances and force field limitations*. Biophys J, 2004. 87(1): p. 227-42.

S209. Harris, D. L., J. Y. Park, L. Gruenke, and L. Waskell, *Theoretical study of the ligand-CYP2B4 complexes: effect of structure on binding free energies and heme spin state*. Proteins, 2004. 55(4): p. 895-914.

S210. AbdulHameed, M. D. M., A. Hamza, and C.-G. Zhan, *Microscopic modes and free energies of 3-phosphoinositide-dependent kinase-1 (PDK1) binding with celecoxib and other inhibitors*. J. Phys. Chem. B, 2006.

Example 8—Expression Levels of PDE5 mRNA in Heart, Whole Brain, Hippocampus and Cerebrum of Humans Quantitative RT-PCR was performed using SYBR green and three different set of primers. Primers specificity was confirmed with a melting curve. Total RNA was prepared by Clontech Laboratories, Inc. The target of Primer-1, 2 and 3 was the 3'UTR of PDE5 mRNA.

```
Primer-1
forward:
                                 (SEQ ID NO: 3)
5'-TGATGCAAAGCAGGTGAAACC-3', Reverse:
                                 (SEQ ID NO: 4)
5'-ATCCAAGGCCATTCCATTTCT-3', Primer-2
forward:
                                 (SEQ ID NO: 5)
5'-TTCCATGTGCTAGCCAGGTAAA', Reverse:
                                 (SEQ ID NO: 6)
5'-GGTCCAAAACCATGCACAATTT-3', Primer-3
forward:
                                 (SEQ ID NO: 7)
5'-ACCGTGCCAATCACAATCCT'-3', Reverse:
                                 (SEQ ID NO: 8)
5'-AGCTGCCTTCTGTGACATTCTG-3'.
```

We have demonstrated that there are very high levels of PDE5 messenger in human hippocampus, even higher than in heart (see FIG. 42). This observation is consistent with database of human brain Gene Logic's ASCENTA System. To perform these experiments was important for our project in view of previous attempts from other groups that cannot demonstrate the presence of messenger in human hippocampi because of two reasons: a) rodent sequence was used to detect human RNA; b) given that the PDE5 gene has a long 3'UTR (more than 5000 bp long). We chose the 3'UTR while others used the coding sequence, and selection of the coding sequence involves more than a 6000 bp long cDNA. Therefore, quantification of mRNA expression carried out by other groups was not correct.

Example 9—Effect of Sildenafil in a Different Animal Model for AD

Fragments of APP which are expressed in the APP/PS1 animals other than Aβ can contribute to alterations in memory. Therefore, we also validated our findings on a different AD model by administering sildenafil (3 mg/kg, i/p.) to mutant human APP(V717F, K670M, N671L) mice, also known as J20 mice. We repeated the same experimental protocol as for the APP/PS1 animals. Mice were divided into 4 groups: J20 with sildenafil (n=10), J20 with vehicle (n=7), WT with sildenafil (n=8) and WT with vehicle (n=8). We found no difference in the freezing behavior among the 4 groups during the training phase of the FC. 24 hrs later we found a decreased freezing in vehicle-treated J20 mice compared to vehicle-treated WT littermates in the analysis of the contextual learning (FIG. 55A). However, sildenafil treatment immediately after the training improved contextual learning in the Tg animals. We did not find a difference in freezing behavior during cued learning among the four groups of mice. Sildenafil also improved spatial working memory in the J20 mice that were daily injected immediately after the training for 3 weeks (FIG. 55B). When the same animals were tested with a visible platform task, no sensory-motor impairment was seen among the four groups.

Example 10—Inhibition of PDE5 and Synaptic Function, Memory and Aβ Load in an AD Mouse Model Memory loss, synaptic dysfunction and accumulation of amyloid β-peptides (Aβ) are major hallmarks of Alzheimer's disease (AD). Down-regulation of the nitric oxide/cGMP/cGMP-dependent-protein kinase/c-AMP Responsive Element Binding Protein (CREB) cascade has been linked to the synaptic deficits following Aβ elevation. Here we report that the phosphodiesterase 5 inhibitor (PDE5) sildenafil (Viagra), a molecule that enhances phosphorylation of the memory molecule CREB through elevation of cGMP levels, is beneficial against the AD phenotype in a mouse model of amyloid deposition. We demonstrate that the inhibitor produces an immediate and long-lasting amelioration of synaptic function, CREB phosphorylation and memory. This effect is also associated with a long-lasting reduction of Aβ levels. Given that side effects of PDE5 inhibitors are largely known and do not preclude their administration to a senile population, these drugs have potential for the treatment of AD and other diseases associated with elevated Aβ levels.

INTRODUCTION

Alzheimer's disease (AD) is characterized by neuronal loss, extracellular senile plaques and intracellular neurofibrillary tangles, leading to memory loss. AD begins as a synaptic disorder produced at least in part, by Aβ (Selkoe, 2002). Long-term-potentiation (LTP), a cellular model of memory, and phosphorylation of CREB, a transcription factor involved in memory, are reduced by Aβ (Vitolo et al., 2002). Interestingly, both nitric oxide (NO) donors and cGMP-analogs counteract the Aβ-induced impairment in LTP and CREB phosphorylation (Puzzo et al., 2005). Vice-versa, genetic ablation of NO-synthase 2 (NOS2) results in worsening of the AD phenotype in mice expressing mutated amyloid precursor protein (APP) (Colton et al., 2006), indicating that up-regulation of the NO pathway may be protective in AD.

One effective way to up-regulate the NO pathway is by increasing cGMP levels through inhibitors of phosphodiesterase 5 (PDE5), an enzyme expressed in several brain regions associated with cognitive function, such as the hippocampus, cortex and cerebellum (Van Staveren et al., 2003; van Staveren et al., 2004) (see also for human brain Gene Logic's ASCENTA System and personal communication from M. Sakurai). Preclinical studies have shown that the selective PDE5 inhibitors sildenafil (Viagra by Pfizer) and vardenafil (Levitra by Bayer) raise hippocampal cGMP levels and improve memory in aged rats (Prickaerts et al., 2002a) and mice (Baratti and Boccia, 1999). Interestingly, FDA has recently approved the daily use of the inhibitor tadalafil (Cialis by Lilly) (see http://www.clinicaspace.com/news_story.aspx?NewsEntityId=82124). Moreover, PDE5 inhibitors are widely used to treat erectile dysfunction and pulmonary hypertension, so that their side effects are known. Without being bound by theory, PDE5 inhibitors can be compatible with administration to a senile population such as AD patients. Based on these elements, in the present study we have investigated whether PDE5 inhibition can exert beneficial effects against the AD phenotype of mice carrying both the mutant amyloid precursor protein (APP; K670N, M671L) and presenilin-1 (PS1; M146L), termed APP/PS1 mice.

Materials and Methods

Animals.

Double transgenic mice expressing both the human APP (K670M:N671L) and PS1 (M146L) (line 6.2) mutations were used and handled as described in EXAMPLE 1.

Drug Preparation.

Drug preparation was carried out as described in EXAMPLE 1.

Drug Administration.

Three-month-old APP/PS1 and WT mice were separated into 4 groups: APP/PS1 mice treated with vehicle, APP/PS1 mice treated with PDE inhibitor, WT mice treated with vehicle, and WT mice treated with PDE inhibitor. In one experimental series we assessed the acute effects of PDE inhibition on synaptic dysfunction by perfusing hippocampal slices with sildenafil (50 nM), or tadalafil (50 nM) or IC354 (1 µM) for 10 min prior to the theta burst. In a separate series of experiments we also examined the acute effect of different concentrations of sildenafil to establish its minimal effective concentration. In the remaining experiments we i.p. injected sildenafil. For assessment of the short-term effects of sildenafil, the drug was given at a concentration of 3 mg/kg immediately after the training. This dose yields concentrations of ~2.5 µM cGMP in the hippocampus (Prickaerts et al., 2002b). In these experiments, we also established the minimal effective concentration of sildenafil and the minimal effective days of sildenafil delivery. For assessment of long-term effects, sildenafil was given daily by i.p. injection at a concentration of 3 mg/kg for 3 weeks and then treatment was stopped for 9-12 weeks prior to behavioral testing. The minimal effective number of days of sildenafil delivery and the minimal sildenafil effective concentration that can still trigger long-term rescue of memory at 6 months were also studied. Contextual and cued fear conditioning was performed for 3 days. Radial-arm water-maze (RAWM) was performed for 3 weeks. Morris water maze lasted 3 days. Then, the animals were sacrificed for electrophysiological recordings.

To decide the time of administration of sildenafil in the short-term effect experiments, we performed a series of preliminary studies in which the inhibitor was injected i.p. at 5 min before the electric shock or at 5 min before the first acquisition trial with the RAWM. We found no beneficial effect both on the freezing time and the number of errors in sildenafil-injected APP/PS1 mice (sildenafil-treated APP/PS1 mice demonstrated a freezing time equal to ~90% that of vehicle-treated APP/PS1 mice; n=7 males for sildenafil-treated transgenics and 6 males for vehicle-treated transgenics, $P>0.05$; ~5 errors in the retention trial for both sildenafil- and vehicle-treated transgenics, n=6 males for sildenafil-treated transgenics and 5 males for vehicle-treated transgenics, $P>0.05$, sildenafil did not affect the behavioral performance of WT mice in both tasks, n=5 males for all the conditions). Thus, all the behavioral experiments on the short-term effects of sildenafil reported in the result section were performed with injection after the training. Finally, in a separate set of experiments, we tested the effect of i.p. injection of tadalafil on memory.

Electrophysiological Analysis.

Electrophysiological analysis was carried out as described in EXAMPLE 1.

Patch clamp experiments were also performed to assess both NMDA and AMPA receptor currents. The technique has been previously described (Puzzo et al., 2008). Briefly, 350 µm hippocampal slices were cut with a vibratome and maintained in a submerged chamber at 29° C., perfused with artificial cerebrospinal fluid containing (in mM): 125 NaCl, 2.5 KCl, 1.25 $Na_2HPO_4$, 25 $NaHCO_3$, 2 $CaCl_2$, 1.4 $MgCl_2$, 25 glucose, 0.1 picrotoxin, pH 7.4 (95% $O_2$, 5% $CO_2$). Slices were permitted to recover for 30 min at 37° C. and then at least for 60 min at room temperature before recordings. Neurons were voltage clamped throughout the experiment. Patch pipettes (4-6 MΩ) contained a solution (in mM): 117.5 Cs-methyl-sulfonate, 17.5 CsCl2, 4 NaCl, 0.1 EGTA, 10 HEPES, 5 QX-314.Cl, 4 MgATP, 0.3 $Na_2GTP$, 10 phosphocreatine-Tris, pH adjusted to 7.3 with CsOH, osmolarity adjusted to 290 mOsm with sucrose. Currents were recorded with a Warner amplifier (PC-501A) and filtered at 1 kHz (holding potential, -70 mV). The amplitude was measured automatically by using the Clampfit program (version 10.1) from Molecular Devices. The AMPAR/NMDAR receptor ratio was calculated by dividing the amplitude of the AMPAR current measured at the peak response at -70 mV by the NMDAR current measured 30 ms after the peak at -50 mV.

Behavioral Studies

Fear conditioning—Studies were carried out as described in EXAMPLE 1.

Spatial working memory—Studies were carried out as described in EXAMPLE 1.

Reference memory—Studies were carried out as described in EXAMPLE 1.

Visible platform testing—Training was carried out as described in EXAMPLE 1.

Immunocytochemical Experiments.

Immunocytochemical experiments and measurements were carried out as described in EXAMPLE 1.

Determination of Aβ Levels.

Frozen hemi-brains were weighed and homogenized in 5 M guanidine HCL/50 mM Tris HCL solution. $A\beta_{40}$ and $A\beta_{42}$ were measured using human β amyloid ELISA kits (Biosource, CA), according to the manufacturer's protocol. ELISA signals were reported as the mean±s.e.m. in nanograms of Aβ per milligram of cortex. Alternatively, Aβ levels can be determined on homogenates of frozen hemi-brains as previously described [Trinchese et al., Ann Neurol, 2004. 55(6): p. 801-14]. Aβ can be trapped with either monoclonal antibody to $A\beta_{40}$ (JRF/cA 40/10) or $A\beta_{42}$ (JRF/cA 42/26) and then be detected with horseradish peroxidase-conjugated JRF/A tot/17 [Janus et al., Nature, 2000. 408 (6815): p. 979-82]. ELISA signals can be reported as the mean of two replica wells in fmol Aβ per mg protein (determined with the BCA Protein Assay Reagent Kit, PIERCE), based on standard curves using synthetic $A\beta_{40}$ and $A\beta_{42}$ peptide standards (American Peptide). Blood can be harvested in a tube containing 10 mM EDTA, then centrifuged at 4000 rpm for 5 min at 40° C. Plasma can then be stored at -80° C. before loading onto ELISA plates.

Statistical Analyses.

Statistical analysis was carried out as described in EXAMPLE 1. Nonlinear regression analysis was used to fit curves for different concentrations using GraphPad Prism software (GraphPad Software Inc., San Diego, Calif.).

Results

Acute Effects of Sildenafil on Synaptic Function in Hippocampal Slices of APP/PS1 Mice.

Our first goal was to determine whether PDE5 inhibition can ameliorate synaptic function. Because sildenafil is reported to cross the blood brain barrier (BBB) (FDA, 1998), whereas evidence for vardenafil is indirect (Prickaerts et al., 2004), and tadalafil does not cross it, we chose this compound as a primary drug inhibiting PDE5 for our CNS studies. Sildenafil has an $IC_{50}$ against PDE5 of 6.0 nM and an in vivo half-life of 0.4 hrs in rodents (~4 hrs in humans) (Walker et al., 1999; Daugan et al., 2003b). We first tested whether a brief application of sildenafil rescued the defect in LTP of slices derived from 3 month-old APP/PS1 mice, when synaptic plasticity impairment is just starting whereas basal synaptic transmission (BST) is normal (Trinchese et al., 2004). BST was determined by plotting the peak amplitude of the fiber volley against the slope of the field excitatory postsynaptic potential (fEPSPs) and also the fEPSP slope at increasing stimulus intensity in APP/PS1 and wild-type (WT) mice. We did not find a difference in BST among different groups (FIG. 56A, FIG. 67). Hippocampal slices were then perfused with sildenafil (50 nM) for 10 min before inducing LTP through tetanic stimulation of the Schaeffer collateral pathway. Potentiation in sildenafil treated APP/PS1 slices was far greater than in vehicle-treated APP/PS1 slices (FIG. 1B). On the other hand, sildenafil did not change the amplitude of LTP in slices of WT mice compared to WT slices treated with vehicle alone (FIG. 1C). Sildenafil had no effect on basal synaptic responses either during its application or 120 minutes after the end of the application in experiments where no tetanus was applied either in slices from APP/PS1 mice or WT littermates (FIGS. 1B-1C). Use of different concentrations of sildenafil showed that 50 nM was the minimum dose of the drug that completely rescued synaptic plasticity in slices from transgenic animals, whereas lower concentrations were less effective (FIG. 56B). The same concentrations of the inhibitor did not have an effect on LTP of WT slices. In additional experiments, 50 nM sildenafil ameliorated LTP in slices from APP/PS1 mice that were potentiated through 1 or 2 series of theta-burst stimulations (FIG. 56C). Interestingly, as previously shown on slices from WT mice that received a weaker tetanic stimulation paired with agonists of the NO pathway (Puzzo et al., 2005), 50 nM sildenafil increased the LTP amplitude in WT slices that received 1 theta-burst stimulation (FIG. 56C).

As a control for PDE5 specificity of the sildenafil effect onto synaptic dysfunction, we next used a more specific PDE5 inhibitor, tadalafil. Differently than sildenafil and vardenafil which are cGMP based inhibitors, tadalafil is a β-carbolines-derived drug with no effect on PDE1 (selectivity ratio >2000) and on PDE6 (selectivity ratio 1000), and an $IC_{50}$ against PDE5 of 5.0 nM (Daugan et al., 2003b). When slices were bathed in tadalafil (50 nM, 10 min prior to tetanus), potentiation in APP/PS1 slices was far greater than in vehicle-treated APP/PS1 slices (FIG. 8A). Tadalafil did not affect baseline and LTP in WT mice (FIG. 8B).

As an additional control for PDE5 specificity, we have also used a highly selective PDE1 inhibitor called IC354, the HCl salt of IC224 [$IC_{50}$ against PDE1 of 80 nM; ratio of $IC_{50}$ value for the next most sensitive PDE to $IC_{50}$ value for PDE1 equal to 127 (Snyder et al., 2005)]. Differently than sildenafil or tadalafil, when APP/PS1 slices were bathed in IC354 (1 µM, 10 min prior to tetanus), LTP was not affected (FIG. 8C). IC354 did not change LTP amplitude in hippocampal slices of WT mice (FIG. 8D). Thus, these results taken together with the experiments with sildenafil and tadalafil demonstrate that inhibition of PDE5 (but not PDE1) protects AD-like animal models against synaptic dysfunction, supporting that inhibition of PDE5 can be beneficial against synaptic dysfunction in AD.

Acute Effects of Sildenafil on the Cognitive Function of APP/PS1 Mice.

As reported above, sildenafil offers the advantage of crossing the BBB and therefore it can be easily utilized in behavioural experiments. We divided 3 month-old mice into 4 groups: APP/PS1 with sildenafil, APP/PS1 with vehicle, WT with sildenafil and WT with vehicle. Sildenafil and vehicle control solutions were administered i.p. at a concentration of 3 mg/kg. This concentration was chosen based on previous studies showing that these amounts of sildenafil raise hippocampal cGMP levels and improve memory in aged rats (Prickaerts et al., 2002a) and mice (Baratti and Boccia, 1999) independent of vascular effects (Prickaerts et al., 2002a). We first examined the effects of acute administration of sildenafil on fear-conditioning learning, a type of learning that is impaired in several AD mouse models (Gong et al., 2004b), and depends on hippocampus and amygdala (Phillips and LeDoux, 1992). For contextual fear conditioning, mice were trained to associate neutral stimuli with an aversive one. They were placed in a novel context (fear conditioning box), exposed to a white noise cue (conditioned stimulus, CS) paired with a mild foot shock (unconditioned stimulus, US), and injected with sildenafil immediately after the training. Fear learning was assessed twenty-four hours later by measuring freezing behaviour—the absence of all movement except for that necessitated by breathing—in response to representation of the context or of the auditory cue within a completely different context. We found no difference in the freezing behaviour among the four groups of mice before the training phase (FIG. 2A). Twenty-four hours later, we found a decrease in the freezing behaviour of vehicle-treated APP/PS1 mice compared with that of vehicle-treated WT littermates in the analysis of the contextual learning (FIG. 2A). Sildenafil treatment improved contextual learning in the transgenic animals (FIG. 2A) whereas sildenafil-treated WT animals did not show a significant increase in freezing (FIG. 2A), probably because maximal levels of memory are already induced in vehicle-treated WT mice after the training session, as has been found both in *Drosophila* and in mice (Tully et al., 2003; Gong et al., 2004a). We next tested cued fear conditioning, a hippocampus-independent task (Phillips and LeDoux, 1992), and did not find a difference in freezing among the 4 groups (FIG. 59), as APP/PS1 mice are known to have a selective hippocampus-dependent impairment in associative learning (Gong et al., 2004b). Moreover, as for the electrophysiological experiments, we determined the minimum concentration of sildenafil needed to improve contextual fear memory in APP/PS1 mice by injecting 1.5 mg/kg, 3 mg/kg and 6 mg/kg inhibitor. A concentration of 3 mg/kg fully restored fear memory (FIG. 58A). No memory enhancement was observed in WT littermates injected with the different concentrations of inhibitor.

Next, we examined the effect of treatment with sildenafil on spatial working memory, a type of short-term memory that can be studied with the RAWM test. This task has already demonstrated memory deficits in other transgenic models of AD (Morgan et al., 2000; Trinchese et al., 2004) and has been shown to depend upon hippocampal function (Diamond et al., 1999). Mice were required to learn and memorize the location of a hidden platform in one of the arms of a maze with respect to spatial cues. APP/PS1 injected with vehicle showed severe abnormalities in spatial memory for platform location during both acquisition and retention of the task compared to vehicle-injected WT littermates (FIG. 2B). However, daily injections of sildenafil for 3 weeks immediately after the 4$^{th}$ acquisition trial ameliorated the behavioural performance of APP/PS1 mice (FIG. 2B). Treatment with sildenafil did not affect the performance of WT mice compared to vehicle-injected WT littermates (FIG. 2B). We also determined the minimum concentration of sildenafil needed to improve spatial working memory in APP/PS1 mice by injecting the drug for 3 weeks with 1.5 mg/kg, 3 mg/kg and 6 mg/kg inhibitor. A concentration of 3 mg/kg fully restored memory (FIG. 58B). Then, we tested the minimum time needed for sildenafil to have a positive effect on spatial working memory. Daily injections of 3 mg/kg sildenafil improved APP/PS1 mouse performance after 2 weeks (FIG. 58C). The four groups of mice showed no difference in the time needed to find the platform in the visible platform task, as well as in swimming speed (FIG. 10). Thus, vision, motor coordination, or motivation were not affected in the four groups of mice and cannot influence the RAWM results.

An interesting difference between the results with RAWM and fear conditioning was related to the fact that sildenafil produces a partial rescue with the RAWM experiments in APP/PS1 mice, whereas rescue was complete with contextual fear conditioning. To exclude that this difference was due to an incomplete formation of memory in the WT mice facilitating the task of sildenafil to equalize memory between transgenic and WT littermates, we performed an additional series of experiments in which we increased the intensity of the foot shock from 0.50 mA to 0.75 mA. This procedure is known to increase the amount of freezing. Regardless of the amounts of freezing, sildenafil fully restores memory in APP/PS1 mice, unlike the RAWM experiments and like the experiments with lower intensity of the foot shock (FIG. 60).

To exclude the possibility that sildenafil produced its behavioural effect through a peripheral vascular action, we repeated the memory studies using tadalafil which is unable to cross the BBB (cLogP=1.43 and information from its manufacturer). Tadalafil (1 mg/kg, i.p.) did not improve either contextual fear conditioning or spatial working memory in APP/PS1 mice. Thus, the effect of sildenafil cannot be due to inhibition of PDE5 in the vascular compartment (FIG. 61).

Persistent Effects of Sildenafil on Cognitive and Synaptic Functions in APP/PS1 Mice.

Previous studies have demonstrated that the PDE4 inhibitor rolipram has a prolonged beneficial effect on synaptic and cognitive abnormalities in APP/PS1 mice that persists beyond the administration of the inhibitor (Gong et al., 2004a). This finding has opened a very interesting therapeutic perspective when using drugs up-regulating CREB phosphorylation in AD: a brief course of treatment can be beneficial for a long time. To check whether the same effect is present following sildenafil treatment, we examined whether the PDE5 inhibitor maintains its protective effect against synaptic dysfunction and memory loss. In these experiments, both APP/PS1 and WT mice of 3 months of age were injected i.p. with 3 mg/kg/day sildenafil for 3 weeks, then the treatment was stopped for 9-12 weeks prior to testing. The mice were next subjected to training for contextual learning. As in the acute experiments, when the animals were reintroduced into the same context in which they had been trained 9-12 weeks before, the freezing time was greatly increased in APP/PS1 mice that had been previously treated with sildenafil compared to vehicle-treated APP/PS1 littermates (FIG. 3A). Sildenafil did not increase the freezing time in WT littermates compared to WT mice treated with vehicle (FIG. 3A). There were no differences between the 4 groups in the cued conditioning test. 3 mg/kg was the minimum dose of inhibitor that produced the prolonged beneficial effect on contextual fear memory (FIG. 62A) and 2 weeks were the minimal effective number of days of sildenafil delivery (FIG. 62B). These data indicate that inhibition of PDE5 protects fear contextual learning in APP/PS1 mice for an extended time beyond the duration of drug administration.

The effects of one course of 3-week treatment with sildenafil on spatial working memory were next tested using the RAWM task. There was a difference between the number of errors made by vehicle-treated APP/PS1 and WT mice (FIG. 3B) (Trinchese et al., 2004). Administration of sildenafil for 3 weeks, 9-12 weeks prior to the testing, reduced the gap between the two groups without affecting performance of the WT animals (FIG. 3B). In addition, consistent with the experiments with fear conditioning, 3 mg/kg was the minimum dose of inhibitor that produced the prolonged beneficial effect on spatial working memory (FIG. 62C) and 2 weeks were the minimal effective number of days of sildenafil delivery (FIG. 62D). These data indicate that one course of long-term treatment with the PDE5 inhibitor protects spatial working memory in APP/PS1 mice.

To investigate sildenafil effect on long-term memory, we tested reference memory with a Morris water maze task that is known to require hippocampal function (Schenk and Morris, 1985) and is impaired after 6 months of age in the APP/PS1 mice (Trinchese et al., 2004). Vehicle-treated transgenic mice needed more time to find the hidden platform after six sessions compared to WT littermates (FIG. 3C). When APP/PS1 mice were previously treated with sildenafil they showed a marked improvement of their behavioural performance. Sildenafil did not affect the performance in WT littermates (FIG. 3C). We also assessed reference memory with the probe trial, another test of spatial reference memory (Schenk and Morris, 1985). After the sixth hidden-platform session the platform was removed from the water and the animals were allowed to search for 60 seconds. The mouse is thus indicating that it knows the position of the platform independently of such tactile cues as hitting the platform. Vehicle-treated WT mice spent more time in the target quadrant (TQ), where the platform had been located during training, than in the other quadrants (FIG. 3D). In addition, sildenafil improved the performance of the APP/PS1 mice which searched in the TQ more than the vehicle-treated APP/PS1 mice (FIG. 3D). Sildenafil-treated WT mice remembered where the platform was the previous days and spent about the same time as vehicle-treated WT littermates. Furthermore, consistent with the experiments with fear conditioning and RAWM, 3 mg/kg was the minimum dose of inhibitor that produced the prolonged beneficial effect on reference memory (FIGS. 62E-62F) and 2 weeks were the minimal effective number of days of sildenafil delivery (FIGS. 62G-62H). A visible platform trial performed after the probe trials did not reveal any difference in the time to reach the platform and swimming speed among the 4 groups (FIG. 11).

To add depth to the analysis of the functional changes that underlie the striking effects of sildenafil on APP/PS1 mice behavioral performance, we examined synaptic function in hippocampi from the same mice. In contrast to 3-month-old double transgenic mice, 8- to 9-month old APP/PS1 animals show a reduction of synaptic strength (Trinchese et al., 2004). Previous treatment with sildenafil in APP/PS1 mice produced greater values of fEPSP slope in slices from 8 to 9 month old mice than in vehicle-treated APP/PS1 slices (FIG. 4A). On the other hand, sildenafil did not change responses in WT littermates. CA3-CA1 connections that had been tested for BST were also assessed for their capacity of undergoing potentiation. LTP values recorded from slices obtained from APP/PS1 that had been previously treated with sildenafil were similar to their sildenafil treated-WT littermates and far greater than those from vehicle-treated APP/PS1 littermates (FIGS. 4B-4C). Eight-to nine-month old WT mice showed similar amounts of potentiation whether treated with sildenafil or with vehicle (FIG. 4C). No differences were noted in the baseline transmission of the four groups of mice in the absence of tetanus (FIGS. 4B-4C). 3 mg/kg was the minimum dose of inhibitor that produced the prolonged beneficial effect on BST and LTP (FIGS. 63A-63B) and 2 weeks were the minimal effective number of days of sildenafil delivery for rescuing these phenomena (FIGS. 63C-63D). These data indicate that one course of sildenafil treatment protects APP/PS1 mice against synaptic dysfunction for a long time.

In an additional experimental series, we also examined whether treatment of hippocampal slices from 6 month-old APP/PS1 mice with sildenafil produces an immediate improvement of synaptic function. In contrast to BST which was not ameliorated by the compound, LTP reached normal levels with 500 nM sildenafil (FIGS. 64A-64B). Thus, once the damage of synaptic function is established, PDE5 inhibition can quickly counteract defects in synaptic plasticity, but not deficits in basal synaptic function.

Effects of Sildenafil on CREB Phosphorylation and Aβ Levels in APP/PS1 Mice.

Given that the duration of action of sildenafil is relatively short, a direct effect of the PDE5 inhibitor cannot be held responsible for its long-term effects. CREB has been implicated in the regulation of genes whose expression results in the formation and stabilization of long-term memory. CREB phosphorylation is required for CREB ability to bind to CREB binding protein (CBP) and to stimulate CRE dependent gene expression (Silva et al., 1998). Aβ elevation is also known to block the tetanus-induced increase in phosphorylation of the memory molecule CREB (Puzzo et al., 2005; Gong et al., 2006). Thus, we measured levels of CREB phosphorylation in sildenafil- and vehicle-treated transgenic and WT mice. Hippocampal slices were treated as described in the electrophysiological experiments, fixed 60 minutes after the treatment, stained with anti-phospho-CREB antibodies at Ser-133, and viewed on a confocal microscope. We confirmed previous findings (Lu et al., 1999; Puzzo et al., 2005) showing an increase in immunofluorescence intensity in the CA1 cell body area of WT mice after tetanus compared to control non-tetanized slices (FIGS. 5A-5B). APP/PS1 animals did not have the physiological increase of CA1 phospho-CREB immunofluorescence after tetanus (FIGS. 5A-5B). However, sildenafil re-established normal phospho-CREB increase in tetanized slices of the double transgenics (FIGS. 5A-5B). Sildenafil did not affect the tetanus-induced increase in immunofluorescence in WT animals (FIG. 5A-5B).

We obtained similar results when we investigated mice that had been injected with 3 mg/kg/day sildenafil or vehicle at the age of 3 months and then left without treatment for 9-12 weeks. Similar to the younger animals we found an increase in immunofluorescence intensity in CA1 cell body area of WT mice after tetanus compared to non-tetanized control slices (FIG. 5C). APP/PS1 mice did not reveal the physiological increase of phospho-CREB after tetanus but previous treatment with sildenafil re-established it (FIG. 5C). Moreover, phospho-CREB immunofluorescence did not vary in slices from sildenafil-treated WT mice with tetanic stimulation (FIG. 5C). Thus, at the root of the long-term improvement in synaptic physiology and behaviour there is the re-establishment of the increase of CREB phosphorylation in APP/PS1 mice following tetanic stimulation of the Schaffer collateral-CA1 connection.

What does it underlie the long-lasting improvement in CREB phosphorylation in the APP/PS1 mice? To address this question, given that Aβ down-regulates phospho-CREB, we examined whether sildenafil affects Aβ levels. ELISA of extracts of cerebral cortices revealed a reduction in human $A\beta_{40}$ and $A\beta_{42}$ levels in sildenafil-treated APP/PS1 mice after 3 week treatment with 3 mg/kg and 6 mg/kg sildenafil at 3 months and 7-10 months (FIGS. 6SA-6SB). Treatment with 1.5 mg/kg, in turn, did not decrease Aβ levels. Finally, when we determined the Aβ levels in animals treated with 3 mg/kg sildenafil for different durations, Aβ levels were already reduced after 2 weeks both in animals that were sacrificed immediately after the treatment (FIG. 65C) and animals that had been injected with 3 mg/kg/day sildenafil at the age of 3 months and then left without treatment for 9-12 weeks (FIG. 65D). Thus, a reduction in Aβ levels is the basis of the prolonged beneficial effect by sildenafil on phospho-CREB.

DISCUSSION

The present study demonstrates that a treatment with the PDE5 inhibitor sildenafil rescues synaptic and memory deficits in a transgenic mouse model of amyloid deposition. Sildenafil also re-establishes the increase in phosphorylation of the transcription factor and memory molecule CREB. In addition, the inhibitor counteracts the negative effects of high levels of Aβ on synaptic function, memory and CREB phosphorylation not only immediately, but also for a prolonged period beyond the drug administration. Finally, sildenafil causes an immediate and long-lasting reduction in $A\beta_{40}$ and $A\beta_{42}$ levels. These findings support a model in which PDE5 inhibitors counteract the deficit in CREB phosphorylation by Aβ not only immediately, but also for a prolonged period of time through regulation of transcription of genes controlling Aβ synthesis/degradation.

A relevant finding of the present study is the reversal of the memory impairment in the APP/PS1 mouse following PDE5 inhibition. These results are in agreement with the observation that NO-mimetic molecules may reverse the cognitive impairment caused by scopolamine (Thatcher et al., 2004), or by forebrain cholinergic depletion (Bennett et al., 2007), indicating that stimulating the NO/cGMP signal transduction system can provide new, effective treatments for cognitive disorders. With regard to the beneficial effect on memory, it is interesting to note that inhibition of PDE5 activity during a narrow time window immediately after training for fear learning or after acquisition of the spatial task (but not 5 min before training for fear learning or acquisition of the spatial task) improves learning in the transgenic animals. Considering that the in vivo half-life of sildenafil is 0.4 hrs in rodents (Walker et al., 1999), there is a time-window during the first 20-25 min after the electric shock or the acquisition of the spatial task during which learning processes are susceptible of improvement by PDE5 inhibition. Moreover, given that the beneficial effect of sildenafil was observed with its injection after the training, inhibition of PDE5 acts on memory consolidation mechanisms, and not on aspects of performance, such as perception of pain or of the environment.

Another discovery reported in our study is the beneficial effect of sildenafil against synaptic dysfunction in the APP/PS1 mouse. This finding is consistent with studies on slices showing that cGMP increase through the use of NO donors or cGMP analogs rescues the reduction of LTP and the inhibition of CREB phosphorylation induced by exogenous application of Aβ (Puzzo et al., 2005). Given that altered synaptic function is a fundamental aspect in the cognitive decline of AD (Masliah, 1995), an advantage of using PDE5 inhibitors in AD can be that this class of compounds will counteract aspects of the disease linked to synaptic dysfunction that can be relevant to memory loss.

Decrease in Aβ levels by PDE5 inhibition in transgenic mice is another important finding of our studies. This result is in agreement with the observation that the NO-releasing drug NCX-2216 reduces Aβ load in APP/PS1 mice (Jantzen et al., 2002). Moreover, genetic deletion of NOS2 increases Aβ levels in APP overexpressing mice (Colton et al., 2006). Interestingly, the decrease in Aβ levels was still present after 3 to 5 months from the end of sildenafil administration. Considering that sildenafil has a short half-life, this effect can be due to an action on expression of genes regulating Aβ production and/or clearance. CREB has been implicated in the regulation of genes whose expression results in the formation and stabilization of long-term memory probably through the formation of new synaptic connections (Tully et al., 2003). When phospho-CREB binds to CBP, it stimulates CRE dependent gene expression. CBP functions as a co-activator that facilitates interactions with the basal transcription machinery by working as an acetyltransferase that catalyzes acetylation of the histone H3 of the chromatin, causing a loss in chromosomal repression and increase in the transcription of memory associated genes. Histone acetylation can be self-perpetuating, creating a functionally stable chromatin state and thus chronic changes in the rates of specific gene expression (Battaglioli et al., 2002; Lunyak et al., 2002; Turner, 2002). Without being bound by theory, the prolonged beneficial effect of sildenafil is due to a permanent increase in hystone acetylation. Consistent with this, we have recently demonstrated that inhibition of histone de-acetylation that is normally due to a group of enzymes with a reverse effect of CBP, re-establishes normal LTP and memory in APP/PS1 mice (Francis, Y. I., et al. in *Soc Neurosci. Abstr.* 548.545, San Diego, 2007).

The beneficial effect of sildenafil resembles many aspects of the effects of rolipram, a PDE4 inhibitor that elevates cAMP levels and therefore activates CREB through PKA in experiments in which it was used the same experimental paradigm as in the present studies (Gong et al., 2004b). Moreover, several nonspecific PDE inhibitors, such as caffeine, papaverine and isobutylmethylxanthine have been reported to improve some behavioral performance in experimental animals, probably by antagonizing adenosine receptors or by acting on intracellular $Ca^{2+}$ stores (Villiger and Dunn, 1981; Randt et al., 1982; Nicholson, 1990; Nehlig et al., 1992). Nevertheless, the beneficial effect of sildenafil can be specific to PDE5 inhibition because tadalafil, a highly selective PDE5 inhibitor reproduced the effect of sildenafil on synaptic dysfunction, whereas IC354, a selective inhibitor of PDE1, another PDE that can be inhibited by sildenafil (selectivity ratio 180) (Daugan et al., 2003b) did not re-establish normal LTP in slices from the double transgenic mice. Moreover, differently than rolipram which did not improve spatial working memory immediately after its administration, sildenafil immediately augmented spatial working memory. Most importantly, a striking difference between the effect of sildenafil and those of rolipram is that the former reduced Aβ levels in the brains of APP/PS1 mice, whereas the latter did not affect Aβ load.

When proposing a new class of drugs as therapeutic agents it is imperative to consider their side effects. This can determine the failure of PDE4 inhibitors to enhance memory. An advantage of using PDE5 inhibitors is that their side effects are known as they have already been utilized for many years, such that FDA has recently authorized the daily use of tadalafil. Priapism has been reported to occurr in a few cases following the intake of PDE5 inhibitors. However, the current view about the cause of priapism is that it is due to a dysregulation of PDE5 function following down-regulation of the NO pathway (Champion et al., 2005), a phenomenon also caused by Aβ increase (Puzzo et al., 2005)—such that, PDE5 inhibitors have been proposed as therapeutic agents against priapism (Burnett et al., 2006; Rajfer et al., 2006). Additional adverse events of the PDE5 inhibitors include mild vasodilatory effects such as headache, flushing, dyspepsia, and nasal congestion or rhinitis, which can warrant caution in proposing PDE5 inhibitors as AD agents. However, although Aβ is primarily accumulating in the CNS, Aβ is also present in the blood of patients affected by AD and other neurological disorders characterized by abnormal Aβ production (Basun et al., 2002; Andreasen et al., 2003). Intriguingly, systemic Aβ potentiates vasoconstriction not only in cerebral vasculature but also in other districts of the vascular system (Pasquier and Leys, 1998; Khalil et al., 2002; Kalaria, 2003; Suhara et al., 2003; Gentile et al., 2004; Price et al., 2004; Smith et al., 2004). Moreover, hypertension is often associated with AD (Pasquier and Leys, 1998; Gentile et al., 2004; Price et al., 2004). Thus, it is very appealing to think that PDE5 inhibitors can counteract not only CNS symptoms, but also vascular symptoms that often affect AD patients.

Our findings strongly support that inhibition of PDE5 can be beneficial against cognitive loss in AD. However, none of the existing commercially available inhibitors, including sildenafil, are optimized for the CNS. A good CNS drug should have high specificity and potency, as well as good pharmacokinetic, bioavailability and CNS penetration, and finally should be safe. For instance, sildenafil is reported to cross the BBB (FDA, 1998) and has an $IC_{50}$ against PDE5 of 6.0 nM and an in vivo half-life of 0.4 hrs in rodents (~4 hrs in humans) (Walker et al., 1999; Daugan et al., 2003b). However, the selectivity ratio for PDE1, which is expressed in myocardium and blood vessels besides the brain and may result in mild vasodilatatory effects is 180, and that for PDE6, which is expressed only in retina and can transiently disturb vision is equal to 12 (Corbin and Francis, 2002; Daugan et al., 2003a). Evidence for Vardenafil ability to cross the BBB is indirect (Prickaerts et al., 2004), and even if its $IC_{50}$ against PDE5 is 0.17 nM, the selectivity ratio for PDE6 is equal to 3.5 (Saenz de Tejada et al., 2001; Zhang et al., 2005). Without being bound by theory, tadalafil, cannot cross the BBB. Thus, our findings support developing new PDE5 inhibitors that are optimized for the CNS that can be used in AD patients.

Supplemental Discussion

AMPA- and NMDA-receptor currents were not altered in 3 month old double transgenic mice. Consistent with these findings basal synaptic transmission was normal in APP/PS1 mice of similar age. A careful analysis of the data published in the literature indicates that AMPA receptors are not affected at the earliest stages of the disease. For instance, Chang et al failed to see an impairment of AMPA receptor currents and basal synaptic transmission in 7-8 month old 2×KI mice, whereas at this age LTP was already impaired (Chang et al., 2006). Consistent with these findings, the concentration of $Aβ_{42}$ that interfered with AMPA receptor function was very high (2 µM) (Hsieh et al., 2006). Moreover, miniature EPSC amplitude was not altered in neurons overexpressing APP in organotypic hippocampal slice cultures (Kamenetz et al., 2003). Similar considerations can be applied to NMDA receptors. The concentration of Aβ was high (1 µM) in a manuscript demonstrating the involvement of NMDA receptors in AD (Snyder et al., 2005). In addition, extracellular Aβ was applied for a prolonged time in order to see an effect on NMDA receptors (Shankar et al., 2007). Thus, AMPA- and NMDA-receptors are not affected at the earliest stages of AD pathology. Rather, our data indicate that LTP intrinsic mechanisms are affected prior to AMPA and NMDA receptor involvement in the disease.

Drugs acting on the NO-cascade have vascular effects that can affect the cognitive performance. Thus, an alternative explanation for the beneficial effect of sildenafil is that the inhibitor works through a vascular effect instead of an intra-neuronal effect. This is unlikely as inhibition of PDE5 re-established normal LTP in slices directly exposed to PDE5 inhibitors. Moreover, although cAMP analogues have been shown to induce more dilatation of cerebral arterioles in the parietal cortex than cGMP analogues (Paterno et al., 1996), only 8-Br-cGMP (but not 8-Br-cAMP) improved memory performance in rodents (Prickaerts et al., 2002) indicating that vascular mechanisms can not account for the cGMP effects. Most importantly, tadalafil that does not cross the BBB did not reproduce the behavioral effects of sildenafil.

Our findings are in agreement with reports showing that upregulation of the NO cascade has a protective effect on Aβ-induced damage in the CNS (McCarty, 1998; Troy et al., 2000; Wirtz-Brugger and Giovanni, 2000). For instance, studies performed on PC12 cells, sympathetic neurons and hippocampal neurons, have shown that treatment with the NO generator S-nitroso penicillamine has a neuroprotective action through nitrosylation that inhibits the pro-apoptotic factor caspase-2 (Troy et al., 2000). Aβ has been found to impair NO generation by different mechanisms including a decrease in NMDA receptor signal transduction (McCarty, 1998), subtraction of NADPH availability to NOS (Venturini et al., 2002), and inhibition of the phosphorylation of the serine-threonine kinase Akt (Suhara et al., 2003). The superior temporal cortex of AD patients shows a reduction in soluble guanylyl cyclase activity (Bonkale et al., 1995). Soluble guanylyl cyclase is decreased following Aβ exposure in brain astroglial cells (Baltrons et al., 2002). PDE activity increase has been found on both isolated blood cells and cultured microglia, in which PDE5 inhibition re-establishes normal vasoactivity and blocks inflammatory response caused by Aβ (Paris et al., 1999). However, NO has also been viewed as a major agent of neuropathology and cell death when it is produced in high quantity. High amounts of NO lead to generation of significant quantity of peroxinitrites that are responsible for oxidative and nitrosative stress in Aβ-induced cell death (McCann, 1997; Tran et al., 2001; Wong et al., 2001; Haas et al., 2002; Xie et al., 2002; Monsonego et al., 2003; Wang et al., 2004). These opposite findings can be reconciled with our findings with the observation that release of low amounts of NO by the constitutive forms of NOS including both the neuronal and the endothelial isoforms, n-NOS and e-NOS, promotes synaptic plasticity and learning, whereas uncontrolled production of high amounts of the gas by the inducible form of NO-synthase (iNOS) may promote oxidative and nitrosative stress via production of peroxinitrite (McCann, 1997; Tran et al., 2001; Wong et al., 2001; Haas et al., 2002; Xie et al., 2002; Monsonego et al., 2003; Wang et al., 2004). The current status of drug research exploiting these discoveries is focused both on finding ways to upregulate the NO cascade and therefore elicit neuroprotection, as well as on finding ways to block peroxinitrite toxic effects in order to limit neuropathology (Contestabile et al., 2003). Our therapeutic strategy intervening with PDE5 offers the advantage of bypassing NO production by focusing on steps at the downstream level of NO generation.

REFERENCES FOR EXAMPLE 11

Andreasen N, Sjogren M, Blennow K (2003) CSF markers for Alzheimer's disease: total tau, phospho-tau and Abeta42. World J Biol Psychiatry 4:147-155.
Baratti C M, Boccia M M (1999) Effects of sildenafil on long-term retention of an inhibitory avoidance response in mice. Behav Pharmacol 10:731-737.
Basun H, Nilsberth C, Eckman C, Lannfelt L, Younkin S (2002) Plasma levels of Abeta42 and Abeta40 in Alzheimer patients during treatment with the acetylcholinesterase inhibitor tacrine. Dement Geriatr Cogn Disord 14:156-160.
Battaglioli E, Andres M E, Rose D W, Chenoweth J G, Rosenfeld M G, Anderson M E, Mandel G (2002) REST repression of neuronal genes requires components of the hSWI.SNF complex. The Journal of biological chemistry 277:41038-41045.
Bennett B M, Reynolds J N, Prusky G T, Douglas R M, Sutherland R J, Thatcher G R (2007) Cognitive deficits in rats after forebrain cholinergic depletion are reversed by a novel N O mimetic nitrate ester. Neuropsychopharmacology 32:505-513.
Burnett A L, Bivalacqua T J, Champion H C, Musicki B (2006) Long-term oral phosphodiesterase 5 inhibitor therapy alleviates recurrent priapism. Urology 67:1043-1048.
Champion H C, Bivalacqua T J, Takimoto E, Kass D A, Burnett A L (2005) Phosphodiesterase-5A dysregulation in penile erectile tissue is a mechanism of priapism. Proceedings of the National Academy of Sciences of the United States of America 102:1661-1666.
Colton C A, Vitek M P, Wink D A, Xu Q, Cantillana V, Previti M L, Van Nostrand W E, Weinberg J B, Dawson H (2006) N O synthase 2 (NOS2) deletion promotes multiple pathologies in a mouse model of Alzheimer's disease. Proceedings of the National Academy of Sciences of the United States of America 103:12867-12872.
Corbin J D, Francis S H (2002) Pharmacology of phosphodiesterase-5 inhibitors. Int J Clin Pract 56:453-459.
Daugan A, Grondin P, Ruault C, Le Monnier de Gouville A C, Coste H, Kirilovsky J, Hyafil F, Labaudiniere R (2003a) The discovery of tadalafil: a novel and highly selective PDE5 inhibitor. 1: 5,6,11,11a-tetrahydro-1H-imidazo[1',5': 1,6]pyrido[3,4-b]indole-1,3(2H)-dio ne analogues. J Med Chem 46:4525-4532.
Daugan A, Grondin P, Ruault C, Le Monnier de Gouville A C, Coste H, Linget J M, Kirilovsky J, Hyafil F, Labaudiniere R (2003b) The discovery of tadalafil: a novel and highly selective PDE5 inhibitor. 2: 2,3,6,7,12,12a-hexahydropyrazino[1',2':1,6]pyrido[3,4-b]indole-1,4-dione analogues. J Med Chem 46:4533-4542.
Diamond D M, Park C R, Heman K L, Rose G M (1999) Exposing rats to a predator impairs spatial working memory in the radial arm water maze. Hippocampus 9:542-552.
FDA (1998) Viagra tablets (sildenafil citrate). Review and evaluation of pharmacology and toxicology data. Report from the Division of Cardio-renal Drug Products (HFD-10). Center for Drug Evaluation and Research. In: Food and Drug Administration, pp 121-122. Washington, D C.
Gentile M T, Vecchione C, Maffei A, Aretini A, Marino G, Poulet R, Capobianco L, Selvetella G, Lembo G (2004) Mechanisms of soluble beta-amyloid impairment of endothelial function. The Journal of biological chemistry 279:48135-48142.
Gong B, Vitolo O V, Trinchese F, Liu S, Shelanski M, Arancio O (2004a) Persistent improvement in synaptic and cognitive functions in an Alzheimer mouse model after rolipram treatment. J Clin Invest 114:1624-1634.
Gong B, Vitolo O V, Trinchese F, Liu S, Shelanski M, Arancio O (2004b) Persistent improvement in synaptic and cognitive functions in an Alzheimer mouse model following rolipram treatment. J Clin Invest 114:1624-1634.
Gong B, Cao Z, Zheng P, Vitolo O V, Liu S, Staniszewski A, Moolman D, Zhang H, Shelanski M, Arancio O (2006) Ubiquitin Hydrolase Uch-L1 Rescues beta-Amyloid-Induced Decreases in Synaptic Function and Contextual Memory. Cell 126:775-788.
Jantzen P T, Connor K E, DiCarlo G, Wenk G L, Wallace J L, Rojiani A M, Coppola D, Morgan D, Gordon M N (2002) Microglial activation and beta-amyloid deposit reduction caused by a nitric oxide-releasing nonsteroidal anti-inflammatory drug in amyloid precursor protein plus presenilin-1 transgenic mice. J Neurosci 22:2246-2254.
Kalaria R N (2003) Vascular factors in Alzheimer's disease. Int Psychogeriatr 15 Suppl 1:47-52.
Khalil Z, Poliviou H, Maynard C J, Beyreuther K, Masters C L, Li Q X (2002) Mechanisms of peripheral microvascular dysfunction in transgenic mice overexpressing the Alzheimer's disease amyloid Abeta protein. J Alzheimers Dis 4:467-478.
Lu Y F, Kandel E R, Hawkins R D (1999) Nitric oxide signaling contributes to late-phase LTP and CREB phosphorylation in the hippocampus. J Neurosci 19:10250-10261.

Lunyak V V, Burgess R, Prefontaine G G, Nelson C, Sze S H, Chenoweth J, Schwartz P, Pevzner P A, Glass C, Mandel G, Rosenfeld M G (2002) Corepressor-dependent silencing of chromosomal regions encoding neuronal genes. Science (New York, N.Y. 298:1747-1752.

Masliah E (1995) Mechanisms of synaptic dysfunction in Alzheimer's disease. Histol Histopathol 10:509-519.

Morgan D, Diamond D M, Gottschall P E, Ugen K E, Dickey C, Hardy J, Duff K, Jantzen P, DiCarlo G, Wilcock D, Connor K, Hatcher J, Hope C, Gordon M, Arendash G W (2000) A beta peptide vaccination prevents memory loss in an animal model of Alzheimer's disease. Nature 408:982-985.

Nehlig A, Daval J L, Debry G (1992) Caffeine and the central nervous system: mechanisms of action, biochemical, metabolic and psychostimulant effects. Brain Res Brain Res Rev 17:139-170.

Nicholson C D (1990) Pharmacology of nootropics and metabolically active compounds in relation to their use in dementia. Psychopharmacology (Berl) 101:147-159.

Pasquier F, Leys D (1998) [Blood pressure and Alzheimer's disease]. Rev Neurol (Paris) 154:743-751.

Phillips R G, LeDoux J E (1992) Differential contribution of amygdala and hippocampus to cued and contextual fear conditioning. Behav Neurosci 106:274-285.

Price J M, Hellermann A, Hellermann G, Sutton E T (2004) Aging enhances vascular dysfunction induced by the Alzheimer's peptide beta-amyloid. Neurol Res 26:305-311.

Prickaerts J, de Vente J, Honig W, Steinbusch H W, Blokland A (2002a) cGMP, but not cAMP, in rat hippocampus is involved in early stages of object memory consolidation. Eur J Pharmacol 436:83-87.

Prickaerts J, van Staveren W C, Sik A, Markerink-van Ittersum M, Niewohner U, van der Staay F J, Blokland A, de Vente J (2002b) Effects of two selective phosphodiesterase type 5 inhibitors, sildenafil and vardenafil, on object recognition memory and hippocampal cyclic GMP levels in the rat. Neuroscience 113:351-361.

Prickaerts J, Sik A, van Staveren W C, Koopmans G, Steinbusch H W, van der Staay F J, de Vente J, Blokland A (2004) Phosphodiesterase type 5 inhibition improves early memory consolidation of object information. Neurochem Int 45:915-928.

Puzzo D, Vitolo O, Trinchese F, Jacob J P, Palmeri A, Arancio O (2005) Amyloid-beta peptide inhibits activation of the nitric oxide/cGMP/cAMP-responsive element-binding protein pathway during hippocampal synaptic plasticity. J Neurosci 25:6887-6897.

Rajfer J, Gore J L, Kaufman J, Gonzalez-Cadavid N (2006) Case report: Avoidance of palpable corporal fibrosis due to priapism with upregulators of nitric oxide. J Sex Med 3:173-176.

Randt C T, Judge M E, Bonnet K A, Quartermain D (1982) Brain cyclic AMP and memory in mice. Pharmacology, biochemistry, and behavior 17:677-680.

Saenz de Tejada I, Angulo J, Cuevas P, Fernandez A, Moncada I, Allona A, Lledo E, Korschen H G, Niewohner U, Haning H, Pages E, Bischoff E (2001) The phosphodiesterase inhibitory selectivity and the in vitro and in vivo potency of the new PDE5 inhibitor vardenafil. Int J Impot Res 13:282-290.

Schenk F, Morris R G (1985) Dissociation between components of spatial memory in rats after recovery from the effects of retrohippocampal lesions. Exp Brain Res 58:11-28.

Selkoe D J (2002) Alzheimer's disease is a synaptic failure. Science (New York, N.Y. 298:789-791.

Silva A J, Kogan J H, Frankland P W, Kida S (1998) CREB and memory. Annu Rev Neurosci 21:127-148.

Smith C C, Stanyer L, Betteridge D J (2004) Soluble beta-amyloid (A beta) 40 causes attenuation or potentiation of noradrenaline-induced vasoconstriction in rats depending upon the concentration employed. Neuroscience letters 367:129-132.

Snyder P B, Esselstyn J M, Loughney K, Wolda S L, Florio V A (2005) The role of cyclic nucleotide phosphodiesterases in the regulation of adipocyte lipolysis. Journal of lipid research 46:494-503.

Suhara T, Magrane J, Rosen K, Christensen R, Kim H S, Zheng B, McPhie D L, Walsh K, Querfurth H (2003) Abeta42 generation is toxic to endothelial cells and inhibits eNOS function through an Akt/GSK-3beta signaling-dependent mechanism. Neurobiol Aging 24:437-451.

Terrett N K, Bell A S, Brown D, Ellis P (1996) Sildenafil (VIAGRA™), a potent and selective inhibitor of type 5 cGMP phosphodiesterase with utility for the treatment of male erectile dysfunction. Bioorg Med Chem Lett 6:1819-1824.

Thatcher G R, Bennett B M, Dringenberg H C, Reynolds J N (2004) Novel nitrates as N O mimetics directed at Alzheimer's disease. J Alzheimers Dis 6:S75-84.

Trinchese F, Liu S, Battaglia F, Walter S, Mathews P M, Arancio O (2004) Progressive age-related development of Alzheimer-like pathology in APP/PS1 mice. Ann Neurol 55:801-814.

Tully T, Bourtchouladze R, Scott R, Tallman J (2003) Targeting the CREB pathway for memory enhancers. Nat Rev Drug Discov 2:267-277.

Turner B M (2002) Cellular memory and the histone code. Cell 111:285-291.

van Staveren W C, Steinbusch H W, Markerink-van Ittersum M, Behrends S, de Vente J (2004) Species differences in the localization of cGMP-producing and N O-responsive elements in the mouse and rat hippocampus using cGMP immunocytochemistry. Eur J Neurosci 19:2155-2168.

Van Staveren W C, Steinbusch H W, Markerink-Van Ittersum M, Repaske D R, Goy M F, Kotera J, Omori K, Beavo J A, De Vente J (2003) mRNA expression patterns of the cGMP-hydrolyzing phosphodiesterases types 2, 5, and 9 during development of the rat brain. J Comp Neurol 467:566-580.

Villiger J W, Dunn A J (1981) Phosphodiesterase inhibitors facilitate memory for passive avoidance conditioning. Behavioral and neural biology 31:354-359.

Vitolo O V, Sant'Angelo A, Costanzo V, Battaglia F, Arancio O, Shelanski M (2002) Amyloid beta-peptide inhibition of the PKA/CREB pathway and long-term potentiation: reversibility by drugs that enhance cAMP signaling. Proc Natl Acad Sci USA 99:13217-13221.

Walker D K, Ackland M J, James G C, Muirhead G J, Rance D J, Wastall P, Wright P A (1999) Pharmacokinetics and metabolism of sildenafil in mouse, rat, rabbit, dog and man. Xenobiotica 29:297-310.

Zhang X, Feng Q, Cote R H (2005) Efficacy and selectivity of phosphodiesterase-targeted drugs in inhibiting photoreceptor phosphodiesterase (PDE6) in retinal photoreceptors. Invest Ophthalmol Vis Sci 46:3060-3066.

Baltrons M A, Pedraza C E, Heneka M T, Garcia A (2002) Beta-amyloid peptides decrease soluble guanylyl cyclase expression in astroglial cells. Neurobiol Dis 10:139-149.

Bonkale W L, Winblad B, Ravid R, Cowburn R F (1995) Reduced nitric oxide responsive soluble guanylyl cyclase activity in the superior temporal cortex of patients with Alzheimer's disease. Neuroscience letters 187:5-8.

Chang E H, Savage M J, Flood D G, Thomas J M, Levy R B, Mahadomrongkul V, Shirao T, Aoki C, Huerta P T (2006) AMPA receptor downscaling at the onset of Alzheimer's disease pathology in double knockin mice. Proceedings of the National Academy of Sciences of the United States of America 103:3410-3415.

Contestabile A, Monti B, Contestabile A, Ciani E (2003) Brain nitric oxide and its dual role in neurodegeneration/neuroprotection: understanding molecular mechanisms to devise drug approaches. Curr Med Chem 10:2147-2174.

Haas J, Storch-Hagenlocher B, Biessmann A, Wildemann B (2002) Inducible nitric oxide synthase and argininosuccinate synthetase: co-induction in brain tissue of patients with Alzheimer's dementia and following stimulation with beta-amyloid 1-42 in vitro. Neuroscience letters 322:121-125.

Hsieh H, Boehm J, Sato C, Iwatsubo T, Tomita T, Sisodia S, Malinow R (2006) AMPAR removal underlies Abeta-induced synaptic depression and dendritic spine loss. Neuron 52:831-843.

Kamenetz F, Tomita T, Hsieh H, Seabrook G, Borchelt D, Iwatsubo T, Sisodia S, Malinow R (2003) APP processing and synaptic function. Neuron 37:925-937.

McCann S M (1997) The nitric oxide hypothesis of brain aging. Exp Gerontol 32:431-440.

McCarty M F (1998) Vascular nitric oxide may lessen Alzheimer's risk. Med Hypotheses 51:465-476.

Monsonego A, Imitola J, Zota V, Oida T, Weiner H L (2003) Microglia-mediated nitric oxide cytotoxicity of T cells following amyloid beta-peptide presentation to Th1 cells. J Immunol 171:2216-2224.

Paris D, Town T, Parker T A, Tan J, Humphrey J, Crawford F, Mullan M (1999) Inhibition of Alzheimer's beta-amyloid induced vasoactivity and proinflammatory response in microglia by a cGMP-dependent mechanism. Exp Neurol 157:211-221.

Paterno R, Faraci F M, Heistad D D (1996) Role of Ca(2+)-dependent K+ channels in cerebral vasodilatation induced by increases in cyclic GMP and cyclic AMP in the rat. Stroke 27:1603-1607; discussion 1607-1608.

Prickaerts J, de Vente J, Honig W, Steinbusch H W, Blokland A (2002) cGMP, but not cAMP, in rat hippocampus is involved in early stages of object memory consolidation. Eur J Pharmacol 436:83-87.

Puzzo D, Privitera L, Leznik E, Fa M, Staniszewski A, Palmeri A, Arancio O (2008) Picomolar amyloid-beta positively modulates synaptic plasticity and memory in hippocampus. J Neurosci 28:14537-14545.

Shankar G M, Bloodgood B L, Townsend M, Walsh D M, Selkoe D J, Sabatini B L (2007). J Neurosci 27:2866-2875.

Snyder E M, Nong Y, Almeida C G, Paul S, Moran T, Choi E Y, Nairn A C, Salter M W, Lombroso P J, Gouras G K, Greengard P (2005) Regulation of NMDA receptor trafficking by amyloid-beta. Nature neuroscience 8:1051-1058.

Suhara T, Magrane J, Rosen K, Christensen R, Kim H S, Zheng B, McPhie D L, Walsh K, Querfurth H (2003) Abeta42 generation is toxic to endothelial cells and inhibits eNOS function through an Akt/GSK-3beta signaling-dependent mechanism. Neurobiol Aging 24:437-451.

Tran M H, Yamada K, Olariu A, Mizuno M, Ren X H, Nabeshima T (2001) Amyloid beta-peptide induces nitric oxide production in rat hippocampus: association with cholinergic dysfunction and amelioration by inducible nitric oxide synthase inhibitors. Faseb J 15:1407-1409.

Troy C M, Rabacchi S A, Friedman W J, Frappier T F, Brown K, Shelanski M L (2000) Caspase-2 mediates neuronal cell death induced by beta-amyloid. J Neurosci 20:1386-1392.

Venturini G, Colasanti M, Persichini T, Fioravanti E, Ascenzi P, Palomba L, Cantoni O, Musci G (2002) Beta-amyloid inhibits NOS activity by subtracting NADPH availability. Faseb J 16:1970-1972.

Wang Q, Rowan M J, Anwyl R (2004) Beta-amyloid-mediated inhibition of NMDA receptor-dependent long-term potentiation induction involves activation of microglia and stimulation of inducible nitric oxide synthase and superoxide. J Neurosci 24:6049-6056.

Wirtz-Brugger F, Giovanni A (2000). Neuroscience 99:737-750.

Wong A, Luth H J, Deuther-Conrad W, Dukic-Stefanovic S, Gasic-Milenkovic J, Arendt T, Munch G (2001). Brain Res 920:32-40.

Xie Z, Wei M, Morgan T E, Fabrizio P, Han D, Finch C E, Longo V D (2002) Peroxynitrite mediates neurotoxicity of amyloid beta-peptide1-42- and lipopolysaccharide-activated microglia. J Neurosci 22:3484-3492.

What is claimed is:

1. A method for treating synaptic dysfunction and memory loss in a subject in need thereof, the method comprising:
administering to the subject an effective amount of a composition comprising a PDE5 inhibitor compound of Formula (V):

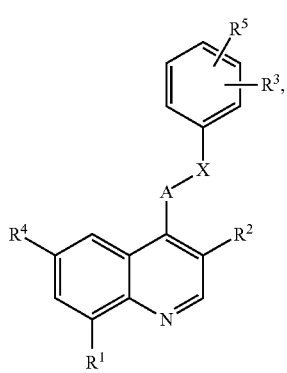

wherein:
A is O or N;
X is —(CH$_2$)$_n$, C(O), S(O), or S(O)$_2$;
R$^1$ is C$_3$-C$_8$ cycloalkyl, NR$^7$R$^8$, or —SR$^7$;
R$^2$ is CH$_2$OR$^6$ or CO$_2$R$^8$;
R$^3$ is hydrogen or halogen;
R$^4$ is —CN or halogen;
R$^5$ is hydrogen or —OR$^6$;
R$^6$ is hydrogen, —C$_1$-C$_6$ alkyl, —C$_3$-C$_8$ cycloalkyl, or —C(O)R$^9$;
R$^7$ and R$^8$ are each independently hydrogen, —C$_1$-C$_6$ alkyl, —C$_3$-C$_8$ cycloalkyl, or —C(O)R$^9$, wherein the C$_1$-C$_6$ alkyl or C$_3$-C$_8$ cycloalkyl are optionally substituted with —C$_1$-C$_6$ alkyl, —C$_3$-C$_8$ cycloalkyl, —NR$^9$R$^{10}$, —SR$^9$, or heterocyclyl; or, R$^7$ and R$^8$ together with the nitrogen atom to which they are attached form a 3 to 8-membered heterocycle, wherein any one of the ring carbon atoms is optionally replaced with a heteroatom, and wherein the heterocycle is optionally substituted with C$_1$-C$_6$ alkyl; and
R$^9$ and R$^{10}$ are each independently hydrogen, C$_1$-C$_6$ alkyl, or C$_3$-C$_8$ cycloalkyl; and n is 1, 2, or 3,
or a pharmaceutically acceptable salt or tautomer thereof.

2. The method of claim 1, wherein the effective amount is at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, or at least about 10 mg/kg body weight.

3. The method of claim 1, wherein A is N.

4. The method of claim 1, wherein R$^5$ is hydrogen.

5. The method of claim 1, wherein R$^5$ is —OCH$_3$.

6. The method of claim 1, wherein the compound is of formula (V-1):

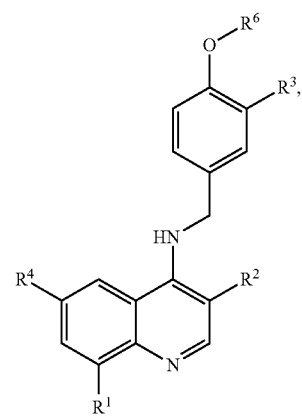

wherein:
R$^1$ is C$_3$-C$_8$ cycloalkyl, NR$^7$R$^8$, or —SR$^7$, or heterocyclyl;
R$^2$ is —CH$_2$OR$^6$ or —CO$_2$R$^8$;
R$^3$ is hydrogen or halogen;
R$^4$ is —CN or halogen;
R$^6$ is hydrogen, —C$_1$-C$_6$ alkyl, —C$_3$-C$_8$ cycloalkyl, or —C(O)R$^9$;
R$^7$ and R$^8$ are each independently hydrogen, —C$_1$-C$_6$ alkyl, —C$_3$-C$_8$ cycloalkyl, or —C(O)R$^9$, wherein the C$_1$-C$_6$ alkyl or C$_3$-C$_8$ cycloalkyl are optionally substituted with —C$_1$-C$_6$ alkyl, —C$_3$-C$_8$ cycloalkyl, —NR$^9$R$^{10}$, —SR$^9$, or heterocyclyl; or, R$^7$ and R$^8$ together with the nitrogen atom to which they are attached form a 3 to 8-membered heterocycle, wherein any one of the ring carbon atoms is optionally replaced with a heteroatom, and wherein the heterocycle is optionally substituted with C$_1$-C$_6$ alkyl; and
R$^9$ and R$^{10}$ are each independently hydrogen, C$_1$-C$_6$ alkyl, or C$_3$-C$_8$ cycloalkyl,
or a pharmaceutically acceptable salt or tautomer thereof.

7. The method of claim 6, wherein R$^6$ is CH$_3$.

8. The method of claim 1, wherein the compound is of formula (V-1a):

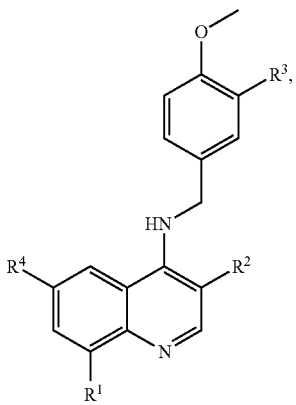

(V-1a)

wherein:
- R¹ is $C_3$-$C_8$ cycloalkyl, —NR⁷R⁸, or —SR⁷;
- R² is —CH₂OR⁶ or —CO₂R⁸;
- R³ is hydrogen or halogen;
- R⁴ is —CN or halogen;
- R⁷ and R⁸ are each independently hydrogen, —$C_1$-$C_6$ alkyl, —$C_3$-$C_8$ cycloalkyl, or —C(O)R⁹, wherein the $C_1$-$C_6$ alkyl or $C_3$-$C_8$ cycloalkyl are optionally substituted with —$C_1$-$C_6$ alkyl, —$C_3$-$C_8$ cycloalkyl, —NR⁹R¹⁰, —SR⁹, or heterocyclyl; or, R⁷ and R⁸ together with the nitrogen atom to which they are attached form a 3 to 8-membered heterocycle, wherein any one of the ring carbon atoms is optionally replaced with a heteroatom, and wherein the heterocycle is optionally substituted with $C_1$-$C_6$ alkyl; and
- R⁹ and R¹⁰ are each independently hydrogen, $C_1$-$C_6$ alkyl, or $C_3$-$C_8$ cycloalkyl, or a pharmaceutically acceptable salt or tautomer thereof.

9. The method of claim 1, wherein R² is CH₂—OH.
10. The method of claim 1, wherein R³ is H.
11. The method of claim 1, wherein R³ is a halogen.
12. The method of claim 1, wherein R³ is chlorine.
13. The method of claim 1, wherein R⁴ is —CN.
14. The method of claim 1, wherein R⁴ is a halogen.
15. The method of claim 1, wherein R⁴ is fluorine.
16. The method of claim 1, wherein the compound is of formula (V-1a1):

17. The method of claim 1, wherein R¹ is $C_3$-$C_8$ cycloalkyl or —NR⁷R⁸.
18. The method of claim 1, wherein R¹ is —NR⁷R⁸.
19. The method of claim 1, wherein R¹ is —NR⁷R⁸, and wherein R⁷ and R⁸ are each independently hydrogen, —$C_1$-$C_6$ alkyl, —$C_3$-$C_8$ cycloalkyl, or —C(O)R⁹, wherein the $C_1$-$C_6$ alkyl or $C_3$-$C_8$ cycloalkyl are optionally substituted with —$C_1$-$C_6$ alkyl, —$C_3$-$C_8$ cycloalkyl, or —NR⁹R¹⁰; or, R⁷ and R⁸ together with the nitrogen atom to which they are attached form a 3 to 8-membered heterocycle, wherein any one of the ring carbon atoms is optionally replaced with O, NR⁹ or N—C(O)R⁹.
20. The method of claim 1, wherein R¹ is —SR⁷.
21. The method of claim 1, wherein R¹ is —S—($C_1$-$C_6$)-alkyl.
22. The method of claim 1, wherein R¹ is $C_3$-$C_8$ cycloalkyl.
23. The method of claim 1, wherein R¹ is cyclopropyl.
24. The method of claim 1, wherein R¹ is dimethylamino.
25. The method of claim 1, wherein the compound is

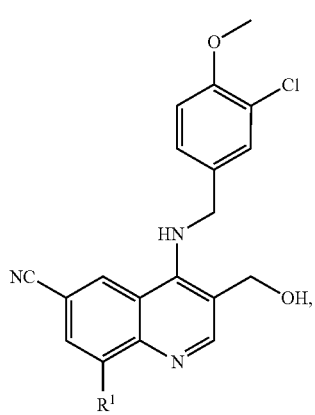

(V-1a1)

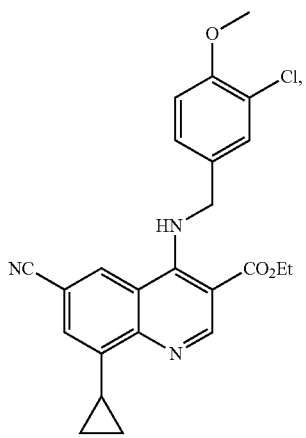

1

-continued
2
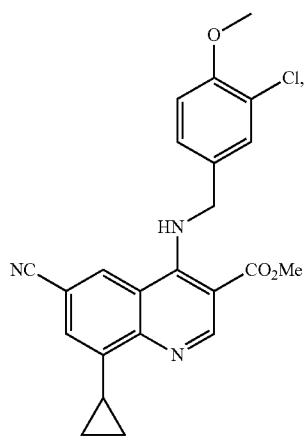
3
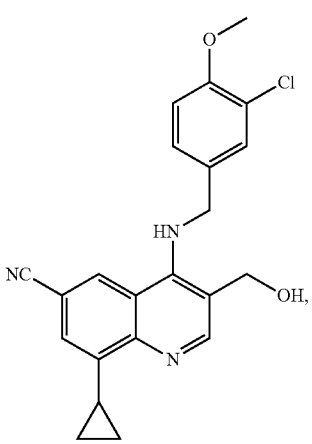
4
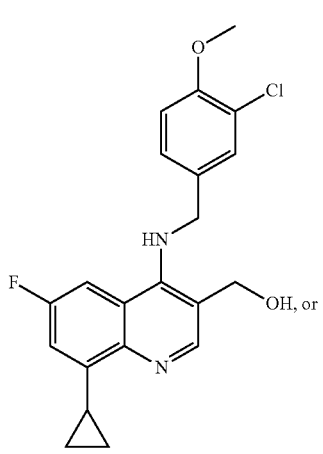
-continued
6
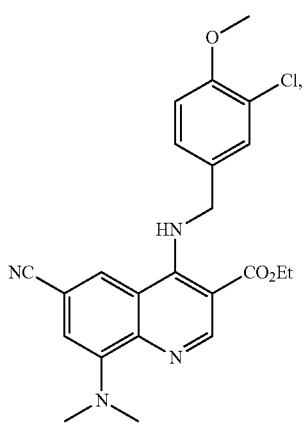
7
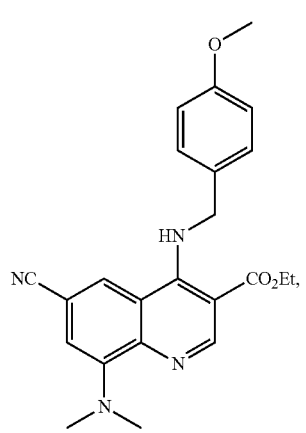
8
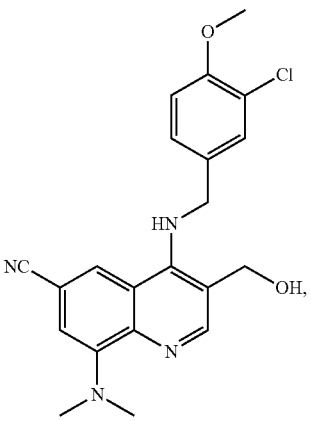

-continued
9
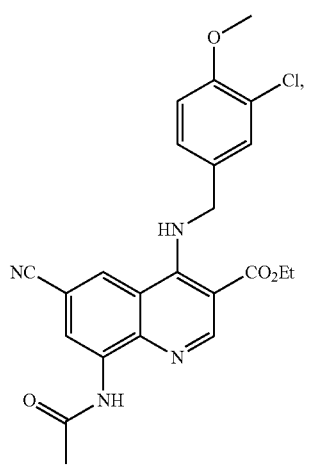
10
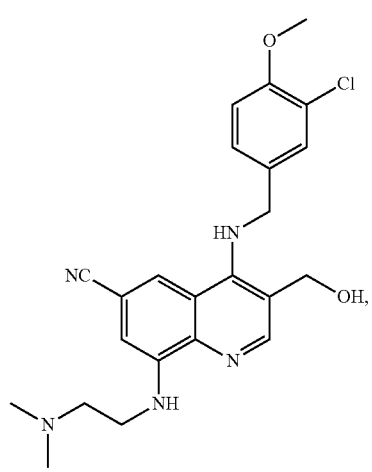
12
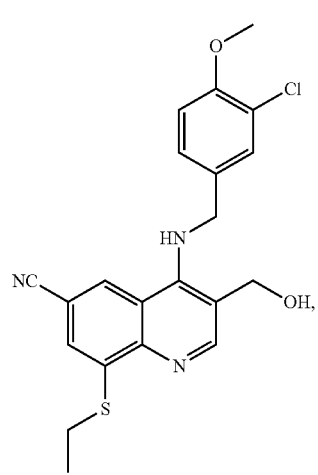
-continued
13
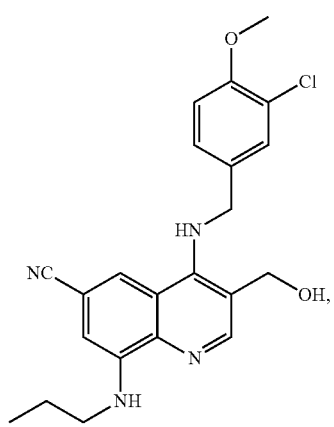
14
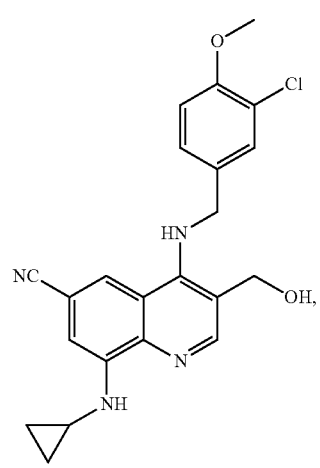
15
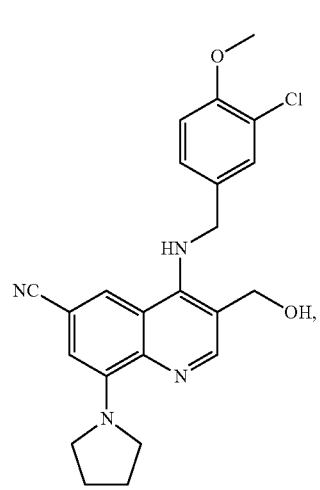

16

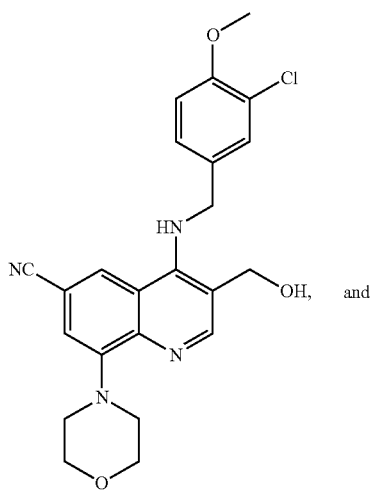

and

17

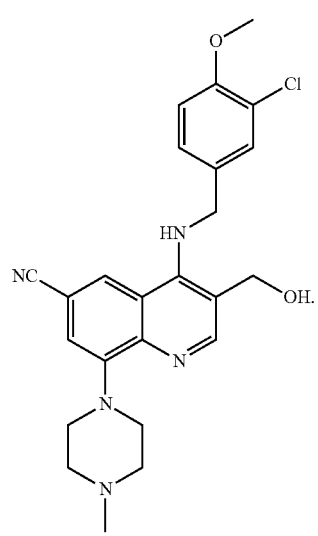

26. The method of claim 1, wherein the compound is

3

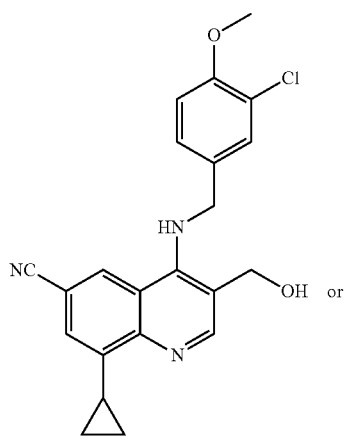

or

8

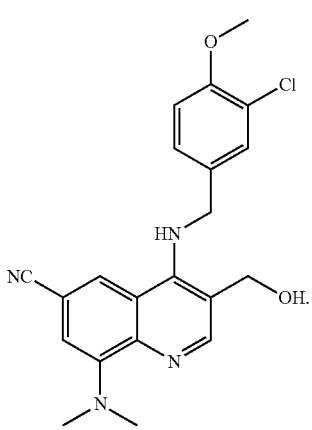

27. The method of claim 1, wherein the composition is administered at least once daily for up to 18 days, up to 19 days, up to 20 days, up to 21 days, up to 22 days, up to 23 days, up to 24 days, or up to 25 days.

28. The method of claim 1, wherein PDE5 activity is inhibited up to 3 months post-treatment, up to 4 months post-treatment, up to 5 months post-treatment, or up to 6 months post-treatment.

* * * * *

SEQUENCE LISTING

```
<160> NUMBER OF SEQ ID NOS: 10

<210> SEQ ID NO 1
<211> LENGTH: 875
<212> TYPE: PRT
<213> ORGANISM: Homo sapiens

<400> SEQUENCE: 1

Met Glu Arg Ala Gly Pro Ser Phe Gly Gln Gln Arg Gln Gln Gln
1               5                   10                  15

Pro Gln Gln Gln Lys Gln Gln Arg Asp Gln Asp Ser Val Glu Ala
                20                  25                  30

Trp Leu Asp Asp His Trp Asp Phe Thr Phe Ser Tyr Phe Val Arg Lys
            35                  40                  45

Ala Thr Arg Glu Met Val Asn Ala Trp Phe Ala Glu Arg Val His Thr
        50                  55                  60
```

```
Ile Pro Val Cys Lys Glu Gly Ile Arg Gly His Thr Glu Ser Cys Ser
 65                  70                  75                  80

Cys Pro Leu Gln Gln Ser Pro Arg Ala Asp Asn Ser Ala Pro Gly Thr
             85                  90                  95

Pro Thr Arg Lys Ile Ser Ala Ser Glu Phe Asp Arg Pro Leu Arg Pro
        100                 105                 110

Ile Val Val Lys Asp Ser Glu Gly Thr Val Ser Phe Leu Ser Asp Ser
        115                 120                 125

Glu Lys Lys Glu Gln Met Pro Leu Thr Pro Pro Arg Phe Asp His Asp
    130                 135                 140

Glu Gly Asp Gln Cys Ser Arg Leu Leu Glu Leu Val Lys Asp Ile Ser
145                 150                 155                 160

Ser His Leu Asp Val Thr Ala Leu Cys His Lys Ile Phe Leu His Ile
                165                 170                 175

His Gly Leu Ile Ser Ala Asp Arg Tyr Ser Leu Phe Leu Val Cys Glu
            180                 185                 190

Asp Ser Ser Asn Asp Lys Phe Leu Ile Ser Arg Leu Phe Asp Val Ala
        195                 200                 205

Glu Gly Ser Thr Leu Glu Glu Val Ser Asn Asn Cys Ile Arg Leu Glu
    210                 215                 220

Trp Asn Lys Gly Ile Val Gly His Val Ala Ala Leu Gly Glu Pro Leu
225                 230                 235                 240

Asn Ile Lys Asp Ala Tyr Glu Asp Pro Arg Phe Asn Ala Glu Val Asp
                245                 250                 255

Gln Ile Thr Gly Tyr Lys Thr Gln Ser Ile Leu Cys Met Pro Ile Lys
            260                 265                 270

Asn His Arg Glu Glu Val Val Gly Val Ala Gln Ala Ile Asn Lys Lys
        275                 280                 285

Ser Gly Asn Gly Gly Thr Phe Thr Glu Lys Asp Glu Lys Asp Phe Ala
    290                 295                 300

Ala Tyr Leu Ala Phe Cys Gly Ile Val Leu His Asn Ala Gln Leu Tyr
305                 310                 315                 320

Glu Thr Ser Leu Leu Glu Asn Lys Arg Asn Gln Val Leu Leu Asp Leu
                325                 330                 335

Ala Ser Leu Ile Phe Glu Glu Gln Gln Ser Leu Glu Val Ile Leu Lys
            340                 345                 350

Lys Ile Ala Ala Thr Ile Ile Ser Phe Met Gln Val Gln Lys Cys Thr
        355                 360                 365

Ile Phe Ile Val Asp Glu Asp Cys Ser Asp Ser Phe Ser Ser Val Phe
    370                 375                 380

His Met Glu Cys Glu Glu Leu Glu Lys Ser Ser Asp Thr Leu Thr Arg
385                 390                 395                 400

Glu His Asp Ala Asn Lys Ile Asn Tyr Met Tyr Ala Gln Tyr Val Lys
                405                 410                 415

Asn Thr Met Glu Pro Leu Asn Ile Pro Asp Val Ser Lys Asp Lys Arg
            420                 425                 430

Phe Pro Trp Thr Thr Glu Asn Thr Gly Asn Val Asn Gln Gln Cys Ile
        435                 440                 445

Arg Ser Leu Leu Cys Thr Pro Ile Lys Asn Gly Lys Lys Asn Lys Val
    450                 455                 460

Ile Gly Val Cys Gln Leu Val Asn Lys Met Glu Glu Asn Thr Gly Lys
465                 470                 475                 480

Val Lys Pro Phe Asn Arg Asn Asp Glu Gln Phe Leu Glu Ala Phe Val
```

```
            485             490             495
Ile Phe Cys Gly Leu Gly Ile Gln Asn Thr Gln Met Tyr Glu Ala Val
            500             505             510

Glu Arg Ala Met Ala Lys Gln Met Val Thr Leu Glu Val Leu Ser Tyr
            515             520             525

His Ala Ser Ala Ala Glu Glu Thr Arg Glu Leu Gln Ser Leu Ala
            530             535             540

Ala Ala Val Val Pro Ser Ala Gln Thr Leu Lys Ile Thr Asp Phe Ser
545             550             555             560

Phe Ser Asp Phe Glu Leu Ser Asp Leu Glu Thr Ala Leu Cys Thr Ile
                565             570             575

Arg Met Phe Thr Asp Leu Asn Leu Val Gln Asn Phe Gln Met Lys His
            580             585             590

Glu Val Leu Cys Arg Trp Ile Leu Ser Val Lys Lys Asn Tyr Arg Lys
            595             600             605

Asn Val Ala Tyr His Asn Trp Arg His Ala Phe Asn Thr Ala Gln Cys
            610             615             620

Met Phe Ala Ala Leu Lys Ala Gly Lys Ile Gln Asn Lys Leu Thr Asp
625             630             635             640

Leu Glu Ile Leu Ala Leu Leu Ile Ala Ala Leu Ser His Asp Leu Asp
                645             650             655

His Arg Gly Val Asn Asn Ser Tyr Ile Gln Arg Ser Glu His Pro Leu
            660             665             670

Ala Gln Leu Tyr Cys His Ser Ile Met Glu His His His Phe Asp Gln
            675             680             685

Cys Leu Met Ile Leu Asn Ser Pro Gly Asn Gln Ile Leu Ser Gly Leu
            690             695             700

Ser Ile Glu Glu Tyr Lys Thr Thr Leu Lys Ile Ile Lys Gln Ala Ile
705             710             715             720

Leu Ala Thr Asp Leu Ala Leu Tyr Ile Lys Arg Arg Gly Glu Phe Phe
                725             730             735

Glu Leu Ile Arg Lys Asn Gln Phe Asn Leu Glu Asp Pro His Gln Lys
            740             745             750

Glu Leu Phe Leu Ala Met Leu Met Thr Ala Cys Asp Leu Ser Ala Ile
            755             760             765

Thr Lys Pro Trp Pro Ile Gln Gln Arg Ile Ala Glu Leu Val Ala Thr
            770             775             780

Glu Phe Phe Asp Gln Gly Asp Arg Glu Arg Lys Glu Leu Asn Ile Glu
785             790             795             800

Pro Thr Asp Leu Met Asn Arg Glu Lys Lys Asn Lys Ile Pro Ser Met
                805             810             815

Gln Val Gly Phe Ile Asp Ala Ile Cys Leu Gln Leu Tyr Glu Ala Leu
            820             825             830

Thr His Val Ser Glu Asp Cys Phe Pro Leu Leu Asp Gly Cys Arg Lys
            835             840             845

Asn Arg Gln Lys Trp Gln Ala Leu Ala Glu Gln Gln Glu Lys Met Leu
            850             855             860

Ile Asn Gly Glu Ser Gly Gln Ala Lys Arg Asn
865             870             875

<210> SEQ ID NO 2
<211> LENGTH: 865
<212> TYPE: PRT
<213> ORGANISM: Mus musculus
```

<400> SEQUENCE: 2

```
Met Glu Arg Ala Gly Pro Asn Ser Val Arg Ser Gln Gln Gln Arg Asp
1               5                   10                  15

Pro Asp Trp Val Glu Ala Trp Leu Asp Asp His Arg Asp Phe Thr Phe
            20                  25                  30

Ser Tyr Phe Ile Arg Lys Ala Thr Arg Asp Met Val Asn Ala Trp Phe
        35                  40                  45

Ser Glu Arg Val His Asn Ile Pro Val Cys Lys Glu Gly Ile Arg Ala
    50                  55                  60

His Thr Glu Ser Cys Ser Cys Ser Leu Gln Gln Ser Pro His Ala Asp
65                  70                  75                  80

Asn Thr Thr Pro Gly Ala Pro Ala Arg Lys Ile Ser Ala Ser Glu Phe
                85                  90                  95

Asp Arg Pro Leu Arg Pro Ile Val Val Lys Asp Ser Glu Gly Thr Val
            100                 105                 110

Ser Phe Leu Ser Asp Ser Gly Lys Lys Glu Gln Met Pro Leu Thr Pro
        115                 120                 125

Pro Arg Phe Asp Ser Asp Glu Gly Asp Gln Cys Ser Arg Leu Leu Glu
    130                 135                 140

Leu Val Lys Asp Ile Ser Ser His Leu Asp Val Thr Ala Leu Cys His
145                 150                 155                 160

Lys Ile Phe Leu His Ile His Gly Leu Ile Ser Ala Asp Arg Tyr Thr
                165                 170                 175

Leu Phe Leu Val Cys Glu Asp Ser Ser Lys Asp Lys Phe Leu Ile Ser
            180                 185                 190

Arg Leu Phe Asp Val Ala Glu Gly Ser Thr Leu Glu Glu Ala Ser Asn
        195                 200                 205

Asn Cys Ile Arg Leu Glu Trp Asn Lys Gly Ile Val Gly His Val Ala
    210                 215                 220

Ala Phe Gly Glu Pro Leu Asn Ile Lys Asp Ala Tyr Glu Asp Pro Arg
225                 230                 235                 240

Phe Asn Ala Glu Val Asp Gln Ile Thr Gly Tyr Lys Thr Gln Ser Ile
                245                 250                 255

Leu Cys Met Pro Ile Lys Asn His Arg Glu Glu Val Val Gly Val Ala
            260                 265                 270

Gln Ala Ile Asn Lys Lys Ser Gly Asn Gly Gly Thr Phe Thr Glu Lys
        275                 280                 285

Asp Glu Lys Asp Phe Ala Ala Tyr Leu Ala Phe Cys Gly Ile Val Leu
    290                 295                 300

His Asn Ala Gln Leu Tyr Glu Thr Ser Leu Leu Glu Asn Lys Arg Asn
305                 310                 315                 320

Gln Val Leu Leu Asp Leu Ala Ser Leu Ile Phe Glu Glu Gln Gln Ser
                325                 330                 335

Leu Glu Val Ile Leu Lys Lys Ile Ala Ala Thr Ile Ile Ser Phe Met
            340                 345                 350

Gln Val Gln Lys Cys Thr Ile Phe Ile Val Asp Glu Asp Cys Pro Asp
        355                 360                 365

Ser Phe Ser Arg Val Phe His Met Glu Cys Glu Glu Val Gly Lys Pro
    370                 375                 380

Ser Asp Pro Leu Thr Arg Glu Gln Asp Ala Asn Lys Ile Asn Tyr Met
385                 390                 395                 400

Tyr Ala Gln Tyr Val Lys Asn Thr Met Glu Pro Leu Asn Ile Pro Asp
```

-continued

```
                405                 410                 415
Val Thr Lys Asp Lys Arg Phe Pro Trp Thr Asn Glu Asn Met Gly His
                420                 425                 430

Val Asn Thr Pro Cys Ile Gly Ser Leu Leu Cys Thr Pro Ile Lys Asn
                435                 440                 445

Gly Lys Lys Asn Lys Val Ile Gly Val Cys Gln Leu Val Asn Lys Met
        450                 455                 460

Glu Glu Asn Thr Gly Lys Ile Lys Ala Phe Asn Gln Asn Asp Glu Gln
465                 470                 475                 480

Phe Leu Glu Ala Phe Val Ile Phe Cys Gly Leu Gly Ile Gln Asn Thr
                485                 490                 495

Gln Met Tyr Glu Ala Val Glu Arg Ala Met Ala Lys Gln Met Val Thr
                500                 505                 510

Leu Glu Val Leu Ser Tyr His Ala Ser Ala Glu Glu Thr Arg
                515                 520                 525

Glu Leu Gln Ala Leu Ser Ala Ala Val Pro Ser Ala Gln Thr Leu
        530                 535                 540

Lys Ile Thr Asp Phe Ser Phe Ser Asp Phe Glu Leu Ser Asp Leu Glu
545                 550                 555                 560

Thr Ala Leu Cys Thr Ile Arg Met Phe Thr Asp Leu Asn Leu Val Gln
                565                 570                 575

Asn Phe Gln Met Lys His Glu Val Leu Cys Arg Trp Ile Leu Ser Val
                580                 585                 590

Lys Lys Asn Tyr Arg Lys Asn Val Ala Tyr His Asn Trp Arg His Ala
        595                 600                 605

Phe Asn Thr Ala Gln Cys Met Phe Ala Ala Leu Lys Ala Gly Lys Ile
        610                 615                 620

Gln Asn Lys Leu Thr Asp Leu Glu Thr Leu Ala Leu Leu Ile Ala Ala
625                 630                 635                 640

Leu Ser His Asp Leu Asp His Arg Gly Val Asn Asn Ser Tyr Ile Gln
                645                 650                 655

Arg Ser Glu His Pro Leu Ala Gln Leu Tyr Cys His Ser Ile Met Glu
                660                 665                 670

His His His Phe Asp Gln Cys Leu Met Ile Leu Asn Ser Pro Gly Asn
        675                 680                 685

Gln Ile Leu Ser Gly Leu Ser Ile Asp Glu Tyr Lys Thr Thr Leu Lys
        690                 695                 700

Ile Ile Lys Gln Ala Ile Leu Ala Thr Asp Leu Ala Leu Tyr Ile Lys
705                 710                 715                 720

Arg Arg Gly Glu Phe Phe Glu Leu Ile Arg Lys Asn Gln Phe Ser Phe
                725                 730                 735

Glu Asp Pro Leu Gln Lys Glu Leu Phe Leu Ala Met Leu Met Thr Ala
                740                 745                 750

Cys Asp Leu Ser Ala Ile Thr Lys Pro Trp Pro Ile Gln Gln Arg Ile
                755                 760                 765

Ala Glu Leu Val Ala Ala Glu Phe Phe Asp Gln Gly Asp Arg Glu Arg
                770                 775                 780

Lys Glu Leu Asn Met Glu Pro Ala Asp Leu Met Asn Arg Glu Lys Lys
785                 790                 795                 800

Asn Lys Ile Pro Ser Met Gln Val Gly Phe Ile Asp Ala Ile Cys Leu
                805                 810                 815

Gln Leu Tyr Glu Ala Leu Thr His Val Ser Glu Asp Cys Leu Pro Leu
                820                 825                 830
```

```
Leu Asp Gly Cys Arg Lys Asn Arg Gln Lys Trp Gln Ala Leu Ala Glu
        835                 840                 845

Gln Gln Glu Lys Met Leu Leu Asn Gly Glu Ser Ser Gln Gly Lys Arg
    850                 855                 860

Asp
865

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgatgcaaag caggtgaaac c                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atccaaggcc attccatttc t                                              21

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttccatgtgc tagccaggta aa                                             22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtccaaaac catgcacaat tt                                             22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
accgtgccaa tcacaatcct                                                20

<210> SEQ ID NO 8
<211> LENGTH: 22
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 8
agctgccttc tgtgacattc tg                                          22

<210> SEQ ID NO 9
<211> LENGTH: 258
<212> TYPE: PRT
<213> ORGANISM: Homo sapiens

<400> SEQUENCE: 9

Glu Glu Thr Arg Glu Leu Gln Ser Leu Ala Ala Val Val Pro Ser
1               5                   10                  15

Ala Gln Thr Leu Lys Ile Thr Asp Phe Ser Phe Ser Asp Phe Glu Leu
            20                  25                  30

Ser Asp Leu Glu Thr Ala Leu Cys Thr Ile Arg Met Phe Thr Asp Leu
        35                  40                  45

Asn Leu Val Gln Asn Phe Gln Met Lys His Glu Val Leu Cys Arg Trp
    50                  55                  60

Ile Leu Ser Val Lys Lys Asn Tyr Arg Lys Asn Val Ala Tyr His Asn
65                  70                  75                  80

Trp Arg His Ala Phe Asn Thr Ala Gln Cys Met Phe Ala Ala Leu Lys
                85                  90                  95

Ala Gly Lys Ile Gln Asn Lys Leu Thr Asp Leu Glu Ile Leu Ala Leu
            100                 105                 110

Leu Ile Ala Ala Leu Ser His Asp Leu Asp His Arg Gly Val Asn Asn
        115                 120                 125

Ser Tyr Ile Gln Arg Ser Glu His Pro Leu Ala Gln Leu Tyr Cys His
    130                 135                 140

Ser Ile Met Glu His His His Phe Asp Gln Cys Leu Met Ile Leu Asn
145                 150                 155                 160

Ser Pro Gly Asn Gln Ile Leu Ser Gly Leu Ser Ile Glu Glu Tyr Lys
                165                 170                 175

Thr Thr Leu Lys Ile Ile Lys Gln Ala Ile Leu Ala Thr Asp Leu Ala
            180                 185                 190

Leu Tyr Ile Lys Arg Arg Gly Glu Phe Phe Glu Leu Ile Arg Lys Asn
        195                 200                 205

Gln Phe Asn Leu Glu Asp Pro His Gln Lys Glu Leu Phe Leu Ala Met
    210                 215                 220

Leu Met Thr Ala Cys Asp Leu Ser Ala Ile Thr Lys Pro Trp Pro Ile
225                 230                 235                 240

Gln Gln Arg Leu Ala Glu Leu Val Ala Thr Glu Phe Phe Asp Gln Gly
                245                 250                 255

Asp Arg

<210> SEQ ID NO 10
<211> LENGTH: 53
<212> TYPE: PRT
<213> ORGANISM: Homo sapiens

<400> SEQUENCE: 10

```
Glu Lys Lys Asn Lys Ile Pro Ser Met Gln Val Gly Phe Ile Asp Ala
1               5                   10                  15

Ile Cys Leu Gln Leu Tyr Glu Ala Leu Thr His Val Ser Glu Asp Cys
            20                  25                  30

Phe Pro Leu Leu Asp Gly Cys Arg Lys Asn Arg Gln Lys Trp Gln Ala
        35                  40                  45

Leu Ala Glu Gln Gln
    50
```